US012723099B2

(12) United States Patent
Campbell et al.

(10) Patent No.: US 12,723,099 B2
(45) Date of Patent: Sep. 1, 2026

(54) TUMOR ACTIVATED ANTIBODIES TARGETING TROP2 AND USES THEREOF

(71) Applicant: Janux Therapeutics, Inc., San Diego, CA (US)

(72) Inventors: David Campbell, San Diego, CA (US); Thomas R. Diraimondo, San Diego, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 644 days.

(21) Appl. No.: 18/314,088

(22) Filed: May 8, 2023

(65) Prior Publication Data

US 2023/0357429 A1 Nov. 9, 2023

Related U.S. Application Data

(63) Continuation of application No. PCT/US2023/066554, filed on May 3, 2023.

(60) Provisional application No. 63/338,172, filed on May 4, 2022.

(51) Int. Cl.

| | |
|---|---|
| ***C07K 16/30*** | (2006.01) |
| ***C07K 16/28*** | (2006.01) |
| *A61K 39/00* | (2006.01) |

(52) U.S. Cl.

CPC .......... *C07K 16/30* (2013.01); *C07K 16/2809* (2013.01); *A61K 2039/505* (2013.01); *C07K 2317/31* (2013.01); *C07K 2317/55* (2013.01); *C07K 2317/622* (2013.01); *C07K 2317/73* (2013.01); *C07K 2317/76* (2013.01); *C07K 2317/92* (2013.01); *C07K 2317/94* (2013.01)

(58) Field of Classification Search

CPC C07K 16/30; C07K 16/2809; C07K 2317/31; C07K 2317/55; C07K 2317/622; C07K 2317/73; C07K 2317/76; C07K 2317/92; C07K 2317/94; C07K 2317/565; C07K 2317/64; C07K 2319/00; A61K 2039/505

See application file for complete search history.

(56) References Cited

U.S. PATENT DOCUMENTS

| | | | |
|---|---|---|---|
| 6,217,866 | B1 | 4/2001 | Schlessinger et al. |
| 7,060,808 | B1 | 6/2006 | Goldstein et al. |
| 8,557,961 | B2 | 10/2013 | Silverman et al. |
| 8,658,175 | B2 | 2/2014 | Dubridge et al. |
| 9,249,211 | B2 | 2/2016 | Schellenberger et al. |
| 9,493,563 | B2 | 11/2016 | Blein et al. |
| 9,540,440 | B2 | 1/2017 | Lowman et al. |
| 9,708,412 | B2 | 7/2017 | Baeuerle et al. |
| 9,916,166 | B2 | 3/2018 | Aizawa |
| 9,976,166 | B2 | 5/2018 | Schellenberger et al. |
| 10,118,966 | B2 | 11/2018 | Qian |
| 10,533,053 | B2 | 1/2020 | Lowman et al. |
| 10,870,874 | B2 | 12/2020 | Schellenberger et al. |
| 11,180,562 | B2 | 11/2021 | Lowman et al. |
| 11,512,113 | B2 | 11/2022 | Campbell et al. |
| 11,649,291 | B2 | 5/2023 | Griswold et al. |
| 11,773,166 | B2 | 10/2023 | Ollier et al. |
| 11,851,502 | B2 | 12/2023 | Blein et al. |
| 11,891,454 | B2 | 2/2024 | Blein et al. |
| 2012/0017338 | A1 | 1/2012 | Wu et al. |
| 2017/0145115 | A1 | 5/2017 | Blein et al. |
| 2018/0112011 | A1 | 4/2018 | Ollier |
| 2018/0118846 | A1* | 5/2018 | Chang ................ A61K 39/3955 |
| 2019/0048095 | A1 | 2/2019 | Tang et al. |
| 2019/0336615 | A1 | 11/2019 | Thompson et al. |
| 2020/0102403 | A1 | 4/2020 | Ollier |
| 2021/0164011 | A1 | 6/2021 | Schellenberger et al. |
| 2022/0054544 | A1 | 2/2022 | Lin et al. |
| 2022/0213227 | A1 | 7/2022 | Ollier |
| 2022/0289853 | A1 | 9/2022 | Lowman et al. |
| 2023/0061715 | A1 | 3/2023 | Schellenberger et al. |
| 2023/0062624 | A1 | 3/2023 | Ollier et al. |
| 2023/0220109 | A1 | 7/2023 | Campbell et al. |
| 2024/0252669 | A1 | 8/2024 | Campbell et al. |
| 2025/0154278 | A1 | 5/2025 | Campbell et al. |

FOREIGN PATENT DOCUMENTS

| | | | |
|---|---|---|---|
| EP | 0359282 | A2 | 3/1990 |
| EP | 3668898 | A1 | 6/2020 |
| WO | WO-03074566 | A2 | 9/2003 |
| WO | WO-2015126548 | A1 | 8/2015 |
| WO | WO-2019034580 | A1 | 2/2019 |
| WO | WO-2019126576 | A1 | 6/2019 |
| WO | WO-2019222278 | A1 | 11/2019 |
| WO | WO-2020191092 | A1 | 9/2020 |
| WO | WO-2020247871 | A2 | 12/2020 |
| WO | WO-2022046658 | A1 | 3/2022 |
| WO | WO-2022094299 | A2 | 5/2022 |
| WO | WO-2022125583 | A1 | 6/2022 |
| WO | WO-2023164513 | A2 | 8/2023 |
| WO | WO-2023215789 | A2 | 11/2023 |

OTHER PUBLICATIONS

Al-Lazikani et al. Standard conformations for the canonical structures of immunoglobulins. J Mol Biol 273(4):927-948 (1997).

Bird et al. Single-chain antigen-binding proteins. Science 242:423-442 (1988).

Chothia et al. Canonical structures for the hypervariable regions of immunoglobulins. J Mol Biol 196:901-917 (1987).

Chothia et al. Structural repertoire of the human VH segments. J Mol Biol 227:799-817 (1992).

Clackson et al. Making antibody fragments using phage display libraries. Nature 352(6336):624-628 (1991).

(Continued)

*Primary Examiner* — Sean E Aeder
*Assistant Examiner* — Yie Chia Lee
(74) *Attorney, Agent, or Firm* — WILSON SONSINI GOODRICH & ROSATI

(57) ABSTRACT

Disclosed herein are isolated polypeptides or polypeptide complexes that comprise a tumor-associated calcium signal transducer 2 (TROP2) binding domain that has been optimized for binding and kinetic properties. In some embodiments, the isolated polypeptides or polypeptide complexes further comprise a CD3 binding domain.

28 Claims, 339 Drawing Sheets

Specification includes a Sequence Listing.

(56) References Cited

OTHER PUBLICATIONS

Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Courtenay-Luck. Chapter 8: Genetic manipulation of monoclonal antibodies. Monoclonal Antibodies: Production, Engineering and Clinical Application pp. 166-179 (1995).
Crouse et al. Expression and amplification of engineered mouse dihydrofolate reductase minigenes. Mol Cell Biol 3(2):257-266 (1983).
Goldspiel et al. Human gene therapy. Clin Pharm 12:488-505 (1993).
Hanes et al. In vitro selection and evolution of functional proteins by using ribosome display. PNAS USA 94:4937-4942 (1997).
Honegger et al. Yet another numbering scheme for immunoglobulin variable domains: an automatic modeling and analysis tool. J Mol Biol 309(3):657-70 (2001).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Huston et al. Protein engineering of single-chain Fv analogs and fusion proteins. Methods Enzymol. 203:46-96 (1991).
Kabat et al. Sequences of proteins of immunological interest. NIH Publ. No. 91-3242 1:647-669 (1991).
Kohler et al. Continuous cultures of fused cells secreting antibody of predefined specificity. Nature 256:495-497 (1975).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Larrick et al. PCR amplification of antibody genes. Methods 2:106-110 (1991).
Lefranc et al.: IMGT unique numbering for immunoglobulin and T cell receptor variable domains and Ig superfamily V-like domains. Dev Comp Immunol 27(1):55-77 (2003).
Lowy et al., Isolation of transforming DNA: Cloning the hamster aprt gene. Cell 22:817-823 (1980).
Maccallum et al.: Antibody-antigen interactions: contact analysis and binding site topography. J Mol Biol. 262(5):732-745 (1996).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Neuberger et al. Recombinant antibodies possessing novel effector functions. Nature 312(5995):604-608 (1984).
O'Hare et al. Transformation of mouse fibroblasts to methotrexate resistance by a recombinant plasmid expressing a prokaryotic dihydrofolate reductase. PNAS USA 78:1527-1531 (1981).
PCT/US2023/063075 International Invitation to Pay Additional Fees dated May 31, 2023.
PCT/US2023/063075 International Search Report and Written Opinion dated Aug. 4, 2023.
PCT/US2023/066554 International Invitation to Pay Additional Fees dated Jul. 21, 2023.
Santerre et al. Expression of prokaryotic genes for hygromycin B and G418 resistance as dominant-selection markers in mouse L cells. Gene 30(1-3):147-156 (1984).
Skerra et al. Assembly of a functional Immunoglobulin Fv fragment in *Escherichia coli*. Science 240(4855):1038-1041 (1988).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Tolstoshev. Gene Therapy, Concepts, Current Trials and Future Directions. Ann. Rev. Pharmacol. Toxicol. 32:573-596 (1993).
Ward et al. Binding activities of a repertoire of single immunoglobulin variable domains secreted from *Escherichia coli*. Nature 341(6242):544-546 (1989).
Ward et al. Genetic Manipulation and Expression of Antibodies. Monoclonal Antibodies: Principles and Applications, Wiley-Liss Inc., pp. 137-185 (1995).
Whitelegg et al. WAM: an improved algorithm for modelling antibodies on the WEB. Protein Eng. 13:819-24 (2000).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wu et al. Delivery systems for gene therapy. Biotherapy 3:87-95 (1991).
Liu, Huicheng et al. Bispecific Antibody Targeting TROP2xCD3 Suppresses Tumor Growth Of Triple Negative Breast Cancer. The Journal for ImmunoTherapy of Cancer 9(10):e003468, 1-12 (2021).
Rossi et al. A new class of bispecific antibodies to redirect T cells for cancer immunotherapy. mabs 6(2):381-391; Mar./Apr. 2014.
U.S. Appl. No. 18/559,201 Notice of Allowance dated Aug. 21, 2024.
PCT/US2023/066554 International Search Report and Written Opinion dated Oct. 13, 2023.

* cited by examiner

| | TBD-2 | TBD-3 | TBD-4 | TBD-5 | TBD-6 | TBD-7 | TBD-8 | TBD-9 | TBD-10 | TBD-11 | TBD-12 | TBD-1 |
|---|---|---|---|---|---|---|---|---|---|---|---|---|
| EC50 nM | 4.71 | 0.27 | >1000 | >1000 | 0.29 | 0.22 | 0.20 | 16.80 | 0.29 | 3.80 | 0.20 | 0.22 |

| | TBD-13 | TBD-14 | TBD-15 | TBD-16 | TBD-17 | TBD-18 | TBD-19 | TBD-20 | TBD-21 | TBD-22 | TBD-23 | TBD-1 |
|---|---|---|---|---|---|---|---|---|---|---|---|---|
| EC50 nM | >1000 | 38.56 | 72.15 | 0.1771 | 0.4324 | 800.7 | 701.9 | 52.25 | 4.105 | 1.098 | 0.2365 | 0.1818 |

TROP2 Fab binding to peptides

OD 450 nm 0.0
0.5
1.0
1.5
2.0
2.5

-5
-4
-3
-2
-1
0
1
2
3

Log [TBD-17, nM]

Peptide-32
Peptide-2
Peptide-33
Peptide-34
Peptide-35
Peptide-36
Peptide-37
Peptide-6
Peptide-38
Peptide-25
Peptide-3
Peptide-8

Peptides inhibit TROP2 Fab, TBD-1, from binding TROP2 antigen

OD 450 nm 2.0
1.5
1.0
0.5
0.0

-7 -6 -5 -4 -3 -2 -1 0 1 2 3

Log [Peptide, uM]

Peptide-43
Peptide-8
Peptide-44
Peptide-45
Peptide-46
Peptide-47
Peptide-48
Peptide-49
Peptide-50
Peptide-51
Peptide-52

Peptides inhibit TROP2 Fab, TBD-6 , from binding TROP2 antigen

- Peptide-25
- Peptide-1
- Peptide-2
- Peptide-3
- Peptide-4
- Peptide-5
- Peptide-6
- Peptide-7

OD 450 nm 1.0
0.5
0.0

-7 -6 -5 -4 -3 -2 -1 0 1 2 3

Log [Peptide, uM]

Peptides inhibit TROP2 Fab, TBD-6 , from binding TROP2 antigen

OD 450 nm 2.0
1.5
1.0
0.5
0.0

-7 -6 -5 -4 -3 -2 -1 0 1 2 3

Log [Peptide, uM]

Peptide-43
Peptide-8
Peptide-53
Peptide-54
Peptide-55
Peptide-56
Peptide-57
Peptide-58
Peptide-59
Peptide-60
Peptide-61

Peptides inhibit TROP2 Fab, TBD-22, from binding TROP2 antigen

OD 450 nm 1.0
0.5
0.0

-7 -6 -5 -4 -3 -2 -1 0 1 2 3

Log [Peptide, uM]

Peptide-25
Peptide-1
Peptide-2
Peptide-3
Peptide-4
Peptide-5
Peptide-6
Peptide-7

| TROP2 | PC-1 | PC-1 + MTSP1 |
|---|---|---|
| $EC_{50}$ nM | 49.40 | 0.48 |

| CD3 | PC-1 | PC-1 + MTSP1 |
|---|---|---|
| EC50 nM | 9.88 | 0.04 |

| | PC-2 | PC-2 + MTSP1 | PC-3 | PC-3 + MTSP1 | PC-4 | PC-4 + MTSP1 |
|---|---|---|---|---|---|---|
| EC50 nM | 78.49 | 0.45 | 64.62 | 0.42 | 32.83 | 0.46 |

| | PC-2 | PC-2 + MTSP1 | PC-3 | PC-3 + MTSP1 | PC-4 | PC-4 + MTSP1 |
|---|---|---|---|---|---|---|
| EC50 nM | 14.39 | 0.07 | 14.69 | 0.06 | 32.69 | 0.11 |

| | TCE-1 | TCE-2 | PC-6 | PC-6 + MTSP1 | PC-7 | PC-7 + MTSP1 | PC-5 | PC-5 + MTSP1 |
|---|---|---|---|---|---|---|---|---|
| TROP2 $EC_{50}$ nM | 0.07 | 0.13 | 32.87 | 0.22 | 24.56 | 0.23 | 24.46 | 0.25 |
| CD3 $EC_{50}$ nM | 0.05 | 0.06 | 86.09 | 0.04 | 72.12 | 0.07 | 3.80 | 0.04 |

| | TCE-3 | TCE-6 | PC-12 | PC-12+ MTSP1 | PC-13 | PC-13+ MTSP1 | TCE-4 | TCE-7 | PC-14 | PC-14+ MTSP1 | PC-15 | PC-15+ MTSP1 |
|---|---|---|---|---|---|---|---|---|---|---|---|---|
| TROP2 $EC_{50}$ nM | 3.18 | 0.46 | 351.7 | 7.45 | 419.0 | 19.75 | 7.29 | 1.41 | 333.4 | 11.29 | 363.0 | 12.93 |
| CD3 $EC_{50}$ nM | 0.05 | 0.04 | 63.43 | 0.05 | 107.6 | 0.07 | 0.11 | 0.07 | 67.76 | 0.06 | 59.11 | 0.06 |

| | TCE-5 | TCE-8 | PC-8 | PC-8 + MTSP1 | PC-9 | PC-9 + MTSP1 | PC-10 | PC-10 + MTSP1 | PC-11 | PC-11 + MTSP1 |
|---|---|---|---|---|---|---|---|---|---|---|
| TROP2 EC50 nM | 1.43 | 0.57 | 186.8 | 3.08 | 193.8 | 3.13 | 181.2 | 2.75 | 379.0 | 6.67 |
| CD3 EC50 nM | 0.05 | 0.05 | 74.67 | 0.05 | 52.38 | 0.06 | 28.42 | 0.04 | 77.50 | 0.12 |

| | TCE-4 | PC-19 | PC-19+MMP9 | PC-13 | PC-23 |
|---|---|---|---|---|---|
| **EC50 nM** | **2.50** | **>1000** | **1.18** | **>1000** | **>1000** |

| | TCE-4 | PC-19 | PC-19+MMP9 | PC-13 | PC-23 |
|---|---|---|---|---|---|
| **EC50 nM** | **0.36** | **130.7** | **0.19** | **671.5** | **218.6** |

| | TCE-5 | PC-21 | PC-21+MMP9 | PC-25 | PC-27 | TCE-1 |
|---|---|---|---|---|---|---|
| EC50 nM | 0.59 | 168.3 | 0.94 | 205.1 | 213.9 | 0.17 |

CD3 binding ELISA

| | TCE-5 | PC-21 | PC-21+MMP9 | PC-25 | PC-27 | TCE-1 |
|---|---|---|---|---|---|---|
| EC50 nM | 0.13 | 490 | 0.18 | 685 | 563.9 | 0.12 |

| | TCE-8 | PC-8 | PC-16 | PC-20 | PC-24 | PC-26 | TCE-6 | PC-22 | TCE-7 | PC-18 |
|---|---|---|---|---|---|---|---|---|---|---|
| TROP2 $EC_{50}$ nM | 0.20 | 86.04 | 69.82 | 74.31 | 87.54 | 54.34 | 0.37 | 142.1 | 0.36 | 301.0 |
| CD3 $EC_{50}$ nM | 0.10 | 170.5 | 72.20 | 23.65 | 183.3 | 8.546 | 0.15 | 19.70 | 0.11 | 390.2 |

| | TCE-1 | TCE-5 | PC-17 | PC-17+MTSP1 |
|---|---|---|---|---|
| EC50 nM | 1.29 | 20.90 | 926.5 | 124.3 |

| | TCE-1 | TCE-5 | PC-17 | PC-17+MTSP1 |
|---|---|---|---|---|
| EC50 nM | 0.26 | 0.28 | 543.6 | 0.36 |

| | TCE-1 | PC-5 | PC-6 | PC-28 | PC-29 |
|---|---|---|---|---|---|
| TROP2 $EC_{50}$ nM | 0.06 | 9.15 | 16.60 | 24.99 | 16.26 |

| | TCE-1 | PC-5 | PC-6 | PC-28 | PC-29 |
|---|---|---|---|---|---|
| CD3 EC50 nM | 0.06 | 16.64 | 201.6 | 44.52 | 18.19 |

| | TCE-8 | PC-8 | PC-30 |
|---|---|---|---|
| TROP2 EC50 nM | 0.16 | 165.4 | 150.6 |

| | TCE-8 | PC-8 | PC-30 |
|---|---|---|---|
| CD3 EC50 nM | 0.07 | 132.7 | 19.12 |

| | TCE-7 | PC-18 |
|---|---|---|
| TROP2 EC50 nM | 0.18 | 205.5 |

| | TCE-7 | PC-18 |
|---|---|---|
| CD3 EC50 nM | 0.05 | 131.0 |

| HCT116 | TCE-1 | PC-1 | PC-1 + MTSP1 |
|---|---|---|---|
| EC50 (pM) | 13.9 | >100,000 | 42.15 |

| HCT116 | TCE-1 | PC-2 | PC-2 + MTSP1 | PC-3 | PC-3 + MTSP1 |
|---|---|---|---|---|---|
| EC50 (pM) | 15.7 | >100,000 | 22.5 | >100,000 | 28.7 |

| HCT116 | TCE-2 | PC-4 | PC-4 + MTSP1 |
|---|---|---|---|
| EC50 (pM) | 2.1 | 4,093 | 1.8 |

| HCT116 | PC-8 | PC-8 + MTSP1 | PC-9 | PC-9 + MTSP1 |
|---|---|---|---|---|
| EC50 (pM) | >100,000 | 669.5 | 70,631 | 42.5 |

| | TCE-3 | TCE-4 | TCE-6 | TCE-7 |
|---|---|---|---|---|
| EC50 pM | 21.1 | 16.9 | 159.8 | 172.5 |

| | TCE-8 | PC-15 | PC-15 + MTSP1 | TCE-4 |
|---|---|---|---|---|
| EC50 pM | 86.6 | >100,000 | 36.0 | 19.3 |

| | TCE-3 | TCE-6 | PC-13 | PC-13 + MTSP1 |
|---|---|---|---|---|
| EC50 pM | 21.0 | 167.6 | 49,789 | 86.5 |

| | TCE-5 | PC-9 | PC-11 | PC-11 + MTSP1 |
|---|---|---|---|---|
| EC50 pM | 5.8 | 27,311 | 53,853 | 21.69 |

| | TCE-1 | PC-5 | PC-6 | PC-6 + MTSP1 |
|---|---|---|---|---|
| EC50 pM | 25.25 | >100,000 | >100,000 | 113.4 |

| | TCE-4 | TCE-7 | PC-15 | PC-15 + MTSP1 |
|---|---|---|---|---|
| EC50 pM | 18.28 | 205.8 | >100,000 | 43.42 |

| | TCE-3 | PC-13 | TCE-4 | PC-15 |
|---|---|---|---|---|
| EC50 pM | 8.7 | 11,421 | 7.3 | 11,964 |

| | TCE-5 | PC-6 | PC-9 | PC-17 |
|---|---|---|---|---|
| EC50 pM | 1.6 | 72,192 | 3,888 | 6,243 |

| | TCE-1 | PC-6 | PC-6 + MMP9 | PC-6 + MTSP1 |
|---|---|---|---|---|
| EC50 pM | 6.8 | >100,000 | 25.91 | 51.93 |

| | TCE-1 | PC-1 | PC-2 | PC-5 |
|---|---|---|---|---|
| EC50 pM | 16.1 | 38,749 | 61,667 | 66,886 |

| | TCE-8 | PC-8 | PC-10 | PC-16 |
|---|---|---|---|---|
| EC50 pM | 26.00 | >100,000 | 89,531 | >100,000 |

| | TCE-7 | PC-14 |
|---|---|---|
| EC50 pM | 51.6 | 96,746 |

| | TCE-6 | PC-12 |
|---|---|---|
| EC50 pM | 76.4 | 50,259 |

| | TCE-8 | PC-21 |
|---|---|---|
| EC50 pM | 69.43 | 15,940 |

| | TCE-5 | PC-21 | PC-25 | PC-27 |
|---|---|---|---|---|
| EC50 pM | 4.094 | 193,75 | 21,133 | 17,678 |

| | PC-19 |
|---|---|
| EC50 pM | 55,027 |

| | TCE-2 | PC-7 | TCE-1 | PC-3 |
|---|---|---|---|---|
| EC50 pM | 1.5 | 4,956 | 37.1 | 40,799 |

| | TCE-8 | PC-20 | PC-24 | PC-26 |
|---|---|---|---|---|
| EC50 pM | 29.5 | >100,000 | 80,193 | 29,329 |

| | TCE-7 | PC-18 | TCE-6 | PC-22 |
|---|---|---|---|---|
| EC50 pM | 46.8 | >100,000 | 78.0 | >100,000 |

| | TCE-8 | PC-8 | PC-16 | PC-20 |
|---|---|---|---|---|
| EC50 pM | 43.41 | >100,000 | >100,000 | >100,000 |

| | TCE-8 | PC-8 | PC-24 | PC-26 |
|---|---|---|---|---|
| EC50 pM | 38.46 | >100,000 | >100,000 | >100,000 |

| | TCE-1 | PC-1 | PC-2 | PC-5 |
|---|---|---|---|---|
| EC50 pM | 1.3 | 4,352 | 4,829 | 7,863 |

| | TCE-8 | PC-8 | PC-10 | PC-16 |
|---|---|---|---|---|
| EC50 pM | 4.3 | 41,623 | 11,303 | 34,848 |

| | TCE-1 | PC-6 | PC-3 | PC-5 |
|---|---|---|---|---|
| EC50 pM | 1.3 | 5,977 | 4,265 | 10,129 |

| | TCE-7 | TCE-4 | PC-15 | PC-19 |
|---|---|---|---|---|
| EC50 pM | 6.5 | 0.4 | 836.9 | 602.3 |

| | TCE-6 | PC-12 | TCE-3 | PC-23 |
|---|---|---|---|---|
| EC50 pM | 9.6 | 4,523 | 0.4 | 2,652 |

| | TCE-5 | PC-16 | PC-25 | PC-27 |
|---|---|---|---|---|
| EC50 pM | 0.1 | 214.6 | 404.2 | 345.4 |

| | TCE-8 | PC-20 | PC-24 | PC-26 |
|---|---|---|---|---|
| EC50 pM | 3.9 | 24,910 | 13,268 | 5,230 |

| | TCE-7 | PC-18 | TCE-6 | PC-22 |
|---|---|---|---|---|
| EC50 pM | 4.7 | >100,000 | 6.3 | 68,363 |

| | TCE-8 | PC-8 | PC-16 | PC-24 |
|---|---|---|---|---|
| EC50 pM | 3.8 | 43,052 | 33,278 | 14,202 |

| | TCE-8 | PC-8 | PC-16 | PC-20 |
|---|---|---|---|---|
| EC50 pM | 7.7 | 69,494 | 56,455 | 54,724 |

| | TCE-8 | PC-8 | PC-24 | PC-26 |
|---|---|---|---|---|
| EC50 pM | 8.3 | 86,338 | 46,704 | 44,008 |

| | TCE-7 | PC-18 | TCE-5 | PC-9 |
|---|---|---|---|---|
| EC50 pM | 7.9 | >100,000 | 0.2 | 530.3 |

| | TCE-1 | TCE-6 | TCE-7 | TCE-8 |
|---|---|---|---|---|
| EC50 pM | 1.0 | 6.3 | 6.8 | 4.3 |

| | TCE-7 | PC-18 | PC-18 + MTSP1 |
|---|---|---|---|
| EC50 pM | 5.6 | >100,000 | 40.2 |

| | TCE-8 | PC-8 |
|---|---|---|
| EC50 pM | 3.7 | 38,219 |

| | TCE-1 | PC-5 | PC-28 |
|---|---|---|---|
| EC50 pM | 0.5 | 4,669 | 3,776 |

| | TCE-8 | PC-8 |
|---|---|---|
| EC50 pM | 1.4 | 30,375 |

| | TCE-7 | PC-18 |
|---|---|---|
| EC50 pM | 5.9 | >100,000 |

| | TCE-1 | PC-5 | PC-28 |
|---|---|---|---|
| EC50 pM | 0.5 | 4,669 | 3,776 |

| | TCE-8 | PC-8 | PC-30 |
|---|---|---|---|
| EC50 pM | 6.1 | 46,987 | 23,214 |

| hTROP2 HEK293 | TCE-7 | PC-18 | TCE-8 | PC-8 |
|---|---|---|---|---|
| EC50 pM | 2.6 | 66,883 | 1.4 | 45,443 |

| cyTROP2 HEK293 | TCE-7 | PC-18 | TCE-8 | PC-8 |
|---|---|---|---|---|
| EC50 pM | 0.1 | 9,081 | 0.1 | 4,683 |

| HEK293 | PC-1 | PC-1+MTSP1 | TCE-1 | TCE-2 |
|---|---|---|---|---|
| EC50 pM | >100,000 | >3,000 | >3,000 | >3,000 |

| | TCE-1 15ug/kg/day | Units |
|---|---|---|
| $C_{MAX}$ | 0.265 | nM |

*Animals died due to severe toxicities at 24-32hrs post the initiation of dosing

*Early termination due to severe clinical signs at 24hrs post the initiation of dosing.

| CD3 ELISA | TCE-1 | TCE-9 | TCE-10 | TCE-11 | TCE-12 | TCE-13 | TCE-14 | TCE-15 | TCE-16 | TCE-17 | TCE-18 |
|---|---|---|---|---|---|---|---|---|---|---|---|
| EC50 (nM) | 0.1798 | 0.1995 | 0.2772 | 0.2707 | 0.2178 | 3.130 | 1.137 | 0.1899 | 0.2016 | 0.2183 | 0.1447 |

| CD3 ELISA | TCE-1 | TCE-1 | TCE-19 | TCE-20 | TCE-21 | TCE-22 | TCE-23 | TCE-24 | TCE-25 | TCE-26 | TCE-27 | TCE-28 |
|---|---|---|---|---|---|---|---|---|---|---|---|---|
| EC50 (nM) | 0.1592 | 0.1681 | 0.2352 | 0.5627 | 732.6 | 0.5611 | 0.1992 | 0.1727 | 0.1972 | 1.810 | 0.1781 | 0.1576 |

| CD3 ELISA | TCE-1 | TCE-29 | TCE-30 | TCE-31 | TCE-32 | TCE-33 | TCE-34 | TCE-35 |
|---|---|---|---|---|---|---|---|---|
| EC50 (nM) | 0.1753 | 0.1753 | 0.1988 | 8.652 | 0.1939 | 0.6010 | 0.2283 | 0.1712 |

TUMOR ACTIVATED ANTIBODIES TARGETING TROP2 AND USES THEREOF

CROSS-REFERENCE

The present application is a continuation of International Application No. PCT/US2023/066554, filed May 3, 2023, which claims the benefit of U.S. Provisional Application No. 63/338,172 filed May 4, 2022 which is incorporated herein by reference in its entirety.

SEQUENCE LISTING

The instant application contains a Sequence Listing which has been submitted electronically in XML format and is hereby incorporated by reference it its entirety. Said XML copy, created on Apr. 27, 2023, is named 52426-742_301 SL.xml and is 487,415 bytes in size.

SUMMARY

Disclosed herein are isolated polypeptide and polypeptide complexes according to Formula I: $A_1$-$L_1$-$P_1$ (Formula I) wherein $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YWX_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease. In some embodiments, $X_1$ is Q, N, D, E, or A; $X_2$ is Q, N, D, E, or A; $X_3$ is I, V, L, or A; $X_4$ is T, S, or A; $X_5$ is P, G, or A; $X_6$ is L, V, I, or A; $X_7$ is T, S, or A; $X_8$ is R, K, or A; $X_9$ is G, S, T, or A; $X_{10}$ is F, Y, or A; $X_{11}$ is G, S, T, or A; $X_{12}$ is S, G, T, or A; $X_{13}$ is S, G, T, or A; $X_{14}$ is Y, W, F. or A; $X_{15}$ is F, Y, W, or A; $X_{16}$ is D, E, Q, N, or A; and $X_{17}$ is V, L, I, or A. In some embodiments, $X_1$ is Q; and $X_6$ is L. In some embodiments, $X_8$ is R; $X_{10}$ is F; $X_{11}$ is G; $X_{14}$ is Y; $X_{15}$ is F; and $X_{16}$ is D.

In some embodiments, $X_1$ is Q, S, T, D, N, E, or A; $X_2$ is Q, S, T, D, N, E, or A; $X_3$ is I, G, P, V, L, M, or A; $X_4$ is T, G, S, M, H, N, Q, or A; $X_5$ is P, G, V, L, I, M, or A; $X_6$ is L, G, P, V, I, M, or A; $X_7$ is T, G, S, M, H, N, Q, or A; $X_8$ is R, H, K, or A; $X_9$ is G, P, V, L, I, M, S, T, or A; $X_{10}$ is F, Y, W, V, L, I, or A; $X_{11}$ is G, P, V, L, I, M, S, T, or A; $X_{12}$ is S, G, T, M, N, Q, or A; $X_{13}$ is S, G, T, M, N, Q, or A; $X_{14}$ is Y, F, W, V, L, I, or A; $X_{15}$ is F, Y, W, V, L, I, or A; $X_{16}$ is D, Q, N, E, S, T, or A; and $X_{17}$ is V, G, P, L, I, M, or A. In some embodiments, $X_1$ is Q, N, or A; $X_2$ is Q, N, or A; $X_3$ is I, V, L, or A; $X_4$ is T, S, or A; $X_5$ is P, G, or A; $X_6$ is L, V, I, or A; $X_7$ is T, S, or A; $X_8$ is R, K, or A; $X_9$ is G, V, S, T, or A; $X_{10}$ is F, Y, or A; $X_{11}$ is G, V, S, T, or A; $X_{12}$ is S, G, T, or A; $X_{13}$ is S, G, T, or A; $X_{14}$ is Y, W, or A; $X_{15}$ is F, Y, or A; $X_{16}$ is D, E, or A; and $X_{17}$ is V, G, L, I, or A. In some embodiments, $X_1$ is Q; and $X_6$ is L. In some embodiments, $X_8$ is R; $X_{10}$ is F; $X_{11}$ is G; $X_{14}$ is Y; $X_{15}$ is F; and $X_{16}$ is D.

In some embodiments, CDR3-L comprises an amino acid selected from SEQ ID NOs: 3-5 and 8-12. In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10, and CDR1-H: SEQ ID NO: 13, CDR2-H: SEQ ID NO: 14, CDR3-H: SEQ ID NO: 15; and CDR1-L: SEQ ID NO: 1, CDR2-L: SEQ ID NO: 2, CDR3-L: SEQ ID NO: 12, and CDR1-H: SEQ ID NO: 13, CDR2-H: SEQ ID NO: 14, CDR3-H: SEQ ID NO: 15.

In some embodiments, CDR3-H comprises an amino acid selected from SEQ ID NOs: 16-17, 19-22, and 25-28. In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14; CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28. In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28.

Disclosed herein are isolated polypeptide or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connects $A_1$ to $P_1$ and is a substrate for a tumor specific protease. In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises a variable domain of an immunoglobulin kappa (IgK) or immunoglobulin lambda (IgL) light chain. In some embodiments, the immunoglobulin heavy chain comprises a variable domain of an IgG1, IgG2, IgG3, or IgG4 heavy chain.

In some embodiments, the immunoglobulin light chain comprises an amino acid sequence with at least 90%, 95%, 96%, 97%, 98%, 99%, or 100% identity to any one of SEQ ID NOs: 31, 33, 35, 37, 39, 41, 43, 45, 47, 49, 51, 53, 55, 57, 59, 61, 63, 65, 67, 69, 71, or 73. In some embodiments, the immunoglobulin heavy chain comprises an amino acid sequence with at least 90%, 95%, 96%, 97%, 98%, 99%, or 100% identity to any one of SEQ ID NOs: 32, 34, 36, 38, 40, 42, 44, 46, 48, 50, 52, 54, 56, 58, 60, 62, 64, 66, 68, 70, 72, or 74. In some embodiments, the immunoglobulin light chain comprises an amino acid sequence with at least 90%, 95%, 96%, 97%, 98%, 99%, or 100% identity to SEQ ID NO: 31 and the immunoglobulin heavy chain comprises an amino acid sequence with at least 90%, 95%, 96%, 97%, 98%, 99%, or 100% identity to SEQ ID NO: 32. In some embodiments, the immunoglobulin light chain comprises an amino acid sequence with at least 90%, 95%, 96%, 97%, 98%, 99%, or 100% identity to SEQ ID NO: 33 and the immunoglobulin heavy chain comprises an amino acid sequence with at least 90%, 95%, 96%, 97%, 98%, 99%, or 100% identity to SEQ ID NO: 34. In some embodiments, the immunoglobulin light chain comprises an amino acid sequence with at least 90%, 95%, 96%, 97%, 98%, 99%, or 100% identity to SEQ ID NO: 35 and the immunoglobulin heavy chain comprises an amino acid sequence with at least 90%, 95%, 96%, 97%, 98%, 99%, or 100% identity to SEQ ID NO: 36. In some embodiments, the immunoglobulin light chain comprises an amino acid sequence with at least 90%, 95%, 96%, 97%, 98%, 99%, or 100% identity to SEQ ID NO: 37 and the immunoglobulin heavy chain comprises an amino acid sequence with at least 90%, 95%, 96%, 97%, 98%, 99%, or 100% identity to SEQ ID NO: 38. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40. In some embodiments, the immunoglobulin light chain comprises an amino acid sequence with at least 90%, 95%, 96%, 97%, 98%, 99%, or 100% identity to SEQ ID NO: 41 and the immunoglobulin heavy chain comprises an amino acid sequence with at least 90%, 95%, 96%, 97%, 98%, 99%, or 100% identity to SEQ ID NO: 42. In some embodiments, the immunoglobulin light chain comprises an amino acid sequence with at least 90%, 95%, 96%, 97%, 98%, 99%, or 100% identity to SEQ ID NO: 43 and the immunoglobulin heavy chain comprises an amino acid sequence with at least 90%, 95%, 96%, 97%, 98%, 99%, or 100% identity to SEQ ID NO: 44. In some embodiments, the immunoglobulin light chain comprises an amino acid sequence with at least 90%, 95%, 96%, 97%, 98%, 99%, or 100% identity to SEQ ID NO: 45 and the immunoglobulin heavy chain comprises an amino acid sequence with at least 90%, 95%, 96%, 97%, 98%, 99%, or 100% identity to SEQ ID NO: 46. In some embodiments, the immunoglobulin light chain comprises an amino acid sequence with at least 90%, 95%, 96%, 97%, 98%, 99%, or 100% identity to SEQ ID NO: 47 and the immunoglobulin heavy chain comprises an amino acid sequence with at least 90%, 95%, 96%, 97%, 98%, 99%, or 100% identity to SEQ ID NO: 48. In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50. In some embodiments, the immunoglobulin light chain comprises an amino acid sequence with at least 90%, 95%, 96%, 97%, 98%, 99%, or 100% identity to SEQ ID NO: 51 and the immunoglobulin heavy chain comprises an amino acid sequence with at least 90%, 95%, 96%, 97%, 98%, 99%, or 100% identity to SEQ ID NO: 52. In some embodiments, the immunoglobulin light chain comprises an amino acid sequence with at least 90%, 95%, 96%, 97%, 98%, 99%, or 100% identity to SEQ ID NO: 53 and the immunoglobulin heavy chain comprises an amino acid sequence with at least 90%, 95%, 96%, 97%, 98%, 99%, or 100% identity to SEQ ID NO: 54. In some embodiments, the immunoglobulin light chain comprises an amino acid sequence with at least 90%, 95%, 96%, 97%, 98%, 99%, or 100% identity to SEQ ID NO: 55 and the immunoglobulin heavy chain comprises an amino acid sequence with at least 90%, 95%, 96%, 97%, 98%, 99%, or 100% identity to SEQ ID NO: 56. In some embodiments, the immunoglobulin light chain comprises an amino acid sequence with at least 90%, 95%, 96%, 97%, 98%, 99%, or 100% identity to SEQ ID NO: 57 and the immunoglobulin heavy chain comprises an amino acid sequence with at least 90%, 95%, 96%, 97%, 98%, 99%, or 100% identity to SEQ ID NO: 58. In some embodiments, the immunoglobulin light chain comprises an amino acid sequence with at least 90%, 95%, 96%, 97%, 98%, 99%, or 100% identity to SEQ ID NO: 59 and the immunoglobulin heavy chain comprises an amino acid sequence with at least 90%, 95%, 96%, 97%, 98%, 99%, or 100% identity to SEQ ID NO: 60. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62. In some embodiments, the immunoglobulin light chain comprises an amino acid sequence with at least 90%, 95%, 96%, 97%, 98%, 99%, or 100% identity to SEQ ID NO: 63 and the immunoglobulin heavy chain comprises an amino acid sequence with at least 90%, 95%, 96%, 97%, 98%, 99%, or 100% identity to SEQ ID NO: 64. In some embodiments, the immunoglobulin light chain comprises an amino acid sequence with at least 90%, 95%, 96%, 97%, 98%, 99%, or 100% identity to SEQ ID NO: 65 and the immunoglobulin heavy chain comprises an amino acid sequence with at least 90%, 95%, 96%, 97%, 98%, 99%, or 100% identity to SEQ ID NO: 66. In some embodiments, the immunoglobulin light chain comprises an amino acid sequence with at least 90%, 95%, 96%, 97%, 98%, 99%, or 100% identity to SEQ ID NO: 67 and the immunoglobulin heavy chain comprises an amino acid sequence with at least 90%, 95%, 96%, 97%, 98%, 99%, or 100% identity to SEQ ID NO: 68. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72. In some embodiments, the immunoglobulin light chain comprises an amino acid sequence with at least 90%, 95%, 96%, 97%, 98%, 99%, or 100% identity to SEQ ID NO: 73 and the immunoglobulin heavy chain comprises an amino acid sequence with at least 90%, 95%, 96%, 97%, 98%, 99%, or 100% identity to SEQ ID NO: 74.

In some embodiments, the TROP2 binding domain has weaker binding to TROP2 as compared to a TROP2 binding domain that comprises an immunoglobulin light chain according to SEQ ID NO: 29 and an immunoglobulin heavy chain according to SEQ ID NO: 30 as measured by ELISA in substantially similar assay conditions. In some embodiments, the TROP2 binding domain has an increased $EC_{50}$ for TROP2 as compared to a TROP2 binding domain that comprises an immunoglobulin light chain according to SEQ ID NO: 29 and an immunoglobulin heavy chain according to SEQ ID NO: 30 as measured by ELISA in substantially similar assay conditions. In some embodiments, the TROP2 binding domain has a faster off rate (larger $k_{diss}$) 1 for TROP2 binding as compared to a TROP2 binding domain that comprises an immunoglobulin light chain according to SEQ ID NO: 29 and an immunoglobulin heavy chain according to SEQ ID NO: 30 as measured under substantially similar kinetic assay conditions.

In some embodiments, $P_1$ impairs binding of $A_1$ to TROP2. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ is bound to $A_1$ at or near an antigen binding site. In some embodiments, $P_1$ becomes unbound from $A_1$ when $L_1$ is cleaved by the tumor specific protease thereby exposing $A_1$ to TROP2. In some embodiments, $P_1$ has less than 75% sequence identity to TROP2. In some embodiments, $P_1$ has less than 80% sequence identity to TROP2. In some embodiments, $P_1$ has less than 85% sequence identity to TROP2. In some embodiments, $P_1$ has less than 90% sequence identity to TROP2. In some embodiments, $P_1$ has less than 95% sequence identity to TROP2. In some embodiments, $P_1$ comprises a de novo amino acid sequence that shares less than 10% sequence identity to TROP2. In some embodiments, $P_1$ comprises at least two cysteine amino acid residues. In some embodiments, $P_1$ comprises a cyclic peptide or a linear peptide. In some embodiments, $P_1$ comprises a cyclic peptide. In some embodiments, $P_1$ comprises a linear peptide. In some embodiments, $P_1$ comprise a modified amino acid or non-natural amino acid, or a modified non-natural amino acid, or a combination thereof. In some embodiments, $P_1$ does not comprise albumin or an albumin fragment. In some embodiments, $P_1$ does not comprise an albumin binding domain.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and wherein $P_1$ comprises an amino acid sequence according to SEQ ID NO: 102 or SEQ ID NO: 107, or an amino acid sequence that has 1, 2, or 3 amino acid mutations, substitutions, or deletions relative to SEQ ID NO: 102 or SEQ ID NO: 107. In some embodiments, the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and wherein $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124. In some embodiments, the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and wherein $P_1$ comprises an amino acid sequence according to SEQ ID NO: 102 or SEQ ID NO; 107, or an amino acid sequence that has 1, 2, or 3 amino acid mutations, substitutions, or deletions relative to SEQ ID NO: 102 or SEQ ID NO: 107.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and wherein $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and wherein $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150. In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and wherein $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO:

27, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 27, and wherein $P_1$ comprises an amino acid sequence according to any one of SEQ ID NOs: 107, 109, 116, 141, 142, 148, 149, 150, 158, or an amino acid sequence that has 1, 2, or 3 amino acid mutations, substitutions, or deletions relative to any one of SEQ ID NOs: 107, 109, 116, 141, 142, 148, 149, 150, 158. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and wherein $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions, or deletions relative to any one of SEQ ID NOs: 107, 109, 116, 141, 142, 148, 149, 150, and 158.

In some embodiments, the isolated polypeptide or polypeptide complex further comprises a CD3 binding domain. In some embodiments, the isolated polypeptide or polypeptide complex is according to the following formula $P_2$-$L_2$-$B_2$-$A_1$-$L_1$-$P_1$(Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 75; CDR2-L comprises the amino acid sequence of SEQ ID NO: 76; CDR3-L comprises the amino acid sequence of SEQ ID NO: 77; CDR1-H comprises the amino acid sequence of SEQ ID NO: 78; CDR2-H comprises the amino acid sequence of SEQ ID NO: 79; and CDR3-H comprises the amino acid sequence of SEQ ID NO: 80.

In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 75 or SEQ ID NO: 259; wherein CDR2-L comprises the amino acid sequence of SEQ ID NO: 76; wherein CDR3-L comprises the amino acid sequence of $Z_1$-$Z_2$-W-$Z_3$-$Z_4$-$Z_5$-$Z_6$-W-$Z_7$-$Z_8$; wherein $Z_1$ is V, G, P, L, I, M, S, T, or A; $Z_2$ is L, G, P, V, I, M, S, T, or A; $Z_3$ is Y, F, W, V, L, I, G, or A; $Z_4$ is S, G, T, M, N, Q, H, or A; $Z_5$ is N, Q, S, T, D, E, H, K, R, or A; $Z_6$ is R, S, T, Q, D, E, H, K, N, or A; $Z_7$ is V, G, P, L, I, M, S, T, or A; and $Z_8$ is F, Y, W, V, L, I, G, or A; wherein CDR1-H comprises the amino acid sequence of SEQ ID NO: 78 or SEQ ID NO: 270; wherein CDR2-H comprises the amino acid sequence of SEQ ID NO: 79; and wherein CDR3-H comprises the amino acid sequence of $Z_9$-$Z_{10}$-$Z_{11}$-$Z_{12}$-N-$Z_{13}$-$Z_{14}$-$Z_{15}$-$Z_{16}$-$Z_{17}$-$Z_{18}$-$Z_{19}$-Y-$Z_{20}$-A-$Z_{21}$; wherein $Z_9$ is V, G, P, L, I, M, S, T, or A; $Z_{10}$ is R, S, T, Q, D, E, H, K, N, or A; $Z_{11}$ is H, R, K, G, T, S, N, Q, or A; $Z_{12}$ is G, P, V, L, I, M, S, T, or A; $Z_{13}$ is F, Y, W, V, L, I, G, or A; $Z_{14}$ is G, P, V, L, I, M, S, T, or A; $Z_{15}$ is N, Q, S, T, D, E, H, K, R, or A; $Z_{16}$ is S, G, T, M, N, Q, H, or A; $Z_{17}$ is Y, F, W, V, L, I, G, or A; $Z_{18}$ is I, G, P, V, L, M, S, T, or A; $Z_{19}$ is S, G, T, M, N, Q, H, or A; $Z_{20}$ is W, F, Y, V, L, I, G, or A; and $Z_{21}$ is Y, F, W, V, L, I, G, or A. In some embodiments, $Z_1$ is V, G, L, I, or A; $Z_2$ is L, V, I, or A; $Z_3$ is Y, W, F, or A; $Z_4$ is S, G, T, or A; $Z_5$ is N, Q, D, E, or A; $Z_6$ is R, K, or A; $Z_7$ is G, L, I, or A; $Z_8$ is F, Y, W, or A; $Z_9$ is V, G, L, I, or A; $Z_{10}$ is R, K, or A; $Z_{12}$ is G, S, T, or A; $Z_{13}$ is F, Y, W, or A; $Z_{14}$ is G, S, T, or A; $Z_{15}$ is N, Q, D, E, or A; $Z_{16}$ is S, G, T, or A; $Z_{17}$ is Y, W, F, or A; $Z_{18}$ is I, V, L, or A; $Z_{19}$ is S, G, T, or A; $Z_{20}$ is W, Y, F, or A; and $Z_{21}$ is Y, W, F, or A. In some embodiments, $Z_8$ is F. In some embodiments, $Z_{10}$ is R; $Z_{11}$ is H; $Z_{13}$ is F; $Z_{18}$ is I; $Z_{19}$ is S; and $Z_{20}$ is W.

In some embodiments, CDR3-L of the CD3 binding domain comprises an amino acid sequence selected from SEQ ID NOs: 77, 260-261, 263-266, and 268-269. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO: 76, CDR3-L: SEQ ID NO: 269, and CDR1-H: SEQ ID NO: 78, CDR2-H: SEQ ID NO: 79, CDR3-H: SEQ ID NO: 80. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80.

In some embodiments, CDR3-H of the CD3 binding domain comprises an amino acid sequence selected from SEQ ID NOs: 80, 271-274, 276-282, and 284-285. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 284; and CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285.

In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; and CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285.

In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 262, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 267, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 269, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274;

CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 275; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 283; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 284; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285; and CDR1-L: SEQ ID NO: 259, CDR2-L: SEQ ID NO: 76, CDR3-L: SEQ ID NO: 260, and CDR1-H: SEQ ID NO: 270, CDR2-H: SEQ ID NO: 79, CDR3-H: SEQ ID NO: 286.

In some embodiments, the immunoglobulin light chain of the CD3 binding domain comprises a variable domain of an immunoglobulin kappa (IgK) or immunoglobulin lambda (IgL) light chain. In some embodiments, the immunoglobulin heavy chain of the CD3 binding domain comprises a variable domain of an IgG1, IgG2, IgG3, or IgG4 heavy chain. In some embodiments, the immunoglobulin light chain of the CD3 binding domain comprises an amino acid sequence with at least 90%, 95%, 96%, 97%, 98%, 99%, or 100% identity to SEQ ID NO: 81. In some embodiments, the immunoglobulin heavy chain of the CD3 binding domain comprises an amino acid sequence with at least 90%, 95%, 96%, 97%, 98%, 99%, or 100% identity to SEQ ID NO: 82. In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82.

In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 303. In some embodiments, the CD3 binding domain comprises an amino acid sequence with at least 90%, 95%, 96%, 97%, 98%, 99%, or 100% identity to SEQ ID NO: 304. In some embodiments, the CD3 binding domain comprises an amino acid sequence with at least 90%, 95%, 96%, 97%, 98%, 99%, or 100% identity to SEQ ID NO: 305. In some embodiments, the CD3 binding domain comprises an amino acid sequence with at least 90%, 95%, 96%, 97%, 98%, 99%, or 100% identity to SEQ ID NO: 306. In some embodiments, the CD3 binding domain comprises an amino acid sequence with at least 90%, 95%, 96%, 97%, 98%, 99%, or 100% identity to SEQ ID NO: 307. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 309. In some embodiments, the CD3 binding domain comprises an amino acid sequence with at least 90%, 95%, 96%, 97%, 98%, 99%, or 100% identity to SEQ ID NO: 310. In some embodiments, the CD3 binding domain comprises an amino acid sequence with at least 90%, 95%, 96%, 97%, 98%, 99%, or 100% identity to SEQ ID NO: 311. In some embodiments, the CD3 binding domain comprises an amino acid sequence with at least 90%, 95%, 96%, 97%, 98%, 99%, or 100% identity to SEQ ID NO: 312. In some embodiments, the CD3 binding domain comprises an amino acid sequence with at least 90%, 95%, 96%, 97%, 98%, 99%, or 100% identity to SEQ ID NO: 313. In some embodiments, the CD3 binding domain comprises an amino acid sequence with at least 90%, 95%, 96%, 97%, 98%, 99%, or 100% identity to SEQ ID NO: 314. In some embodiments, the CD3 binding domain comprises an amino acid sequence with at least 90%, 95%, 96%, 97%, 98%, 99%, or 100% identity to SEQ ID NO: 315. In some embodiments, the CD3 binding domain comprises an amino acid sequence with at least 90%, 95%, 96%, 97%, 98%, 99%, or 100% identity to SEQ ID NO: 316. In some embodiments, the CD3 binding domain comprises an amino acid sequence with at least 90%, 95%, 96%, 97%, 98%, 99%, or 100% identity to SEQ ID NO: 317. In some embodiments, the CD3 binding domain comprises an amino acid sequence with at least 90%, 95%, 96%, 97%, 98%, 99%, or 100% identity to SEQ ID NO: 318. In some embodiments, the CD3 binding domain comprises an amino acid sequence with at least 90%, 95%, 96%, 97%, 98%, 99%, or 100% identity to SEQ ID NO: 319. In some embodiments, the CD3 binding domain comprises an amino acid sequence with at least 90%, 95%, 96%, 97%, 98%, 99%, or 100% identity to SEQ ID NO: 320. In some embodiments, the CD3 binding domain comprises an amino acid sequence with at least 90%, 95%, 96%, 97%, 98%, 99%, or 100% identity to SEQ ID NO: 321. In some embodiments, the CD3 binding domain comprises an amino acid sequence with at least 90%, 95%, 96%, 97%, 98%, 99%, or 100% identity to SEQ ID NO: 322. In some embodiments, the CD3 binding domain comprises an amino acid sequence with at least 90%, 95%, 96%, 97%, 98%, 99%, or 100% identity to SEQ ID NO: 323. In some embodiments, the CD3 binding domain comprises an amino acid sequence with at least 90%, 95%, 96%, 97%, 98%, 99%, or 100% identity to SEQ ID NO: 324. In some embodiments, the CD3 binding domain comprises an amino acid sequence with at least 90%, 95%, 96%, 97%, 98%, 99%, or 100% identity to SEQ ID NO: 325. In some embodiments, the CD3 binding domain comprises an amino acid sequence with at least 90%, 95%, 96%, 97%, 98%, 99%, or 100% identity to SEQ ID NO: 326. In some embodiments, the CD3 binding domain comprises an amino acid sequence with at least 90%, 95%, 96%, 97%, 98%, 99%, or 100% identity to SEQ ID NO: 327. In some embodiments, the CD3 binding domain comprises an amino acid sequence with at least 90%, 95%, 96%, 97%, 98%, 99%, or 100% identity to SEQ ID NO: 328. In some embodiments, the CD3 binding domain comprises an amino acid sequence with at least 90%, 95%, 96%, 97%, 98%, 99%, or 100% identity to SEQ ID NO: 329.

In some embodiments, the CD3 binding domain comprises a Fab, Fab', $(Fab')_2$ or a single chain variable fragment (scFv). In some embodiments, the CD3 binding domain is the scFv. In some embodiments, the N-term of the immunoglobulin heavy chain of the TROP2 binding domain is bound to the C-term of the immunoglobulin light chain of the CD3 binding domain. In some embodiments, the C-term of the immunoglobulin heavy chain of the TROP2 binding domain is bound to the N-term of the immunoglobulin light chain of the CD3 binding domain. In some embodiments, the N-term of the immunoglobulin heavy chain of the TROP2 binding domain is bound to the C-term of the immunoglobulin heavy chain of the CD3 binding domain. In some embodiments, the C-term of the immunoglobulin heavy chain of the TROP2 binding domain is bound to the N-term of the immunoglobulin heavy chain of the CD3 binding domain. In some embodiments, the N-term of the immunoglobulin light chain of the TROP2 binding domain is bound to the C-term of the immunoglobulin light chain of the CD3 binding domain. In some embodiments, the C-term of the immunoglobulin light chain of the TROP2 binding domain is bound to the N-term of the immunoglobulin light chain of the CD3 binding domain. In some embodiments, the N-term of the immunoglobulin light chain of the TROP2 binding domain is bound to the C-term of the immunoglobulin heavy chain of the CD3 binding domain. In some embodiments, the C-term of the immunoglobulin light chain of the TROP2 binding domain is bound to the N-term of the immunoglobulin heavy chain of the CD3 binding domain.

In some embodiments, the CD3 binding domain is a scFv and the TROP2 binding domain is a Fab or Fab'. In some embodiments, the scFv is bound to the immunoglobulin heavy chain of the Fab or Fab'. In some embodiments, the scFv is bound to the immunoglobulin light chain of the Fab or Fab'. In some embodiments, the immunoglobulin light chain of the scFv is bound to the immunoglobulin heavy chain of the Fab or Fab'. In some embodiments, the immunoglobulin light chain of the scFv is bound to the immunoglobulin light chain of the Fab or Fab'. In some embodiments, the immunoglobulin heavy chain of the scFv is bound to the immunoglobulin heavy chain of the Fab or Fab'. In some embodiments, the immunoglobulin heavy chain of the scFv is bound to the immunoglobulin light chain of the Fab or Fab'.

In some embodiments, the recombinant antibody or antigen binding fragment thereof comprises amino acid sequences with at least 90%, 95%, 96%, 97%, 98%, 99%, or 100% identity to SEQ ID NO: 87 and SEQ ID NO: 88. In some embodiments, the recombinant antibody or antigen binding fragment thereof comprises amino acid sequences with at least 90%, 95%, 96%, 97%, 98%, 99%, or 100% identity to SEQ ID NO: 89 and SEQ ID NO: 90. In some embodiments, the recombinant antibody or antigen binding fragment thereof comprises amino acid sequences with at least 90%, 95%, 96%, 97%, 98%, 99%, or 100% identity to SEQ ID NO: 91 and SEQ ID NO: 92. In some embodiments, the recombinant antibody or antigen binding fragment thereof comprises amino acid sequences with at least 90%, 95%, 96%, 97%, 98%, 99%, or 100% identity to SEQ ID NO: 93 and SEQ ID NO: 94. In some embodiments, the recombinant antibody or antigen binding fragment thereof comprises amino acid sequences with at least 90%, 95%, 96%, 97%, 98%, 99%, or 100% identity to SEQ ID NO: 95 and SEQ ID NO: 96. In some embodiments, the recombinant antibody or antigen binding fragment thereof comprises amino acid sequences with at least 90%, 95%, 96%, 97%, 98%, 99%, or 100% identity to SEQ ID NO: 97 and SEQ ID NO: 98.

In some embodiments, the recombinant antibody or antigen binding fragment thereof comprises amino acid sequences with at least 90%, 95%, 96%, 97%, 98%, 99%, or 100% identity to SEQ ID NO: 330 and SEQ ID NO: 331. In some embodiments, the recombinant antibody or antigen binding fragment thereof comprises amino acid sequences with at least 90%, 95%, 96%, 97%, 98%, 99%, or 100% identity to SEQ ID NO: 332 and SEQ ID NO: 333. In some embodiments, the recombinant antibody or antigen binding fragment thereof comprises amino acid sequences with at least 90%, 95%, 96%, 97%, 98%, 99%, or 100% identity to SEQ ID NO: 332 and SEQ ID NO: 333. In some embodiments, the recombinant antibody or antigen binding fragment thereof comprises amino acid sequences with at least 90%, 95%, 96%, 97%, 98%, 99%, or 100% identity to SEQ ID NO: 334 and SEQ ID NO: 335. In some embodiments, the recombinant antibody or antigen binding fragment thereof comprises amino acid sequences with at least 90%, 95%, 96%, 97%, 98%, 99%, or 100% identity to SEQ ID NO: 336 and SEQ ID NO: 337. In some embodiments, the recombinant antibody or antigen binding fragment thereof comprises amino acid sequences with at least 90%, 95%, 96%, 97%, 98%, 99%, or 100% identity to SEQ ID NO: 338 and SEQ ID NO: 339. In some embodiments, the recombinant antibody or antigen binding fragment thereof comprises amino acid sequences with at least 90%, 95%, 96%, 97%, 98%, 99%, or 100% identity to SEQ ID NO: 340 and SEQ ID NO: 341. In some embodiments, the recombinant antibody or antigen binding fragment thereof comprises amino acid sequences with at least 90%, 95%, 96%, 97%, 98%, 99%, or 100% identity to SEQ ID NO: 342 and SEQ ID NO: 343. In some embodiments, the recombinant antibody or antigen binding fragment thereof comprises amino acid sequences with at least 90%, 95%, 96%, 97%, 98%, 99%, or 100% identity to SEQ ID NO: 344 and SEQ ID NO: 345. In some embodiments, the recombinant antibody or antigen binding fragment thereof comprises amino acid sequences with at least 90%, 95%, 96%, 97%, 98%, 99%, or 100% identity to SEQ ID NO: 346 and SEQ ID NO: 347. In some embodiments, the recombinant antibody or antigen binding fragment thereof comprises amino acid sequences with at least 90%, 95%, 96%, 97%, 98%, 99%, or 100% identity to SEQ ID NO: 348 and SEQ ID NO: 349. In some embodiments, the recombinant antibody or antigen binding fragment thereof comprises amino acid sequences with at least 90%, 95%, 96%, 97%, 98%, 99%, or 100% identity to SEQ ID NO: 350 and SEQ ID NO: 351.

In some embodiments, the recombinant antibody or antigen binding fragment thereof has weaker cytotoxicity activity as compared to a recombinant antibody or antigen binding fragment thereof that comprises an immunoglobulin light chain according to SEQ ID NO: 83 or 85 and an immunoglobulin heavy chain according to SEQ ID NO: 84 or 86 as measured in an in vitro tumor cell killing assay under substantially similar assay conditions.

In some embodiments, $P_2$ impairs binding of $B_2$ to CD3. In some embodiments, $P_2$ is bound to $B_2$ through ionic interactions, electrostatic interactions, hydrophobic interactions, Pi-stacking interactions, and H-bonding interactions, or a combination thereof. In some embodiments, $P_2$ is bound to $B_2$ at or near an antigen binding site. In some embodiments, $P_2$ becomes unbound from $B_2$ when $L_2$ is cleaved by the tumor specific protease thereby exposing $B_2$ to the CD3. In some embodiments, $P_2$ has less than 70% sequence identity to CD3. In some embodiments, $P_2$ has less than 75% sequence identity to CD3. In some embodiments, $P_2$ has less than 80% sequence identity to CD3. In some embodiments, $P_2$ has less than 85% sequence identity to CD3. In some embodiments, $P_2$ has less than 90% sequence identity to CD3. In some embodiments, $P_2$ has less than 95% sequence identity to CD3. In some embodiments, $P_2$ comprises a de novo amino acid sequence that shares less than 10% sequence identity to CD3. In some embodiments, $P_2$ comprises a peptide sequence of at least 5 amino acids in length. In some embodiments, $P_2$ comprises a peptide sequence of at least 6 amino acids in length. In some embodiments, $P_2$ comprises a peptide sequence of at least 10 amino acids in length. In some embodiments, $P_2$ comprises a peptide sequence of at least 10 amino acids in length and no more than 20 amino acids in length. In some embodiments, $P_2$ comprises a peptide sequence of at least 16 amino acids in length. In some embodiments, $P_2$ comprises a peptide sequence of no more than 40 amino acids in length. In some embodiments, $P_2$ comprises at least two cysteine amino acid residues. In some embodiments, $P_2$ comprises a cyclic peptide or a linear peptide. In some embodiments, $P_2$ comprises a cyclic peptide. In some embodiments, $P_2$ comprises a linear peptide. In some embodiments, $P_2$ comprises a modified amino acid or non-natural amino acid, or a modified non-natural amino acid, or a combination thereof. In some embodiments, $P_2$ does not comprise albumin or an albumin fragment. In some embodiments, $P_2$ does not comprise an albumin binding domain. In some embodiments, $P_2$ comprises the amino acid sequence of SEQ ID NO: 289 or SEQ ID NO: 292.

In some embodiments, $P_2$ comprises an amino acid sequence according to any one of SEQ ID NOs: 287-302, or an amino acid sequence that has 1, 2, or 3 amino acid mutations, substitutions or deletions relative to any one of SEQ ID NOs: 287-302. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 305, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the CD3 binding domain comprises an amino acid sequence with at least 90%, 95%, 96%, 97%, 98%, 99%, or 100% identity to SEQ ID NO: 305, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 305, and wherein $P_2$ comprises an amino acid sequence according to SEQ ID NO: 295.

In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 276, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 276, and wherein $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 308, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 308, and wherein $P_2$ comprises an amino acid sequence according to SEQ ID NO: 295. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 329, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the CD3 binding domain comprises an amino acid sequence according to SEQ ID NO: 329, and wherein $P_2$ comprises an amino acid sequence according to SEQ ID NO: 295.

In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 261, CDR1-H: SEQ ID NO: 78, CDR2-H: SEQ ID NO: 79, and CDR3-H: SEQ ID NO: 80, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 261, CDR1-H: SEQ ID NO: 78, CDR2-H: SEQ ID NO: 79, and CDR3-H: SEQ ID NO: 80, and wherein $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 319, and wherein $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 319, and wherein $P_2$ comprises an amino acid sequence according to SEQ ID NO: 295.

In some embodiments, $L_1$ or $L_2$ is a peptide sequence having at least 5 to no more than 50 amino acids. In some embodiments, $L_1$ or $L_2$ is a peptide sequence having at least 10 to no more than 30 amino acids. In some embodiments, $L_1$ or $L_2$ is a peptide sequence having at least 10 amino acids. In some embodiments, $L_1$ or $L_2$ is a peptide sequence having at least 18 amino acids. In some embodiments, $L_1$ or $L_2$ is a peptide sequence having at least 26 amino acids. In some embodiments, $L_1$ or $L_2$ comprises a formula comprising $(G_2S)_n$, wherein n is an integer from 1 to 3. In some embodiments, $L_1$ or $L_2$ comprises a formula comprising $(G_2S)_n$, wherein n is an integer of at least 1. In some embodiments, $L_1$ or $L_2$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1. In some embodiments, the tumor specific protease is selected from the group consisting of metalloprotease, serine protease, cysteine protease, threonine protease, and aspartic protease. In some embodiments, $L_1$ or $L_2$ comprises a urokinase cleavable amino acid sequence, a matriptase cleavable amino acid sequence, or a matrix metalloprotease cleavable amino acid sequence. In some embodiments, $L_1$ or $L_2$ comprises a sequence according to any one of SEQ ID NOs: 226-254. In some embodiments, $L_1$ is bound to N-terminus of $A_1$. In some embodiments, $L_1$ is bound to C-terminus of $A_1$. In some embodiments, $L_2$ is bound to N-terminus of $B_2$. In some embodiments, $L_2$ is bound to C-terminus of $B_2$.

In some embodiments, the isolated polypeptide or polypeptide complex further comprises a half-life extending molecule ($H_1$). In some embodiments, $H_1$ is connected to $P_1$. In some embodiments, $H_1$ is connected to $P_2$. In some embodiments, $H_1$ does not block the CD3 binding domain to CD3. In some embodiments, the half-life extending molecule ($H_1$) does not have binding affinity to CD3. In some embodiments, the half-life extending molecule ($H_1$) does not shield the isolated polypeptide or polypeptide complex from CD3. In some embodiments, $H_1$ comprises a sequence according to SEQ ID NOs: 255-258. In some embodiments, $H_1$ comprises an amino acid sequence that has repetitive sequence motifs. In some embodiments, $H_1$ comprises an amino acid sequence that has highly ordered secondary structure. In some embodiments, $H_1$ comprises a polymer. In some embodiments, the polymer is polyethylene glycol (PEG). In some embodiments, $H_1$ comprises albumin. In some embodiments, $H_1$ comprises an Fc domain. In some embodiments, the albumin is serum albumin. In some embodiments, the albumin is human serum albumin. In some embodiments, $H_1$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the single domain antibody comprises a single domain antibody that binds to albumin. In some embodiments, the single domain antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 255, HC-CDR2: SEQ ID NO: 256, and HC-CDR3: SEQ ID NO: 257; and wherein the CDRs comprise from 0-2 amino acid modifications in at least one of the HC-CDR1, HC-CDR2, or HC-CDR3. In some embodiments, $H_1$ comprises an amino acid sequence according to SEQ ID NO: 258. In some embodiments, $H_1$ comprises an amino acid sequence that has at least 80% sequence identity to SEQ ID NO: 258. In some embodiments, $H_1$ comprises an amino acid sequence that has at least 85% sequence identity to SEQ ID NO: 258. In some embodiments, $H_1$ comprises an amino acid sequence that has at least 90% sequence identity to SEQ ID NO: 258. In some embodiments, $H_1$ comprises an amino acid sequence that has at least 95% sequence identity to SEQ ID NO: 258. In some embodiments, $H_1$ comprises an amino acid sequence that has at least 99% sequence identity to SEQ ID NO: 258. In some embodiments, $H_1$ comprise a modified amino acid or non-natural amino acid, or a modified non-natural amino acid, or a combination thereof. In some embodiments, the modified amino acid or a modified non-natural amino acid comprises a post-translational modification. In some embodiments, $H_1$ comprises a linking moiety ($L_3$) that connects $H_1$ to $P_1$ or $P_2$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1.

In some embodiments, the isolated polypeptide or polypeptide complex comprises amino acid sequences with at least 90%, 95%, 96%, 97%, 98%, 99%, or 100% identity to SEQ ID NO: 166 and SEQ ID NO: 167. In some embodiments, the isolated polypeptide or polypeptide complex comprises amino acid sequences with at least 90%, 95%, 96%, 97%, 98%, 99%, or 100% identity to SEQ ID NO: 168 and SEQ ID NO: 169. In some embodiments, the isolated polypeptide or polypeptide complex comprises amino acid sequences with at least 90%, 95%, 96%, 97%, 98%, 99%, or 100% identity to SEQ ID NO: 170 and SEQ ID NO: 171. In some embodiments, the isolated polypeptide or polypeptide complex comprises amino acid sequences with at least 90%, 95%, 96%, 97%, 98%, 99%, or 100% identity to SEQ ID NO: 172 and SEQ ID NO: 173. In some embodiments, the isolated polypeptide or polypeptide complex comprises amino acid sequences with at least 90%, 95%, 96%, 97%, 98%, 99%, or 100% identity to SEQ ID NO: 174 and SEQ ID NO: 175. In some embodiments, the isolated polypeptide or polypeptide complex comprises amino acid sequences with at least 90%, 95%, 96%, 97%, 98%, 99%, or 100% identity to SEQ ID NO: 176 and SEQ ID NO: 177. In some embodiments, the isolated polypeptide or polypeptide complex comprises amino acid sequences with at least 90%, 95%, 96%, 97%, 98%, 99%, or 100% identity to SEQ ID NO: 178 and SEQ ID NO: 179. In some embodiments, the isolated polypeptide or polypeptide complex comprises amino acid sequences with at least 90%, 95%, 96%, 97%, 98%, 99%, or 100% identity to SEQ ID NO: 180 and SEQ ID NO: 181. In some embodiments, the isolated polypeptide or polypeptide complex comprises amino acid sequences with at least 90%, 95%, 96%, 97%, 98%, 99%, or 100% identity to SEQ ID NO: 182 and SEQ ID NO: 183. In some embodiments, the isolated polypeptide or polypeptide complex comprises amino acid sequences with at least 90%, 95%, 96%, 97%, 98%, 99%, or 100% identity to SEQ ID NO: 184 and SEQ ID NO: 185. In some embodiments, the isolated polypeptide or polypeptide complex comprises amino acid sequences with at least 90%, 95%, 96%, 97%, 98%, 99%, or 100% identity to SEQ ID NO: 186 and SEQ ID NO: 187. In some embodiments, the isolated polypeptide or polypeptide complex comprises amino acid sequences with at least 90%, 95%, 96%, 97%, 98%, 99%, or 100% identity to SEQ ID NO: 188 and SEQ ID NO: 189. In some embodiments, the isolated polypeptide or polypeptide complex comprises amino acid sequences with at least 90%, 95%, 96%, 97%, 98%, 99%, or 100% identity to SEQ ID NO: 190 and SEQ ID NO: 191. In some embodiments, the isolated polypeptide or polypeptide complex comprises amino acid sequences with at least 90%, 95%, 96%, 97%, 98%, 99%, or 100% identity to SEQ ID NO: 192 and SEQ ID NO: 193. In some embodiments, the isolated polypeptide or polypeptide complex comprises amino acid sequences with at least 90%, 95%, 96%, 97%, 98%, 99%, or 100% identity to SEQ ID NO: 194 and SEQ ID NO: 195. In some embodiments, the isolated polypeptide or polypeptide complex comprises amino acid sequences with at least 90%, 95%, 96%, 97%, 98%, 99%, or 100% identity to SEQ ID NO: 196 and SEQ ID NO: 197. In some embodiments, the isolated polypeptide or polypeptide complex comprises amino acid sequences with at least 90%, 95%, 96%, 97%, 98%, 99%, or 100% identity to SEQ ID NO: 198 and SEQ ID NO: 199. In some embodiments, the isolated polypeptide or polypeptide complex comprises amino acid sequences with at least 90%, 95%, 96%, 97%, 98%, 99%, or 100% identity to SEQ ID NO: 200 and SEQ ID NO: 201. In some embodiments, the isolated polypeptide or polypeptide complex comprises amino acid sequences with at least 90%, 95%, 96%, 97%, 98%, 99%, or 100% identity to SEQ ID NO: 202 and SEQ ID NO: 203. In some embodiments, the isolated polypeptide or polypeptide complex comprises amino acid sequences with at least 90%, 95%, 96%, 97%, 98%, 99%, or 100% identity to SEQ ID NO: 204 and SEQ ID NO: 205. In some embodiments, the isolated polypeptide or polypeptide complex comprises amino acid sequences with at least 90%, 95%, 96%, 97%, 98%, 99%, or 100% identity to SEQ ID NO: 206 and SEQ ID NO: 207. In some embodiments, the isolated polypeptide or polypeptide complex comprises amino acid sequences with at least 90%, 95%, 96%, 97%, 98%, 99%, or 100% identity to SEQ ID NO: 208 and SEQ ID NO: 209. In some embodiments, the isolated polypeptide or polypeptide complex comprises amino acid sequences with at least 90%, 95%, 96%, 97%, 98%, 99%, or 100% identity to SEQ ID NO: 210 and SEQ ID NO: 211. In some embodiments, the isolated polypeptide or polypeptide complex comprises amino acid sequences with at least 90%, 95%, 96%, 97%, 98%, 99%, or 100% identity to SEQ ID NO: 212 and SEQ ID NO: 213. In some embodiments, the isolated polypeptide or polypeptide complex comprises amino acid sequences with at least 90%, 95%, 96%, 97%, 98%, 99%, or 100% identity to SEQ ID NO: 214 and SEQ ID NO: 215. In some embodiments, the isolated polypeptide or polypeptide complex comprises amino acid sequences with at least 90%, 95%, 96%, 97%, 98%, 99%, or 100% identity to SEQ ID NO: 216 and SEQ ID NO: 217. In some embodiments, the isolated polypeptide or polypeptide complex comprises amino acid sequences with at least 90%, 95%, 96%, 97%, 98%, 99%, or 100% identity to SEQ ID NO: 218 and SEQ ID NO: 219. In some embodiments, the isolated polypeptide or polypeptide complex comprises amino acid sequences with at least 90%, 95%, 96%, 97%, 98%, 99%, or 100% identity to SEQ ID NO: 220 and SEQ ID NO: 221. In some embodiments, the isolated polypeptide or polypeptide complex comprises amino acid sequences with at least 90%, 95%, 96%, 97%, 98%, 99%, or 100% identity to SEQ ID NO: 222 and SEQ ID NO: 223. In some embodiments, the isolated polypeptide or polypeptide complex comprises amino acid sequences with at least 90%, 95%, 96%, 97%, 98%, 99%, or 100% identity to SEQ ID NO: 224 and SEQ ID NO: 225.

In some embodiments, the isolated polypeptide or polypeptide complex comprises amino acid sequences with at least 90%, 95%, 96%, 97%, 98%, 99%, or 100% identity to SEQ ID NO: 352 and SEQ ID NO: 353. In some embodiments, the isolated polypeptide or polypeptide complex comprises amino acid sequences with at least 90%, 95%, 96%, 97%, 98%, 99%, or 100% identity to SEQ ID NO: 354 and SEQ ID NO: 355. In some embodiments, the isolated polypeptide or polypeptide complex comprises amino acid sequences with at least 90%, 95%, 96%, 97%, 98%, 99%, or 100% identity to SEQ ID NO: 356 and SEQ ID NO: 357. In some embodiments, the isolated polypeptide or polypeptide complex comprises amino acid sequences with at least 90%, 95%, 96%, 97%, 98%, 99%, or 100% identity to SEQ ID NO: 358 and SEQ ID NO: 359. In some embodiments, the isolated polypeptide or polypeptide complex comprises amino acid sequences with at least 90%, 95%, 96%, 97%, 98%, 99%, or 100% identity to SEQ ID NO: 360 and SEQ ID NO: 361. In some embodiments, the isolated polypeptide or polypeptide complex comprises amino acid sequences with at least 90%, 95%, 96%, 97%, 98%, 99%, or 100% identity to SEQ ID NO: 362 and SEQ ID NO: 363. In some embodiments, the isolated polypeptide or polypeptide complex comprises amino acid sequences with at least 90%, 95%, 96%, 97%, 98%, 99%, or 100% identity to SEQ ID NO: 364 and SEQ ID NO: 365. In some embodiments, the isolated polypeptide or polypeptide complex comprises amino acid sequences with at least 90%, 95%, 96%, 97%, 98%, 99%, or 100% identity to SEQ ID NO: 366 and SEQ ID NO: 367. In some embodiments, the isolated polypeptide or polypeptide complex comprises amino acid sequences with at least 90%, 95%, 96%, 97%, 98%, 99%, or 100% identity to SEQ ID NO: 368 and SEQ ID NO: 369. In some embodiments, the isolated polypeptide or polypeptide complex comprises amino acid sequences with at least 90%, 95%, 96%, 97%, 98%, 99%, or 100% identity to SEQ ID NO: 370 and SEQ ID NO: 371. In some embodiments, the isolated polypeptide or polypeptide complex comprises amino acid sequences with at least 90%, 95%, 96%, 97%, 98%, 99%, or 100% identity to SEQ ID NO: 372 and SEQ ID NO: 373. In some embodiments, the isolated polypeptide or polypeptide complex comprises amino acid sequences with at least 90%, 95%, 96%, 97%, 98%, 99%, or 100% identity to SEQ ID NO: 374 and SEQ ID NO: 375. In some embodiments, the isolated polypeptide or polypeptide complex comprises amino acid sequences with at least 90%, 95%, 96%, 97%, 98%, 99%, or 100% identity to SEQ ID NO: 376 and SEQ ID NO: 377. In some embodiments, the isolated polypeptide or polypeptide complex comprises amino acid sequences with at least 90%, 95%, 96%, 97%, 98%, 99%, or 100% identity to SEQ ID NO: 378 and SEQ ID NO: 379. In some embodiments, the isolated polypeptide or polypeptide complex comprises amino acid sequences with at least 90%, 95%, 96%, 97%, 98%, 99%, or 100% identity to SEQ ID NO: 380 and SEQ ID NO: 381. In some embodiments, the isolated polypeptide or polypeptide complex comprises amino acid sequences with at least 90%, 95%, 96%, 97%, 98%, 99%, or 100% identity to SEQ ID NO: 382 and SEQ ID NO: 383. In some embodiments, the isolated polypeptide or polypeptide complex comprises amino acid sequences with at least 90%, 95%, 96%, 97%, 98%, 99%, or 100% identity to SEQ ID NO: 384 and SEQ ID NO: 385. In some embodiments, the isolated polypeptide or polypeptide complex comprises amino acid sequences with at least 90%, 95%, 96%, 97%, 98%, 99%, or 100% identity to SEQ ID NO: 386 and SEQ ID NO: 387. In some embodiments, the isolated polypeptide or polypeptide complex comprises amino acid sequences with at least 90%, 95%, 96%, 97%, 98%, 99%, or 100% identity to SEQ ID NO: 388 and SEQ ID NO: 389. In some embodiments, the isolated polypeptide or polypeptide complex comprises amino acid sequences with at least 90%, 95%, 96%, 97%, 98%, 99%, or 100% identity to SEQ ID NO: 390 and SEQ ID NO: 391. In some embodiments, the isolated polypeptide or polypeptide complex comprises amino acid sequences with at least 90%, 95%, 96%, 97%, 98%, 99%, or 100% identity to SEQ ID NO: 392 and SEQ ID NO: 393. In some embodiments, the isolated polypeptide or polypeptide complex comprises amino acid sequences with at least 90%, 95%, 96%, 97%, 98%, 99%, or 100% identity to SEQ ID NO: 394 and SEQ ID NO: 395.

Disclosed herein are isolated polypeptide and polypeptide complexes according to Formula I: $A_1$-$L_1$-$P_1$ (Formula I) wherein $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 26; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease. In some embodiments, $P_1$ comprises an amino acid sequence according to any one of SEQ ID NOs: 107, 141, 142, and 150, or an amino acid sequence that has 1, 2, or 3 amino acid mutations, substitutions or deletions relative to any one of SEQ ID NOs: 107, 141, 142, and 150. In some embodiments, $P_1$ comprises an amino acid sequence according to SEQ ID NO: 142. In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises an amino acid sequence with at least 85% identity to SEQ ID NO: 69 and the immunoglobulin heavy chain comprises an amino acid sequence with at least 85% identity to SEQ ID NO: 70. In some embodiments, the immunoglobulin light chain comprises an amino acid sequence with at least 90% identity to SEQ ID NO: 69 and the immunoglobulin heavy chain comprises an amino acid sequence with at least 90% identity to SEQ ID NO: 70. In some embodiments, the immunoglobulin light chain comprises an amino acid sequence with at least 92% identity to SEQ ID NO: 69 and the immunoglobulin heavy chain comprises an amino acid sequence with at least 92% identity to SEQ ID NO: 70. In some embodiments, the immunoglobulin light chain comprises an amino acid sequence with at least 95% identity to SEQ ID NO: 69 and the immunoglobulin heavy chain comprises an amino acid sequence with at least 95% identity to SEQ ID NO: 70. In some embodiments, the immunoglobulin light chain comprises an amino acid sequence with at least 98% identity to SEQ ID NO: 69 and the immunoglobulin heavy chain comprises an amino acid sequence with at least 98% identity to SEQ ID NO: 70. In some embodiments, the immunoglobulin light chain comprises an amino acid sequence with at least 99% identity to SEQ ID NO: 69 and the immunoglobulin heavy chain comprises an amino acid sequence with at least 99% identity to SEQ ID NO: 70. In some embodiments, the immunoglobulin light chain comprises an amino acid sequence of SEQ ID NO: 69 and the immunoglobulin heavy chain comprises an amino acid sequence of SEQ ID NO: 70.

In some embodiments, the isolated polypeptide or polypeptide complex further comprises a CD3 binding domain. In some embodiments, the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 80.

In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 276. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76, CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 273.

In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82. In some embodiments, the CD3 binding domain comprises a Fab, Fab', $(Fab')_2$ or a single chain variable fragment (scFv). In some embodiments, the CD3 binding domain is the scFv. In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 329. In some embodiments, the CD3 binding domain comprises an amino acid sequence with at least 90%, 95%, 96%, 97%, 98%, 99%, or 100% identity to SEQ ID NO: 305.

In some embodiments, $P_2$ comprises the amino acid sequence of SEQ ID NO: 289 or SEQ ID NO: 292. In some embodiments, $P_2$ comprises the amino acid sequence of SEQ ID NO: 295. In some embodiments, the isolated polypeptide or polypeptide complex comprises amino acid sequences with at least 90%, 95%, 96%, 97%, 98%, 99%, or 100% identity to SEQ ID NO: 200 and SEQ ID NO: 201. In some embodiments, the isolated polypeptide or polypeptide complex comprises amino acid sequences of SEQ ID NO: 200 and SEQ ID NO: 201. In some embodiments, the isolated polypeptide or polypeptide complex comprises amino acid sequences with at least 90%, 95%, 96%, 97%, 98%, 99%, or 100% identity to SEQ ID NO: 362 and SEQ ID NO: 363. In some embodiments, the isolated polypeptide or polypeptide complex comprises amino acid sequences with at least 90%, 95%, 96%, 97%, 98%, 99%, or 100% identity to SEQ ID NO: 382 and SEQ ID NO: 383. In some embodiments, the isolated polypeptide or polypeptide complex comprises amino acid sequences with at least 90%, 95%, 96%, 97%, 98%, 99%, or 100% identity to SEQ ID NO: 390 and SEQ ID NO: 391.

Disclosed herein are isolated polypeptide and polypeptide complexes according to Formula I: $A_1$-$L_1$-$P_1$ (Formula I) wherein $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 27; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease. In some embodiments, $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions or deletions relative to any one of SEQ ID NOs: 107, 109, 116, 141, 142, 148, 149, 150, and 158. In some embodiments, $P_1$ comprises an amino acid sequence according to SEQ ID NO: 107.

In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises an amino acid sequence with at least 85% identity to SEQ ID NO: 71 and the immunoglobulin heavy chain comprises an amino acid sequence with at least 85% identity to SEQ ID NO: 72. In some embodiments, the immunoglobulin light chain comprises an amino acid sequence with at least 90% identity to SEQ ID NO: 71 and the immunoglobulin heavy chain comprises an amino acid sequence with at least 90% identity to SEQ ID NO: 72. In some embodiments, the immunoglobulin light chain comprises an amino acid sequence with at least 92% identity to SEQ ID NO: 71 and the immunoglobulin heavy chain comprises an amino acid sequence with at least 92% identity to SEQ ID NO: 72. In some embodiments, the immunoglobulin light chain comprises an amino acid sequence with at least 95% identity to SEQ ID NO: 71 and the immunoglobulin heavy chain comprises an amino acid sequence with at least 95% identity to SEQ ID NO: 72. In some embodiments, the immunoglobulin light chain comprises an amino acid sequence with at least 98% identity to SEQ ID NO: 71 and the immunoglobulin heavy chain comprises an amino acid sequence with at least 98% identity to SEQ ID NO: 72. In some embodiments, the immunoglobulin light chain comprises an amino acid sequence with at least 99% identity to SEQ ID NO: 71 and the immunoglobulin heavy chain comprises an amino acid sequence with at least 99% identity to SEQ ID NO: 72. In some embodiments, the immunoglobulin light chain comprises an amino acid sequence of SEQ ID NO: 71 and the immunoglobulin heavy chain comprises an amino acid sequence of SEQ ID NO: 72.

In some embodiments, the isolated polypeptide or polypeptide complex further comprises a CD3 binding domain. In some embodiments, the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 80.

In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 276. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76, CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286.

In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82. In some embodiments, the CD3 binding domain comprises a Fab, Fab', $(Fab')_2$ or a single chain variable fragment (scFv). In some embodiments, the CD3 binding domain is the scFv. In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 329.

In some embodiments, $P_2$ comprises the amino acid sequence of SEQ ID NO: 289 or SEQ ID NO: 292. In some embodiments, $P_2$ comprises the amino acid sequence of SEQ ID NO: 295. In some embodiments, the isolated polypeptide or polypeptide complex comprises amino acid sequences with at least 90%, 95%, 96%, 97%, 98%, 99%, or 100% identity to SEQ ID NO: 180 and SEQ ID NO: 181. In some embodiments, the isolated polypeptide or polypeptide complex comprises amino acid sequences of SEQ ID NO: 180 and SEQ ID NO: 181. In some embodiments, the isolated polypeptide or polypeptide complex comprises amino acid sequences with at least 90%, 95%, 96%, 97%, 98%, 99%, or 100% identity to SEQ ID NO: 352 and SEQ ID NO: 353. In some embodiments, the isolated polypeptide or polypeptide complex comprises amino acid sequences with at least 90%, 95%, 96%, 97%, 98%, 99%, or 100% identity to SEQ ID NO: 354 and SEQ ID NO: 355.

Disclosed herein are pharmaceutical compositions comprising (i) the isolated polypeptide or polypeptide complex thereof of any one of the above embodiments, and (ii) a pharmaceutically acceptable excipient.

Disclosed herein are isolated recombinant nucleic acid molecules encoding an isolated polypeptide or polypeptide complex of any one of the above embodiments.

Disclosed herein are methods of treating a cancer in a subject in need thereof comprising administering to the subject an isolated polypeptide or polypeptide complex of any one of the above embodiments. In some embodiments, the cancer comprises breast cancer, lung cancer, urothelial cancer, endometrial cancer, ovarian cancer, prostate cancer, pancreatic cancer, gastric cancer, colon cancer, head and neck cancer, or glioma. In some embodiments, the breast cancer comprises triple-negative breast cancer. In some embodiments, the lung cancer comprises non-small cell lung cancer.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 121 illustrates binding curves for binding of CD3 by TCEs and PCs as measured by ELISA.

FIG. 122 illustrates binding curves for binding of TROP2 by TCEs and PCs as measured by ELISA.

FIG. 123 illustrates binding curves for binding of CD3 by TCEs and PCs as measured by ELISA.

FIG. 124 illustrates binding curves for binding of TROP2 by TCEs and PCs as measured by ELISA.

FIG. 125 illustrates binding curves for binding of CD3 by TCEs and PCs as measured by ELISA.

FIGS. 126-129 illustrate killing of TROP2 positive HCT116 tumor cells by TCEs and PCs in the presence of CD8+ T-cells.

FIGS. 130-146 illustrate killing of TROP2 positive H292 tumor cells by TCEs and PCs in the presence of CD8+ T-cells.

FIGS. 147-162 illustrate killing of cynomolgus HEK293 tumor cells expressing TROP2 by TCEs and PCs in the presence of CD8+ T-cells.

FIG. 163 illustrates results of pharmacokinetic and toxicity studies of TCE-8 in cynomolgus monkey.

FIG. 164 illustrates results of pharmacokinetic and toxicity studies of TCE-7 in cynomolgus monkey.

FIG. 165 shows cytokine release in cynomolgus monkey after continuous IV infusion of TCE-8.

FIG. 166 shows cytokine release in cynomolgus monkey after continuous IV infusion of TCE-7.

FIGS. 167A-167F show clinical chemistry parameters in cynomolgus monkeys after continuous IV infusion of TCE-8.

FIGS. 168A-168F show clinical chemistry parameters in cynomolgus monkeys after continuous IV infusion of TCE-7.

Figure 169:
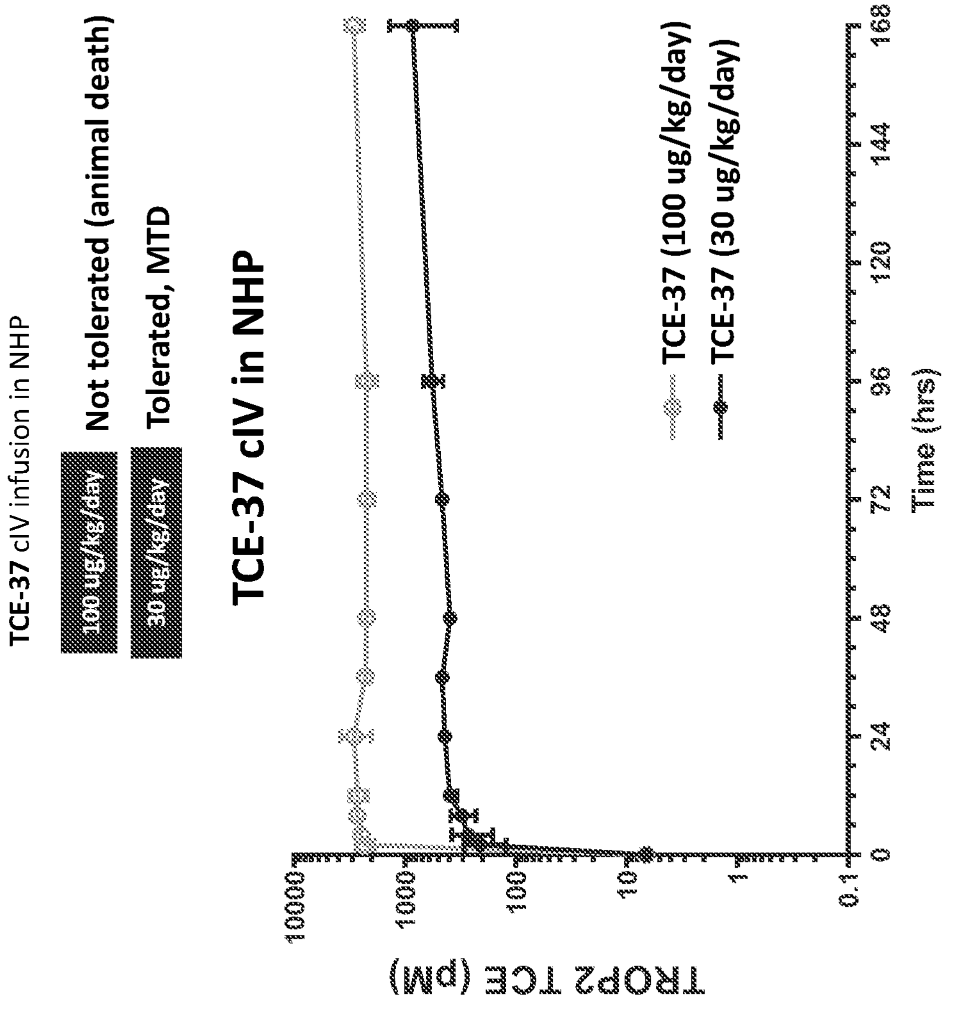

FIG. 169 illustrates pharmacokinetic and toxicity studies of TCE-37 in cynomolgus monkey.

Figure 170:
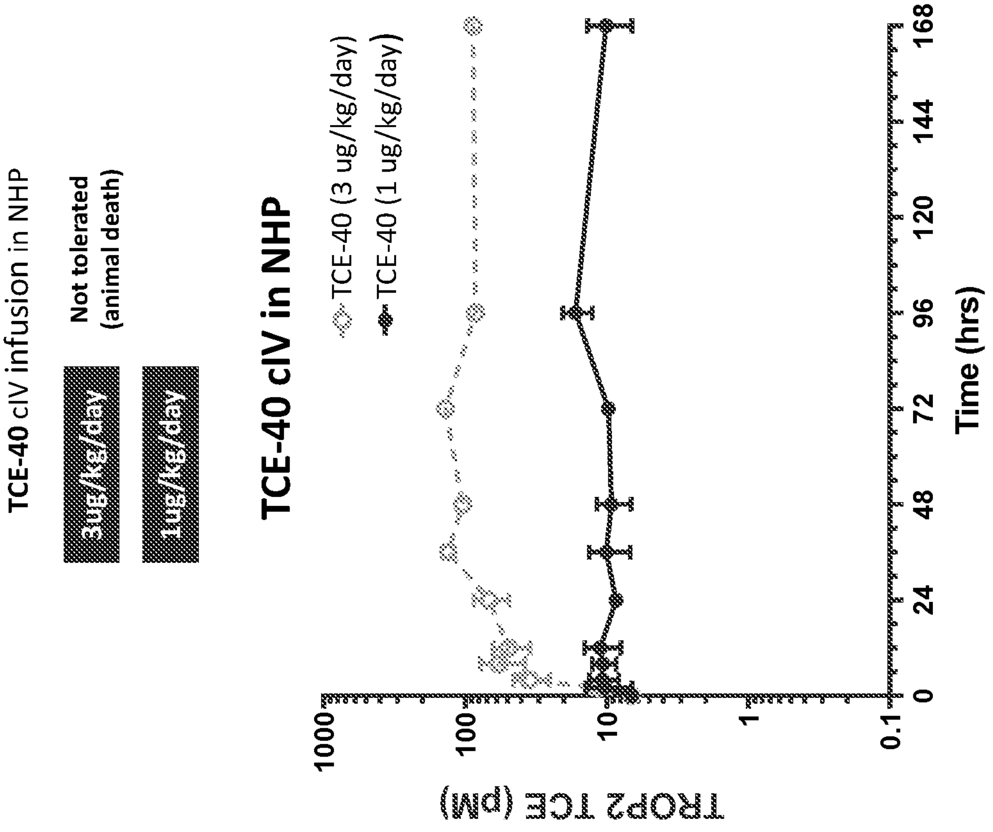

FIG. 170 illustrates pharmacokinetic and toxicity studies of TCE-40 in cynomolgus monkey.

Figure 171:
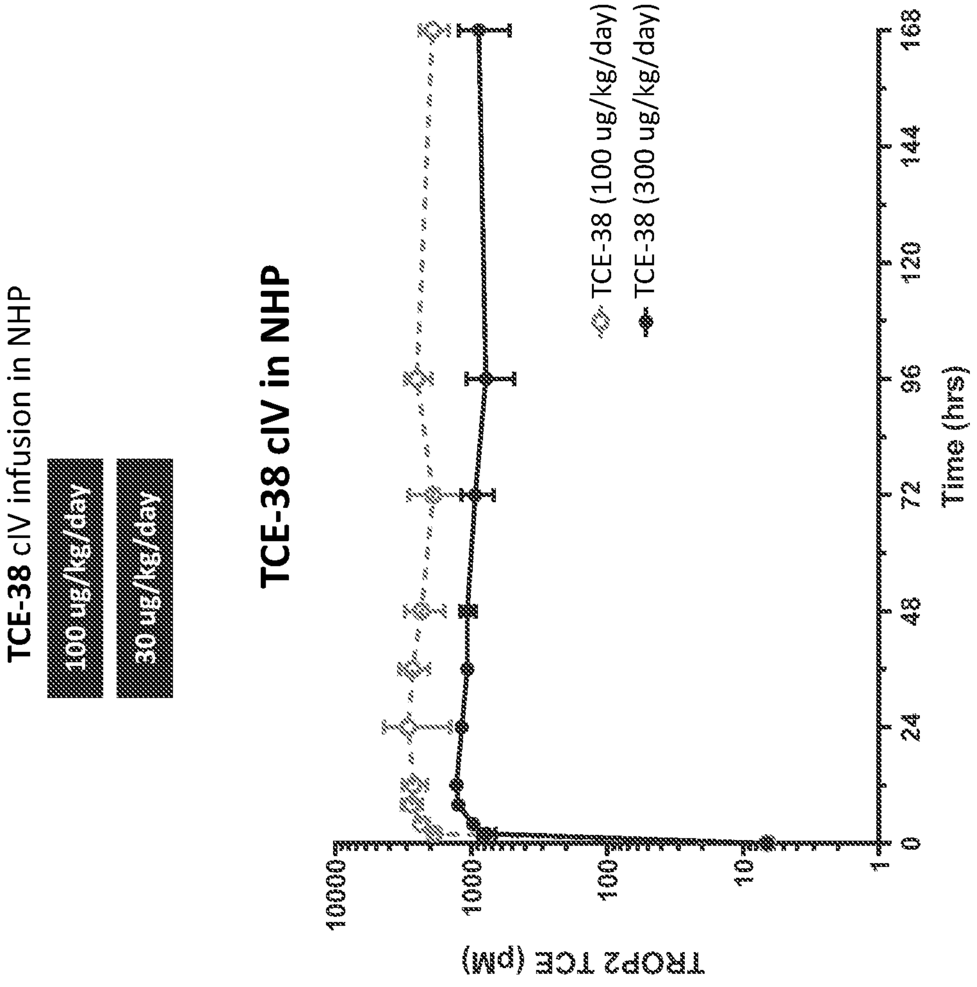
Figure 172A:
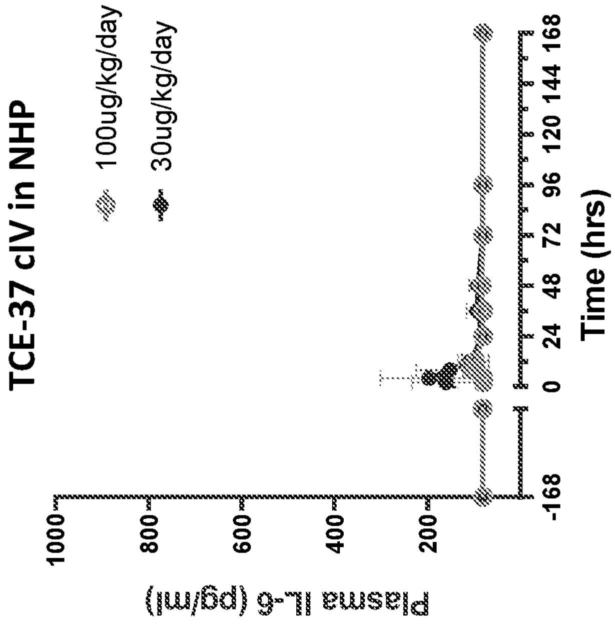
Figure 172B:
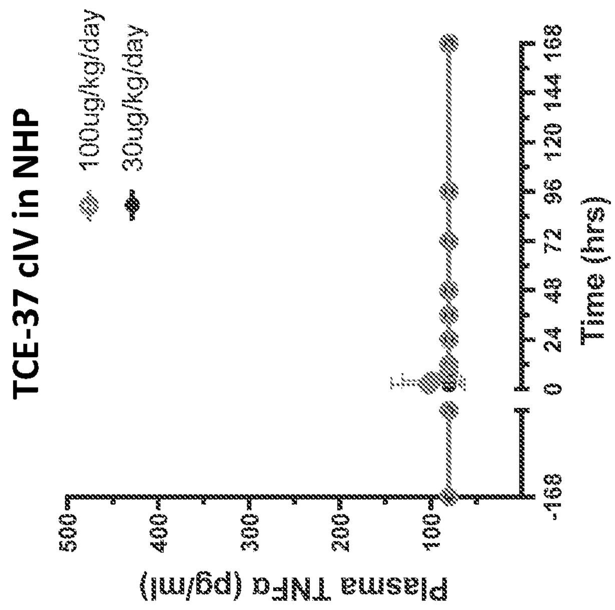
Figure 172C:
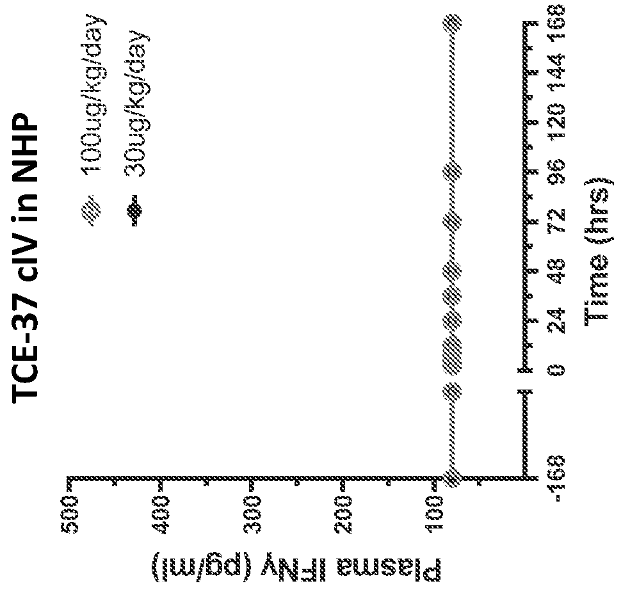
Figure 172D:
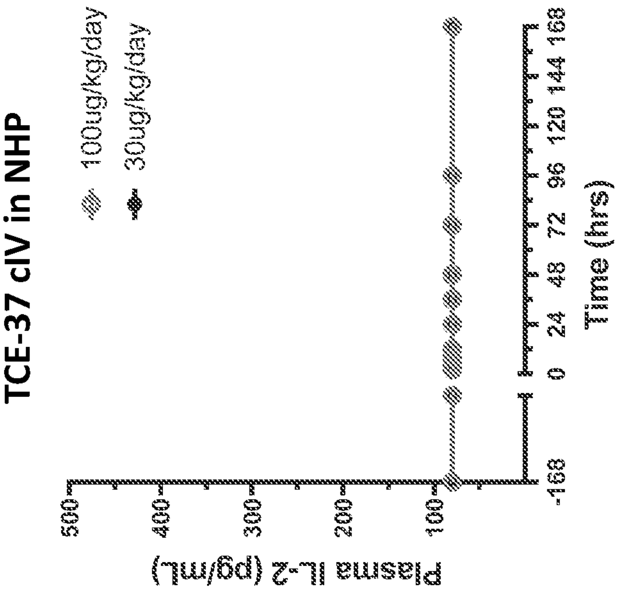
Figure 173B:
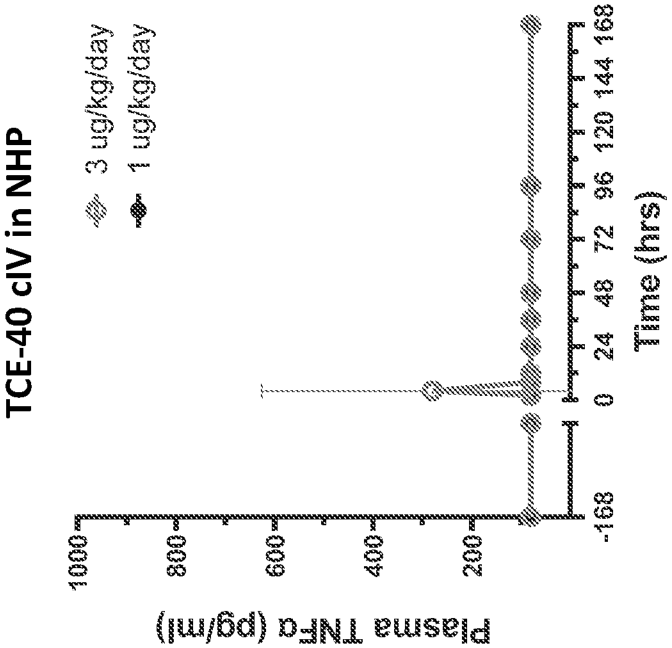
Figure 173A:
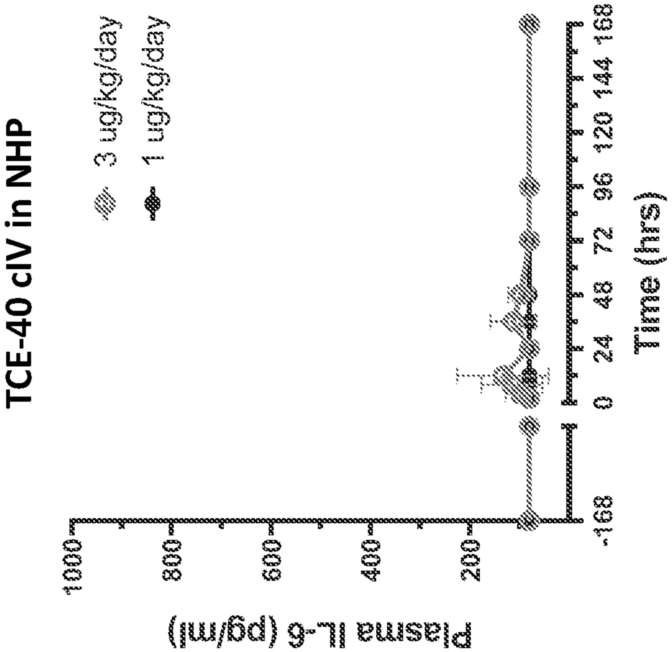
Figure 173D:
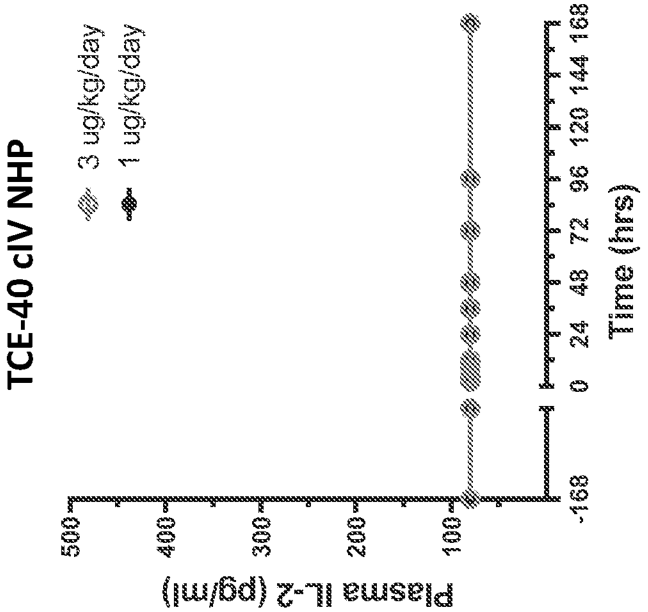
Figure 173C:
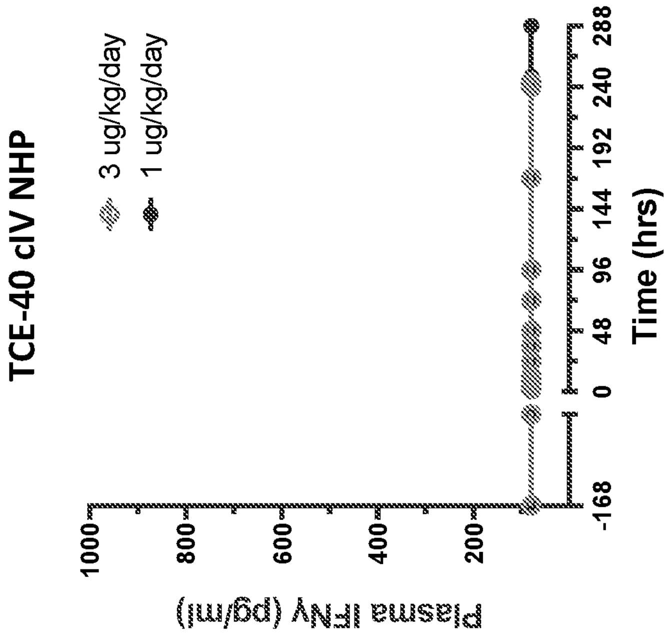

FIG. 171 illustrates pharmacokinetic and toxicity studies of TCE-38 in cynomolgus monkey.

FIGS. 172A-172D show cytokine release in cynomolgus monkeys after continuous IV infusion of TCE-37.

FIGS. 173A-173D show cytokine release in cynomolgus monkeys after continuous IV infusion of TCE-40.

Figure 174:
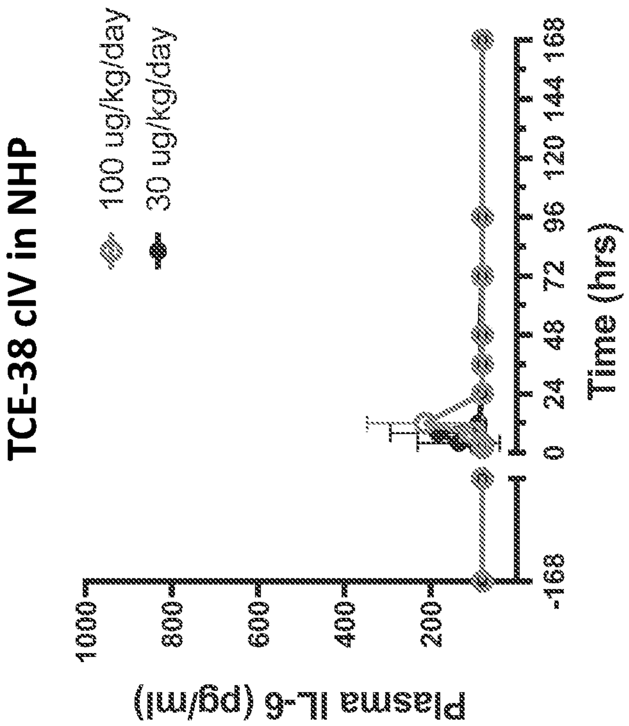
Figure 175A:
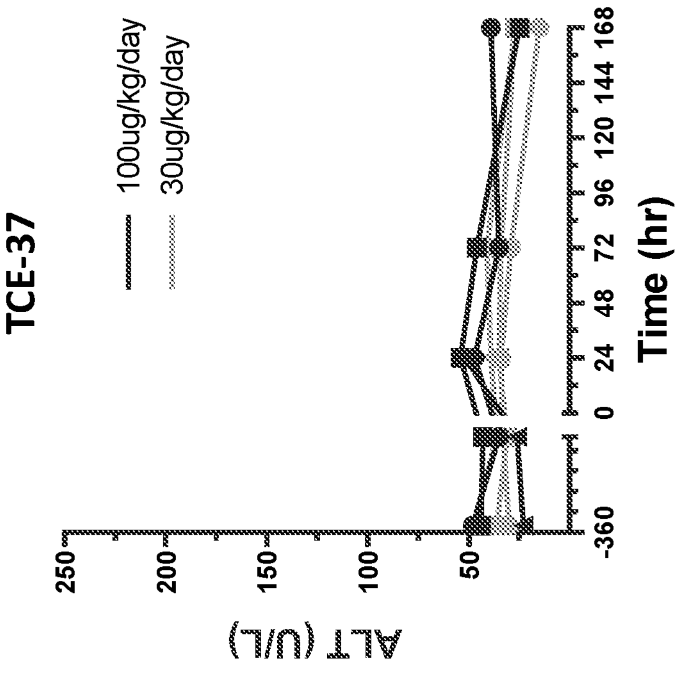
Figure 175B:
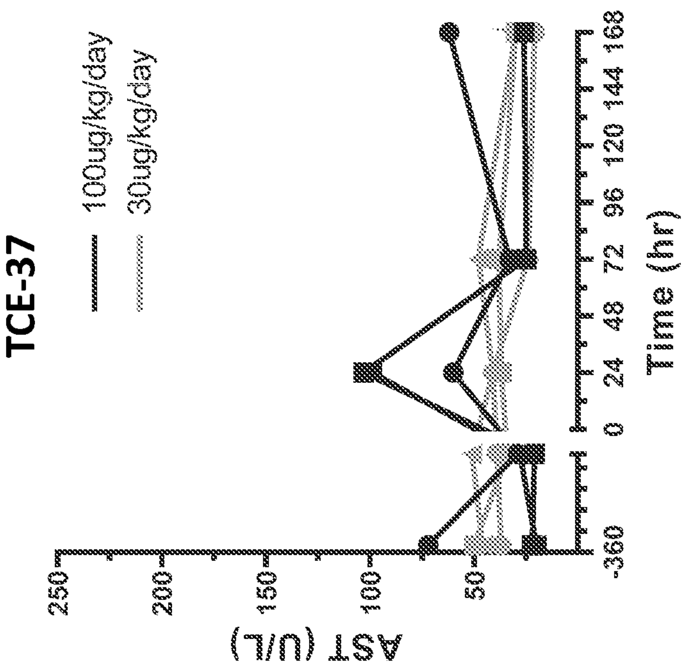
Figure 175C:
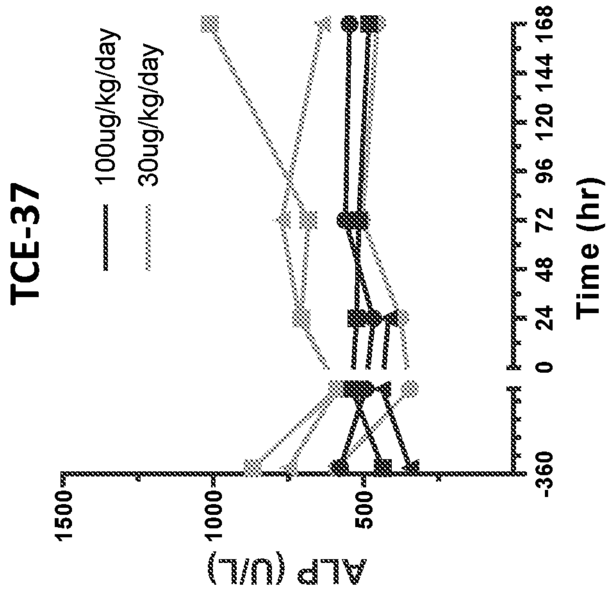
Figure 175D:
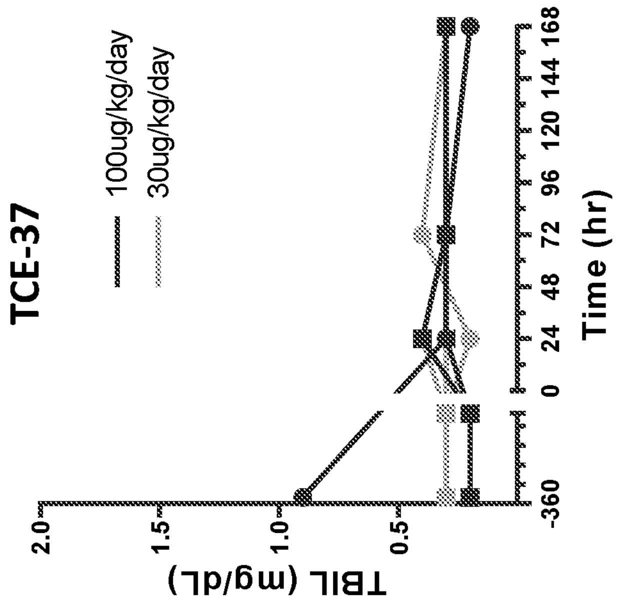
Figure 175F:
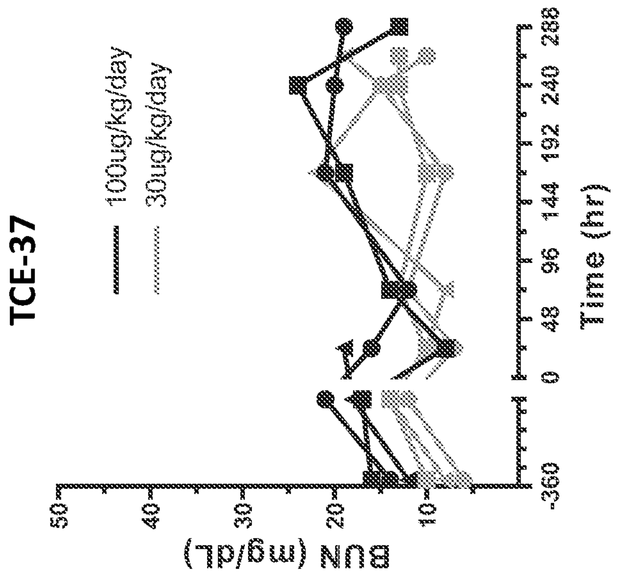
Figure 175E:
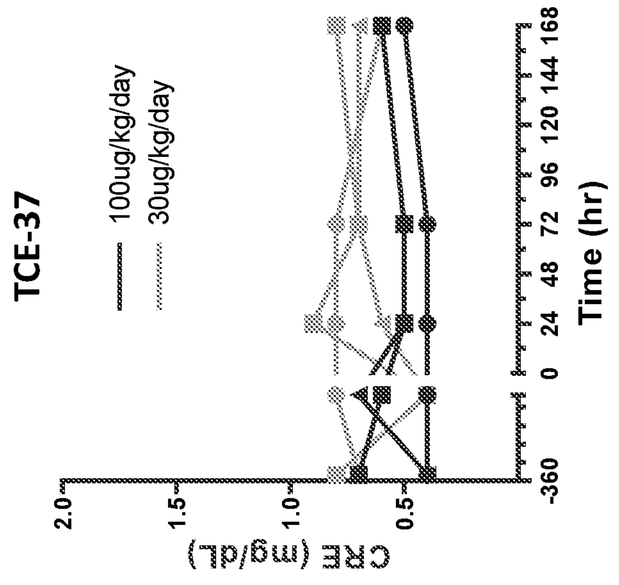
Figure 176B:
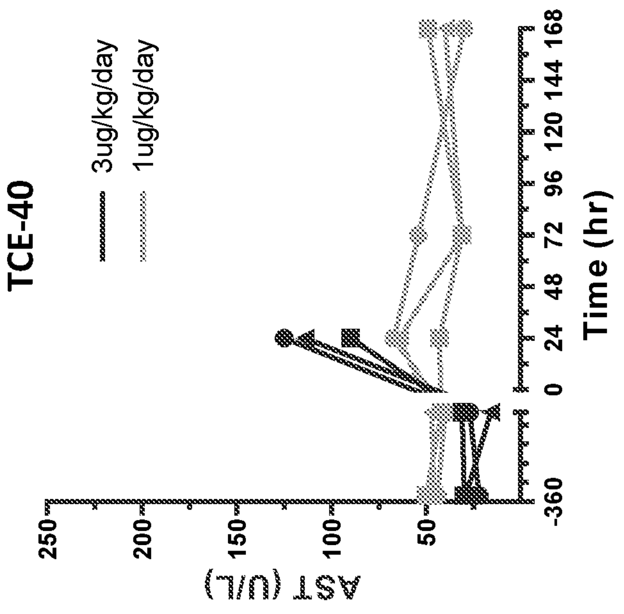
Figure 176A:
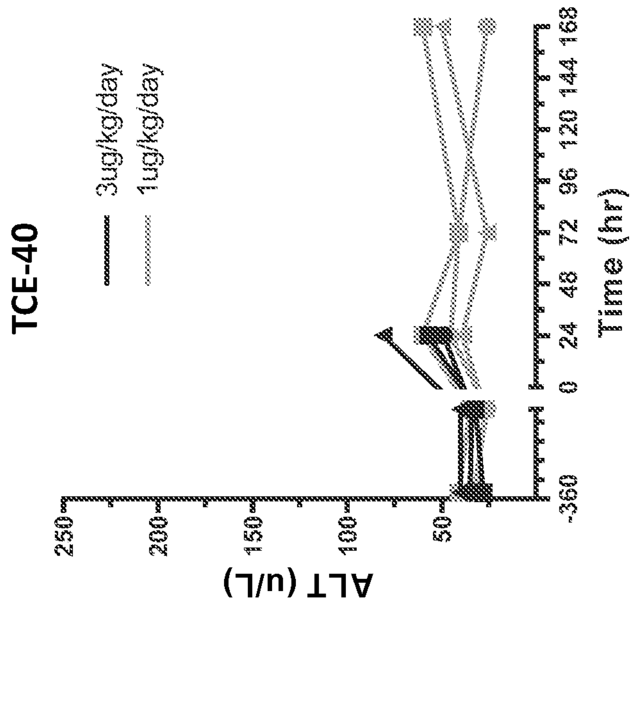
Figure 176C:
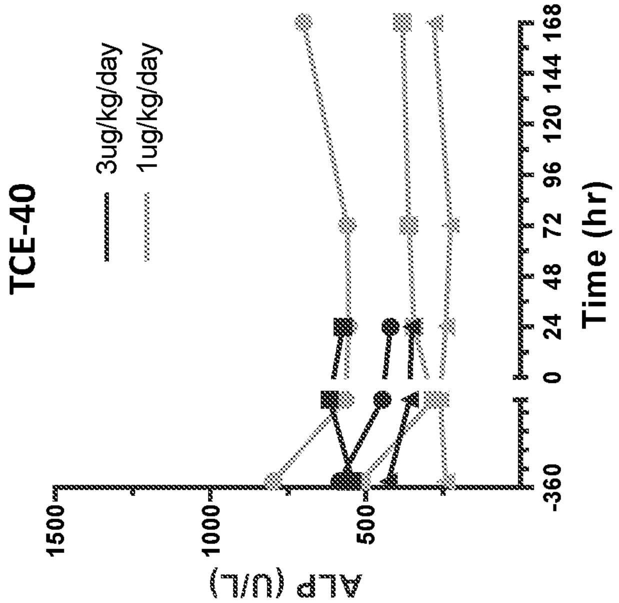
Figure 176D:
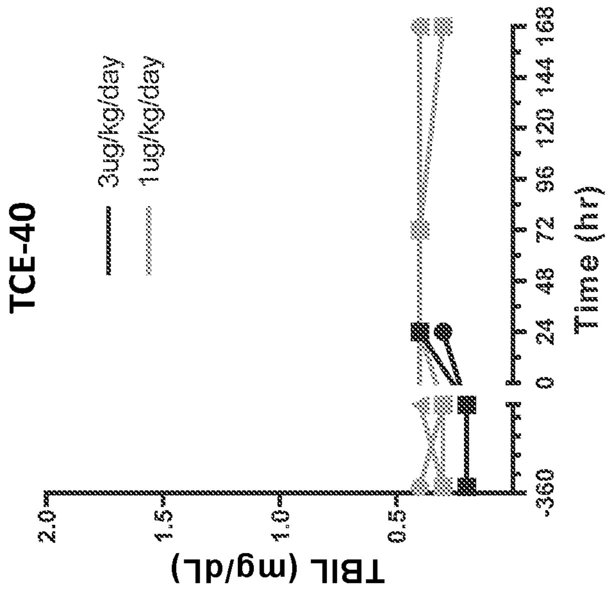
Figure 176E:
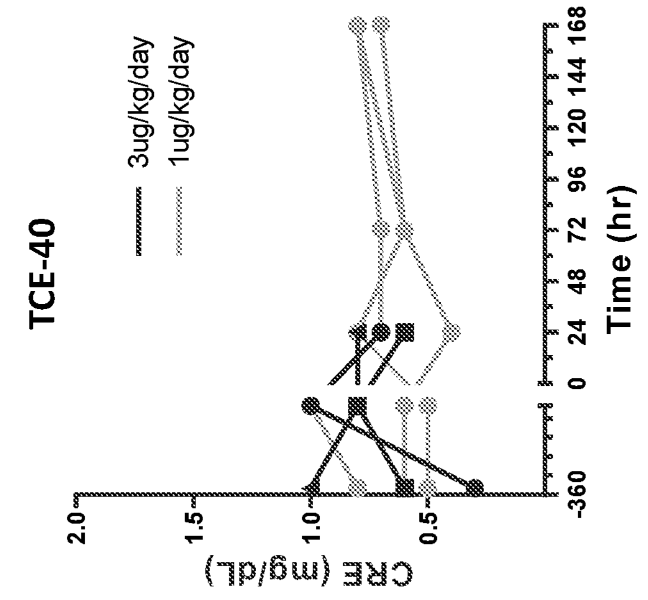
Figure 176F:
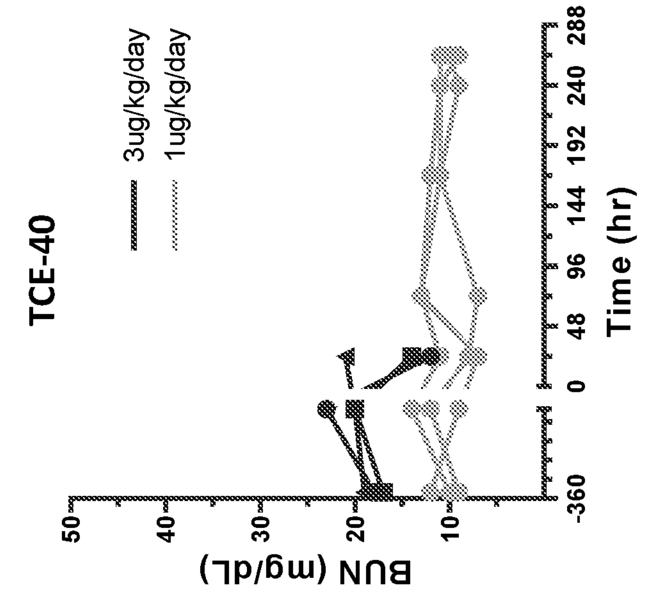
Figure 177B:
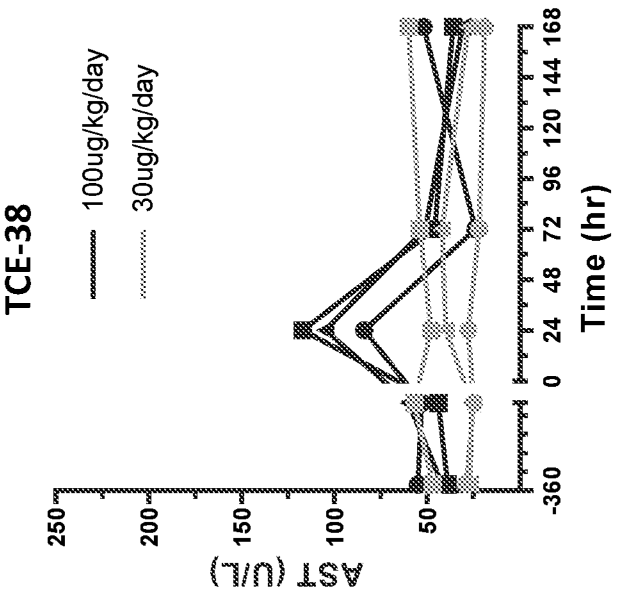
Figure 177A:
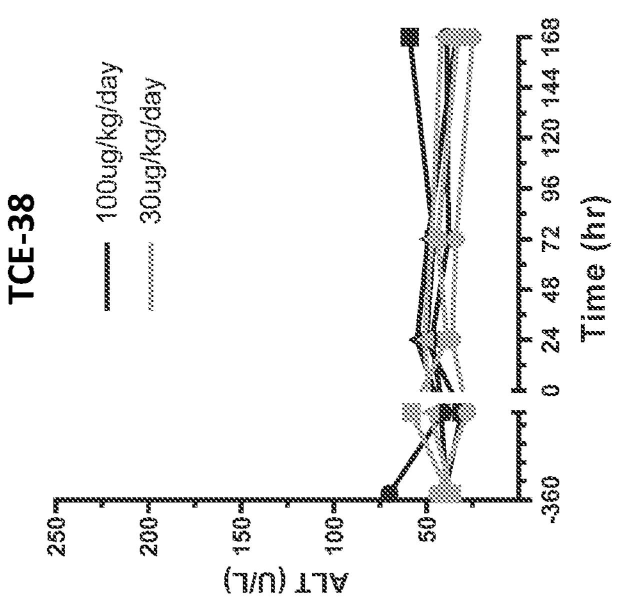
Figure 177C:
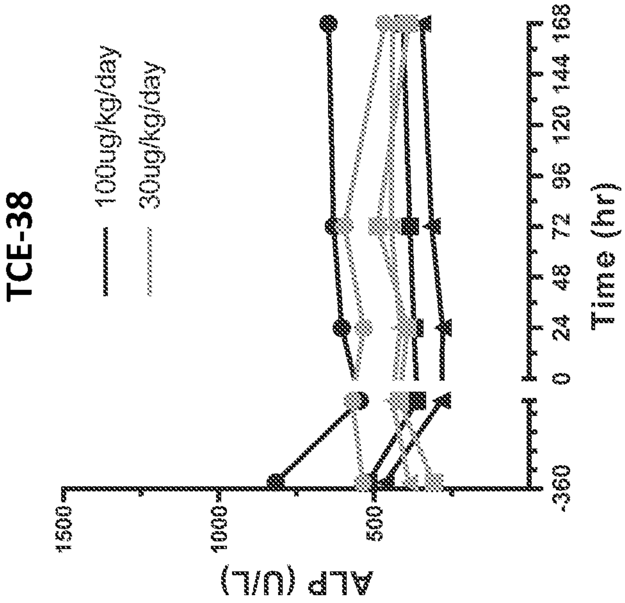
Figure 177D:
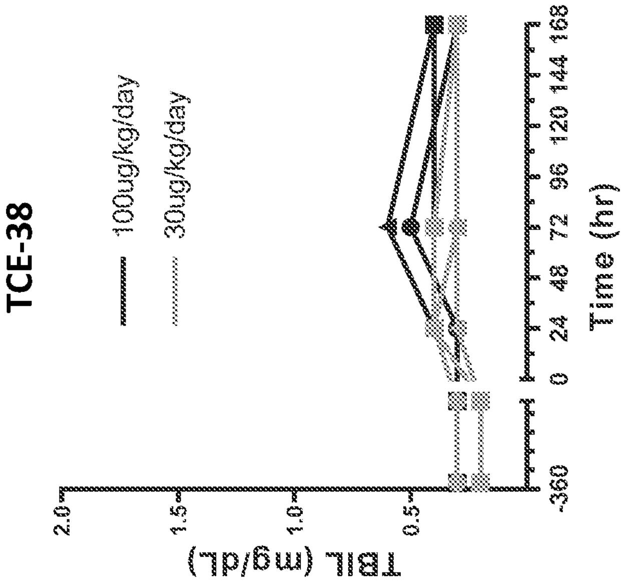
Figure 177F:
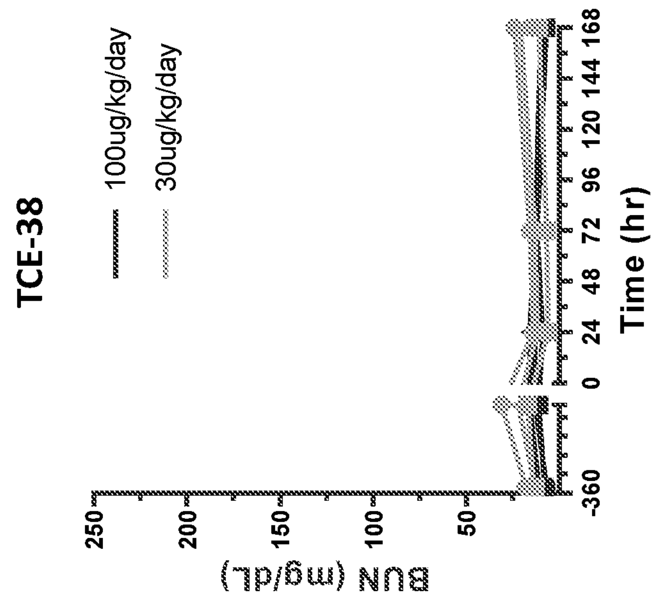
Figure 177E:
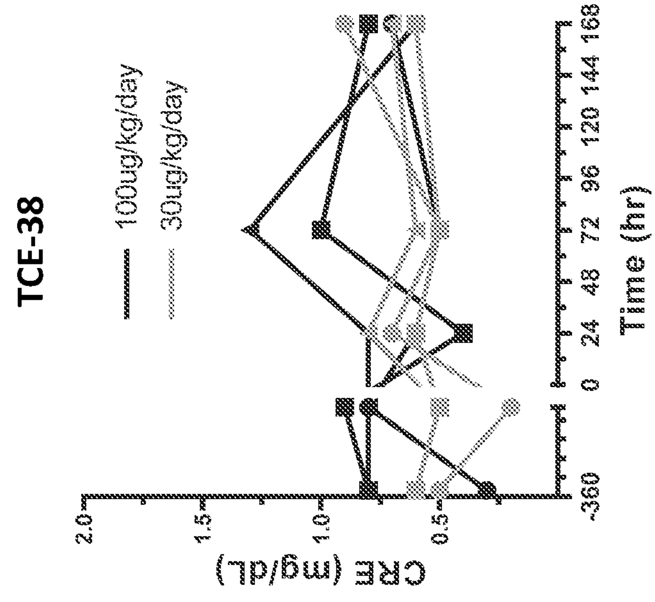

FIG. 174 shows cytokine release in cynomolgus monkeys after continuous IV infusion of TCE-38.

FIGS. 175A-175F show clinical chemistry parameters in cynomolgus monkeys after continuous IV infusion of TCE-37.

FIGS. 176A-176F show clinical chemistry parameters in cynomolgus monkeys after continuous IV infusion of TCE-40.

FIGS. 177A-177F show clinical chemistry parameters in cynomolgus monkeys after continuous IV infusion of TCE-38.

DETAILED DESCRIPTION OF THE INVENTION

TROP2 (also known as tumor-associated calcium signal transducer 2 or epithelial glycoprotein-1) is the protein product of the TACSTD2 gene, and is a transmembrane glycoprotein that functions in variety of cell signaling pathways, many of which are associated with tumorigenesis. TROP2 has been shown to be overexpressed in multiple human carcinomas, including lung, breast, cervical, ovarian, colorectal, pancreatic, and gastric cancers, and its expression has been correlated with poor patient prognosis. Furthermore, TROP2 functions as an oncogene capable of driving both tumorigenesis and metastasis in epithelial cancers such as colorectal cancer. TROP2 expression in cancer cells has long been correlated with drug resistance, and high levels of TROP2 expression have been shown to correlate with poor prognosis in a variety of cancer types. In a meta-analysis, including data from approximately 2,500 patients, increased TROP2 expression was associated with poor overall survival and disease-free survival outcomes across several solid tumors.

Disclosed herein are recombinant antibodies or antigen binding fragments thereof that comprise a tumor-associated calcium signal transducer 2 (TROP2) binding domain that has been optimized for certain properties. In some embodiments, the TROP2 binding domain has TROP2 binding properties that improve safety and reduce accumulation in healthy tissue. For instance, in some embodiments, the TROP2 binding domain has faster off rates ($k_{diss}$) and/or weaker (higher) $EC_{50}$s for TROP2 binding which may help reduce accumulation in healthy tissues. Furthermore, in some embodiments, the TROP2 binding domain has faster off rates ($k_{diss}$) and/or weaker (higher) $EC_{50}$s for TROP2 binding while maintaining TROP2 binding capabilities and activity. In some embodiments, the recombinant antibodies or antigen binding fragments thereof exhibit weaker cytotoxicity activity to help reduce off tumor on target toxicity in healthy tissues.

Disclosed herein are recombinant antibodies or antigen binding fragments thereof that comprise a tumor-associated calcium signal transducer 2 (TROP2) binding domain that have been optimized through alanine scanning mutagenesis Alanine scanning of the TROP2 binding domain was performed to optimize certain properties of the recombinant antibodies or antigen binding fragments thereof. Alanine scanning was accomplished by systematically mutating individual residues to alanine in the TROP2 binding domain relative to a non-mutated or "wild-type" TROP2 binding domain. Specifically, residues in the third complementarity determining regions (CDR3) of the immunoglobulin light chain and the immunoglobulin heavy chain were systematically mutated to alanine in order to both establish CDR3 related structure activity relationships (SAR) and to identify TROP2 binding domains that maintain binding and activity while exhibiting faster off rates to reduce accumulation in healthy tissues.

Disclosed herein, are recombinant antibodies or antigen binding fragments thereof that comprise a TROP2 binding domain that is paired with a peptide that impairs binding of the TROP2 binding domain to TROP2 in healthy tissue. The peptide is linked to the TROP2 binding domain via a linking moiety that is a substrate for a tumor specific protease. In the tumor microenvironment, the linking moiety is cleaved by a tumor specific protease thereby releasing the peptide.

In some embodiments, the TROP2 binding domain is linked to a CD3 binding domain that is also paired with a peptide mask that binds to the CD3 binding domain and impairs binding of the CD3 binding domain to CD3 in healthy tissue. The peptide mask is linked to the CD3 binding domain via a linking moiety that is a substrate for a tumor specific protease. In the tumor microenvironment, the linking moiety is cleaved by a tumor specific protease thereby releasing the peptide mask from the CD3 binding domain. Applicant has found that, in some embodiments, mutations in the CD3 binding domain decreased binding affinity to CD3 but increased binding affinity to peptide masks, thereby improving masking efficiency. The stronger masking efficiency is demonstrated by a larger difference between cell killing potency between non-masked T cell engager (TCE) constructs and masked polypeptide complexes that harbor a particular CD3 binding domain mutation relative to the difference in cell killing potency between non-masked TCE and masked polypeptide complexes harboring the non-mutated CD3 binding domain.

In some embodiments, a half-life extending moiety, such as an anti-albumin domain, is linked to the peptide that is paired with the CD3 binding domain. In some embodiments, the polypeptides or polypeptide complexes described herein are optimized for strong pairs of TROP2 binding domains and peptides that impair binding of the TROP2 binding domain to TROP2 in healthy tissue while optimizing a faster off rate of the TROP2 binding domain from TROP2.

In some embodiments, the recombinant antibodies or antigen fragments that comprise a TROP2 binding domain that have been optimized for certain properties further comprise a CD3 binding domain. Multispecific antibodies for redirecting T cells to cancers have shown promise in both pre-clinical and clinical studies. This approach relies on binding of one antigen interacting portion of the antibody to a tumor-associated antigen or marker such as TROP2, while a second antigen interacting portion can bind to an effector cell antigen on a T cell, such as CD3, which then triggers cytotoxic activity. Disclosed herein are multispecific antibody compositions that target TROP2 and CD3 for triggering cytotoxic activity.

In some embodiments, the recombinant antibodies or antigen binding fragments thereof described herein are used in a method of treating cancer. In some embodiments, the cancer has cells that express TROP2. In some instances, the cancer is a solid tumor cancer. In some embodiments, the cancer is lung, breast (e.g. HER2+; ER/PR+; TNBC), cervical, ovarian, colorectal, pancreatic or gastric. In some embodiments, the polypeptides or polypeptide complexes described herein are used in a method of treating triple-negative breast cancer (TNBC), urothelial cancer (UC), non-small cell lung cancer (NSCLC), small cell lung cancer (SCLC), gastric cancer, esophageal cancer, head and neck cancer, prostate cancer, or endometrial cancer. In some embodiments, the polypeptides or polypeptide complexes described herein are used in a method of treating breast cancer, lung cancer, urothelial cancer, endometrial cancer, ovarian cancer, prostate cancer, pancreatic cancer, gastric cancer, colon cancer, head and neck cancer, and glioma.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "antibody" is used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

The term "Fab" refers to a protein that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 June 8; 309(3):657-70, ("Aho" numbering scheme); and Whitelegg N R and Rees A R, "WAM: an improved algorithm for modelling antibodies on the WEB," Protein Eng. 2000 December; 13(12):819-24 ("AbM" numbering scheme. In certain embodiments the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Isolated Polypeptide or Polypeptide Complex Compositions TROP2 Binding Domain and Peptide Masks ($P_1$)

Disclosed herein, are isolated polypeptides or polypeptide complexes that comprise a recombinant antibody or antigen binding fragment that comprise an associated calcium signal transducer 2 (TROP2) binding domain that are selectively activated in tumor microenvironments. In some embodiments, the TROP2 binding domain is linked to a peptide ($P_1$) that comprises an amino acid sequence according to any one of SEQ ID NOs: 100-163, or an amino acid sequence that has 1, 2, or 3 amino acid mutations, substitutions or deletions relative to any one of SEQ ID NOs: 100-163. In some embodiments, $P_1$ masks the TROP2 binding domain from binding TROP2 in healthy tissue and is released from the TROP2 binding domain in tumor microenvironments by a tumor specific protease.

Disclosed herein are isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YW\ X_{14}X_{15}X_{16}\ X_{17}$; wherein $X_8$ is R, S, T, Q, D, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease.

Disclosed herein are isolated polypeptides or polypeptide complexes comprising the following Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO:

2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YW X_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease.

Disclosed herein are isolated polypeptides or polypeptide complexes comprising the following Formula I: $A_1$-$L_1$-$P_1$ wherein: $A_1$ is a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YW X_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ is a peptide that binds to $A_1$, wherein $P_1$ is an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ is a linking moiety that connects $A_1$ to $P_1$ and is a substrate for a tumor specific protease.

Disclosed herein are isolated polypeptides or polypeptide complexes according to Formula I: $A_1$-$L_1$-$P_1$ wherein: $A_1$ is a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YW X_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ is a peptide that binds to $A_1$, wherein $P_1$ is an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ is a linking moiety that connects $A_1$ to $P_1$ and is a substrate for a tumor specific protease.

TABLE 1

TROP2 binding domain light chain complementarity determining regions (CDRs) as based on IMGT CDR numbering system.

| Construct Description | Amino Acid Sequence (N to C) | SEQ ID NO: |
|---|---|---|
| CDR1-L | QDVSIA | 1 |
| CDR2-L | SA | 2 |
| CDR3-L hRS7 | QQHYITPLT | 3 |
| CDR3-L Q89A | **A**QHYITPLT | 4 |
| CDR3-L Q90A | Q**A**HYITPLT | 5 |
| CDR3-L H91A | QQ**A**YITPLT | 6 |
| CDR3-L Y92A | QQH**A**ITPLT | 7 |
| CDR3-L I93A | QQHY**A**TPLT | 8 |
| CDR3-L T94A | QQHYI**A**PLT | 9 |
| CDR3-L P95A | QQHYIT**A**LT | 10 |
| CDR3-L L96A | QQHYITP**A**T | 11 |
| CDR3-L T97A | QQHYITPL**A** | 12 |

TABLE 2

TROP2 binding domain heavy chain complementarity determining regions (CDRs) as based on IMGT CDR numbering system.

| Construct Description | Amino Acid Sequence (N to C) | SEQ ID NO: |
|---|---|---|
| CDR1-H | GYTFTNYG | 13 |
| CDR2-H | INTYTGEP | 14 |
| CDR3-H hRS7 | ARGGFGSSYWYFDV | 15 |

TABLE 2-continued

TROP2 binding domain heavy chain complementarity determining regions (CDRs) as based on IMGT CDR numbering system.

| Construct Description | Amino Acid Sequence (N to C) | SEQ ID NO: |
|---|---|---|
| CDR3-H R98A | **A**AGGFGSSYWYFDV | 16 |
| CDR3-H G99A | AR**A**GFGSSYWYFDV | 17 |
| CDR3-H G100A | ARG**A**FGSSYWYFDV | 18 |
| CDR3-H F101A | ARGG**A**GSSYWYFDV | 19 |
| CDR3-H G102A | ARGGF**A**SSYWYFDV | 20 |
| CDR3-H S103A | ARGGFG**A**SYWYFDV | 21 |
| CDR3-H S104A | ARGGFGS**A**YWYFDV | 22 |
| CDR3-H Y105A | ARGGFGSS**A**WYFDV | 23 |
| CDR3-H W106A | ARGGFGSSY**A**YFDV | 24 |
| CDR3-H Y107A | ARGGFGSSYW**A**FDV | 25 |
| CDR3-H F108A | ARGGFGSSYWY**A**DV | 26 |
| CDR3-H D109A | ARGGFGSSYWYF**A**V | 27 |
| CDR3-H V110A | ARGGFGSSYWYFD**A** | 28 |

TABLE 3

Peptide mask sequences for TROP2 Fab alanine scanning sequences

| Peptide | Amino Acid Sequence (N to C) | SEQ ID NO: |
|---|---|---|
| Peptide-1 | IDFCAMYQWPICDT | 100 |
| Peptide-2 | IDFCAVYKWPVCQV | 101 |
| Peptide-3 | IDFCMLYNWPICAG | 102 |
| Peptide-4 | VDFCKIYAWPICGS | 103 |
| Peptide-5 | VDFCKLYNWPVCQT | 104 |
| Peptide-6 | IDFCLIYNWPVCDT | 105 |
| Peptide-7 | EDFCKLYNWPICYQ | 106 |
| Peptide-8 | VDFCGLYHWPICYQ | 107 |
| Peptide-9 | VDFCYLYNWPVCSK | 108 |
| Peptide-10 | IDFCAIYQWPVCRS | 109 |
| Peptide-11 | VDFCALYNWPVCET | 110 |
| Peptide-12 | PDFCAVYRWPICYQ | 111 |
| Peptide-13 | VDFCELYRWPICNS | 112 |
| Peptide-14 | LDFCKIYDWPICHL | 113 |
| Peptide-15 | LDFCKLYQWPVCFT | 114 |
| Peptide-16 | IDFCLLYDWPVCAS | 115 |
| Peptide-17 | IDFCLLYDWPICGR | 116 |
| Peptide-18 | MDFCQIYDWPICRL | 117 |

TABLE 3-continued

Peptide mask sequences for TROP2 Fab alanine scanning sequences

| Peptide | Amino Acid Sequence (N to C) | SEQ ID NO: |
|---|---|---|
| Peptide-19 | PDFCQLYNWPVCAG | 118 |
| Peptide-20 | VDFCSFYRWPICET | 119 |
| Peptide-21 | IDFCSLYQWPVCGT | 120 |
| Peptide-22 | VDFCTIYKWPVCEG | 121 |
| Peptide-23 | VDFCYQYGWPICSR | 122 |
| Peptide-24 | SVLFCVKNLYCWVT | 123 |
| Peptide-25 | VDFCKIYSWPVCHQ | 124 |
| Peptide-26 | DNLICVKNLWCWIA | 125 |
| Peptide-27 | FSLVCVRNLYCWNV | 126 |
| Peptide-28 | NYLLCVKNLYCWIV | 127 |
| Peptide-29 | SYLVCVKNVYCWTA | 128 |
| Peptide-30 | TSLICFRNVYCWNV | 129 |
| Peptide-31 | YSLVCVKNLYCWNL | 130 |
| Peptide-32 | PDFCYMYGWPICDS | 131 |
| Peptide-33 | PDFCYMYNWPVCVT | 132 |
| Peptide-34 | WTFCATSMWRYCVD | 133 |
| Peptide-35 | EDFCYWYQWPICSD | 134 |
| Peptide-36 | VDFCYQYGWPICSR | 135 |
| Peptide-37 | VDFCYLYNWPVCSK | 136 |
| Peptide-38 | VDFCSIYHWPVCYV | 137 |
| Peptide-39 | VDFCGLYHWPICYQVD | 138 |
| Peptide-40 | VDFCYLYSWPICTK | 139 |
| Peptide-41 | VDFCGLYHWPICYQVY | 140 |
| Peptide-42 | IDFCAMYHWPICDT | 141 |
| Peptide-43 | VDFCALYHWPICYQ | 142 |
| Peptide-44 | VEFCKQWTWFGCMT | 143 |
| Peptide-45 | VDFCYQYGWPICSRVD | 144 |
| Peptide-46 | VEFCAIYSWPICKI | 145 |
| Peptide-47 | VDFCYQYGWPICSRLY | 146 |
| Peptide-48 | VDFCYMYKWPVCYP | 147 |
| Peptide-49 | IDFCLLYKWPVCEL | 148 |
| Peptide-50 | VDFCAIYSWPICKI | 149 |
| Peptide-51 | VDFCGLYHWPICYQV | 150 |
| Peptide-52 | VDFCYQYAWPVCSTGD | 151 |
| Peptide-53 | IDFCRVYDWPVCSL | 152 |
| Peptide-54 | VDFCYRYSWPVCWA | 153 |
| Peptide-55 | VDFCYKYNWPICSR | 154 |

TABLE 3-continued

Peptide mask sequences for TROP2 Fab alanine scanning sequences

| Peptide | Amino Acid Sequence (N to C) | SEQ ID NO: |
|---|---|---|
| Peptide-56 | VDFCYQYGWPICSRV | 155 |
| Peptide-57 | IDFCYRYGWPVCQT | 156 |
| Peptide-58 | VEICKQWFYTVCLS | 157 |
| Peptide-59 | VDFCALYNWPVCAI | 158 |
| Peptide-60 | VDFCNLYHWPICAI | 159 |
| Peptide-61 | VDFCALYHWPVCGL | 160 |
| Peptide-62 | IDFCAVYKWPVCQV | 161 |
| Peptide-63 | IDFCLIYNWPVCDT | 162 |
| Peptide-64 | PDFCAVYRWPICYQ | 163 |

In some embodiments, $X_1$ is Q, N, D, E, or A; $X_2$ is Q, N, D, E, or A; $X_3$ is I, V, L, or A; $X_4$ is T, S, or A; $X_5$ is P, G, or A; $X_6$ is L, V, I, or A; $X_7$ is T, S, or A; $X_8$ is R, K, or A; $X_9$ is G, S, T, or A; $X_{10}$ is F, Y, or A; $X_{11}$ is G, S, T, or A; $X_{12}$ is S, G, T, or A; $X_{13}$ is S, G, T, or A; $X_{14}$ is Y, W, F, or A; $X_{15}$ is F, Y, W, or A; $X_{16}$ is D, E, Q, N, or A; and $X_{17}$ is V, L, I, or A. In some embodiments, $X_1$ is Q; and $X_6$ is L. In some embodiments, $X_8$ is R; $X_{10}$ is F; $X_{11}$ is G; $X_{14}$ is Y; $X_{15}$ is F; and $X_{16}$ is D. In some embodiments, $X_1$ is Q, S, T, D, N, E, or A; $X_2$ is Q, S, T, D, N, E, or A; $X_3$ is I, G166, P, V, L, M, or A; $X_4$ is T, G, S, M, H, N, Q, or A; $X_5$ is P, G, V, L, I, M, or A; $X_6$ is L, G, P, V, I, M, or A; $X_7$ is T, G, S, M, H, N, Q, or A; $X_8$ is R, H, K, or A; $X_9$ is G, P, V, L, I, M, S, T, or A; $X_{10}$ is F, Y, W, V, L, I, or A; $X_{11}$ is G, P, V, L, I, M, S, T, or A; $X_{12}$ is S, G, T, M, N, Q, or A; $X_{13}$ is S, G, T, M, N, Q, or A; $X_{14}$ is Y, F, W, V, L, I, or A; $X_{15}$ is F, Y, W, V, L, I, or A; $X_{16}$ is D, Q, N, E, S, T, or A; and $X_{17}$ is V, G, P, L, I, M, or A. In some embodiments, $X_1$ is Q, N, or A; $X_2$ is Q, N, or A; $X_3$ is I, V, L, or A; $X_4$ is T, S, or A; $X_5$ is P, G, or A; $X_6$ is L, V, I, or A; $X_7$ is T, S, or A; $X_8$ is R, K, or A; $X_9$ is G, V, S, T, or A; $X_{10}$ is F, Y, or A; $X_{11}$ is G, V, S, T, or A; $X_{12}$ is S, G, T, or A; $X_{13}$ is S, G, T, or A; $X_{14}$ is Y, W, or A; $X_{15}$ is F, Y, or A; $X_{16}$ is D, E, or A; and $X_{17}$ is V, G, L, I, or A. In some embodiments, $X_1$ is Q; and $X_6$ is L. In some embodiments, $X_8$ is R; $X_{10}$ is F; $X_{11}$ is G; $X_{14}$ is Y; $X_{15}$ is F; and $X_{16}$ is D.

In some embodiments, CDR3-L comprises an amino acid selected from SEQ ID NOs: 3-5 and 8-12.

In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2; CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11, and CDR1-H: SEQ ID NO: 13, CDR2-H: SEQ ID NO: 14, CDR3-H: SEQ ID NO: 15; and CDR1-L: SEQ ID NO: 1, CDR2-L: SEQ ID NO: 2, CDR3-L: SEQ ID NO: 12, and CDR1-H: SEQ ID NO: 13, CDR2-H: SEQ ID NO: 14, CDR3-H: SEQ ID NO: 15.

In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 5, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 8, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 9, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 10, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 11, and CDR1-H: SEQ ID NO: 13, CDR2-H: SEQ ID NO: 14, CDR3-H: SEQ ID NO: 15. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 12, and CDR1-H: SEQ ID NO: 13, CDR2-H: SEQ ID NO: 14, CDR3-H: SEQ ID NO: 15.

In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10, and CDR1-H: SEQ ID NO: 13, CDR2-H: SEQ ID NO: 14, CDR3-H: SEQ ID NO: 15; and CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15.

In some embodiments, CDR3-H comprises an amino acid selected from SEQ ID NOs: 16-17, 19-22, and 25-28. In some embodiments, the immunoglobulin light chain and the immunoglobulin heavy chain comprise a set of CDRs selected from the group consisting of: CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28.

In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 21. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27. In some embodiments, the immunoglobulin light chain and the immunoglobulin heavy chain comprise a set of CDR sequences comprising CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28.

In some embodiments, the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28.

Disclosed herein are isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3 and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connect $A_1$ to $P_1$ and is a substrate for a tumor specific protease.

Disclosed herein are isolated polypeptides or polypeptide complexes comprising the Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ comprises a peptide that bind to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connect $A_1$ to $P_1$ and is a substrate for a tumor specific protease.

Disclosed herein are isolated polypeptides or polypeptide complexes comprising Formula I: $A_1$-$L_1$-$P_1$ wherein: $A_1$ is a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ is a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ is a linking moiety that connect $A_1$ to $P_1$ and is a substrate for a tumor specific protease.

Disclosed herein are isolated polypeptides or polypeptide complexes according to Formula I: $A_1$-$L_1$-$P_1$ wherein: $A_1$ is a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ is a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ is a linking moiety that connect $A_1$ to $P_1$ and is a substrate for a tumor specific protease.

In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises a variable domain of immunoglobulin kappa (IgK) or immunoglobulin lambda (IgL) light chain. In some embodiments, the immunoglobulin heavy chain comprises a variable domain of an IgG1, IgG2, IgG3, or IgG4 heavy chain.

In some embodiments, the immunoglobulin light chain comprises an amino acid sequence with at least 90%, 95%, 96%, 97%, 98%, 99%, or 100% identity to any one of SEQ ID NOs: 31, 33, 35, 37, 39, 41, 43, 45, 47, 49, 51, 53, 55, 57, 59, 61, 63, 65, 67, 69, 71, or 73. In some embodiments, the immunoglobulin heavy chain comprises an amino acid sequence with at least 90%, 95%, 96%, 97%, 98%, 99%, or 100% identity to any one of SEQ ID NOs: 32, 34, 36, 38, 40, 42, 44, 46, 48, 50, 52, 54, 56, 58, 60, 62, 64, 66, 68, 70, 72, or 74.

In some embodiments, the immunoglobulin light chain comprises an amino acid sequence with at least 90%, 95%, 96%, 97%, 98%, 99%, or 100% identity to SEQ ID NO: 31 and the immunoglobulin heavy chain comprises an amino acid sequence with at least 90%, 95%, 96%, 97%, 98%, 99%, or 100% identity to SEQ ID NO: 32. In some embodiments, the immunoglobulin light chain comprises an amino acid sequence with at least 90%, 95%, 96%, 97%, 98%, 99%, or 100% identity to SEQ ID NO: 33 and the immunoglobulin heavy chain comprises an amino acid sequence with at least 90%, 95%, 96%, 97%, 98%, 99%, or 100% identity to SEQ ID NO: 34. In some embodiments, the immunoglobulin light chain comprises an amino acid sequence with at least 90%, 95%, 96%, 97%, 98%, 99%, or 100% identity to SEQ ID NO: 35 and the immunoglobulin heavy chain comprises an amino acid sequence with at least 90%, 95%, 96%, 97%, 98%, 99%, or 100% identity to SEQ ID NO: 36. In some embodiments, the immunoglobulin light chain comprises an amino acid sequence with at least 90%, 95%, 96%, 97%, 98%, 99%, or 100% identity to SEQ ID NO: 37 and the immunoglobulin heavy chain comprises an amino acid sequence with at least 90%, 95%, 96%, 97%, 98%, 99%, or 100% identity to SEQ ID NO: 38. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40. In some embodiments, the immunoglobulin light chain comprises an amino acid sequence with at least 90%, 95%, 96%, 97%, 98%, 99%, or 100% identity to SEQ ID NO: 41 and the immunoglobulin heavy chain comprises an amino acid sequence with at least 90%, 95%, 96%, 97%, 98%, 99%, or 100% identity to SEQ ID NO: 42. In some embodiments, the immunoglobulin light chain comprises an amino acid sequence with at least 90%, 95%, 96%, 97%, 98%, 99%, or 100% identity to SEQ ID NO: 43 and the immunoglobulin heavy chain comprises an amino acid sequence with at least 90%, 95%, 96%, 97%, 98%, 99%, or 100% identity to SEQ ID NO: 44. In some embodiments, the immunoglobulin light chain comprises an amino acid sequence with at least 90%, 95%, 96%, 97%, 98%, 99%, or 100% identity to SEQ ID NO: 45 and the immunoglobulin heavy chain comprises an amino acid sequence with at least 90%, 95%, 96%, 97%, 98%, 99%, or 100% identity to SEQ ID NO: 46. In some embodiments, the immunoglobulin light chain comprises an amino acid sequence with at least 90%, 95%, 96%, 97%, 98%, 99%, or 100% identity to SEQ ID NO: 47 and the immunoglobulin heavy chain comprises an amino acid sequence with at least 90%, 95%, 96%, 97%, 98%, 99%, or 100% identity to SEQ ID NO: 48.

In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50. In some embodiments, the immunoglobulin light chain comprises an amino acid sequence with at least 90%, 95%, 96%, 97%, 98%, 99%, or 100% identity to SEQ ID NO: 51 and the immunoglobulin heavy chain comprises an amino acid sequence with at least 90%, 95%, 96%, 97%, 98%, 99%, or 100% identity to SEQ ID NO: 52. In some embodiments, the immunoglobulin light chain comprises an amino acid sequence with at least 90%, 95%, 96%, 97%, 98%, 99%, or 100% identity to SEQ ID NO: 53 and the immunoglobulin heavy chain comprises an amino acid sequence with at least 90%, 95%, 96%, 97%, 98%, 99%, or 100% identity to SEQ ID NO: 54. In some embodiments, the immunoglobulin light chain comprises an amino acid sequence with at least 90%, 95%, 96%, 97%, 98%, 99%, or 100% identity to SEQ ID NO: 55 and the immunoglobulin heavy chain comprises an amino acid sequence with at least 90%, 95%, 96%, 97%, 98%, 99%, or 100% identity to SEQ ID NO: 56. In some embodiments, the immunoglobulin light chain comprises an amino acid sequence with at least 90%, 95%, 96%, 97%, 98%, 99%, or 100% identity to SEQ ID NO: 57 and the immunoglobulin heavy chain comprises an amino acid sequence with at least 90%, 95%, 96%, 97%, 98%, 99%, or 100% identity to SEQ ID NO: 58. In some embodiments, the immunoglobulin light chain comprises an amino acid sequence with at least 90%, 95%, 96%, 97%, 98%, 99%, or 100% identity to SEQ ID NO: 59 and the immunoglobulin heavy chain comprises an amino acid sequence with at least 90%, 95%, 96%, 97%, 98%, 99%, or 100% identity to SEQ ID NO: 60. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62. In some embodiments, the immunoglobulin light chain comprises an amino acid sequence with at least 90%, 95%, 96%, 97%, 98%, 99%, or 100% identity to SEQ ID NO: 63 and the immunoglobulin heavy chain comprises an amino acid sequence with at least 90%, 95%, 96%, 97%, 98%, 99%, or 100% identity to SEQ ID NO: 64. In some embodiments, the immunoglobulin light chain comprises an amino acid sequence with at least 90%, 95%, 96%, 97%, 98%, 99%, or 100% identity to SEQ ID NO: 65 and the immunoglobulin heavy chain comprises an amino acid sequence with at least 90%, 95%, 96%, 97%, 98%, 99%, or 100% identity to SEQ ID NO: 66. In some embodiments, the immunoglobulin light chain comprises an amino acid sequence with at least 90%, 95%, 96%, 97%, 98%, 99%, or 100% identity to SEQ ID NO: 67 and the immunoglobulin heavy chain comprises an amino acid sequence with at least 90%, 95%, 96%, 97%, 98%, 99%, or 100% identity to SEQ ID NO: 68. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72. In some embodiments, the immunoglobulin light chain comprises an amino acid sequence with at least 90%, 95%, 96%, 97%, 98%, 99%, or 100% identity to SEQ ID NO: 73 and the immunoglobulin heavy chain comprises an amino acid sequence with at least 90%, 95%, 96%, 97%, 98%, 99%, or 100% identity to SEQ ID NO: 74.

TABLE 4

TROP2 binding domain (TBD) heavy chain and light chain sequences

| Construct Description | Amino Acid Sequence (N to C) | SEQ ID NO: |
|---|---|---|
| TBD-1 LC wt | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29 |
| TBD-1 HC wt | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 30 |
| TBD-2 LC Q89A | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**AQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 31 |
| TBD-2 HC | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 32 |
| TBD-3 LC Q90A | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QAHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 33 |
| TBD-3 HC | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 34 |
| TBD-4 LC H91A | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQAYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 35 |

TABLE 4-continued

TROP2 binding domain (TBD) heavy chain and light chain sequences

| Construct Description | Amino Acid Sequence (N to C) | SEQ ID NO: |
|---|---|---|
| TBD-4 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 36 |
| TBD-5 LC Y92A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHAITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 37 |
| TBD-5 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 38 |
| TBD-6 LC I93A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYATPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 39 |
| TBD-6 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 40 |
| TBD-7 LC T94A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYIAPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 41 |
| TBD-7 HC | QUQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 42 |
| TBD-8 LC P95A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITALT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 43 |
| TBD-8 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 44 |
| TBD-9 LC L96A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPAT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 45 |

TABLE 4-continued

TROP2 binding domain (TBD) heavy chain and light chain sequences

| Construct Description | Amino Acid Sequence (N to C) | SEQ ID NO: |
|---|---|---|
| TBD-9 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 46 |
| TBD-10 LC<br>T97A | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLA**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 47 |
| TBD-10 HC | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 48 |
| TBD-11 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 49 |
| TBD-11 HC<br>R98A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**AAGGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 50 |
| TBD-12 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 51 |
| TBD-12 HC<br>G99A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARAGFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 52 |
| TBD-13 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 53 |
| TBD-13 HC<br>G100A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGAFGSSYWYFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 54 |
| TBD-14 LC | DIQLTQSPSSLSASVGDRVSITCKAS**QDVSIAVA**WYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 55 |

TABLE 4-continued

TROP2 binding domain (TBD) heavy chain and light chain sequences

| Construct Description | Amino Acid Sequence (N to C) | SEQ ID NO: |
|---|---|---|
| TBD-14 HC F101A | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGAGSSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 56 |
| TBD-15 LC | DIQLTQSPSSLSASVGDRVSITCKAS**QDVSIAVA**WYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 57 |
| TBD-15 HC G102A | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFASSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 58 |
| TBD-16 LC | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 59 |
| TBD-16 HC S103A | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGASYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 60 |
| TBD-17 LC | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 61 |
| TBD-17 HC S104A | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSAYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 62 |
| TBD-18 LC | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 63 |
| TBD-18 HC Y105A | QVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSAWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 64 |
| TBD-19 LC | DIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 65 |

TABLE 4-continued

TROP2 binding domain (TBD) heavy chain and light chain sequences

| Construct Description | Amino Acid Sequence (N to C) | SEQ ID NO: |
|---|---|---|
| TBD-19 HC<br>W106A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYAYFDVW**<br>GQGSLVTVSSASTKGPSVFPLAPSSKSTSGGTAALGCLV<br>KDYFPEPVTVSWNSGALTSGVHTFPAVLQSSGLYSLSSV<br>VTVPSSSLGTQTYICNVNHKPSNTKVDKKVEPKSC | 66 |
| TBD-20 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 67 |
| TBD-20 HC<br>Y107A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWAFDV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 68 |
| TBD-21 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 69 |
| TBD-21 HC<br>F108A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYADV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 70 |
| TBD-22 LC | DIQLTQSPSSLSASVGDRVSITCKA**SQDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 71 |
| TBD-22 HC<br>D109A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFAV**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 72 |
| TBD-23 LC | DIQLTQSPSSLSASVGDRVSITCKAS**QDVSIA**VAWYQQK<br>PGKAPKLLIY**SAS**YRYTGVPDRFSGSGSGTDFTLTISSLQ<br>PEDFAVYYC**QQHYITPLT**FGAGTKVEIKRTVAAPSVFIF<br>PPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 73 |
| TBD-23 HC<br>V110A | QVQLQQSGSELKKPGASVKVSCKAS**GYTFTNYG**MNW<br>VKQAPGQGLKWMGW**INTYTGEP**TYTDDFKGRFAFSLD<br>TSVSTAYLQISSLKADDTAVYFC**ARGGFGSSYWYFDA**<br>WGQGSLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKKVEPKSC | 74 |

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 31 and the immunoglobulin heavy chain comprises an amino acid sequence with at least 90% identity to SEQ ID NO: 32.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 33 and the immunoglobulin heavy chain comprises an amino acid sequence with at least 90% identity to SEQ ID NO: 34.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 39 and the immunoglobulin heavy chain comprises an amino acid sequence with at least 90% identity to SEQ ID NO: 40.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 41 and the immunoglobulin heavy chain comprises an amino acid sequence with at least 90% identity to SEQ ID NO: 42.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 43 and the immunoglobulin heavy chain comprises an amino acid sequence with at least 90% identity to SEQ ID NO: 44.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 45 and the immunoglobulin heavy chain comprises an amino acid sequence with at least 90% identity to SEQ ID NO: 46.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; and the immunoglobulin light chain comprises an amino acid sequence with at least 90% identity to SEQ ID NO: 47 and the immunoglobulin heavy chain comprises an amino acid sequence with at least 90% identity to SEQ ID NO: 48.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; and the immunoglobulin light chain comprises an amino acid sequence with at least 90% identity to SEQ ID NO: 49 and the immunoglobulin heavy chain comprises an amino acid sequence with at least 90% identity to SEQ ID NO: 50.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; and the immunoglobulin light chain comprises an amino acid sequence with at least 90% identity to SEQ ID NO: 51 and the immunoglobulin heavy chain comprises an amino acid sequence with at least 90% identity to SEQ ID NO: 52.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; and the immunoglobulin light chain comprises an amino acid sequence with at least 90% identity to SEQ ID NO: 55 and the immunoglobulin heavy chain comprises an amino acid sequence with at least 90% identity to SEQ ID NO: 56.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; and the immunoglobulin light chain comprises an amino acid sequence with at least 90% identity to SEQ ID NO: 57 and the immunoglobulin heavy chain comprises an amino acid sequence with at least 90% identity to SEQ ID NO: 58.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO:21; and the immunoglobulin light chain comprises an amino acid sequence with at least 90% identity to SEQ ID NO: 59 and the immunoglobulin heavy chain comprises an amino acid sequence with at least 90% identity to SEQ ID NO: 60.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 22; and the immunoglobulin light chain comprises an amino acid sequence with at least 90% identity to SEQ ID NO: 61 and the immunoglobulin heavy chain comprises an amino acid sequence with at least 90% identity to SEQ ID NO: 62.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; and the immunoglobulin light chain comprises an amino acid sequence with at least 90% identity to SEQ ID NO: 67 and the immunoglobulin heavy chain comprises an amino acid sequence with at least 90% identity to SEQ ID NO: 68.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; and the immunoglobulin light chain comprises an amino acid sequence with at least 90% identity to SEQ ID NO: 69 and the immunoglobulin heavy chain comprises an amino acid sequence with at least 90% identity to SEQ ID NO: 70.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and the immunoglobulin light chain comprises an amino acid sequence with at least 90% identity to SEQ ID NO: 71 and the immunoglobulin heavy chain comprises an amino acid sequence with at least 90% identity to SEQ ID NO: 72.

In some embodiments, the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H wherein the amino acid sequences comprise CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28; and the immunoglobulin light chain comprises an amino acid sequence with at least 90% identity to SEQ ID NO: 73 and the immunoglobulin heavy chain comprises an amino acid sequence with at least 90% identity to SEQ ID NO: 74.

In some embodiments, the TROP2 binding domain has a faster off rate (larger $k_{diss}$) for TROP2 binding as compared to a TROP2 binding domain that comprises an immunoglobulin light chain according to SEQ ID NO: 29 and an immunoglobulin heavy chain according to SEQ ID NO: 30 as measured under substantially similar kinetic assay conditions. In some embodiments, the TROP2 binding domain has weaker binding to TROP2 as compared to a TROP2 binding domain that comprises an immunoglobulin light chain according to SEQ ID NO: 29 and an immunoglobulin heavy chain according to SEQ ID NO: 30 as measured by enzyme-linked immunosorbent assay (ELISA) in substantially similar assay conditions. In some embodiments, the TROP2 binding domain has an increased $EC_{50}$ for TROP2 as compared to a TROP2 binding domain that comprises an immunoglobulin light chain according to SEQ ID NO: 29 and an immunoglobulin heavy chain according to SEQ ID NO: 30 as measured by ELISA in substantially similar assay conditions. In some embodiments, the TROP2 comprises an amino acid sequence according to SEQ ID NO: 396 (see Table 13).

In some embodiments, $P_1$ impairs binding of $A_1$ to TROP2. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ is bound to $A_1$ at or near an antigen binding site. In some embodiments, $P_1$ becomes unbound from $A_1$ when $L_1$ is cleaved by the tumor specific protease thereby exposing $A_1$ to TROP2. In some embodiments, $P_1$ has less than 75% sequence identity to TROP2. In some embodiments, $P_1$ has less than 80% sequence identity to TROP2. In some embodiments, $P_1$ has less than 85% sequence identity to TROP2. In some embodiments, $P_1$ has less than 90% sequence identity to TROP2. In some embodiments, $P_1$ has less than 95% sequence identity to TROP2. In some embodiments, $P_1$ comprises a de novo amino acid sequence that shares less than 10% sequence identity to TROP2. In some embodiments, $P_1$ comprises at least two cysteine amino acid residues. In some embodiments, $P_1$ comprises a cyclic peptide or a linear peptide. In some embodiments, $P_1$ comprises a cyclic peptide. In some embodiments, $P_1$ comprises a linear peptide. In some embodiments, $P_1$ comprise a modified amino acid or non-natural amino acid, or a modified non-natural amino acid, or a combination thereof. In some embodiments, $P_1$ does not comprise albumin or an albumin fragment. In some embodiments, $P_1$ does not comprise an albumin binding domain.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and $P_1$ comprises an amino acid sequence according to SEQ ID NO: 102 or SEQ ID NO: 107, or an amino acid sequence that has 1, 2, or 3 amino acid mutations, substitutions, or deletions relative to SEQ ID NO: 102 or SEQ ID NO: 107. In some embodiments, the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124. In some embodiments, the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and $P_1$ comprises an amino acid sequence according to SEQ ID NO: 102 or SEQ ID NO: 107, or an amino acid sequence that has 1, 2, or 3 amino acid mutations, substitutions, or deletions relative to SEQ ID NO: 102 or SEQ ID NO: 107.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150. In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 27, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 27, and $P_1$ comprises an amino acid sequence according to any one of SEQ ID NOs: 107, 109, 116, 141, 142, 148, 149, 150, 158, or an amino acid sequence that has 1, 2, or 3 amino acid mutations, substitutions, or deletions relative to any one of SEQ ID NOs: 107, 109, 116, 141, 142, 148, 149, 150, 158. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163. In some embodiments, the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions, or deletions relative to any one of SEQ ID NOs: 107, 109, 116, 141, 142, 148, 149, 150, and 158.

CD3 Binding Domain

In some embodiments, the isolated polypeptide or polypeptide complex further comprises a CD3 binding domain. In some embodiments, the isolated polypeptide or polypeptide complex is according to the following formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the isolated polypeptide or polypeptide complex comprises the following formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the isolated polypeptide or polypeptide complex comprises the following formula $P_2$-$L_2$-$B_2$-$A_1$-$L_1$-$P_1$ (Formula Ia), wherein $B_2$ is the CD3 binding domain, $P_2$ is a peptide that binds to $B_2$ and $L_2$ is a linking moiety that connects $B_2$ to $P_2$ and is a substrate for a tumor specific protease. In some embodiments, the isolated polypeptide or polypeptide complex is according to the following formula $P_2$-$L_2$-$B_2$-$A_1$-$L_1$-$P_1$ (Formula Ia), wherein $B_2$ is the CD3 binding domain, $P_2$ is a peptide that binds to $B_2$ and $L_2$ is a linking moiety that connects $B_2$ to $P_2$ and is a substrate for a tumor specific protease.

In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, CDR1-L comprises the amino acid sequence of SEQ ID NO: 75; CDR2-L comprises the amino acid sequence of SEQ ID NO:

76; CDR3-L comprises the amino acid sequence of SEQ ID NO: 77; CDR1-H comprises the amino acid sequence of SEQ ID NO: 78; and CDR2-H comprises the amino acid sequence of SEQ ID NO: 79; and CDR3-H comprises the amino acid sequence of SEQ ID NO: 80.

In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 75 or SEQ ID NO: 259; wherein CDR2-L comprises the amino acid sequence of SEQ ID NO: 76; wherein CDR3-L comprises the amino acid sequence of $Z_1$-$Z_2$-W-$Z_3$-$Z_4$-$Z_5$-$Z_6$-W-$Z_7$-$Z_8$; wherein $Z_1$ is V, G, P, L, I, M, S, T, or A; $Z_2$ is L, G, P, V, I, M, S, T, or A; $Z_3$ is Y, F, W, V, L, I, G, or A; $Z_4$ is S, G, T, M, N, Q, H, or A; $Z_5$ is N, Q, S, T, D, E, H, K, R, or A; $Z_6$ is R, S, T, Q, D, E, H, K, N, or A; $Z_7$ is V, G, P, L, I, M, S, T, or A; and $Z_8$ is F, Y, W, V, L, I, G, or A; wherein CDR1-H comprises the amino acid sequence of SEQ ID NO: 78 or SEQ ID NO: 270; wherein CDR2-H comprises the amino acid sequence of SEQ ID NO: 79; and wherein CDR3-H comprises the amino acid sequence of $Z_9$-$Z_{10}$-$Z_{11}$-$Z_{12}$-N-$Z_{13}$-$Z_{14}$-$Z_{15}$-$Z_{16}$-$Z_{17}$-$Z_{18}$-$Z_{19}$-Y-$Z_{20}$-A-$Z_{21}$; wherein $Z_9$ is V, G, P, L, I, M, S, T, or A; $Z_{10}$ is R, S, T, Q, D, E, H, K, N, or A; $Z_{11}$ is H, R, K, G, T, S, N, Q, or A; $Z_{12}$ is G, P, V, L, I, M, S, T, or A; $Z_{13}$ is F, Y, W, V, L, I, G, or A; $Z_{14}$ is G, P, V, L, I, M, S, T, or A; $Z_{15}$ is N, Q, S, T, D, E, H, K, R, or A; $Z_{16}$ is S, G, T, M, N, Q, H, or A; $Z_{17}$ is Y, F, W, V, L, I, G, or A; $Z_{18}$ is I, G, P, V, L, M, S, T, or A; $Z_{19}$ is S, G, T, M, N, Q, H, or A; $Z_{20}$ is W, F, Y, V, L, I, G, or A; and $Z_{21}$ is Y, F, W, V, L, I, G, or A. In some embodiments, $Z_1$ is V, G, L, I, or A; $Z_2$ is L, V, I, or A; $Z_3$ is Y, W, F, or A; $Z_4$ is S, G, T, or A; $Z_5$ is N, Q, D, E, or A; $Z_6$ is R, K, or A; $Z_7$ is V, G, L, I, or A; $Z_8$ is F, Y, W, or A; $Z_9$ is V, G, L, I, or A; $Z_{10}$ is R, K, or A; $Z_{12}$ is G, S, T, or A; $Z_{13}$ is F, Y, W, or A; $Z_{14}$ is G, S, T, or A; $Z_{15}$ is N, Q, D, E, or A; $Z_{16}$ is S, G, T, or A; $Z_{17}$ is Y, W, F, or A; $Z_{18}$ is I, V, L, or A; $Z_{19}$ is S, G, T, or A; $Z_{20}$ is W, Y, F, or A; and $Z_{21}$ is Y, W, F, or A. In some embodiments, $Z_8$ is F. In some embodiments, $Z_{10}$ is R; $Z_{11}$ is H; $Z_{13}$ is F; $Z_{18}$ is I; $Z_{19}$ is S; and $Z_{20}$ is W.

TABLE 5

CD3 binding domain light chain complementarity determining regions (CDRs) as based on IMGT CDR numbering system.

| Construct Description | Amino Acid Sequence (N to C) | SEQ ID NO: |
|---|---|---|
| CDR1-L | TGAVTSGNY | 75 |
| CDR2-L | GTK | 76 |
| CDR3-L | VLWYSNRWV | 77 |
| CDR1-L | TGAVTSANY | 259 |
| CDR3-L V231A | **A**LWYSNRWV | 260 |
| CDR3-L L232A | V**A**WYSNRWV | 261 |
| CDR3-L W233A | VL**A**YSNRWV | 262 |
| CDR3-L Y234A | VLW**A**SNRWV | 263 |
| CDR3-L S235A | VLWY**A**NRWV | 264 |
| CDR3-L N236A | VLWYS**A**RWV | 265 |

TABLE 5-continued

CD3 binding domain light chain complementarity determining regions (CDRs) as based on IMGT CDR numbering system.

| Construct Description | Amino Acid Sequence (N to C) | SEQ ID NO: |
|---|---|---|
| CDR3-L R237A | VLWYSN**A**WV | 266 |
| CDR3-L W238A | VLWYSNR**A**V | 267 |
| CDR3-L V239A | VLWYSNRW**A** | 268 |
| CDR3-L F240A | VLWYSNRWV**A** | 269 |

TABLE 6

CD3 binding domain heavy chain complementarity determining regions (CDRs) as based on IMGT CDR numbering system.

| Construct Description | Amino Acid Sequence (N to C) | SEQ ID NO: |
|---|---|---|
| CDR1-H | GFTFNKYA | 78 |
| CDR2-H | IRSKYNNYAT | 79 |
| CDR3-H | VRHGNFGNSYISYWAY | 80 |
| CDR1-H | GFTFQKYA | 270 |
| CDR3-H V99A | ARHGNFGNSYISYWAY | 271 |
| CDR3-H R100A | VAHGNFGNSYISYWAY | 272 |
| CDR3-H H101A | VRAGNFGNSYISYWAY | 273 |
| CDR3-H G102A | VRHANFGNSYISYWAY | 274 |
| CDR3-H N103A | VRHGAFGNSYISYWAY | 275 |
| CDR3-H F104A | VRHGNAGNSYISYWAY | 276 |
| CDR3-H G105A | VRHGNFANSYISYWAY | 277 |
| CDR3-H N106A | VRHGNFGASYISYWAY | 278 |
| CDR3-H S107A | VRHGNFGNAYISYWAY | 279 |
| CDR3-H Y108A | VRHGNFGNSAISYWAY | 280 |
| CDR3-H I109A | VRHGNFGNSYASYWAY | 281 |
| CDR3-H S110A | VRHGNFGNSYIAYWAY | 282 |
| CDR3-H Y111A | VRHGNFGNSYISAWAY | 283 |
| CDR3-H W112A | VRHGNFGNSYISYAAY | 284 |
| CDR3-H Y114A | VRHGNFGNSYISYWAA | 285 |
| CDR3-H I109V | VRHGNFGNSYVSYWAY | 286 |

In some embodiments, CDR3-L of the CD3 binding domain comprises an amino acid sequence selected from SEQ ID NOs: 77, 260-261, 263-266, and 268-269. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO: 76, CDR3-L: SEQ ID NO: 269, and CDR1-H: SEQ ID NO: 78, CDR2-H: SEQ ID NO: 79, CDR3-H: SEQ ID NO: 80. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80.

In some embodiments, CDR3-H of the CD3 binding domain comprises an amino acid sequence selected from SEQ ID NOs: 80, 271-274, 276-282, and 284-285. In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 284; and CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285.

In some embodiments, the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; and CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285.

In some embodiments, the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 75, CDR2-L: SEQ ID NO: 76, CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 262, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 264, and CDR1-H: SEQ ID NO: 78, CDR2-H: SEQ ID NO: 79, CDR3-H: SEQ ID NO: 80;

CDR1-L: SEQ ID NO: 75, CDR2-L: SEQ ID NO: 76, CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 266, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 267, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 268, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 269, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 275; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 283; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 284; CDR1-L: SEQ ID NO: 75, CDR2-L: SEQ ID NO: 76, CDR3-L: SEQ ID NO: 77, and CDR1-H: SEQ ID NO: 78, CDR2-H: SEQ ID NO: 79, CDR3-H: SEQ ID NO: 285; and CDR1-L: SEQ ID NO: 259, CDR2-L: SEQ ID NO: 76, CDR3-L: SEQ ID NO: 260, and CDR1-H: SEQ ID NO: 270, CDR2-H: SEQ ID NO: 79, CDR3-H: SEQ ID NO: 286.

In some embodiments, the immunoglobulin light chain of the CD3 binding domain comprises a variable domain of an immunoglobulin kappa (IgK) or immunoglobulin lambda (IgL) light chain. In some embodiments, the immunoglobulin heavy chain of the CD3 binding domain comprises a variable domain of an IgG1, IgG2, IgG3, or IgG4 heavy chain. In some embodiments, the immunoglobulin light chain of the CD3 binding domain comprises an amino acid sequence with at least 90%, 95%, 96%, 97%, 98%, 99%, or 100% identity to SEQ ID NO: 81. In some embodiments, the immunoglobulin heavy chain of the CD3 binding domain comprises an amino acid sequence with at least 90%, 95%, 96%, 97%, 98%, 99%, or 100% identity to SEQ ID NO: 82. In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82.

In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 303. In some embodiments, the CD3 binding domain comprises an amino acid sequence with at least 90%, 95%, 96%, 97%, 98%, 99%, or 100% identity to SEQ ID NO: 304. In some embodiments, the CD3 binding domain comprises an amino acid sequence with at least 90%, 95%, 96%, 97%, 98%, 99%, or 100% identity to SEQ ID NO: 305. In some embodiments, the CD3 binding domain comprises an amino acid sequence with at least 90%, 95%, 96%, 97%, 98%, 99%, or 100% identity to SEQ ID NO: 306. In some embodiments, the CD3 binding domain comprises an amino acid sequence with at least 90%, 95%, 96%, 97%, 98%, 99%, or 100% identity to SEQ ID NO: 307. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 309. In some embodiments, the CD3 binding domain comprises an amino acid sequence with at least 90%, 95%, 96%, 97%, 98%, 99%, or 100% identity to SEQ ID NO: 310. In some embodiments, the CD3 binding domain comprises an amino acid sequence with at least 90%, 95%, 96%, 97%, 98%, 99%, or 100% identity to SEQ ID NO: 311. In some embodiments, the CD3 binding domain comprises an amino acid sequence with at least 90%, 95%, 96%, 97%, 98%, 99%, or 100% identity to SEQ ID NO: 312. In some embodiments, the CD3 binding domain comprises an amino acid sequence with at least 90%, 95%, 96%, 97%, 98%, 99%, or 100% identity to SEQ ID NO: 313. In some embodiments, the CD3 binding domain comprises an amino acid sequence with at least 90%, 95%, 96%, 97%, 98%, 99%, or 100% identity to SEQ ID NO: 314. In some embodiments, the CD3 binding domain comprises an amino acid sequence with at least 90%, 95%, 96%, 97%, 98%, 99%, or 100% identity to SEQ ID NO: 315. In some embodiments, the CD3 binding domain comprises an amino acid sequence with at least 90%, 95%, 96%, 97%, 98%, 99%, or 100% identity to SEQ ID NO: 316. In some embodiments, the CD3 binding domain comprises an amino acid sequence with at least 90%, 95%, 96%, 97%, 98%, 99%, or 100% identity to SEQ ID NO: 317. In some embodiments, the CD3 binding domain comprises an amino acid sequence with at least 90%, 95%, 96%, 97%, 98%, 99%, or 100% identity to SEQ ID NO: 318. In some embodiments, the CD3 binding domain comprises an amino acid sequence with at least 90%, 95%, 96%, 97%, 98%, 99%, or 100% identity to SEQ ID NO: 319. In some embodiments, the CD3 binding domain comprises an amino acid sequence with at least 90%, 95%, 96%, 97%, 98%, 99%, or 100% identity to SEQ ID NO: 320. In some embodiments, the CD3 binding domain comprises an amino acid sequence with at least 90%, 95%, 96%, 97%, 98%, 99%, or 100% identity to SEQ ID NO: 321. In some embodiments, the CD3 binding domain comprises an amino acid sequence with at least 90%, 95%, 96%, 97%, 98%, 99%, or 100% identity to SEQ ID NO: 322. In some embodiments, the CD3 binding domain comprises an amino acid sequence with at least 90%, 95%, 96%, 97%, 98%, 99%, or 100% identity to SEQ ID NO: 323. In some embodiments, the CD3 binding domain comprises an amino acid sequence with at least 90%, 95%, 96%, 97%, 98%, 99%, or 100% identity to SEQ ID NO: 324. In some embodiments, the CD3 binding domain comprises an amino acid sequence with at least 90%, 95%, 96%, 97%, 98%, 99%, or 100% identity to SEQ ID NO: 325. In some embodiments, the CD3 binding domain comprises an amino acid sequence with at least 90%, 95%, 96%, 97%, 98%, 99%, or 100% identity to SEQ ID NO: 326. In some embodiments, the CD3 binding domain comprises an amino acid sequence with at least 90%, 95%, 96%, 97%, 98%, 99%, or 100% identity to SEQ ID NO: 327. In some embodiments, the CD3 binding domain comprises an amino acid sequence with at least 90%, 95%, 96%, 97%, 98%, 99%, or 100% identity to SEQ ID NO: 328. In some embodiments, the CD3 binding domain comprises an amino acid sequence with at least 90%, 95%, 96%, 97%, 98%, 99%, or 100% identity to SEQ ID NO: 329.

TABLE 7

CD3 binding domain heavy chain and light chain sequences

| Construct Description | Amino Acid Sequence (N to C) | SEQ ID NO: |
|---|---|---|
| CD3 light chain | QTVVTQEPSLTVSPGGTVTLTCGSS**TGAVTSGNY**PNW<br>VQQKPGQAPRGLIG**GTK**FLAPGTPARFSGSLLGGKAA<br>LTLSGVQPEDEAEYYC**VLWYSNRWV**FGGGTKLTVL | 81 |
| CD3 heavy chain | EVQLVESGGGLVQPGGSLKLSCAAS**GFTFNKYA**MNW<br>VRQAPGKGLEWVAR**IRSKYNNYAT**YYADSVKDRFTI<br>SRDDSKNTAYLQMNNLKTEDTAVYYC**VRHGNFGNS**<br>YISYWAYWGQGTLVTVSS | 82 |
| CD3 scFv (SP34.185) wt | EVQLVESGGGLVQPGGSLKLSCAAS**GFTFNKYA**MNW<br>VRQAPGKGLEWVAR**IRSKYNNYAT**YYADSVKDRFTI<br>SRDDSKNTAYLQMNNLKTEDTAVYYC**VRHGNFGNS**<br>**YISYWAY**WGQGTLVTVSSGGGGSGGGGSGGGGSQTV<br>VTQEPSLTVSPGGTVTLTCGSS**TGAVTSGNY**PNWVQQ<br>KPGQAPRGLIG**GTK**FLAPGTPARFSGSLLGGKAALTLS<br>GVQPEDEAEYYC**VLWYSNRWV**FGGGTKLTVL | 99 |
| CD3 scFv V99A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**ARHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 303 |
| CD3 scFv R100A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VAHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 304 |
| CD3 scFv H101A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRAGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 305 |
| CD3 scFv G102A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHANFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 306 |
| CD3 scFv N103A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGAFGNSYI**<br>**SYWAY**WGQGTLVTVSSGGGGSGGGGSGGGGSQTVV | 307 |

TABLE 7-continued

CD3 binding domain heavy chain and light chain sequences

| Construct Description | Amino Acid Sequence (N to C) | SEQ ID NO: |
|---|---|---|
| | TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | |
| CD3 scFv F104A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNAGNSY**<br>**ISYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 308 |
| CD3 scFv G105A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFANSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 309 |
| CD3 scFv N106A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGASYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 310 |
| CD3 scFv S107A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNAY**<br>**ISYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 311 |
| CD3 scFv Y108A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSAI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 312 |
| CD3 scFv I109A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSY**<br>**ASYWAY**WGQGTLVTVSSGGGGSGGGGSGGGGSQTV<br>VTQEPSLTVSPGGTVTLTCGSSTGAVTSGNYPNWVQQ<br>KPGQAPRGLIGGTKFLAPGTPARFSGSLLGGKAALTLS<br>GVQPEDEAEYYC**VLWYSNRWV**FGGGTKLTVL | 313 |
| CD3 scFv S110A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**AYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 314 |
| CD3 scFv Y111A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SAWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 315 |
| CD3 scFv W112A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYAAY**WGQGTLVTVSSGGGGSGGGGSGGGGSQTVVT<br>QEPSLTVSPGGTVTLTCGSSTGAVTSGNYPNWVQQKP<br>GQAPRGLIGGTKFLAPGTPARFSGSLLGGKAALTLSGV<br>QPEDEAEYYC**VLWYSNRWV**FGGGTKLTVL | 316 |

TABLE 7-continued

CD3 binding domain heavy chain and light chain sequences

| Construct Description | Amino Acid Sequence (N to C) | SEQ ID NO: |
|---|---|---|
| CD3 scFv Y114A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAA**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWV**FGGGTKLTVL | 317 |
| CD3 scFv V231A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**ALWYSNRWVF**GGGTKLTVL | 318 |
| CD3 scFv L232A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VAWYSNRWVF**GGGTKLTVL | 319 |
| CD3 scFv W233A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLAYSNRWV**FGGGTKLTVL | 320 |
| CD3 scFv Y234A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWASNRWVF**GGGTKLTVL | 321 |
| CD3 scFv S235A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYANRWVF**GGGTKLTVL | 322 |
| CD3 scFv N236A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSARWVF**GGGTKLTVL | 323 |
| CD3 scFv R237A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNAWV**FGGGTKLTVL | 324 |
| CD3 scFv W238A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYY**CVLWYSNRAVF**GGGTKLTVL | 325 |

TABLE 7-continued

CD3 binding domain heavy chain and light chain sequences

| Construct Description | Amino Acid Sequence (N to C) | SEQ ID NO: |
|---|---|---|
| CD3 scFv V239A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWAF**GGGTKLTVL | 326 |
| CD3 scFv F240A | EVQLVESGGGLVQPGGSLKLSCAASGFTFNKYAMNW<br>VRQAPGKGLEWVARIRSKYNNYATYYADSVKDRFTIS<br>RDDSKNTAYLQMNNLKTEDTAVYYC**VRHGNFGNSYI**<br>**SYWAY**WGQGTLVTVSSGGGGSGGGGSGGGGSQTVV<br>TQEPSLTVSPGGTVTLTCGSSTGAVTSGNYPNWVQQK<br>PGQAPRGLIGGTKFLAPGTPARFSGSLLGGKAALTLSG<br>VQPEDEAEYYC**VLWYSNRWVA**GGGTKLTVL | 327 |
| CD3 scFv P41S, A49G, N87S, L150F, T151S, G163R, P175A, K181T, T200V, A202D, L208I, G211N, L217I, S218T, V220A, P222A, E223D, A226S, E227D | EVQLVESGGGLVQPGGSLKLSCAASGFTFNKYAMNW<br>VRQASGKGLEWVGRIRSKYNNYATYYADSVKDRFTIS<br>RDDSKNTAYLQMNSLKTEDTAVYYCVRHGNFGNSYI<br>SYWAYWGQGTLVTVSSGGGGSGGGGSGGGGSQTVV<br>TQEPSFSVSPGGTVTLTCRSSTGAVTSGNYANWVQQT<br>PGQAPRGLIGGTKFLAPGVPDRFSGSILGNKAALTITGA<br>QADDESDYYCVLWYSNRWVFGGGTKLTVL | 328 |
| CD3 scFv N30Q, I109V, G172A, V231A | EVQLVESGGGLVQPGGSLKLSCAASGFTFQKYAMNW<br>VRQAPGKGLEWVARIRSKYNNYATYYADSVKDRFTIS<br>RDDSKNTAYLQMNNLKTEDTAVYYCVRHGNFGNSY<br>VSYWAYWGQGTLVTVSSGGGGSGGGGSGGGGSQTV<br>VTQEPSLTVSPGGTVTLTCGSSTGAVTSANYPNWVQQ<br>KPGQAPRGLIGGTKFLAPGTPARFSGSLLGGKAALTLS<br>GVQPEDEAEYYCALWYSNRWVFGGGTKLTVL | 329 |

In some embodiments, the CD3 binding domain comprises a Fab, Fab', $(Fab')_2$ or a single chain variable fragment (scFv). In some embodiments, the CD3 binding domain is the scFv. In some embodiments, the N-term of the immunoglobulin heavy chain of the TROP2 binding domain is bound to the C-term of the immunoglobulin light chain of the CD3 binding domain. In some embodiments, the C-term of the immunoglobulin heavy chain of the TROP2 binding domain is bound to the N-term of the immunoglobulin light chain of the CD3 binding domain. In some embodiments, the N-term of the immunoglobulin heavy chain of the TROP2 binding domain is bound to the C-term of the immunoglobulin heavy chain of the CD3 binding domain. In some embodiments, the C-term of the immunoglobulin heavy chain of the TROP2 binding domain is bound to the N-term of the immunoglobulin heavy chain of the CD3 binding domain. In some embodiments, the N-term of the immunoglobulin light chain of the TROP2 binding domain is bound to the C-term of the immunoglobulin light chain of the CD3 binding domain. In some embodiments, the C-term of the immunoglobulin light chain of the TROP2 binding domain is bound to the N-term of the immunoglobulin light chain of the CD3 binding domain. In some embodiments, the N-term of the immunoglobulin light chain of the TROP2 binding domain is bound to the C-term of the immunoglobulin heavy chain of the CD3 binding domain. In some embodiments, the C-term of the immunoglobulin light chain of the TROP2 binding domain is bound to the N-term of the immunoglobulin heavy chain of the CD3 binding domain. In some embodiments, the CD3 binding domain is a scFv and the TROP2 binding domain is a Fab or Fab'. In some embodiments, the scFv is bound to the immunoglobulin heavy chain of the Fab or Fab'. In some embodiments, the scFv is bound to the immunoglobulin light chain of the Fab or Fab'. In some embodiments, the immunoglobulin light chain of the scFv is bound to the immunoglobulin heavy chain of the Fab or Fab'. In some embodiments, the immunoglobulin light chain of the scFv is bound to the immunoglobulin light chain of the Fab or Fab'. In some embodiments, the immunoglobulin heavy chain of the scFv is bound to the immunoglobulin heavy chain of the Fab or Fab'. In some embodiments, the immunoglobulin heavy chain of the scFv is bound to the immunoglobulin light chain of the Fab or Fab'.

T Cell Engager (TCE) Compositions

In some embodiments, the recombinant antibody or antigen binding fragment thereof comprises amino acid sequences with at least 90%, 95%, 96%, 97%, 98%, 99%, or 100% identity to SEQ ID NO: 87 and SEQ ID NO: 88. In some embodiments, the recombinant antibody or antigen binding fragment thereof comprises amino acid sequences with at least 90%, 95%, 96%, 97%, 98%, 99%, or 100% identity to SEQ ID NO: 89 and SEQ ID NO: 90. In some embodiments, the recombinant antibody or antigen binding fragment thereof comprises amino acid sequences with at least 90%, 95%, 96%, 97%, 98%, 99%, or 100% identity to SEQ ID NO: 91 and SEQ ID NO: 92. In some embodiments, the recombinant antibody or antigen binding fragment thereof comprises amino acid sequences with at least 90%, 95%, 96%, 97%, 98%, 99%, or 100% identity to SEQ ID NO: 93 and SEQ ID NO: 94. In some embodiments, the recombinant antibody or antigen binding fragment thereof comprises amino acid sequences with at least 90%, 95%, 96%, 97%, 98%, 99%, or 100% identity to SEQ ID NO: 95 and SEQ ID NO: 96. In some embodiments, the recombinant antibody or antigen binding fragment thereof comprises amino acid sequences with at least 90%, 95%, 96%, 97%, 98%, 99%, or 100% identity to SEQ ID NO: 97 and SEQ ID NO: 98.

In some embodiments, the recombinant antibody or antigen binding fragment thereof comprises amino acid sequences with at least 90%, 95%, 96%, 97%, 98%, 99%, or 100% identity to SEQ ID NO: 330 and SEQ ID NO: 331. In some embodiments, the recombinant antibody or antigen binding fragment thereof comprises amino acid sequences with at least 90%, 95%, 96%, 97%, 98%, 99%, or 100% identity to SEQ ID NO: 332 and SEQ ID NO: 333. In some embodiments, the recombinant antibody or antigen binding fragment thereof comprises amino acid sequences with at least 90%, 95%, 96%, 97%, 98%, 99%, or 100% identity to SEQ ID NO: 332 and SEQ ID NO: 333. In some embodiments, the recombinant antibody or antigen binding fragment thereof comprises amino acid sequences with at least 90%, 95%, 96%, 97%, 98%, 99%, or 100% identity to SEQ ID NO: 334 and SEQ ID NO: 335. In some embodiments, the recombinant antibody or antigen binding fragment thereof comprises amino acid sequences with at least 90%, 95%, 96%, 97%, 98%, 99%, or 100% identity to SEQ ID NO: 336 and SEQ ID NO: 337. In some embodiments, the recombinant antibody or antigen binding fragment thereof comprises amino acid sequences with at least 90%, 95%, 96%, 97%, 98%, 99%, or 100% identity to SEQ ID NO: 338 and SEQ ID NO: 339. In some embodiments, the recombinant antibody or antigen binding fragment thereof comprises amino acid sequences with at least 90%, 95%, 96%, 97%, 98%, 99%, or 100% identity to SEQ ID NO: 340 and SEQ ID NO: 341. In some embodiments, the recombinant antibody or antigen binding fragment thereof comprises amino acid sequences with at least 90%, 95%, 96%, 97%, 98%, 99%, or 100% identity to SEQ ID NO: 342 and SEQ ID NO: 343. In some embodiments, the recombinant antibody or antigen binding fragment thereof comprises amino acid sequences with at least 90%, 95%, 96%, 97%, 98%, 99%, or 100% identity to SEQ ID NO: 344 and SEQ ID NO: 345. In some embodiments, the recombinant antibody or antigen binding fragment thereof comprises amino acid sequences with at least 90%, 95%, 96%, 97%, 98%, 99%, or 100% identity to SEQ ID NO: 346 and SEQ ID NO: 347. In some embodiments, the recombinant antibody or antigen binding fragment thereof comprises amino acid sequences with at least 90%, 95%, 96%, 97%, 98%, 99%, or 100% identity to SEQ ID NO: 348 and SEQ ID NO: 349. In some embodiments, the recombinant antibody or antigen binding fragment thereof comprises amino acid sequences with at least 90%, 95%, 96%, 97%, 98%, 99%, or 100% identity to SEQ ID NO: 350 and SEQ ID NO: 351.

TABLE 8

TROP2-T cell engager (TCE) sequences

| Construct Description | Amino Acid Sequence (N to C) | SEQ ID NO: |
|---|---|---|
| TCE-1 LC | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 83 |
| TCE-1 HC | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 84 |
| TCE-2 LC | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSDI<br>QLTQSPSSLSASVGDRVSITCKASQDVSIA<br>VAWYQQKPGKAPKLLIYSASYRYTGVPD<br>RFSGSGSGTDFTLTISSLQPEDFAVYYCQQ<br>HYITPLTFGAGTKVEIKRTVAAPSVFIFPPS<br>DEQLKSGTASVVCLLNNFYPREAKVQWK | 85 |

TABLE 8-continued

TROP2-T cell engager (TCE) sequences

| Construct Description | Amino Acid Sequence (N to C) | SEQ ID NO: |
|---|---|---|
| | VDNALQSGNSQESVTEQDSKDSTYSLSSTL<br>TLSKADYEKHKVYACEVTHQGLSSPVTKS<br>FNRGEC | |
| TCE-2 HC | QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 86 |
| TCE-3 LC<br>anti-TROP2 R98A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSDI<br>QLTQSPSSLSASVGDRVSITCKASQDVSIA<br>VAWYQQKPGKAPKLLIYSASYRYTGVPD<br>RFSGSGSGTDFTLTISSLQPEDFAVYYCQQ<br>HYITPLTFGAGTKVEIKRTVAAPSVFIFPPS<br>DEQLKSGTASVVCLLNNFYPREAKVQWK<br>VDNALQSGNSQESVTEQDSKDSTYSLSSTL<br>TLSKADYEKHKVYACEVTHQGLSSPVTKS<br>FNRGEC | 87 |
| TCE-3 HC<br>anti-TROP2 R98A | QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFC**AAGGFGSSYWYFDV**WG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 88 |
| TCE-4 LC<br>anti-TROP2 F108A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSDI<br>QLTQSPSSLSASVGDRVSITCKASQDVSIA<br>VAWYQQKPGKAPKLLIYSASYRYTGVPD<br>RFSGSGSGTDFTLTISSLQPEDFAVYYCQQ<br>HYITPLTFGAGTKVEIKRTVAAPSVFIFPPS<br>DEQLKSGTASVVCLLNNFYPREAKVQWK<br>VDNALQSGNSQESVTEQDSKDSTYSLSSTL<br>TLSKADYEKHKVYACEVTHQGLSSPVTKS<br>FNRGEC | 89 |
| TCE-4 HC<br>anti-TROP2 F108A | QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFC**ARGGFGSSYWYADV**WG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 90 |
| TCE-5 LC<br>anti-TROP2 D109A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSDI | 91 |

TABLE 8-continued

| TROP2-T cell engager (TCE) sequences | | |
|---|---|---|
| Construct Description | Amino Acid Sequence (N to C) | SEQ ID NO: |
| | QLTQSPSSLSASVGDRVSITCKASQDVSIA<br>VAWYQQKPGKAPKLLIYSASYRYTGVPD<br>RFSGSGSGTDFTLTISSLQPEDFAVYYCQQ<br>HYITPLTFGAGTKVEIKRTVAAPSVFIFPPS<br>DEQLKSGTASVVCLLNNFYPREAKVQWK<br>VDNALQSGNSQESVTEQDSKDSTYSLSSTL<br>TLSKADYEKHKVYACEVTHQGLSSPVTKS<br>FNRGEC | |
| TCE-5 HC<br>anti-TROP2 D109A | QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFC**ARGGFGSSYWYFAV**WG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 92 |
| TCE-6 LC<br>anti-TROP2 R98A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 93 |
| TCE-6 HC<br>anti-TROP2 R98A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFC**AAGGFGSSYWYFDV**WGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 94 |
| TCE-7 LC<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 95 |
| TCE-7 HC<br>anti-TROP2 F108A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFC**ARGGFGSSYWYADV**WGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 96 |
| TCE-8 LC<br>anti-TROP2 D109A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP | 97 |

TABLE 8-continued

| TROP2-T cell engager (TCE) sequences | | |
|---|---|---|
| Construct Description | Amino Acid Sequence (N to C) | SEQ ID NO: |
| | SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | |
| TCE-8 HC<br>anti-TROP2 D109A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YCVLWYSNRWVFGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFC**ARGGFGSSYWYFAV**WGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 98 |
| TCE-9 LC<br>anti-CD3 scFv V99A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 400 |
| TCE-9 HC<br>anti-CD3 scFv V99A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**ARHGNFGNSYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 401 |
| TCE-10 LC<br>anti-CD3 scFv R100A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 402 |
| TCE-10 HC<br>anti-CD3 scFv R100A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VAHGNFGNSYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 403 |

TABLE 8-continued

TROP2-T cell engager (TCE) sequences

| Construct Description | Amino Acid Sequence (N to C) | SEQ ID NO: |
|---|---|---|
| TCE-11 LC anti-CD3 scFv H101A anti-TROP2 wt | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 404 |
| TCE-11 HC anti-CD3 scFv H101A anti-TROP2 wt | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYC**VRAGNFGNSYISYWAY**WGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGSQVQLQQSGSELKKPGASVKVSCKASGYTFTNYGMNWVKQAPGQGLKWMGWINTYTGEPTYTDDFKGRFAFSLDTSVSTAYLQISSLKADDTAVYFCARGGFGSSYWYFDVWGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 405 |
| TCE-12 LC anti-CD3 scFv G102A anti-TROP2 wt | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 406 |
| TCE-12 HC anti-CD3 scFv G102A anti-TROP2 wt | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYC**VRHANFGNSYISYWAY**WGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGSQVQLQQSGSELKKPGASVKVSCKASGYTFTNYGMNWVKQAPGQGLKWMGWINTYTGEPTYTDDFKGRFAFSLDTSVSTAYLQISSLKADDTAVYFCARGGFGSSYWYFDVWGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 407 |
| TCE-13 LC anti-CD3 scFv N103A anti-TROP2 wt | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 408 |
| TCE-13 HC anti-CD3 scFv N103A anti-TROP2 wt | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYC**VRHGAFGNSYISYWAY**WGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGSQVQLQQSGSELKKPGASVKVSCKASGYTFTNYGMNWVKQAPGQGLKWMGWINTYTGEPTYTDDFKGRFAFSLDTSVSTAYLQISS | 409 |

TABLE 8-continued

| TROP2-T cell engager (TCE) sequences | | |
|---|---|---|
| Construct Description | Amino Acid Sequence (N to C) | SEQ ID NO: |
| | LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | |
| TCE-14 LC<br>anti-CD3 scFv F104A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 410 |
| TCE-14 HC<br>anti-CD3 scFv F104A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNAGNSYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 411 |
| TCE-15 LC<br>anti-CD3 scFv G105A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 412 |
| TCE-15 HC<br>anti-CD3 scFv G105A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFANSYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 413 |
| TCE-16 LC<br>anti-CD3 scFv N106A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 414 |
| TCE-16 HC<br>anti-CD3 scFv N106A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFGASYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA | 415 |

TABLE 8-continued

TROP2-T cell engager (TCE) sequences

| Construct Description | Amino Acid Sequence (N to C) | SEQ ID NO: |
|---|---|---|
| | PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | |
| TCE-17 LC<br>anti-CD3 scFv S107A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 416 |
| TCE-17 HC<br>anti-CD3 scFv S107A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFGNAYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 417 |
| TCE-18 LC<br>anti-CD3 scFv Y108A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 418 |
| TCE-18 HC<br>anti-CD3 scFv Y108A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFGNSAISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 419 |
| TCE-19 LC<br>anti-CD3 scFv I109A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 420 |

TABLE 8-continued

TROP2-T cell engager (TCE) sequences

| Construct Description | Amino Acid Sequence (N to C) | SEQ ID NO: |
|---|---|---|
| TCE-19 HC<br>anti-CD3 scFv I109A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFGNSYASY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 421 |
| TCE-20 LC<br>anti-CD3 scFv S110A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 422 |
| TCE-20 HC<br>anti-CD3 scFv S110A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRHGNFGNSYIAY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 423 |
| TCE-21 LC<br>anti-CD3 scFv Y111A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 424 |
| TCE-21 HC<br>anti-CD3 scFv Y111A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCV**RHGNFGNSYISA**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 425 |
| TCE-22 LC<br>anti-CD3 scFv W112A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP | 426 |

TABLE 8-continued

TROP2-T cell engager (TCE) sequences

| Construct Description | Amino Acid Sequence (N to C) | SEQ ID NO: |
|---|---|---|
| | SDEQLKSGTASVVCLLNNFYPREAKVQW KVDNALQSGNSQESVTEQDSKDSTYSLSS TLTLSKADYEKHKVYACEVTHQGLSSPVT KSFNRGEC | |
| TCE-22 HC anti-CD3 scFv W112A anti-TROP2 wt | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYC**VRHGNFGNSYISYA AY**WGQGTLVTVSSGGGGSGGGGSGGGGS QTVVTQEPSLTVSPGGTVTLTCGSSTGAVT SGNYPNWVQQKPGQAPRGLIGGTKFLAPG TPARFSGSLLGGKAALTLSGVQPEDEAEY YCVLWYSNRWVFGGGTKLTVLGGGGSQ VQLQQSGSELKKPGASVKVSCKASGYTFT NYGMNWVKQAPGQGLKWMGWINTYTG EPTYTDDFKGRFAFSLDTSVSTAYLQISSL KADDTAVYFCARGGFGSSYWYFDVWGQ GSLVTVSSASTKGPSVFPLAPSSKSTSGGT AALGCLVKDYFPEPVTVSWNSGALTSGVH TFPAVLQSSGLYSLSSVVTVPSSSLGTQTYI CNVNHKPSNTKVDKKVEPKSC | 427 |
| TCE-23 LC anti-CD3 scFv Y114A anti-TROP2 wt | DIQLTQSPSSLSASVGDRVSITCKASQDVSI AVAWYQQKPGKAPKLLIYSASYRYTGVP DRFSGSGSGTDFTLTISSLQPEDFAVYYCQ QHYITPLTFGAGTKVEIKRTVAAPSVFIFPP SDEQLKSGTASVVCLLNNFYPREAKVQW KVDNALQSGNSQESVTEQDSKDSTYSLSS TLTLSKADYEKHKVYACEVTHQGLSSPVT KSFNRGEC | 428 |
| TCE-23 HC anti-CD3 scFv Y114A anti-TROP2 wt | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYC**VRHGNFGNSYISY WAA**WGQGTLVTVSSGGGGSGGGGSGGG GSQTVVTQEPSLTVSPGGTVTLTCGSSTGA VTSGNYPNWVQQKPGQAPRGLIGGTKFLA PGTPARFSGSLLGGKAALTLSGVQPEDEAE YYCVLWYSNRWVFGGGTKLTVLGGGGS QVQLQQSGSELKKPGASVKVSCKASGYTF TNYGMNWVKQAPGQGLKWMGWINTYT GEPTYTDDFKGRFAFSLDTSVSTAYLQISS LKADDTAVYFCARGGFGSSYWYFDVWG QGSLVTVSSASTKGPSVFPLAPSSKSTSGG TAALGCLVKDYFPEPVTVSWNSGALTSGV HTFPAVLQSSGLYSLSSVVTVPSSSLGTQT YICNVNHKPSNTKVDKKVEPKSC | 429 |
| TCE-24 LC anti-CD3 scFv V231A anti-TROP2 wt | DIQLTQSPSSLSASVGDRVSITCKASQDVSI AVAWYQQKPGKAPKLLIYSASYRYTGVP DRFSGSGSGTDFTLTISSLQPEDFAVYYCQ QHYITPLTFGAGTKVEIKRTVAAPSVFIFPP SDEQLKSGTASVVCLLNNFYPREAKVQW KVDNALQSGNSQESVTEQDSKDSTYSLSS TLTLSKADYEKHKVYACEVTHQGLSSPVT KSFNRGEC | 430 |
| TCE-24 HC anti-CD3 scFv V231A anti-TROP2 wt | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYCVRHGNFGNSYISYW AYWGQGTLVTVSSGGGGSGGGGSGGGGS QTVVTQEPSLTVSPGGTVTLTCGSSTGAVT SGNYPNWVQQKPGQAPRGLIGGTKFLAPG TPARFSGSLLGGKAALTLSGVQPEDEAEY YC**ALWYSNRWV**FGGGTKLTVLGGGGSQ VQLQQSGSELKKPGASVKVSCKASGYTFT NYGMNWVKQAPGQGLKWMGWINTYTG EPTYTDDFKGRFAFSLDTSVSTAYLQISSL KADDTAVYFCARGGFGSSYWYFDVWGQ GSLVTVSSASTKGPSVFPLAPSSKSTSGGT AALGCLVKDYFPEPVTVSWNSGALTSGVH TFPAVLQSSGLYSLSSVVTVPSSSLGTQTYI CNVNHKPSNTKVDKKVEPKSC | 431 |

TABLE 8-continued

TROP2-T cell engager (TCE) sequences

| Construct Description | Amino Acid Sequence (N to C) | SEQ ID NO: |
|---|---|---|
| TCE-25 LC<br>anti-CD3 scFv L232A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 432 |
| TCE-25 HC<br>anti-CD3 scFv L232A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VAWYSNRWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 433 |
| TCE-26 LC<br>anti-CD3 scFv W233A<br>anti-TROP2 HC wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 434 |
| TCE-26 HC<br>anti-CD3 scFv W233A<br>anti-TROP2 HC wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLAYSNRWV**FGGGTKLTVLGGGGSQV<br>QLQQSGSELKKPGASVKVSCKASGYTFTN<br>YGMNWVKQAPGQGLKWMGWINTYTGEP<br>TYTDDFKGRFAFSLDTSVSTAYLQISSLKA<br>DDTAVYFCARGGFGSSYWYFDVWGQGSL<br>VTVSSASTKGPSVFPLAPSSKSTSGGTAAL<br>GCLVKDYFPEPVTVSWNSGALTSGVHTFP<br>AVLQSSGLYSLSSVVTVPSSSLGTQTYICN<br>VNHKPSNTKVDKKVEPKSC | 435 |
| TCE-27 LC<br>anti-CD3 scFv Y234A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 436 |
| TCE-27 HC<br>anti-CD3 scFv Y234A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWASNRWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL | 437 |

TABLE 8-continued

TROP2-T cell engager (TCE) sequences

| Construct Description | Amino Acid Sequence (N to C) | SEQ ID NO: |
|---|---|---|
| | KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | |
| TCE-28 LC<br>anti-CD3 scFv S235A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 438 |
| TCE-28 HC<br>anti-CD3 scFv S235A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYANRWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 439 |
| TCE-29 LC<br>anti-CD3 scFv N236A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 440 |
| TCE-29 HC<br>anti-CD3 scFv N236A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYSARWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 441 |
| TCE-30 LC<br>anti-CD3 scFv R237A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 442 |
| TCE-30 HC<br>anti-CD3 scFv R237A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG | 443 |

TABLE 8-continued

| TROP2-T cell engager (TCE) sequences | | |
|---|---|---|
| Construct Description | Amino Acid Sequence (N to C) | SEQ ID NO: |
| | TPARFSGSLLGGKAALTLSGVQPEDEAEY<br>YC**VLWYSNAWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | |
| TCE-31 LC<br>anti-CD3 scFv W238A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 444 |
| TCE-31 HC<br>anti-CD3 scFv W238A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYSNRAV**FGGGTKLTVLGGGGSQV<br>QLQQSGSELKKPGASVKVSCKASGYTFTN<br>YGMNWVKQAPGQGLKWMGWINTYTGEP<br>TYTDDFKGRFAFSLDTSVSTAYLQISSLKA<br>DDTAVYFCARGGFGSSYWYFDVWGQGSL<br>VTVSSASTKGPSVFPLAPSSKSTSGGTAAL<br>GCLVKDYFPEPVTVSWNSGALTSGVHTFP<br>AVLQSSGLYSLSSVVTVPSSSLGTQTYICN<br>VNHKPSNTKVDKKVEPKSC | 445 |
| TCE-32 LC<br>anti-CD3 scFv V239A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 446 |
| TCE-32 HC<br>anti-CD3 scFv V239A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYSNRWA**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 447 |
| TCE-33 LC<br>anti-CD3 scFv F240A<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 448 |

TABLE 8-continued

TROP2-T cell engager (TCE) sequences

| Construct Description | Amino Acid Sequence (N to C) | SEQ ID NO: |
|---|---|---|
| TCE-33 HC<br>anti-CD3 scFv F240A<br>anti-TROP2 wt | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYSNRWVA**GGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFCARGGFGSSYWYFDVWGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 449 |
| TCE-34 LC<br>anti-CD3 scFv (P41S, A49G,<br>N87S, L150F, T151S, G163R,<br>P175A, K181T, T200V, A202D,<br>L208I, G211N, L217I, S218T,<br>V220A, P222A, E223D, A226S,<br>E227D)<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 450 |
| TCE-34 HC<br>anti-CD3 scFv (P41S, A49G,<br>N87S, L150F, T151S, G163R,<br>P175A, K181T, T200V, A202D,<br>L2081, G211N, L217I, S218T,<br>V220A, P222A, E223D, A226S,<br>E227D)<br>anti-TROP2 wt | EVQLVESGGGLVQPGGSLKLSCAASGFTF<br>NKYAMNWVRQASGKGLEWVGRIRSKYN<br>NYATYYADSVKDRFTISRDDSKNTAYLQ<br>MNSLKTEDTAVYYCVRHGNFGNSYISYW<br>AYWGQGTLVTVSSGGGGSGGGGSGGGGS<br>QTVVTQEPSFSVSPGGTVTLTCRSSTGAVT<br>SGNYANWVQQTPGQAPRGLIGGTKFLAPG<br>VPDRFSGSILGNKAALTITGAQADDESDYY<br>CVLWYSNRWVFGGGTKLTVLGGGGSQV<br>QLQQSGSELKKPGASVKVSCKASGYTFTN<br>YGMNWVKQAPGQGLKWMGWINTYTGEP<br>TYTDDFKGRFAFSLDTSVSTAYLQISSLKA<br>DDTAVYFCARGGFGSSYWYFDVWGQGSL<br>VTVSSASTKGPSVFPLAPSSKSTSGGTAAL<br>GCLVKDYFPEPVTVSWNSGALTSGVHTFP<br>AVLQSSGLYSLSSVVTVPSSSLGTQTYICN<br>VNHKPSNTKVDKKVEPKSC | 451 |
| TCE-35 LC<br>anti-CD3 scFv (N30Q, I109V,<br>G172A, V231A)<br>anti-TROP2 wt | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 452 |
| TCE-35 HC<br>anti-CD3 scFv (N30Q, I109V,<br>G172A, V231A)<br>anti-TROP2 wt | EVQLVESGGGLVQPGGSLKLSCAASGFTF<br>QKYAMNWVRQAPGKGLEWVARIRSKYN<br>NYATYYADSVKDRFTISRDDSKNTAYLQ<br>MNNLKTEDTAVYYCVRHGNFGNSYVSY<br>WAYWGQGTLVTVSSGGGGSGGGGSGGG<br>GSQTVVTQEPSLTVSPGGTVTLTCGSSTGA<br>VTSANYPNWVQQKPGQAPRGLIGGTKFLA<br>PGTPARFSGSLLGGKAALTLSGVQPEDEAE<br>YYCALWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFCARGGFGSSYWYFDVWG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 453 |
| TCE-36 LC<br>anti-CD3 scFv H101A<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP | 330 |

TABLE 8-continued

| TROP2-T cell engager (TCE) sequences | | |
|---|---|---|
| Construct Description | Amino Acid Sequence (N to C) | SEQ ID NO: |
| | SDEQLKSGTASVVCLLNNFYPREAKVQW KVDNALQSGNSQESVTEQDSKDSTYSLSS TLTLSKADYEKHKVYACEVTHQGLSSPVT KSFNRGEC | |
| TCE-36 HC anti-CD3 scFv H101A anti-TROP2 F108A | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYC**VRAGNFGNSYISY WAY**WGQGTLVTVSSGGGGSGGGGSGGG GSQTVVTQEPSLTVSPGGTVTLTCGSSTGA VTSGNYPNWVQQKPGQAPRGLIGGTKFLA PGTPARFSGSLLGGKAALTLSGVQPEDEAE YYCVLWYSNRWVFGGGTKLTVLGGGGS QVQLQQSGSELKKPGASVKVSCKASGYTF TNYGMNWVKQAPGQGLKWMGWINTYT GEPTYTDDFKGRFAFSLDTSVSTAYLQISS LKADDTAVYFC**ARGGFGSSYWYADV**WG QGSLVTVSSASTKGPSVFPLAPSSKSTSGG TAALGCLVKDYFPEPVTVSWNSGALTSGV HTFPAVLQSSGLYSLSSVVTVPSSSLGTQT YICNVNHKPSNTKVDKKVEPKSC | 331 |
| TCE-37 LC anti-CD3 scFv F104A anti-TROP2 F108A | DIQLTQSPSSLSASVGDRVSITCKASQDVSI AVAWYQQKPGKAPKLLIYSASYRYTGVP DRFSGSGSGTDFTLTISSLQPEDFAVYYCQ QHYITPLTFGAGTKVEIKRTVAAPSVFIFPP SDEQLKSGTASVVCLLNNFYPREAKVQW KVDNALQSGNSQESVTEQDSKDSTYSLSS TLTLSKADYEKHKVYACEVTHQGLSSPVT KSFNRGEC | 332 |
| TCE-37 HC anti-CD3 scFv F104A anti-TROP2 F108A | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYC**VRHGNAGNSYISY WAY**WGQGTLVTVSSGGGGSGGGGSGGG GSQTVVTQEPSLTVSPGGTVTLTCGSSTGA VTSGNYPNWVQQKPGQAPRGLIGGTKFLA PGTPARFSGSLLGGKAALTLSGVQPEDEAE YYCVLWYSNRWVFGGGTKLTVLGGGGS QVQLQQSGSELKKPGASVKVSCKASGYTF TNYGMNWVKQAPGQGLKWMGWINTYT GEPTYTDDFKGRFAFSLDTSVSTAYLQISS LKADDTAVYFC**ARGGFGSSYWYADV**WG QGSLVTVSSASTKGPSVFPLAPSSKSTSGG TAALGCLVKDYFPEPVTVSWNSGALTSGV HTFPAVLQSSGLYSLSSVVTVPSSSLGTQT YICNVNHKPSNTKVDKKVEPKSC | 333 |
| TCE-38 LC anti-CD3 scFv F240A anti-TROP2 F108A | DIQLTQSPSSLSASVGDRVSITCKASQDVSI AVAWYQQKPGKAPKLLIYSASYRYTGVP DRFSGSGSGTDFTLTISSLQPEDFAVYYCQ QHYITPLTFGAGTKVEIKRTVAAPSVFIFPP SDEQLKSGTASVVCLLNNFYPREAKVQW KVDNALQSGNSQESVTEQDSKDSTYSLSS TLTLSKADYEKHKVYACEVTHQGLSSPVT KSFNRGEC | 334 |
| TCE-38 HC anti-CD3 scFv F240A anti-TROP2 F108A | EVQLVESGGGLVQPGGSLKLSCAASGFTF NKYAMNWVRQAPGKGLEWVARIRSKYN NYATYYADSVKDRFTISRDDSKNTAYLQ MNNLKTEDTAVYYCVRHGNFGNSYISYW AYWGQGTLVTVSSGGGGSGGGGSGGGGS QTVVTQEPSLTVSPGGTVTLTCGSSTGAVT SGNYPNWVQQKPGQAPRGLIGGTKFLAPG TPARFSGSLLGGKAALTLSGVQPEDEAEY YC**VLWYSNRWVA**GGGTKLTVLGGGGSQ VQLQQSGSELKKPGASVKVSCKASGYTFT NYGMNWVKQAPGQGLKWMGWINTYTG EPTYTDDFKGRFAFSLDTSVSTAYLQISSL KADDTAVYFC**ARGGFGSSYWYADV**WGQ GSLVTVSSASTKGPSVFPLAPSSKSTSGGT AALGCLVKDYFPEPVTVSWNSGALTSGVH TFPAVLQSSGLYSLSSVVTVPSSSLGTQTYI CNVNHKPSNTKVDKKVEPKSC | 335 |

TABLE 8-continued

| TROP2-T cell engager (TCE) sequences | | |
|---|---|---|
| Construct Description | Amino Acid Sequence (N to C) | SEQ ID NO: |
| TCE-39 LC<br>anti-CD3 scFv (P41S, A49G, N87S, L150F, T151S, G163R, P175A, K181T, T200V, A202D, L2081, G211N, L217I, S218T, V220A, P222A, E223D, A226S, E227D)<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 336 |
| TCE-39 HC<br>anti-CD3 scFv (P41S, A49G, N87S, L150F, T151S, G163R, P175A, K181T, T200V, A202D, L208I, G211N, L217I, S218T, V220A, P222A, E223D, A226S, E227D)<br>anti-TROP2 F108A | EVQLVESGGGLVQPGGSLKLSCAASGFTF<br>NKYAMNWVRQASGKGLEWVGRIRSKYN<br>NYATYYADSVKDRFTISRDDSKNTAYLQ<br>MNSLKTEDTAVYYCVRHGNFGNSYISYW<br>AYWGQGTLVTVSSGGGGSGGGGSGGGGS<br>QTVVTQEPSFSVSPGGTVTLTCRSSTGAVT<br>SGNYANWVQQTPGQAPRGLIGGTKFLAPG<br>VPDRFSGSILGNKAALTITGAQADDESDYY<br>CVLWYSNRWVFGGGTKLTVLGGGGSQV<br>QLQQSGSELKKPGASVKVSCKASGYTFTN<br>YGMNWVKQAPGQGLKWMGWINTYTGEP<br>TYTDDFKGRFAFSLDTSVSTAYLQISSLKA<br>DDTAVYFC**ARGGFGSSYWYADV**WGQGS<br>LVTVSSASTKGPSVFPLAPSSKSTSGGTAA<br>LGCLVKDYFPEPVTVSWNSGALTSGVHTF<br>PAVLQSSGLYSLSSVVTVPSSSLGTQTYIC<br>NVNHKPSNTKVDKKVEPKSC | 337 |
| TCE-40 LC<br>anti-CD3 scFv (N30Q, I109V, G172A, V231A)<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 338 |
| TCE-40 HC<br>anti-CD3 scFv (N30Q, I109V, G172A, V231A)<br>anti-TROP2 F108A | EVQLVESGGGLVQPGGSLKLSCAASGFTF<br>QKYAMNWVRQAPGKGLEWVARIRSKYN<br>NYATYYADSVKDRFTISRDDSKNTAYLQ<br>MNNLKTEDTAVYYCVRHGNFGNSYVSY<br>WAYWGQGTLVTVSSGGGGSGGGGSGGG<br>GSQTVVTQEPSLTVSPGGTVTLTCGSSTGA<br>VTSANYPNWVQQKPGQAPRGLIGGTKFLA<br>PGTPARFSGSLLGGKAALTLSGVQPEDEAE<br>YYCALWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFC**ARGGFGSSYWYADV**WG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | 339 |
| TCE-41 LC<br>anti-CD3 scFv H101A<br>anti-TROP2 D109A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 340 |
| TCE-41 HC<br>anti-CD3 scFv H101A<br>anti-TROP2 D109A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYC**VRAGNFGNSYISY**<br>**WAY**WGQGTLVTVSSGGGGSGGGGSGGG<br>GSQTVVTQEPSLTVSPGGTVTLTCGSSTGA<br>VTSGNYPNWVQQKPGQAPRGLIGGTKFLA<br>PGTPARFSGSLLGGKAALTLSGVQPEDEAE<br>YYCVLWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS | 341 |

TABLE 8-continued

| TROP2-T cell engager (TCE) sequences | | |
|---|---|---|
| Construct Description | Amino Acid Sequence (N to C) | SEQ ID NO: |
| | LKADDTAVYFC**ARGGFGSSYWYFAV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | |
| TCE-42 LC<br>anti-CD3 scFv F104A<br>anti-TROP2 D109A | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 342 |
| TCE-42 HC<br>anti-CD3 scFv F104A<br>anti-TROP2 D109A | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYC**VRHGNAGNSYISYWAY**WGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGSQVQLQQSGSELKKPGASVKVSCKASGYTFTNYGMNWVKQAPGQGLKWMGWINTYTGEPTYTDDFKGRFAFSLDTSVSTAYLQISSLKADDTAVYFC**ARGGFGSSYWYFAV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 343 |
| TCE-43 LC<br>anti-CD3 scFv F240A<br>anti-TROP2 D109A | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 344 |
| TCE-43 HC<br>anti-CD3 scFv F240A<br>anti-TROP2 D109A | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYC**VLWYSNRWVA**GGGTKLTVLGGGGSQVQLQQSGSELKKPGASVKVSCKASGYTFTNYGMNWVKQAPGQGLKWMGWINTYTGEPTYTDDFKGRFAFSLDTSVSTAYLQISSLKADDTAVYFC**ARGGFGSSYWYFAV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 345 |
| TCE-44 LC<br>anti-CD3 scFv (N30Q, I109V, G172A, V231A)<br>anti-TROP2 D109A | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 346 |
| TCE-44 HC<br>anti-CD3 scFv (N30Q, I109V, G172A, V231A)<br>anti-TROP2 D109A | EVQLVESGGGLVQPGGSLKLSCAASGFTFQKYAMNWVRQAPGKGLEWVARIRSKYNNYATYYADSVKDRFTISRDDSKNTAYLQMNNLKTEDTAVYYCVRHGNFGNSYVSYWAYWGQGTLVTVSSGGGGSGGGGSGGGGSQTVVTQEPSLTVSPGGTVTLTCGSSTGAVTSANYPNWVQQKPGQAPRGLIGGTKFLA | 347 |

TABLE 8-continued

| TROP2-T cell engager (TCE) sequences | | |
|---|---|---|
| Construct Description | Amino Acid Sequence (N to C) | SEQ ID NO: |
| | PGTPARFSGSLLGGKAALTLSGVQPEDEAE<br>YYCALWYSNRWVFGGGTKLTVLGGGGS<br>QVQLQQSGSELKKPGASVKVSCKASGYTF<br>TNYGMNWVKQAPGQGLKWMGWINTYT<br>GEPTYTDDFKGRFAFSLDTSVSTAYLQISS<br>LKADDTAVYFC**ARGGFGSSYWYFAV**WG<br>QGSLVTVSSASTKGPSVFPLAPSSKSTSGG<br>TAALGCLVKDYFPEPVTVSWNSGALTSGV<br>HTFPAVLQSSGLYSLSSVVTVPSSSLGTQT<br>YICNVNHKPSNTKVDKKVEPKSC | |
| TCE-48 LC<br>anti-CD3 scFv L232A<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 348 |
| TCE-48 HC<br>anti-CD3 scFv L232A<br>anti-TROP2 F108A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VAWYSNRWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFC**ARGGFGSSYWYADV**WGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 349 |
| TCE-49 LC<br>anti-CD3 scFv N236A<br>anti-TROP2 F108A | DIQLTQSPSSLSASVGDRVSITCKASQDVSI<br>AVAWYQQKPGKAPKLLIYSASYRYTGVP<br>DRFSGSGSGTDFTLTISSLQPEDFAVYYCQ<br>QHYITPLTFGAGTKVEIKRTVAAPSVFIFPP<br>SDEQLKSGTASVVCLLNNFYPREAKVQW<br>KVDNALQSGNSQESVTEQDSKDSTYSLSS<br>TLTLSKADYEKHKVYACEVTHQGLSSPVT<br>KSFNRGEC | 350 |
| TCE-49 HC<br>anti-CD3 scFv N236A<br>anti-TROP2 F108A | EVQLVESGGGLVQPGGSLKLSCAASGFTF<br>NKYAMNWVRQAPGKGLEWVARIRSKYN<br>NYATYYADSVKDRFTISRDDSKNTAYLQ<br>MNNLKTEDTAVYYCVRHGNFGNSYISYW<br>AYWGQGTLVTVSSGGGGSGGGGSGGGGS<br>QTVVTQEPSLTVSPGGTVTLTCGSSTGAVT<br>SGNYPNWVQQKPGQAPRGLIGGTKFLAPG<br>TPARFSGSLLGGKAALTLSGVQPEDEAEY<br>YC**VLWYSARWV**FGGGTKLTVLGGGGSQ<br>VQLQQSGSELKKPGASVKVSCKASGYTFT<br>NYGMNWVKQAPGQGLKWMGWINTYTG<br>EPTYTDDFKGRFAFSLDTSVSTAYLQISSL<br>KADDTAVYFC**ARGGFGSSYWYADV**WGQ<br>GSLVTVSSASTKGPSVFPLAPSSKSTSGGT<br>AALGCLVKDYFPEPVTVSWNSGALTSGVH<br>TFPAVLQSSGLYSLSSVVTVPSSSLGTQTYI<br>CNVNHKPSNTKVDKKVEPKSC | 351 |

In some embodiments, the recombinant antibody or antigen binding fragment thereof has weaker cytotoxicity activity as compared to a recombinant antibody or antigen binding fragment thereof that comprises an immunoglobulin light chain according to SEQ ID NO: 83 or 85 and an immunoglobulin heavy chain according to SEQ ID NO: 84 or 86 as measured in an in vitro tumor cell killing assay under substantially similar assay conditions.

CD3 Binding Domain Peptide Masks ($P_2$)

In some embodiments, $P_2$ impairs binding of $B_2$ to CD3. In some embodiments, $P_2$ is bound to $B_2$ through ionic interactions, electrostatic interactions, hydrophobic interactions, Pi-stacking interactions, and H-bonding interactions, or a combination thereof. In some embodiments, $P_2$ is bound to $B_2$ at or near an antigen binding site. In some embodiments, $P_2$ becomes unbound from $B_2$ when $L_2$ is cleaved by the tumor specific protease thereby exposing $B_2$ to CD3. In some embodiments, $P_2$ has less than 70% sequence identity to CD3. In some embodiments, $P_2$ has less than 75% sequence identity to CD3. In some embodiments, $P_2$ has less than 80% sequence identity to CD3. In some embodiments, $P_2$ has less than 85% sequence identity to CD3. In some embodiments, $P_2$ has less than 90% sequence identity to CD3. In some embodiments, $P_2$ has less than 95% sequence identity to CD3. In some embodiments, $P_2$ comprises a de novo amino acid sequence that shares less than 10% sequence identity to CD3. In some embodiments, $P_2$ comprises a peptide sequence of at least 5 amino acids in length. In some embodiments, $P_2$ comprises a peptide sequence of at least 6 amino acids in length. In some embodiments, $P_2$ comprises a peptide sequence of at least 10 amino acids in length. In some embodiments, $P_2$ comprises a peptide sequence of at least 10 amino acids in length and no more than 20 amino acids in length. In some embodiments, $P_2$ comprises a peptide sequence of at least 16 amino acids in length. In some embodiments, $P_2$ comprises a peptide sequence of no more than 40 amino acids in length. In some embodiments, $P_2$ comprises at least two cysteine amino acid residues. In some embodiments, $P_2$ comprises a cyclic peptide or a linear peptide. In some embodiments, $P_2$ comprises a cyclic peptide. In some embodiments, $P_2$ comprises a linear peptide. In some embodiments, $P_2$ comprise a modified amino acid or non-natural amino acid, or a modified non-natural amino acid, or a combination thereof. In some embodiments, $P_2$ does not comprise albumin or an albumin fragment. In some embodiments, $P_2$ does not comprise an albumin binding domain. In some embodiments, $P_2$ comprises the amino acid sequence of SEQ ID NO: 289 or SEQ ID NO: 292. I n some embodiments, $P_2$ comprises the amino acid sequence of SEQ ID NO: 289. In some embodiments, $P_2$ comprises the amino acid sequence of SEQ ID NO: 292.

In some embodiments, $P_2$ comprises an amino acid sequence according to any one of SEQ ID NOs: 287-302, or an amino acid sequence that has 1, 2, or 3 amino acid mutations, substitutions or deletions relative to any one of SEQ ID NOs: 287-302. In some embodiments, $P_2$ comprises the amino acid sequence of SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 273, and $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 305, and $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the CD3 binding domain comprises an amino acid sequence with at least 90%, 95%, 96%, 97%, 98%, 99%, or 100% identity to SEQ ID NO: 305, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 305, and $P_2$ comprises an amino acid sequence according to SEQ ID NO: 295.

In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 276, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 77, CDR1-H: SEQ ID NO: 78, CDR2-H: SEQ ID NO: 79, and CDR3-H: SEQ ID NO: 276, and $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 308, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 308, and $P_2$ comprises an amino acid sequence according to SEQ ID NO: 295. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 259, CDR2-L: SEQ ID NO: 76, CDR3-L: SEQ ID NO: 260, CDR1-H: SEQ ID NO: 270, CDR2-H: SEQ ID NO: 79, and CDR3-H: SEQ ID NO: 286, and $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 329, and $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298. In some embodiments, the CD3 binding domain comprises an amino acid sequence with at least 90%, 95%, 96%, 97%, 98%, 99%, or 100% identity to SEQ ID NO: 329, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 329, and $P_2$ comprises an amino acid sequence according to SEQ ID NO: 295.

In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 261, CDR1-H: SEQ ID NO: 78, CDR2-H: SEQ ID NO: 79, and CDR3-H: SEQ ID NO: 80, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the immunoglobulin light chain and the immunoglobulin heavy chain of the CD3 binding domain comprise a set of CDRs comprising CDR1-L: SEQ ID NO: 75, CDR2-L: SEQ ID NO: 76, CDR3-L: SEQ ID NO: 261, CDR1-H: SEQ ID NO: 78, CDR2-H: SEQ ID NO: 79, and CDR3-H: SEQ ID NO: 80, and $P_2$ comprises an amino acid sequence according to SEQ ID NO: 295. In some embodiments, the CD3 binding domain comprises an amino acid sequence with at least 90%, 95%, 96%, 97%, 98%, 99%, or 100% identity to SEQ ID NO: 319, and $P_2$ comprises an amino acid sequence according to SEQ ID NO: 295, or an amino acid sequence that has 1, 2, or 3 amino acid mutations, substitutions, or deletions relative to SEQ ID NO: 295. In some embodiments, the CD3 binding domain comprises an amino acid sequence according to SEQ ID NO: 319, and $P_2$ comprises an amino acid sequence according to SEQ ID NO: 295.

TABLE 9

Peptide masks for CD3 scFv sequences

| Peptide | Amino Acid Sequence (N to C) | SEQ ID NO: |
|---|---|---|
| Peptide-65 | QGCGTIADPEPHCW | 287 |
| Peptide-66 | GSQCLGPEWEVCPY | 288 |
| Peptide-67 | VYCGPEFDESVGCM | 289 |
| Peptide-68 | DWCWYSPDNDGLCD | 290 |
| Peptide-69 | SECLVDLQSDPCYW | 291 |
| Peptide-70 | YLCGPDGDETLACY | 292 |
| Peptide-71 | VDCGPDGDESILCY | 293 |
| Peptide-72 | AYCGPEFDESVGCM | 294 |
| Peptide-73 | VYCGPEFDESVGCA | 295 |
| Peptide-74 | ASQCLGPEWEVCPY | 296 |

TABLE 9-continued

Peptide masks for CD3 scFv sequences

| Peptide | Amino Acid Sequence (N to C) | SEQ ID NO: |
|---|---|---|
| Peptide-75 | GSACLGPEWEVCPY | 297 |
| Peptide-76 | YLCGPDADETLACY | 298 |
| Peptide-77 | YLCGPDTDETLACY | 299 |
| Peptide-78 | IDFCAVYKWPVCQV | 300 |
| Peptide-79 | IDFCLIYNWPVCDT | 301 |
| Peptide-80 | PDFCAVYRWPICYQ | 302 |

Linking Moiety ($L_1$ or $L_2$)

In some embodiments, $L_1$ or $L_2$ is a peptide sequence having at least 5 to no more than 50 amino acids. In some embodiments, $L_1$ or $L_2$ is a peptide sequence having at least 10 to no more than 30 amino acids. In some embodiments, $L_1$ or $L_2$ is a peptide sequence having at least 10 amino acids. In some embodiments, $L_1$ or $L_2$ is a peptide sequence having at least 18 amino acids. In some embodiments, $L_1$ or $L_2$ is a peptide sequence having at least 26 amino acids. In some embodiments, $L_1$ or $L_2$ comprises a formula comprising $(G_2S)_n$, wherein n is an integer from 1 to 3. In some embodiments, $L_1$ or $L_2$ comprises a formula comprising $(G_2S)_n$, wherein n is an integer of at least 1. In some embodiments, $L_1$ or $L_2$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1. In some embodiments, the tumor specific protease is selected from the group consisting of metalloprotease, serine protease, cysteine protease, threonine protease, and aspartic protease. In some embodiments, $L_1$ or $L_2$ comprises a urokinase cleavable amino acid sequence, a matriptase cleavable amino acid sequence, or a matrix metalloprotease cleavable amino acid sequence. In some embodiments, $L_1$ or $L_2$ comprises a sequence according to any one of SEQ ID NOs: 226-254. In some embodiments, $L_1$ is bound to N-terminus of $A_1$. In some embodiments, $L_1$ is bound to C-terminus of $A_1$. In some embodiments, $L_2$ is bound to N-terminus of $B_2$. In some embodiments, $L_2$ is bound to C-terminus of $B_2$.

TABLE 10

$L_1$ or $L_2$

| | Construct Description | Amino Acid Sequence (N to C) | SEQ ID NO: |
|---|---|---|---|
| Half | Linker 1 | GGGGSGGGGSGGGGS | 226 |
| | Linker 2 | GGGGS | 227 |
| | Linker 3 | GGGGSGGGS | 228 |
| | Cleavable linker | GGGGSGGGLSGRSDAGSPLGL AGSGGGS | 229 |
| | Linker 4 | GGGGSLSGRSDNHGSSGT | 230 |
| | Linker 5 | GGGGSSGGSGGSGLSGRSDNH GSSGT | 231 |
| | Linker 6 | ASGRSDNH | 232 |

TABLE 10-continued

| $L_1$ or $L_2$ | | |
|---|---|---|
| Construct Description | Amino Acid Sequence (N to C) | SEQ ID NO: |
| Linker 7 | LAGRSDNH | 233 |
| Linker 8 | ISSGLASGRSDNH | 234 |
| Linker 9 | ISSGLLAGRSDNH | 235 |
| Linker 10 | LSGRSDNH | 236 |
| Linker 11 | ISSGLLSGRSDNP | 237 |
| Linker 12 | ISSGLLSGRSDNH | 238 |
| Linker 13 | LSGRSDNHSPLGLAGS | 239 |
| Linker 14 | SPLGLAGSLSGRSDNH | 240 |
| Linker 15 | SPLGLSGRSDNH | 241 |
| Linker 16 | LAGRSDNHSPLGLAGS | 242 |
| Linker 17 | LSGRSDNHVPLSLKMG | 243 |
| Linker 18 | LSGRSDNHVPLSLSMG | 244 |
| Linker 19 | GSSGGSGGSGGSGISSGLLSGR SDNHGSSGT | 245 |
| Linker 20 | GSSGGSGGSGGISSGLLSGRSD NHGGGS | 246 |
| Linker 21 | ASGRSDNH | 247 |
| Linker 22 | LAGRSDNH | 248 |
| Linker 23 | ISSGLASGRSDNH | 249 |
| Linker 24 | LSGRSDAG | 250 |
| Linker 25 | ISSGLLSGRSDAG | 251 |
| Linker 26 | AAGLLAPPGGLSGRSDAG | 252 |
| Linker 27 | SPLGLSGRSDAG | 253 |
| Linker 28 | LSGRSDAGSPLGLAG | 254 |

Life-Extending Molecule ($H_1$)

In some embodiments, the isolated polypeptide or polypeptide complex further comprises a half-life extending molecule ($H_1$). In some embodiments, $H_1$ is connected to $P_1$. In some embodiments, $H_1$ is connected to $P_2$. In some embodiments, $H_1$ does not block the CD3 binding domain to CD3. In some embodiments, the half-life extending molecule ($H_1$) does not have binding affinity to CD3. In some embodiments, the half-life extending molecule ($H_1$) does not shield the isolated polypeptide or polypeptide complex from CD3. In some embodiments, $H_1$ comprises a sequence according to SEQ ID NOs: 255-258. In some embodiments, $H_1$ comprises an amino acid sequence that has repetitive sequence motifs. In some embodiments, $H_1$ comprises an amino acid sequence that has highly ordered secondary structure. In some embodiments, $H_1$ comprises a polymer. In some embodiments, the polymer is polyethylene glycol (PEG). In some embodiments, $H_1$ comprises albumin. In some embodiments, $H_1$ comprises an Fc domain. In some embodiments, the albumin is serum albumin. In some embodiments, the albumin is human serum albumin. In some embodiments, $H_1$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, slgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the single domain antibody comprises a single domain antibody that binds to albumin. In some embodiments, the single domain antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 255, HC-CDR2: SEQ ID NO: 256, and HC-CDR3: SEQ ID NO: 257; and wherein the CDRs comprise from 0-2 amino acid modifications in at least one of the HC-CDR1, HC-CDR2, or HC-CDR3. In some embodiments, $H_1$ comprises an amino acid sequence according to SEQ ID NO: 258. In some embodiments, $H_1$ comprises an amino acid sequence that has at least 80% sequence identity to SEQ ID NO: 258. In some embodiments, $H_1$ comprises an amino acid sequence that has at least 85% sequence identity to SEQ ID NO: 258. In some embodiments, $H_1$ comprises an amino acid sequence that has at least 90% sequence identity to SEQ ID NO: 258. In some embodiments, $H_1$ comprises an amino acid sequence that has at least 95% sequence identity to SEQ ID NO: 258. In some embodiments, $H_1$ comprises an amino acid sequence that has at least 99% sequence identity to SEQ ID NO: 258. In some embodiments, $H_1$ comprises a modified amino acid or non-natural amino acid, or a modified non-natural amino acid, or a combination thereof. In some embodiments, the modified amino acid or a modified non-natural amino acid comprises a post-translational modification. In some embodiments, $H_1$ comprises a linking moiety ($L_3$) that connects $H_1$ to $P_1$ or $P_2$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1. In some embodiments, $L_3$ comprises a sequence according to any one of SEQ ID NOs: 226-254.

TABLE 11

H$_1$ Sequences

| Construct Description | Amino Acid Sequence (N to C) | SEQ ID NO: |
|---|---|---|
| Anti-Albumin: CDR-H1 | GSTFYTAV | 255 |
| Anti-Albumin: CDR-H2 | IRWTALTT | 256 |
| Anti-Albumin: CDR-H3 | AARGTLGLFTTADSYDY | 257 |
| Anti-albumin (HE-1) | EVQLVESGGGLVQPGGSLRLSCAAS **GSTFYTAV**MGWVRQAPGKGLEWV AA**IRWTALTT**SYADSVKGRFTISRD GAKTTLYLQMNSLRPEDTAVYYC**A ARGTLGLFTTADSYDY**WGQGTLV TVSS | 258 |

Polypeptide Complexes

In some embodiments, the isolated polypeptide or polypeptide complex comprises amino acid sequences with at least 90%, 95%, 96%, 97%, 98%, 99%, or 100% identity to SEQ ID NO: 166 and SEQ ID NO: 167. In some embodiments, the isolated polypeptide or polypeptide complex comprises amino acid sequences with at least 90%, 95%, 96%, 97%, 98%, 99%, or 100% identity to SEQ ID NO: 168 and SEQ ID NO: 169. In some embodiments, the isolated polypeptide or polypeptide complex comprises amino acid sequences with at least 90%, 95%, 96%, 97%, 98%, 99%, or 100% identity to SEQ ID NO: 170 and SEQ ID NO: 171. In some embodiments, the isolated polypeptide or polypeptide complex comprises amino acid sequences with at least 90%, 95%, 96%, 97%, 98%, 99%, or 100% identity to SEQ ID NO: 172 and SEQ ID NO: 173. In some embodiments, the isolated polypeptide or polypeptide complex comprises amino acid sequences with at least 90%, 95%, 96%, 97%, 98%, 99%, or 100% identity to SEQ ID NO: 174 and SEQ ID NO: 175. In some embodiments, the isolated polypeptide or polypeptide complex comprises amino acid sequences with at least 90%, 95%, 96%, 97%, 98%, 99%, or 100% identity to SEQ ID NO: 176 and SEQ ID NO: 177. In some embodiments, the isolated polypeptide or polypeptide complex comprises amino acid sequences with at least 90%, 95%, 96%, 97%, 98%, 99%, or 100% identity to SEQ ID NO: 178 and SEQ ID NO: 179. In some embodiments, the isolated polypeptide or polypeptide complex comprises amino acid sequences with at least 90%, 95%, 96%, 97%, 98%, 99%, or 100% identity to SEQ ID NO: 180 and SEQ ID NO: 181. In some embodiments, the isolated polypeptide or polypeptide complex comprises amino acid sequences with at least 90%, 95%, 96%, 97%, 98%, 99%, or 100% identity to SEQ ID NO: 182 and SEQ ID NO: 183. In some embodiments, the isolated polypeptide or polypeptide complex comprises amino acid sequences with at least 90%, 95%, 96%, 97%, 98%, 99%, or 100% identity to SEQ ID NO: 184 and SEQ ID NO: 185. In some embodiments, the isolated polypeptide or polypeptide complex comprises amino acid sequences with at least 90%, 95%, 96%, 97%, 98%, 99%, or 100% identity to SEQ ID NO: 186 and SEQ ID NO: 187. In some embodiments, the isolated polypeptide or polypeptide complex comprises amino acid sequences with at least 90%, 95%, 96%, 97%, 98%, 99%, or 100% identity to SEQ ID NO: 188 and SEQ ID NO: 189. In some embodiments, the isolated polypeptide or polypeptide complex comprises amino acid sequences with at least 90%, 95%, 96%, 97%, 98%, 99%, or 100% identity to SEQ ID NO: 190 and SEQ ID NO: 191. In some embodiments, the isolated polypeptide or polypeptide complex comprises amino acid sequences with at least 90%, 95%, 96%, 97%, 98%, 99%, or 100% identity to SEQ ID NO: 192 and SEQ ID NO: 193. In some embodiments, the isolated polypeptide or polypeptide complex comprises amino acid sequences with at least 90%, 95%, 96%, 97%, 98%, 99%, or 100% identity to SEQ ID NO: 194 and SEQ ID NO: 195. In some embodiments, the isolated polypeptide or polypeptide complex comprises amino acid sequences with at least 90%, 95%, 96%, 97%, 98%, 99%, or 100% identity to SEQ ID NO: 196 and SEQ ID NO: 197. In some embodiments, the isolated polypeptide or polypeptide complex comprises amino acid sequences with at least 90%, 95%, 96%, 97%, 98%, 99%, or 100% identity to SEQ ID NO: 198 and SEQ ID NO: 199. In some embodiments, the isolated polypeptide or polypeptide complex comprises amino acid sequences with at least 90%, 95%, 96%, 97%, 98%, 99%, or 100% identity to SEQ ID NO: 200 and SEQ ID NO: 201. In some embodiments, the isolated polypeptide or polypeptide complex comprises amino acid sequences with at least 90%, 95%, 96%, 97%, 98%, 99%, or 100% identity to SEQ ID NO: 202 and SEQ ID NO: 203. In some embodiments, the isolated polypeptide or polypeptide complex comprises amino acid sequences with at least 90%, 95%, 96%, 97%, 98%, 99%, or 100% identity to SEQ ID NO: 204 and SEQ ID NO: 205. In some embodiments, the isolated polypeptide or polypeptide complex comprises amino acid sequences with at least 90%, 95%, 96%, 97%, 98%, 99%, or 100% identity to SEQ ID NO: 206 and SEQ ID NO: 207. In some embodiments, the isolated polypeptide or polypeptide complex comprises amino acid sequences with at least 90%, 95%, 96%, 97%, 98%, 99%, or 100% identity to SEQ ID NO: 208 and SEQ ID NO: 209. In some embodiments, the isolated polypeptide or polypeptide complex comprises amino acid sequences with at least 90%, 95%, 96%, 97%, 98%, 99%, or 100% identity to SEQ ID NO: 210 and SEQ ID NO: 211. In some embodiments, the isolated polypeptide or polypeptide complex comprises amino acid sequences with at least 90%, 95%, 96%, 97%, 98%, 99%, or 100% identity to SEQ ID NO: 212 and SEQ ID NO: 213. In some embodiments, the isolated polypeptide or polypeptide complex comprises amino acid sequences with at least 90%, 95%, 96%, 97%, 98%, 99%, or 100% identity to SEQ ID NO: 214 and SEQ ID NO: 215. In some embodiments, the isolated polypeptide or polypeptide complex comprises amino acid sequences with at least 90%, 95%, 96%, 97%, 98%, 99%, or 100% identity to SEQ ID NO: 216 and SEQ ID NO: 217. In some embodiments, the isolated polypeptide or polypeptide complex comprises amino acid sequences with at least 90%, 95%, 96%, 97%, 98%, 99%, or 100% identity to SEQ ID NO: 218 and SEQ ID NO: 219. In some embodiments, the isolated polypeptide or polypeptide complex comprises amino acid sequences with at least 90%, 95%, 96%, 97%, 98%, 99%, or 100% identity to SEQ ID NO: 220 and SEQ ID NO: 221. In some embodiments, the isolated polypeptide or polypeptide complex comprises amino acid sequences with at least 90%, 95%, 96%, 97%, 98%, 99%, or 100% identity to SEQ ID NO: 222 and SEQ ID NO: 223. In some embodiments, the isolated polypeptide or polypeptide complex comprises amino acid sequences with at least 90%, 95%, 96%, 97%, 98%, 99%, or 100% identity to SEQ ID NO: 224 and SEQ ID NO: 225.

In some embodiments, the isolated polypeptide or polypeptide complex comprises amino acid sequences with at least 90%, 95%, 96%, 97%, 98%, 99%, or 100% identity to SEQ ID NO: 352 and SEQ ID NO: 353. In some embodiments, the isolated polypeptide or polypeptide complex comprises amino acid sequences with at least 90%, 95%, 96%, 97%, 98%, 99%, or 100% identity to SEQ ID NO: 354 and SEQ ID NO: 355. In some embodiments, the isolated polypeptide or polypeptide complex comprises amino acid sequences with at least 90%, 95%, 96%, 97%, 98%, 99%, or 100% identity to SEQ ID NO: 356 and SEQ ID NO: 357. In some embodiments, the isolated polypeptide or polypeptide complex comprises amino acid sequences with at least 90%, 95%, 96%, 97%, 98%, 99%, or 100% identity to SEQ ID NO: 358 and SEQ ID NO: 359. In some embodiments, the isolated polypeptide or polypeptide complex comprises amino acid sequences with at least 90%, 95%, 96%, 97%, 98%, 99%, or 100% identity to SEQ ID NO: 360 and SEQ ID NO: 361. In some embodiments, the isolated polypeptide or polypeptide complex comprises amino acid sequences with at least 90%, 95%, 96%, 97%, 98%, 99%, or 100% identity to SEQ ID NO: 362 and SEQ ID NO: 363. In some embodiments, the isolated polypeptide or polypeptide complex comprises amino acid sequences with at least 90%, 95%, 96%, 97%, 98%, 99%, or 100% identity to SEQ ID NO: 364 and SEQ ID NO: 365. In some embodiments, the isolated polypeptide or polypeptide complex comprises amino acid sequences with at least 90%, 95%, 96%, 97%, 98%, 99%, or 100% identity to SEQ ID NO: 366 and SEQ ID NO: 367. In some embodiments, the isolated polypeptide or polypeptide complex comprises amino acid sequences with at least 90%, 95%, 96%, 97%, 98%, 99%, or 100% identity to SEQ ID NO: 368 and SEQ ID NO: 369. In some embodiments, the isolated polypeptide or polypeptide complex comprises amino acid sequences with at least 90%, 95%, 96%, 97%, 98%, 99%, or 100% identity to SEQ ID NO: 370 and SEQ ID NO: 371. In some embodiments, the isolated polypeptide or polypeptide complex comprises amino acid sequences with at least 90%, 95%, 96%, 97%, 98%, 99%, or 100% identity to SEQ ID NO: 372 and SEQ ID NO: 373. In some embodiments, the isolated polypeptide or polypeptide complex comprises amino acid sequences with at least 90%, 95%, 96%, 97%, 98%, 99%, or 100% identity to SEQ ID NO: 374 and SEQ ID NO: 375. In some embodiments, the isolated polypeptide or polypeptide complex comprises amino acid sequences with at least 90%, 95%, 96%, 97%, 98%, 99%, or 100% identity to SEQ ID NO: 376 and SEQ ID NO: 377. In some embodiments, the isolated polypeptide or polypeptide complex comprises amino acid sequences with at least 90%, 95%, 96%, 97%, 98%, 99%, or 100% identity to SEQ ID NO: 378 and SEQ ID NO: 379. In some embodiments, the isolated polypeptide or polypeptide complex comprises amino acid sequences with at least 90%, 95%, 96%, 97%, 98%, 99%, or 100% identity to SEQ ID NO: 380 and SEQ ID NO: 381. In some embodiments, the isolated polypeptide or polypeptide complex comprises amino acid sequences with at least 90%, 95%, 96%, 97%, 98%, 99%, or 100% identity to SEQ ID NO: 382 and SEQ ID NO: 383. In some embodiments, the isolated polypeptide or polypeptide complex comprises amino acid sequences with at least 90%, 95%, 96%, 97%, 98%, 99%, or 100% identity to SEQ ID NO: 384 and SEQ ID NO: 385. In some embodiments, the isolated polypeptide or polypeptide complex comprises amino acid sequences with at least 90%, 95%, 96%, 97%, 98%, 99%, or 100% identity to SEQ ID NO: 386 and SEQ ID NO: 387. In some embodiments, the isolated polypeptide or polypeptide complex comprises amino acid sequences with at least 90%, 95%, 96%, 97%, 98%, 99%, or 100% identity to SEQ ID NO: 388 and SEQ ID NO: 389. In some embodiments, the isolated polypeptide or polypeptide complex comprises amino acid sequences with at least 90%, 95%, 96%, 97%, 98%, 99%, or 100% identity to SEQ ID NO: 390 and SEQ ID NO: 391. In some embodiments, the isolated polypeptide or polypeptide complex comprises amino acid sequences with at least 90%, 95%, 96%, 97%, 98%, 99%, or 100% identity to SEQ ID NO: 392 and SEQ ID NO: 393. In some embodiments, the isolated polypeptide or polypeptide complex comprises amino acid sequences with at least 90%, 95%, 96%, 97%, 98%, 99%, or 100% identity to SEQ ID NO: 394 and SEQ ID NO: 395.

TABLE 12

Polypeptide complex sequences (masked sequences that bind to TROP2 and CD3e)

| Construct Description | Amino Acid Sequence (N to C) | SEQ ID NO: |
|---|---|---|
| PC-1 LC wt | GGVDFCKIYSWPVCHQGGGGSGGLSGRSDAGSPLGLAG SGGSDIQLTQSPSSLSASVGDRVSITCKAS**QDVSIA**VAW YQQKPGKAPKLLIY**SA**SYRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 166 |
| PC-1 HC wt | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCMG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM | 167 |

TABLE 12-continued

| Polypeptide complex sequences (masked sequences that bind to TROP2 and CD3e) | | |
|---|---|---|
| Construct Description | Amino Acid Sequence (N to C) | SEQ ID NO: |
| | NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFDV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | |
| PC-2 LC wt | GGIDFCMLYNWPICAGGGGGSSGGSAAGLLAPPGGLSG<br>RSDAGGGGSDIQLTQSPSSLSASVGDRVSITCKAS**QDVSI**<br>**A**VAWYQQKPGKAPKLLIY**SA**SYRYTGVPDRFSGSGSGT<br>DFTLTISSLQPEDFAVYYC**QQHYITPLT**FGAGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 168 |
| PC-2 HC wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>SSGGSAAGLLAPPGGLSGRSDAGGGGSEVQLVESGGGL<br>VQPGGSLKLSCAAS**GFTFNKY**AMNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFDV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 169 |
| PC-3 LC wt | GGVDFCKIYSWPVCHQGGGGSSGGSAAGLLAPPGGLSG<br>RSDAGGGGSDIQLTQSPSSLSASVGDRVSITCKAS**QDVS**<br>**IA**VAWYQQKPGKAPKLLIY**SA**SYRYTGVPDRFSGSGSGT<br>DFTLTISSLQPEDFAVYYC**QQHYITPLT**FGAGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 170 |
| PC-3 HC wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>SSGGSAAGLLAPPGGLSGRSDAGGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFDV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 171 |
| PC-4 LC wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>SSGGSAAGLLAPPGGLSGRSDAGGGGSEVQLVESGGGL<br>VQPGGSLKLSCAAS**GFTFNKY**AMNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT | 172 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | LTCGSSTGAVTSGNYPNWVQQKPGQAPRGLIGGTKFL<br>APGTPARFSGSLLGGKAALTLSGVQPEDEAEYYCVLWY<br>SNRWVFGGGTKLTVLGGGGSDIQLTQSPSSLSASVGDR<br>VSITCKASQDVSIAVAWYQQKPGKAPKLLIYSASYRYT<br>GVPDRFSGSGSGTDFTLTISSLQPEDFAVYYCQQHYITP<br>LTFGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | |
| PC-4 HC wt | GGIDFCMLYNWPICAGGGGGSSGGSAAGLLAPPGGLSG<br>RSDAGGGGSQVQLQQSGSELKKPGASVKVSCKASGYTF<br>TNYGMNWVKQAPGQGLKWMGWINTYTGEPTYTDDF<br>KGRFAFSLDTSVSTAYLQISSLKADDTAVYFCARGGFGS<br>SYWYFDVWGQGSLVTVSSASTKGPSVFPLAPSSKSTSG<br>GTAALGCLVKDYFPEPVTVSWNSGALTSGVHTFPAVLQ<br>SSGLYSLSSVVTVPSSSLGTQTYICNVNHKPSNTKVDKK<br>VEPKSC | 173 |
| PC-5 LC wt | GGIDFCMLYNWPICAGGGGGSGGLSGRSDAGSPLGLAG<br>SGGSDIQLTQSPSSLSASVGDRVSITCKASQDVSIAVAW<br>YQQKPGKAPKLLIYSASYRYTGVPDRFSGSGSGTDFTLTI<br>SSLQPEDFAVYYCQQHYITPLTFGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 174 |
| PC-5 HC wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAASGFTFNKYAMNWVRQAPGKGLEW<br>VARIRSKYNNYATYYADSVKDRFTISRDDSKNTAYLQM<br>NNLKTEDTAVYYCVRHGNFGNSYISYWAYWGQGTLV<br>TVSSGGGGSGGGGSGGGGSQTVVTQEPSLTVSPGGTVT<br>LTCGSSTGAVTSGNYPNWVQQKPGQAPRGLIGGTKFL<br>APGTPARFSGSLLGGKAALTLSGVQPEDEAEYYCVB LWY<br>SNRWVFGGGTKLTVLGGGGSQVQLQQSGSELKKPGAS<br>VKVSCKASGYTFTNYGMNWVKQAPGQGLKWMGWIN<br>TYTGEPTYTDDFKGRFAFSLDTSVSTAYLQISSLKADDT<br>AVYFCARGGFGSSYWYFDVWGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 175 |
| PC-6 LC wt | GGVDFCGLYHWPICYQGGGGSGGLSGRSDAGSPLGLAG<br>SGGSDIQLTQSPSSLSASVGDRVSITCKASQDVSIAVAW<br>YQQKPGKAPKLLIYSASYRYTGVPDRFSGSGSGTDFTLTI<br>SSLQPEDFAVYYCQQHYITPLTFGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 176 |
| PC-6 HC wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAASGFTFNKYAMNWVRQAPGKGLEW<br>VARIRSKYNNYATYYADSVKDRFTISRDDSKNTAYLQM<br>NNLKTEDTAVYYCVRHGNFGNSYISYWAYWGQGTLV<br>TVSSGGGGSGGGGSGGGGSQTVVTQEPSLTVSPGGTVT<br>LTCGSSTGAVTSGNYPNWVQQKPGQAPRGLIGGTKFL<br>APGTPARFSGSLLGGKAALTLSGVQPEDEAEYYCVB LWY<br>SNRWVFGGGTKLTVLGGGGSQVQLQQSGSELKKPGAS<br>VKVSCKASGYTFTNYGMNWVKQAPGQGLKWMGWIN<br>TYTGEPTYTDDFKGRFAFSLDTSVSTAYLQISSLKADDT<br>AVYFCARGGFGSSYWYFDVWGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 177 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-7 LC<br>wt | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKY**AMNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLQPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 178 |
| PC-7 HC<br>wt | GGVDFCGLYHWPICYQGGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**ARGGFGSSYWY**<br>**FDV**WGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 179 |
| PC-8 LC<br>anti-TROP2<br>D109A | GGVDFCGLYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 180 |
| PC-8 HC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFAV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 181 |
| PC-9 LC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLQPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 182 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-9 HC<br>anti-TROP2<br>D109A | GGVDFCGLYHWPICYQGGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**ARGGFGS**SYWY<br>FAVWGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 183 |
| PC-10 LC<br>anti-TROP2<br>D109A | GGVDFCGLYHWPICYQGGGGSSGGSAAGLLAPPGGLSG<br>RSDAGGGGSDIQLTQSPSSLSASVGDRVSITCKAS**QDVSI**<br>AVAWYQQKPGKAPKLLIY**SA**SYRYTGVPDRFSGSGSGT<br>DFTLTISSLQPEDFAVYYC**QQHYITPLT**FGAGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 184 |
| PC-10 HC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>SSGGSAAGLLAPPGGLSGRSDAGGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFAV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 185 |
| PC-11 LC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>SSGGSAAGLLAPPGGLSGRSDAGGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLQPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 186 |
| PC-11 HC<br>anti-TROP2<br>D109A | GGVDFCGLYHWPICYQGGGGSSGGSAAGLLAPPGGLSG<br>RSDAGGGGSQVQLQQSGSELKKPGASVKVSCKAS**GYTF**<br>**TNYG**MNWVKQAPGQGLKWMGW**INTYTGEP**TYTDDF<br>KGRFAFSLDTSVSTAYLQISSLKADDTAVYFC**ARGGFGS**<br>**SYWYFAV**WGQGSLVTVSSASTKGPSVFPLAPSSKSTSG<br>GTAALGCLVKDYFPEPVTVSWNSGALTSGVHTFPAVLQ<br>SSGLYSLSSVVTVPSSSLGTQTYICNVNHKPSNTKVDKK<br>VEPKSC | 187 |
| PC-12 LC<br>anti-TROP2 R98A | GGVDFCGLYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 188 |
| PC-12 HC<br>anti-TROP2 R98A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY | 189 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYCVB LWY<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**AAGGFGSSYWYFDV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | |
| PC-13 LC<br>anti-TROP2 R98A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLQPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 190 |
| PC-13 HC<br>anti-TROP2 R98A | GGVDFCGLYHWPICYQGGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**AAGGFGSSYWY**<br>**FDV**WGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 191 |
| PC-14 LC<br>anti-TROP2 F108A | GGVDFCGLYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 192 |
| PC-14 HC<br>anti-TROP2 F108A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 193 |
| PC-15 LC<br>anti-TROP2 F108A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG | 194 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSDIQLTQSPSSLSASVGDR VSITCKAS**QDVSIA**VAWYQQKPGKAPKLLIY**SA**SYRYT GVPDRFSGSGSGTDFTLTISSLOPEDFAVYYC**QQHYITP LT**FGAGTKVEIKRTVAAPSVFIFPPSDEQLKSGTASVVCL LNNFYPREAKVQWKVDNALQSGNSQESVTEQDSKDST YSLSSTLTLSKADYEKHKVYACEVTHQGLSSPVTKSFNR GEC | |
| PC-15 HC anti-TROP2 F108A | GGVDFCGLYHWPICYQGGGGSGGLSGRSDAGSPLGLAG SGGSQVQLQQSGSELKKPGASVKVSCKAS**GYTFTNYG** MNWVKQAPGQGLKWMGW**INTYTGEP**TYTDDFKGRFA FSLDTSVSTAYLQISSLKADDTAVYFC**ARGGFGSSYWY ADV**WGQGSLVTVSSASTKGPSVFPLAPSSKSTSGGTAAL GCLVKDYFPEPVTVSWNSGALTSGVHTFPAVLQSSGLY SLSSVVTVPSSSLGTQTYICNVNHKPSNTKVDKKVEPKS C | 195 |
| PC-16 LC<br><br>anti-TROP2 D109A | GGIDFCAIYQWPVCRSGGGGSGGLSGRSDAGSPLGLAGS GGSDIQLTQSPSSLSASVGDRVSITCKAS**QDVSIA**VAWY QQKPGKAPKLLIY**SA**SYRYTGVPDRFSGSGSGTDFTLTIS SLOPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 196 |
| PC-16 HC anti-TROP2 D109A | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCMG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSQVQLQQSGSELKKPGAS VKVSCKAS**GYTFTNYG**MNWVKQAPGQGLKWMGW**IN TYTGEP**TYTDDFKGRFAFSLDTSVSTAYLQISSLKADDT AVYFC**ARGGFGSSYWYFAV**WGQGSLVTVSSASTKGPS VFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | 197 |
| PC-17 LC anti-TROP2 D109A | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCMG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSDIQLTQSPSSLSASVGDR VSITCKAS**QDVSIA**VAWYQQKPGKAPKLLIY**SA**SYRYT GVPDRFSGSGSGTDFTLTISSLOPEDFAVYYC**QQHYITP LT**FGAGTKVEIKRTVAAPSVFIFPPSDEQLKSGTASVVCL LNNFYPREAKVQWKVDNALQSGNSQESVTEQDSKDST YSLSSTLTLSKADYEKHKVYACEVTHQGLSSPVTKSFNR GEC | 198 |
| PC-17 HC anti-TROP2 D109A | GGIDFCAIYQWPVCRSGGGGSGGLSGRSDAGSPLGLAGS GGSQVQLQQSGSELKKPGASVKVSCKAS**GYTFTNYG**M NWVKQAPGQGLKWMGW**INTYTGEP**TYTDDFKGRFAF SLDTSVSTAYLQISSLKADDTAVYFC**ARGGFGSSYWYF AV**WGQGSLVTVSSASTKGPSVFPLAPSSKSTSGGTAALG | 199 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | CLVKDYFPEPVTVSWNSGALTSGVHTFPAVLQSSGLYSL<br>SSVVTVPSSSLGTQTYICNVNHKPSNTKVDKKVEPKSC | |
| PC-18 LC<br>anti-TROP2 F108A | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 200 |
| PC-18 HC<br>anti-TROP2 F108A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 201 |
| PC-19 LC<br>anti-TROP2 F108A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLQPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 202 |
| PC-19 HC<br>anti-TROP2 F108A | GGVDFCALYHWPICYQGGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**ARGGFGSSYWY**<br>**ADV**WGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 203 |
| PC-20 LC<br>anti-TROP2<br>D109A | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 204 |
| PC-20 HC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKY**AMNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV | 205 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | TVSSGGGGSGGGGSGGGGSQTVVTQEPSLTVSPGGTVTLTCGSS**TGAVTSGNY**PNWVQQKPGQAPRGLIG**GTK**FLAPGTPARFSGSLLGGKAALTLSGVQPEDEAEYYC**VLWYSNRWV**FGGGTKLTVLGGGGSQVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYFAV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | |
| PC-21 LC anti-TROP2 D109A | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGVYCGPEFDESVGCMGGGGSGGGLSGRSDAGSPLGLAGSGGGSEVQLVESGGGLVQPGGSLKLSCAAS**GFTFNKY**AMNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GTK**FLAPGTPARFSGSLLGGKAALTLSGVQPEDEAEYYC**VLWYSNRWV**FGGGTKLTVLGGGGSDIQLTQSPSSLSASVGDRVSITCKAS**QDVSIA**VAWYQQKPGKAPKLLIY**SA**SYRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 206 |
| PC-21 HC anti-TROP2 D109A | GGVDFCALYHWPICYQGGGGSGGLSGRSDAGSPLGLAGSGGSQVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYFAV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 207 |
| PC-22 LC anti-TROP2 R98A | GGVDFCGLYHWPICYQVGGGSGGLSGRSDAGSPLGLAGSGGSDIQLTQSPSSLSASVGDRVSITCKAS**QDVSIA**VAWYQQKPGKAPKLLIY**SA**SYRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 208 |
| PC-22 HC anti-TROP2 R98A | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGVYCGPEFDESVGCMGGGGSGGGLSGRSDAGSPLGLAGSGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSS**TGAVTSGNY**PNWVQQKPGQAPRGLIG**GTK**FLAPGTPARFSGSLLGGKAALTLSGVQPEDEAEYYC**VLWYSNRWV**FGGGTKLTVLGGGGSQVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**AAGGFGSSYWYFDV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 209 |
| PC-23 LC anti-TROP2 R98A | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGVYCGPEFDESVGCMGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVT | 210 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLOPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | |
| PC-23 HC<br>anti-TROP2 R98A | GGVDFCGLYHWPICYQVGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**AAGGFGSSYWY**<br>**FDV**WGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 211 |
| PC-24 LC<br>anti-TROP2<br>D109A | GGVDFCGLYHWPICYQVGGGSGGLSGRSDAGSPLGLAG<br>SGGSDIQLTQSPSSLSASVGDRVSITCKAS**QDVSIA**VAW<br>YQQKPGKAPKLLIY**SA**SYRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 212 |
| PC-24 HC<br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFAV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 213 |
| PC-25 LC<br><br>anti-TROP2<br>D109A | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSDIQLTQSPSSLSASVGDR<br>VSITCKAS**QDVSIA**VAWYQQKPGKAPKLLIY**SA**SYRYT<br>GVPDRFSGSGSGTDFTLTISSLOPEDFAVYYC**QQHYITP**<br>**LT**FGAGTKVEIKRTVAAPSVFIFPPSDEQLKSGTASVVCL<br>LNNFYPREAKVQWKVDNALQSGNSQESVTEQDSKDST<br>YSLSSTLTLSKADYEKHKVYACEVTHQGLSSPVTKSFNR<br>GEC | 214 |
| PC-25 HC<br>anti-TROP2<br>D109A | GGVDFCALYHWPICYQGGGGSGGLSGRSDAGSPLGLAG<br>SGGSQVQLQQSGSELKKPGASVKVSCKAS**GYTFTNYG**<br>MNWVKQAPGQGLKWMGW**INTYTGEP**TYTDDFKGRFA<br>FSLDTSVSTAYLQISSLKADDTAVYFC**ARGGFGSSYWY**<br>**FAV**WGQGSLVTVSSASTKGPSVFPLAPSSKSTSGGTAAL<br>GCLVKDYFPEPVTVSWNSGALTSGVHTFPAVLQSSGLY<br>SLSSVVTVPSSSLGTQTYICNVNHKPSNTKVDKKVEPKS<br>C | 215 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-26 LC anti-TROP2 D109A | GGVDFCAIYSWPICKIGGGGSGGLSGRSDAGSPLGLAGS GGSDIQLTQSPSSLSASVGDRVSITCKAS**QDVSIA**VAWY QQKPGKAPKLLIY**SA**SYRYTGVPDRFSGSGSGTDFTLTIS SLOPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 216 |
| PC-26 HC anti-TROP2 D109A | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCMG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSQVQLQQSGSELKKPGAS VKVSCKAS**GYTFTNYG**MNWVKQAPGQGLKWMGW**IN TYTGEP**TYTDDFKGRFAFSLDTSVSTAYLQISSLKADDT AVYFC**ARGGFGSSYWYFAV**WGQGSLVTVSSASTKGPS VFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | 217 |
| PC-27 LC anti-TROP2 D109A | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCMG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSDIQLTQSPSSLSASVGDR VSITCKAS**QDVSIA**VAWYQQKPGKAPKLLIY**SA**SYRYT GVPDRFSGSGSGTDFTLTISSLOPEDFAVYYC**QQHYITP LT**FGAGTKVEIKRTVAAPSVFIFPPSDEQLKSGTASVVCL LNNFYPREAKVQWKVDNALQSGNSQESVTEQDSKDST YSLSSTLTLSKADYEKHKVYACEVTHQGLSSPVTKSFNR GEC | 218 |
| PC-27 HC anti-TROP2 D109A | GGVDFCAIYSWPICKIGGGGSGGLSGRSDAGSPLGLAGS GGSQVQLQQSGSELKKPGASVKVSCKAS**GYTFTNYG**M NWVKQAPGQGLKWMGW**INTYTGEP**TYTDDFKGRFAF SLDTSVSTAYLQISSLKADDTAVYFC**ARGGFGSSYWYF AV**WGQGSLVTVSSASTKGPSVFPLAPSSKSTSGGTAALG CLVKDYFPEPVTVSWNSGALTSGVHTFPAVLQSSGLYSL SSVVTVPSSSLGTQTYICNVNHKPSNTKVDKKVEPKSC | 219 |
| PC-28 LC wt | GGIDFCMLYNWPICAGGGGGSGGLSGRSDAGSPLGLAG SGGSDIQLTQSPSSLSASVGDRVSITCKAS**QDVSIA**VAW YQQKPGKAPKLLIY**SA**SYRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 220 |
| PC-28 HC wt | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGYLCGPDGDETLACYG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSQVQLQQSGSELKKPGAS VKVSCKAS**GYTFTNYG**MNWVKQAPGQGLKWMGW**IN** | 221 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | **TYTGEP**TYTDDFKGRFAFSLDTSVSTAYLQISSLKADDT AVYFC**ARGGFGSSYWYFDV**WGQGSLVTVSSASTKGPS VFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | |
| PC-29 LC wt | GGVDFCGLYHWPICYQGGGGSGGLSGRSDAGSPLGLAG SGGSDIQLTQSPSSLSASVGDRVSITCKAS**QDVSIA**VAW YQQKPGKAPKLLIY**SA**SYRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 222 |
| PC-29 HC wt | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGYLCGPDGDETLACYG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSQVQLQQSGSELKKPGAS VKVSCKAS**GYTFTNYG**MNWVKQAPGQGLKWMGW**IN TYTGEP**TYTDDFKGRFAFSLDTSVSTAYLQISSLKADDT AVYFC**ARGGFGSSYWYFDV**WGQGSLVTVSSASTKGPS VFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | 223 |
| PC-30 LC anti-TROP2 D109A | GGVDFCGLYHWPICYQGGGGSGGLSGRSDAGSPLGLAG SGGSDIQLTQSPSSLSASVGDRVSITCKAS**QDVSIA**VAW YQQKPGKAPKLLIY**SA**SYRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 224 |
| PC-30 HC anti-TROP2 D109A | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGYLCGPDGDETLACYG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SNRWV**FGGGTKLTVLGGGGSQVQLQQSGSELKKPGAS VKVSCKAS**GYTFTNYG**MNWVKQAPGQGLKWMGW**IN TYTGEP**TYTDDFKGRFAFSLDTSVSTAYLQISSLKADDT AVYFC**ARGGFGSSYWYFAV**WGQGSLVTVSSASTKGPS VFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | 225 |
| PC-31 LC (anti-TROP2 D109A; anti-CD3 F104A) | GGVDFCGLYHWPICYQGGGGSGGLSGRSDAGSPLGLAG SGGSDIQLTQSPSSLSASVGDRVSITCKAS**QDVSIA**VAW YQQKPGKAPKLLIY**SAS**YRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 352 |
| PC-31 HC (anti-TROP2 D109A; anti-CD3 F104A) | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCAG GGGSGGGLSGRSDAGSPLGLAGSGGGSEVQLVESGGGL VQPGGSLKLSCAAS**GFTFNKYA**MNWVRQAPGKGLEW VAR**IRSKYNNYAT**YYADSVKDRFTISRDDSKNTAYLQM | 353 |

TABLE 12-continued

| Construct Description | Amino Acid Sequence (N to C) | SEQ ID NO: |
|---|---|---|
| Polypeptide complex sequences (masked sequences that bind to TROP2 and CD3e) | | |
| | NNLKTEDTAVYYC**VRHGNAGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFAV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | |
| PC-32 LC (anti-TROP2 D109A; anti-CD3 N30Q, I109V, G172A, V231A) | GGVDFCGLYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 354 |
| PC-32 HC (anti-TROP2 D109A; anti-CD3 N30Q, I109V, G172A, V231A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAASGFTFQKYAMNWVRQAPGKGLEWV<br>ARIRSKYNNYATYYADSVKDRFTISRDDSKNTAYLQMN<br>NLKTEDTAVYYCVRHGNFGNSYVSYWAYWGQGTLVT<br>VSSGGGGSGGGGSGGGGSQTVVTQEPSLTVSPGGTVTL<br>TCGSSTGAVTSANYPNWVQQKPGQAPRGLIG**GTK**FLAP<br>GTPARFSGSLLGGKAALTLSGVQPEDEAEYYCALWYSN<br>RWVFGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYFAV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 355 |
| PC-33 LC (anti-TROP2 F108A; anti-CD3 wt) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 356 |
| PC-33 HC (anti-TROP2 F108A; anti-CD3 wt) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGYLCGPDGDETLACYG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 357 |
| PC-34 LC (anti-TROP2 F108A; anti-CD3 H101A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 358 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-34 HC<br>(anti-TROP2<br>F108A; anti-CD3<br>H101A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGYLCGPDGDETLACYG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYCV**RAGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>VKVSCKAS**GYTFTNYG**MNWVKQAPGQGLKWMGW**IN**<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 359 |
| PC-35 LC<br>(anti-TROP2<br>F108A; anti-CD3<br>H101A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC<br>**SNRWV**FGGGTKLTVLGGGGSQVQLQQSGSELKKPGAS | 360 |
| PC-35 HC<br>(anti-TROP2<br>F108A; anti-CD3<br>H101A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGYLCGPDADETLACYG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYCV**RAGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 361 |
| PC-36 LC<br>(anti-TROP2<br>F108A; anti-CD3<br>F104A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC<br>**TYTGEP**TYTDDFKGRFAFSLDTSVSTAYLQISSLKADDT | 362 |
| PC-36 HC<br>(anti-TROP2<br>F108A; anti-CD3<br>F104A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNAGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 363 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-37 LC (anti-TROP2 F108A; anti-CD3 F240A) | GGVDFCALYHWPICYQGGGGSGGLSGRSDAGSPLGLAGSGGSDIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 364 |
| PC-37 HC (anti-TROP2 F108A; anti-CD3 F240A) | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGYLCGPDGDETLACYGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GTK**FLAPGTPARFSGSLLGGKAALTLSGVQPEDEAEYYC**VLWYSNRWVA**GGGTKLTVLGGGGSQVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYADV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 365 |
| PC-38 LC (anti-TROP2 F108A; anti-CD3 F240A) | GGVDFCALYHWPICYQGGGGSGGLSGRSDAGSPLGLAGSGGSDIQLTQSPSSLSASVGDRVSITCKASQDVSIAVAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 366 |
| PC-38 HC (anti-TROP2 F108A; anti-CD3 F240A) | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGYLCGPDADETLACYGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GTK**FLAPGTPARFSGSLLGGKAALTLSGVQPEDEAEYYC**VLWYSNRWVA**GGGTKLTVLGGGGSQVQLQQSGSELKKPGASVKVSCKAS**GYTFTNYG**MNWVKQAPGQGLKWMGW**INTYTGEP**TYTDDFKGRFAFSLDTSVSTAYLQISSLKADDTAVYFC**ARGGFGSSYWYADV**WGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 367 |
| PC-39 LC (anti-TROP2 F108A; anti-CD3 P41S, A49G, N87S, L150F, T151S, G163R, P175A, K181T, T200V, A202D, L208I, G211N, L2171, S218T, V220A, P222A, E223D, A226S, E227D) | GGVDFCALYHWPICYQGGGGSGGLSGRSDAGSPLGLAGSGGSDIQLTQSPSSLSASVGDRVSITCKAS**QDVSIA**VAWYQQKPGKAPKLLIY**SAS**YRYTGVPDRFSGSGSGTDFTLTISSLQPEDFAVYYC**QQHYITPLT**FGAGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 368 |
| PC-39 HC (anti-TROP2 F108A; anti-CD3 P41S, A49G, N87S, L150F, T151S, G163R, P175A, K181T, | EVQLVESGGGLVQPGGSLRLSCAASGSTFYTAVMGWVRQAPGKGLEWVAAIRWTALTTSYADSVKGRFTISRDGAKTTLYLQMNSLRPEDTAVYYCAARGTLGLFTTADSYDYWGQGTLVTVSSGGGGSGGGSGGYLCGPDGDETLACYGGGGSGGGLSGRSDAGSPLGLAGSGGGSEVQLVESGGGLVQPGGSLKLSCAAS**GFTFNKYA**MNWVRQASGKGLEWVGR**IRSKYNNYAT**YYADSVKDRFTISRDDSKNTAYLQM | 369 |

TABLE 12-continued

Polypeptide complex sequences (masked sequences that bind to TROP2 and CD3e)

| Construct Description | Amino Acid Sequence (N to C) | SEQ ID NO: |
|---|---|---|
| T200V, A202D, L208I, G211N, L2171, S218T, V220A, P222A, E223D, A226S, E227D) | NSLKTEDTAVYYC**VRHGNFGNSYISYWAY**WGQGTLV TVSSGGGGSGGGGSGGGGSQTVVTQEPSFSVSPGGTVTL TCRSS**TGAVTSGNY**ANWVQQTPGQAPRGLIG**GTK**FLAP GVPDRFSGSILGNKAALTITGAQADDESDYYC**VLWYSN RWV**FGGGTKLTVLGGGGSQVQLQQSGSELKKPGASVK VSCKAS**GYTFTNYG**MNWVKQAPGQGLKWMGW**INTY TGEP**TYTDDFKGRFAFSLDTSVSTAYLQISSLKADDTAV YFC**ARGGFGSSYWYADV**WGQGSLVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSC | |
| PC-40 LC (anti-TROP2 F108A; anti-CD3 P41S, A49G, N87S, L150F, T151S, G163R, P175A, K181T, T200V, A202D, L208I, G211N, L2171, S218T, V220A, P222A, E223D, A226S, E227D) | GGVDFCALYHWPICYQGGGGSGGLSGRSDAGSPLGLAG SGGSDIQLTQSPSSLSASVGDRVSITCKAS**QDVSIA**VAW YQQKPGKAPKLLIY**SAS**YRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 370 |
| PC-40 HC (anti-TROP2 F108A; anti-CD3 P41S, A49G, N87S, L150F, T151S, G163R, P175A, K181T, T200V, A202D, L208I, G211N, L2171, S218T, V220A, P222A, E223D, A226S, E227D) | KTTLYLQMNSLRPEDTAVYYCAARGTLGLFTTADSYDY WGQGTLVTVSSGGGGSGGGSGGYLCGPDADETLACYG GGGSGGGLSGRSDAGSPLGLAGSGGGSEVQLVESGGGL VQPGGSLKLSCAAS**GFTFNKYA**MNWVRQASGKGLEW VGR**IRSKYNNYAT**YYADSVKDRFTISRDDSKNTAYLQM NSLKTEDTAVYYC**VRHGNFGNSYISYWAY**WGQGTLV TVSSGGGGSGGGGSGGGGSQTVVTQEPSFSVSPGGTVTL TCRSS**TGAVTSGNY**ANWVQQTPGQAPRGLIG**GTK**FLAP GVPDRFSGSILGNKAALTITGAQADDESDYYC**VLWYSN RWV**FGGGTKLTVLGGGGSQVQLQQSGSELKKPGASVK VSCKAS**GYTFTNYG**MNWVKQAPGQGLKWMGW**INTY TGEP**TYTDDFKGRFAFSLDTSVSTAYLQISSLKADDTAV YFC**ARGGFGSSYWYADV**WGQGSLVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSC | 371 |
| PC-41 LC F108A; anti-CD3 (anti-TROP2 P41S, A49G, N87S, L150F, T151S, G163R, P175A, K181T, T200V, A202D, L2081, G211N, L2171, S218T, V220A, P222A, E223D, A226S, E227D) | GGVDFCALYHWPICYQGGGGSGGLSGRSDAGSPLGLAG SGGSDIQLTQSPSSLSASVGDRVSITCKAS**QDVSIA**VAW YQQKPGKAPKLLIY**SAS**YRYTGVPDRFSGSGSGTDFTLTI SSLQPEDFAVYYC**QQHYITPLT**FGAGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 372 |
| PC-41 HC (anti-TROP2 F108A; anti-CD3 P41S, A49G, N87S, L150F, T151S, G163R, P175A, K181T, T200V, A202D, L208I, G211N, L2171, S218T, V220A, P222A, E223D, A226S, E227D) | EVQLVESGGGLVQPGGSLRLSCAASGSTFYTAVMGWV RQAPGKGLEWVAAIRWTALTTSYADSVKGRFTISRDGA KTTLYLQMNSLRPEDTAVYYCAARGTLGLFTTADSYDY WGQGTLVTVSSGGGGSGGGSGGVYCGPEFDESVGCAG GGGSGGGLSGRSDAGSPLGLAGSGGGSEVQLVESGGGL VQPGGSLKLSCAAS**GFTFNKYA**MNWVRQASGKGLEW VGR**IRSKYNNYAT**YYADSVKDRFTISRDDSKNTAYLQM NSLKTEDTAVYYC**VRHGNFGNSYISYWAY**WGQGTLV TVSSGGGGSGGGGSGGGGSQTVVTQEPSFSVSPGGTVTL TCRSS**TGAVTSGNY**ANWVQQTPGQAPRGLIG**GTK**FLAP GVPDRFSGSILGNKAALTITGAQADDESDYYC**VLWYSN RWV**FGGGTKLTVLGGGGSQVQLQQSGSELKKPGASVK VSCKAS**GYTFTNYG**MNWVKQAPGQGLKWMGW**INTY TGEP**TYTDDFKGRFAFSLDTSVSTAYLQISSLKADDTAV YFC**ARGGFGSSYWYADV**WGQGSLVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSC | 373 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-42 LC<br>(anti-TROP2<br>F108A; anti-CD3<br>P41S, A49G,<br>N87S, L150F,<br>T151S, G163R,<br>P175A, K181T,<br>T200V, A202D,<br>L208I, G211N,<br>L2171, S218T,<br>V220A, P222A,<br>E223D, A226S,<br>E227D) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 374 |
| PC-42 HC<br>(anti-TROP2<br>F108A; anti-CD3<br>P41S, A49G,<br>N87S, L150F,<br>T151S, G163R,<br>P175A, K181T,<br>T200V, A202D,<br>L208I, G211N,<br>L2171, S218T,<br>V220A, P222A,<br>E223D, A226S,<br>E227D) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGASQCLGPEWEVCPYG<br>GGGSGGGLSGRSDAGSPLGLAGSGGGSEVQLVESGGGL<br>VQPGGSLKLSCAAS**GFTFNKYA**MNWVRQASGKGLEW<br>VGR**IRSKYNNYAT**YYADSVKDRFTISRDDSKNTAYLQM<br>NSLKTEDTAVYYC**VRHGNFGNSYISYWAY**WGQGTLV<br>TVSSGGGGSGGGGSGGGGSQTVVTQEPSFSVSPGGTVTL<br>TCRSS**TGAVTSGNY**ANWVQQTPGQAPRGLIG**GTK**FLAP<br>GVPDRFSGSILGNKAALTITGAQADDESDYYC**VLWYSN**<br>**RWV**FGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 375 |
| PC-43 LC<br>(anti-TROP2<br>F108A; anti-CD3<br>P41S, A49G,<br>N87S, L150F,<br>T151S, G163R,<br>P175A, K181T,<br>T200V, A202D,<br>L208I, G211N,<br>L2171, S218T,<br>V220A, P222A,<br>E223D, A226S,<br>E227D) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 376 |
| PC-43 HC<br>(anti-TROP2<br>F108A; anti-CD3<br>P41S, A49G,<br>N87S, L150F,<br>T151S, G163R,<br>P175A, K181T,<br>T200V, A202D,<br>L208I, G211N,<br>L217I, S218T,<br>V220A, P222A,<br>E223D, A226S,<br>E227D) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGGSACLGPEWEVCPYG<br>GGGSGGGLSGRSDAGSPLGLAGSGGGSEVQLVESGGGL<br>VQPGGSLKLSCAAS**GFTFNKYA**MNWVRQASGKGLEW<br>VGR**IRSKYNNYAT**YYADSVKDRFTISRDDSKNTAYLQM<br>NSLKTEDTAVYYC**VRHGNFGNSYISYWAY**WGQGTLV<br>TVSSGGGGSGGGGSGGGGSQTVVTQEPSFSVSPGGTVTL<br>TCRSS**TGAVTSGNY**ANWVQQTPGQAPRGLIG**GTK**FLAP<br>GVPDRFSGSILGNKAALTITGAQADDESDYYC**VLWYSN**<br>**RWV**FGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 377 |
| PC-44 LC<br>(anti-TROP2<br>F108A; anti-CD3<br>N30Q, I109V,<br>G172A, V231A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 378 |

TABLE 12-continued

| Polypeptide complex sequences (masked sequences that bind to TROP2 and CD3e) | | |
|---|---|---|
| Construct Description | Amino Acid Sequence (N to C) | SEQ ID NO: |
| PC-44 HC (anti-TROP2 F108A; anti-CD3 N30Q, I109V, G172A, V231A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGYLCGPDGDETLACYG<br>GGGSGGGLSGRSDAGSPLGLAGSGGGSEVQLVESGGGL<br>VQPGGSLKLSCAASGFTFQKYAMNWVRQAPGKGLEWV<br>ARIRSKYNNYATYYADSVKDRFTISRDDSKNTAYLQMN<br>NLKTEDTAVYYCVRHGNFGNSYVSYWAYWGQGTLVT<br>VSSGGGGSGGGGSGGGGSQTVVTQEPSLTVSPGGTVTL<br>TCGSSTGAVTSANYPNWVQQKPGQAPRGLIGGTKFLAP<br>GTPARFSGSLLGGKAALTLSGVQPEDEAEYYCALWYSN<br>RWVFGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 379 |
| PC-45 LC (anti-TROP2 F108A; anti-CD3 N30Q, I109V, G172A, V231A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 380 |
| PC-45 HC (anti-TROP2 F108A; anti-CD3 N30Q, I109V, G172A, V231A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGYLCGPDADETLACYG<br>GGGSGGGLSGRSDAGSPLGLAGSGGGSEVQLVESGGGL<br>VQPGGSLKLSCAASGFTFQKYAMNWVRQAPGKGLEWV<br>ARIRSKYNNYATYYADSVKDRFTISRDDSKNTAYLQMN<br>NLKTEDTAVYYCVRHGNFGNSYVSYWAYWGQGTLVT<br>VSSGGGGSGGGGSGGGGSQTVVTQEPSLTVSPGGTVTL<br>TCGSSTGAVTSANYPNWVQQKPGQAPRGLIGGTKFLAP<br>GTPARFSGSLLGGKAALTLSGVQPEDEAEYYCALWYSN<br>RWVFGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 381 |
| PC-46 LC (anti-TROP2 F108A; anti-CD3 N30Q, I109V, G172A, V231A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 382 |
| PC-46 HC (anti-TROP2 F108A; anti-CD3 N30Q, I109V, G172A, V231A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAASGFTFQKYAMNWVRQAPGKGLEWV<br>ARIRSKYNNYATYYADSVKDRFTISRDDSKNTAYLQMN<br>NLKTEDTAVYYCVRHGNFGNSYVSYWAYWGQGTLVT<br>VSSGGGGSGGGGSGGGGSQTVVTQEPSLTVSPGGTVTL<br>TCGSSTGAVTSANYPNWVQQKPGQAPRGLIGGTKFLAP<br>GTPARFSGSLLGGKAALTLSGVQPEDEAEYYCALWYSN<br>RWVFGGGTKLTVLGGGGSQVQLQQSGSELKKPGASVK<br>VSCKAS**GYTFTNYG**MNWVKQAPGQGLKWMGW**INTY**<br>**TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | 383 |

TABLE 12-continued

Polypeptide complex sequences (masked sequences that bind to TROP2 and CD3e)

| Construct Description | Amino Acid Sequence (N to C) | SEQ ID NO: |
|---|---|---|
| PC-47 LC (non-cleavable linker) (anti-TROP2 D109A; anti-CD3 wt) | GGVDFCGLYHWPICYQGGGGSGGGGSGGGGSGGASS<br>GAGGSDIQLTQSPSSLSASVGDRVSITCKAS**QDVSIA**VA<br>WYQQKPGKAPKLLIY**SAS**YRYTGVPDRFSGSGSGTDFTL<br>TISSLQPEDFAVYYC**QQHYITPLT**FGAGTKVEIKRTVAA<br>PSVFIFPPSDEQLKSGTASVVCLLNNFYPREAKVQWKVD<br>NALQSGNSQESVTEQDSKDSTYSLSSTLTLSKADYEKHK<br>VYACEVTHQGLSSPVTKSFNRGEC | 384 |
| PC-47 HC (non-cleavable linker) (anti-TROP2 D109A; anti-CD3 wt) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGSGGGGSGGASSGAGGSGGGSEVQLVESGGG<br>LVQPGGSLKLSCAAS**GFTFNKYA**MNWVRQAPGKGLE<br>WVAR**IRSKYNNY**ATYYADSVKDRFTISRDDSKNTAYLQ<br>MNNLKTEDTAVYYC**VRHGNFGNSYISYWAY**WGQGTL<br>VTVSSGGGGSGGGGSGGGGSQTVVTQEPSLTVSPGGTV<br>TLTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW**IN**<br>**TYTGEP**TYTDDFKGRFAFSLDTSVSTAYLQISSLKADDT<br>AVYFC**ARGGFGSSYWYFAV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 385 |
| PC-48 LC (non-cleavable linker) (anti-TROP2 F108A; anti-CD3 wt) | GGVDFCALYHWPICYQGGGGSGGGSGGSGGASSGAGG<br>SGGGSDIQLTQSPSSLSASVGDRVSITCKAS**QDVSIA**VA<br>WYQQKPGKAPKLLIY**SAS**YRYTGVPDRFSGSGSGTDFTL<br>TISSLQPEDFAVYYC**QQHYITPLT**FGAGTKVEIKRTVAA<br>PSVFIFPPSDEQLKSGTASVVCLLNNFYPREAKVQWKVD<br>NALQSGNSQESVTEQDSKDSTYSLSSTLTLSKADYEKHK<br>VYACEVTHQGLSSPVTKSFNRGEC | 386 |
| PC-48 HC (non-cleavable linker) (anti-TROP2 F108A; anti-CD3 wt) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGGSGGGGSGGASSGAGGSGGGSEVQLVESGGG<br>LVQPGGSLKLSCAAS**GFTFNKYA**MNWVRQAPGKGLE<br>WVAR**IRSKYNNYAT**YYADSVKDRFTISRDDSKNTAYL<br>QMNNLKTEDTAVYYC**VRHGNFGNSYISYWAY**WGQGT<br>LVTVSSGGGGSGGGGSGGGGSQTVVTQEPSLTVSPGGT<br>VTLTCGSS**TGAVTSGNY**PNWVQQKPGQAPRGLIG**GTK**<br>FLAPGTPARFSGSLLGGKAALTLSGVQPEDEAEYYC**VL**<br>**WYSNRWV**FGGGTKLTVLGGGGSQVQLQQSGSELKKPG<br>ASVKVSCKAS**GYTFTNYG**MNWVKQAPGQGLKWMG<br>W**INTYTGEP**TYTDDFKGRFAFSLDTSVSTAYLQISSLKAD<br>DTAVYFC**ARGGFGSSYWYADV**WGQGSLVTVSSASTK<br>GPSVFPLAPSSKSTSGGTAALGCLVKDYFPEPVTVSWNS<br>GALTSGVHTFPAVLQSSGLYSLSSVVTVPSSSLGTQTYIC<br>NVNHKPSNTKVDKKVEPKSC | 387 |
| PC-49 LC (CL2 cleavable linker) (anti-TROP2 F108A; anti-CD3 wt) | GGVDFCALYHWPICYQGGGSGGSGGISSGLLSGRSDAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 388 |
| PC-49 HC (CL2 cleavable linker) (anti-TROP2 F108A; anti-CD3 wt) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCMG<br>GGGSGGSGGISSGLLSGRSDAGSGGGSEVQLVESGGGLV<br>QPGGSLKLSCAAS**GFTFNKYA**MNWVRQAPGKGLEWV<br>AR**IRSKYNNYAT**YYADSVKDRFTISRDDSKNTAYLQMN<br>NLKTEDTAVYYC**VRHGNFGNSYISYWAY**WGQGTLVT<br>VSSGGGGSGGGGSGGGGSQTVVTQEPSLTVSPGGTVTL<br>TCGSS**TGAVTSGNY**PNWVQQKPGQAPRGLIG**GTK**FLAP<br>GTPARFSGSLLGGKAALTLSGVQPEDEAEYYC**VLWYSN**<br>**RWV**FGGGTKLTVLGGGGSQVQLQQSGSELKKPGASVK<br>VSCKAS**GYTFTNYG**MNWVKQAPGQGLKWMGW**INTY** | 389 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | **TGEP**TYTDDFKGRFAFSLDTSVSTAYLQISSLKADDTAV<br>YFC**ARGGFGSSYWYADV**WGQGSLVTVSSASTKGPSVF<br>PLAPSSKSTSGGTAALGCLVKDYFPEPVTVSWNSGALTS<br>GVHTFPAVLQSSGLYSLSSVVTVPSSSLGTQTYICNVNH<br>KPSNTKVDKKVEPKSC | |
| PC-50 LC<br>(anti-TROP2<br>F108A; anti-CD3<br>H101A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 390 |
| PC-50 HC<br>(anti-TROP2<br>F108A; anti-CD3<br>H101A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYCV**RAGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VLWY**<br>**SNRWV**FGGGTKLTVLGGGGSQVQLQQSGSELKKPGAS<br>VKVSCKAS**GYTFTNYG**MNWVKQAPGQGLKWMGW<br>**INTYTGEP**TYTDDFKGRFAFSLDTSVSTAYLQISSLKAD<br>DTAVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNV<br>NHKPSNTKVDKKVEPKSC | 391 |
| PC-51 LC<br>(anti-TROP2<br>F108A; anti-CD3<br>L232A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 392 |
| PC-51 HC<br>(anti-TROP2<br>F108A; anti-CD3<br>L232A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM<br>NNLKTEDTAVYYC**VRHGNFGNSYISYWAY**WGQGTLV<br>TVSSGGGGSGGGGSGGGGSQTVVTQEPSLTVSPGGTVT<br>LTCGSS**TGAVTSGNY**PNWVQQKPGQAPRGLIG**GTK**FL<br>APGTPARFSGSLLGGKAALTLSGVQPEDEAEYYC**VAWY**<br>**SNRWV**FGGGTKLTVLGGGGSQVQLQQSGSELKKPGAS<br>VKVSCKAS**GYTFTNYG**MNWVKQAPGQGLKWMGW<br>**INTYTGEP**TYTDDFKGRFAFSLDTSVSTAYLQISSLKAD<br>DTAVYFC**ARGGFGSSYWYADV**WGQGSLVTVSSASTKGPS<br>VFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSC | 393 |
| PC-52 LC<br>(anti-TROP2<br>F108A; anti-CD3<br>N236A) | GGVDFCALYHWPICYQGGGGSGGLSGRSDAGSPLGLAG<br>SGGSDIQLTQSPSSLSASVGDRVSITCKAS**QDVSIA**VAW<br>YQQKPGKAPKLLIY**SAS**YRYTGVPDRFSGSGSGTDFTLTI<br>SSLQPEDFAVYYC**QQHYITPLT**FGAGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC | 394 |
| PC-52 HC<br>(anti-TROP2<br>F108A; anti-CD3<br>N236A) | EVQLVESGGGLVQPGGSLRLSCAASGSTFYTAVMGWV<br>RQAPGKGLEWVAAIRWTALTTSYADSVKGRFTISRDGA<br>KTTLYLQMNSLRPEDTAVYYCAARGTLGLFTTADSYDY<br>WGQGTLVTVSSGGGGSGGGSGGVYCGPEFDESVGCAG<br>GGGSGGGLSGRSDAGSPLGLAGSGGGSEVQLVESGGGL<br>VQPGGSLKLSCAAS**GFTFNKYA**MNWVRQAPGKGLEW<br>VAR**IRSKYNNYAT**YYADSVKDRFTISRDDSKNTAYLQM | 395 |

TABLE 12-continued

Polypeptide complex sequences (masked sequences that bind to TROP2 and CD3e)

| Construct Description | Amino Acid Sequence (N to C) | SEQ ID NO: |
|---|---|---|
| | NNLKTEDTAVYYC**VRHGNFGNSYISYWAY**WGQGTLV TVSSGGGGSGGGGSGGGGSQTVVTQEPSLTVSPGGTVT LTCGSS**TGAVTSGNY**PNWVQQKPGQAPRGLIG**GTK**FL APGTPARFSGSLLGGKAALTLSGVQPEDEAEYYC**VLWY SARWV**FGGGTKLTVLGGGGSQVQLQQSGSELKKPGAS VKVSCKAS**GYTFTNYG**MNWVKQAPGQGLKWMGW **INTYTGEP**TYTDDFKGRFAFSLDTSVSTAYLQISSLKAD AVYFC**ARGGFGSSYWYADV**WGQGSLVTVSSASTKGPS DTVFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSC | |

Disclosed herein are isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 26; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease. In some embodiments, $P_1$ comprises an amino acid sequence according to any one of SEQ ID NOs: 107, 141, 142, and 150, or an amino acid sequence that has 1, 2, or 3 amino acid mutations, substitutions or deletions relative to any one of SEQ ID NOs: 107, 141, 142, and 150. In some embodiments, $P_1$ comprises the amino acid sequence according to any one of SEQ ID NOs: 100-107, 109, 111-113, 116-117, 119, and 123-163. In some embodiments, $P_1$ comprises the amino acid sequence according to any one of SEQ ID NOs: 107, 141, 142, and 150. In some embodiments, $P_1$ comprises an amino acid sequence according to SEQ ID NO: 142, or an amino acid sequence that has 1, 2, or 3 amino acid mutations, substitutions or deletions relative to SEQ ID NO: 142. In some embodiments, $P_1$ comprises an amino acid sequence according to SEQ ID NO: 142.

In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises an amino acid sequence with at least 85% identity to SEQ ID NO: 69 and the immunoglobulin heavy chain comprises an amino acid sequence with at least 85% identity to SEQ ID NO: 70. In some embodiments, the immunoglobulin light chain comprises an amino acid sequence with at least 90% identity to SEQ ID NO: 69 and the immunoglobulin heavy chain comprises an amino acid sequence with at least 90% identity to SEQ ID NO: 70. In some embodiments, the immunoglobulin light chain comprises an amino acid sequence with at least 92% identity to SEQ ID NO: 69 and the immunoglobulin heavy chain comprises an amino acid sequence with at least 92% identity to SEQ ID NO: 70. In some embodiments, the immunoglobulin light chain comprises an amino acid sequence with at least 95% identity to SEQ ID NO: 69 and the immunoglobulin heavy chain comprises an amino acid sequence with at least 95% identity to SEQ ID NO: 70. In some embodiments, the immunoglobulin light chain comprises an amino acid sequence with at least 98% identity to SEQ ID NO: 69 and the immunoglobulin heavy chain comprises an amino acid sequence with at least 98% identity to SEQ ID NO: 70. In some embodiments, the immunoglobulin light chain comprises an amino acid sequence with at least 99% identity to SEQ ID NO: 69 and the immunoglobulin heavy chain comprises an amino acid sequence with at least 99% identity to SEQ ID NO: 70. In some embodiments, the immunoglobulin light chain comprises an amino acid sequence of SEQ ID NO: 69 and the immunoglobulin heavy chain comprises an amino acid sequence of SEQ ID NO: 70.

In some embodiments, the isolated polypeptide or polypeptide complex further comprises a CD3 binding domain. In some embodiments, the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 80.

In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 276. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76, CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 273.

In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82. In some embodiments, the CD3 binding domain comprises a Fab, Fab', $(Fab')_2$ or a single chain variable fragment (scFv). In some embodiments, the CD3 binding domain is the scFv. In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 329. In some embodiments, the CD3 binding domain comprises an amino acid sequence with at least 90%, 95%, 96%, 97%, 98%, 99%, or 100% identity to SEQ ID NO: 305.

In some embodiments, $P_2$ comprises the amino acid sequence of SEQ ID NO: 289 or SEQ ID NO: 292. In some embodiments, $P_2$ comprises the amino acid sequence of SEQ ID NO: 295. In some embodiments, the isolated polypeptide or polypeptide complex comprises amino acid sequences with at least 90%, 95%, 96%, 97%, 98%, 99%, or 100% identity to SEQ ID NO: 200 and SEQ ID NO: 201. In some embodiments, the isolated polypeptide or polypeptide complex comprises amino acid sequences of SEQ ID NO: 200 and SEQ ID NO: 201. In some embodiments, the isolated polypeptide or polypeptide complex comprises amino acid sequences with at least 90%, 95%, 96%, 97%, 98%, 99%, or 100% identity to SEQ ID NO: 362 and SEQ ID NO: 363. In some embodiments, the isolated polypeptide or polypeptide complex comprises amino acid sequences with at least 90%, 95%, 96%, 97%, 98%, 99%, or 100% identity to SEQ ID NO: 382 and SEQ ID NO: 383. In some embodiments, the isolated polypeptide or polypeptide complex comprises amino acid sequences with at least 90%, 95%, 96%, 97%, 98%, 99%, or 100% identity to SEQ ID NO: 390 and SEQ ID NO: 391.

Disclosed herein are isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 27; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease. In some embodiments, $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions or deletions relative to any one of SEQ ID NOs: 107, 109, 116, 141, 142, 148, 149, 150, and 158. In some embodiments, $P_1$ comprises the amino acid sequence according to any one of SEQ ID NOs: 100-107, 109, 111-113, 116-117, 119, and 123-163. In some embodiments, $P_1$ comprises the amino acid sequence according to any one of SEQ ID NOs: 107, 109, 116, 141, 142, 148, 149, 150, and 158. In some embodiments, $P_1$ comprises an amino acid sequence according to SEQ ID NO: 107, or an amino acid sequence that has 1, 2, or 3 amino acid mutations, substitutions or deletions relative to SEQ ID NO: 107.

In some embodiments, the TROP2 binding domain comprises a Fab, Fab', $(Fab')_2$ or a single chain variable fragment (scFv). In some embodiments, the TROP2 binding domain is a Fab. In some embodiments, the immunoglobulin light chain comprises an amino acid sequence with at least 85% identity to SEQ ID NO: 71 and the immunoglobulin heavy chain comprises an amino acid sequence with at least 85% identity to SEQ ID NO: 72. In some embodiments, the immunoglobulin light chain comprises an amino acid sequence with at least 90% identity to SEQ ID NO: 71 and the immunoglobulin heavy chain comprises an amino acid sequence with at least 90% identity to SEQ ID NO: 72. In some embodiments, the immunoglobulin light chain comprises an amino acid sequence with at least 92% identity to SEQ ID NO: 71 and the immunoglobulin heavy chain comprises an amino acid sequence with at least 92% identity to SEQ ID NO: 72. In some embodiments, the immunoglobulin light chain comprises an amino acid sequence with at least 95% identity to SEQ ID NO: 71 and the immunoglobulin heavy chain comprises an amino acid sequence with at least 95% identity to SEQ ID NO: 72. In some embodiments, the immunoglobulin light chain comprises an amino acid sequence with at least 98% identity to SEQ ID NO: 71 and the immunoglobulin heavy chain comprises an amino acid sequence with at least 98% identity to SEQ ID NO: 72. In some embodiments, the immunoglobulin light chain comprises an amino acid sequence with at least 99% identity to SEQ ID NO: 71 and the immunoglobulin heavy chain comprises an amino acid sequence with at least 99% identity to SEQ ID NO: 72. In some embodiments, the immunoglobulin light chain comprises an amino acid sequence of SEQ ID NO: 71 and the immunoglobulin heavy chain comprises an amino acid sequence of SEQ ID NO: 72.

In some embodiments, the isolated polypeptide or polypeptide complex further comprises a CD3 binding domain. In some embodiments, the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 80.

In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76, CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 276. In some embodiments, the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76, CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286.

In some embodiments, the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82. In some embodiments, the CD3 binding domain comprises a Fab, Fab', $(Fab')_2$ or a single chain variable fragment (scFv). In some embodiments, the CD3 binding domain is the scFv. In some embodiments, the CD3 binding domain comprises an amino acid sequence with at least 90%, 95%, 96%, 97%, 98%, 99%, or 100% identity to SEQ ID NO: 99. In some embodiments, the CD3 binding domain comprises an amino acid sequence with at least 90%, 95%, 96%, 97%, 98%, 99%, or 100% identity to SEQ ID NO: 308. In some embodiments, the CD3 binding domain comprises an amino acid sequence with at least 90%, 95%, 96%, 97%, 98%, 99%, or 100% identity to SEQ ID NO: 329.

In some embodiments, $P_2$ comprises the amino acid sequence of SEQ ID NO: 289 or SEQ ID NO: 292. In some embodiments, the isolated polypeptide or polypeptide complex comprises amino acid sequences with at least 90%, 95%, 96%, 97%, 98%, 99%, or 100% identity to SEQ ID NO: 180 and SEQ ID NO: 181. In some embodiments, the isolated polypeptide or polypeptide complex comprises amino acid sequences of SEQ ID NO: 180 and SEQ ID NO: 181. In some embodiments, the isolated polypeptide or polypeptide complex comprises amino acid sequences with at least 90%, 95%, 96%, 97%, 98%, 99%, or 100% identity to SEQ ID NO: 352 and SEQ ID NO: 353. In some embodiments, the isolated polypeptide or polypeptide complex comprises amino acid sequences with at least 90%, 95%, 96%, 97%, 98%, 99%, or 100% identity to SEQ ID NO: 354 and SEQ ID NO: 355.

Polynucleotides Encoding Recombinant Isolated Polypeptide or Polypeptide Complex Compositions Disclosed herein, in some embodiments, are isolated recombinant nucleic acid molecules encoding isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}$ $X_{13}YWX_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease.

Disclosed herein, in some embodiments, are isolated recombinant nucleic acid molecules encoding isolated polypeptides or polypeptide complexes according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1; CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connect $A_1$ to $P_1$ and is a substrate for a tumor specific protease.

Pharmaceutical Compositions

Disclosed herein, in some embodiments, are pharmaceutical compositions comprising: (a) the isolated polypeptide or polypeptide complex according to any of the embodiments disclosed herein and (b) a pharmaceutically acceptable excipient.

In some embodiments, the isolated polypeptide or polypeptide complex is according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; and wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q, or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YWX_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that bind to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease.

In some embodiments, the polypeptide or polypeptide complex is according to Formula I: $A_1$-$L_1$-$P_1$ wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2, CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 5 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 6 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 7 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 8 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 9 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 10 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 11 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 12 and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2; CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2, CDR3-L: SEQ ID NO: 3, and CDR1-H: SEQ ID NO: 13, CDR2-H: SEQ ID NO: 14, CDR3-H: SEQ ID NO: 28, $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connect $A_1$ to $P_1$ and is a substrate for a tumor specific protease.

For administration to a subject, the recombinant antibodies or antigen binding fragments thereof as disclosed herein, may be provided in a pharmaceutical composition together with one or more pharmaceutically acceptable carriers or excipients. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Methods of Treatment

In some embodiments, are methods of treating cancer in a subject need in need thereof comprising administering to the subject an isolated polypeptide or polypeptide complex as described herein. In some embodiments, the cancer has cells that express TROP2. In some instances, the cancer is a solid tumor cancer. In some embodiments, the cancer is lung, breast (e.g. HER2+; ER/PR+; TNBC), cervical, ovarian, colorectal, pancreatic or gastric.

In some embodiments, are methods of treating triple-negative breast cancer (TNBC), urothelial cancer (UC), non-small cell lung cancer (NSCLC), small cell lung cancer (SCLC), gastric cancer, esophageal cancer, head and neck cancer, prostate cancer, or endometrial cancer in a subject need in need thereof comprising administering to the subject a polypeptide or polypeptide complex as described herein. In some embodiments, are methods of treating breast cancer, lung cancer, urothelial cancer, endometrial cancer, ovarian cancer, prostate cancer, pancreatic cancer, gastric cancer, colon cancer, head and neck cancer, and glioma in a subject need in need thereof comprising administering to the subject a polypeptide or polypeptide complex as described herein.

Production of Antibodies

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk−, hgprt− or aprt− cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac 1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4 Mammalian stable expression vector may include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-*Thermus*, Fibrobacteres-Chlorobi/Bacteroidetes (FCB group), Fusobacteria, Gemmatimonadetes, Nitrospirae, Planctomycetes—Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli* bacilli.

Exemplary prokaryotic host cells include, but are not limited to, BL21, Mach1™, $DH_{10}B$™, TOP10, DH5a, DH10Bac™, OmniMax™, MegaX™, DH12S™, INV110, TOP10F', INVαF, TOP10/P3, ccdB Survival, PIR1, PIR2, Stb12™, Stb13™, or Stb14™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis,*

*Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to CD3 and a second antigen-binding site that specifically binds to TROP2 as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EMBODIMENTS

Embodiment 1 comprises an isolated polypeptide or polypeptide complex according to Formula I: $A_1$-$L_1$-$P_1$(Formula I) wherein $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2 (SA); and wherein CDR3-L comprises wherein CDR3-L comprises an amino acid sequence of $X_1X_2HYX_3X_4X_5X_6X_7$; wherein $X_1$ is Q, S, T, D, N, E, H, K, R, or A; $X_2$ is Q, S, T, D, N, E, H, K, R, or A; $X_3$ is I, G, P, V, L, M, S, T, or A; $X_4$ is T, G, S, M, H, N, Q or A; $X_5$ is P, G, V, L, I, M, S, T, or A; $X_6$ is L, G, P, V, I, M, S, T, or A; and $X_7$ is T, G, S, M, H, N, Q, or A; wherein CDR1-H comprises the amino acid sequence of SEQ ID NO: 13; wherein CDR1-H comprises the amino acid sequence of SEQ ID NO: 13; wherein CDR2-H comprises the amino acid sequence of SEQ ID NO: 14; and wherein CDR3-H comprises an amino acid sequence of $AX_8X_9GX_{10}X_{11}X_{12}X_{13}YWX_{14}X_{15}X_{16}X_{17}$; wherein $X_8$ is R, S, T, Q, D, E, H, K, N, or A; $X_9$ is G, P, V, L, I, M, S, T, or A; $X_{10}$ is F, Y, W, V, L, I, G, or A; $X_{11}$ is G, P, V, L, I, M, S, T, or A; $X_{12}$ is S, G, T, M, N, Q, H, or A; $X_{13}$ is S, G, T, M, N, Q, H, or A; $X_{14}$ is Y, F, W, V, L, I, G, or A; $X_{15}$ is F, Y, W, V, L, I, G, or A; $X_{16}$ is D, Q, N, E, S, T, H, K, R, or A; and $X_{17}$ is V, G, P, L, I, M, S, T, or A; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one of SEQ ID NOs: 100-163; and $L_1$ comprises a linking moiety that connects $A_1$ to $P_1$ and is a substrate for a tumor specific protease.

Embodiment 2 comprises the isolated polypeptide or polypeptide complex according to embodiment 1, wherein $X_1$ is Q, N, D, E, or A; $X_2$ is Q, N, D, E, or A; $X_3$ is I, V, L, or A; $X_4$ is T, S, or A; $X_5$ is P, G, or A; $X_6$ is L, V, I, or A;

$X_7$ is T, S, or A; $X_8$ is R, K, or A; $X_9$ is G, S, T, or A; $X_{10}$ is F, Y, or A; $X_{11}$ is G, S, T, or A; $X_{12}$ is S, G, T, or A; $X_{13}$ is S, G, T, or A; $X_{14}$ is Y, W, F, or A; $X_{15}$ is F, Y, W, or A; $X_{16}$ is D, E, Q, N, or A; and $X_{17}$ is V, L, I, or A.

Embodiment 3 comprises the isolated polypeptide or polypeptide complex according to embodiments 1 or 2, wherein $X_1$ is Q; and $X_6$ is L.

Embodiment 4 comprises the isolated polypeptide or polypeptide complex according to any one of embodiments 1 to 3, wherein $X_8$ is R; $X_{10}$ is F; $X_{11}$ is G; $X_{14}$ is Y; $X_{15}$ is F; and $X_{16}$ is D.

Embodiment 5 comprises the isolated polypeptide or polypeptide complex according to embodiment 1, wherein $X_1$ is Q, S, T, D, N, E, or A; $X_2$ is Q, S, T, D, N, E, or A; $X_3$ is I, G, P, V, L, M, or A; $X_4$ is T, G, S, M, H, N, Q, or A; $X_5$ is P, G, V, L, I, M, or A; $X_6$ is L, G, P, V, I, M, or A; $X_7$ is T, G, S, M, H, N, Q, or A; $X_8$ is R, H, K, or A; $X_9$ is G, P, V, L, I, M, S, T, or A; $X_{10}$ is F, Y, W, V, L, I, or A; $X_{11}$ is G, P, V, L, I, M, S, T, or A; $X_{12}$ is S, G, T, M, N, Q, or A; $X_{13}$ is S, G, T, M, N, Q, or A; $X_{14}$ is Y, F, W, V, L, I, or A; $X_{15}$ is F, Y, W, V, L, I, or A; $X_{16}$ is D, Q, N, E, S, T, or A; and $X_{17}$ is V, G, P, L, I, M, or A.

Embodiment 6 comprises the isolated polypeptide or polypeptide complex according to embodiment 5, wherein $X_1$ is Q, N, or A; $X_2$ is Q, N, or A; $X_3$ is I, V, L, or A; $X_4$ is T, S, or A; $X_5$ is P, G, or A; $X_6$ is L, V, I, or A; $X_7$ is T, S, or A; $X_8$ is R, K, or A; $X_9$ is G, V, S, T, or A; $X_{10}$ is F, Y, or A; $X_{11}$ is G, V, S, T, or A; $X_{12}$ is S, G, T, or A; $X_{13}$ is S, G, T, or A; $X_{14}$ is Y, W, or A; $X_{15}$ is F, Y, or A; $X_{16}$ is D, E, or A; and $X_{17}$ is V, G, L, I, or A.

Embodiment 7 comprises the isolated polypeptide or polypeptide complex according to embodiment 5, wherein $X_1$ is Q; and $X_6$ is L.

Embodiment 8 comprises the isolated polypeptide or polypeptide complex according to embodiment 7, wherein $X_8$ is R; $X_{10}$ is F; $X_{11}$ is G; $X_{14}$ is Y; $X_{15}$ is F; and $X_{16}$ is D.

Embodiment 9 comprises the isolated polypeptide or polypeptide complex according to embodiment 1, wherein CDR3-L comprises an amino acid selected from SEQ ID NOs: 3-5 and 8-12.

Embodiment 10 comprises the isolated polypeptide or polypeptide complex according to embodiment 1, wherein the immunoglobulin light chain and the immunoglobulin heavy chain comprise a set of CDR sequences selected from the group consisting of: CDR1-L: SEQ ID NO: 1, CDR2-L: SEQ ID NO: 2 (SA), CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 10, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 11, and CDR1-H: SEQ ID NO: 13, CDR2-H: SEQ ID NO: 14, CDR3-H: SEQ ID NO: 15; and CDR1-L: SEQ ID NO: 1, CDR2-L: SEQ ID NO: 2 (SA), CDR3-L: SEQ ID NO: 12, and CDR1-H: SEQ ID NO: 13, CDR2-H: SEQ ID NO: 14, CDR3-H: SEQ ID NO: 15.

Embodiment 11 comprises the isolated polypeptide or polypeptide complex according to embodiment 1, wherein the immunoglobulin light chain and the immunoglobulin heavy chain comprise a set of CDR sequences selected from the group consisting of: CDR1-L: SEQ ID NO: 1, CDR2-L: SEQ ID NO: 2 (SA), CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 10, and CDR1-H: SEQ ID NO: 13, CDR2-H: SEQ ID NO: 14, CDR3-H: SEQ ID NO: 15; and CDR1-L: SEQ ID NO: 1, CDR2-L: SEQ ID NO: 2 (SA), CDR3-L: SEQ ID NO: 12, and CDR1-H: SEQ ID NO: 13, CDR2-H: SEQ ID NO: 14, CDR3-H: SEQ ID NO: 15.

Embodiment 12 comprises the isolated polypeptide or polypeptide complex according to embodiment 1, wherein CDR3-H comprises an amino acid selected from SEQ ID NOs: 16-17, 19-22, and 25-28.

Embodiment 13 comprises the isolated polypeptide or polypeptide complex according to embodiment 1, wherein the immunoglobulin light chain and the immunoglobulin heavy chain comprise a set of CDR sequences selected from the group consisting of: CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14; CDR3-H: SEQ ID NO: 16; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 22; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 28.

Embodiment 14 comprises the isolated polypeptide or polypeptide complex according to embodiment 1, wherein the immunoglobulin light chain and the immunoglobulin heavy chain comprise a set of CDR sequences selected from the group consisting of: CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 22; and CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 28.

Embodiment 15 comprises an isolated polypeptide or polypeptide complex according to Formula I: $A_1$-$L_1$-$P_1$ (Formula I) wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 1, CDR2-L: SEQ ID NO: 2 (SA), CDR3-L: SEQ ID NO: 4, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 5, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 6, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 7, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 8, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 9, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 10, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 11, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 12, and CDR1-H: SEQ ID NO: 13, CDR2-H: SEQ ID NO: 14, CDR3-H: SEQ ID NO: 15; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 16; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 17; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 18; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 19; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 20; CDR1-L: SEQ ID NO: 1, CDR2-L: SEQ ID NO: 2 (SA); CDR3-L: SEQ ID NO: 3, and CDR1-H: SEQ ID NO: 13, CDR2-H: SEQ ID NO: 14, CDR3-H: SEQ ID NO: 21; CDR1-L: SEQ ID NO: 1, CDR2-L: SEQ ID NO: 2 (SA); CDR3-L: SEQ ID NO: 3, and CDR1-H: SEQ ID NO: 13, CDR2-H: SEQ ID NO: 14; CDR3-H: SEQ ID NO: 22; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 23; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 24; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 25; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 26; CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 27; and CDR1-L: SEQ ID NO: 1, CDR2-L: SEQ ID NO: 2 (SA), CDR3-L: SEQ ID NO: 3, and CDR1-H: SEQ ID NO: 13, CDR2-H: SEQ ID NO: 14, CDR3-H: SEQ ID NO: 28; $P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connects $A_1$ to $P_1$ and is a substrate for a tumor specific protease.

Embodiment 16 comprises the isolated polypeptide or polypeptide complex according to any one of embodiments 1-15, wherein the TROP2 binding domain comprises a Fab, Fab', $(Fab')_2$ or a single chain variable fragment (scFv).

Embodiment 17 comprises the isolated polypeptide or polypeptide complex according to any one of embodiments 1-16, wherein the TROP2 binding domain is a Fab.

Embodiment 18 comprises the isolated polypeptide or polypeptide complex according to any one of embodiments 1-17, wherein the immunoglobulin light chain comprises a variable domain of an immunoglobulin kappa (IgK) or immunoglobulin lambda (IgL) light chain.

Embodiment 19 comprises the isolated polypeptide or polypeptide complex according to any one of embodiments 1-18, wherein the immunoglobulin heavy chain comprises a variable domain of an IgG1, IgG2, IgG3, or IgG4 heavy chain.

Embodiment 20 comprises the isolated polypeptide or polypeptide complex according to any one of embodiments 1-19, wherein the immunoglobulin light chain comprises an amino acid sequence with at least 90%, 95%, 96%, 97%, 98%, 99%, or 100% identity to any one of SEQ ID NOs: 31, 33, 35, 37, 39, 41, 43, 45, 47, 49, 51, 53, 55, 57, 59, 61, 63, 65, 67, 69, 71, or 73.

Embodiment 21 comprises the isolated polypeptide or polypeptide complex according to any one of embodiments 1-20, wherein the immunoglobulin heavy chain comprises an amino acid sequence with at least 90%, 95%, 96%, 97%, 98%, 99%, or 100% identity to any one of SEQ ID NOs: 32, 34, 36, 38, 40, 42, 44, 46, 48, 50, 52, 54, 56, 58, 60, 62, 64, 66, 68, 70, 72, or 74.

Embodiment 22 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 31 and the immunoglobulin heavy chain comprises an amino acid sequence with at least 90%, 95%, 96%, 97%, 98%, 99%, or 100% identity to SEQ ID NO: 32.

Embodiment 23 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 33 and the immunoglobulin heavy chain comprises an amino acid sequence with at least 90%, 95%, 96%, 97%, 98%, 99%, or 100% identity to SEQ ID NO: 34.

Embodiment 24 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 35 and the immunoglobulin heavy chain comprises an amino acid sequence with at least 90%, 95%, 96%, 97%, 98%, 99%, or 100% identity to SEQ ID NO: 36.

Embodiment 25 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 37 and the immunoglobulin heavy chain comprises an amino acid sequence with at least 90%, 95%, 96%, 97%, 98%, 99%, or 100% identity to SEQ ID NO: 38.

Embodiment 26 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40.

Embodiment 27 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 41 and the immunoglobulin heavy chain comprises an amino acid sequence with at least 90%, 95%, 96%, 97%, 98%, 99%, or 100% identity to SEQ ID NO: 42.

Embodiment 28 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 43 and the immunoglobulin heavy chain comprises an amino acid sequence with at least 90%, 95%, 96%, 97%, 98%, 99%, or 100% identity to SEQ ID NO: 44.

Embodiment 29 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 45 and the immunoglobulin heavy chain comprises an amino acid sequence with at least 90%, 95%, 96%, 97%, 98%, 99%, or 100% identity to SEQ ID NO: 46.

Embodiment 30 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 47 and the immunoglobulin heavy chain comprises an amino acid sequence with at least 90%, 95%, 96%, 97%, 98%, 99%, or 100% identity to SEQ ID NO: 48.

Embodiment 31 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50.

Embodiment 32 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 51 and the immunoglobulin heavy chain comprises an amino acid sequence with at least 90%, 95%, 96%, 97%, 98%, 99%, or 100% identity to SEQ ID NO: 52.

Embodiment 33 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 53 and the immunoglobulin heavy chain comprises an amino acid sequence with at least 90%, 95%, 96%, 97%, 98%, 99%, or 100% identity to SEQ ID NO: 54.

Embodiment 34 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 55 and the immunoglobulin heavy chain comprises an amino acid sequence with at least 90%, 95%, 96%, 97%, 98%, 99%, or 100% identity to SEQ ID NO: 56.

Embodiment 35 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 59 and the immunoglobulin heavy chain comprises an amino acid sequence with at least 90%, 95%, 96%, 97%, 98%, 99%, or 100% identity to SEQ ID NO: 60.

Embodiment 36 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62.

Embodiment 37 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 63 and the immunoglobulin heavy chain comprises an amino acid sequence with at least 90%, 95%, 96%, 97%, 98%, 99%, or 100% identity to SEQ ID NO: 64.

Embodiment 38 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 65 and the immunoglobulin heavy chain comprises an amino acid sequence with at least 90%, 95%, 96%, 97%, 98%, 99%, or 100% identity to SEQ ID NO: 66.

Embodiment 39 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 67 and the immunoglobulin heavy chain comprises an amino acid sequence with at least 90%, 95%, 96%, 97%, 98%, 99%, or 100% identity to SEQ ID NO: 68.

Embodiment 40 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70.

Embodiment 41 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72.

Embodiment 42 comprises the isolated polypeptide or polypeptide complex according to any one of embodiments 1 and 15-21, wherein the immunoglobulin light chain comprises an amino acid sequence with at least 90%, 95%, 96%, 97%, 98%, 99%, or 100% identity to SEQ ID NO: 73 and the immunoglobulin heavy chain comprises an amino acid sequence with at least 90%, 95%, 96%, 97%, 98%, 99%, or 100% identity to SEQ ID NO: 74.

Embodiment 43 comprises the isolated polypeptide or polypeptide complex according to any one of the preceding embodiments, wherein the TROP2 binding domain has weaker binding to TROP2 as compared to a TROP2 binding domain that comprises an immunoglobulin light chain according to SEQ ID NO: 29 and an immunoglobulin heavy chain according to SEQ ID NO: 30 as measured by ELISA in substantially similar assay conditions.

Embodiment 44 comprises the isolated polypeptide or polypeptide complex according to any one of the preceding embodiments, wherein the TROP2 binding domain has an increased $EC_{50}$ for TROP2 as compared to a TROP2 binding domain that comprises an immunoglobulin light chain according to SEQ ID NO: 29 and an immunoglobulin heavy chain according to SEQ ID NO: 30 as measured by ELISA in substantially similar assay conditions.

Embodiment 45 comprises the isolated polypeptide or polypeptide complex according to any one of the preceding embodiments, wherein the TROP2 binding domain has a faster off rate (larger $k_{diss}$) for TROP2 binding as compared to a TROP2 binding domain that comprises an immunoglobulin light chain according to SEQ ID NO: 29 and an immunoglobulin heavy chain according to SEQ ID NO: 30 as measured under substantially similar kinetic assay conditions.

Embodiment 46 comprises the isolated polypeptide or polypeptide complex according to any one of the preceding embodiments, wherein $P_1$ impairs binding of $A_1$ to TROP2.

Embodiment 47 comprises the isolated polypeptide or polypeptide complex according to any one of the preceding embodiments, wherein $P_1$ is bound to $A_1$ through ionic interactions, electrostatic interactions, hydrophobic interactions, Pi-stacking interactions, and H-bonding interactions, or a combination thereof.

Embodiment 48 comprises the isolated polypeptide or polypeptide complex according to any one of the preceding embodiments, wherein $P_1$ is bound to $A_1$ at or near an antigen binding site.

Embodiment 49 comprises the isolated polypeptide or polypeptide complex according to any one of the preceding embodiments, wherein $P_1$ becomes unbound from $A_1$ when $L_1$ is cleaved by the tumor specific protease thereby exposing $A_1$ to TROP2.

Embodiment 50 comprises the isolated polypeptide or polypeptide complex according to any one of the preceding embodiments, wherein $P_1$ has less than 75% sequence identity to TROP2.

Embodiment 51 comprises the isolated polypeptide or polypeptide complex according to any one of the preceding embodiments, wherein $P_1$ has less than 80% sequence identity to TROP2.

Embodiment 52 comprises the isolated polypeptide or polypeptide complex according to any one of the preceding embodiments, wherein $P_1$ has less than 85% sequence identity to TROP2.

Embodiment 53 comprises the isolated polypeptide or polypeptide complex according to any one of the preceding embodiments, wherein $P_1$ has less than 90% sequence identity to TROP2.

Embodiment 54 comprises the isolated polypeptide or polypeptide complex according to any one of the preceding embodiments, wherein $P_1$ has less than 95% sequence identity to TROP2.

Embodiment 55 comprises the isolated polypeptide or polypeptide complex according to any one of the preceding embodiments, wherein $P_1$ comprises a de novo amino acid sequence that shares less than 10% sequence identity to TROP2.

Embodiment 56 comprises the isolated polypeptide or polypeptide complex according to any one of the preceding embodiments, wherein $P_1$ comprises at least two cysteine amino acid residues.

Embodiment 57 comprises the isolated polypeptide or polypeptide complex according to any one of the preceding embodiments, wherein $P_1$ comprises a cyclic peptide or a linear peptide.

Embodiment 58 comprises the isolated polypeptide or polypeptide complex according to any one of the preceding embodiments, wherein $P_1$ comprises a cyclic peptide.

Embodiment 59 comprises the isolated polypeptide or polypeptide complex according to any one of embodiments 1-57, wherein $P_1$ comprises a linear peptide.

Embodiment 60 comprises the isolated polypeptide or polypeptide complex according to any one of the preceding embodiments, wherein $P_1$ comprise a modified amino acid or non-natural amino acid, or a modified non-natural amino acid, or a combination thereof.

Embodiment 61 comprises the isolated polypeptide or polypeptide complex according to any one of the preceding embodiments, wherein $P_1$ does not comprise albumin or an albumin fragment.

Embodiment 62 comprises the isolated polypeptide or polypeptide complex according to any one of the preceding embodiments, wherein $P_1$ does not comprise an albumin binding domain.

Embodiment 63 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124.

Embodiment 64 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 15, and wherein $P_1$ comprises an amino acid sequence according to SEQ ID NO: 102 or SEQ ID NO: 107, or an amino acid sequence that has 1, 2, or 3 amino acid mutations, substitutions, or deletions relative to SEQ ID NO: 102 or SEQ ID NO: 107.

Embodiment 65 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and wherein $P_1$ comprises an amino acid sequence according to any one of SEQ ID NOs: 102, 107, 123, and 124, or an amino acid sequence that has 1, 2, or 3 amino acid mutations, substitutions, or deletions relative to any one of SEQ ID NOs: 102, 107, 123, and 124.

Embodiment 66 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 29 and the immunoglobulin heavy chain comprises an amino acid sequence with at least 90%, 95%, 96%, 97%, 98%, 99%, or 100% identity to SEQ ID NO: 30, and wherein $P_1$ comprises an amino acid sequence according to SEQ ID NO: 102 or SEQ ID NO: 107, or an amino acid sequence that has 1, 2, or 3 amino acid mutations, substitutions, or deletions relative to SEQ ID NO: 102 or SEQ ID NO: 107.

Embodiment 67 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 68 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 8, CDR1-H: SEQ ID NO: 13, CDR2-H: SEQ ID NO: 14, and CDR3-H: SEQ ID NO: 15, and wherein $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150.

Embodiment 69 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 70 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 39 and the immunoglobulin heavy chain comprises an amino acid sequence with at least 90%, 95%, 96%, 97%, 98%, 99%, or 100% identity to SEQ ID NO: 40, and wherein $P_1$ comprises an amino acid sequence according to any one of SEQ ID NOs: 100, 102, 103, 107, 141, 142, and 150, or an amino acid sequence that has 1, 2, or 3 amino acid mutations, substitutions, or deletions relative to any one of SEQ ID NOs: 100, 102, 103, 107, 141, 142, and 150.

Embodiment 71 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 72 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 16, and wherein $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150.

Embodiment 73 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 74 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 49 and the immunoglobulin heavy chain comprises an amino acid sequence with at least 90%, 95%, 96%, 97%, 98%, 99%, or 100% identity to SEQ ID NO: 50, and wherein $P_1$ comprises an amino acid sequence according to any one of SEQ ID NOs: 107, 142, and 150, or an amino acid sequence that has 1, 2, or 3 amino acid mutations, substitutions, or deletions relative to any one of SEQ ID NOs: 107, 142, and 150.

Embodiment 75 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 76 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 22, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

Embodiment 77 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 78 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 61 and the immunoglobulin heavy chain comprises an amino acid sequence with at least 90%, 95%, 96%, 97%, 98%, 99%, or 100% identity to SEQ ID NO: 62, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

Embodiment 79 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 80 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

Embodiment 81 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 82 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

Embodiment 83 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 27, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 84 comprises the isolated polypeptide or polypeptide complex according to any one of embodiments 1, 15-21, and 43-62, wherein the immunoglobulin light chain and the immunoglobulin heavy chain comprise a set of CDRs comprising CDR1-L: SEQ ID NO: 1, CDR2-L: SEQ ID NO: 2, CDR3-L: SEQ ID NO: 3, CDR1-H: SEQ ID NO: 13, CDR2-H: SEQ ID NO: 14, and CDR3-H: SEQ ID NO: 27, and wherein $P_1$ comprises an amino acid sequence according to any one of SEQ ID NOs: 107, 109, 116, 141, 142, 148, 149, 150, 158, or an amino acid sequence that has 1, 2, or 3 amino acid mutations, substitutions, or deletions relative to any one of SEQ ID NOs: 107, 109, 116, 141, 142, 148, 149, 150, 158.

Embodiment 85 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

Embodiment 86 comprises the isolated polypeptide or polypeptide complex according to any one of embodiments 1, 15-21, and 43-62, wherein the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and wherein $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions, or deletions relative to any one of SEQ ID NOs: 107, 109, 116, 141, 142, 148, 149, 150, and 158.

Embodiment 87 comprises the isolated polypeptide or polypeptide complex according to any one of the preceding embodiments, wherein the isolated polypeptide or polypeptide complex further comprises a CD3 binding domain.

Embodiment 88 comprises the isolated polypeptide or polypeptide complex according to embodiment 87, wherein the isolated polypeptide or polypeptide complex is according to the following formula $P_2$-$L_2$-$B_2$-$A_1$-$L_1$-$P_1$(Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease.

Embodiment 89 comprises the isolated polypeptide or polypeptide complex according to embodiment 87 or 88, wherein the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 75; wherein CDR2-L comprises the amino acid sequence of SEQ ID NO: 76 (GTK); wherein CDR3-L comprises the amino acid sequence of SEQ ID NO: 77; wherein CDR1-H comprises the amino acid sequence of SEQ ID NO: 78; wherein CDR2-H comprises the amino acid sequence of SEQ ID NO: 79; and wherein CDR3-H comprises the amino acid sequence of SEQ ID NO: 80.

Embodiment 90 comprises the isolated polypeptide or polypeptide complex according to embodiment 87 or 88, wherein the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 75 or SEQ ID NO: 259; wherein CDR2-L comprises the amino acid sequence of SEQ ID NO: 76 (GTK); wherein CDR3-L comprises the amino acid sequence of $Z_1$-$Z_2$-W-$Z_3$-$Z_4$-$Z_5$-$Z_6$-W-$Z_7$-$Z_8$; wherein $Z_1$ is V, G, P, L, I, M, S, T, or A; $Z_2$ is L, G, P, V, I, M, S, T, or A; $Z_3$ is Y, F, W, V, L, I, G, or A; $Z_4$ is S, G, T, M, N, Q, H, or A; $Z_5$ is N, Q, S, T, D, E, H, K, R, or A; $Z_6$ is R, S, T, Q, D, E, H, K, N, or A; $Z_7$ is V, G, P, L, I, M, S, T, or A; and $Z_8$ is F, Y, W, V, L, I, G, or A; wherein CDR1-H comprises the amino acid sequence of SEQ ID NO: 78 or SEQ ID NO: 270; wherein CDR2-H comprises the amino acid sequence of SEQ ID NO: 79; and wherein CDR3-H comprises the amino acid sequence of $Z_9$-$Z_{10}$-$Z_{11}$$Z_{12}$-N-$Z_{13}$-$Z_{14}$-$Z_{15}$-$Z_{16}$-$Z_{17}$-$Z_{18}$-$Z_{19}$-Y-$Z_{20}$-A-$Z_{21}$; wherein $Z_9$ is V, G, P, L, I, M, S, T, or A; $Z_{10}$ is R, S, T, Q, D, E, H, K, N, or A; $Z_{11}$ is H, R, K, G, T, S, N, Q, or A; $Z_{12}$ is G, P, V, L, I, M, S, T, or A; $Z_{13}$ is F, Y, W, V, L, I, G, or A; $Z_{14}$ is G, P, V, L, I, M, S, T, or A; $Z_{15}$ is N, Q, S, T, D, E, H, K, R, or A; $Z_{16}$ is S, G, T, M, N, Q, H, or A; $Z_{17}$ is Y, F, W, V, L, I, G, or A; $Z_{18}$ is I, G, P, V, L, M, S, T, or A; $Z_{19}$ is S, G, T, M, N, Q, H, or A; $Z_{20}$ is W, F, Y, V, L, I, G, or A; and $Z_{21}$ is Y, F, W, V, L, I, G, or A.

Embodiment 91 comprises the isolated polypeptide or polypeptide complex according to embodiment 90, wherein $Z_1$ is V, G, L, I, or A; $Z_2$ is L, V, I, or A; $Z_3$ is Y, W, F, or A; $Z_4$ is S, G, T, or A; $Z_5$ is N, Q, D, E, or A; $Z_6$ is R, K, or A; $Z_7$ is V, G, L, I, or A; $Z_8$ is F, Y, W, or A; $Z_9$ is V, G, L, I, or A; $Z_{10}$ is R, K, or A; $Z_{12}$ is G, S, T, or A; $Z_{13}$ is F, Y, W, or A; $Z_{14}$ is G, S, T, or A; $Z_{15}$ is N, Q, D, E, or A; $Z_{16}$ is S, G, T, or A; $Z_{17}$ is Y, W, F, or A; $Z_{18}$ is I, V, L, or A; $Z_{19}$ is S, G, T, or A; $Z_{20}$ is W, Y, F, or A; and $Z_{21}$ is Y, W, F, or A.

Embodiment 92 comprises the isolated polypeptide or polypeptide complex according to embodiment 90 or 91, wherein: $Z_8$ is F.

Embodiment 93 comprises the isolated polypeptide or polypeptide complex according to any one of embodiments 90-92, wherein: $Z_{10}$ is R; $Z_{11}$ is H; $Z_{13}$ is F; $Z_{18}$ is I; $Z_{19}$ is S; and $Z_{20}$ is W.

Embodiment 94 comprises the isolated polypeptide or polypeptide complex according to embodiment 90, wherein CDR3-L comprises an amino acid sequence selected from SEQ ID NOs: 77, 260-261, 263-266, and 268-269.

Embodiment 95 comprises the isolated polypeptide or polypeptide complex according to embodiment 90, wherein the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76 (GTK), CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 266, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 268, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO:

76 (GTK), CDR3-L: SEQ ID NO: 269, and CDR1-H: SEQ ID NO: 78, CDR2-H: SEQ ID NO: 79, CDR3-H: SEQ ID NO: 80.

Embodiment 96 comprises the isolated polypeptide or polypeptide complex according to embodiment 90, wherein the immunoglobulin light chain and the immunoglobulin heavy chain comprise a set of CDR sequences selected from the group consisting of: CDR1-L: SEQ ID NO: 75, CDR2-L: SEQ ID NO: 76 (GTK), CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 266, and CDR1-H: SEQ ID NO: 78, CDR2-H: SEQ ID NO: 79, CDR3-H: SEQ ID NO: 80; and CDR1-L: SEQ ID NO: 75, CDR2-L: SEQ ID NO: 76 (GTK), CDR3-L: SEQ ID NO: 268, and CDR1-H: SEQ ID NO: 78, CDR2-H: SEQ ID NO: 79, CDR3-H: SEQ ID NO: 80.

Embodiment 97 comprises the isolated polypeptide or polypeptide complex according to embodiment 90, wherein CDR3-H comprises an amino acid sequence selected from SEQ ID NOs: 80, 271-274, 276-282, and 284-285.

Embodiment 98 comprises the isolated polypeptide or polypeptide complex according to embodiment 90, wherein the immunoglobulin light chain and the immunoglobulin heavy chain of the CD3 binding domain comprise a set of CDR sequences selected from the group consisting of: CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 284; and CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 285.

Embodiment 99 comprises the isolated polypeptide or polypeptide complex according to embodiment 90, wherein the immunoglobulin light chain and the immunoglobulin heavy chain comprise a set of CDR sequences selected from the group consisting of: CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 280; and CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 285.

Embodiment 100 comprises the isolated polypeptide or polypeptide complex according to embodiment 87 or 88, wherein the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of: CDR1-L: SEQ ID NO: 75, CDR2-L: SEQ ID NO: 76 (GTK), CDR3-L: SEQ ID NO: 260, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 261, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 262, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 263, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 264, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 265, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 266, and CDR1-H: SEQ ID NO: 78, CDR2-H: SEQ ID NO: 79, CDR3-H: SEQ ID NO:

80; CDR1-L: SEQ ID NO: 75, CDR2-L: SEQ ID NO: 76 (GTK), CDR3-L: SEQ ID NO: 267, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 268, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 269, and CDR1-H: SEQ ID NO: 78, CDR2-H: SEQ ID NO: 79, CDR3-H: SEQ ID NO: 80; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 271; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 272; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 273; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 274; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 275; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 276; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 277; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 278; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 279; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 280; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 281; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 282; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 283; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 284; CDR1-L: SEQ ID NO: 75, CDR2-L: SEQ ID NO: 76 (GTK), CDR3-L: SEQ ID NO: 77, and CDR1-H: SEQ ID NO: 78, CDR2-H: SEQ ID NO: 79, CDR3-H: SEQ ID NO: 285; and CDR1-L: SEQ ID NO: 259, CDR2-L: SEQ ID NO: 76 (GTK), CDR3-L: SEQ ID NO: 260, and CDR1-H: SEQ ID NO: 270, CDR2-H: SEQ ID NO: 79, CDR3-H: SEQ ID NO: 286.

Embodiment 101 comprises the isolated polypeptide or polypeptide complex according to any one of embodiments 87-100, wherein the immunoglobulin light chain of the CD3 binding domain comprises a variable domain of an immunoglobulin kappa (IgK) or immunoglobulin lambda (IgL) light chain.

Embodiment 102 comprises the isolated polypeptide or polypeptide complex according to any one of embodiments 87-101, wherein the immunoglobulin heavy chain of the CD3 binding domain comprises a variable domain of an IgG1, IgG2, IgG3, or IgG4 heavy chain.

Embodiment 103 comprises the isolated polypeptide or polypeptide complex according to any one of embodiments 87-102, wherein the immunoglobulin light chain of the CD3 binding domain comprises an amino acid sequence with at least 90%, 95%, 96%, 97%, 98%, 99%, or 100% identity to SEQ ID NO: 81.

Embodiment 104 comprises the isolated polypeptide or polypeptide complex according to any one of embodiments 87-103, wherein the immunoglobulin heavy chain of the CD3 binding domain comprises an amino acid sequence with at least 90%, 95%, 96%, 97%, 98%, 99%, or 100% identity to SEQ ID NO: 82.

Embodiment 105 comprises the isolated polypeptide or polypeptide complex according to any one of embodiments 87-102, wherein the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82.

Embodiment 106 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to any one of SEQ ID NOs: 99 and 303-329.

Embodiment 107 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 303.

Embodiment 108 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 304.

Embodiment 109 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 305.

Embodiment 110 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 306.

Embodiment 111 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 307.

Embodiment 112 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 308.

Embodiment 113 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 309.

Embodiment 114 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 310.

Embodiment 115 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 311.

Embodiment 116 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 312.

Embodiment 117 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 313.

Embodiment 118 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 314.

Embodiment 119 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 315.

Embodiment 120 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 316.

Embodiment 121 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 317.

Embodiment 122 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 318.

Embodiment 123 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 319.

Embodiment 124 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 320.

Embodiment 125 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 321.

Embodiment 126 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 322.

Embodiment 127 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 323.

Embodiment 128 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 324.

Embodiment 129 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 325.

Embodiment 130 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 326.

Embodiment 131 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 327.

Embodiment 132 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 328.

Embodiment 133 comprises the isolated polypeptide or polypeptide complex according to embodiments 87 or 88, wherein the CD3 binding domain comprises an amino acid sequence with at least 90%, 95%, 96%, 97%, 98%, 99%, or 100% identity to SEQ ID NO: 329.

Embodiment 134 comprises the isolated polypeptide or polypeptide complex according to any one of embodiments 87 to 133, wherein the CD3 binding domain comprises a Fab, Fab', $(Fab')_2$ or a single chain variable fragment (scFv).

Embodiment 135 comprises the isolated polypeptide or polypeptide complex according to embodiment 134, wherein the CD3 binding domain is the scFv.

Embodiment 136 comprises the isolated polypeptide or polypeptide complex according to any one of embodiments 89 to 135, wherein the N-term of the immunoglobulin heavy chain of the TROP2 binding domain is bound to the C-term of the immunoglobulin light chain of the CD3 binding domain.

Embodiment 137 comprises the isolated polypeptide or polypeptide complex according to any one of embodiments 89 to 135, wherein the C-term of the immunoglobulin heavy chain of the TROP2 binding domain is bound to the N-term of the immunoglobulin light chain of the CD3 binding domain.

Embodiment 138 comprises the isolated polypeptide or polypeptide complex according to any one of embodiments 89 to 135, wherein the N-term of the immunoglobulin heavy chain of the TROP2 binding domain is bound to the C-term of the immunoglobulin heavy chain of the CD3 binding domain.

Embodiments 139 comprises the isolated polypeptide or polypeptide complex according to any one of embodiments 89 to 135, wherein the C-term of the immunoglobulin heavy chain of the TROP2 binding domain is bound to the N-term of the immunoglobulin heavy chain of the CD3 binding domain.

Embodiment 140 comprises the isolated polypeptide or polypeptide complex according to any one of embodiments 89 to 135, wherein the N-term of the immunoglobulin light chain of the TROP2 binding domain is bound to the C-term of the immunoglobulin light chain of the CD3 binding domain.

Embodiment 141 comprises the isolated polypeptide or polypeptide complex according to any one of embodiments 89 to 135, wherein the C-term of the immunoglobulin light chain of the TROP2 binding domain is bound to the N-term of the immunoglobulin light chain of the CD3 binding domain.

Embodiment 142 comprises the isolated polypeptide or polypeptide complex according to any one of embodiments 89 to 135, wherein the N-term of the immunoglobulin light chain of the TROP2 binding domain is bound to the C-term of the immunoglobulin heavy chain of the CD3 binding domain.

Embodiment 143 comprises the isolated polypeptide or polypeptide complex according to any one of embodiments 89 to 135, wherein the C-term of the immunoglobulin light chain of the TROP2 binding domain is bound to the N-term of the immunoglobulin heavy chain of the CD3 binding domain.

Embodiment 144 comprises the isolated polypeptide or polypeptide complex according to any one of embodiments 89 to 135, wherein the CD3 binding domain is a scFv and the TROP2 binding domain is a Fab or Fab'.

Embodiment 145 comprises the isolated polypeptide or polypeptide complex according to embodiment 144, wherein the scFv is bound to the immunoglobulin heavy chain of the Fab or Fab'.

Embodiment 146 comprises the isolated polypeptide or polypeptide according to embodiment 144, wherein the scFv is bound to the immunoglobulin light chain of the Fab or Fab'.

Embodiment 147 comprises the isolated polypeptide or polypeptide complex according to embodiment 144, wherein the immunoglobulin light chain of the scFv is bound to the immunoglobulin heavy chain of the Fab or Fab'.

Embodiment 148 comprises the isolated polypeptide or polypeptide complex according to embodiment 144, wherein the immunoglobulin light chain of the scFv is bound to the immunoglobulin light chain of the Fab or Fab'.

Embodiment 149 comprises the isolated polypeptide or polypeptide complex according to embodiment 144, wherein the immunoglobulin heavy chain of the scFv is bound to the immunoglobulin heavy chain of the Fab or Fab'.

Embodiment 150 comprises the isolated polypeptide or polypeptide complex of according to embodiment 144, the immunoglobulin heavy chain of the scFv is bound to the immunoglobulin light chain of the Fab or Fab'.

Embodiment 151 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 87 and SEQ ID NO: 88.

Embodiment 152 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 89 and SEQ ID NO: 90.

Embodiment 153 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 91 and SEQ ID NO: 92.

Embodiment 154 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 93 and SEQ ID NO: 94.

Embodiment 155 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 95 and SEQ ID NO: 96.

Embodiment 156 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 97 and SEQ ID NO: 98.

Embodiment 157 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 330 and SEQ ID NO: 331.

Embodiment 158 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 332 and SEQ ID NO: 333.

Embodiment 159 comprises the isolated polypeptide or polypeptide complex according to any one of embodiments 87-89 and 100-102, wherein the recombinant antibody or antigen binding fragment thereof comprises amino acid sequences with at least 90%, 95%, 96%, 97%, 98%, 99%, or 100% identity to SEQ ID NO: 334 and SEQ ID NO: 335.

Embodiment 160 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 336 and SEQ ID NO: 337.

Embodiment 161 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 338 and SEQ ID NO: 339.

Embodiment 162 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 340 and SEQ ID NO: 341.

Embodiment 163 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 342 and SEQ ID NO: 343.

Embodiment 164 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 344 and SEQ ID NO: 345.

Embodiment 165 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 346 and SEQ ID NO: 347.

Embodiment 166 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 348 and SEQ ID NO: 349.

Embodiment 167 comprises the isolated polypeptide or polypeptide complex according to any one of embodiments 87-90 and 100-102, wherein the recombinant antibody or antigen binding fragment thereof comprises amino acid sequences with at least 90%, 95%, 96%, 97%, 98%, 99%, or 100% identity to SEQ ID NO: 350 and SEQ ID NO: 351.

Embodiment 168 comprises the isolated polypeptide or polypeptide complex according to any one of embodiments 151-167, wherein the recombinant antibody or antigen binding fragment thereof has weaker cytotoxicity activity as compared to a recombinant antibody or antigen binding fragment thereof that comprises an immunoglobulin light chain according to SEQ ID NO: 83 or 85 and an immunoglobulin heavy chain according to SEQ ID NO: 84 or 86 as measured in an in vitro tumor cell killing assay under substantially similar assay conditions.

Embodiment 169 comprises the isolated polypeptide or polypeptide complex according to any one of embodiments 88-168, wherein $P_2$ impairs binding of $B_2$ to CD3.

Embodiment 170 comprises the isolated polypeptide or polypeptide complex according to any one of embodiments 88-168, wherein $P_2$ is bound to $B_2$ through ionic interactions, electrostatic interactions, hydrophobic interactions, Pi-stacking interactions, and H-bonding interactions, or a combination thereof.

Embodiment 171 comprises the isolated polypeptide or polypeptide complex according to any one of embodiments 88-168, wherein $P_2$ is bound to $B_2$ at or near an antigen binding site.

Embodiment 172 comprises the isolated polypeptide or polypeptide complex according to any one of embodiments 88-168, wherein $P_2$ becomes unbound from $B_2$ when $L_2$ is cleaved by the tumor specific protease thereby exposing $B_2$ to the CD3.

Embodiment 173 comprises the isolated polypeptide or polypeptide complex of any one of embodiments 88-168, wherein $P_2$ has less than 70% sequence identity to CD3.

Embodiment 174 comprises the isolated polypeptide or polypeptide complex according to any one of embodiments 88-168, wherein $P_2$ has less than 75% sequence identity to CD3.

Embodiment 175 comprises the isolated polypeptide or polypeptide complex according to any one of embodiments 88-168, wherein $P_2$ has less than 80% sequence identity to CD3.

Embodiment 176 comprises the isolated polypeptide or polypeptide complex according to any one of embodiments 88-168, wherein $P_2$ has less than 85% sequence identity to CD3.

Embodiment 177 comprises the isolated polypeptide or polypeptide complex according to any one of embodiments 88-168, wherein $P_2$ has less than 90% sequence identity to CD3.

Embodiment 178 comprises the isolated polypeptide or polypeptide complex according to any one of embodiments 88-168, wherein $P_2$ has less than 95% sequence identity to CD3.

Embodiment 179 comprises the isolated polypeptide or polypeptide complex according to any one of embodiments 88-168, wherein $P_2$ comprises a de novo amino acid sequence that shares less than 10% sequence identity to CD3.

Embodiment 180 comprises the isolated polypeptide or polypeptide complex according to any one of embodiments 88-179, wherein $P_2$ comprises a peptide sequence of at least 5 amino acids in length.

Embodiment 181 comprises the isolated polypeptide or polypeptide complex according to any one of embodiments 88-179, wherein $P_2$ comprises a peptide sequence of at least 6 amino acids in length.

Embodiment 182 comprises the isolated polypeptide or polypeptide complex according to any one of embodiments 88-179, wherein $P_2$ comprises a peptide sequence of at least 10 amino acids in length.

Embodiment 183 comprises the isolated polypeptide or polypeptide complex according to any one of embodiments 88-179, wherein $P_2$ comprises a peptide sequence of at least 10 amino acids in length and no more than 20 amino acids in length.

Embodiment 184 comprises the isolated polypeptide or polypeptide complex according to any one of embodiments 88-179, wherein $P_2$ comprises a peptide sequence of at least 16 amino acids in length.

Embodiment 185 comprises the isolated polypeptide or polypeptide complex according to any one of embodiments 88-179, wherein $P_2$ comprises a peptide sequence of no more than 40 amino acids in length.

Embodiment 186 comprises the isolated polypeptide or polypeptide complex according to any one of embodiments 88-179, wherein $P_2$ comprises at least two cysteine amino acid residues.

Embodiment 187 comprises the isolated polypeptide or polypeptide complex according to any one of embodiments 88-186, wherein $P_2$ comprises a cyclic peptide or a linear peptide.

Embodiment 188 comprises the isolated polypeptide or polypeptide complex according to any one of embodiments 88-186, wherein $P_2$ comprises a cyclic peptide.

Embodiment 189 comprises the isolated polypeptide or polypeptide complex according to any one of embodiments 88-186, wherein $P_2$ comprises a linear peptide.

Embodiment 190 comprises the isolated polypeptide or polypeptide complex according to any one of embodiments 88-189, wherein $P_2$ comprises a modified amino acid or non-natural amino acid, or a modified non-natural amino acid, or a combination thereof.

Embodiment 191 comprises the isolated polypeptide or polypeptide complex according to any one of embodiments 88-190, wherein $P_2$ does not comprise albumin or an albumin fragment.

Embodiment 192 comprises the isolated polypeptide or polypeptide complex according to any one of embodiments 88-191, wherein $P_2$ does not comprise an albumin binding domain.

Embodiment 193 comprises the isolated polypeptide or polypeptide complex according to any one of embodiments 88-192, wherein $P_2$ comprises the amino acid sequence of SEQ ID NO: 289 or SEQ ID NO: 292.

Embodiment 194 comprises the isolated polypeptide or polypeptide complex according to any one of embodiments 88-192, wherein $P_2$ comprises an amino acid sequence according to any one of SEQ ID NOs: 287-302, or an amino acid sequence that has 1, 2, or 3 amino acid mutations, substitutions or deletions relative to any one of SEQ ID NOs: 287-302.

Embodiment 195 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298.

Embodiment 196 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 197 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 77, CDR1-H: SEQ ID NO: 78, CDR2-H: SEQ ID NO: 79, and CDR3-H: SEQ ID NO: 273, and wherein $P_2$ comprises an amino acid sequence according to SEQ ID NO: 295.

Embodiment 198 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 305, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298.

Embodiment 199 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 305, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 200 comprises the isolated polypeptide or polypeptide complex according to embodiment 194, wherein the CD3 binding domain comprises an amino acid sequence according to SEQ ID NO: 305, and wherein $P_2$ comprises an amino acid sequence according to SEQ ID NO: 295.

Embodiment 201 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 77, CDR1-H: SEQ ID NO: 78, CDR2-H: SEQ ID NO: 79, and CDR3-H: SEQ ID NO: 276, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 202 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 77, CDR1-H: SEQ ID NO: 78, CDR2-H: SEQ ID NO: 79, and CDR3-H: SEQ ID NO: 276, and wherein $P_2$ comprises an amino acid sequence according to SEQ ID NO: 295.

Embodiment 203 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 308, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 204 comprises the isolated polypeptide or polypeptide complex according to embodiment 194, wherein the CD3 binding domain comprises an amino acid sequence according to SEQ ID NO: 308, and wherein $P_2$ comprises an amino acid sequence according to SEQ ID NO: 295.

Embodiment 205 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 259, CDR2-L: SEQ ID NO: 76 (GTK), CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298.

Embodiment 206 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 259, CDR2-L: SEQ ID NO: 76 (GTK), CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 207 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 259, CDR2-L: SEQ ID NO: 76 (GTK), CDR3-L: SEQ ID NO: 260, CDR1-H: SEQ ID NO: 270, CDR2-H: SEQ ID NO: 79, and CDR3-H: SEQ ID NO: 286, and wherein $P_2$ comprises an amino acid sequence according to SEQ ID NO: 295.

Embodiment 208 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 329, and wherein $P_2$ comprises an amino acid sequence according to any one of SEQ ID NOs: 292, 295, and 298, or an amino acid sequence that has 1, 2, or 3 amino acid mutations, substitutions, or deletions relative to any one of SEQ ID NOs: 292, 295, and 298.

Embodiment 209 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 329, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 210 comprises the isolated polypeptide or polypeptide complex according to embodiment 194, wherein the CD3 binding domain comprises an amino acid sequence according to SEQ ID NO: 329, and wherein $P_2$ comprises an amino acid sequence according to SEQ ID NO: 295.

Embodiment 211 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 261, CDR1-H: SEQ ID NO: 78, CDR2-H: SEQ ID NO: 79, and CDR3-H: SEQ ID NO: 80, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 212 comprises the isolated polypeptide or polypeptide complex according to embodiment 194, wherein the immunoglobulin light chain and the immunoglobulin heavy chain of the CD3 binding domain comprise a set of CDRs comprising CDR1-L: SEQ ID NO: 75, CDR2-L: SEQ ID NO: 76 (GTK), CDR3-L: SEQ ID NO: 261, CDR1-H: SEQ ID NO: 78, CDR2-H: SEQ ID NO: 79, and CDR3-H: SEQ ID NO: 80, and wherein $P_2$ comprises an amino acid sequence according to SEQ ID NO: 295.

Embodiment 213 comprises the isolated polypeptide or polypeptide complex according to embodiment 194, wherein the CD3 binding domain comprises an amino acid sequence with at least 90%, 95%, 96%, 97%, 98%, 99%, or 100% identity to SEQ ID NO: 319, and wherein $P_2$ comprises an amino acid sequence according to SEQ ID NO: 295, or an amino acid sequence that has 1, 2, or 3 amino acid mutations, substitutions, or deletions relative to SEQ ID NO: 295.

Embodiment 214 comprises the isolated polypeptide or polypeptide complex according to embodiment 194, wherein the CD3 binding domain comprises an amino acid sequence according to SEQ ID NO: 319, and wherein $P_2$ comprises an amino acid sequence according to SEQ ID NO: 295.

Embodiment 215 comprises the isolated polypeptide or polypeptide complex according to any one of the preceding embodiments, wherein $L_1$ or $L_2$ is a peptide sequence having at least 5 to no more than 50 amino acids.

Embodiment 216 comprises the isolated polypeptide or polypeptide complex according to embodiment 215, wherein $L_1$ or $L_2$ is a peptide sequence having at least 10 to no more than 30 amino acids.

Embodiment 217 comprises the isolated polypeptide or polypeptide complex according to embodiment 215, wherein $L_1$ or $L_2$ is a peptide sequence having at least 10 amino acids.

Embodiment 218 comprises the isolated polypeptide or polypeptide complex according to embodiment 215, wherein $L_1$ or $L_2$ is a peptide sequence having at least 18 amino acids.

Embodiment 219 comprises the isolated polypeptide or polypeptide complex according to embodiment 215, wherein $L_1$ or $L_2$ is a peptide sequence having at least 26 amino acids.

Embodiment 220 comprises the isolated polypeptide or polypeptide complex according to embodiment 215, wherein $L_1$ or $L_2$ comprises a formula comprising $(G_2S)_n$, wherein n is an integer from 1 to 3.

Embodiment 221 comprises the isolated polypeptide or polypeptide complex according to embodiment 215, wherein $L_1$ or $L_2$ comprises a formula comprising $(G_2S)_n$, wherein n is an integer of at least 1.

Embodiment 222 comprises the isolated polypeptide or polypeptide complex according to embodiment 215, wherein $L_1$ or $L_2$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1.

Embodiment 223 comprises the isolated polypeptide or polypeptide complex according to any one of the preceding embodiments, wherein the tumor specific protease is selected from the group consisting of metalloprotease, serine protease, cysteine protease, threonine protease, and aspartic protease.

Embodiment 224 comprises the isolated polypeptide or polypeptide complex according to any one of the preceding embodiments, wherein $L_1$ or $L_2$ comprises a urokinase cleavable amino acid sequence, a matriptase cleavable amino acid sequence, or a matrix metalloprotease cleavable amino acid sequence.

Embodiment 225 comprises the isolated polypeptide or polypeptide complex according to any one of the preceding embodiments, wherein $L_1$ or $L_2$ comprises a sequence according to any one of SEQ ID NOs: 226-254.

Embodiment 226 comprises the isolated polypeptide or polypeptide complex according to any one of the preceding embodiments, wherein $L_1$ is bound to N-terminus of $A_1$.

Embodiment 227 comprises the isolated polypeptide or polypeptide complex according to any one of embodiments 1 to 225, wherein $L_1$ is bound to C-terminus of $A_1$.

Embodiment 228 comprises the isolated polypeptide or polypeptide complex according to any one of embodiments 88 to 225, wherein $L_2$ is bound to N-terminus of $B_2$.

Embodiment 229 comprises the isolated polypeptide or polypeptide complex according to any one of embodiments 88 to 225, wherein $L_2$ is bound to C-terminus of $B_2$.

Embodiment 230 comprises the isolated polypeptide or polypeptide complex according to any one of the preceding embodiments, wherein the isolated polypeptide or polypeptide complex further comprises a half-life extending molecule ($H_1$).

Embodiment 231 comprises the isolated polypeptide or polypeptide complex according to embodiment 230, wherein $H_1$ is connected to $P_1$.

Embodiment 232 comprises the isolated polypeptide or polypeptide complex according to embodiment 230, wherein $H_1$ is connected to $P_2$.

Embodiment 233 comprises the isolated polypeptide or polypeptide complex according to any one of embodiments 230-232, wherein $H_1$ does not block the CD3 binding domain to CD3.

Embodiment 234 comprises the isolated polypeptide or polypeptide complex according to any one of embodiments 230-233, wherein the half-life extending molecule ($H_1$) does not have binding affinity to CD3.

Embodiment 235 comprises the isolated polypeptide or polypeptide complex according to any one of embodiments 230-234, wherein the half-life extending molecule ($H_1$) does not shield the isolated polypeptide or polypeptide complex from CD3.

Embodiment 236 comprises the isolated polypeptide or polypeptide complex according to any one of embodiments 230-235, wherein $H_1$ comprises a sequence according to SEQ ID NOs: 255-258.

Embodiment 237 comprises the isolated polypeptide or polypeptide complex according to any one of embodiments 230-236, wherein $H_1$ comprises an amino acid sequence that has repetitive sequence motifs.

Embodiment 238 comprises the isolated polypeptide or polypeptide complex according to any one of embodiments 230-237, wherein $H_1$ comprises an amino acid sequence that has highly ordered secondary structure.

Embodiment 239 comprises the isolated polypeptide or polypeptide complex according to any one of embodiments 230-235, wherein $H_1$ comprises a polymer.

Embodiment 240 comprises the isolated polypeptide or polypeptide complex according to any one of embodiments 230-235, wherein the polymer is polyethylene glycol (PEG).

Embodiment 241 comprises the isolated polypeptide or polypeptide complex according to any one of embodiments 230-235, wherein $H_1$ comprises albumin.

Embodiment 242 comprises the isolated polypeptide or polypeptide complex according to any one of embodiments 230-235, wherein $H_1$ comprises an Fc domain.

Embodiment 243 comprises the isolated polypeptide or polypeptide complex according to embodiment 241, wherein the albumin is serum albumin.

Embodiment 244 comprises the isolated polypeptide or polypeptide complex according to embodiment 241, wherein the albumin is human serum albumin.

Embodiment 245 comprises the isolated polypeptide or polypeptide complex according to any one of embodiments 230-244, wherein $H_1$ comprises a polypeptide, a ligand, or a small molecule.

Embodiment 246 comprises the isolated polypeptide or polypeptide complex according to embodiment 245, wherein the polypeptide, the ligand or the small molecule binds serum protein or a fragment thereof, a circulating immunoglobulin or a fragment thereof, or CD35/CR1.

Embodiment 247 comprises the isolated polypeptide or polypeptide complex according to embodiment 246, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 248 comprises the isolated polypeptide or polypeptide complex according to embodiment 246, wherein the circulating immunoglobulin molecule comprises IgG1, IgG2, IgG3, IgG4, slgA, IgM or IgD.

Embodiment 249 comprises the isolated polypeptide or polypeptide complex according to embodiment 246, wherein the serum protein is albumin.

Embodiment 250 comprises the isolated polypeptide or polypeptide complex according to embodiment 245, wherein the polypeptide is an antibody.

Embodiment 251 comprises the isolated polypeptide or polypeptide complex according to embodiment 250, wherein the antibody comprises a single domain antibody, a single chain variable fragment or a Fab.

Embodiment 252 comprises the isolated polypeptide or polypeptide complex according to embodiment 251, wherein the single domain antibody comprises a single domain antibody that binds to albumin.

Embodiment 253 comprises the isolated polypeptide or polypeptide complex according to embodiments 251-252, wherein the single domain antibody is a human or humanized antibody.

Embodiment 254 comprises the isolated polypeptide or polypeptide complex according to embodiment 251, wherein the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21.

Embodiment 255 comprises the isolated polypeptide or polypeptide complex according to embodiment 251, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 255, HC-CDR2: SEQ ID NO: 256, and HC-CDR3: SEQ ID NO: 257; and wherein the CDRs comprise from 0-2 amino acid modifications in at least one of the HC-CDR1, HC-CDR2, or HC-CDR3.

Embodiment 256 comprises the isolated polypeptide or polypeptide complex according to embodiment 255, wherein $H_1$ comprises an amino acid sequence according to SEQ ID NO: 258.

Embodiment 257 comprises the isolated polypeptide or polypeptide complex according to embodiment 255, wherein $H_1$ comprises an amino acid sequence that has at least 80% sequence identity to SEQ ID NO: 258.

Embodiment 258 comprises the isolated polypeptide or polypeptide complex according to embodiment 255, wherein $H_1$ comprises an amino acid sequence that has at least 85% sequence identity to SEQ ID NO: 258.

Embodiment 259 comprises the isolated polypeptide or polypeptide complex according to embodiment 255, wherein $H_1$ comprises an amino acid sequence that has at least 90% sequence identity to SEQ ID NO: 258.

Embodiment 260 comprises the isolated polypeptide or polypeptide complex according to embodiment 255, wherein $H_1$ comprises an amino acid sequence that has at least 95% sequence identity to SEQ ID NO: 258.

Embodiment 261 comprises the isolated polypeptide or polypeptide complex according to embodiment 255, wherein $H_1$ comprises an amino acid sequence that has at least 99% sequence identity to SEQ ID NO: 258.

Embodiment 262 comprises the isolated polypeptide or polypeptide complex according to any one of embodiments 230-261, wherein $H_1$ comprise a modified amino acid or non-natural amino acid, or a modified non-natural amino acid, or a combination thereof.

Embodiment 263 comprises the isolated polypeptide or polypeptide complex according to embodiment 262, wherein the modified amino acid or a modified non-natural amino acid comprises a post-translational modification.

Embodiment 264 comprises the isolated polypeptide or polypeptide complex according to any one of embodiments 230-262, wherein $H_1$ comprises a linking moiety ($L_3$) that connects $H_1$ to $P_1$ or $P_2$.

Embodiment 265 comprises the isolated polypeptide or polypeptide complex according to embodiment 264, wherein $L_3$ is a peptide sequence having at least 10 to no more than 30 amino acids.

Embodiment 266 comprises the isolated polypeptide or polypeptide complex according to embodiment 264, wherein $L_3$ is a peptide sequence having at least 10 amino acids.

Embodiment 267 comprises the isolated polypeptide or polypeptide according to embodiment 264, wherein $L_3$ is a peptide sequence having at least 18 amino acids.

Embodiment 268 comprises the isolated polypeptide or polypeptide complex according to embodiment 264, wherein $L_3$ is a peptide sequence having at least 26 amino acids.

Embodiment 269 comprises the isolated polypeptide or polypeptide complex according to embodiment 264, wherein $L_3$ comprises a formula selected from the group consisting of $(G_2S)_n$, $(GS)_n$, $(GSGGS)_n$, $(GGGS)_n$, $(GGGGS)_n$, and $(GSSGGS)_n$, wherein n is an integer of at least 1.

Embodiment 270 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 166 and SEQ ID NO: 167.

Embodiment 271 comprises the isolated polypeptide or polypeptide complex according to embodiment 1 or 15, wherein the isolated polypeptide or polypeptide complex comprises amino acid sequences with at least 90%, 95%, 96%, 97%, 98%, 99%, or 100% identity to SEQ ID NO: 168 and SEQ ID NO: 169.

Embodiment 272 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 170 and SEQ ID NO: 171.

Embodiment 273 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 172 and SEQ ID NO: 173.

Embodiment 274 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 174 and SEQ ID NO: 175.

Embodiment 275 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 176 and SEQ ID NO: 177.

Embodiment 276 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 178 and SEQ ID NO: 179.

Embodiment 277 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 180 and SEQ ID NO: 181.

Embodiment 278 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 182 and SEQ ID NO: 183.

Embodiment 279 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 184 and SEQ ID NO: 185.

Embodiment 280 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 186 and SEQ ID NO: 187.

Embodiment 281 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 188 and SEQ ID NO: 189.

Embodiments 282 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 190 and SEQ ID NO: 191.

Embodiments 283 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 192 and SEQ ID NO: 193.

Embodiment 284 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 194 and SEQ ID NO: 195.

Embodiment 285 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 196 and SEQ ID NO: 197.

Embodiment 286 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 198 and SEQ ID NO: 199.

Embodiment 287 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 200 and SEQ ID NO: 201.

Embodiment 288 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 202 and SEQ ID NO: 203.

Embodiment 289 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 204 and SEQ ID NO: 205.

Embodiment 290 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 206 and SEQ ID NO: 207.

Embodiment 291 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 208 and SEQ ID NO: 209.

Embodiment 292 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 210 and SEQ ID NO: 211.

Embodiment 293 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 212 and SEQ ID NO: 213.

Embodiment 294 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 214 and SEQ ID NO: 215.

Embodiment 295 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 216 and SEQ ID NO: 217.

Embodiment 296 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 218 and SEQ ID NO: 219.

Embodiments 297 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 220 and SEQ ID NO: 221.

Embodiment 298 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 222 and SEQ ID NO: 223.

Embodiment 299 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 224 and SEQ ID NO: 225.

Embodiment 300 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 352 and SEQ ID NO: 353.

Embodiment 301 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 354 and SEQ ID NO: 355.

Embodiment 302 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 356 and SEQ ID NO: 357.

Embodiment 303 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 358 and SEQ ID NO: 359.

Embodiment 304 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 360 and SEQ ID NO: 361.

Embodiment 305 the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 362 and SEQ ID NO: 363.

Embodiment 306 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 364 and SEQ ID NO: 365.

Embodiment 307 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 366 and SEQ ID NO: 367.

Embodiment 308 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 368 and SEQ ID NO: 369.

Embodiment 309 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 370 and SEQ ID NO: 371.

Embodiment 310 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 372 and SEQ ID NO: 373.

Embodiment 311 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 374 and SEQ ID NO: 375.

Embodiment 312 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 376 and SEQ ID NO: 377.

Embodiment 313 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 378 and SEQ ID NO: 379.

Embodiment 314 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 380 and SEQ ID NO: 381.

Embodiment 315 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 382 and SEQ ID NO: 383.

Embodiment 316 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 384 and SEQ ID NO: 385.

Embodiment 317 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 386 and SEQ ID NO: 387.

Embodiment 318 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 388 and SEQ ID NO: 389.

Embodiment 319 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 390 and SEQ ID NO: 391.

Embodiment 320 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 392 and SEQ ID NO: 393.

Embodiment 321 comprises the isolated polypeptide or polypeptide complex according to embodiments 1 or 15, wherein the isolated polypeptide or polypeptide complex comprises amino acid sequences with at least 90%, 95%, 96%, 97%, 98%, 99%, or 100% identity to SEQ ID NO: 394 and SEQ ID NO: 395.

Embodiment 322 comprises an isolated polypeptide or polypeptide complex according to Formula I: $A_1$-$L_1$-$P_1$ (Formula I) wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 26; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease.

Embodiment 323 comprises the isolated polypeptide or polypeptide complex according to embodiment 322, wherein $P_1$ comprises an amino acid sequence according to any one of SEQ ID NOs: 107, 141, 142, and 150, or an amino acid sequence that has 1, 2, or 3 amino acid mutations, substitutions or deletions relative to any one of SEQ ID NOs: 107, 141, 142, and 150.

Embodiment 324 comprises the isolated polypeptide or polypeptide complex according to embodiments 322 or 323, wherein $P_1$ comprises an amino acid sequence according to SEQ ID NO: 142.

Embodiment 325 comprises the isolated polypeptide or polypeptide complex according to any one of embodiments 322-324, wherein the TROP2 binding domain comprises a Fab, Fab', $(Fab')_2$ or a single chain variable fragment (scFv).

Embodiment 326 comprises the isolated polypeptide or polypeptide complex according to embodiment 325, wherein the TROP2 binding domain is a Fab.

Embodiment 327 comprises the isolated polypeptide or polypeptide complex according to any one of embodiments 322-326, wherein the immunoglobulin light chain comprises an amino acid sequence with at least 85% identity to SEQ ID NO: 69 and the immunoglobulin heavy chain comprises an amino acid sequence with at least 85% identity to SEQ ID NO: 70.

Embodiment 328 comprises the isolated polypeptide or polypeptide complex according to any one of embodiments 322-326, wherein the immunoglobulin light chain comprises an amino acid sequence with at least 90% identity to SEQ ID NO: 69 and the immunoglobulin heavy chain comprises an amino acid sequence with at least 90% identity to SEQ ID NO: 70.

Embodiment 329 comprises the isolated polypeptide or polypeptide complex according to any one of embodiments 322-326, wherein the immunoglobulin light chain comprises an amino acid sequence with at least 92% identity to SEQ ID NO: 69 and the immunoglobulin heavy chain comprises an amino acid sequence with at least 92% identity to SEQ ID NO: 70.

Embodiment 330 comprises the isolated polypeptide or polypeptide complex according to any one of embodiments 322-326, wherein the immunoglobulin light chain comprises an amino acid sequence with at least 95% identity to SEQ ID NO: 69 and the immunoglobulin heavy chain comprises an amino acid sequence with at least 95% identity to SEQ ID NO: 70.

Embodiment 331 comprises the isolated polypeptide or polypeptide complex according to any one of embodiments 322-326, wherein the immunoglobulin light chain comprises an amino acid sequence with at least 98% identity to SEQ ID NO: 69 and the immunoglobulin heavy chain comprises an amino acid sequence with at least 98% identity to SEQ ID NO: 70.

Embodiment 332 comprises the isolated polypeptide or polypeptide complex according to any one of embodiments 322-326, wherein the immunoglobulin light chain comprises an amino acid sequence with at least 99% identity to SEQ ID NO: 69 and the immunoglobulin heavy chain comprises an amino acid sequence with at least 99% identity to SEQ ID NO: 70.

Embodiment 333 comprises the isolated polypeptide or polypeptide complex according to any one of embodiments 322-326, wherein the immunoglobulin light chain comprises an amino acid sequence of SEQ ID NO: 69 and the immunoglobulin heavy chain comprises an amino acid sequence of SEQ ID NO: 70.

Embodiment 334 comprises the isolated polypeptide or polypeptide complex according to any one of embodiments 322-333, wherein the isolated polypeptide or polypeptide complex further comprises a CD3 binding domain.

Embodiment 335 comprises the isolated polypeptide or polypeptide complex according to embodiment 334, wherein the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease.

Embodiment 336 comprises the isolated polypeptide or polypeptide complex according to embodiments 334 or 335, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76 (GTK), CDR3-L comprises an amino acid sequence of SEQ ID NO: 77, CDR1-H SEQ ID NO: 79, and CDR3-L comprises an amino acid sequence of SEQ ID NO: 80.

Embodiment 337 comprises the isolated polypeptide or polypeptide complex according to embodiments 334 or 335, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76 (GTK), CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 276.

Embodiment 338 comprises the isolated polypeptide or polypeptide complex according to embodiments 334 or 335, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76 (GTK), CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286.

Embodiment 339 comprises the isolated polypeptide or polypeptide complex according to embodiments 334 or 335, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76 (GTK), CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 273.

Embodiment 340 comprises the isolated polypeptide or polypeptide complex according to embodiments 334 or 335, wherein the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82.

Embodiment 341 comprises the isolated polypeptide or polypeptide complex according to any one of embodiments 334-340, wherein the CD3 binding domain comprises a Fab, Fab', $(Fab')_2$ or a single chain variable fragment (scFv).

Embodiment 342 comprises the isolated polypeptide or polypeptide complex according to embodiment 341, wherein the CD3 binding domain is the scFv.

Embodiment 343 comprises the isolated polypeptide or polypeptide complex according to embodiments 334 or 335, wherein the CD3 binding domain comprises an amino acid sequence with at least 90%, 95%, 96%, 97%, 98%, 99%, or 100% identity to SEQ ID NO: 99.

Embodiment 344 comprises the isolated polypeptide or polypeptide complex according to embodiments 334 or 335, wherein the CD3 binding domain comprises an amino acid sequence with at least 90%, 95%, 96%, 97%, 98%, 99%, or 100% identity to SEQ ID NO: 308.

Embodiment 345 comprises the isolated polypeptide or polypeptide complex according to embodiments 334 or 335, wherein the CD3 binding domain comprises an amino acid sequence with at least 90%, 95%, 96%, 97%, 98%, 99%, or 100% identity to SEQ ID NO: 329.

Embodiment 346 comprises the isolated polypeptide or polypeptide complex according to embodiments 334 or 335, wherein the CD3 binding domain comprises an amino acid sequence with at least 90%, 95%, 96%, 97%, 98%, 99%, or 100% identity to SEQ ID NO: 305.

Embodiment 347 comprises the isolated polypeptide or polypeptide complex according to embodiment 335, wherein $P_2$ comprises the amino acid sequence of SEQ ID NO: 289 or SEQ ID NO: 292.

Embodiment 348 comprises the isolated polypeptide or polypeptide complex according to embodiment 335, wherein $P_2$ comprises the amino acid sequence of SEQ ID NO: 295.

Embodiment 349 comprises the isolated polypeptide or polypeptide complex according to embodiment 322, wherein the isolated polypeptide or polypeptide complex comprises amino acid sequences with at least 90%, 95%, 96%, 97%, 98%, 99%, or 100% identity to SEQ ID NO: 200 and SEQ ID NO: 201.

Embodiment 350 comprises the isolated polypeptide or polypeptide complex according to embodiment 322, wherein the isolated polypeptide or polypeptide complex comprises amino acid sequences of SEQ ID NO: 200 and SEQ ID NO: 201.

Embodiment 351 comprises the isolated polypeptide or polypeptide complex according to embodiment 322, wherein the isolated polypeptide or polypeptide complex comprises amino acid sequences with at least 90%, 95%, 96%, 97%, 98%, 99%, or 100% identity to SEQ ID NO: 362 and SEQ ID NO: 363.

Embodiment 352 comprises the isolated polypeptide or polypeptide complex according to embodiment 322, wherein the isolated polypeptide or polypeptide complex comprises amino acid sequences with at least 90%, 95%, 96%, 97%, 98%, 99%, or 100% identity to SEQ ID NO: 382 and SEQ ID NO: 383.

Embodiment 353 comprises the isolated polypeptide or polypeptide complex according to embodiment 322, wherein the isolated polypeptide or polypeptide complex comprises amino acid sequences with at least 90%, 95%, 96%, 97%, 98%, 99%, or 100% identity to SEQ ID NO: 390 and SEQ ID NO: 391.

Embodiment 354 comprises an isolated polypeptide or polypeptide complex according to Formula I: $A_1$-$L_1$-$P_1$ (Formula I) wherein: $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein CDR1-L comprises the amino acid sequence of SEQ ID NO: 1; wherein CDR2-L comprises the amino acid sequence of SEQ ID NO: 2; wherein CDR3-L comprises the amino acid sequence of SEQ ID NO: 3; wherein CDR1-H comprises the amino acid sequence of SEQ ID NO: 13; wherein CDR2-H comprises the amino acid sequence of SEQ ID NO: 14; and wherein CDR3-H comprises the amino acid sequence of SEQ ID NO: 27; $P_1$ comprises a peptide that binds to $A_1$, wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions or deletions relative to any one of SEQ ID NOs: 100-107, 109, 111-113, 116-117, 119, and 123-163; and $L_1$ comprises a linking moiety that connects $A_1$ to $P_1$ and is a substrate for a tumor specific protease.

Embodiment 355 comprises the isolated polypeptide or polypeptide complex according to embodiment 354, wherein $P_1$ comprises an amino acid sequence according to any one of SEQ ID NOs: 107, 109, 116, 141, 142, 148, 149, 150, and 158, or an amino acid sequence that has 1, 2, or 3 amino acid mutations, substitutions or deletions relative to any one of SEQ ID NOs: 107, 109, 116, 141, 142, 148, 149, 150, and 158.

Embodiment 356 comprises the isolated polypeptide or polypeptide complex according to embodiments 354 or 355, wherein $P_1$ comprises an amino acid sequence according to SEQ ID NO: 107.

Embodiment 357 comprises the isolated polypeptide or polypeptide complex according to any one of embodiment 354-356, wherein the TROP2 binding domain comprises a Fab, Fab', $(Fab')_2$ or a single chain variable fragment (scFv).

Embodiment 358 comprises the isolated polypeptide or polypeptide complex according to embodiment 357, wherein the TROP2 binding domain is a Fab.

Embodiment 359 comprises the isolated polypeptide or polypeptide complex according to any one of embodiments 354-358, wherein the immunoglobulin light chain comprises an amino acid sequence with at least 85% identity to SEQ ID NO: 71 and the immunoglobulin heavy chain comprises an amino acid sequence with at least 85% identity to SEQ ID NO: 72.

Embodiment 360 comprises the isolated polypeptide or polypeptide complex according to any one of embodiments 354-358, wherein the immunoglobulin light chain comprises an amino acid sequence with at least 90% identity to SEQ ID NO: 71 and the immunoglobulin heavy chain comprises an amino acid sequence with at least 90% identity to SEQ ID NO: 72.

Embodiment 361 comprises the isolated polypeptide or polypeptide complex according to any one of embodiments 354-358, wherein the immunoglobulin light chain comprises an amino acid sequence with at least 92% identity to SEQ ID NO: 71 and the immunoglobulin heavy chain comprises an amino acid sequence with at least 92% identity to SEQ ID NO: 72.

Embodiment 362 comprises the isolated polypeptide or polypeptide complex according to any one of embodiments 354-358, wherein the immunoglobulin light chain comprises an amino acid sequence with at least 95% identity to SEQ ID NO: 71 and the immunoglobulin heavy chain comprises an amino acid sequence with at least 95% identity to SEQ ID NO: 72.

Embodiment 363 comprises the isolated polypeptide or polypeptide complex according to any one of embodiments 354-358, wherein the immunoglobulin light chain comprises an amino acid sequence with at least 98% identity to SEQ ID NO: 71 and the immunoglobulin heavy chain comprises an amino acid sequence with at least 98% identity to SEQ ID NO: 72.

Embodiment 364 comprises the isolated polypeptide or polypeptide complex according to any one of embodiments 354-358, wherein the immunoglobulin light chain comprises an amino acid sequence with at least 99% identity to SEQ ID NO: 71 and the immunoglobulin heavy chain comprises an amino acid sequence with at least 99% identity to SEQ ID NO: 72.

Embodiment 365 comprises the isolated polypeptide or polypeptide complex according to any one of embodiments 354-358, wherein the immunoglobulin light chain comprises an amino acid sequence of SEQ ID NO: 71 and the immunoglobulin heavy chain comprises an amino acid sequence of SEQ ID NO: 72.

Embodiment 366 comprises the isolated polypeptide or polypeptide complex according to any one of embodiments 354-365, wherein the isolated polypeptide or polypeptide complex further comprises a CD3 binding domain.

Embodiment 367 comprises the isolated polypeptide or polypeptide complex according to embodiment 366, wherein the isolated polypeptide or polypeptide complex is according to the formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease.

Embodiment 368 comprises the isolated polypeptide or polypeptide complex according to embodiments 366 or 367, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76 (GTK), CDR3-L comprises an amino acid sequence of SEQ ID NO: 77, CDR1-H comprises an amino acid sequence of SEQ ID NO: 78, CDR2-H comprises an amino acid sequence of SEQ ID NO: 79, and CDR3-L comprises an amino acid sequence of SEQ ID NO: 80.

Embodiment 369 comprises the isolated polypeptide or polypeptide complex according to embodiments 366 or 367, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 75, CDR2-L comprises an amino acid sequence of SEQ ID NO: 76 (GTK), CDR3-L comprises an amino acid sequence of SEQ ID NO: 77, CDR1-H SEQ ID NO: 79, and CDR3-L comprises an amino acid sequence of SEQ ID NO: 276.

Embodiment 370 comprises the isolated polypeptide or polypeptide complex according to embodiments 366 or 367, wherein the CD3 binding domain comprises an immunoglobulin light chain comprising complementary determining regions (CDRs) CDR1-L, CDR2-L, and CDR3-L, and an immunoglobulin heavy chain comprising CDRs: CDR1-H, CDR2-H, and CDR3-H, and wherein CDR1-L comprises an amino acid sequence of SEQ ID NO: 259, CDR2-L comprises an amino acid sequence of SEQ ID NO: 76 (GTK), CDR3-L comprises an amino acid sequence of SEQ ID NO: 260, CDR1-H comprises an amino acid sequence of SEQ ID NO: 270, CDR2-H comprises an amino acid sequence of SEQ ID NO: 79, and CDR3-L comprises an amino acid sequence of SEQ ID NO: 286.

Embodiment 371 comprises the isolated polypeptide or polypeptide complex according to embodiments 366 or 367, wherein the immunoglobulin light chain of the CD3 binding domain comprises an amino acid sequence with at least 90%, 95%, 96%, 97%, 98%, 99%, or 100% identity to SEQ ID NO: 81 and the immunoglobulin heavy chain of the CD3 binding domain comprises an amino acid sequence with at least 90%, 95%, 96%, 97%, 98%, 99%, or 100% identity to SEQ ID NO: 82.

Embodiment 372 comprises the isolated polypeptide or polypeptide complex according to embodiments 366 or 367, wherein the CD3 binding domain comprises a Fab, Fab', $(Fab')_2$ or a single chain variable fragment (scFv).

Embodiment 373 comprises the isolated polypeptide or polypeptide complex according to embodiment 372, wherein the CD3 binding domain is the scFv.

Embodiment 374 comprises the isolated polypeptide or polypeptide complex according to embodiments 366 or 367, wherein the CD3 binding domain comprises an amino acid sequence with at least 90%, 95%, 96%, 97%, 98%, 99%, or 100% identity to SEQ ID NO: 99.

Embodiment 375 comprises the isolated polypeptide or polypeptide complex according to embodiments 366 or 367, wherein the CD3 binding domain comprises an amino acid sequence with at least 90%, 95%, 96%, 97%, 98%, 99%, or 100% identity to SEQ ID NO: 308.

Embodiment 376 comprises the isolated polypeptide or polypeptide complex according to embodiments 366 or 367, wherein the CD3 binding domain comprises an amino acid sequence with at least 90%, 95%, 96%, 97%, 98%, 99%, or 100% identity to SEQ ID NO: 329.

Embodiment 377 comprises the isolated polypeptide or polypeptide complex according to embodiment 367, wherein $P_2$ comprises the amino acid sequence of SEQ ID NO: 289 or SEQ ID NO: 292.

Embodiment 378 comprises the isolated polypeptide or polypeptide complex according to embodiment 367, wherein $P_2$ comprises the amino acid sequence of SEQ ID NO: 295.

Embodiment 379 comprises the isolated polypeptide or polypeptide complex according to embodiment 354, wherein the isolated polypeptide or polypeptide complex comprises amino acid sequences with at least 90%, 95%, 96%, 97%, 98%, 99%, or 100% identity to SEQ ID NO: 180 and SEQ ID NO: 181.

Embodiment 380 comprises the isolated polypeptide or polypeptide complex according to embodiment 354, wherein the isolated polypeptide or polypeptide complex comprises amino acid sequences of SEQ ID NO: 180 and SEQ ID NO: 181.

Embodiment 381 comprises the isolated polypeptide or polypeptide complex according to embodiment 354, wherein the isolated polypeptide or polypeptide complex comprises amino acid sequences with at least 90%, 95%, 96%, 97%, 98%, 99%, or 100% identity to SEQ ID NO: 352 and SEQ ID NO: 353.

Embodiment 382 comprises the isolated polypeptide or polypeptide complex according to embodiment 354, wherein the isolated polypeptide or polypeptide complex comprises amino acid sequences with at least 90%, 95%, 96%, 97%, 98%, 99%, or 100% identity to SEQ ID NO: 354 and SEQ ID NO: 355.

Embodiment 383 comprises a pharmaceutical composition comprising: (i) the isolated polypeptide or polypeptide complex thereof according to any one of the preceding embodiments; and (ii) a pharmaceutically acceptable excipient.

Embodiment 384 comprises an isolated recombinant nucleic acid molecule encoding an isolated polypeptide or polypeptide complex according to any one of embodiments 1-382.

Embodiment 385 comprises a method of treating a cancer in a subject in need thereof comprising administering to the subject the isolated polypeptide or polypeptide complex according to any one of embodiments 1-382.

Embodiment 386 comprises the method of embodiment 385, wherein the cancer comprises breast cancer, lung cancer, urothelial cancer, endometrial cancer, ovarian cancer, prostate cancer, pancreatic cancer, gastric cancer, colon cancer, head and neck cancer, or glioma.

Embodiment 387 comprises the method of embodiment 386, wherein the breast cancer comprises triple-negative breast cancer.

Embodiment 388 comprises the method of embodiment 386, wherein the lung cancer comprises non-small cell lung cancer.

EXAMPLES

Example 1: Alanine Scanning of TROP2 Binding Domain CDR3s

Alanine scanning of the TROP2 binding domain (TBD) was carried out in order to establish CDR3 related sequence activity relationships (SAR). TROP2 Fabs were mutated in the CDR3 light chain (LC) region or the CDR3 heavy chain (HC) region of the Immunomedics TROP2 Fab (hRS7) Alanine scanning was accomplished by mutating individual residues in the CDR3 LC region and the CDR3 HC region of the anti-TROP2 Fab starting sequence to alanine. The amino acid sequences of the non-mutated (or "wild-type") and mutated TBD constructs are shown in Table 4. TBD-1 is the "wild-type" or starting sequence anti-TROP2 Fab. TBD-2 to TBD-10 are the TBDs having individual alanine mutations in the CDR3 LC region, and TBD-11 to TBD-23 are the TBDs having individual alanine mutations in the CDR3 HC region.

Example 2: Binding of TBDs to TROP2

Kinetic Binding to TROP2 Via BLI

The wild-type and alanine mutated TBDs of Example 1 were evaluated for their ability to bind TROP2. Kinetic binding was measured using biolayer interferometry (BLI). Briefly, biotinylated human TROP2 was loaded onto a streptavidin coated Octet® SAX biosensor, quenched in biocytin, and baselined in buffer. The TBDs diluted in buffer were then associated onto the antigen loaded biosensors. Sensors were then transferred to buffer where the TBD constructs then dissociated from the sensors. Association and dissociation rates were measured in real time using an Octet® instrument. Example sensorgrams for non-mutated (TBD-1) and CDR3 LC alanine scanning mutants (TBD-2 to TBD-10) are shown in FIGS. 1A-1J. Example sensorgrams for CDR3 HC alanine scanning mutants (TBD-11 to TBD-23) are shown in FIGS. 2A-2M. Exemplary experimental conditions and steps used for the kinetic binding measurements are shown in Table 14. For both the kinetic and equilibrium binding studies, the extracellular domain (ECD) of TROP2 was used (Table 13; SEQ ID NO: 396). The amino acid sequence of the extracellular domain of cynomolgus monkey TROP2 (SEQ ID NO: 397) as well as the full length amino acid sequences for human and cynomolgus monkey TROP2 (SEQ ID NO: 398 and SEQ ID NO: 399) are also provided in Table 13.

TABLE 13

Human and cynomolgus monkey TROP2 sequences.

| Description | Amino Acid Sequence (N to C) | SEQ ID NO: |
|---|---|---|
| Human TROP2 ECD (31-274 AA) | QDNCTCPTNKMTVCSPDGPG<br>GRCQCRALGSGMAVDCSTLT<br>SKCLLLKARMSAPKNARTLV<br>RPSEHALVDNDGLYDPDCDP<br>EGRFKARQCNQTSVCWCVNS<br>VGVRRTDKGDLSLRCDELVR<br>THHILIDLRHRPTAGAFNHS<br>DLDAELRRLFRERYRLHPKF<br>VAAVHYEQPTIQIELRONTS<br>QKAAGDVDIGDAAYYFERDI<br>KGESLFQGRGGLDLRVRGEP<br>LQVERTLIYYLDEIPPKFSM<br>KRLT | 396 |
| Cyno TROP2 ECD (31-274 AA) | QDNCTCPTNKMTVCSPDGPG<br>GRCQCRALGSGVAVDCSTLT<br>SKCLLLKARMSAPKNARTLV<br>RPNEHALVDNDGLYDPDCDP<br>EGRFKARQCNQTSVCWCVNS<br>VGVRRTDKGDLSLRCDELVR<br>THHILIDLRHRPTAGAFNHS<br>DLDAELRRLFRERYRLHPKF<br>VAAVHYEQPTIQIELRONTS<br>QKAAGDVDIGDAAYYFERDV<br>KGESLFQGRGGLDLRVRGEP<br>LQVERTLIYYLDEIPPKFSM<br>KRLT | 397 |
| Human TROP2 Full length | QDNCTCPTNKMTVCSPDGPG<br>GRCQCRALGSGMAVDCSTLT<br>SKCLLLKARMSAPKNARTLV<br>RPSEHALVDNDGLYDPDCDP<br>EGRFKARQCNQTSVCWCVNS<br>VGVRRTDKGDLSLRCDELVR<br>THHILIDLRHRPTAGAFNHS<br>DLDAELRRLFRERYRLHPKF<br>VAAVHYEQPTIQIELRONTS<br>QKAAGDVDIGDAAYYFERDI<br>KGESLFQGRGGLDLRVRGEP<br>LQVERTLIYYLDEIPPKFSM<br>KRLTAGLIAVIVVVVVALVA<br>GMAVLVITNRRKSGKYKKVE<br>IKELGELRKEPSL | 398 |
| Cyno TROP2 Full length | QDNCTCPTNKMTVCSPDGPG<br>GRCQCRALGSGVAVDCSTLT<br>SKCLLLKARMSAPKNARTLV<br>RPNEHALVDNDGLYDPDCDP<br>EGRFKARQCNQTSVCWCVNS<br>VGVRRTDKGDLSLRCDELVR<br>THHILIDLRHRPTAGAFNHS<br>DLDAELRRLFRERYRLHPKF<br>VAAVHYEQPTIQIELRQNTS<br>QKAAGDVDIGDAAYYFERDV<br>KGESLFQGRGGLDLRVRGEP<br>LQVERTLIYYLDEIPPKFSM<br>KRLTAGLIAVIVVVVVALVA<br>GVAVLVISNRRKSGKYKKVE<br>IKELGELRKEPSL | 399 |

TABLE 14

| Step | Time |
|---|---|
| Sensor: SAX | |
| Baseline: Octet buffer | 60 seconds |
| Loading: Human TROP2-biotin (10 nM) | 300 seconds |
| Biocytin quench (100 μM) | 300 seconds |
| Baseline: Octet buffer | 300 seconds |
| Association: | 300 seconds |
| 50 nM Fab | |
| 25 nM Fab | |
| 12.5 nM Fab | |
| 6.25 nM Fab | |
| Dissociation: Octet buffer | 600 seconds |

Equilibrium Binding to TROP2 Via ELISA

Figure 1A:
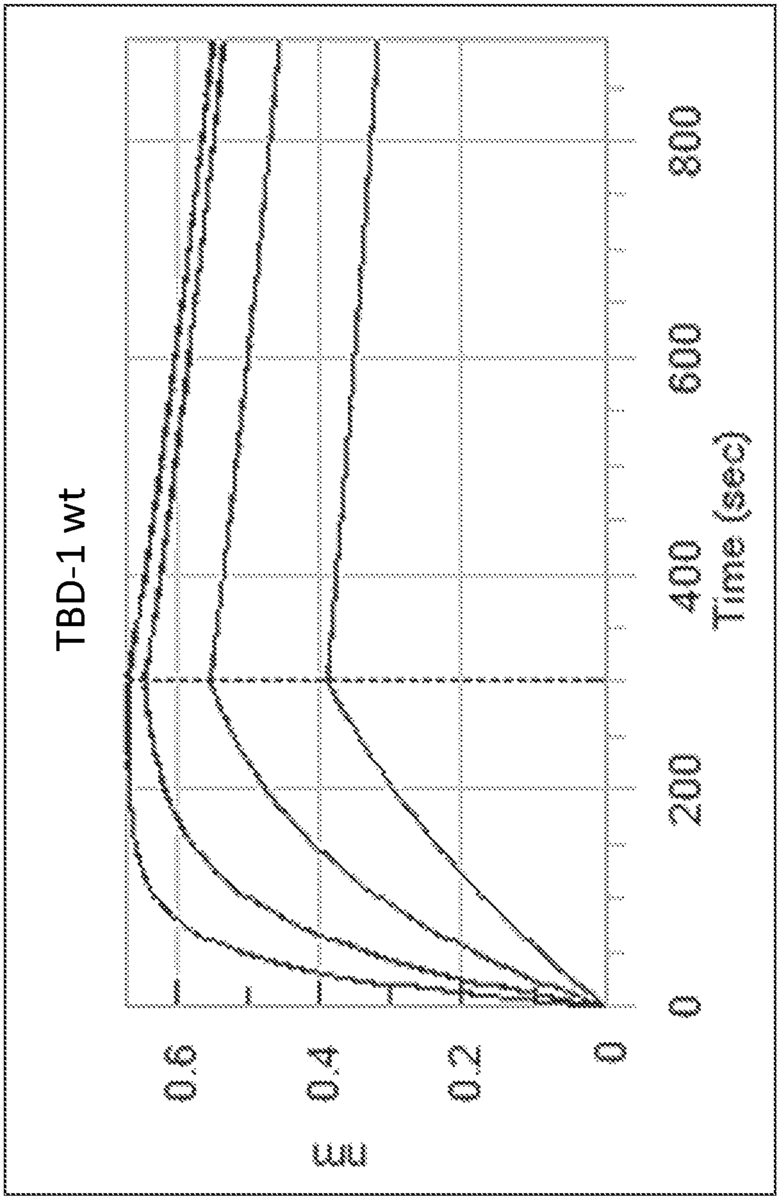
FIGS. 1A-1J illustrate biolayer interferometry (BLI) titration data for TROP2 binding by non-mutated and mutated TROP2 binding domains (TBDs).
Figure 1B:
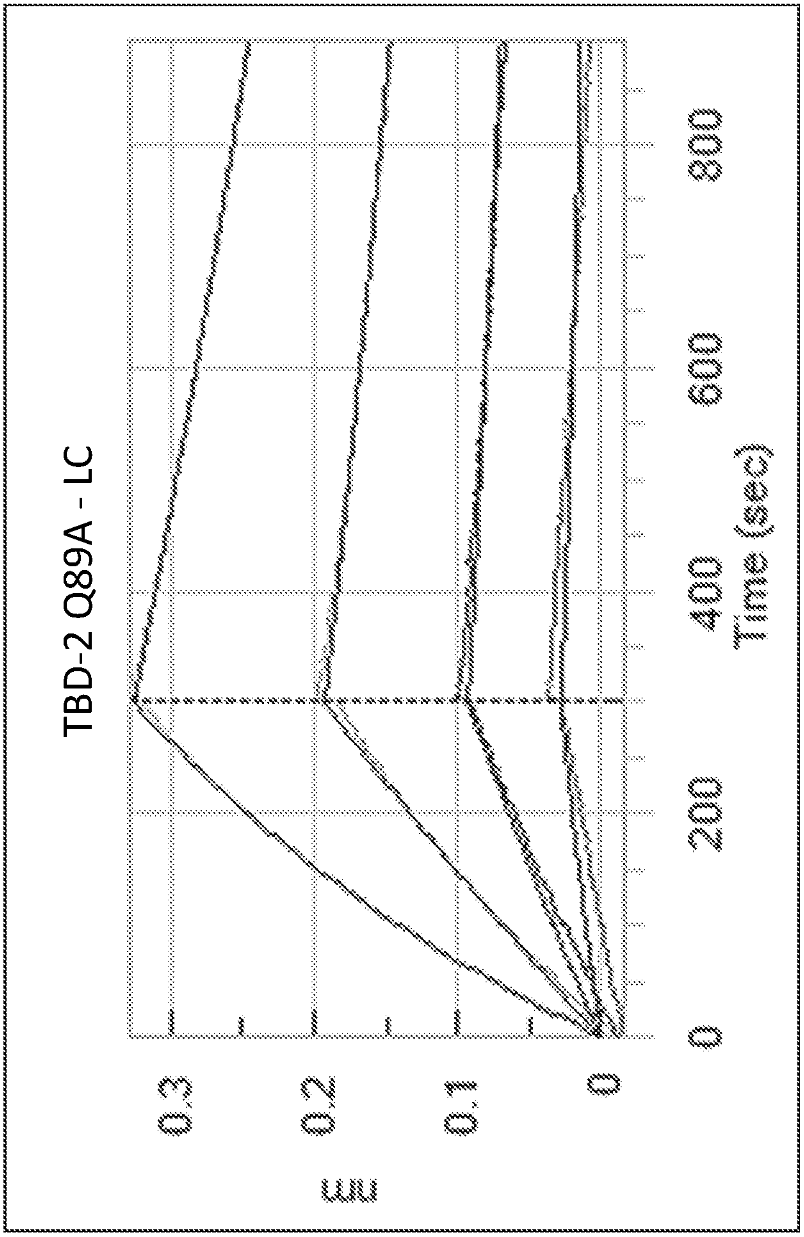
Figure 1C:
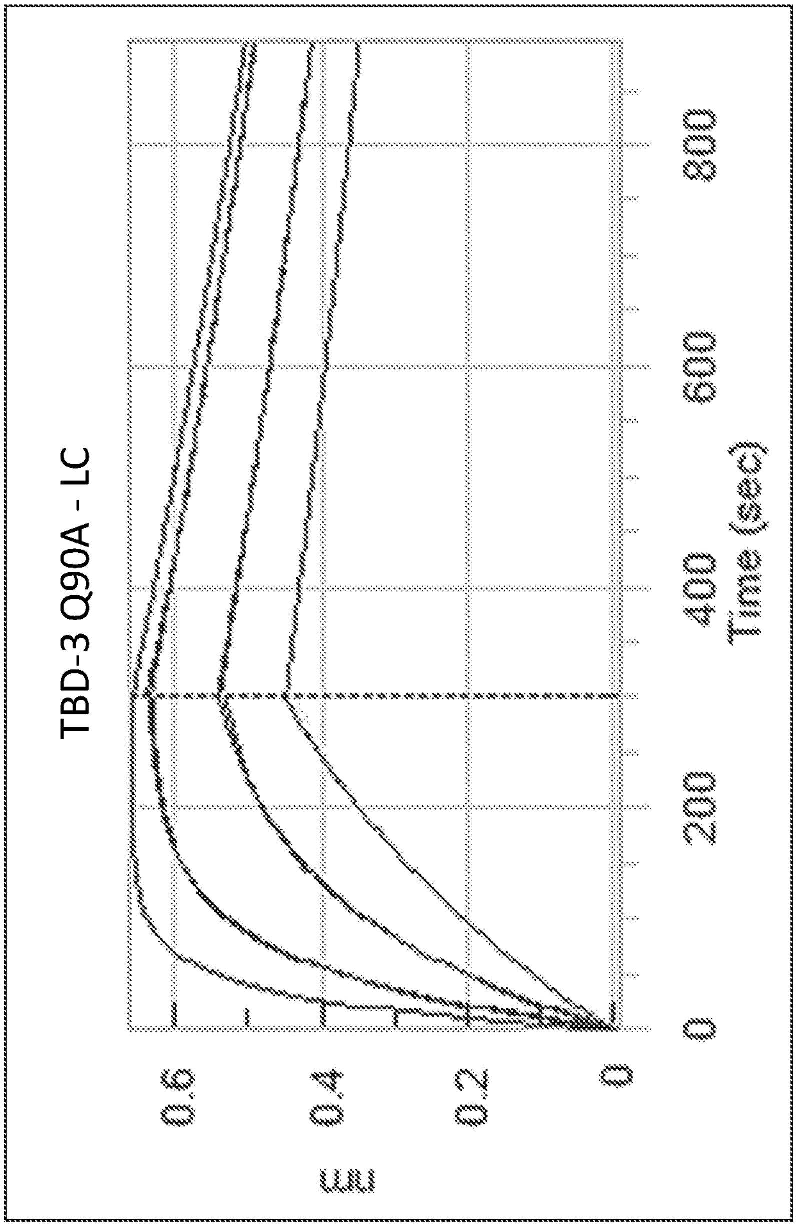
Figure 1D:
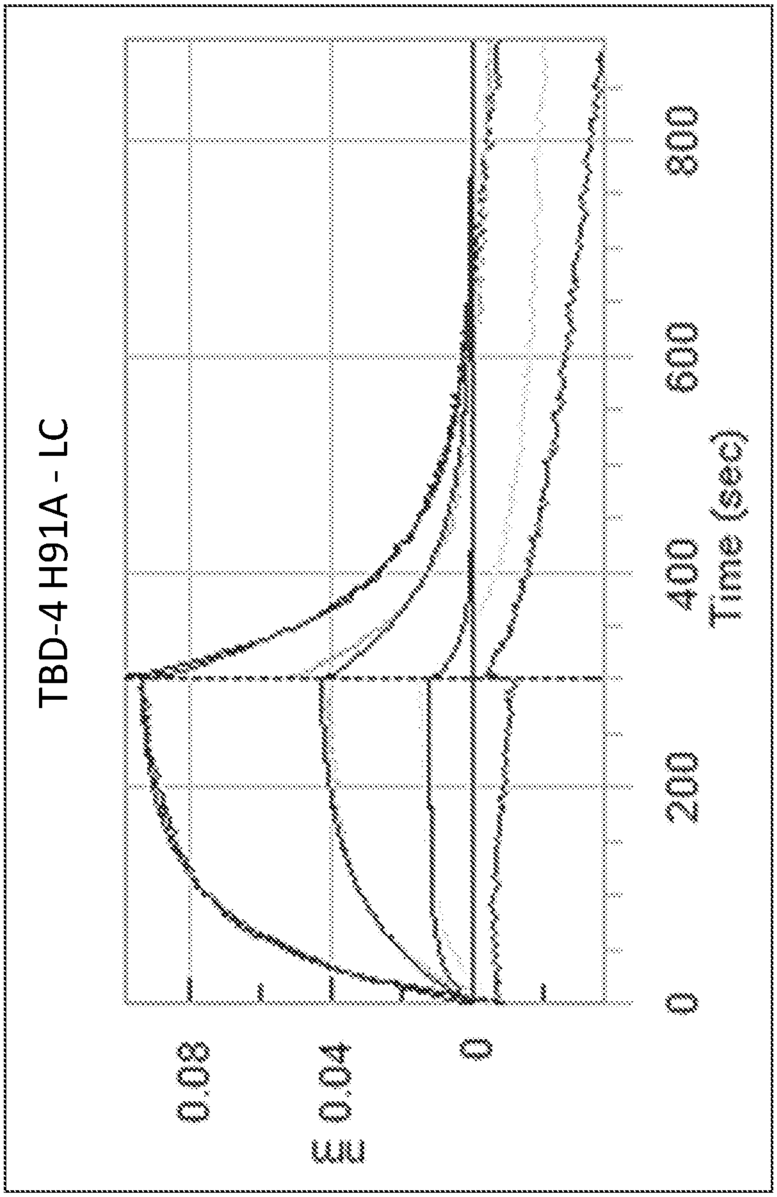
Figure 1E:
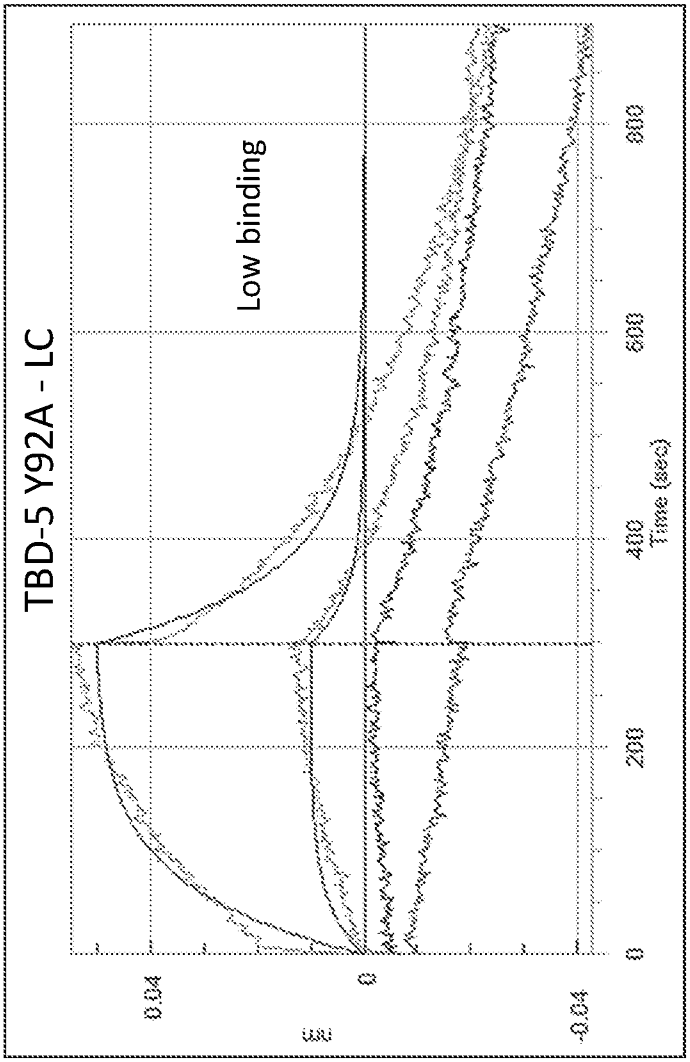
Figure 1F:
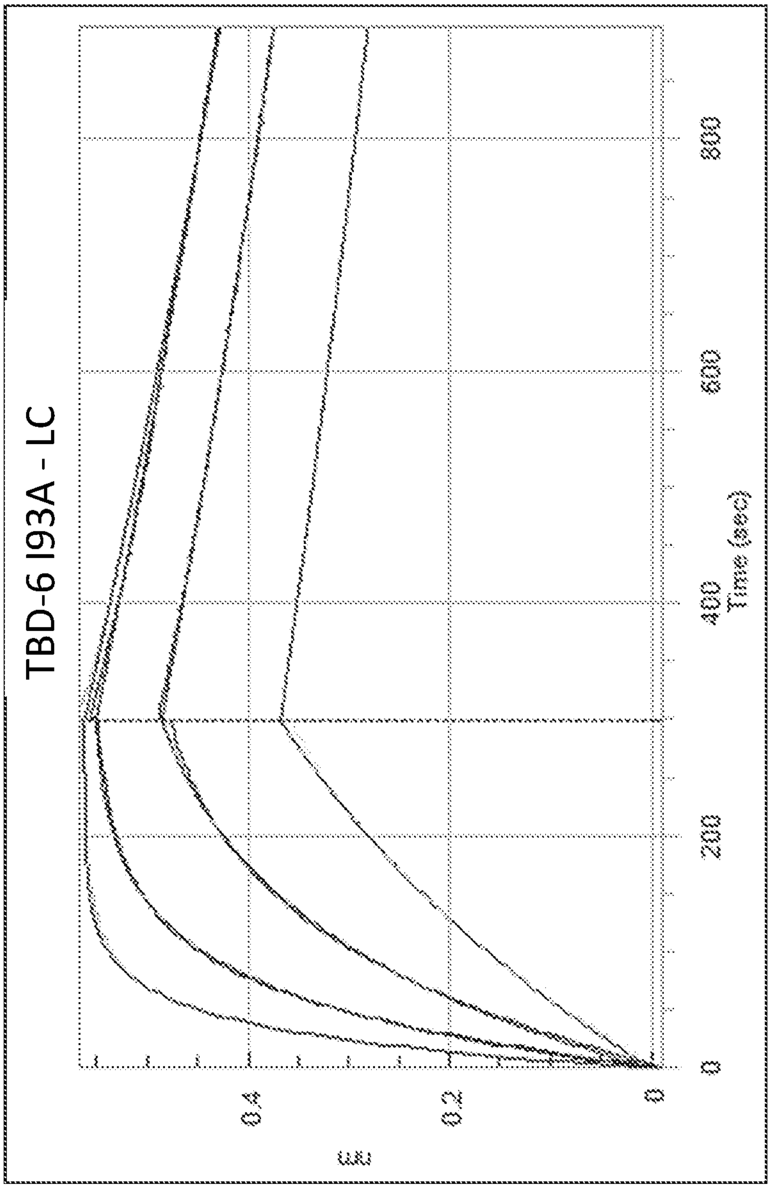
Figure 1G:
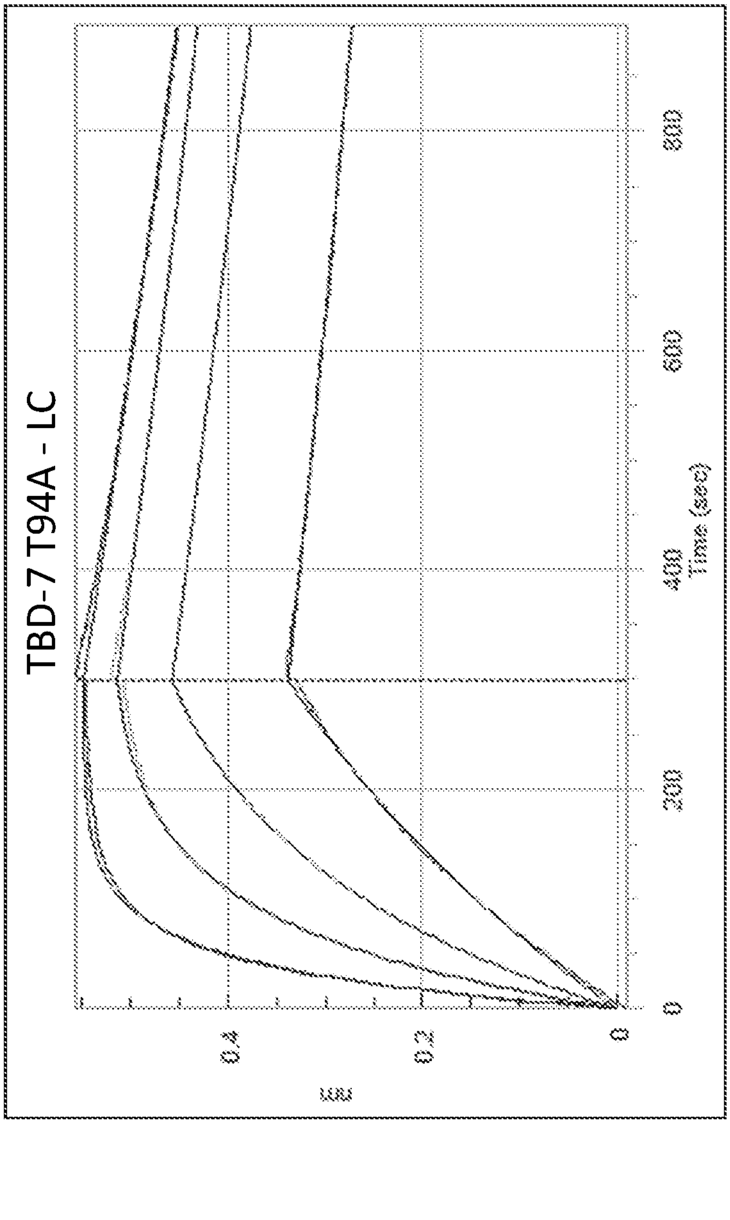
Figure 1H:
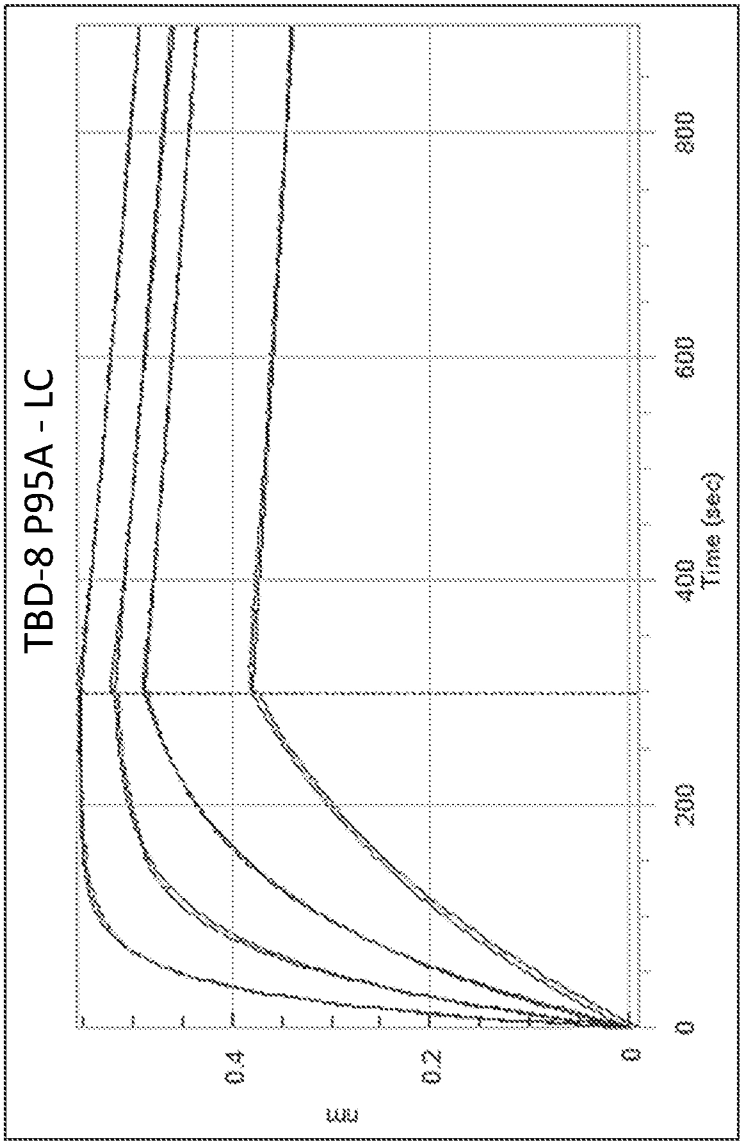
Figure 1I:
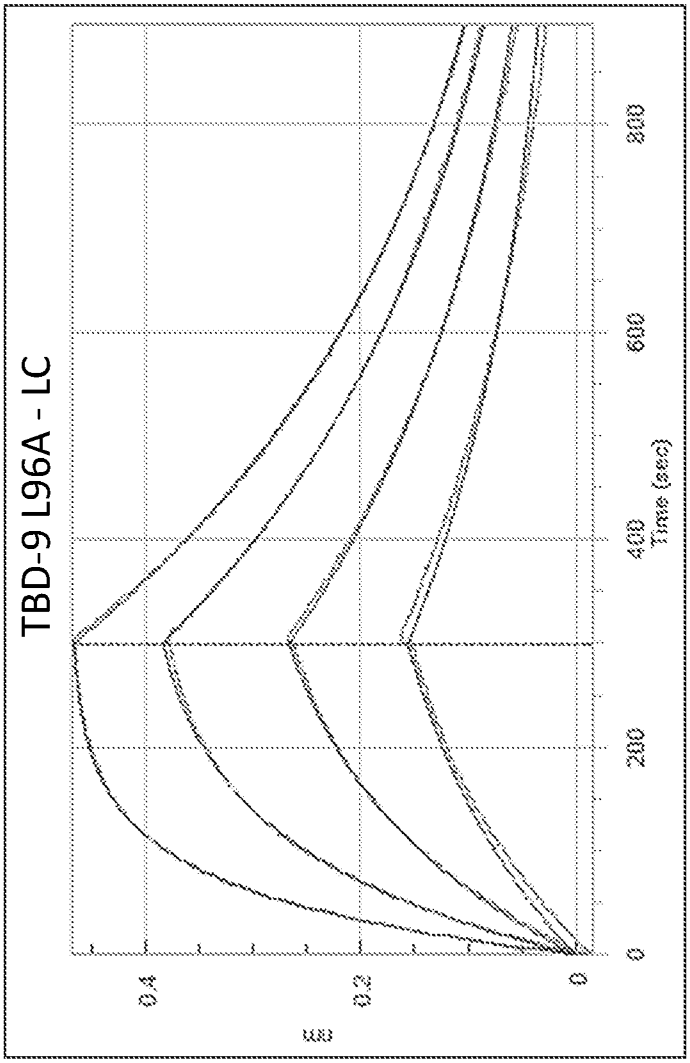
Figure 1J:
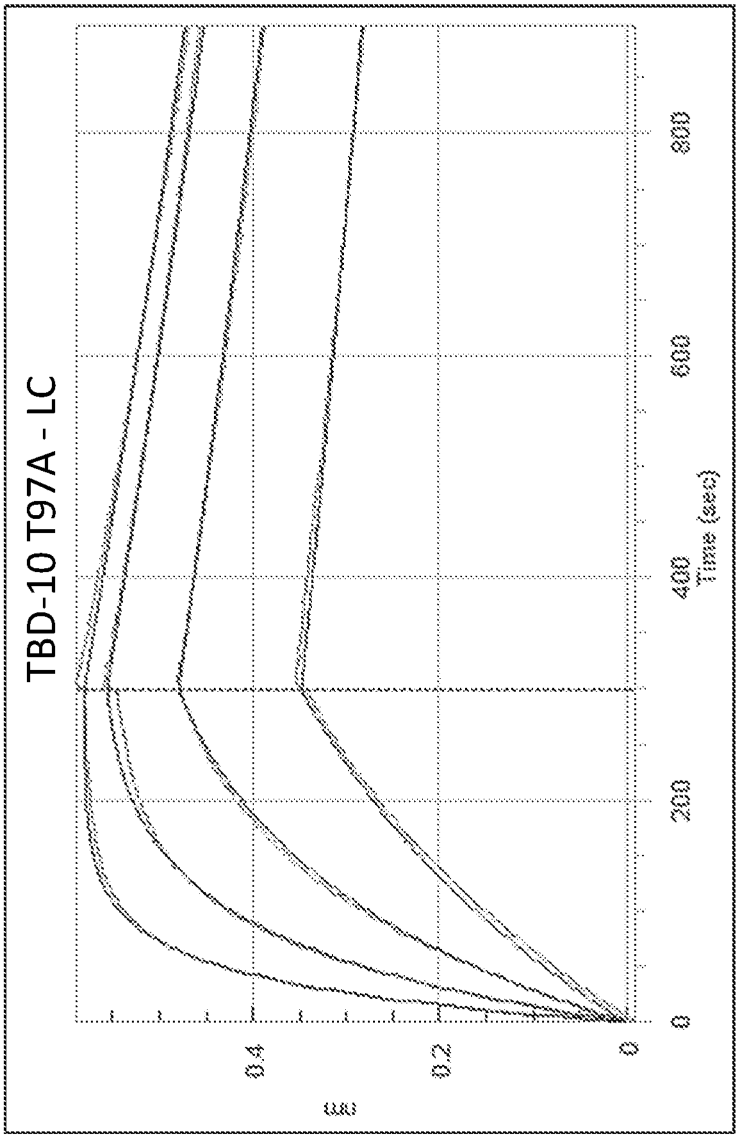
Figure 2A:
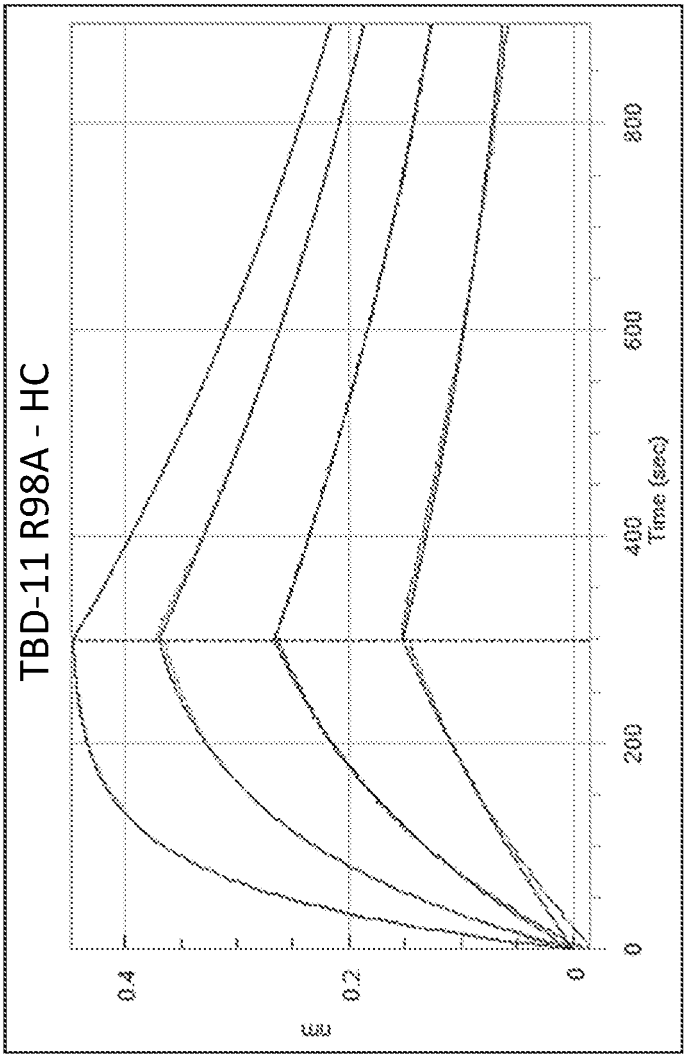
FIGS. 2A-2M illustrate BLI titration data for TROP2 binding by mutated TBDs.
Figure 2B:
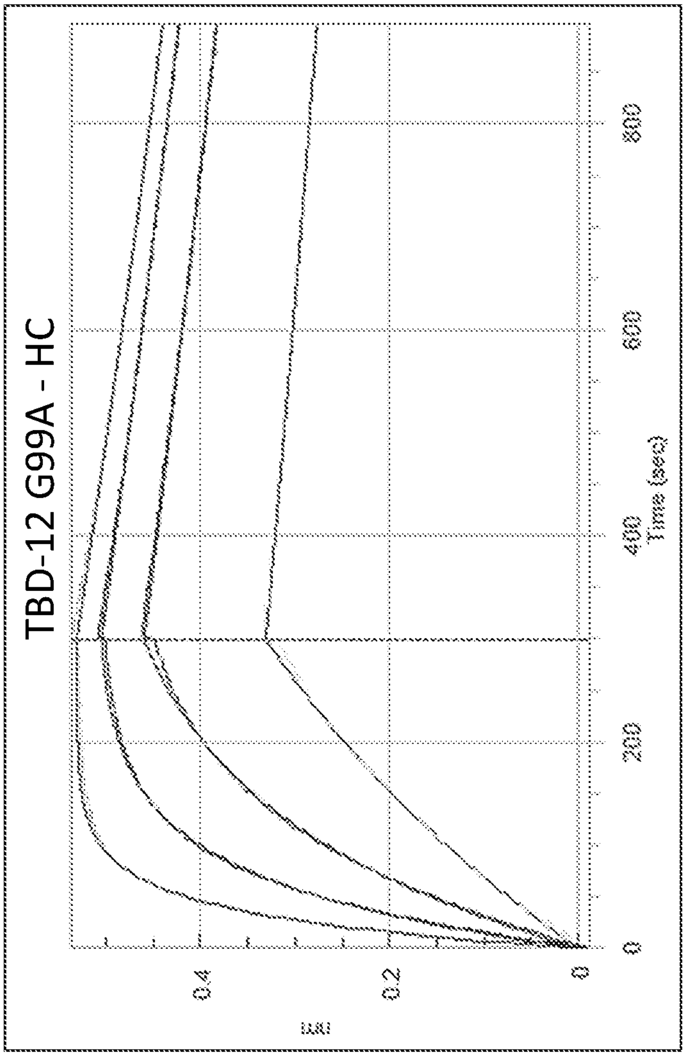
Figure 2C:
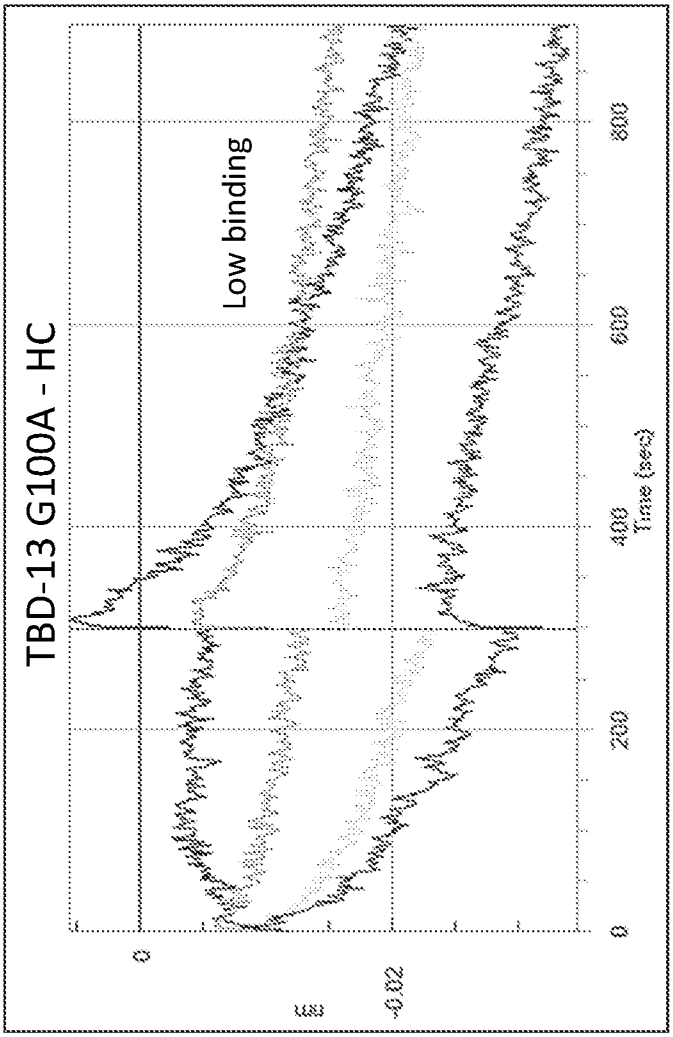
Figure 2D:
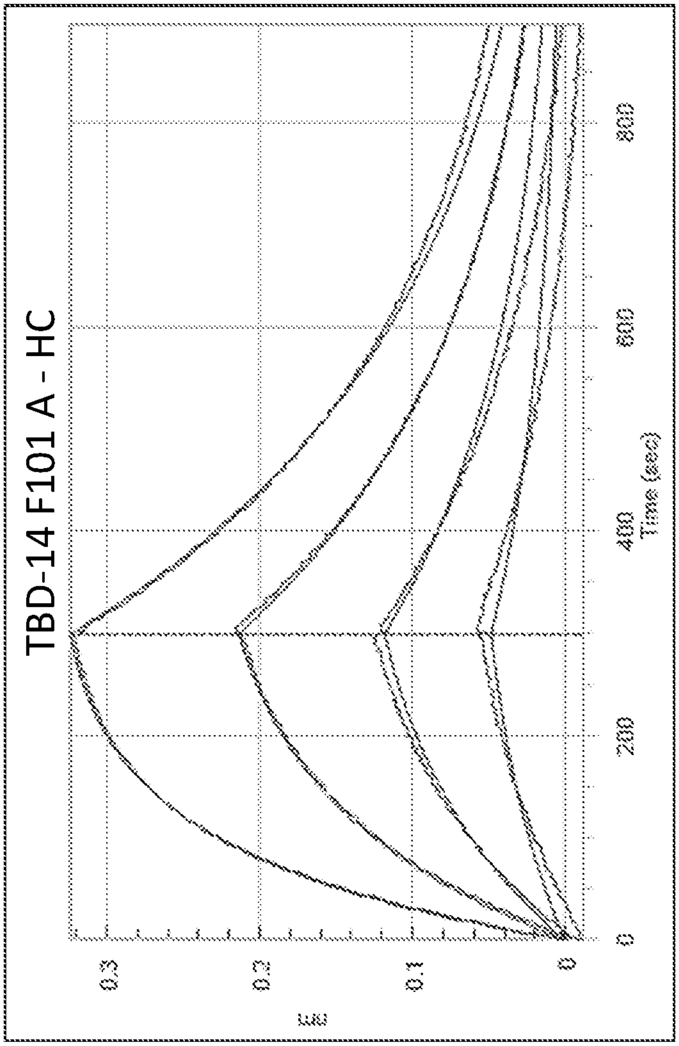
Figure 2E:
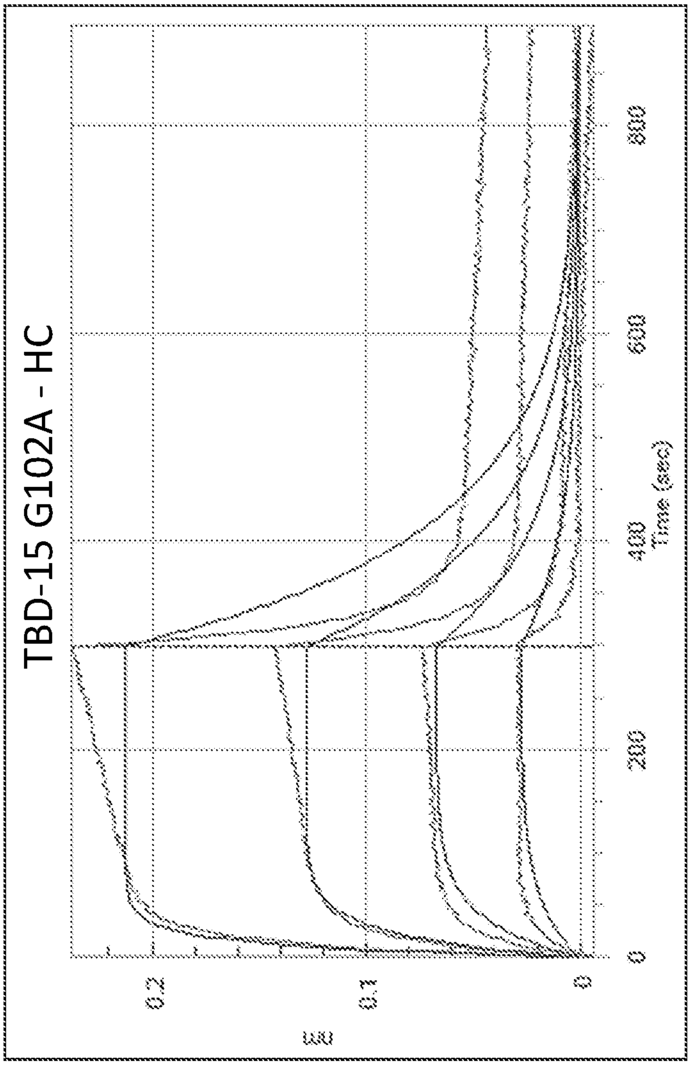
Figure 2F:
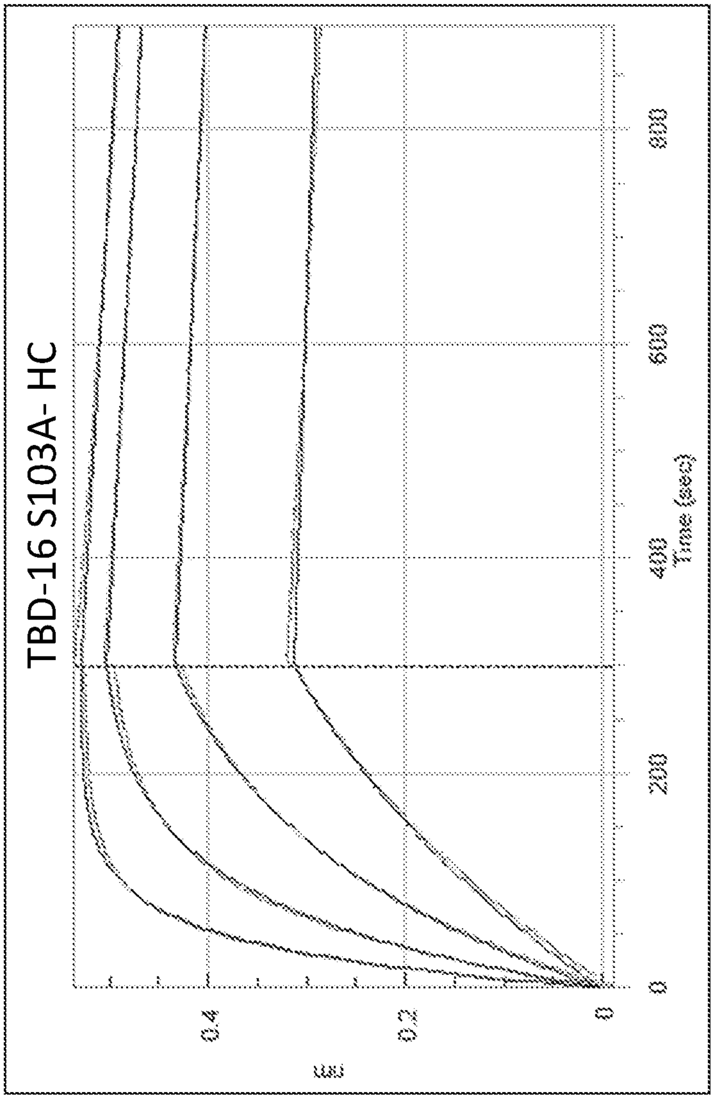
Figure 2G:
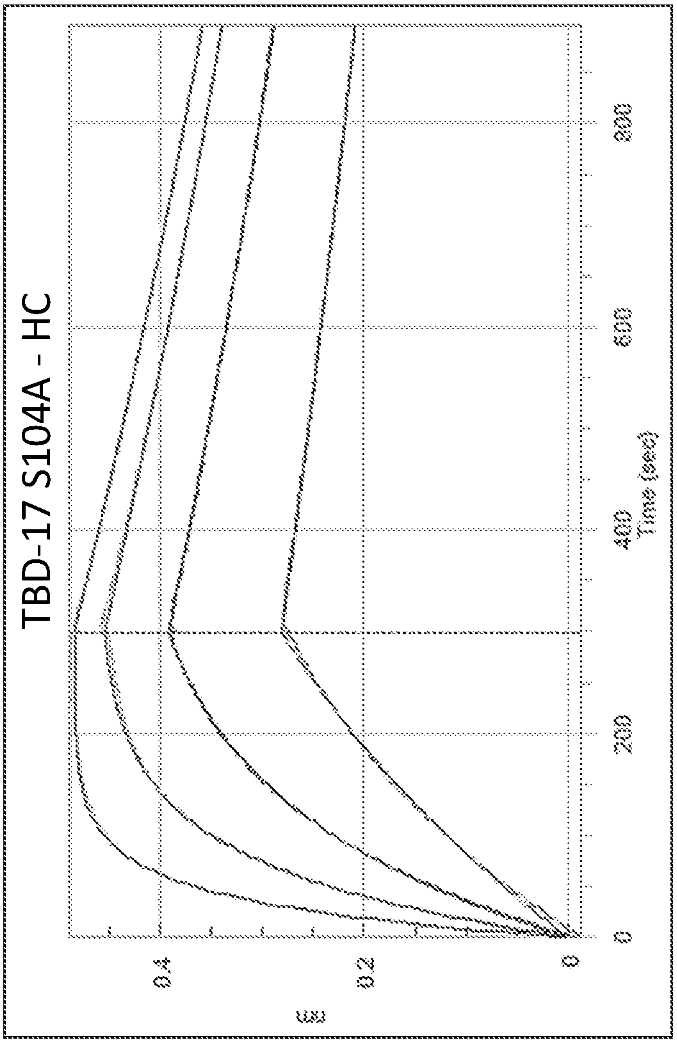
Figure 2H:
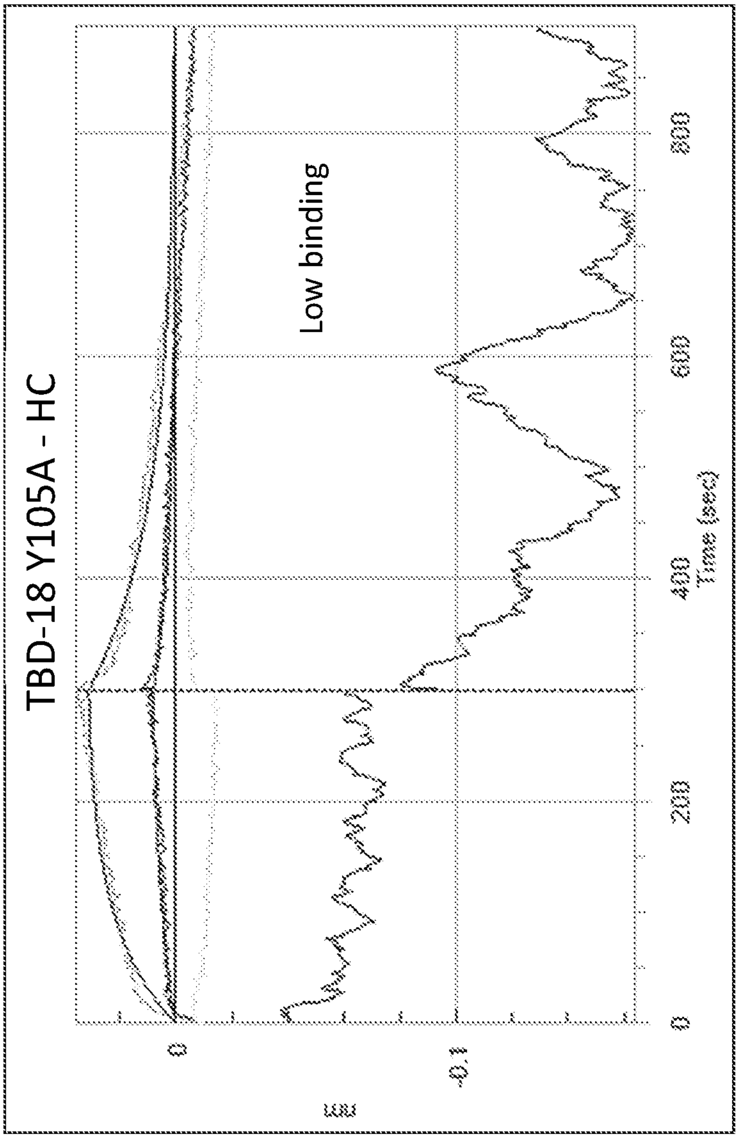
Figure 2I:
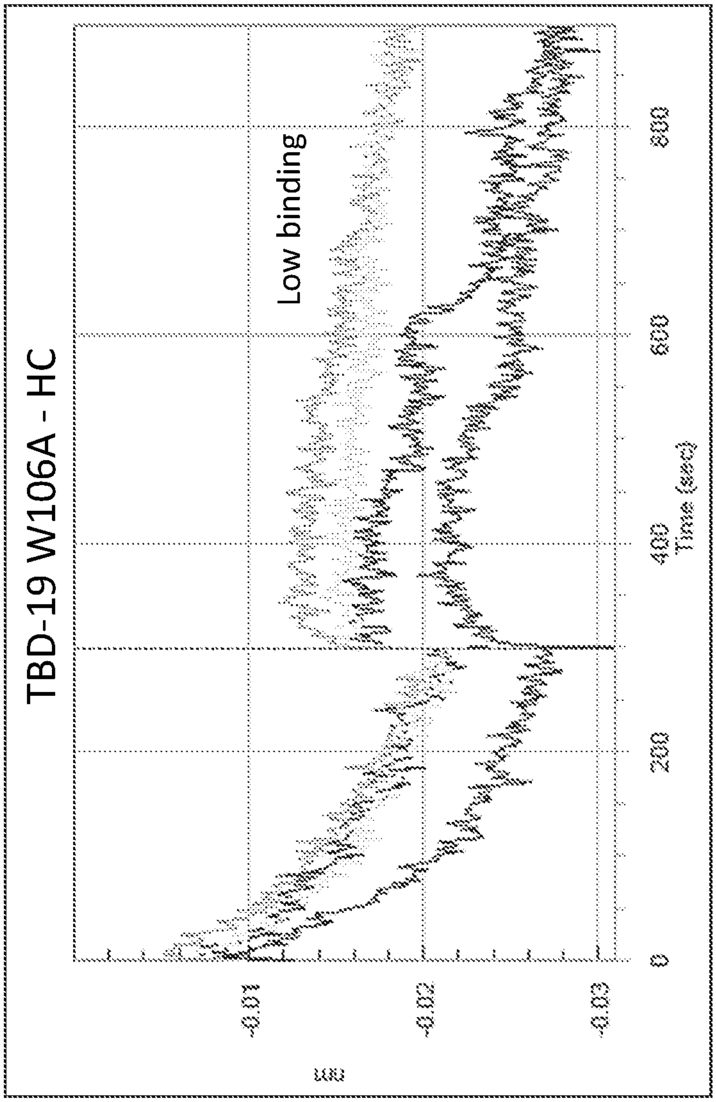
Figure 2J:
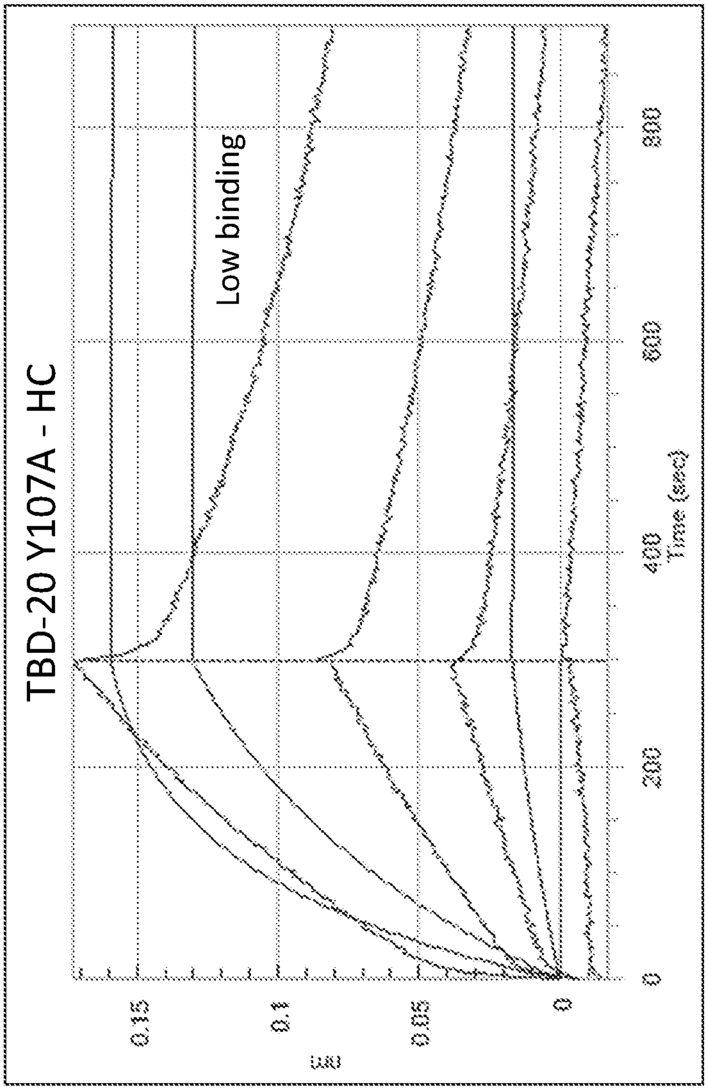
Figure 2K:
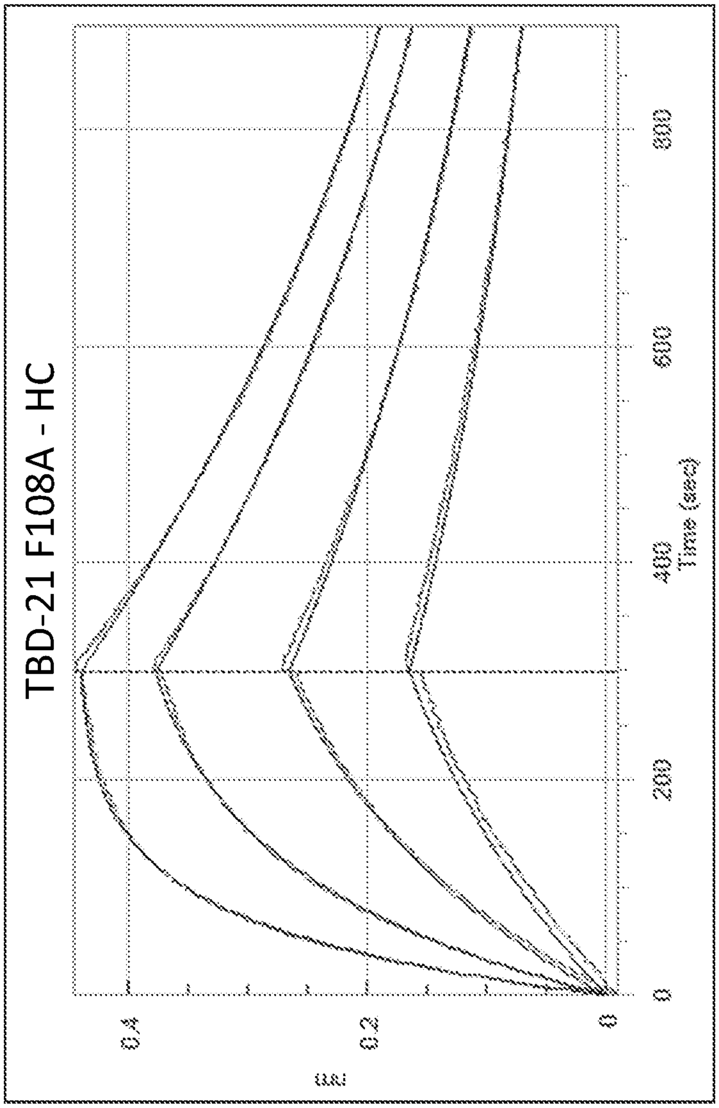
Figure 2L:
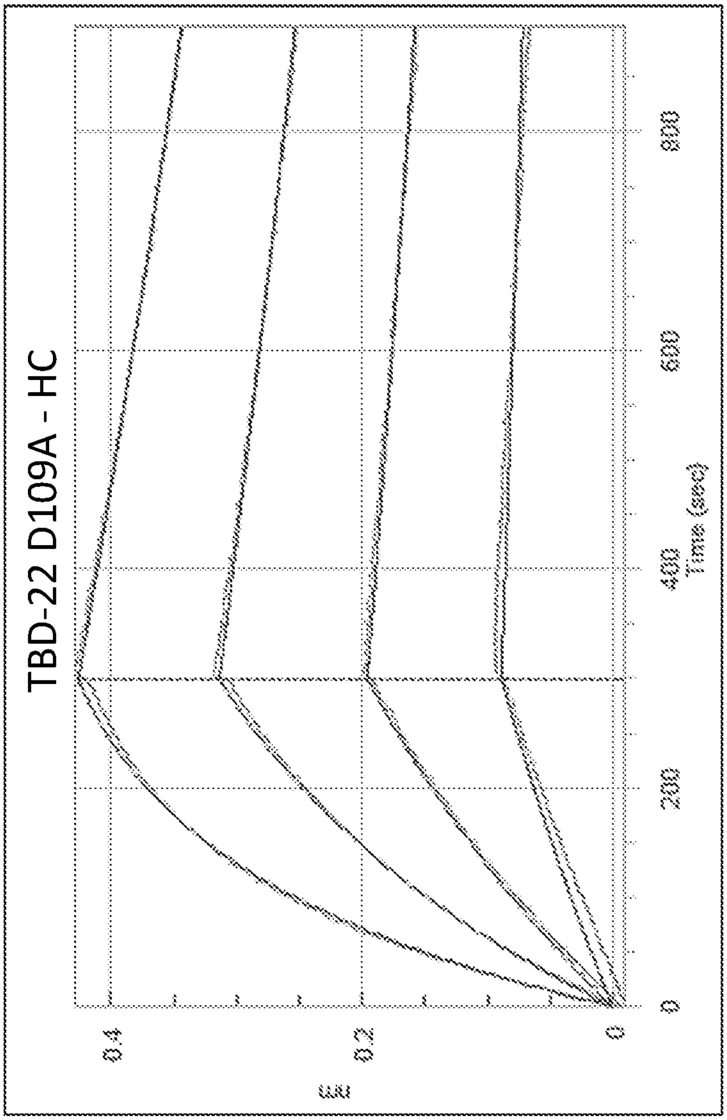
Figure 2M:
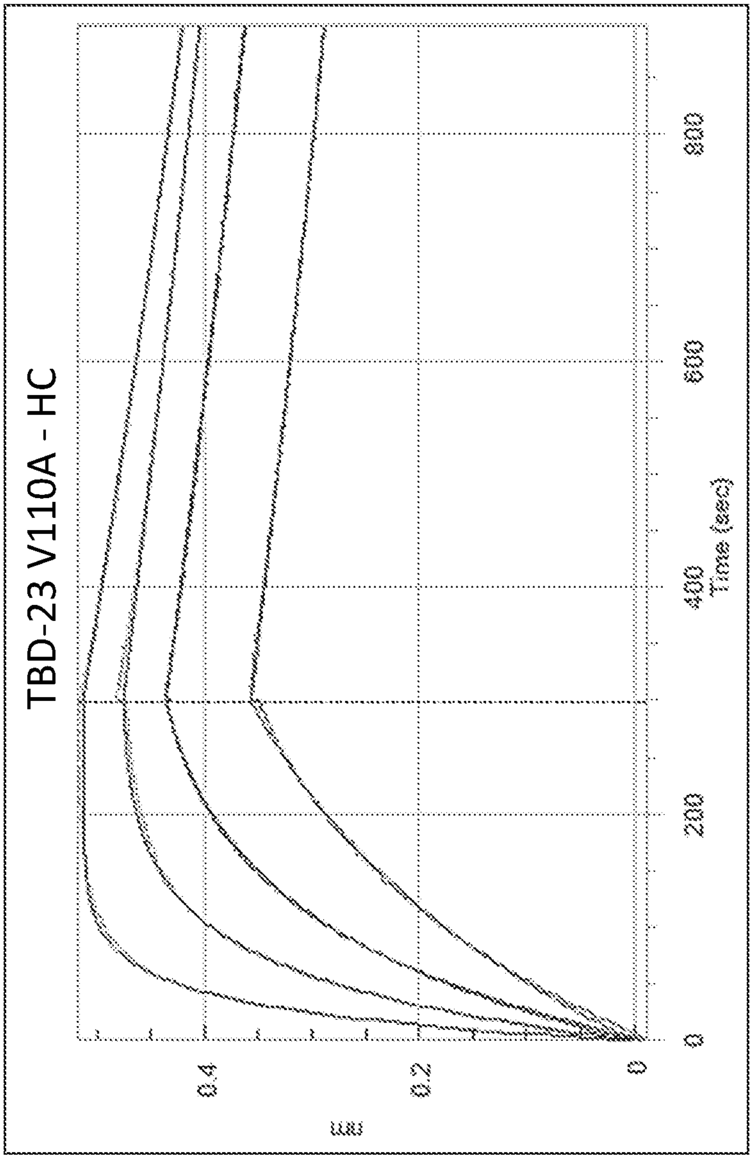
Figure 3:
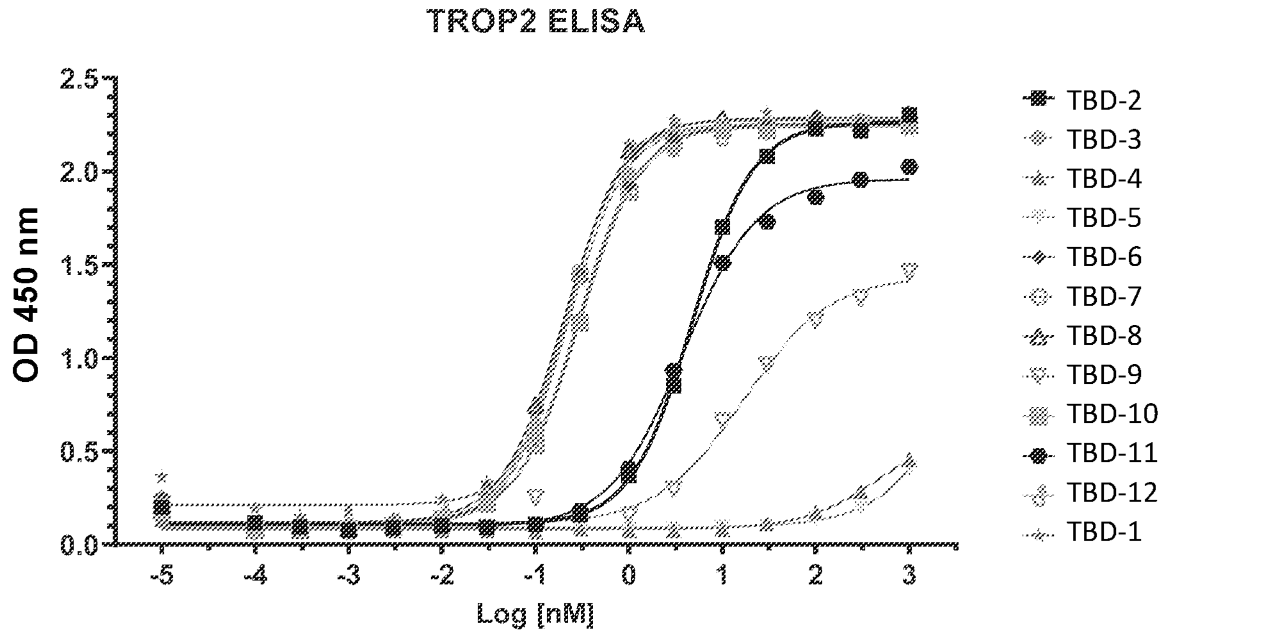
FIG. 3 illustrates binding curves and $EC_{50}$s for binding of TROP2 by non-mutated and mutated TBDs as measured by ELISA.
Figure 4:
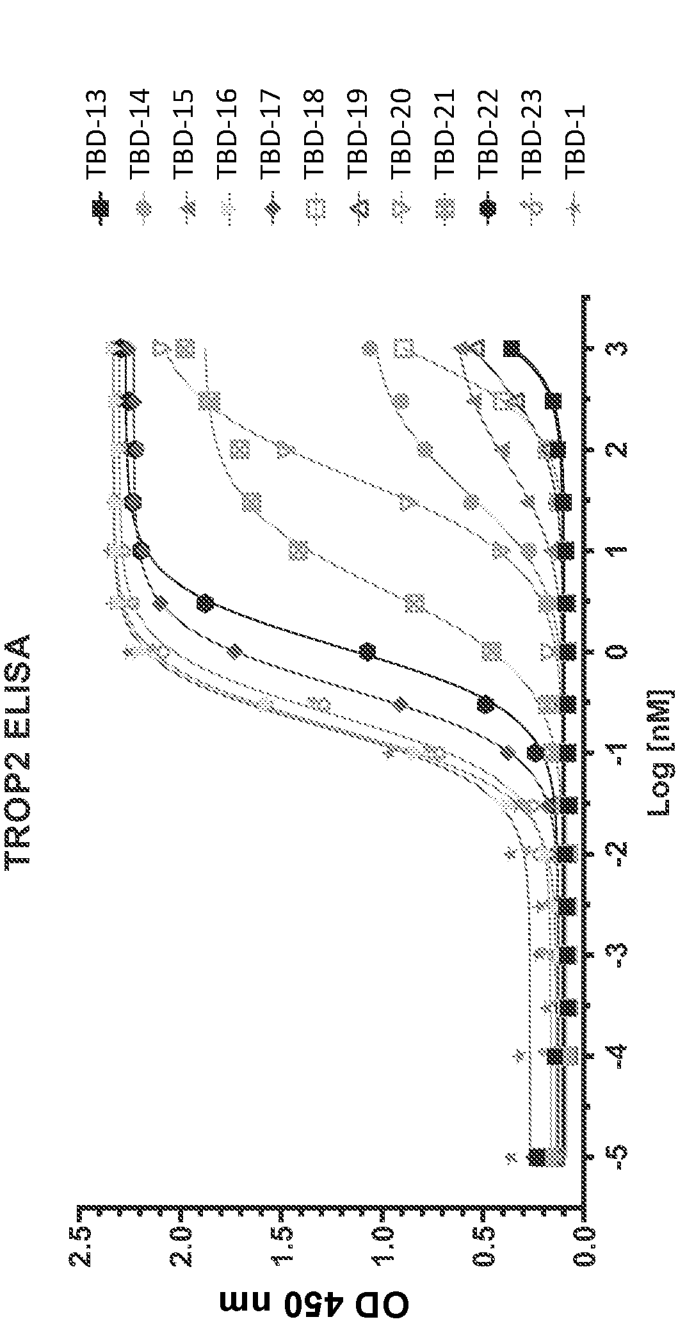
FIG. 4 illustrates binding curves and $EC_{50}$s for binding of TROP2 by non-mutated and mutated TBDs as measured by ELISA.
Figure 5A:
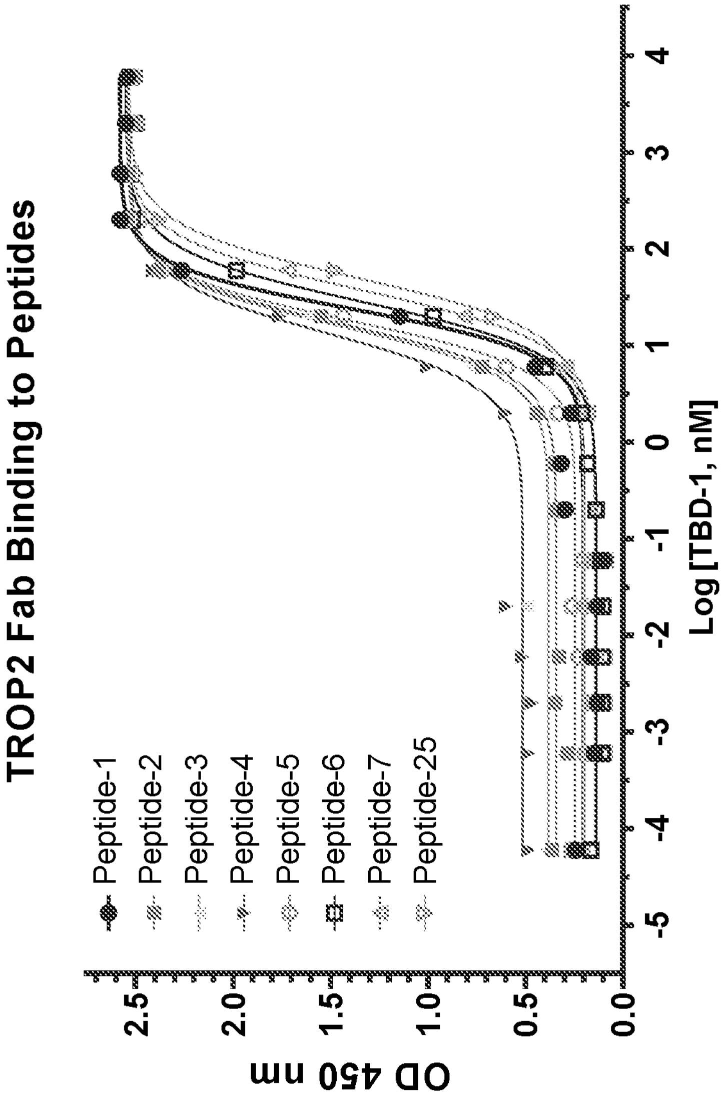
FIGS. 5A-5G illustrate binding curves for peptide binding to TBD-1 as measured by ELISA.
Figure 5B:
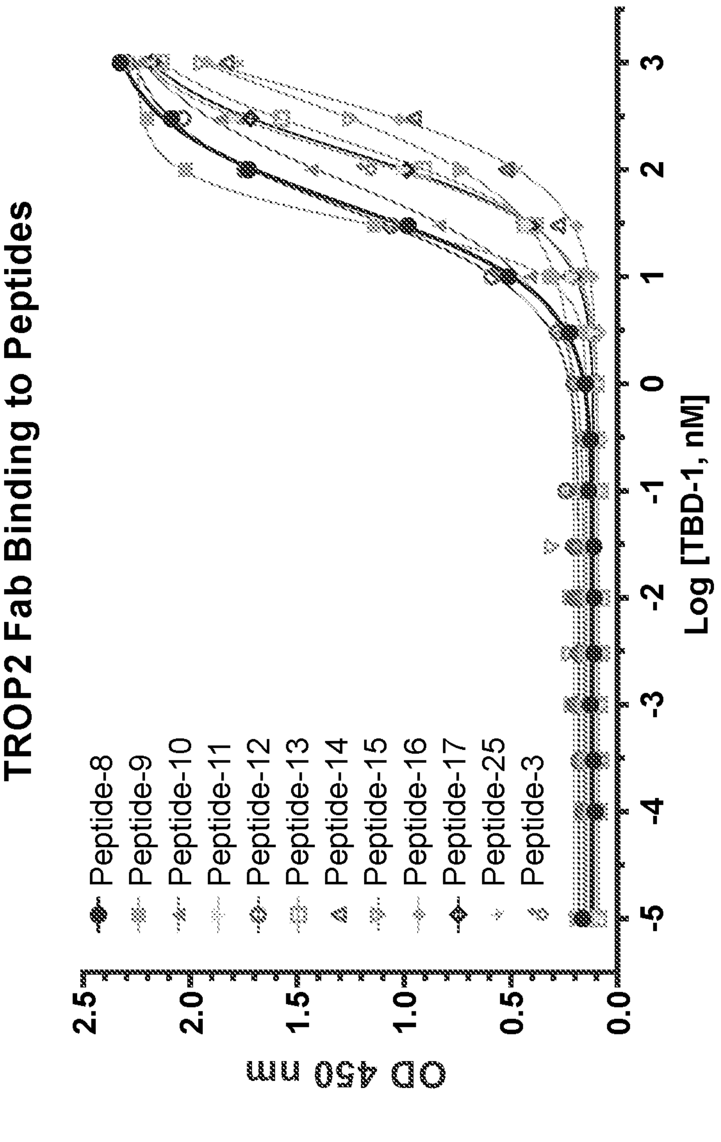
Figure 5C:
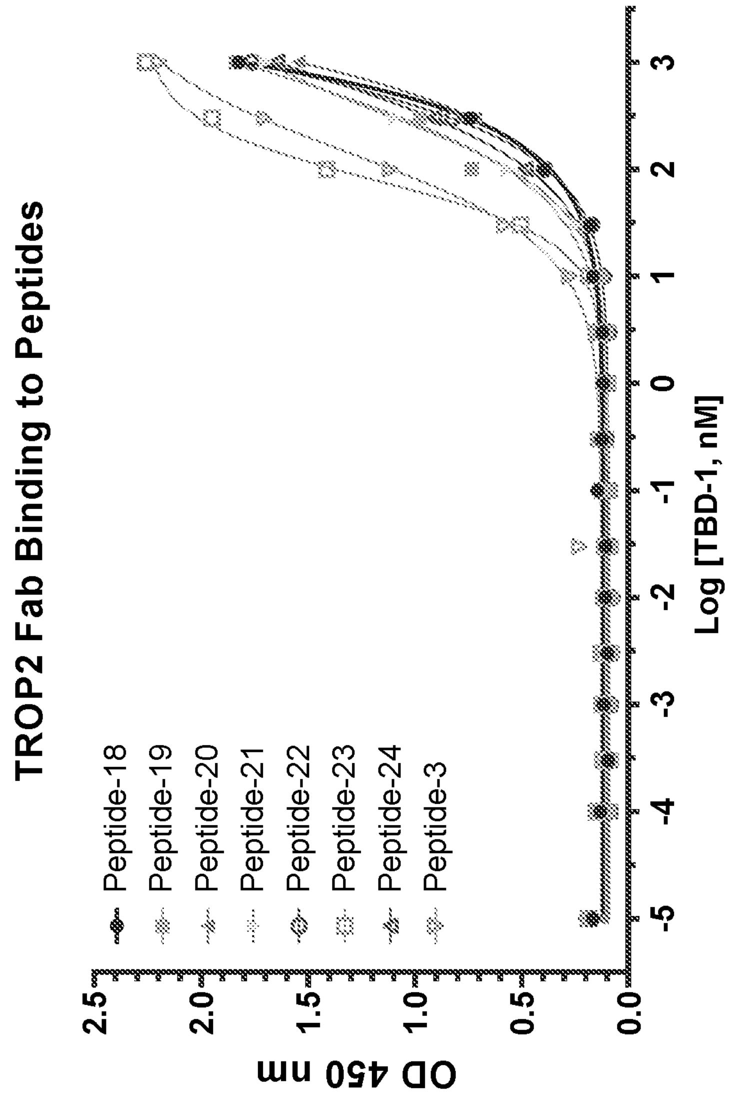
Figure 5D:
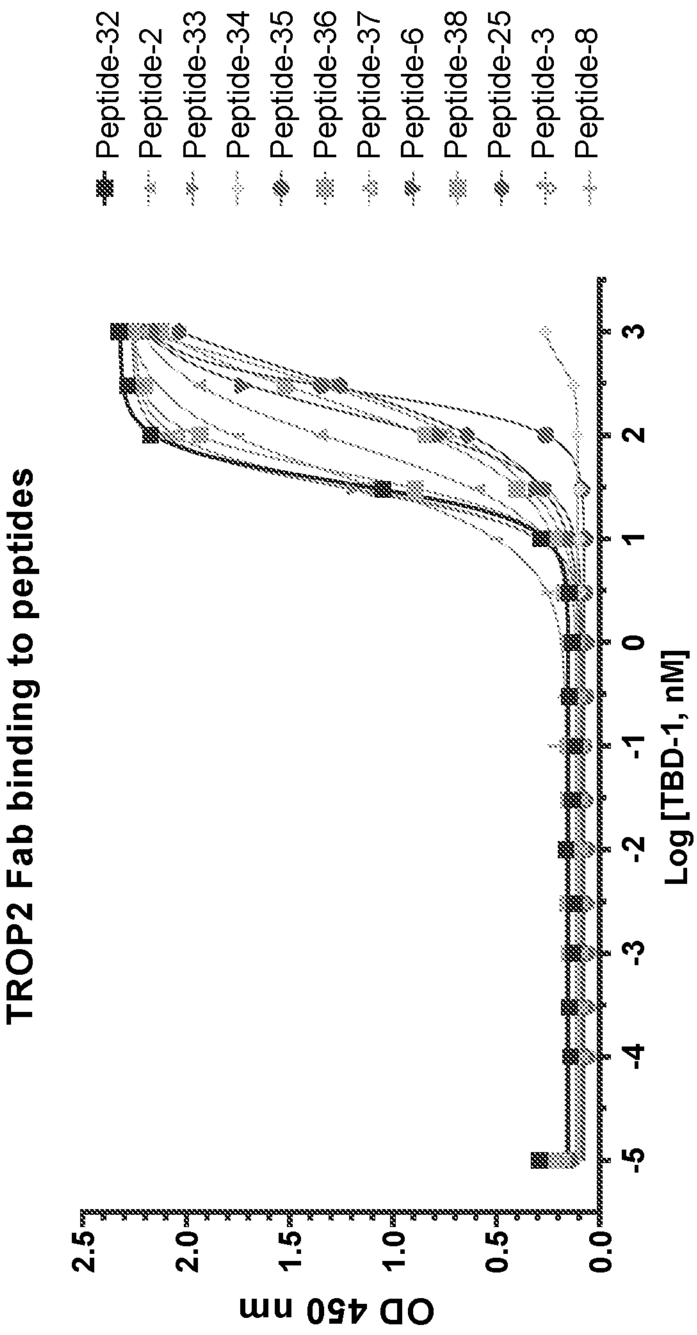
Figure 5E:
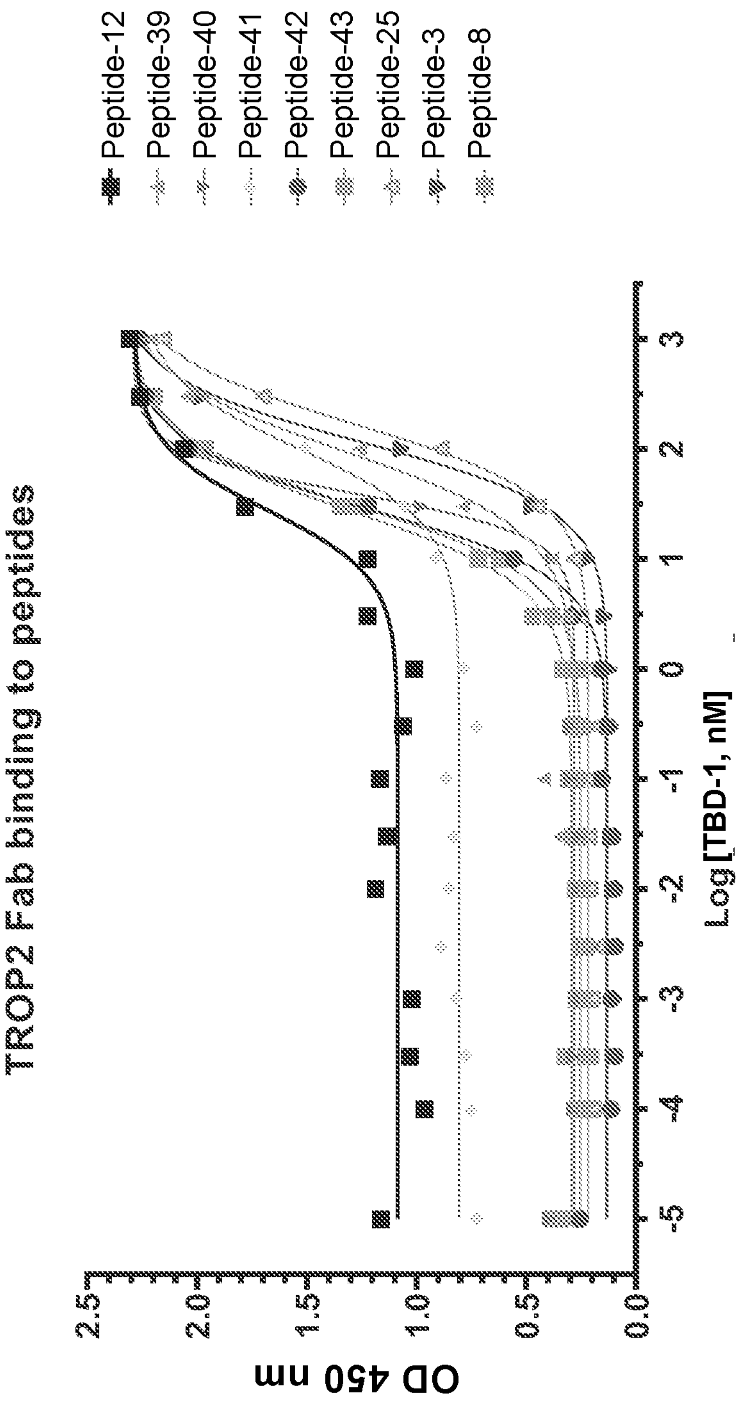
Figure 5F:
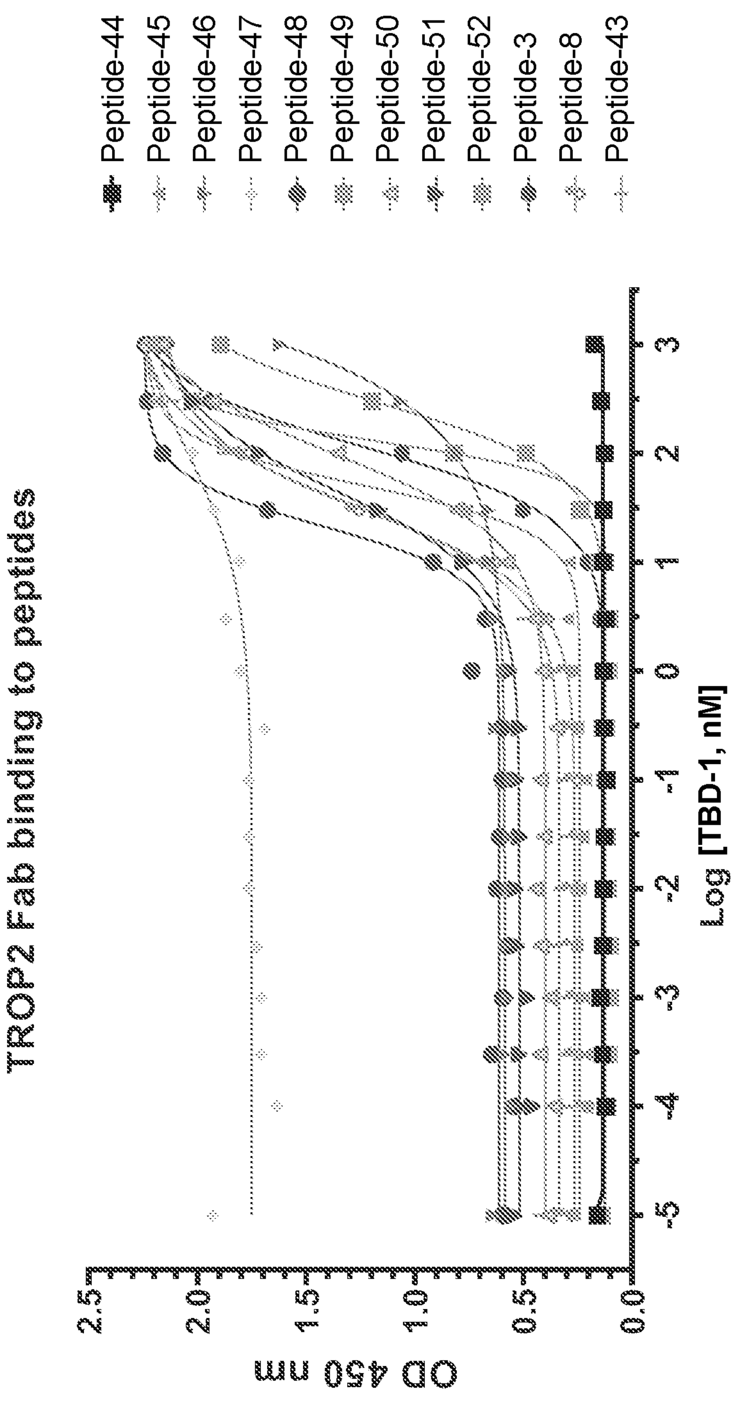
Figure 5G:
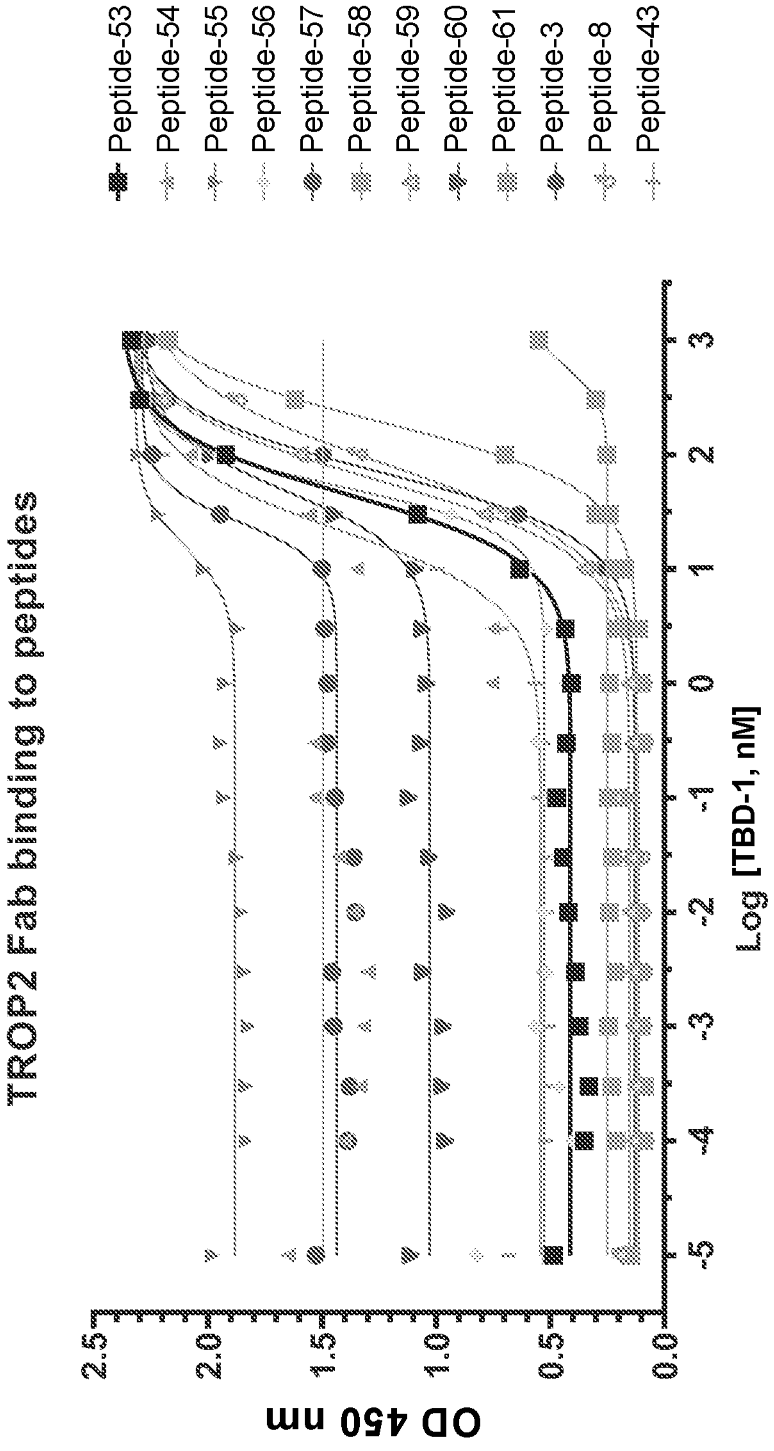
Figure 6A:
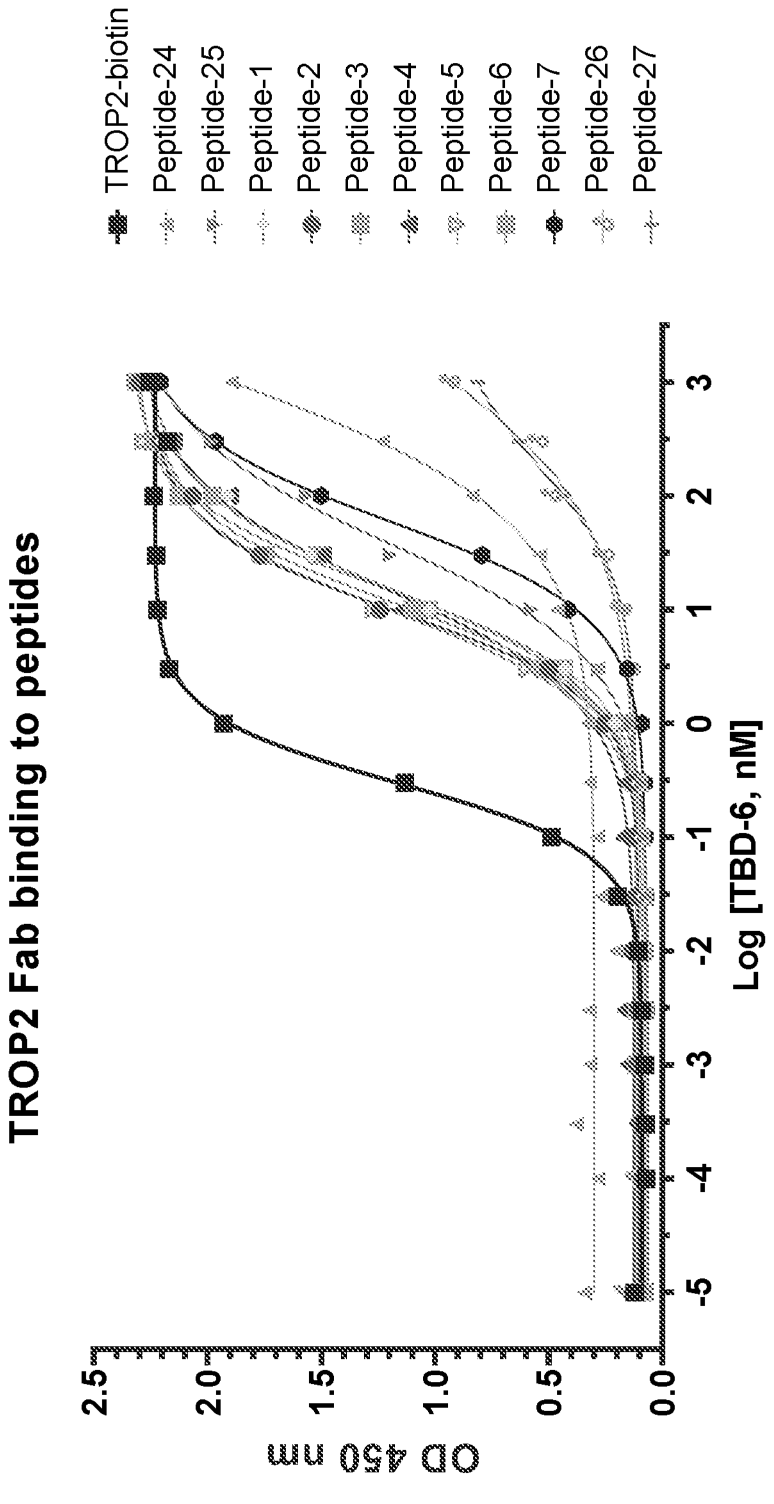
FIGS. 6A-6F illustrate binding curves for peptide binding to TBD-6 as measured by ELISA.
Figure 6B:
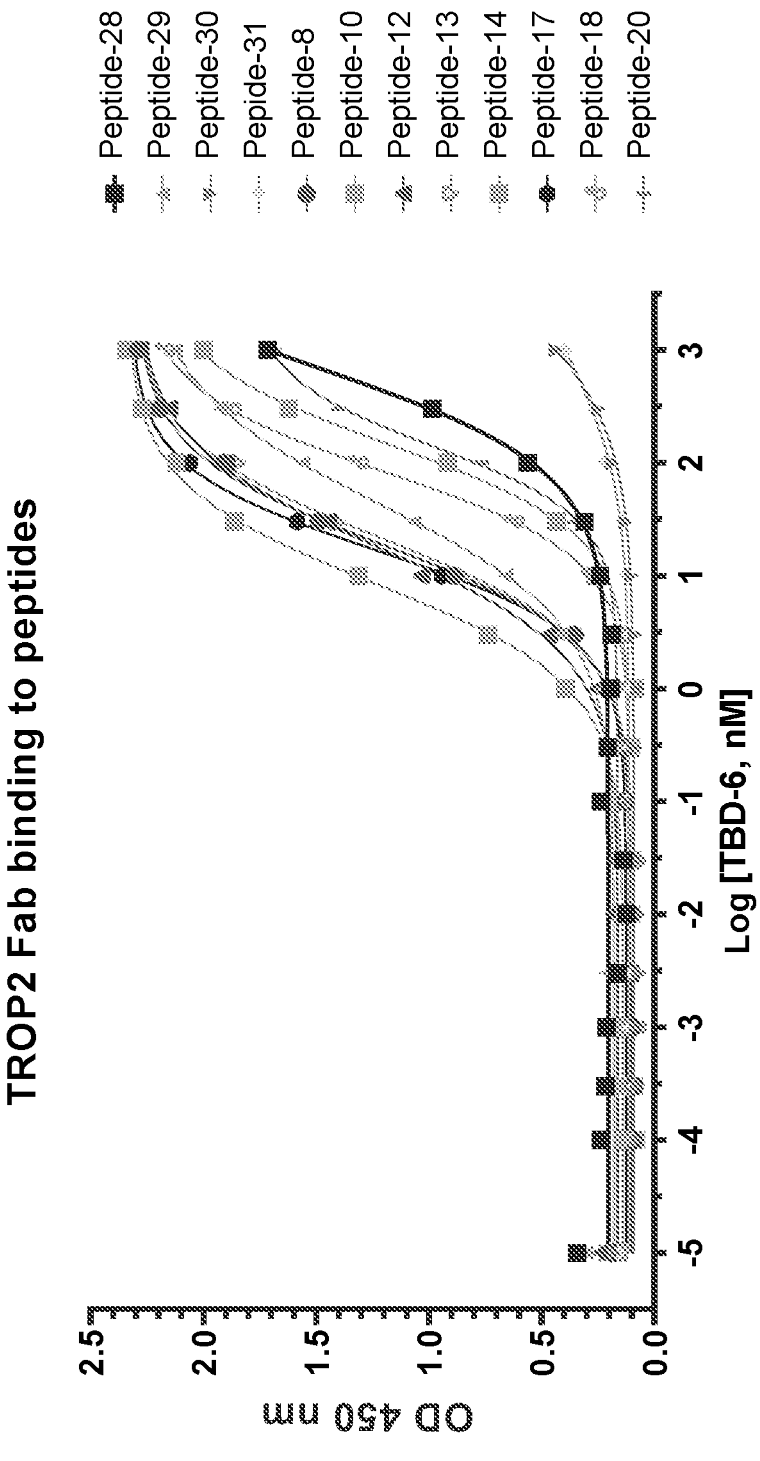
Figure 6C:
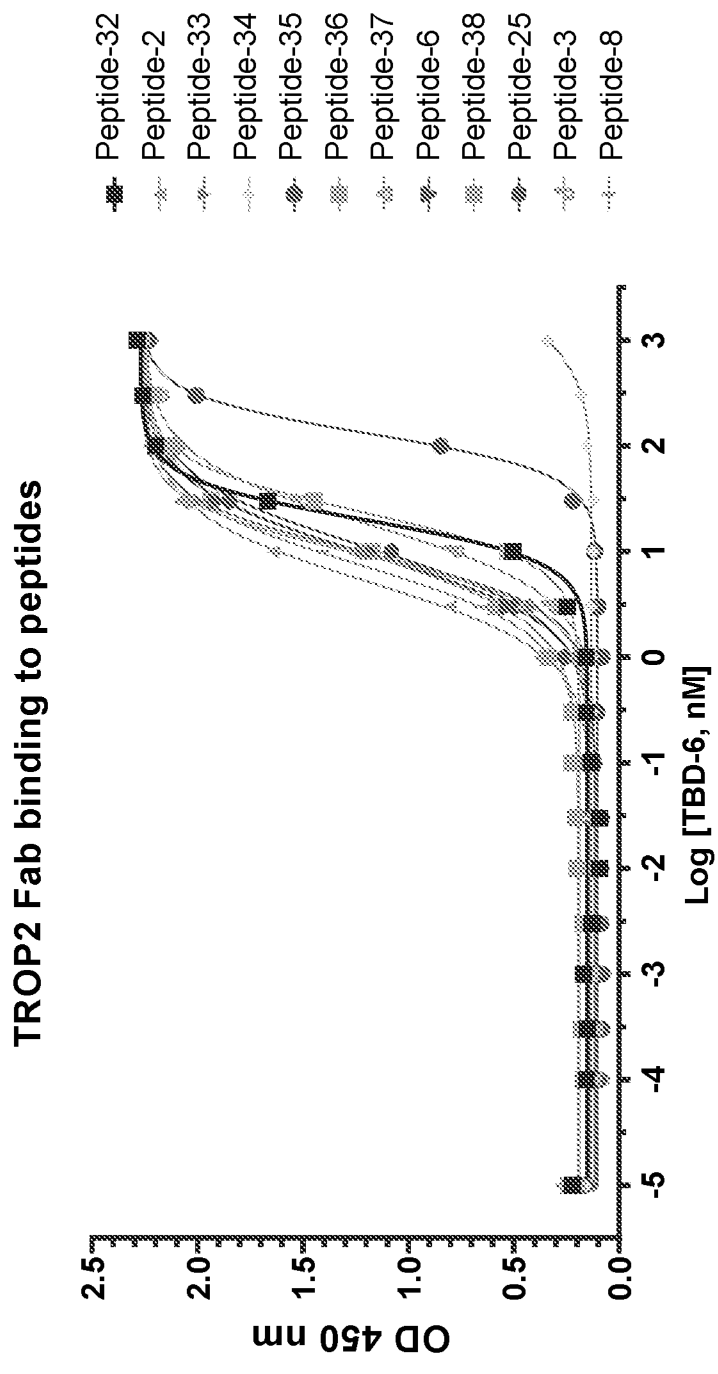
Figure 6D:
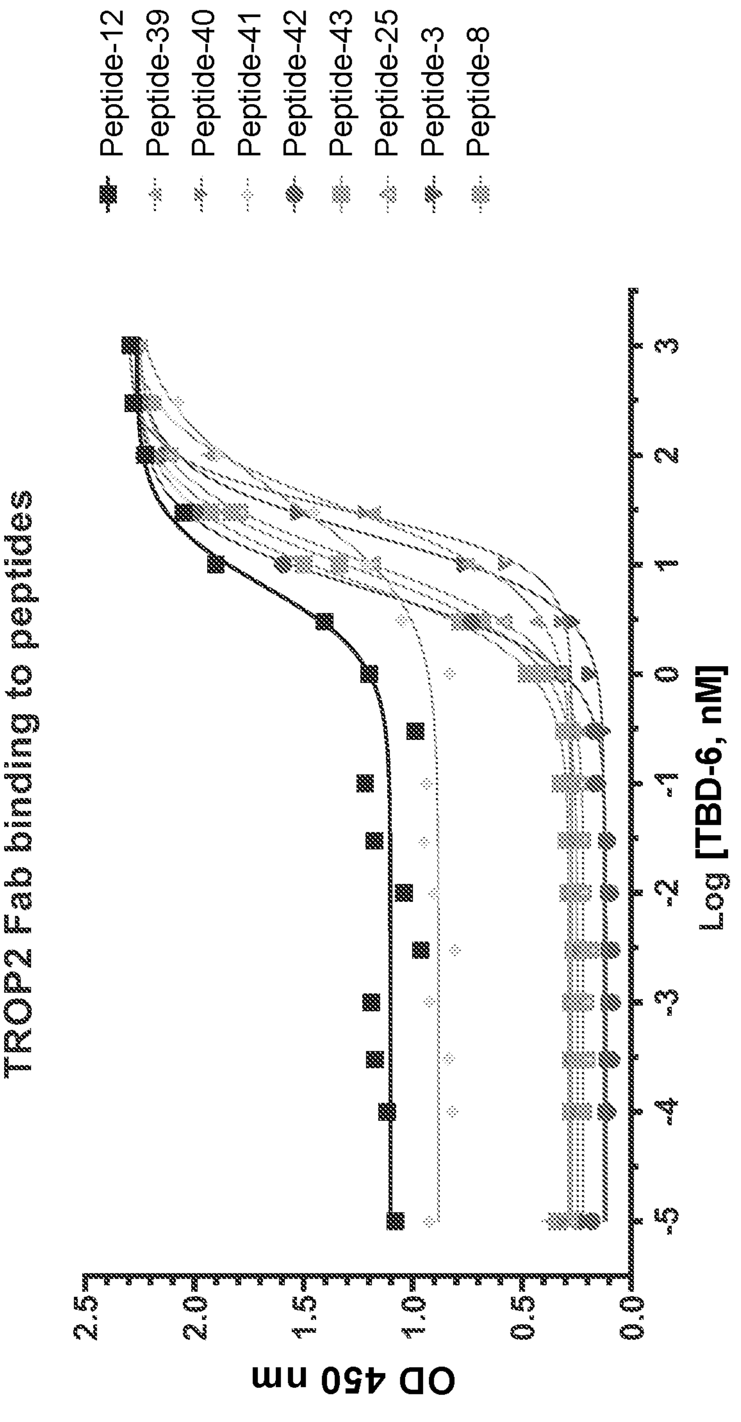
Figure 6E:
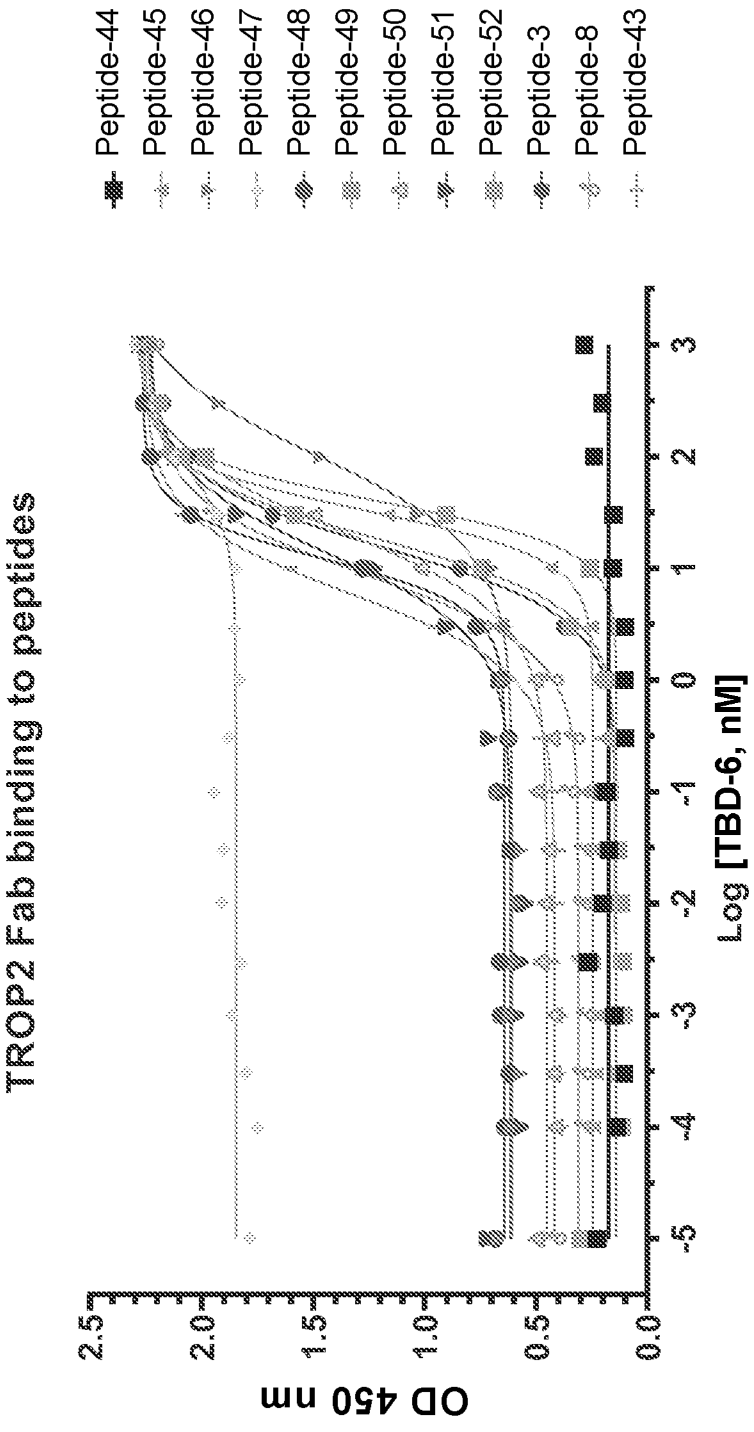
Figure 6F:
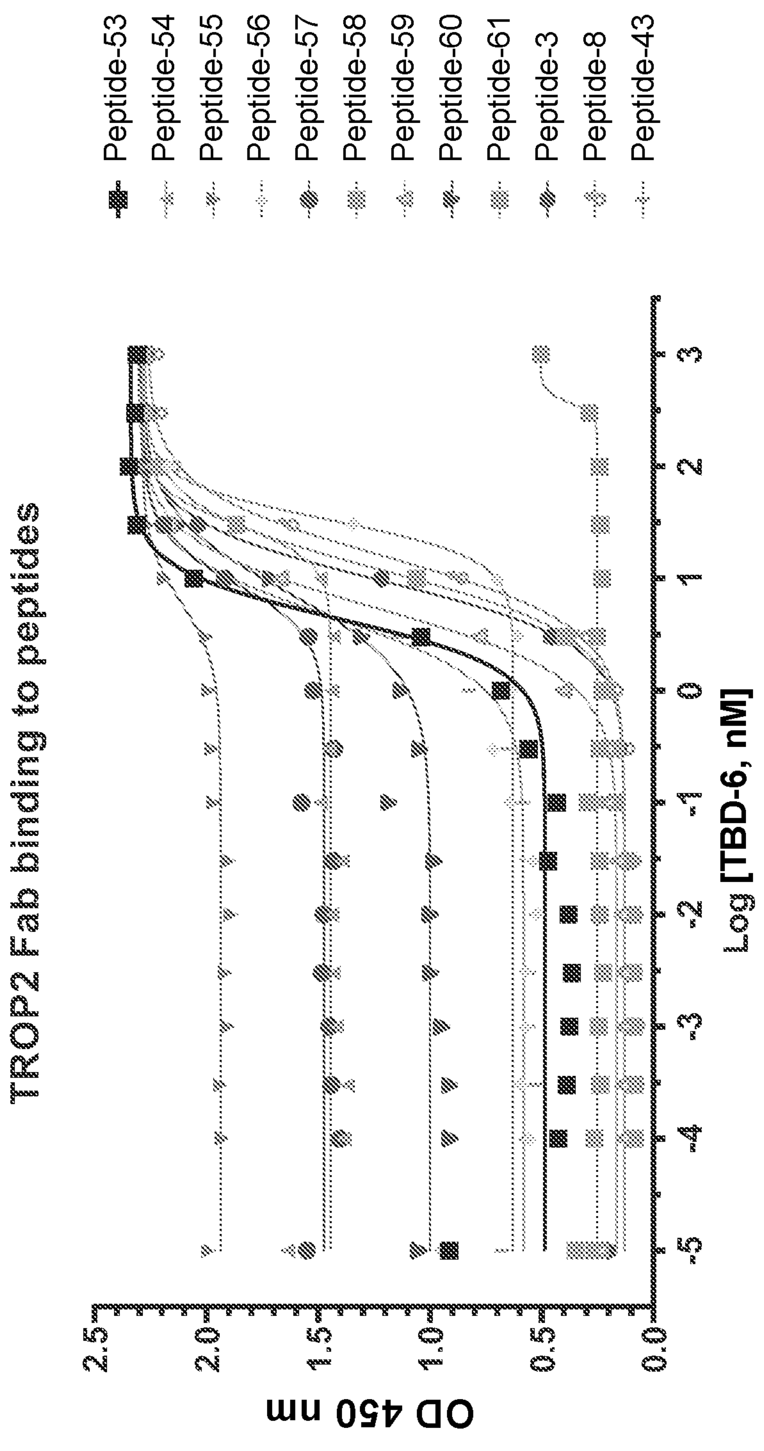
Figure 7A:
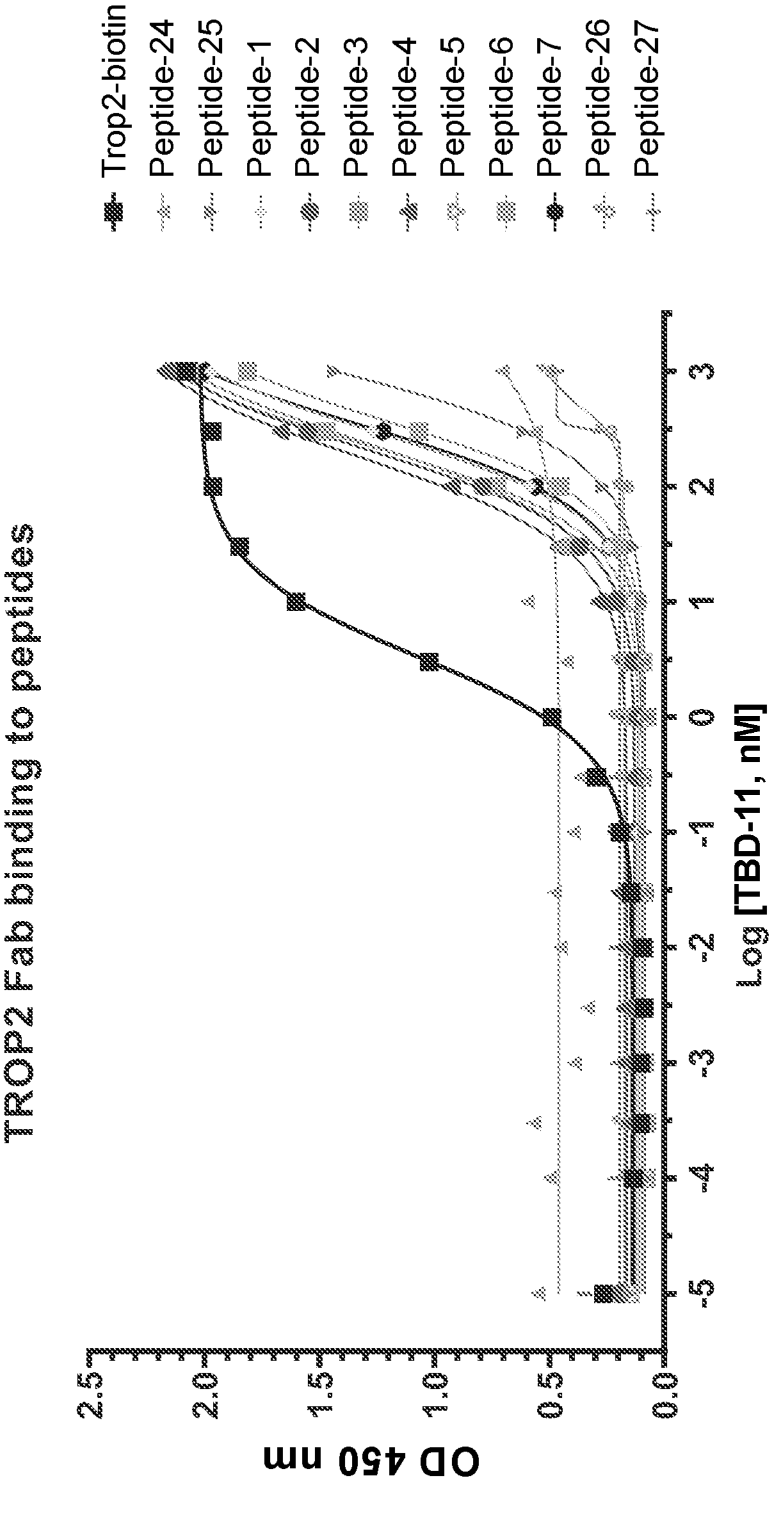
FIGS. 7A-7F illustrate binding curves for peptide binding to TBD-11 as measured by ELISA.
Figure 7B:
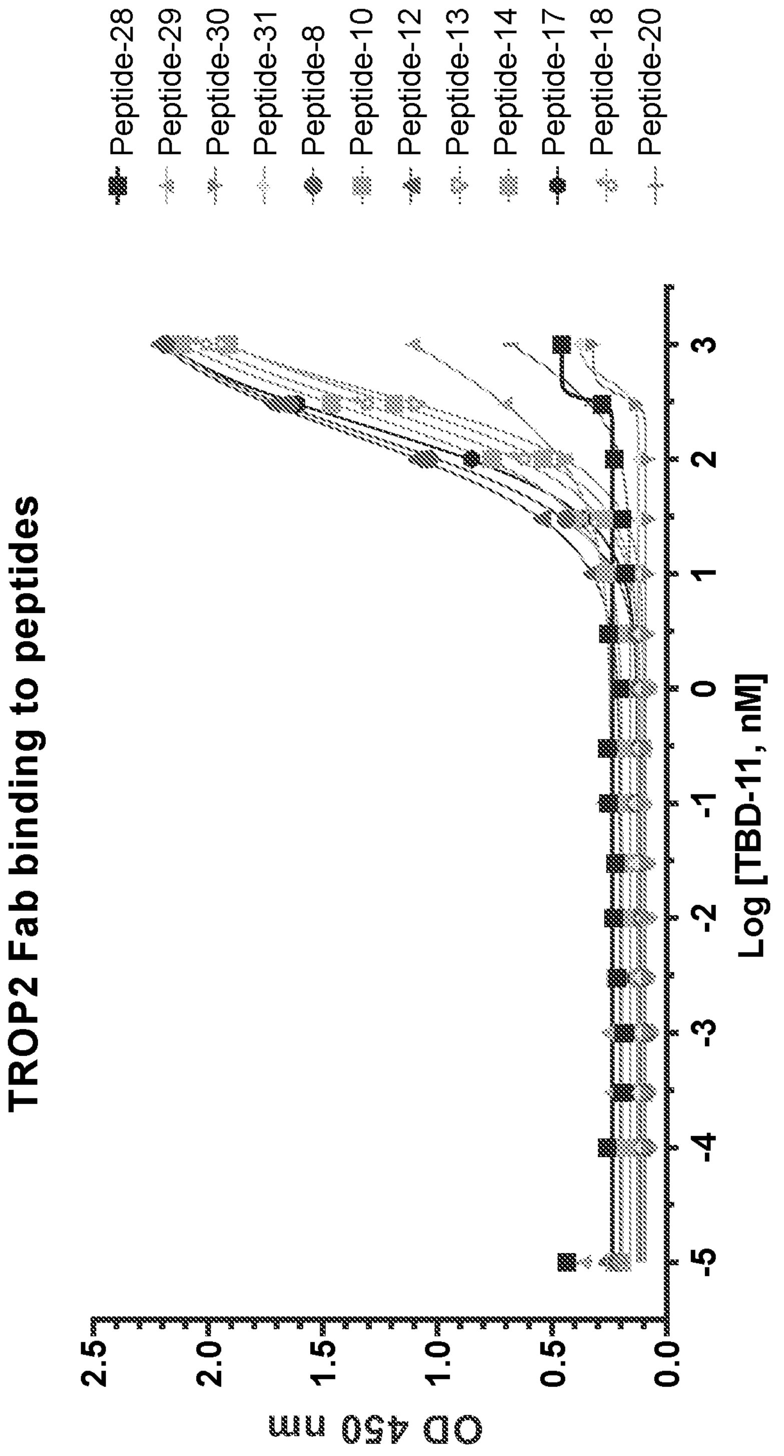
Figure 7C:
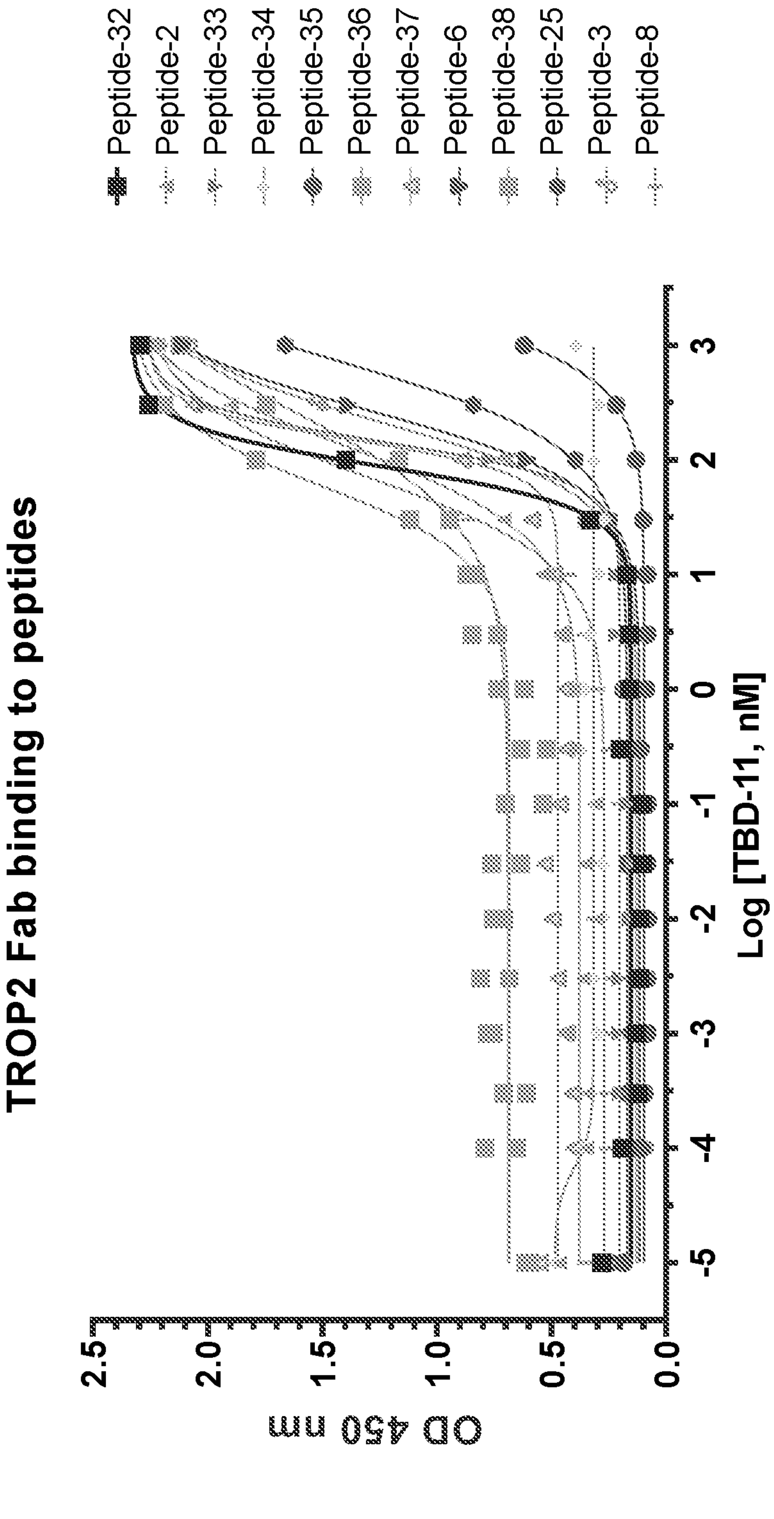
Figure 7D:
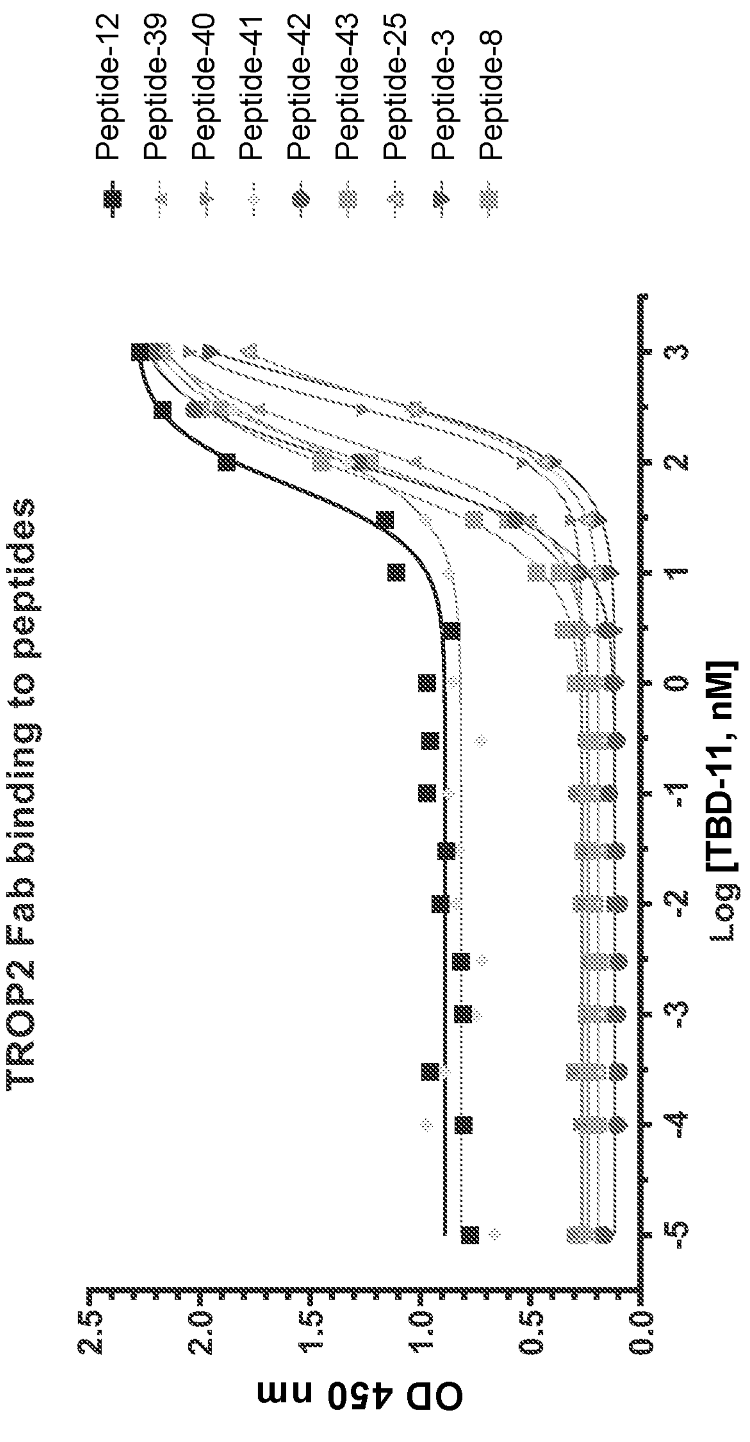
Figure 7E:
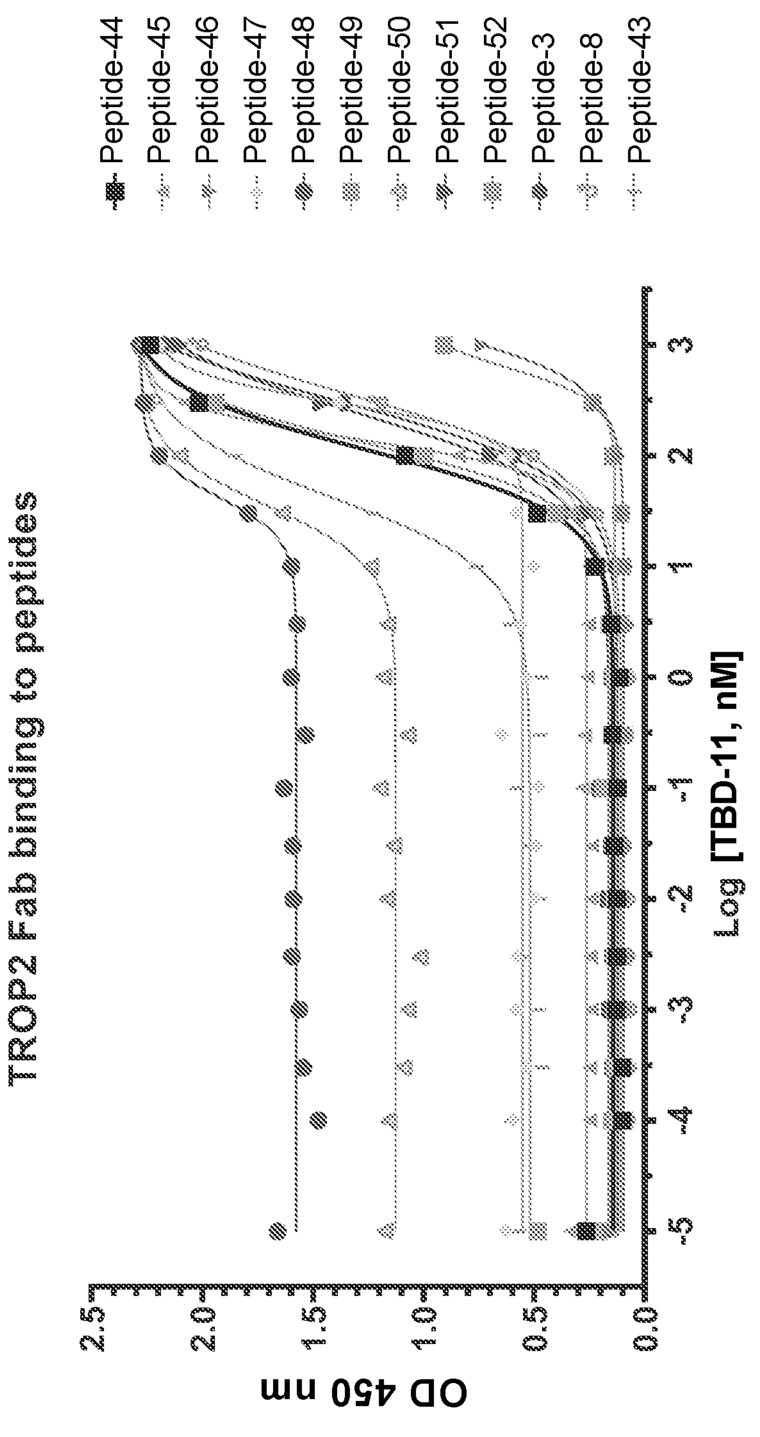
Figure 7F:
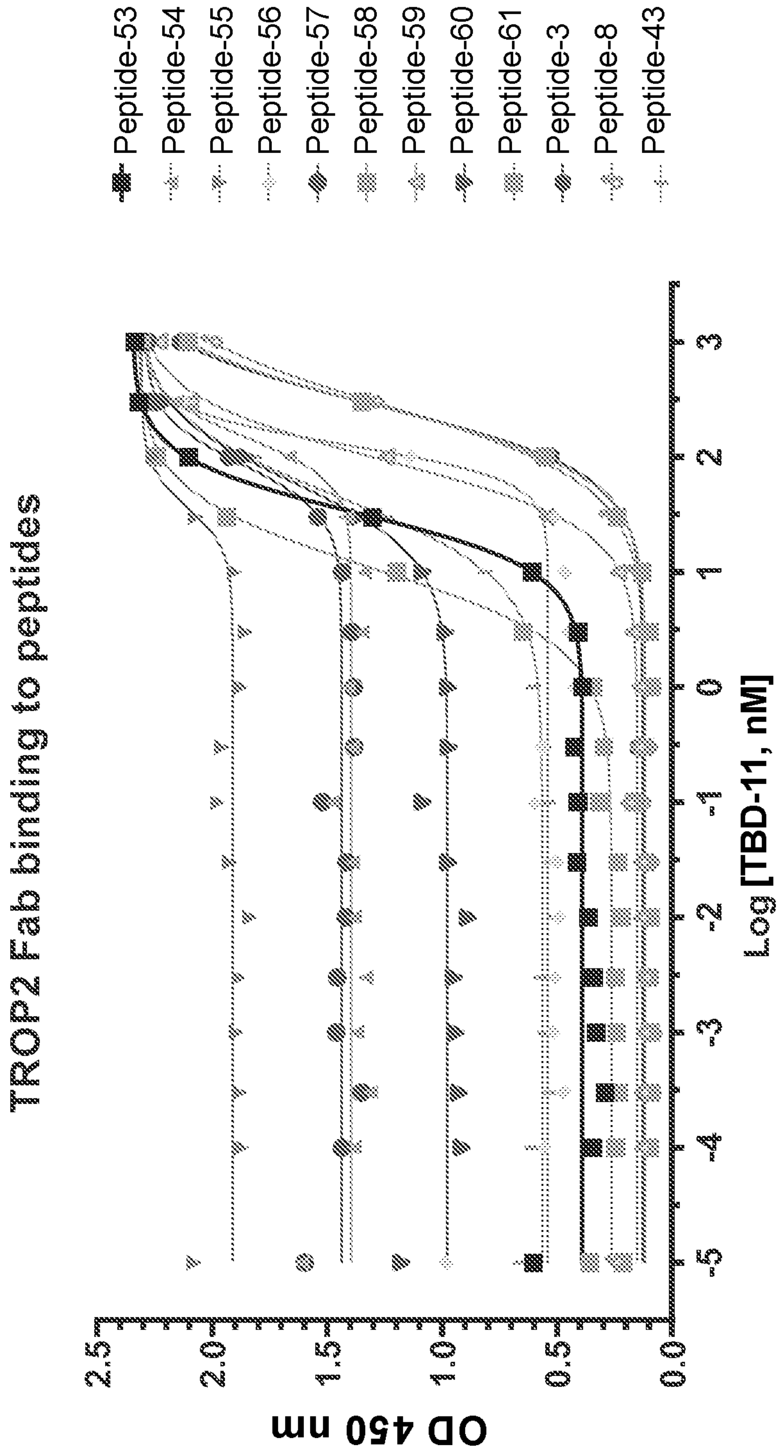
Figure 8A:
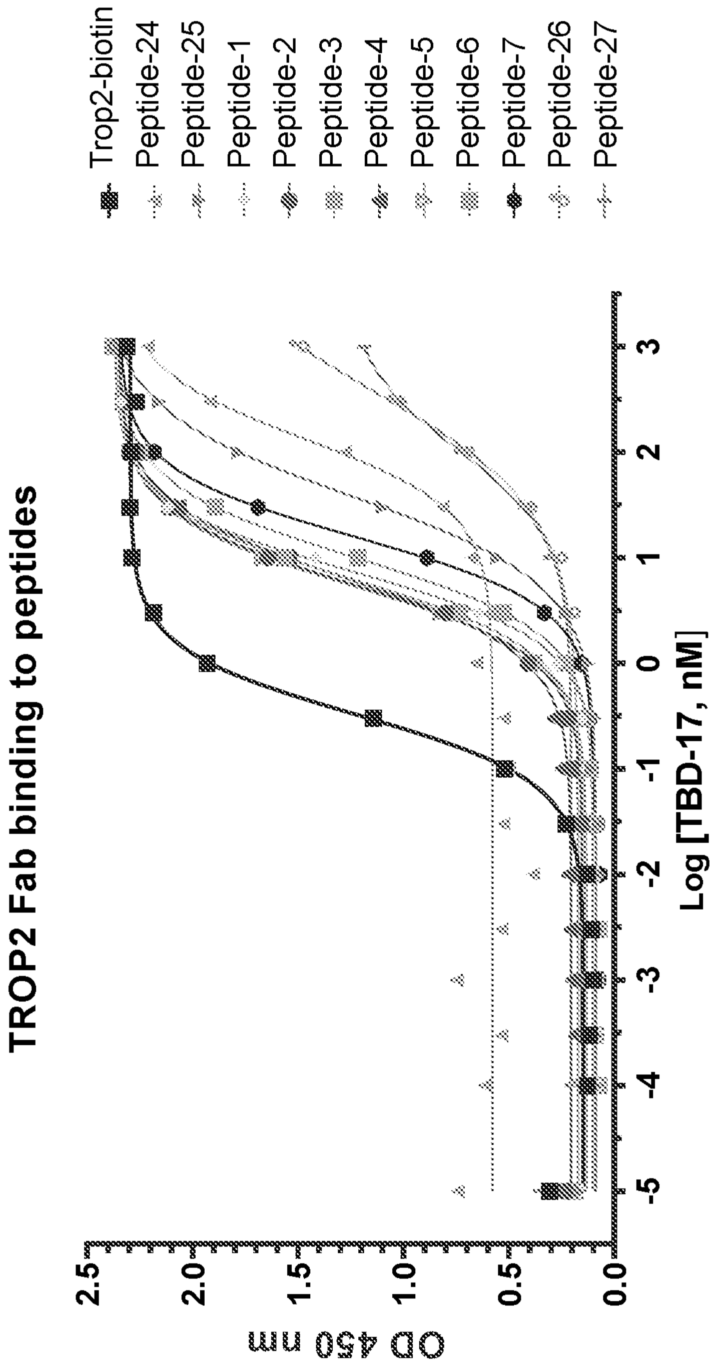
FIGS. 8A-8D illustrate binding curves for peptide binding to TBD-17 as measured by ELISA.
Figure 8B:
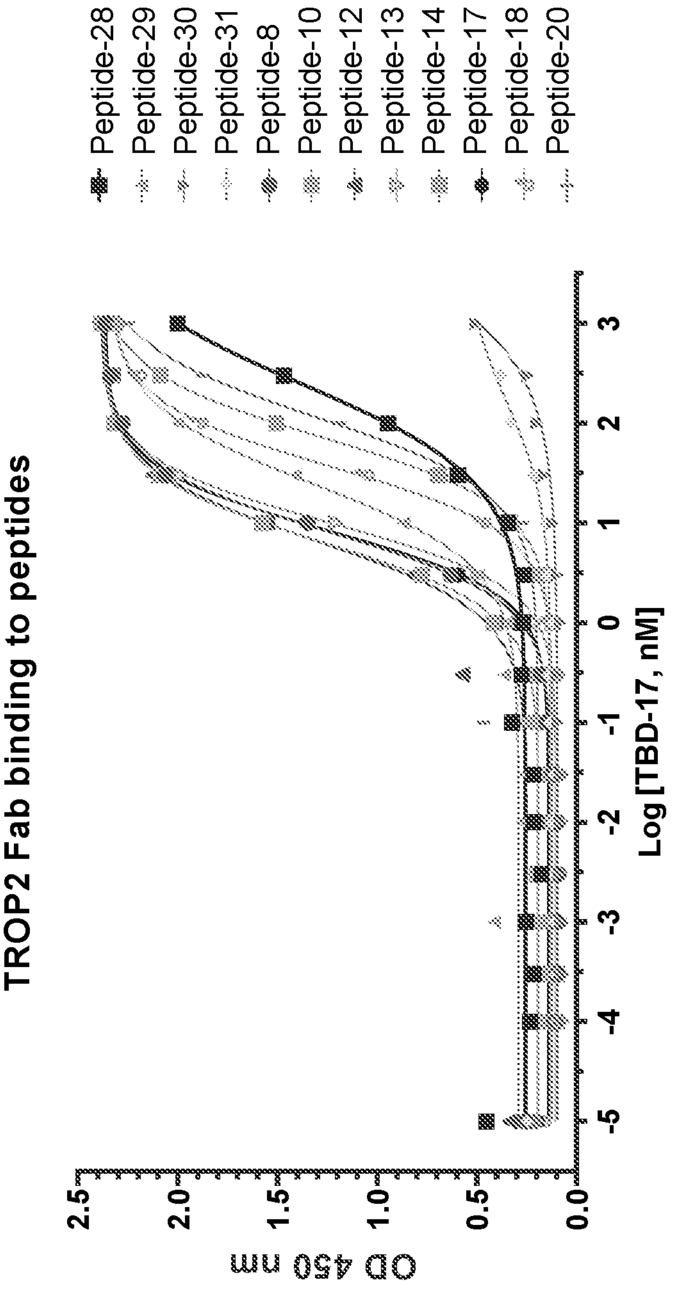
Figure 8C:
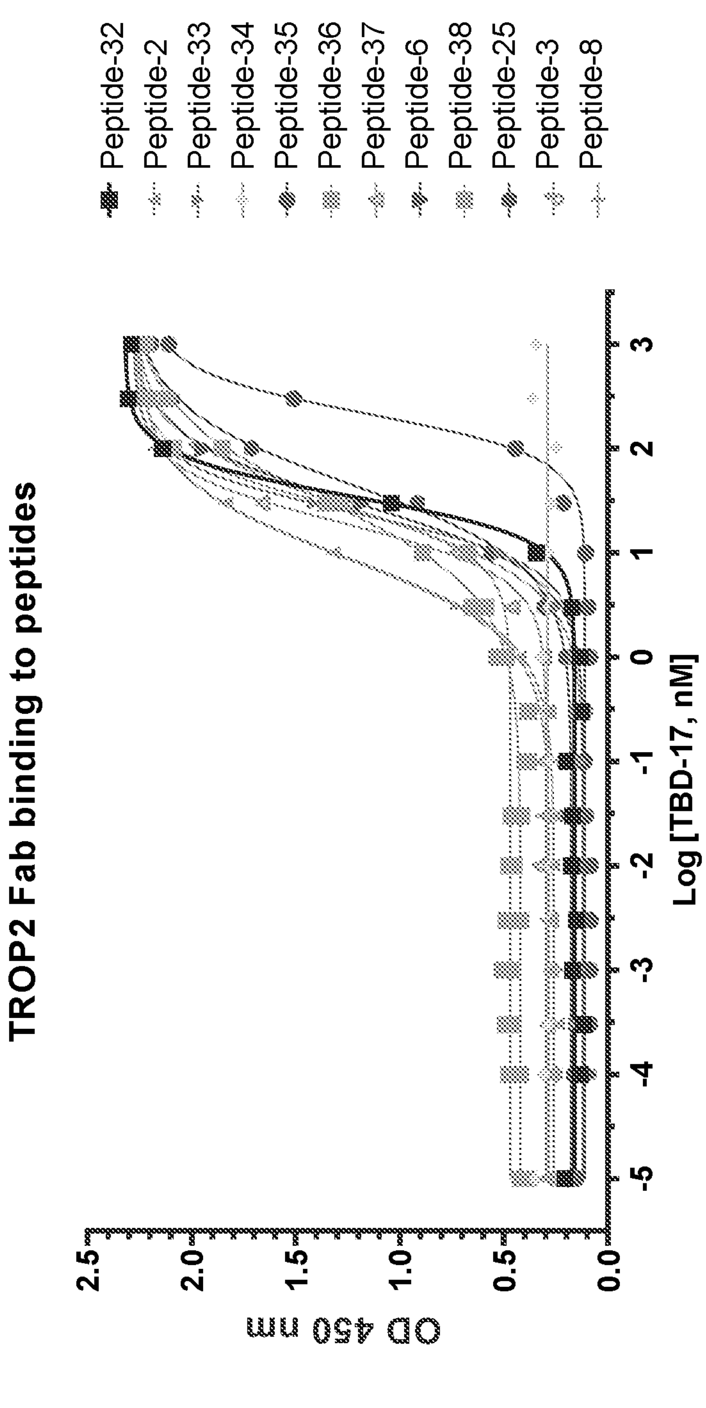
Figure 8D:
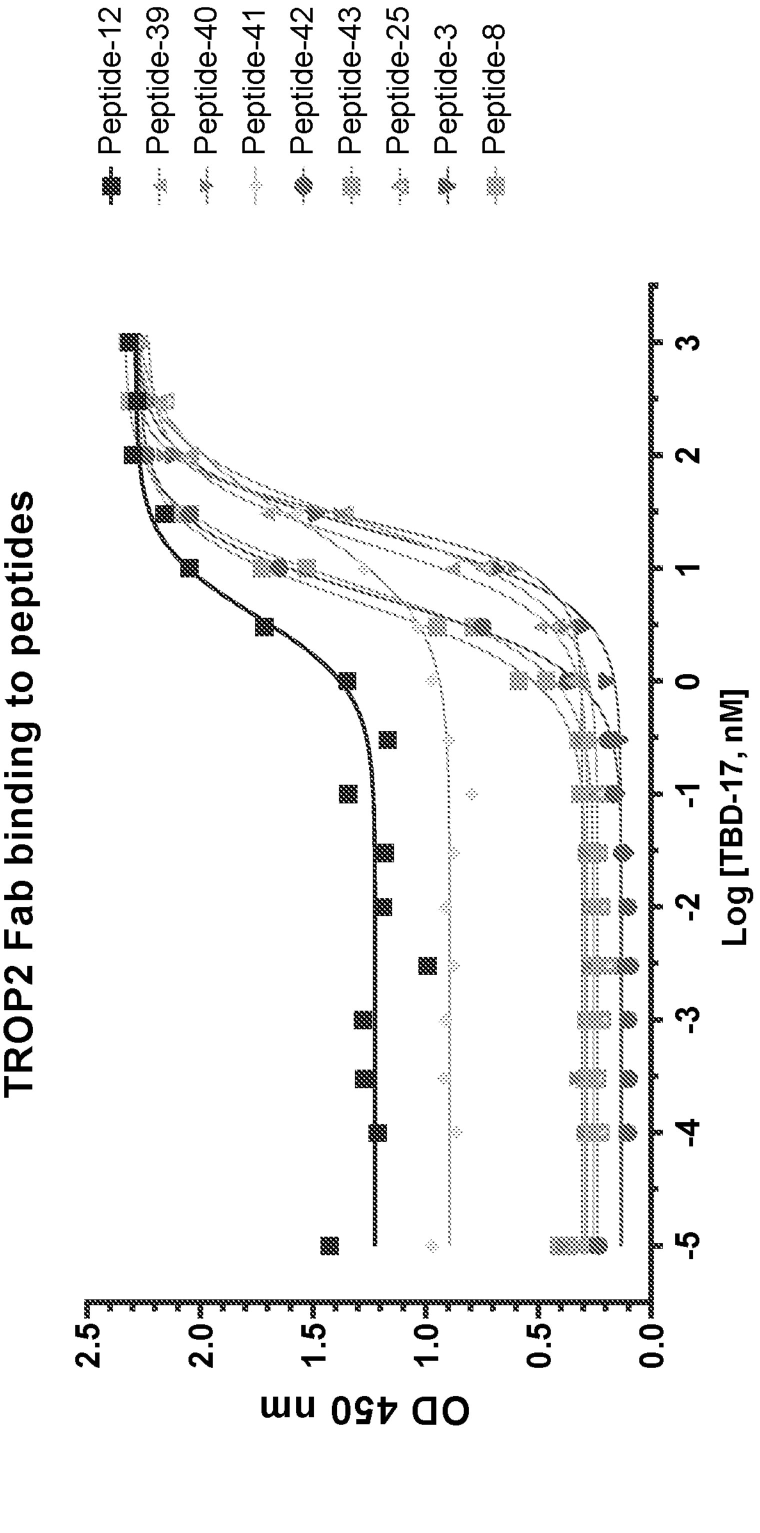
Figure 9A:
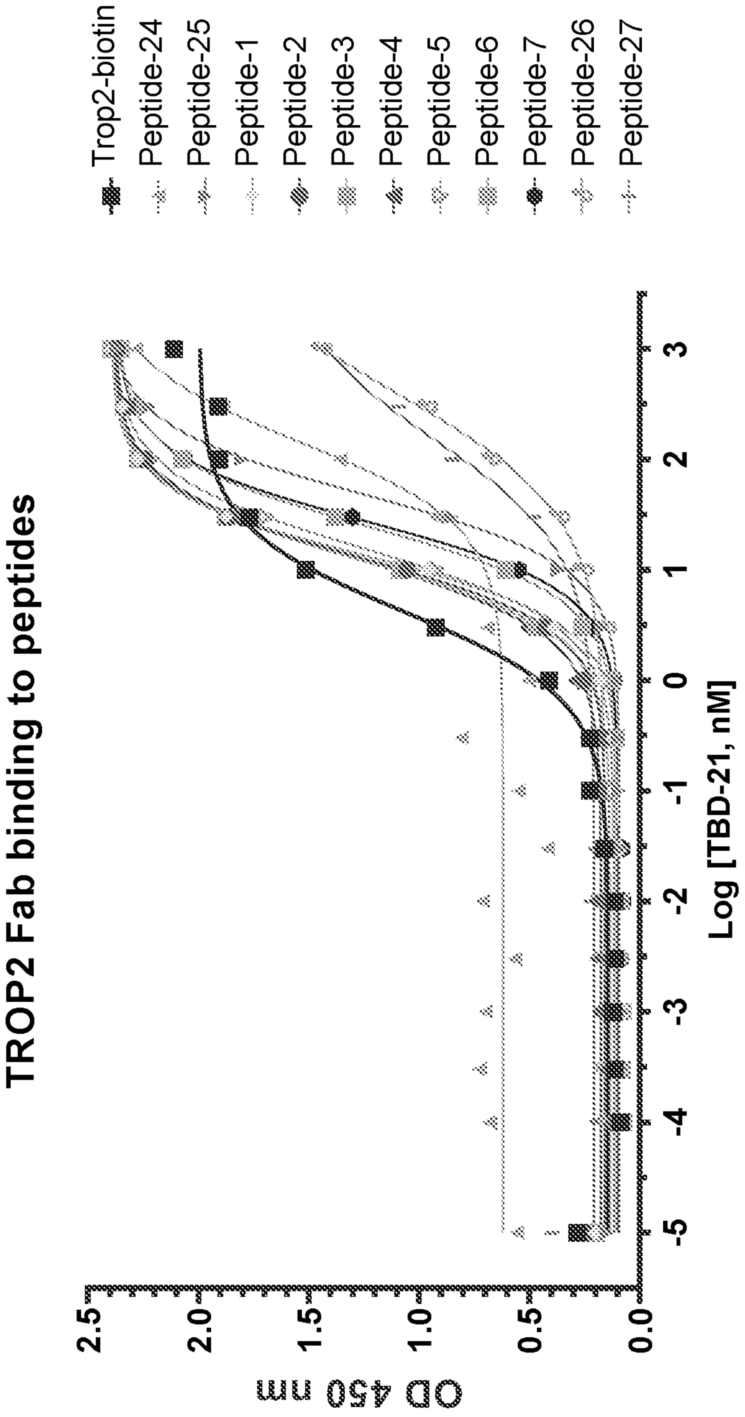
FIGS. 9A-9D illustrate binding curves for peptide binding to TBD-21 as measured by ELISA.
Figure 9B:
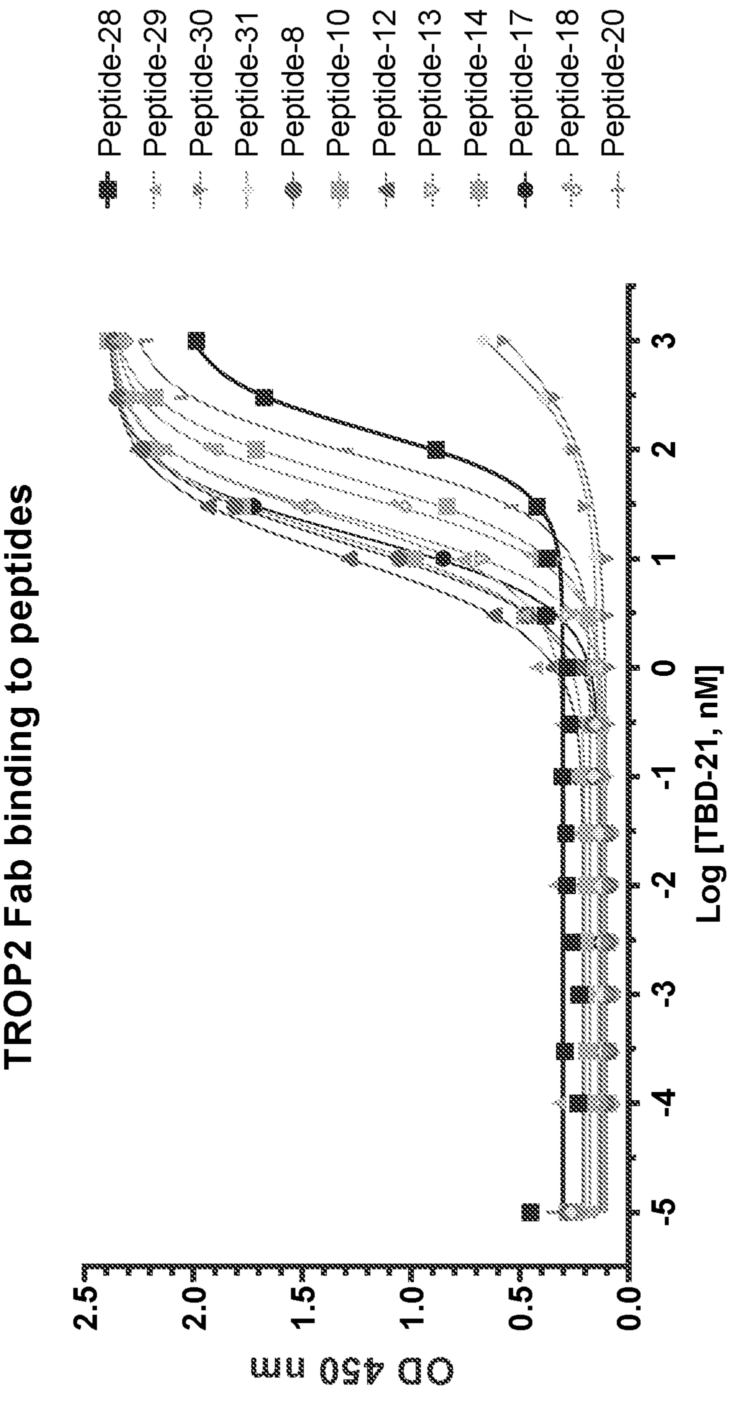
Figure 9C:
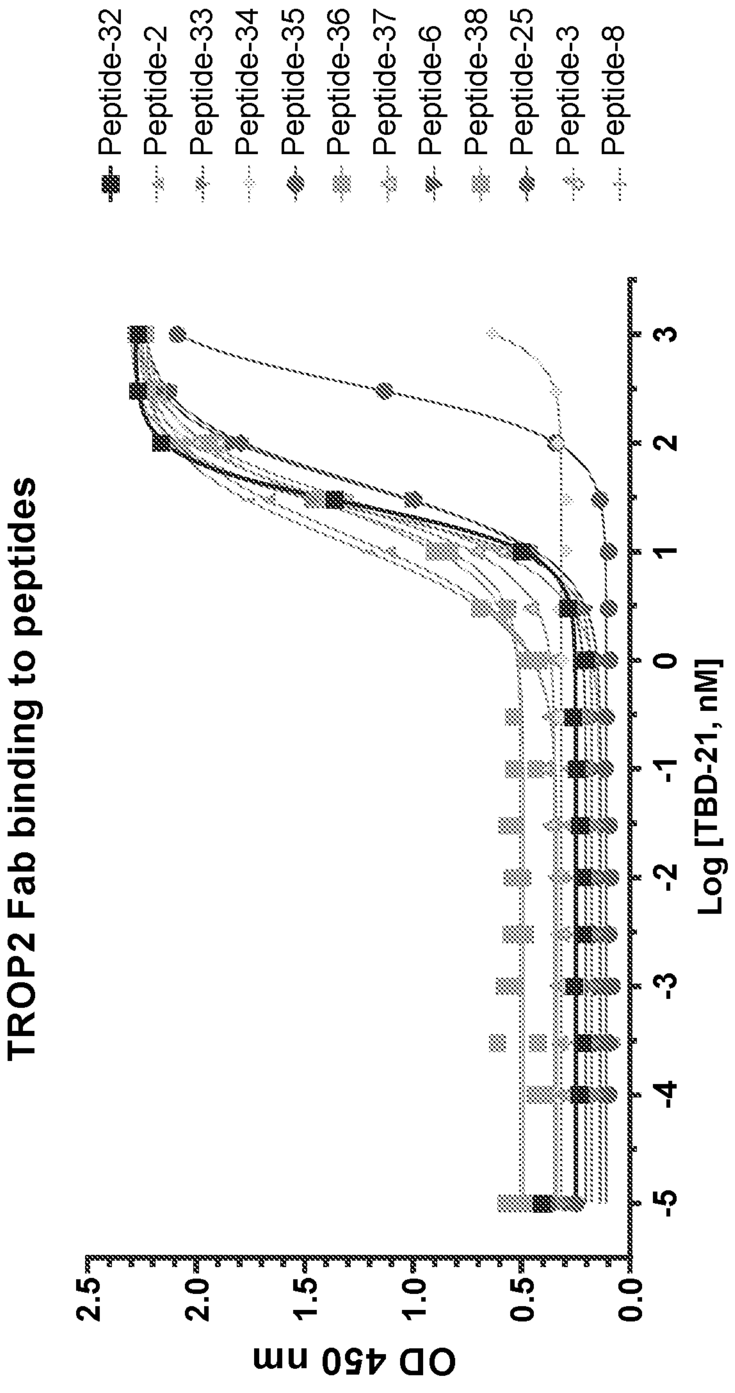
Figure 9D:
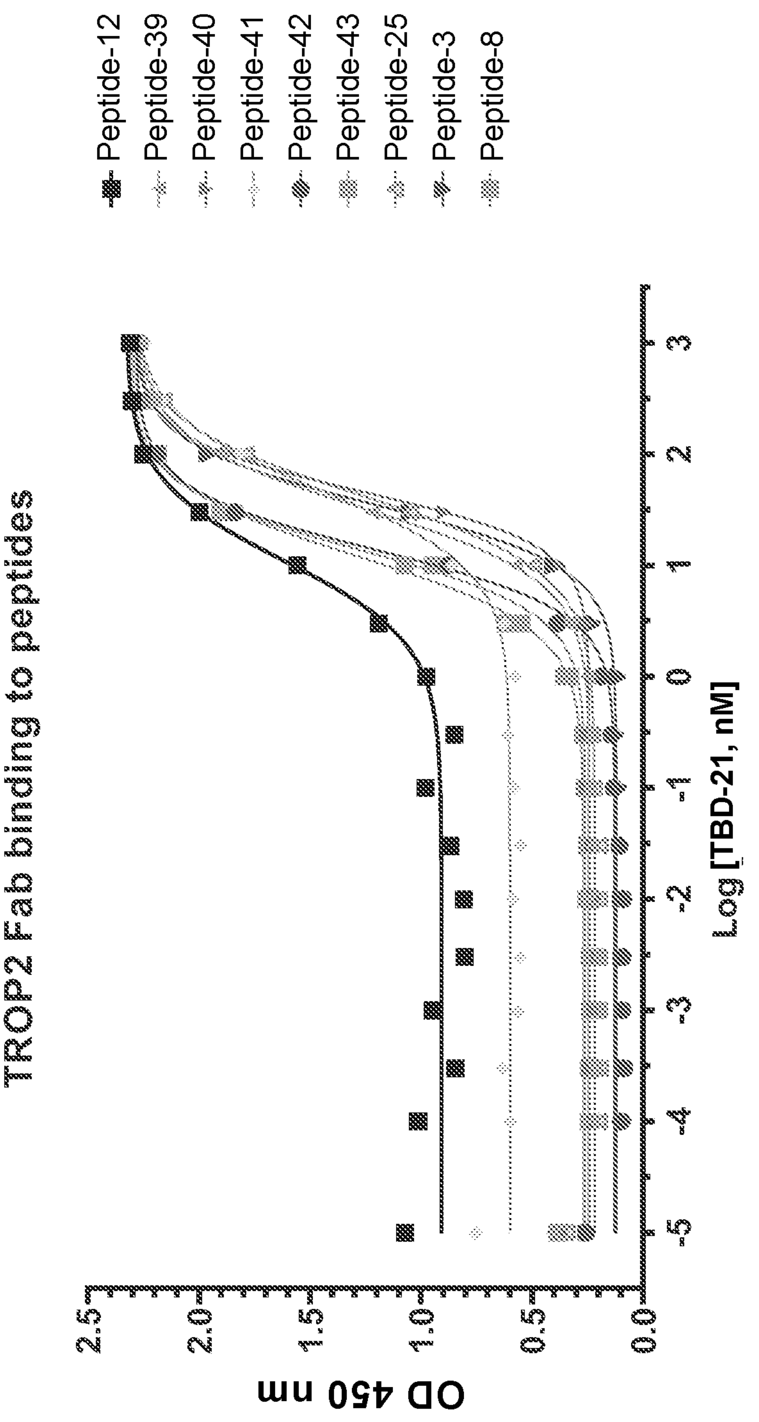
Figure 10A:
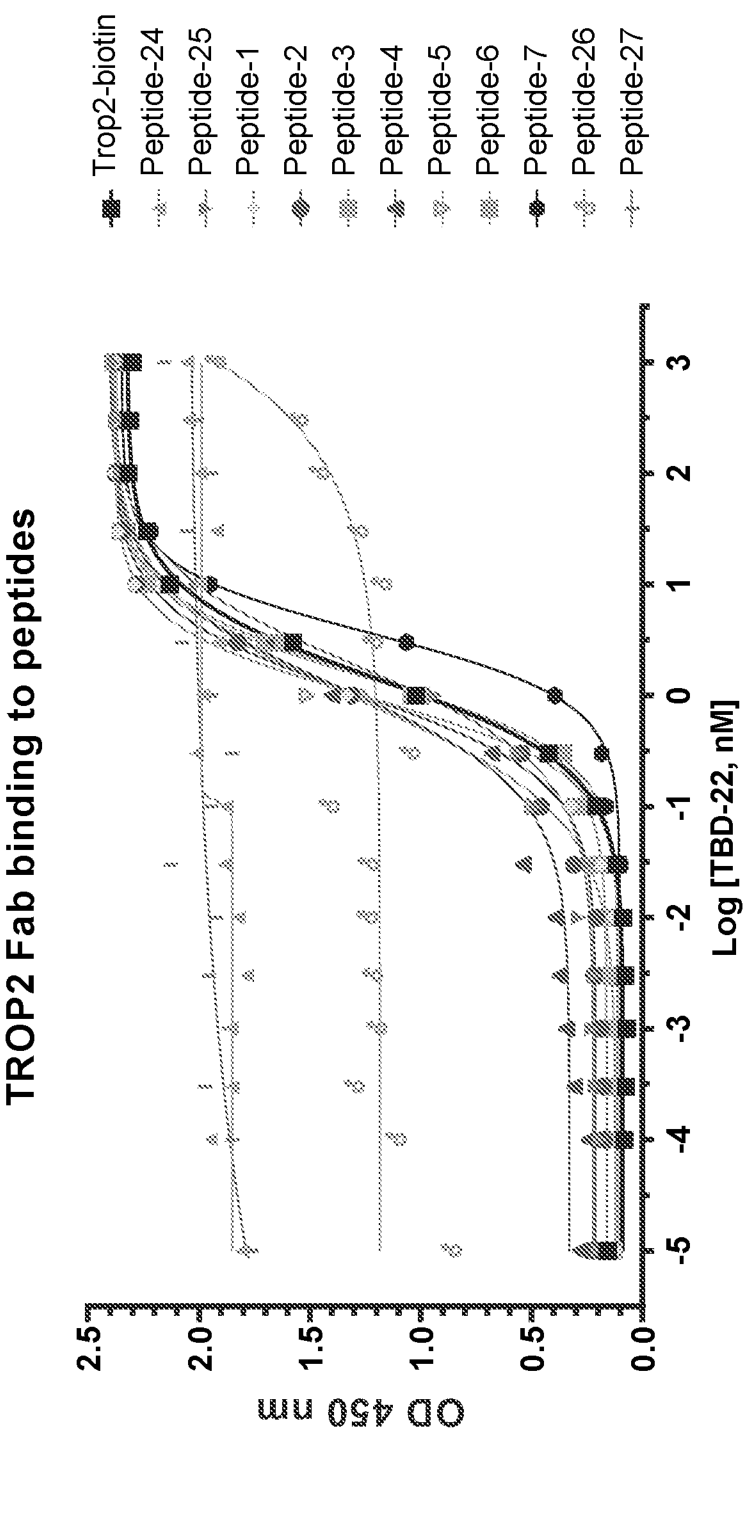
FIGS. 10A-10D illustrate binding curves for peptide binding to TBD-22 as measured by ELISA.
Figure 10B:
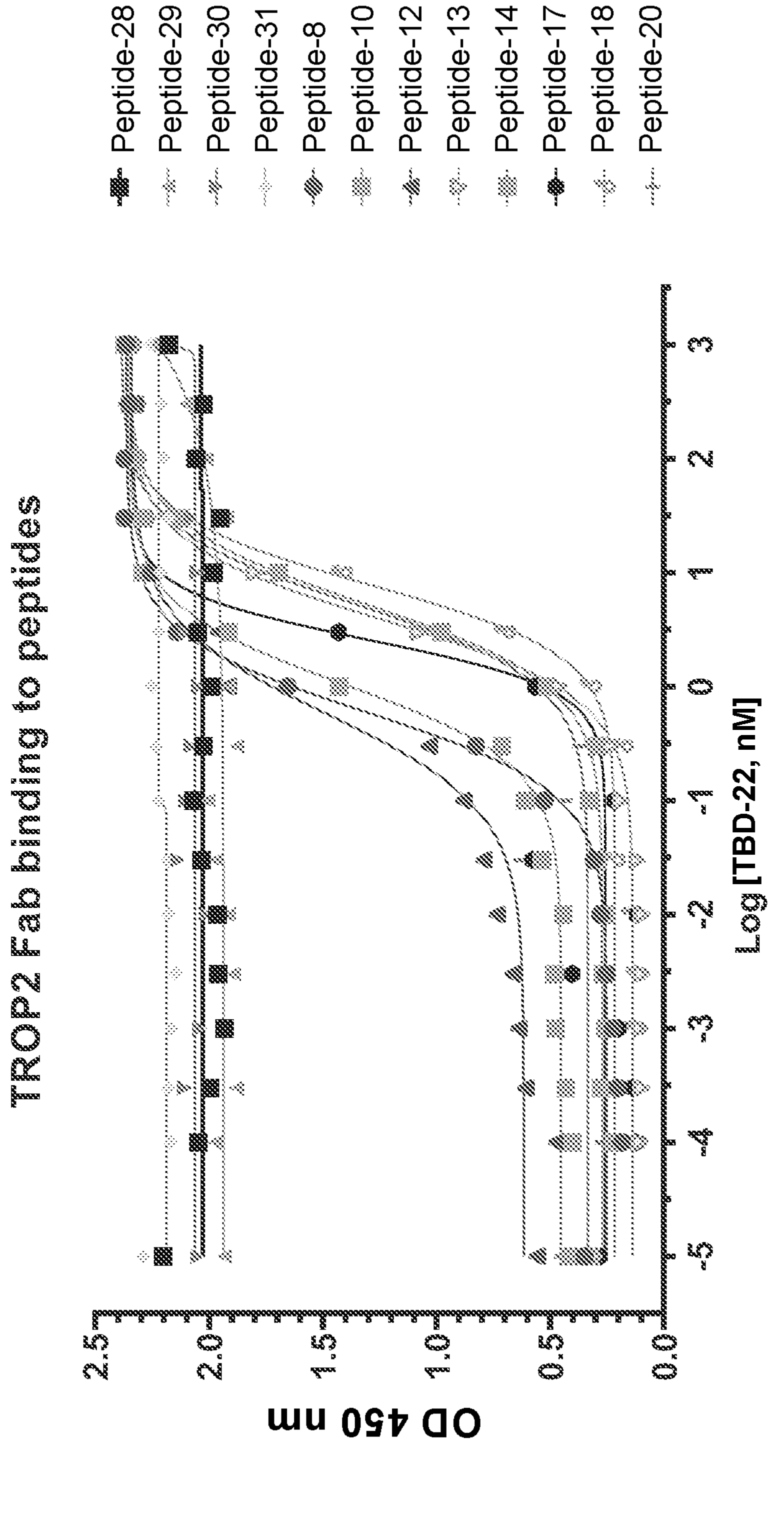
Figure 10C:
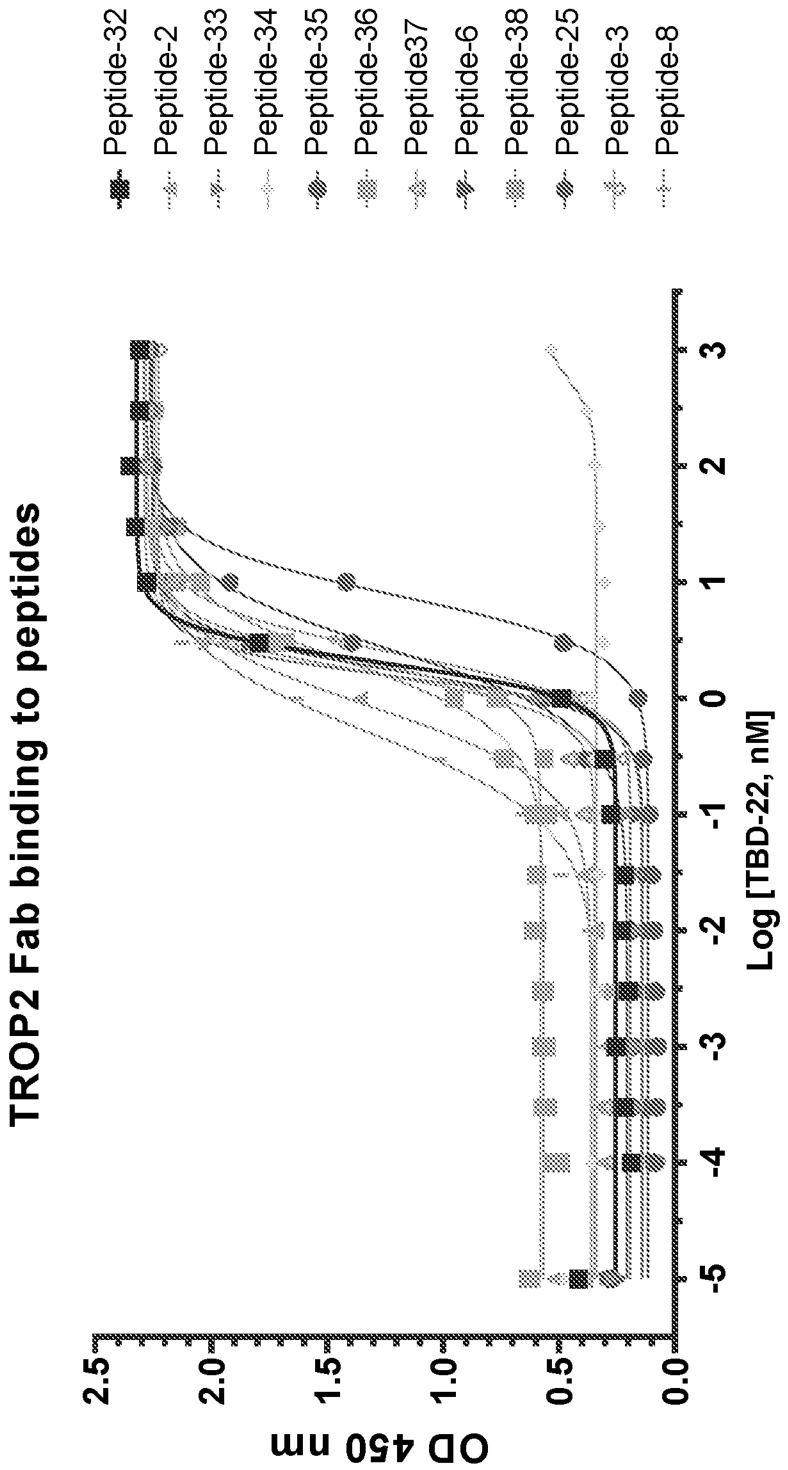
Figure 10D:
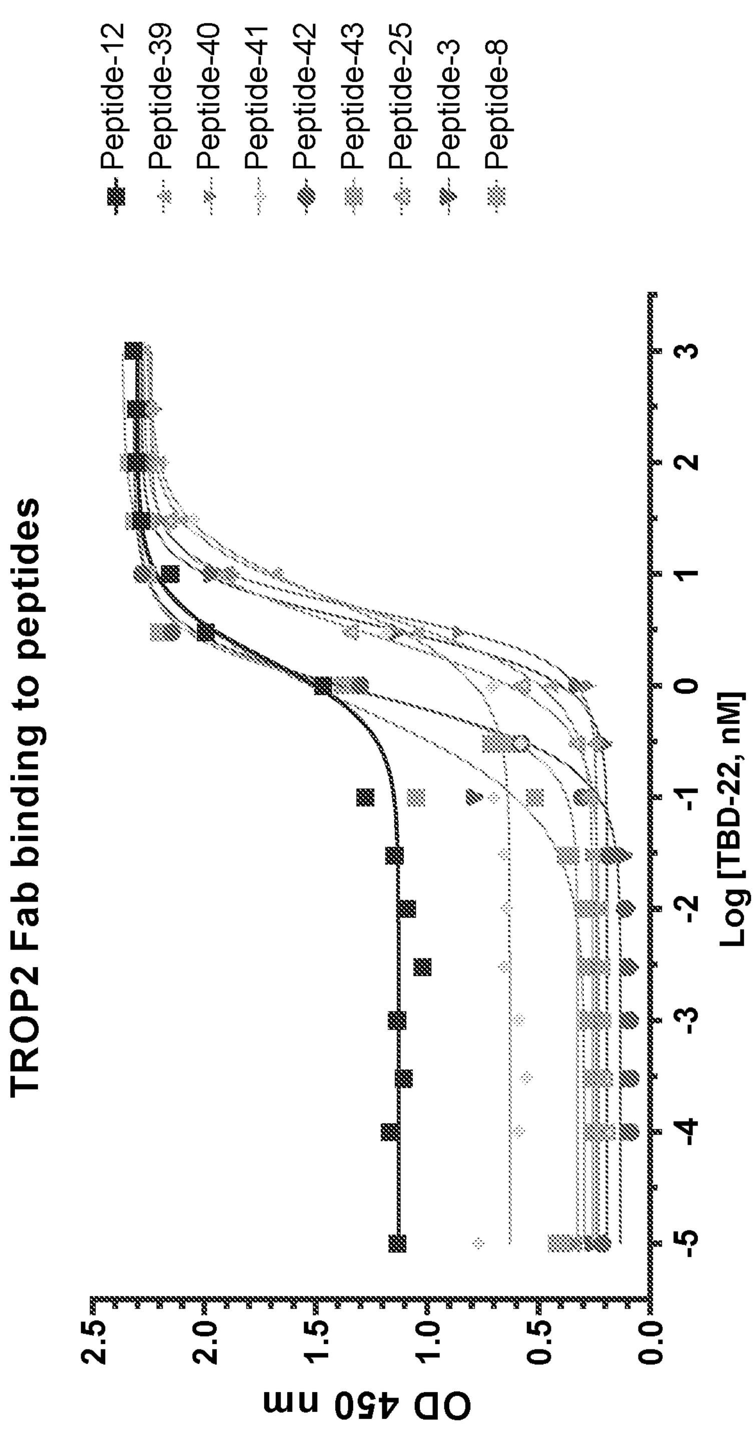
Figure 11A:
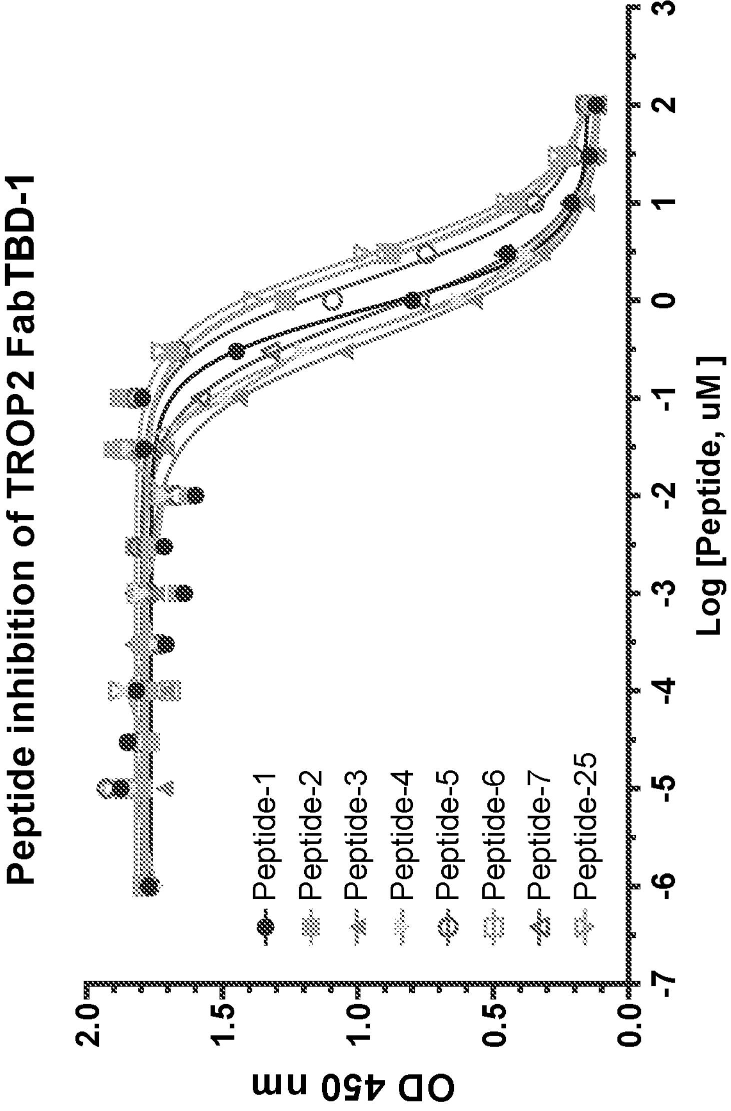
FIGS. 11A-11G illustrate inhibition of TBD-1 binding to TROP2 by peptides of the present disclosure.
Figure 11B:
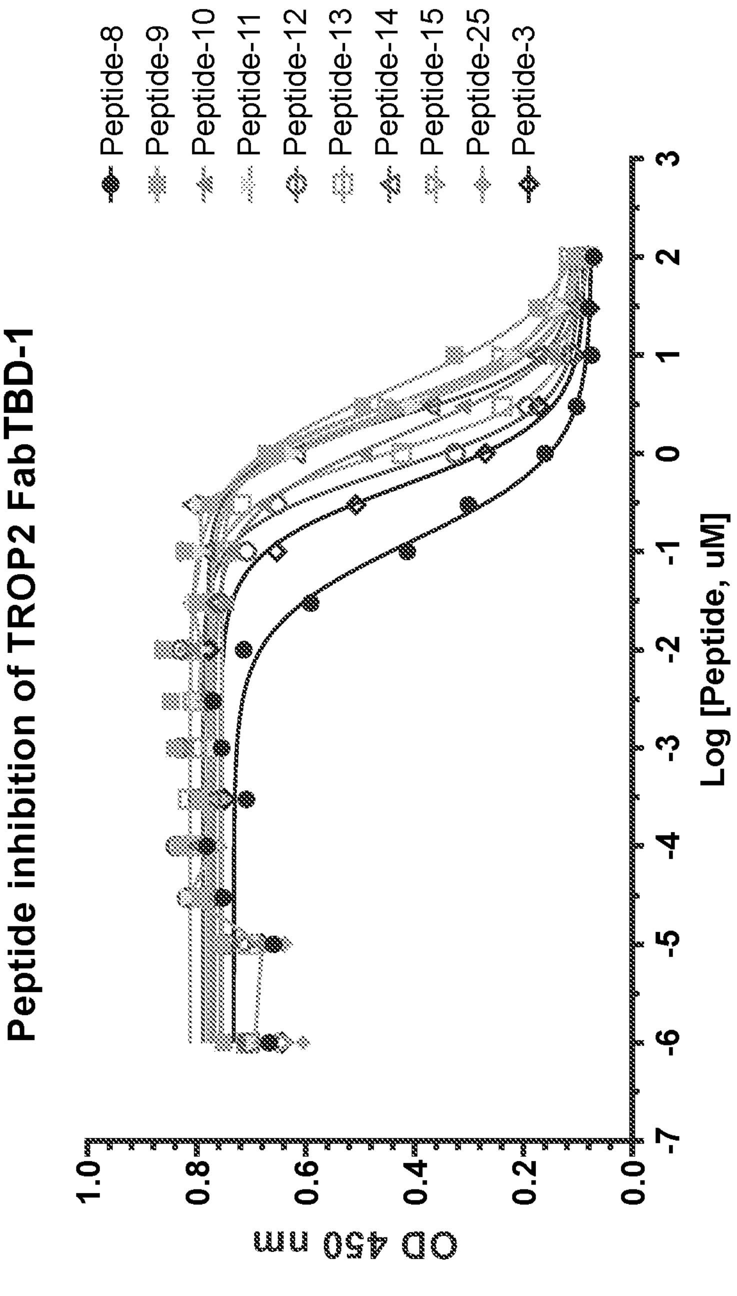
Figure 11C:
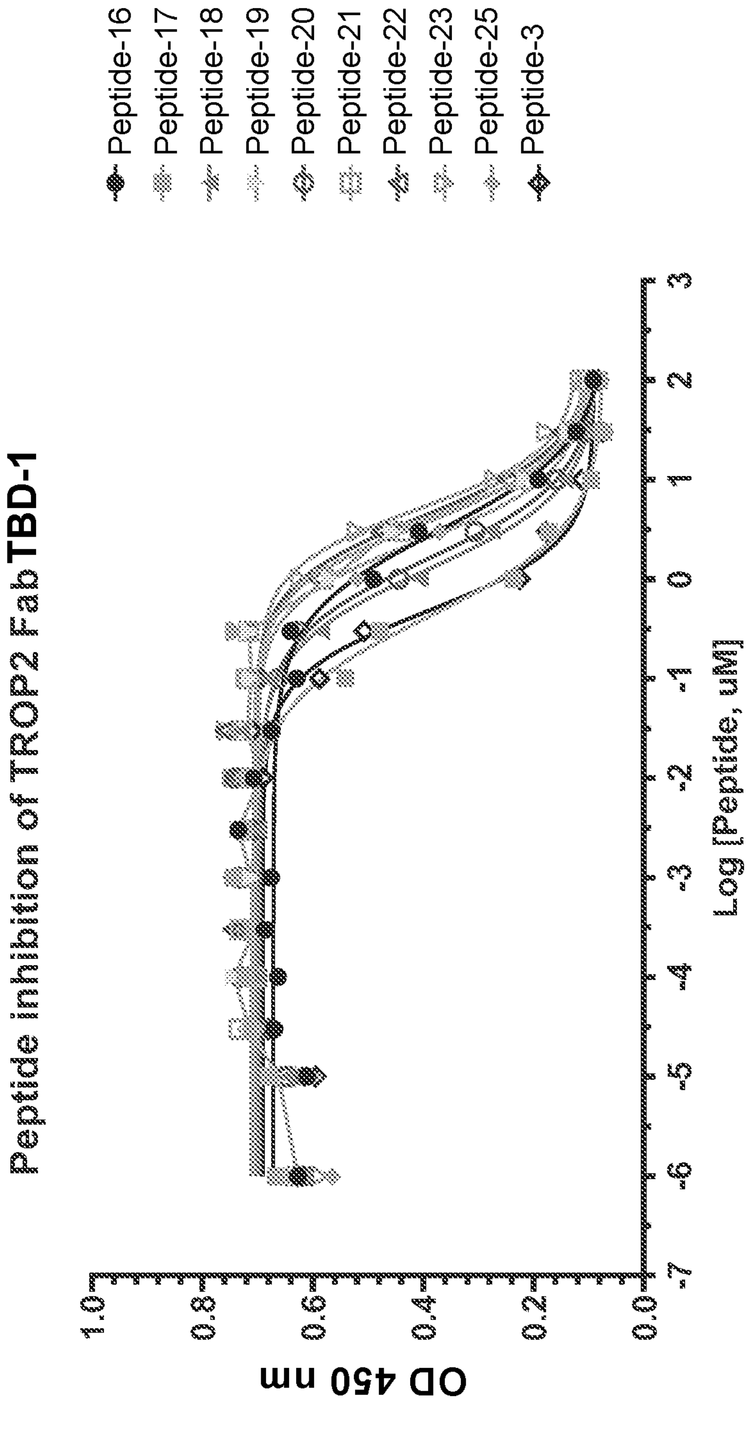
Figure 11D:
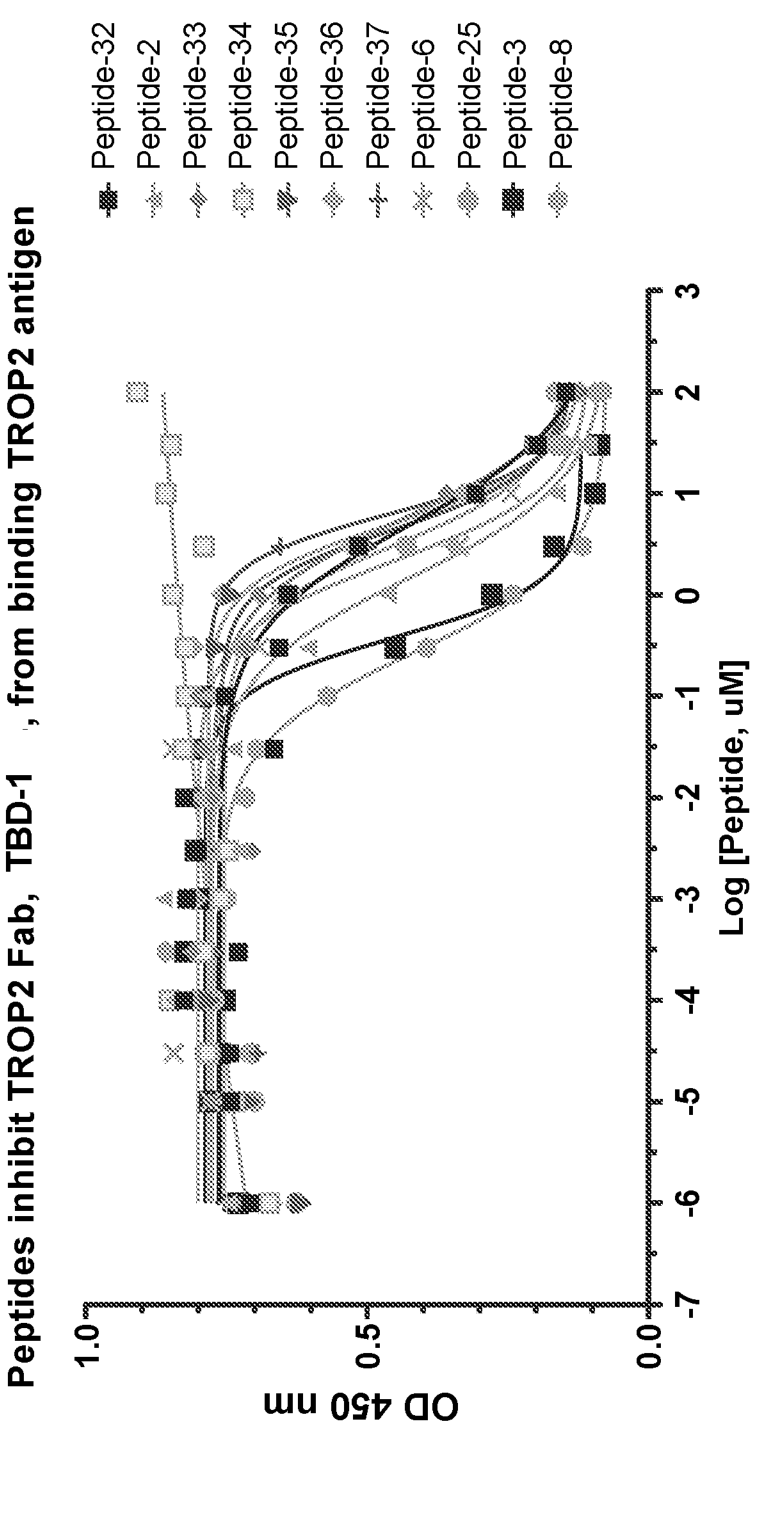
Figure 11E:
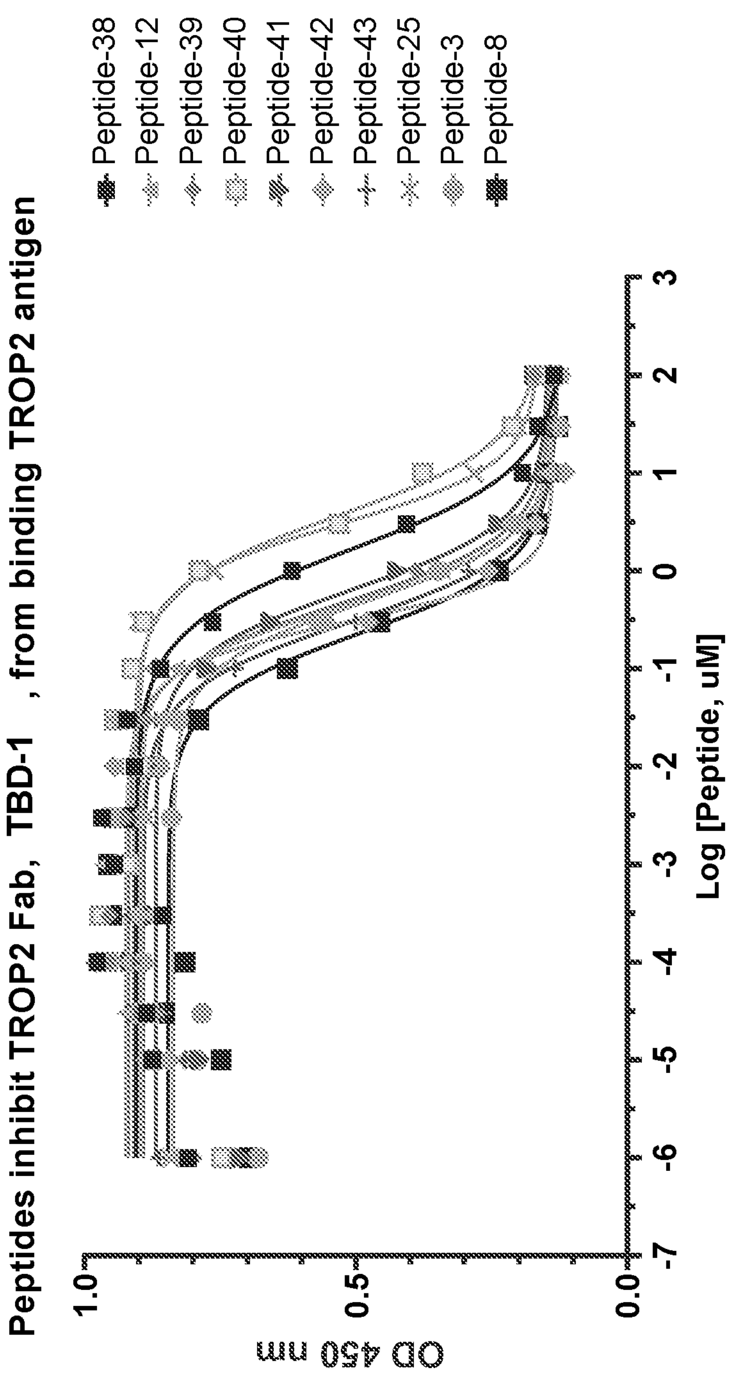
Figure 11F:
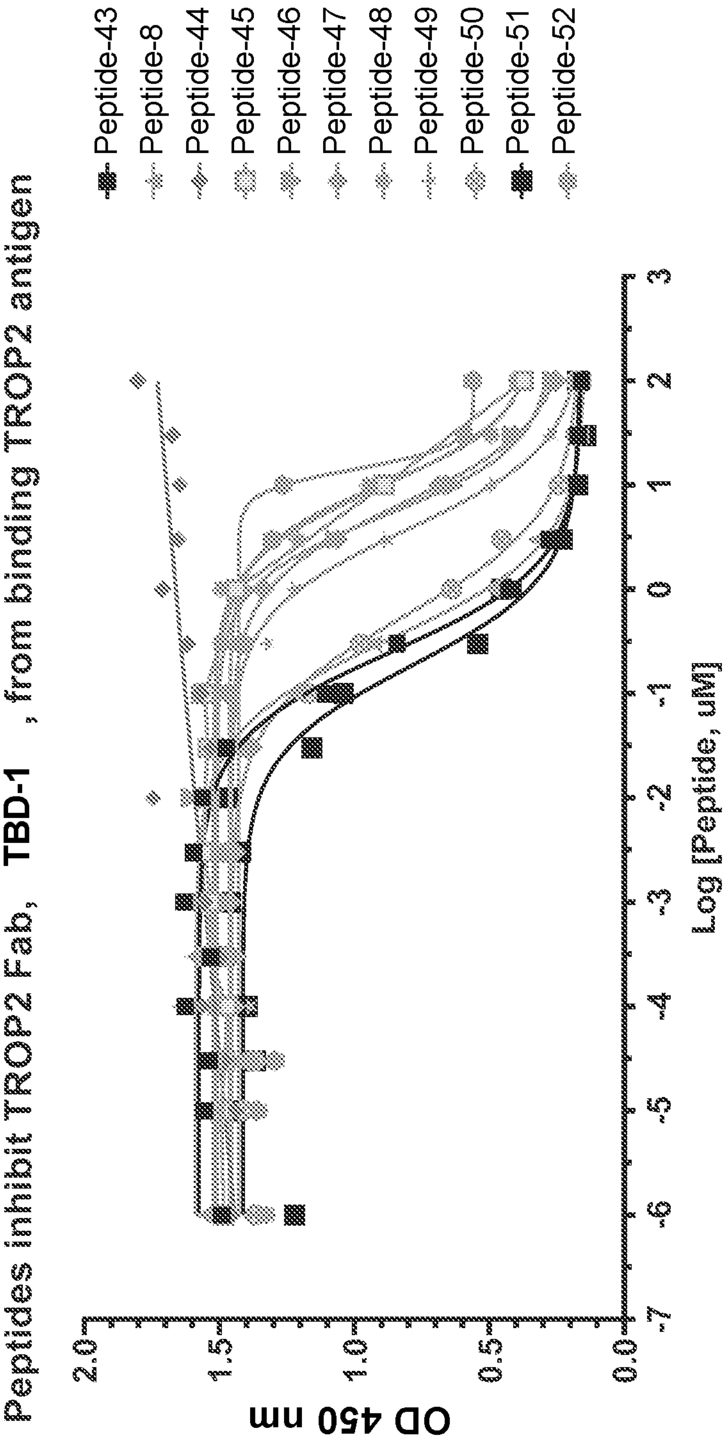
Figure 11G:
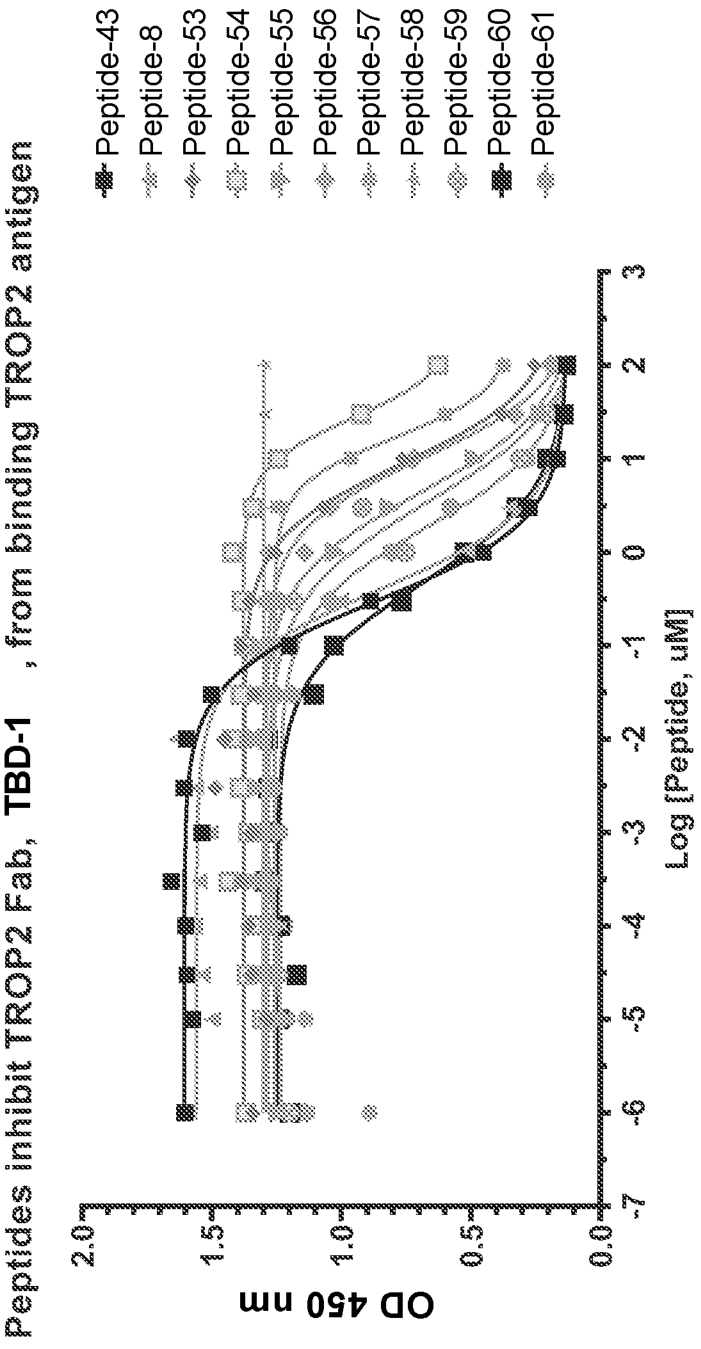
Figure 12A:
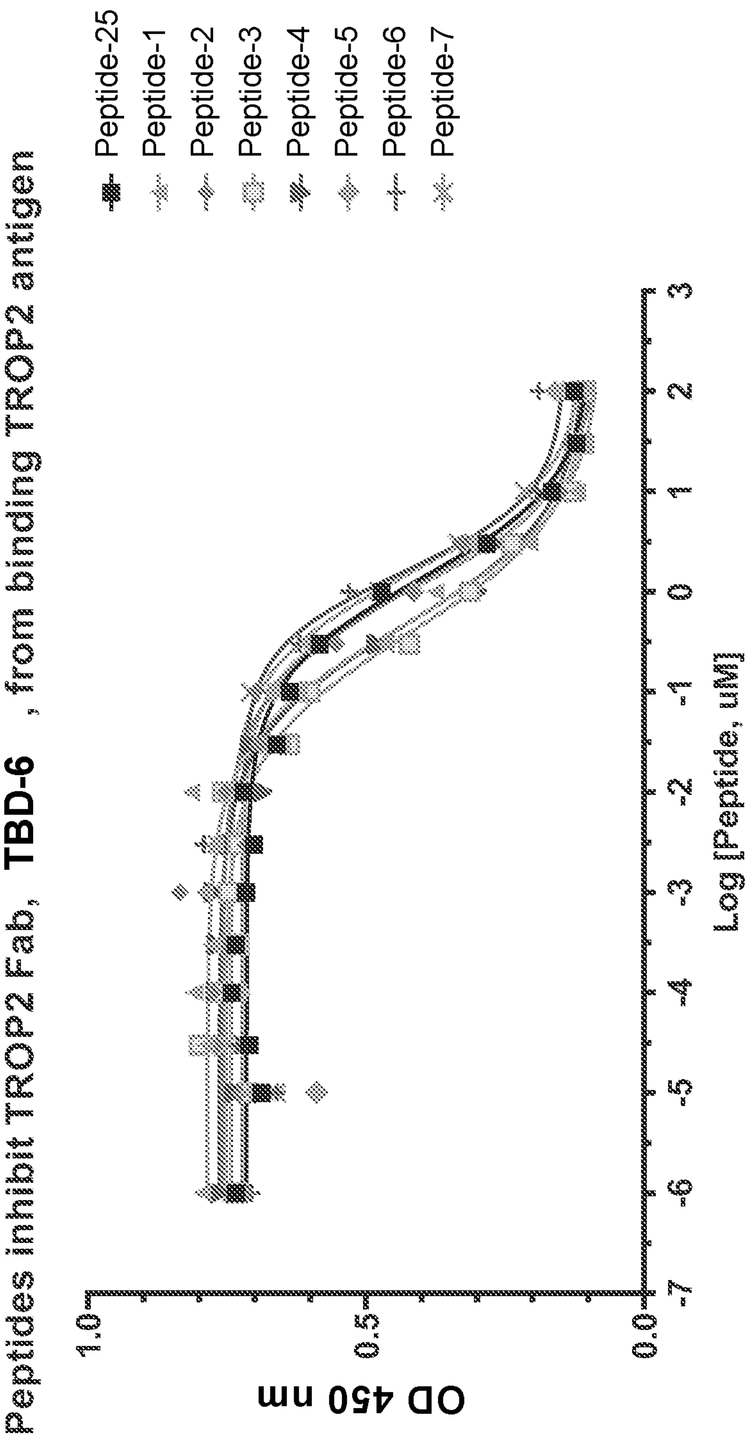
FIGS. 12A-12F illustrate inhibition of TBD-6 binding to TROP2 by peptides of the present disclosure.
Figure 12B:
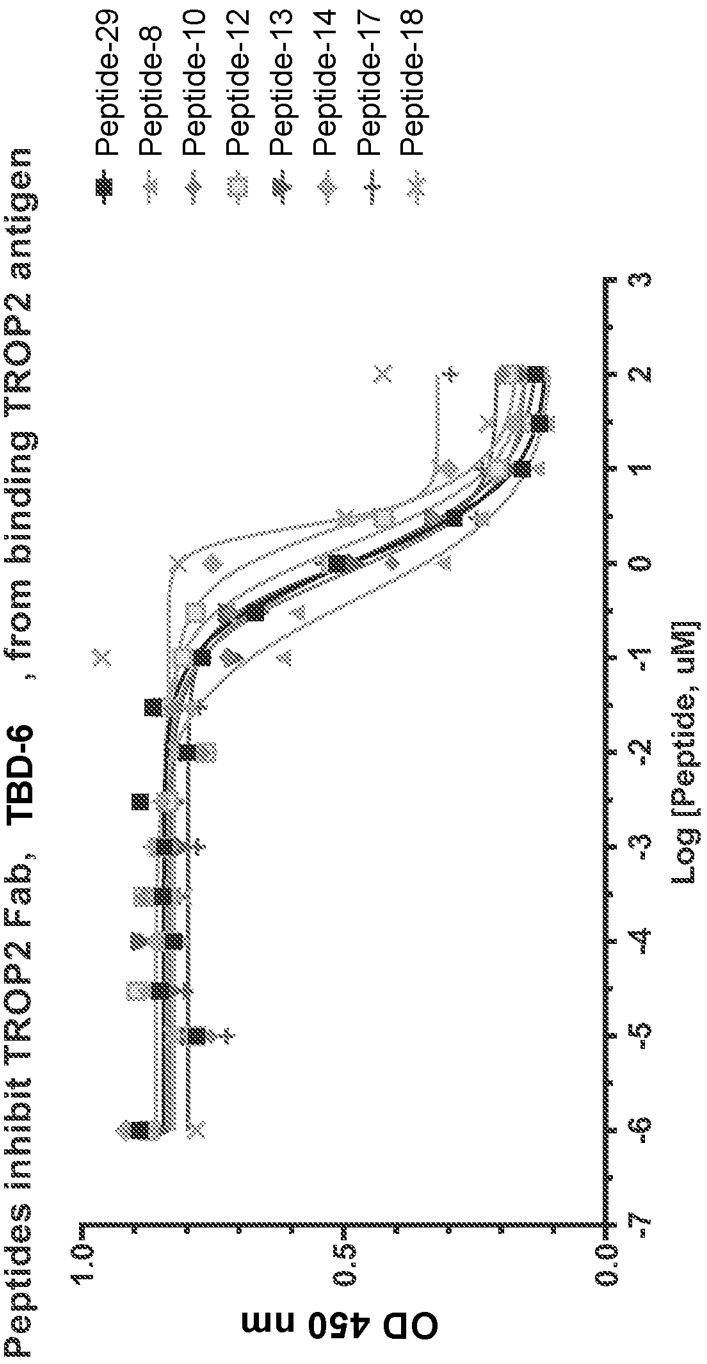
Figure 12C:
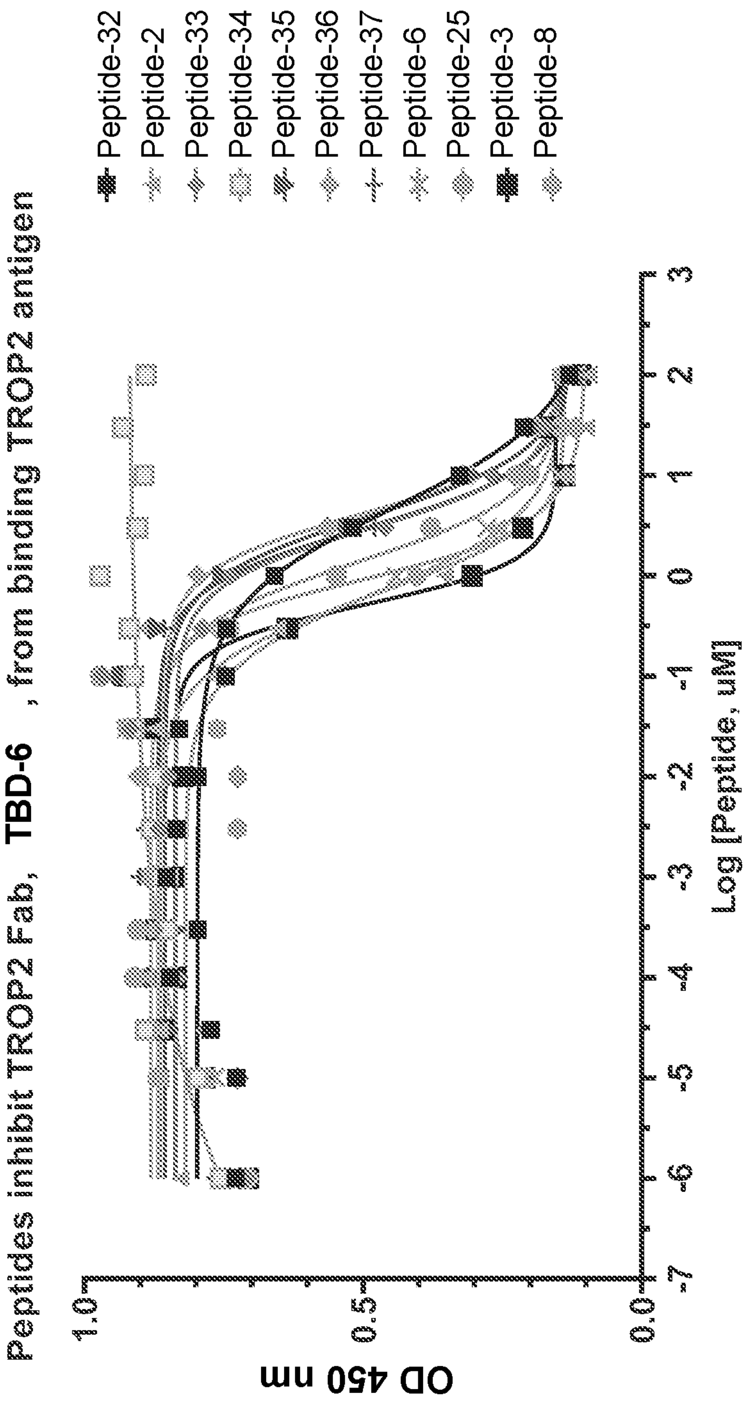
Figure 12D:
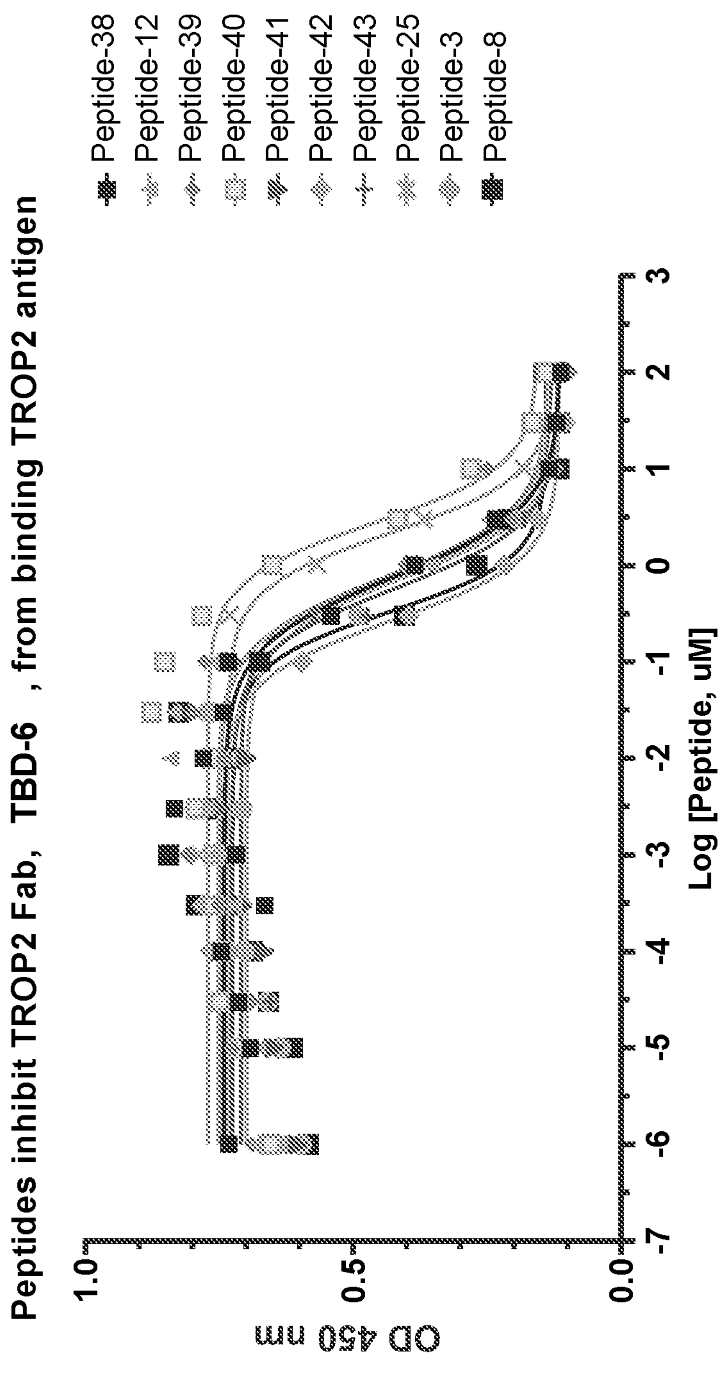
Figure 12E:
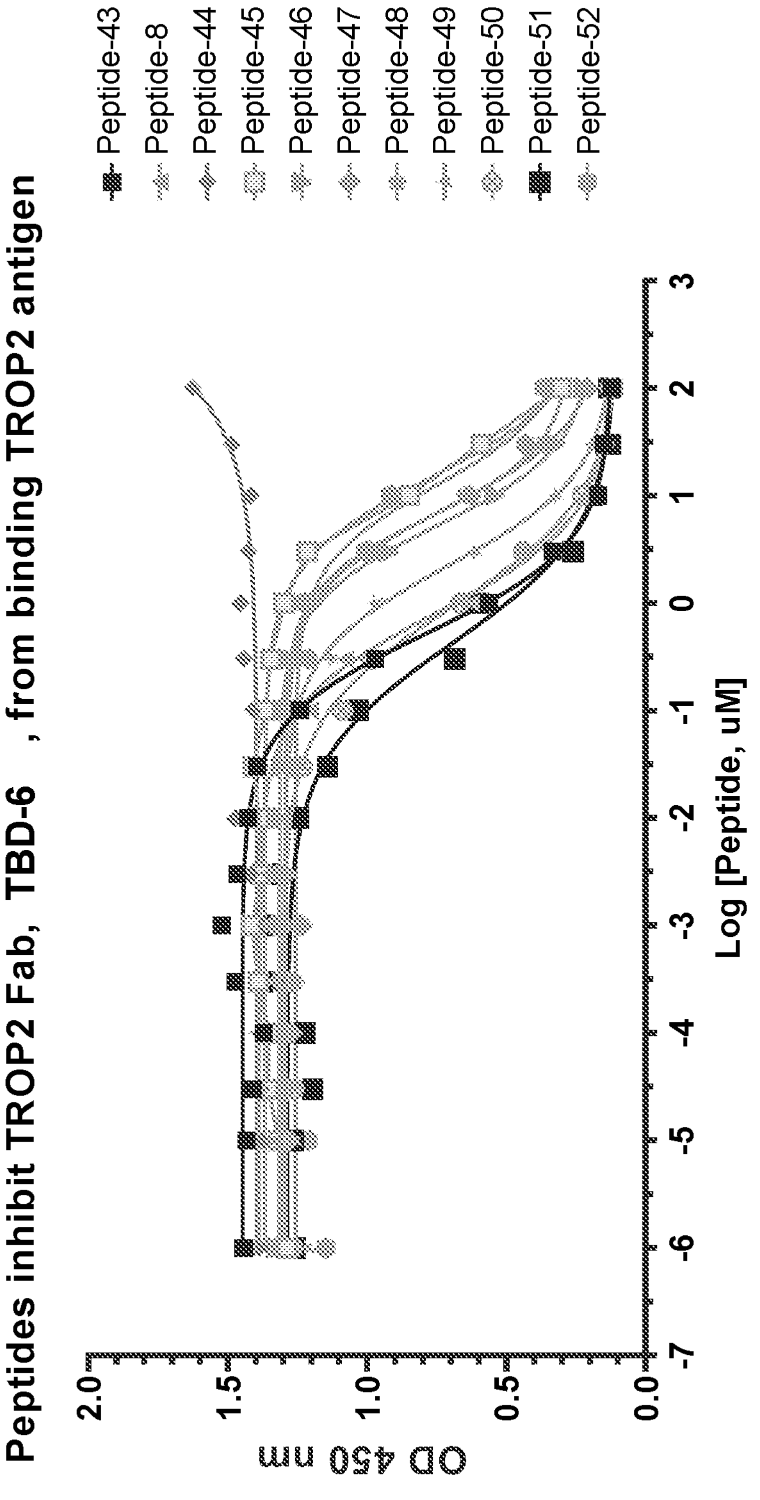
Figure 12F:
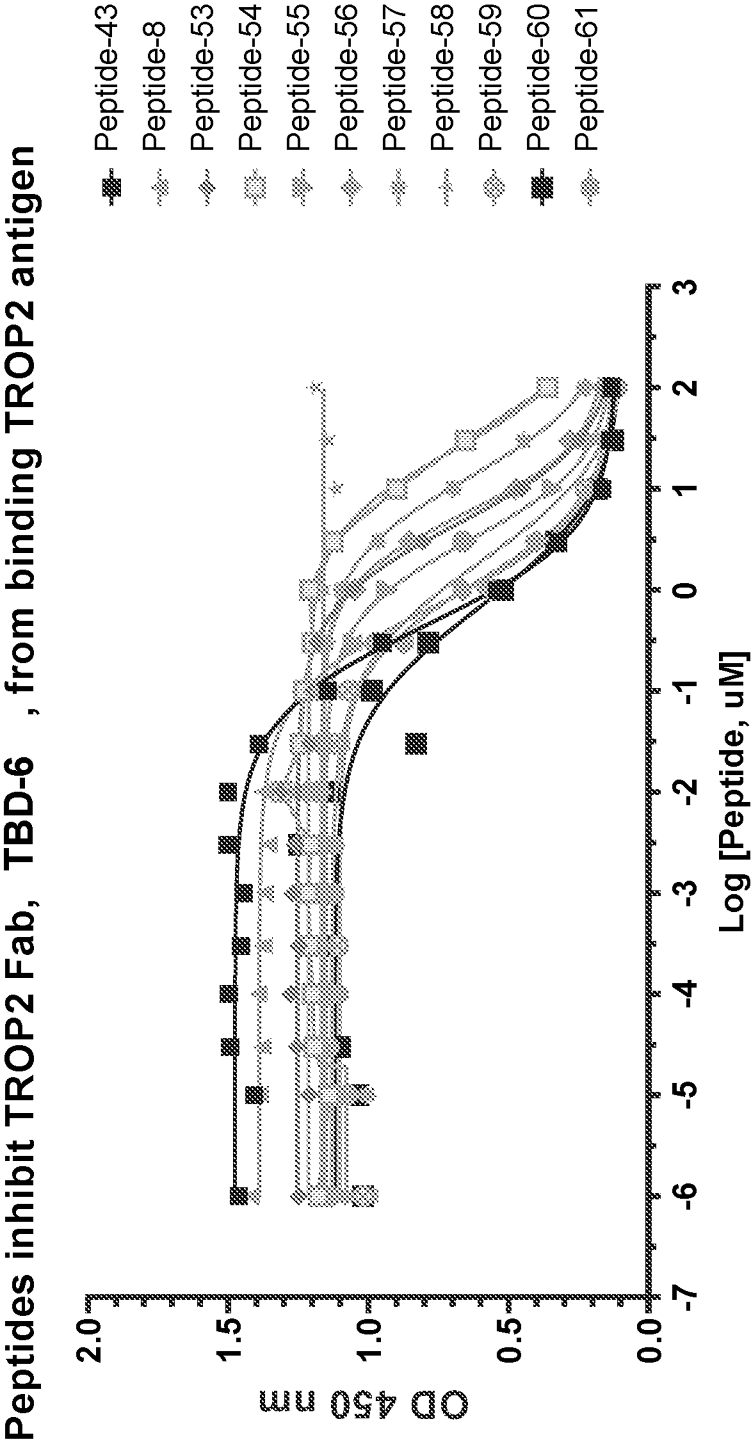
Figure 13A:
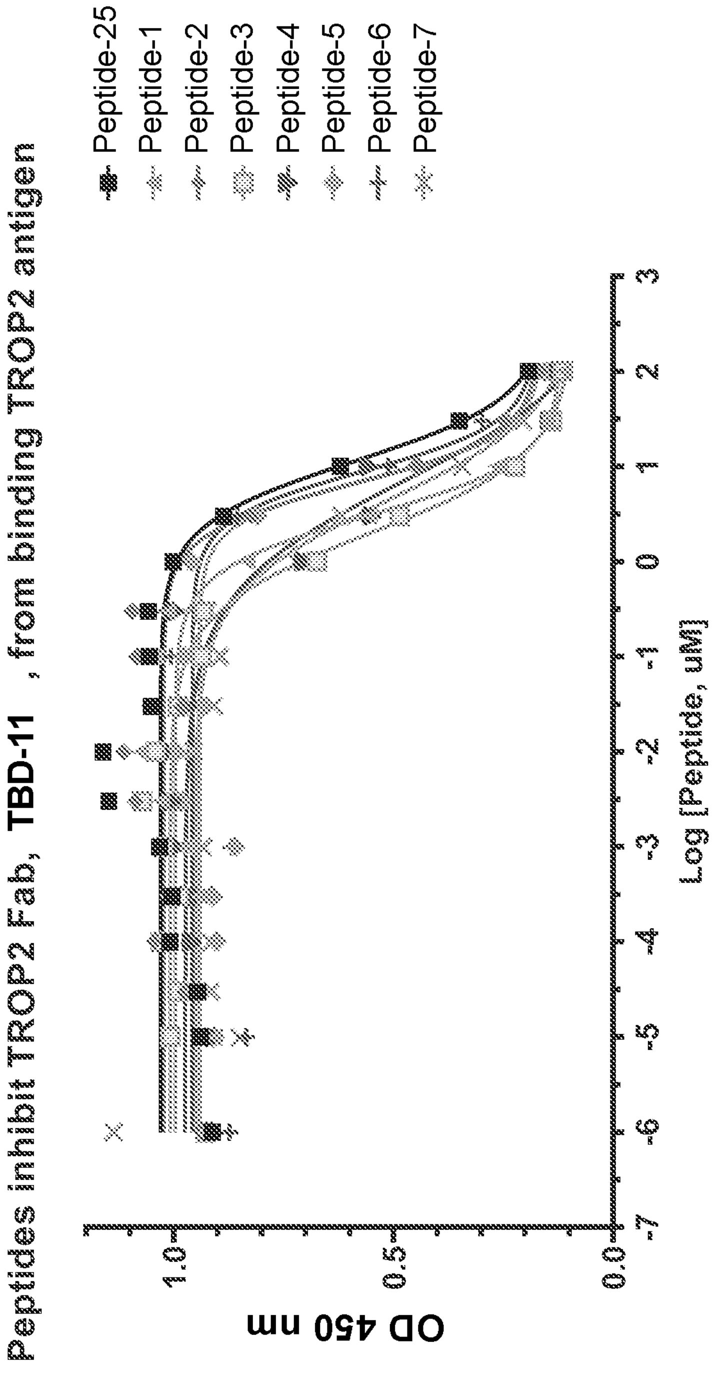
FIGS. 13A-13F illustrate inhibition of TBD-11 binding to TROP2 by peptides of the present disclosure.
Figure 13B:
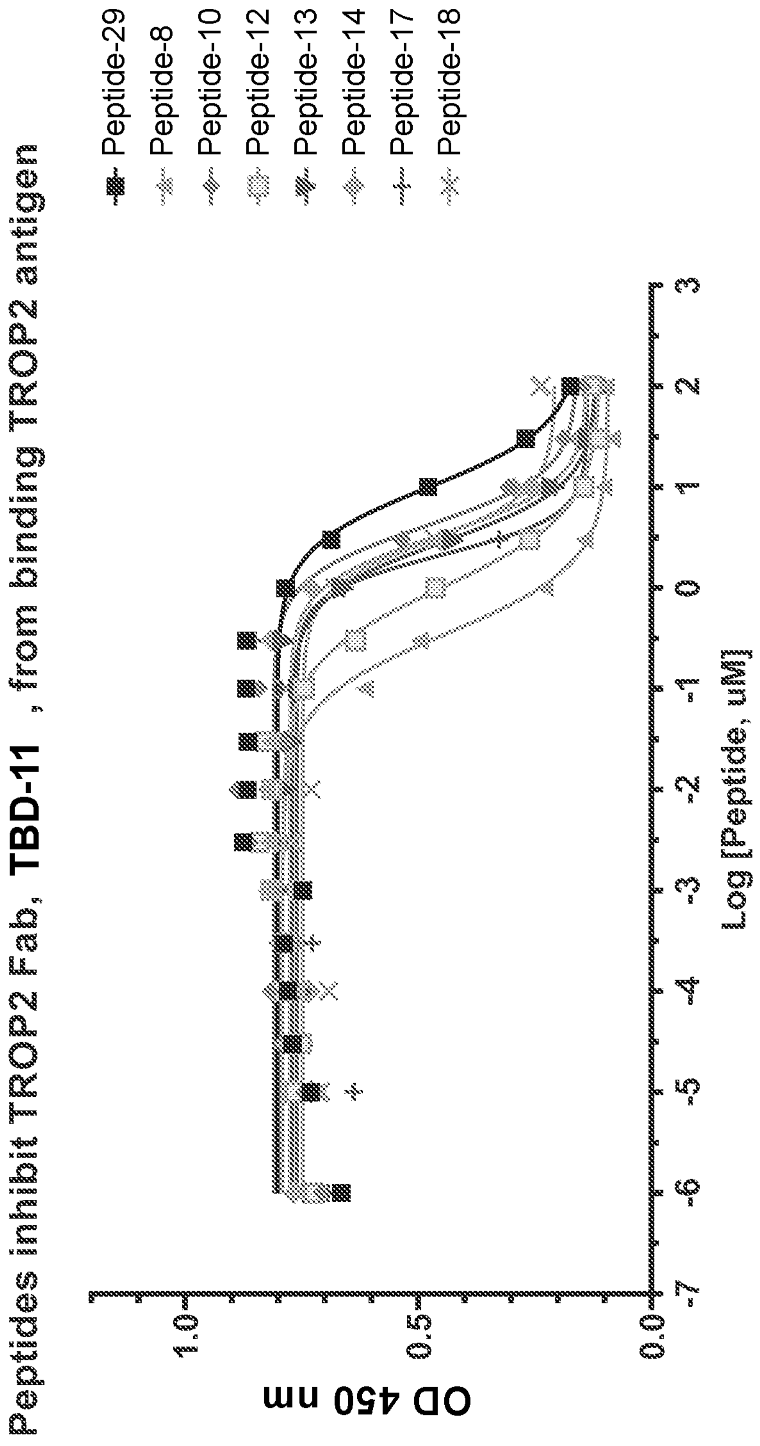
Figure 13C:
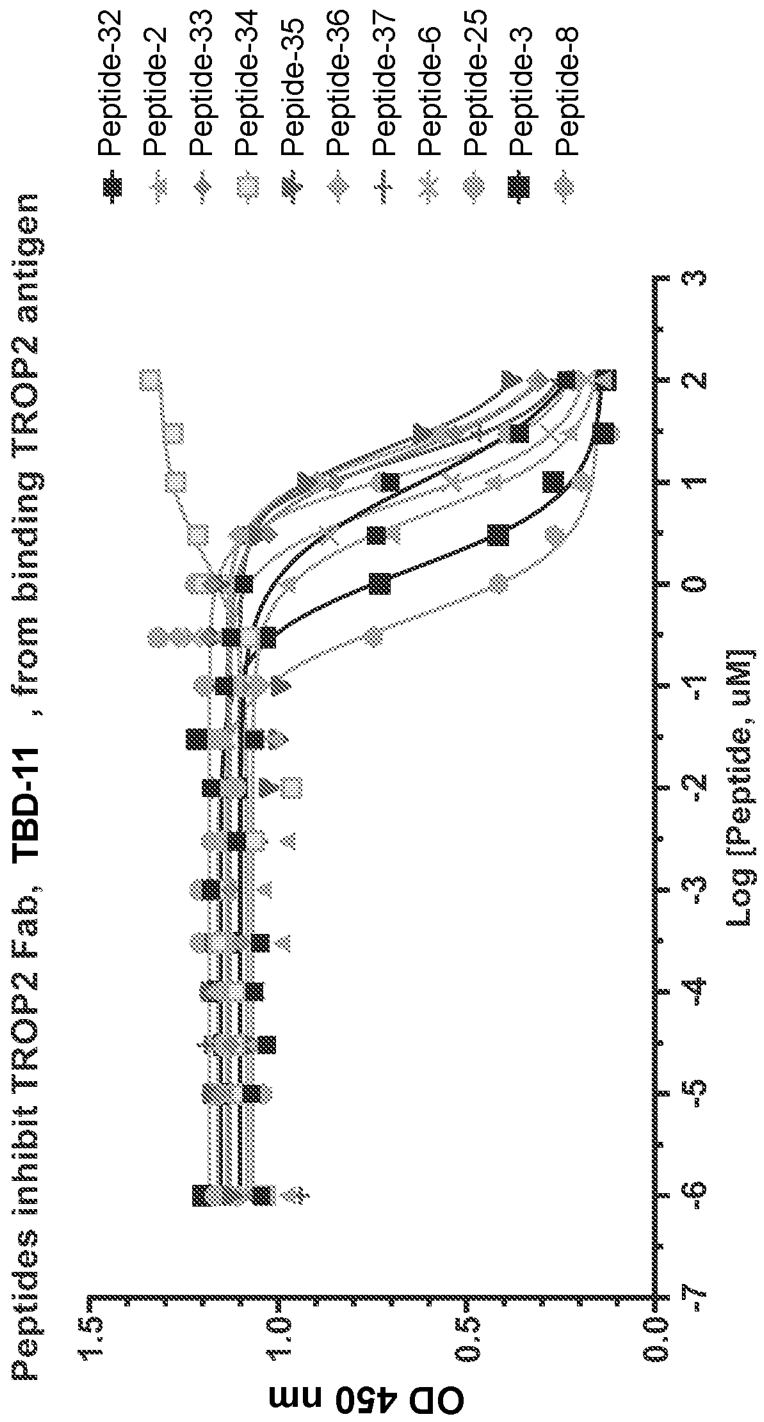
Figure 13D:
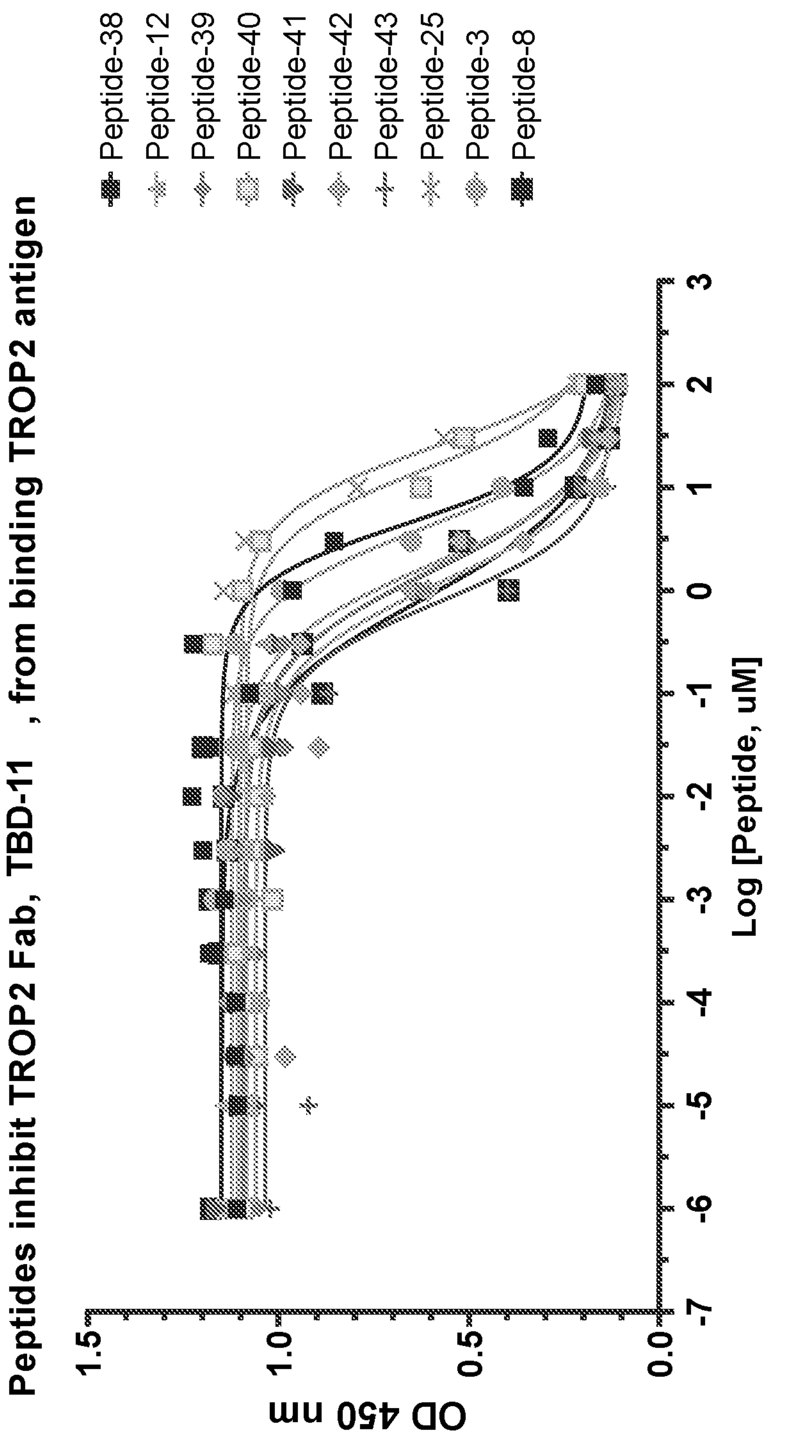
Figure 13E:
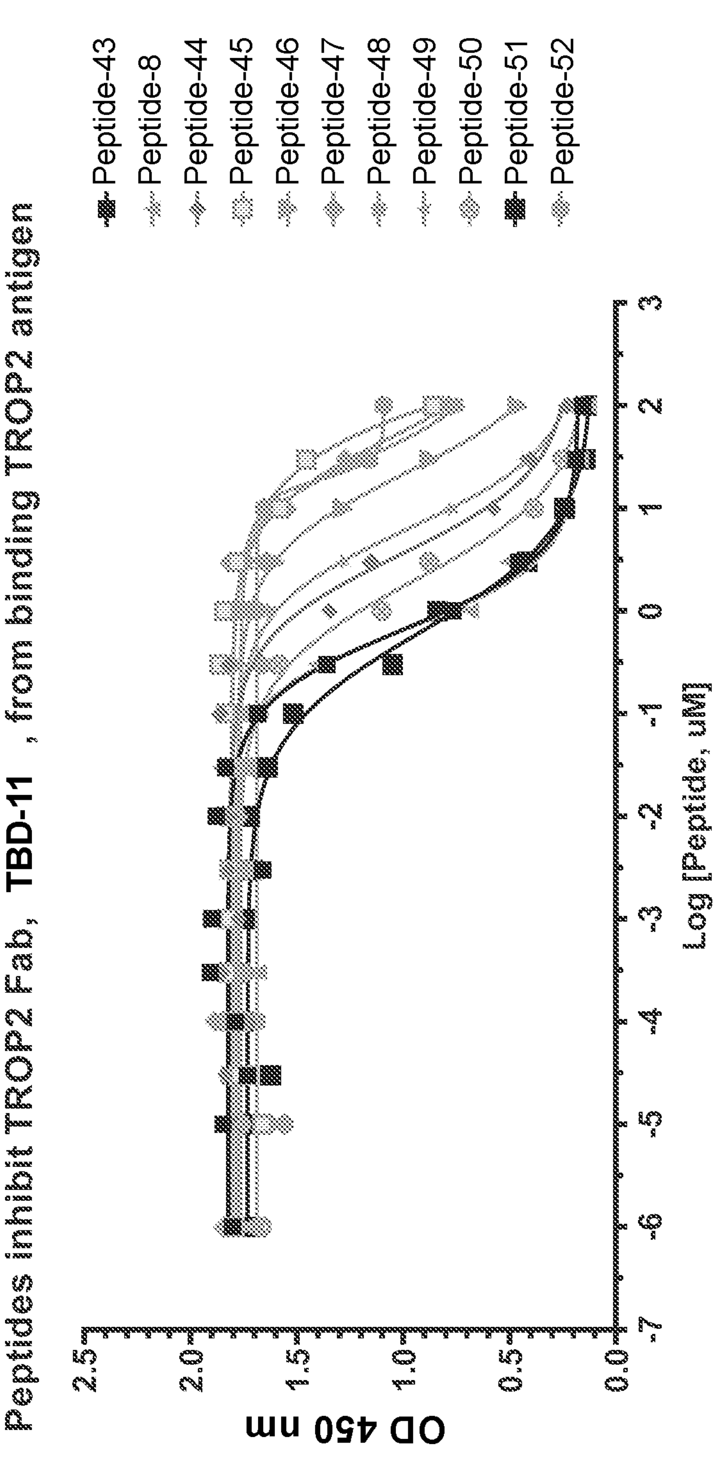
Figure 13F:
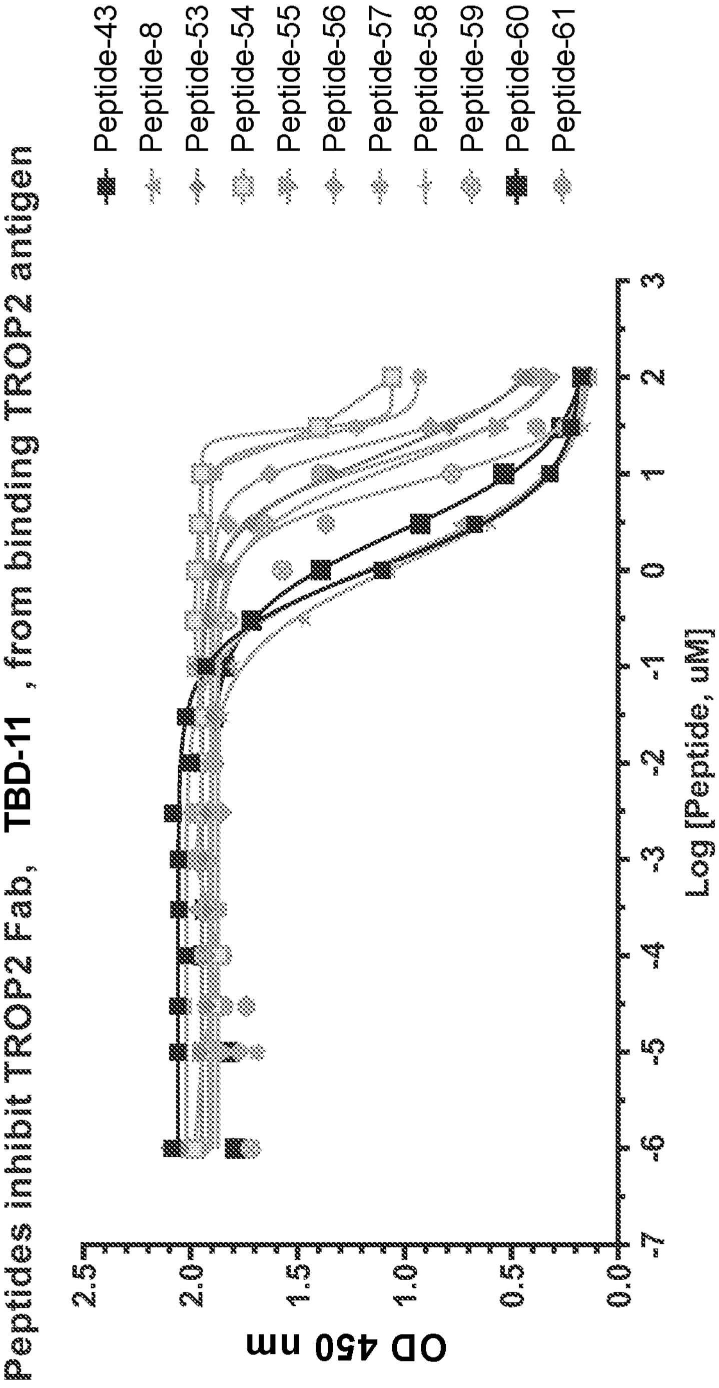
Figure 14A:
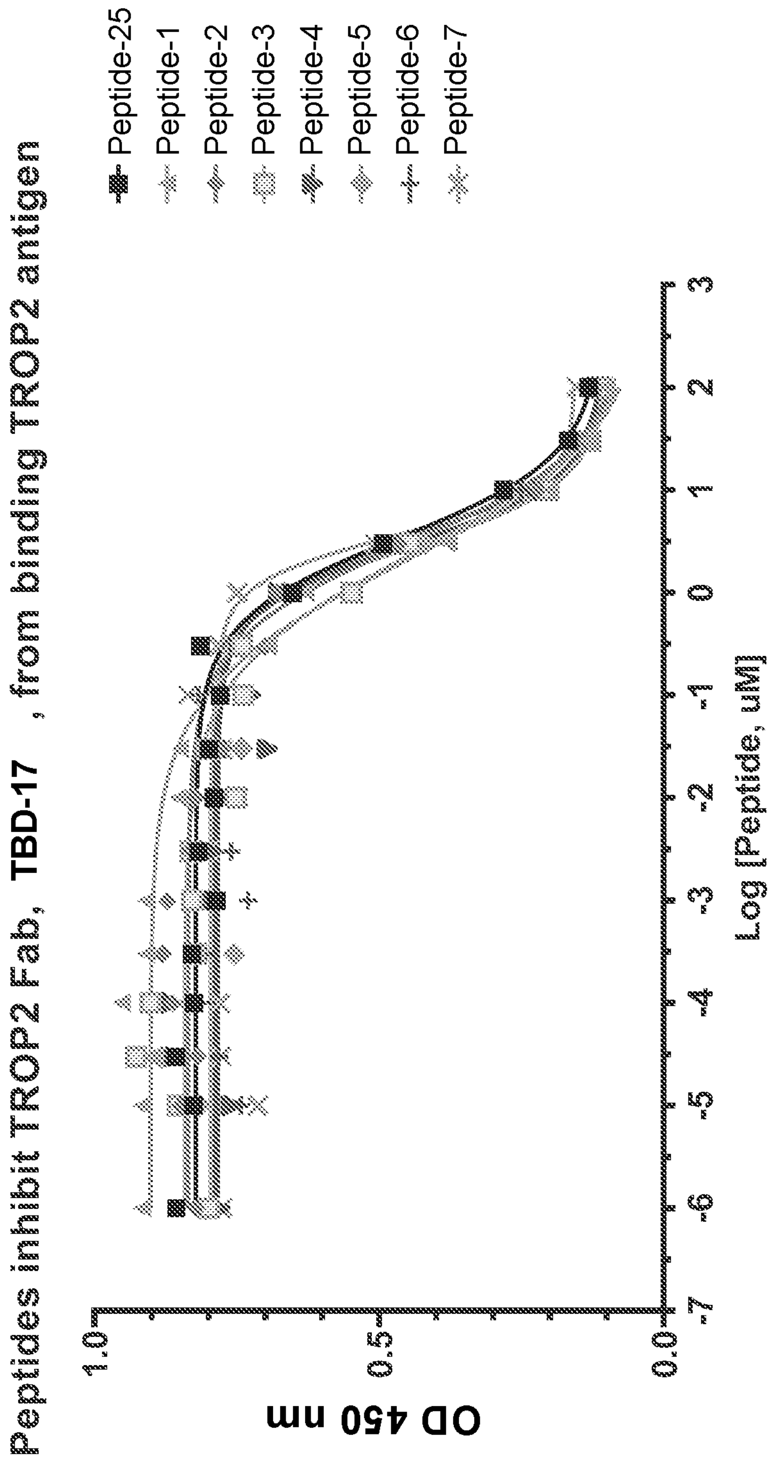
FIGS. 14A-14F illustrate inhibition of TBD-17 binding to TROP2 by peptides of the present disclosure.
Figure 14B:
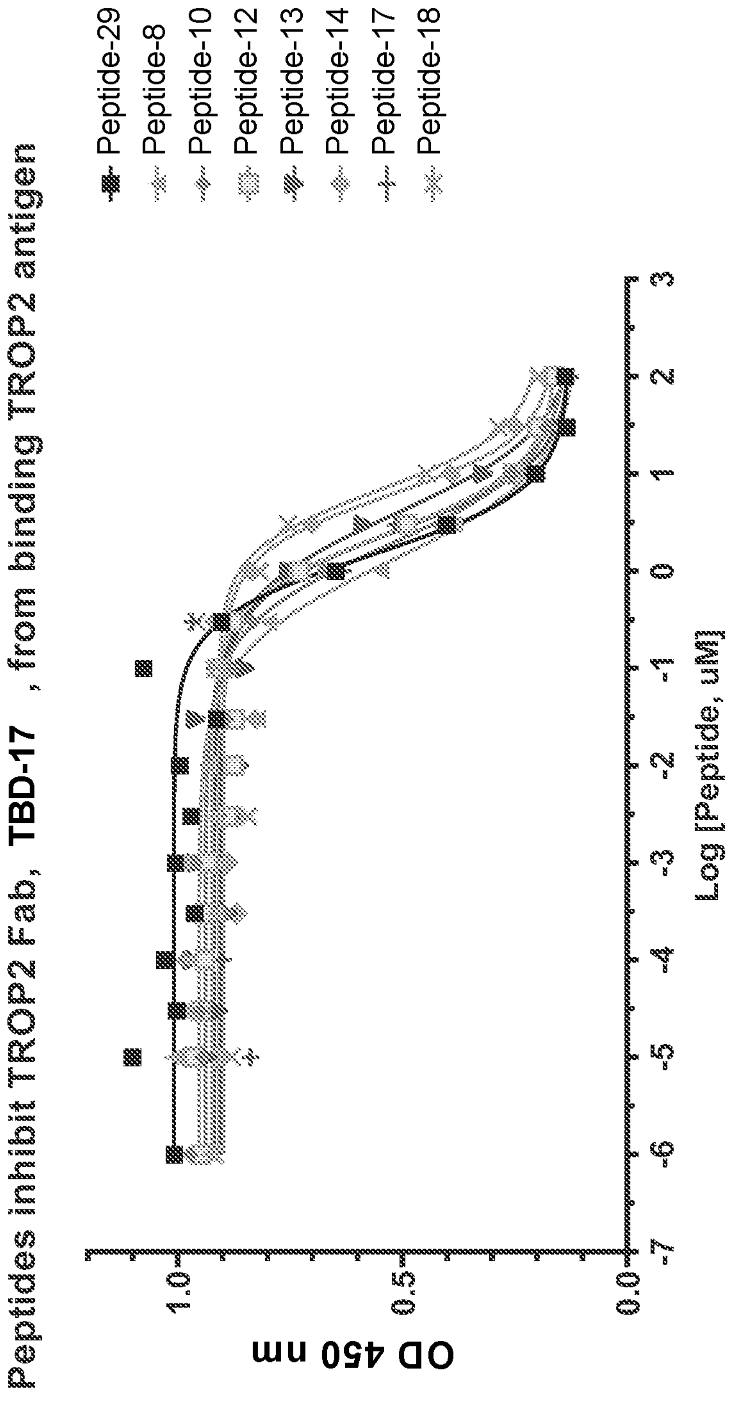
Figure 14C:
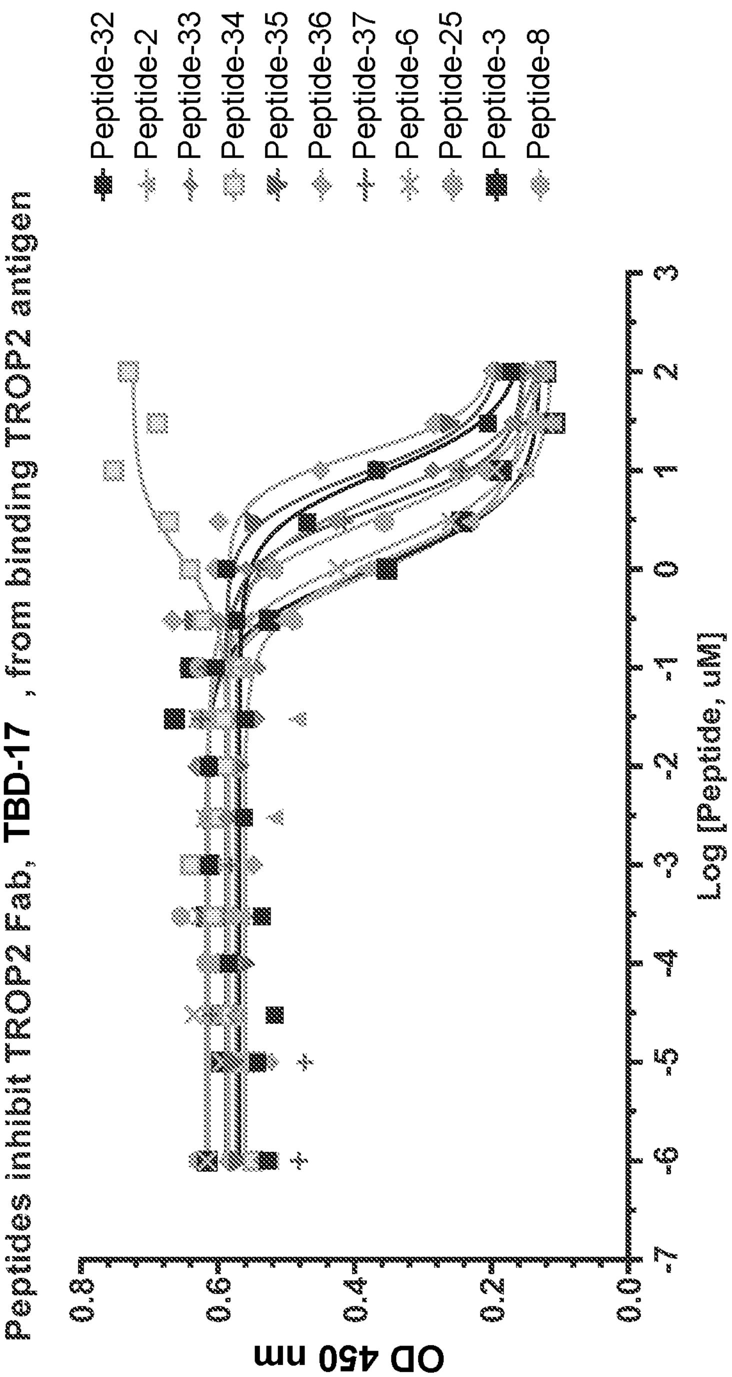
Figure 14D:
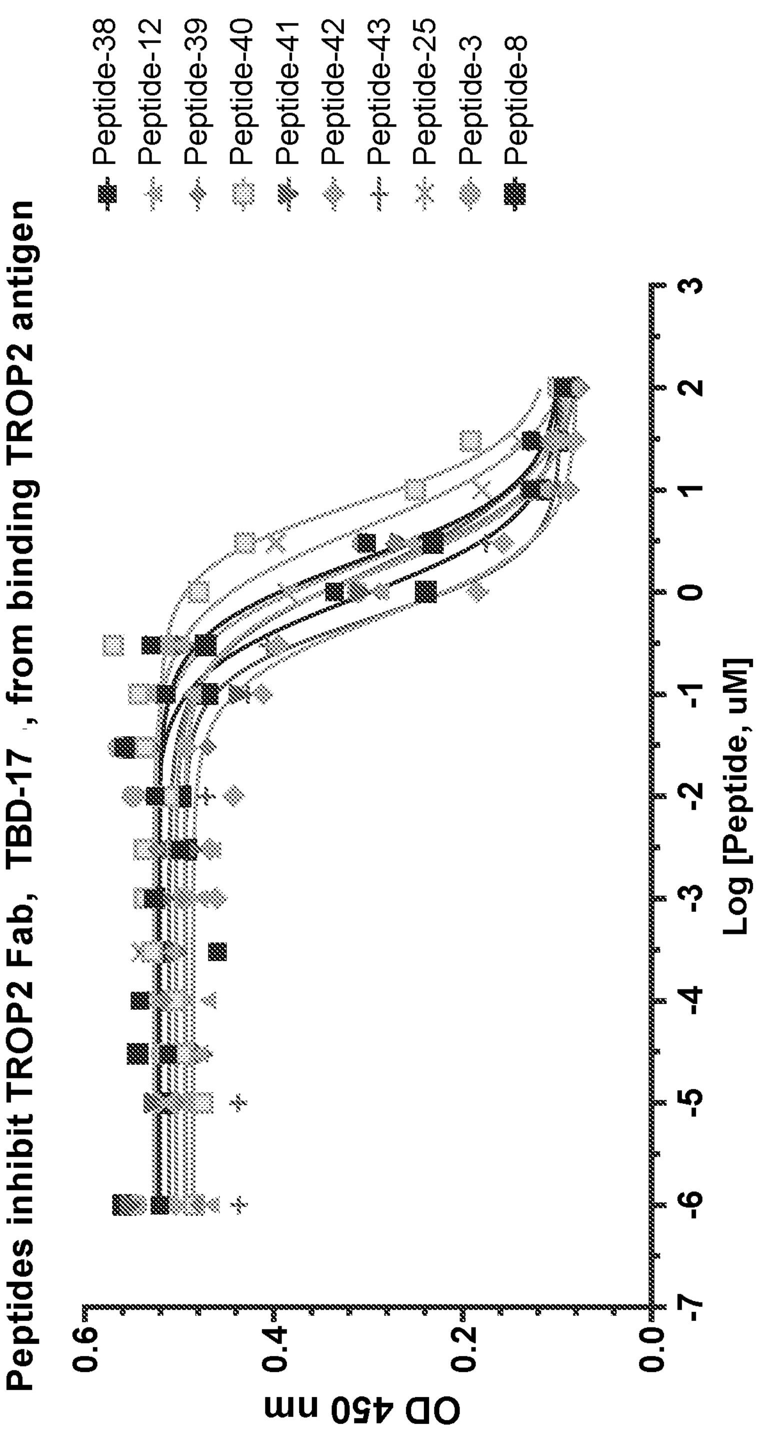
Figure 14E:
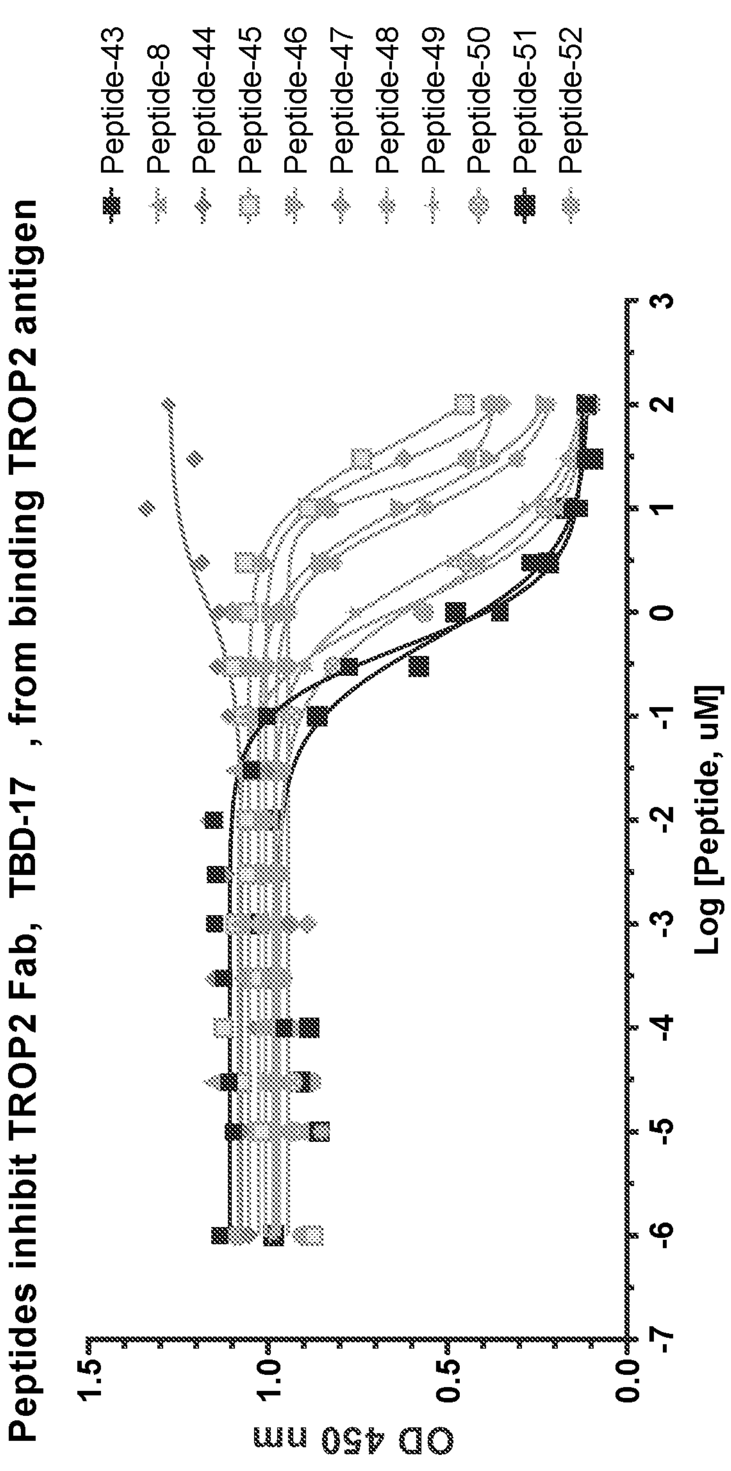
Figure 14F:
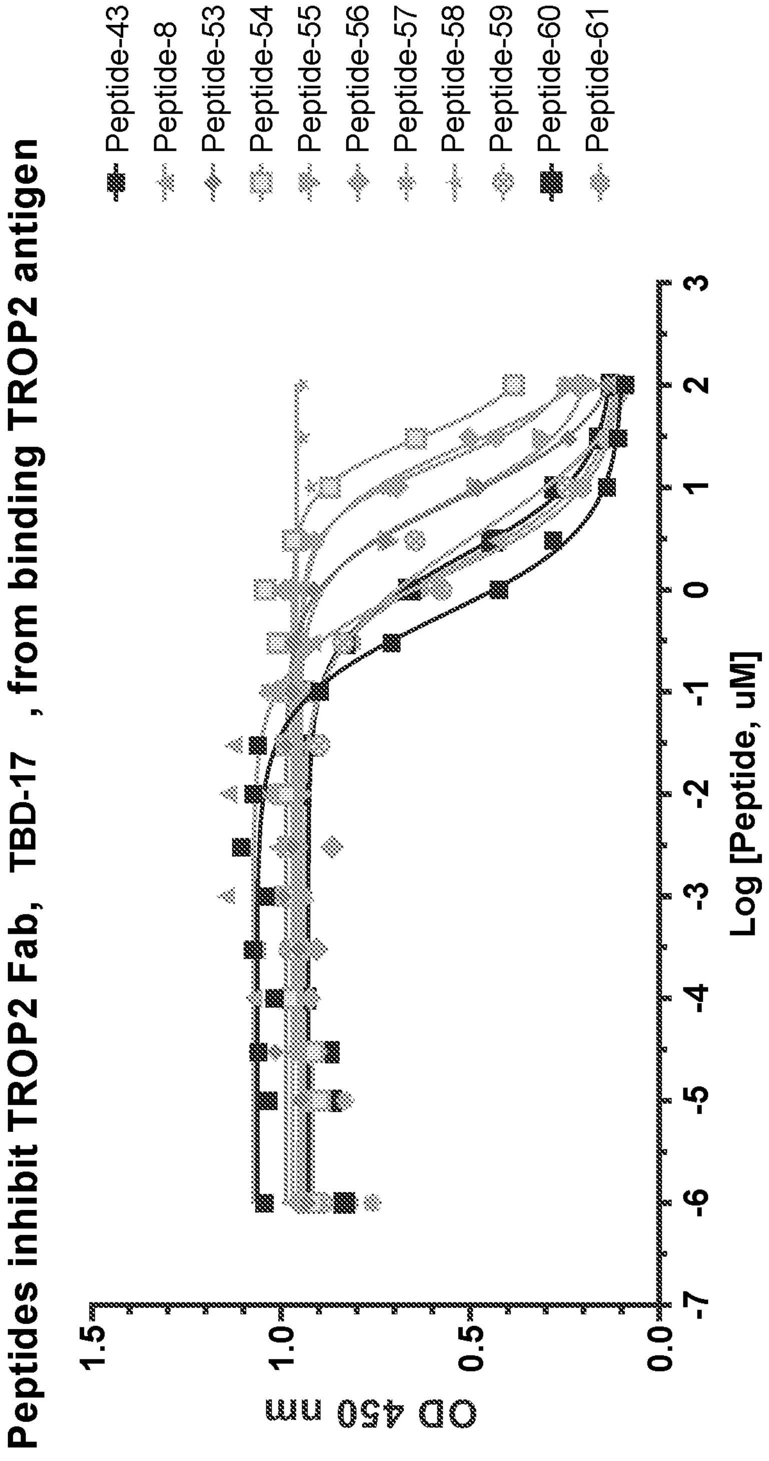
Figure 15A:
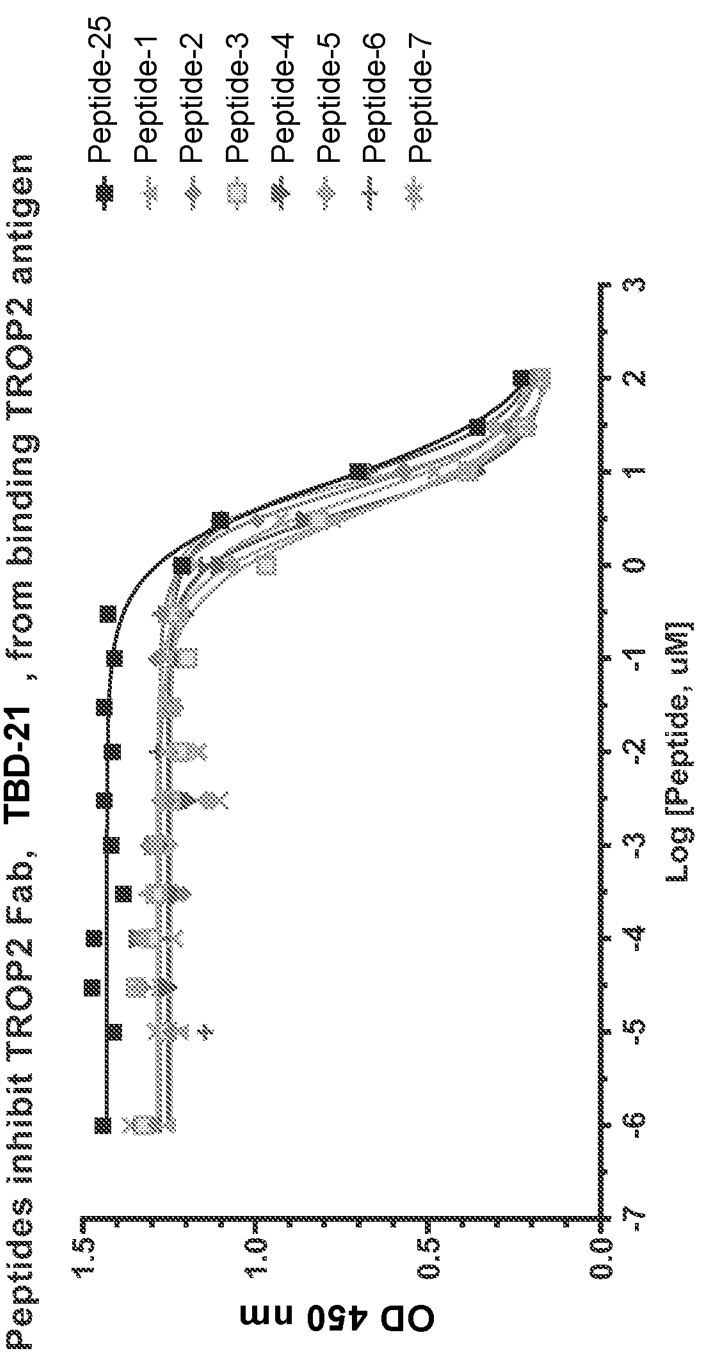
FIGS. 15A-15F illustrate inhibition of TBD-21 binding to TROP2 by peptides of the present disclosure.
Figure 15B:
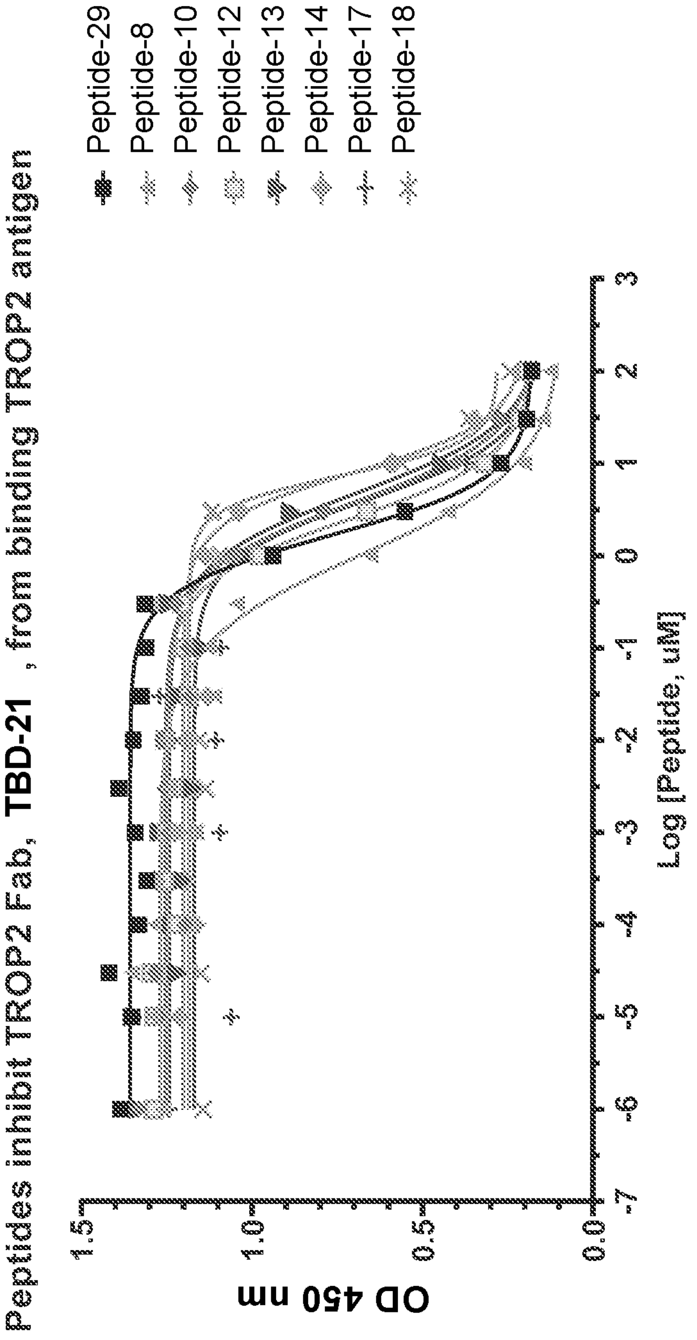
Figure 15C:
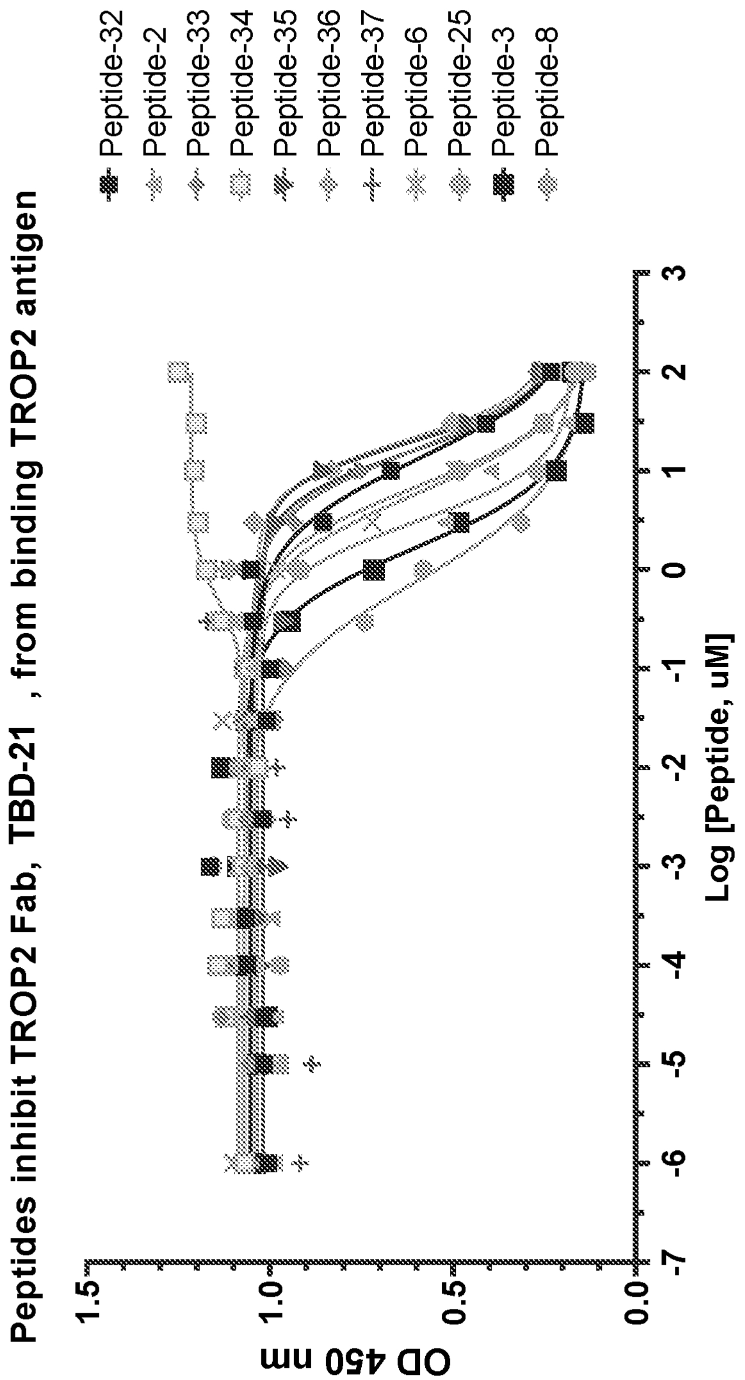
Figure 15D:
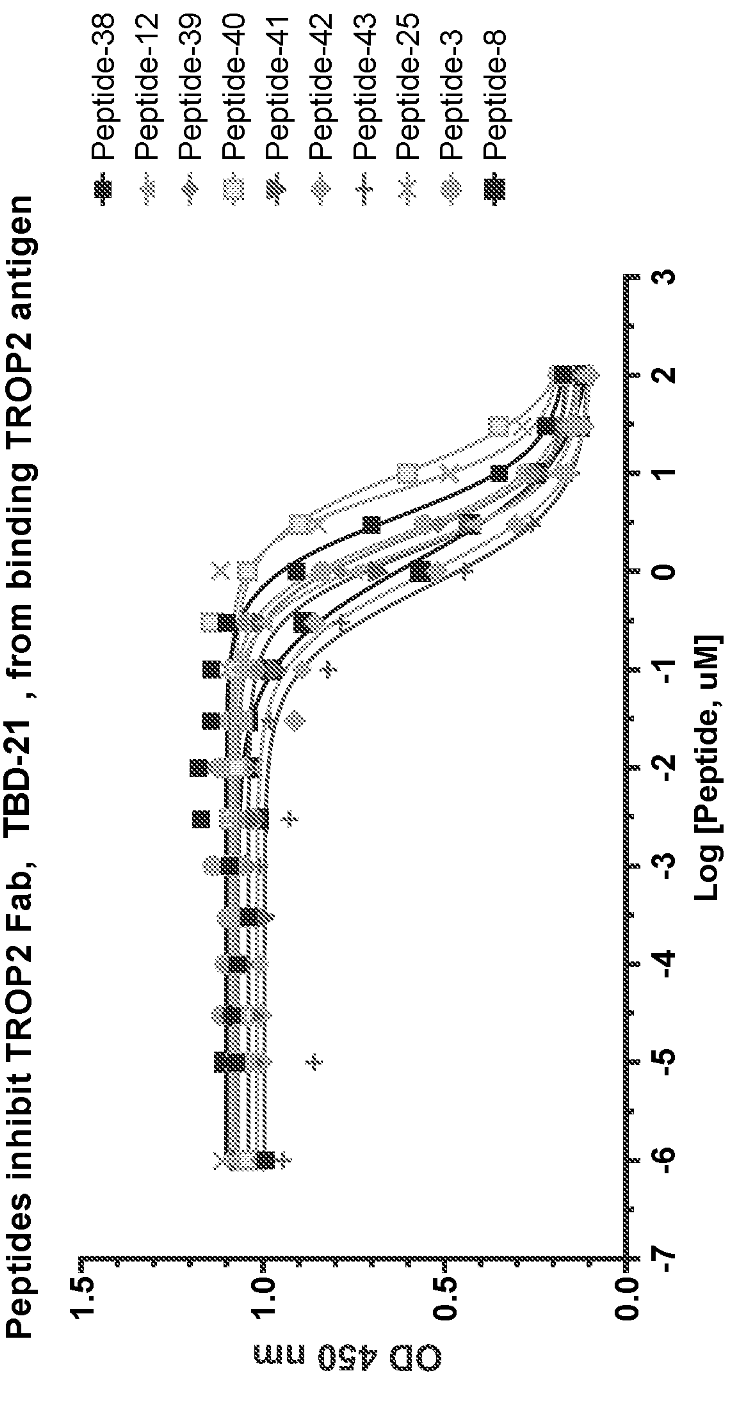
Figure 15E:
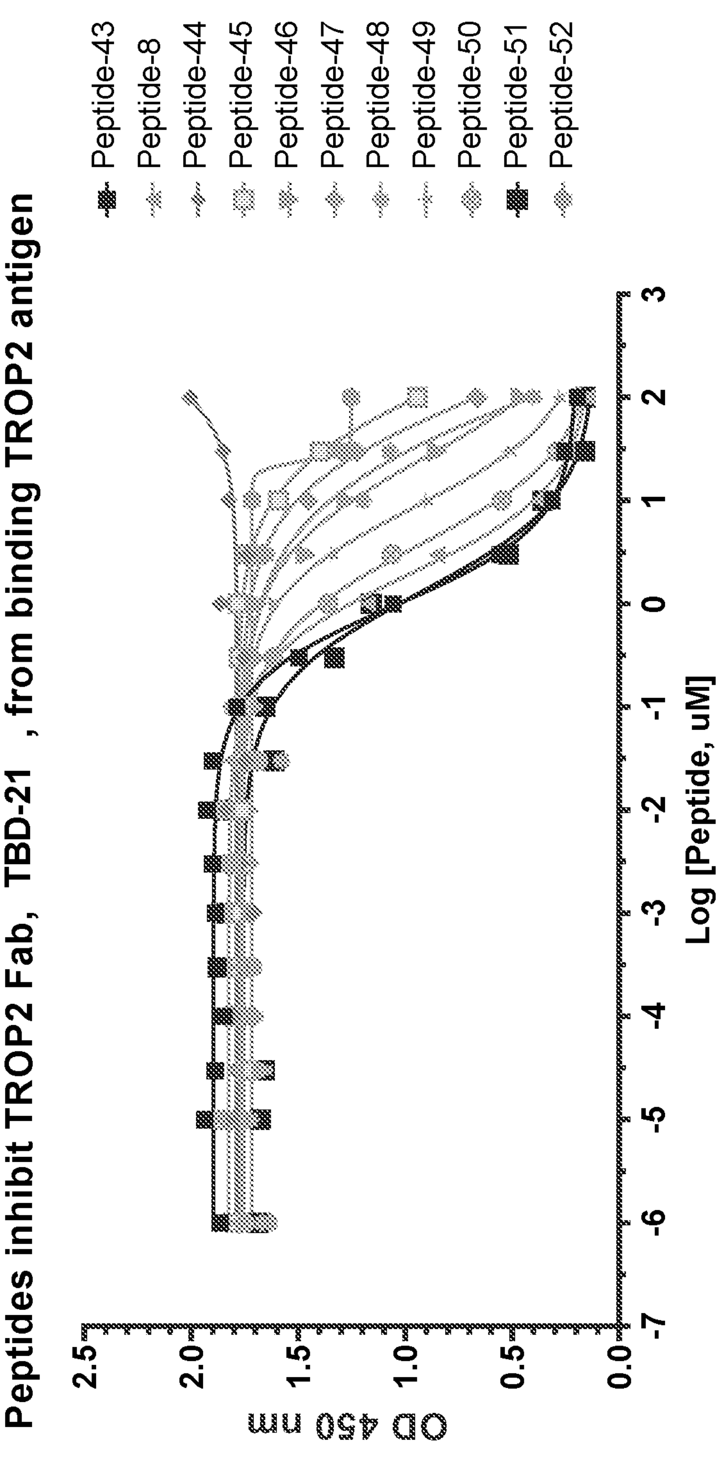
Figure 15F:
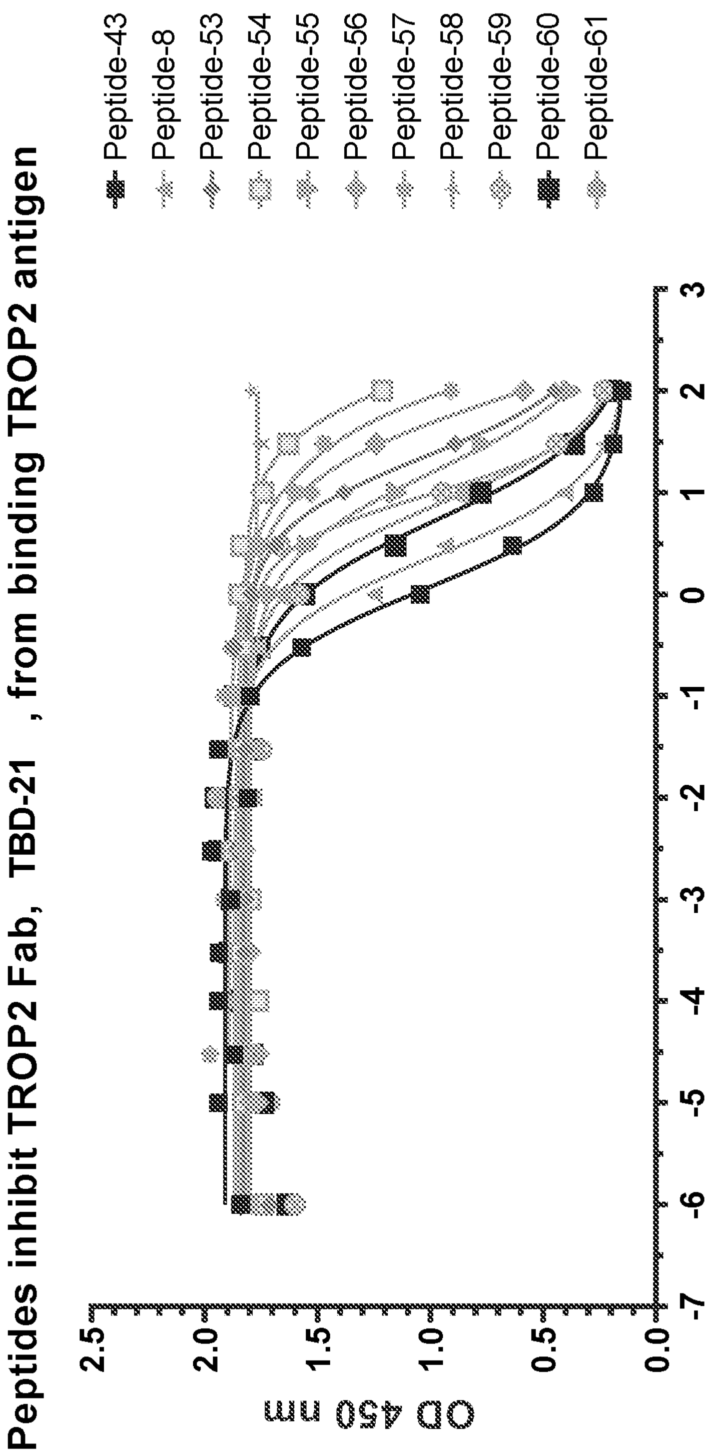
Figure 16A:
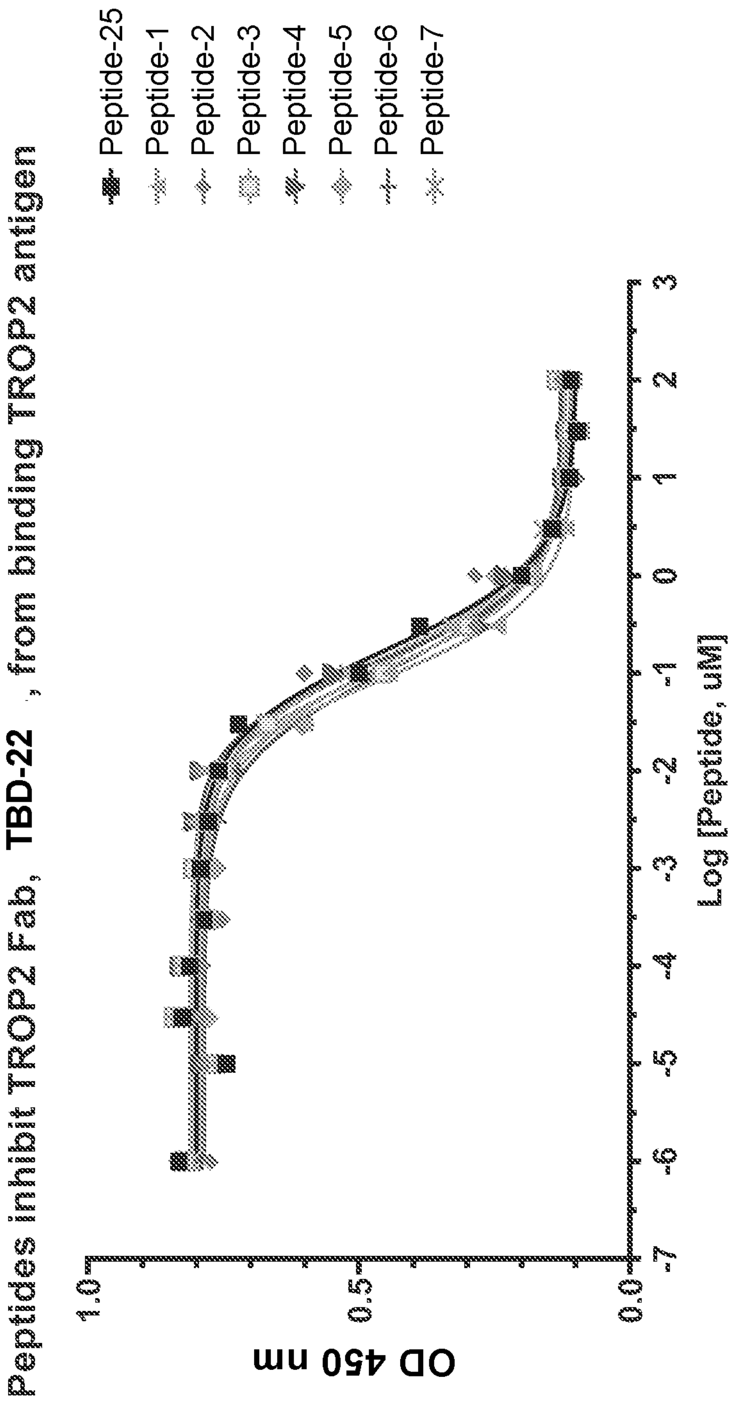
FIGS. 16A-16F illustrate inhibition of TBD-22 binding to TROP2 by peptides of the present disclosure.
Figure 16B:
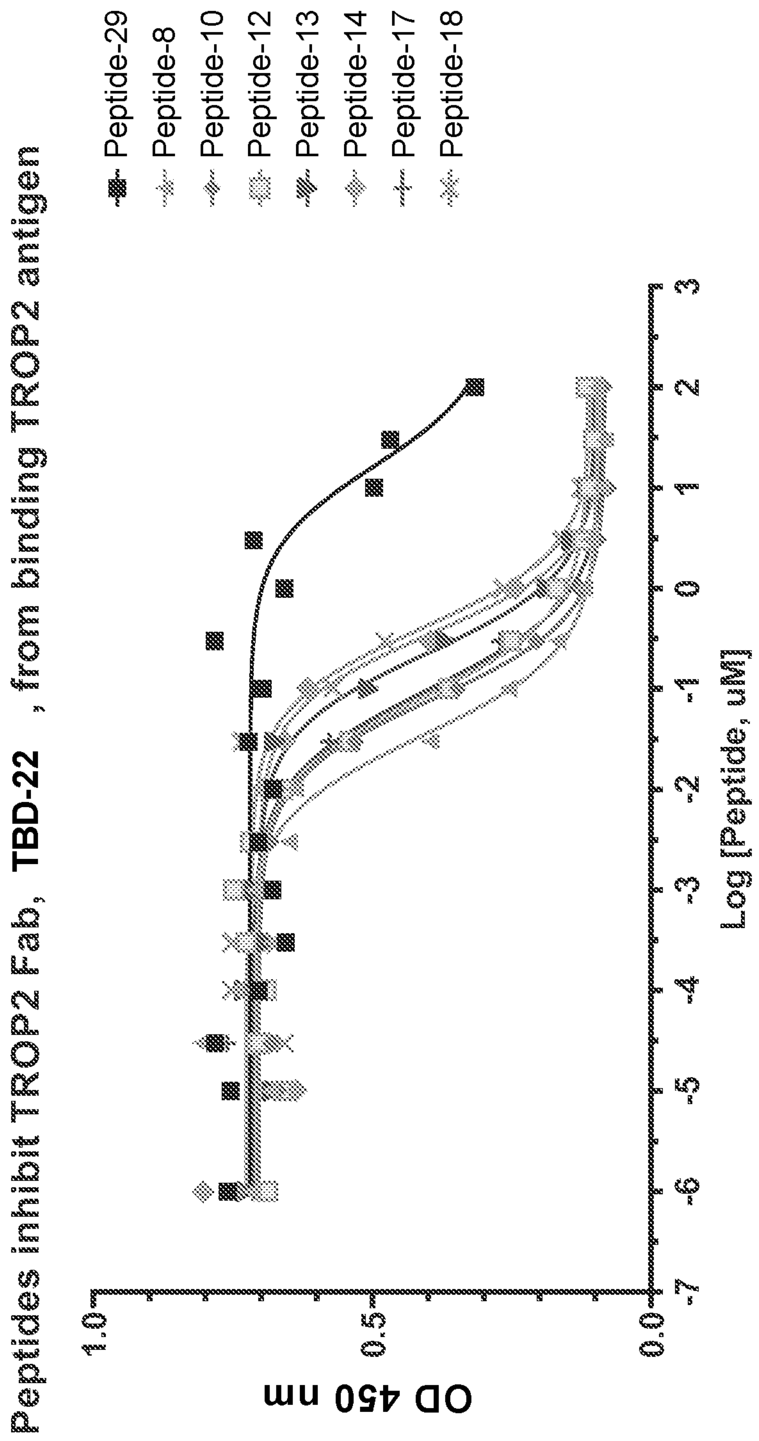
Figure 16C:
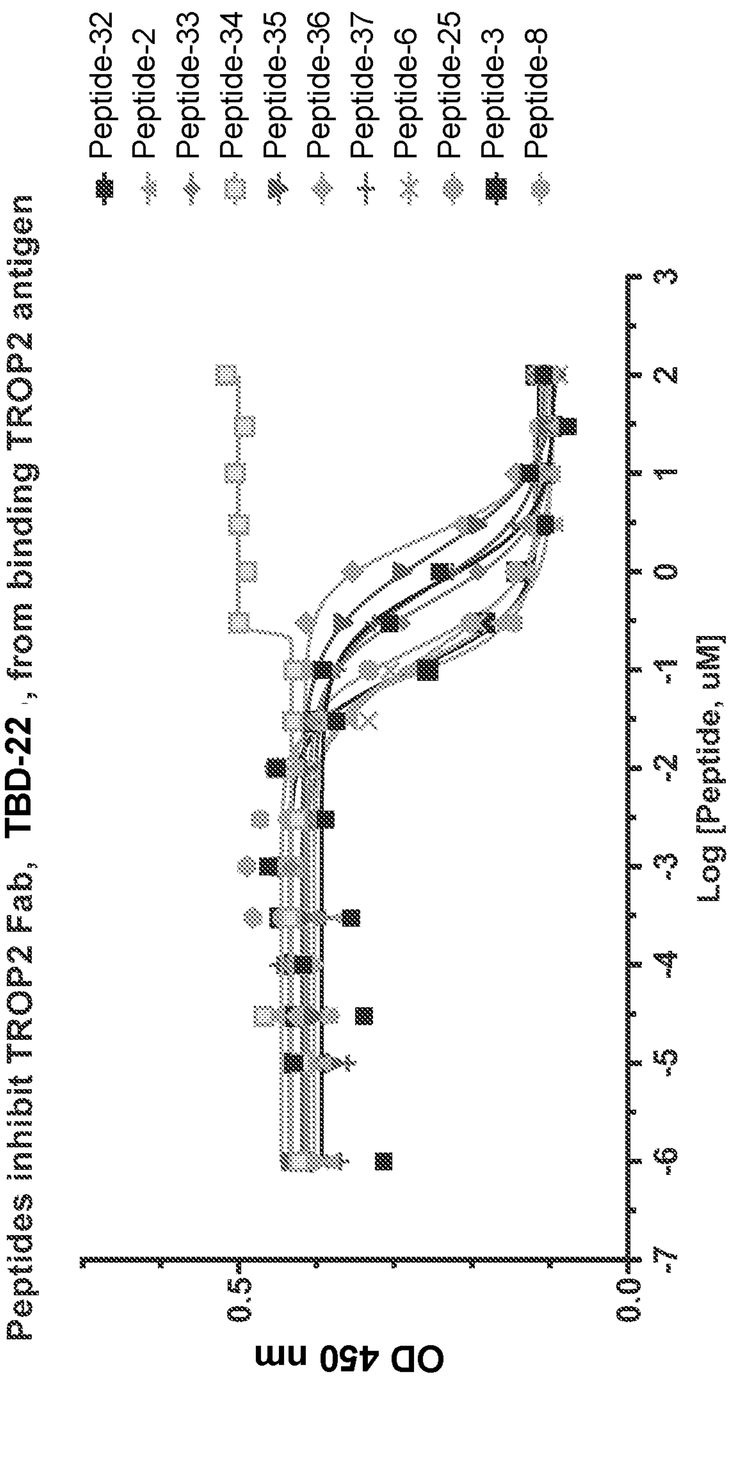
Figure 16D:
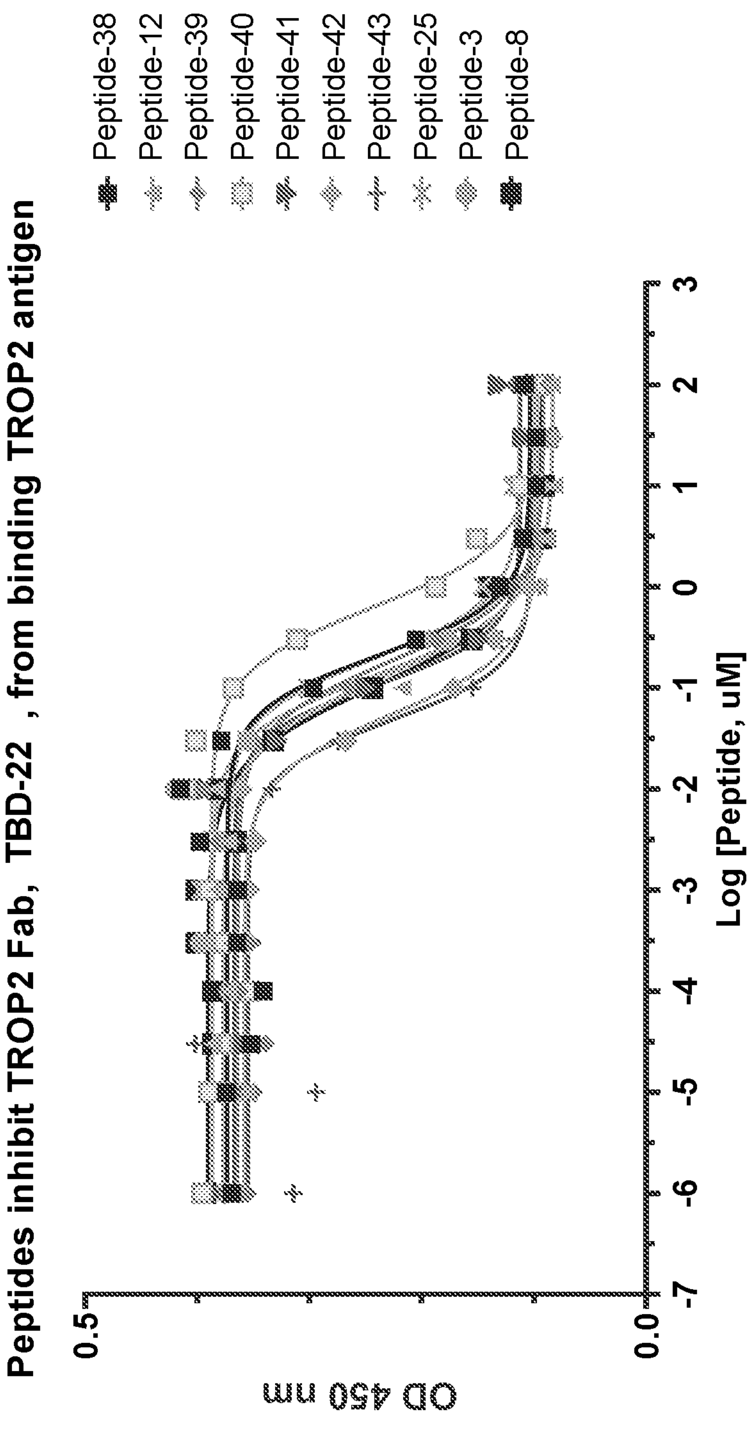
Figure 16E:
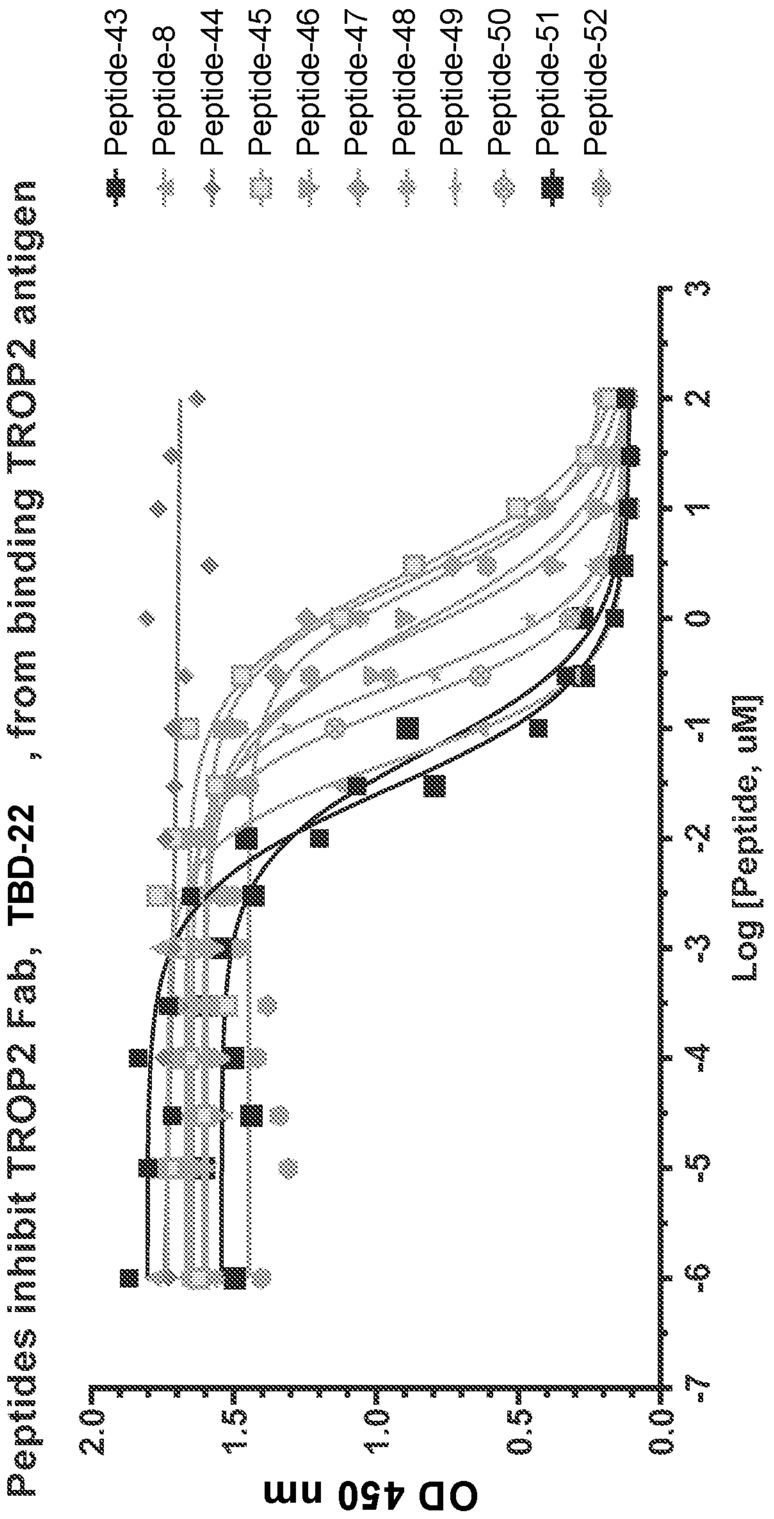
Figure 16F:
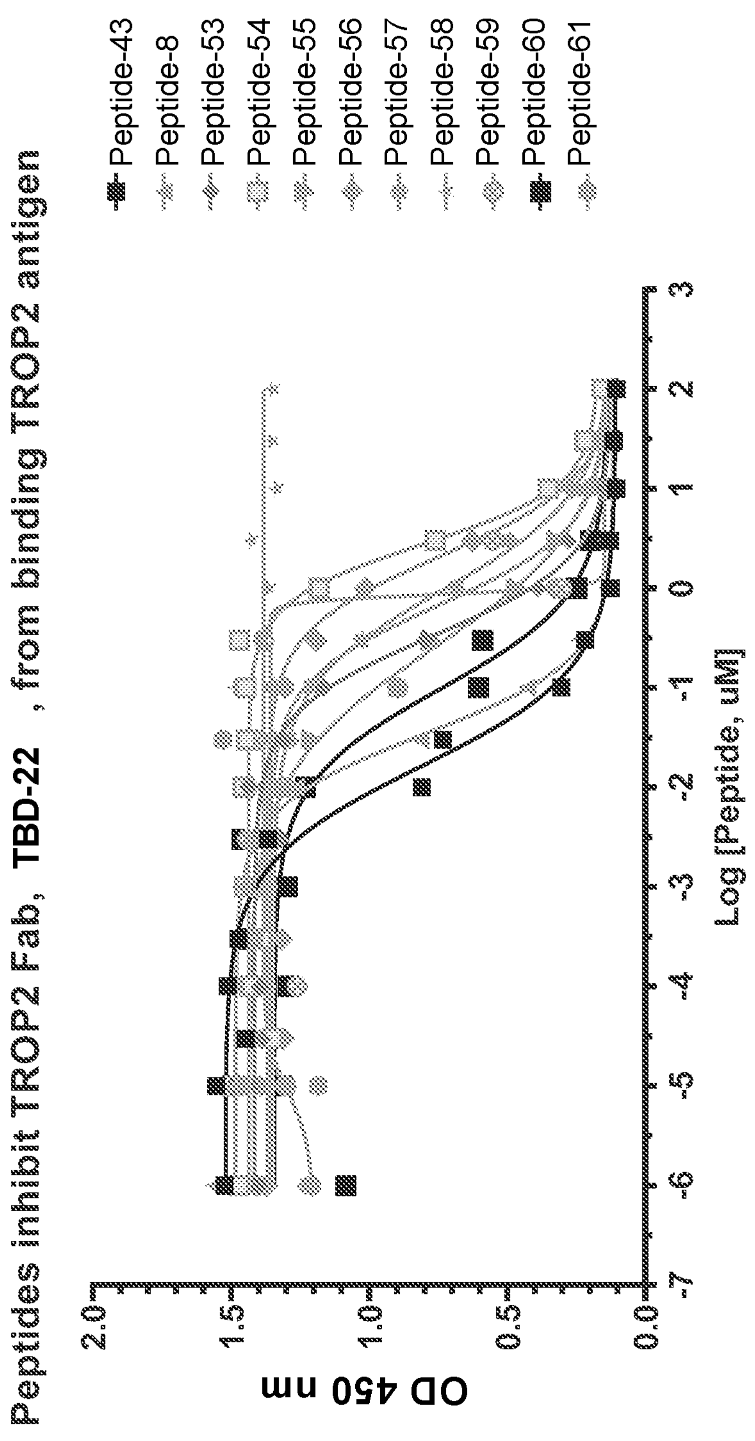
Figure 17A:
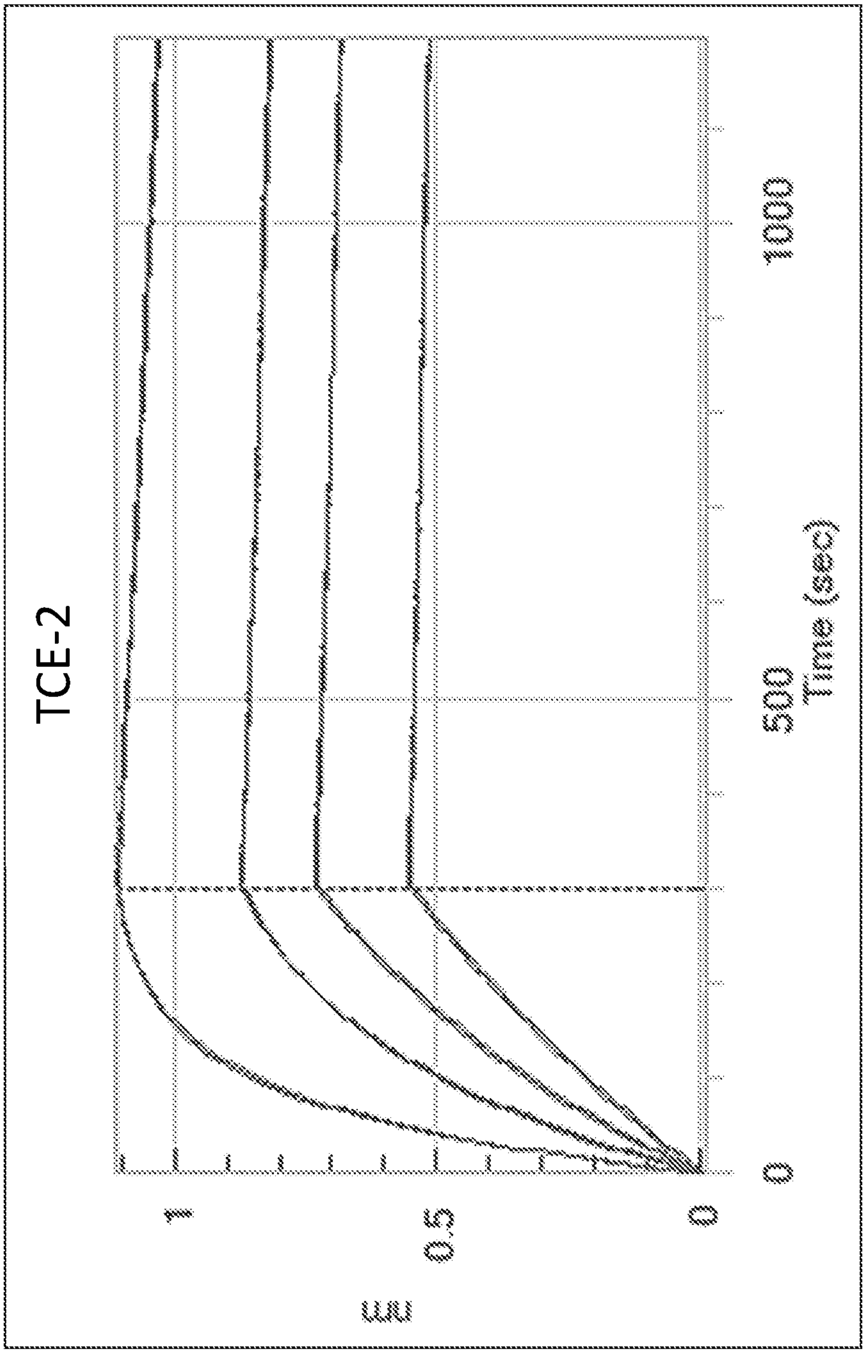
FIGS. 17A-17D illustrate BLI titration data for TROP2 binding by non-mutated and mutated T-cell engagers (TCEs).
Figure 17B:
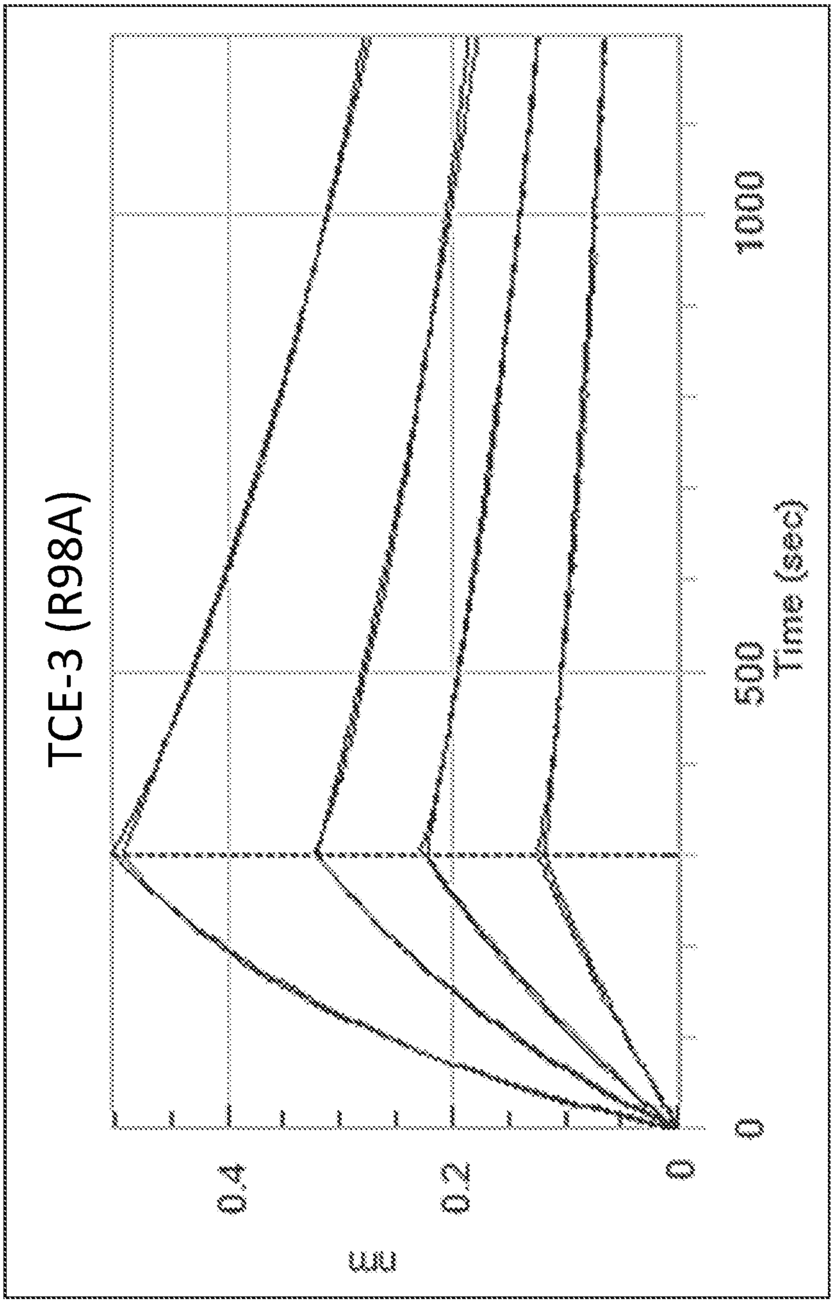
Figure 17C:
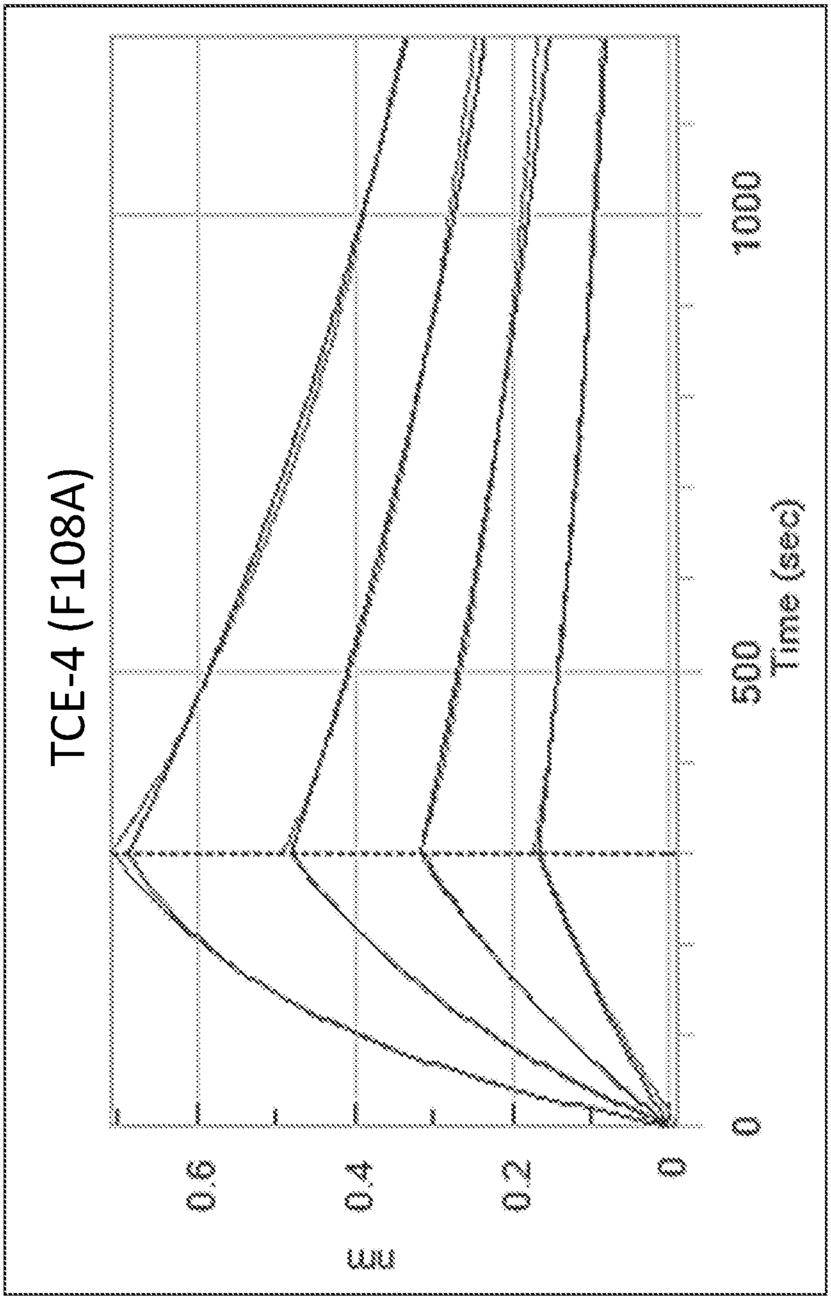
Figure 17D:
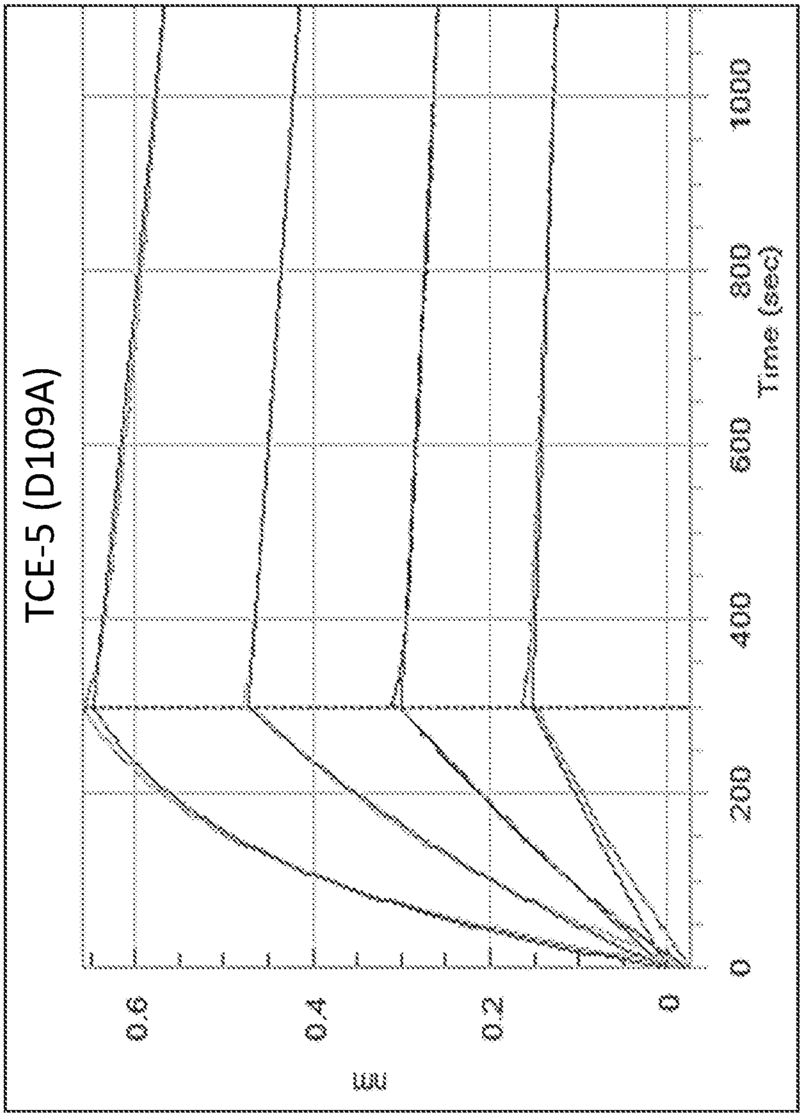
Figure 18A:
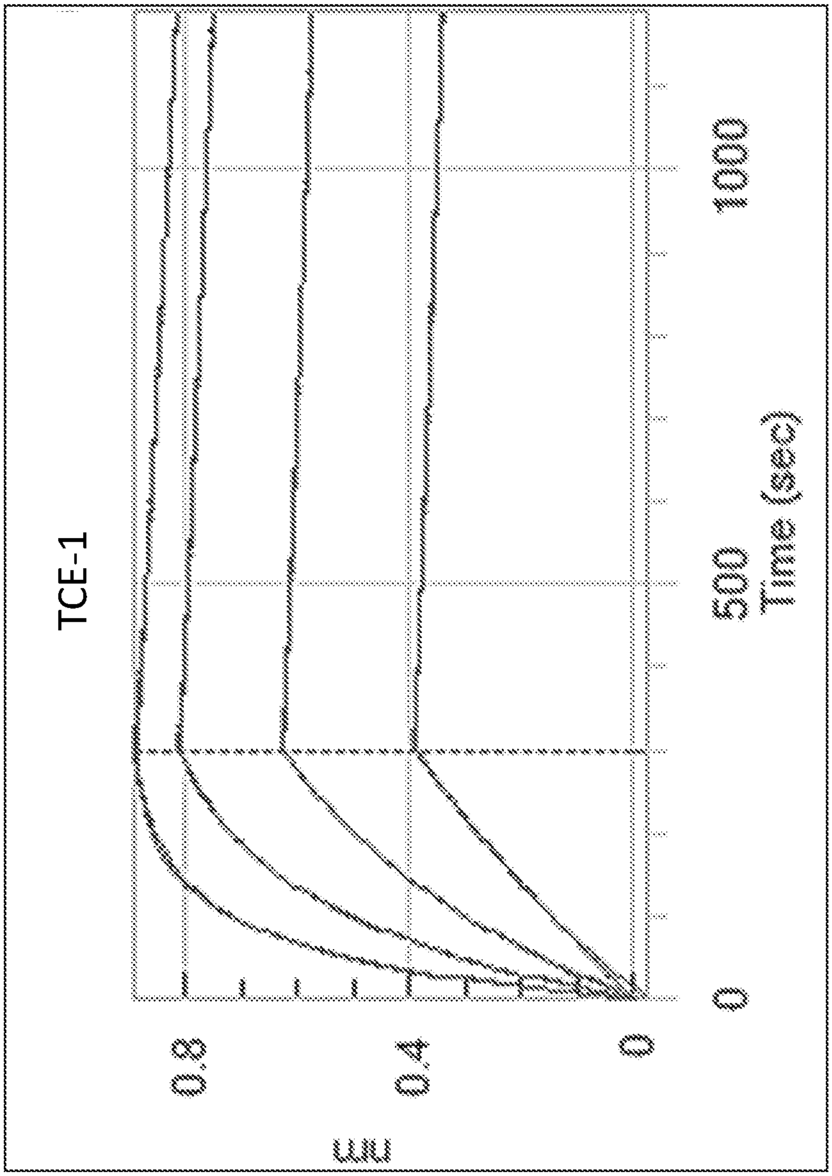
FIGS. 18A-18D illustrate BLI titration data for TROP2 binding by non-mutated and mutated TCEs.
Figure 18B:
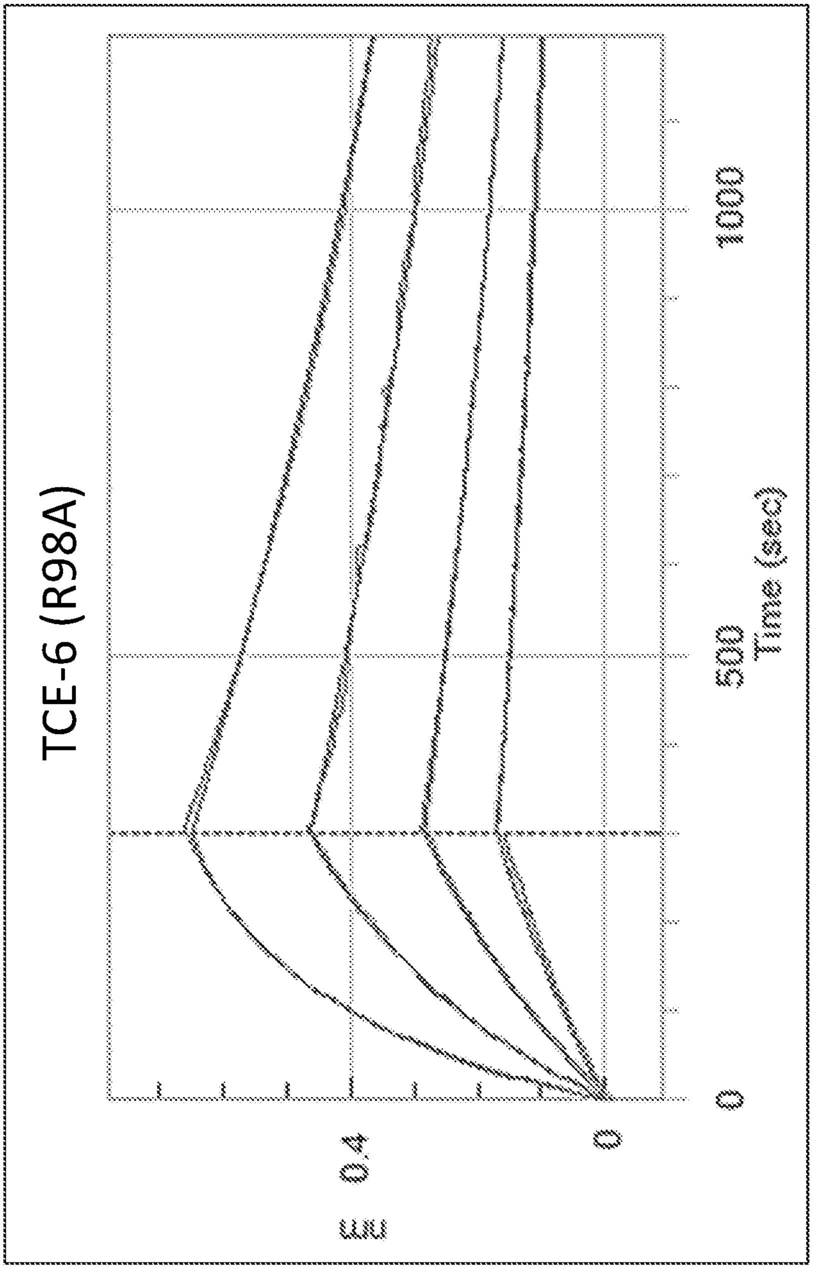
Figure 18C:
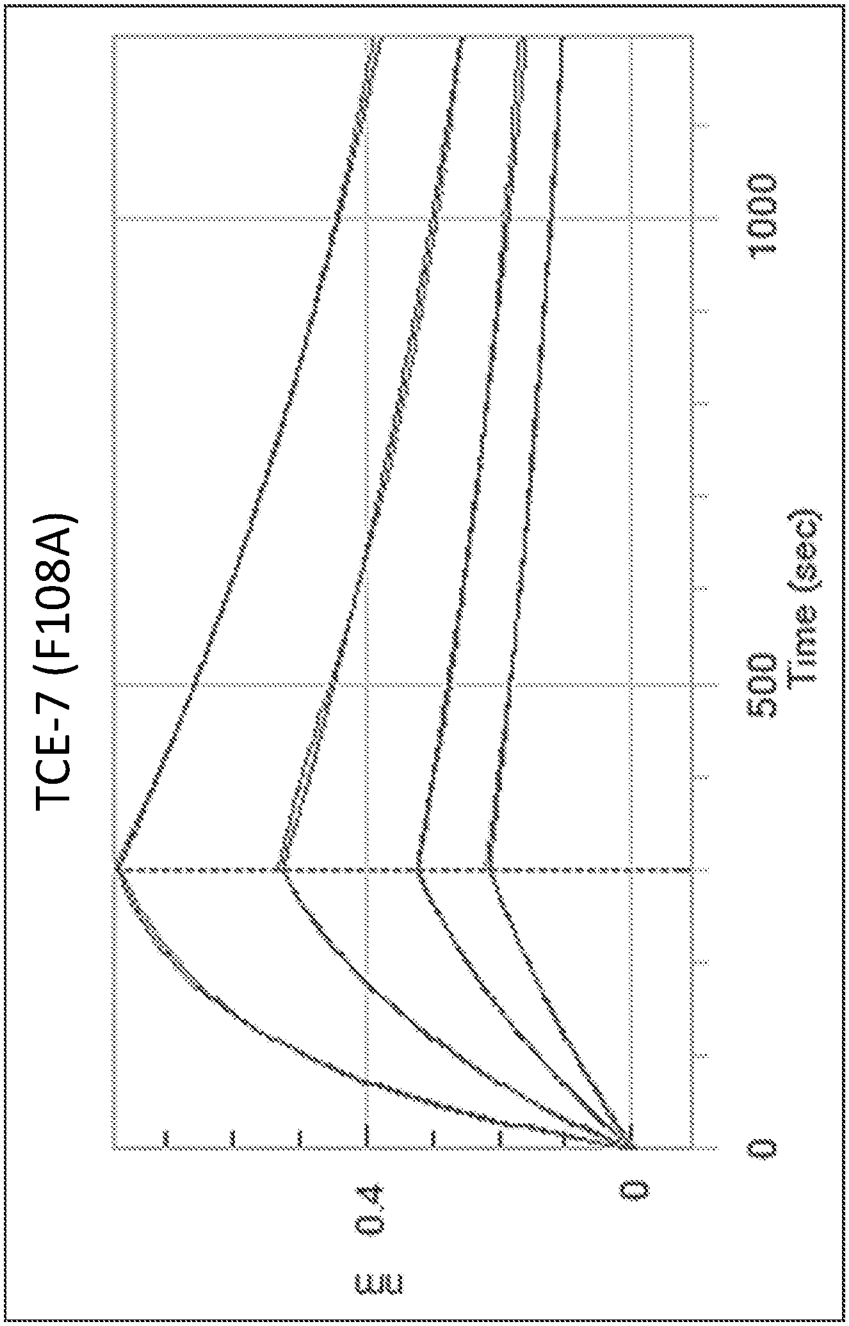
Figure 18D:
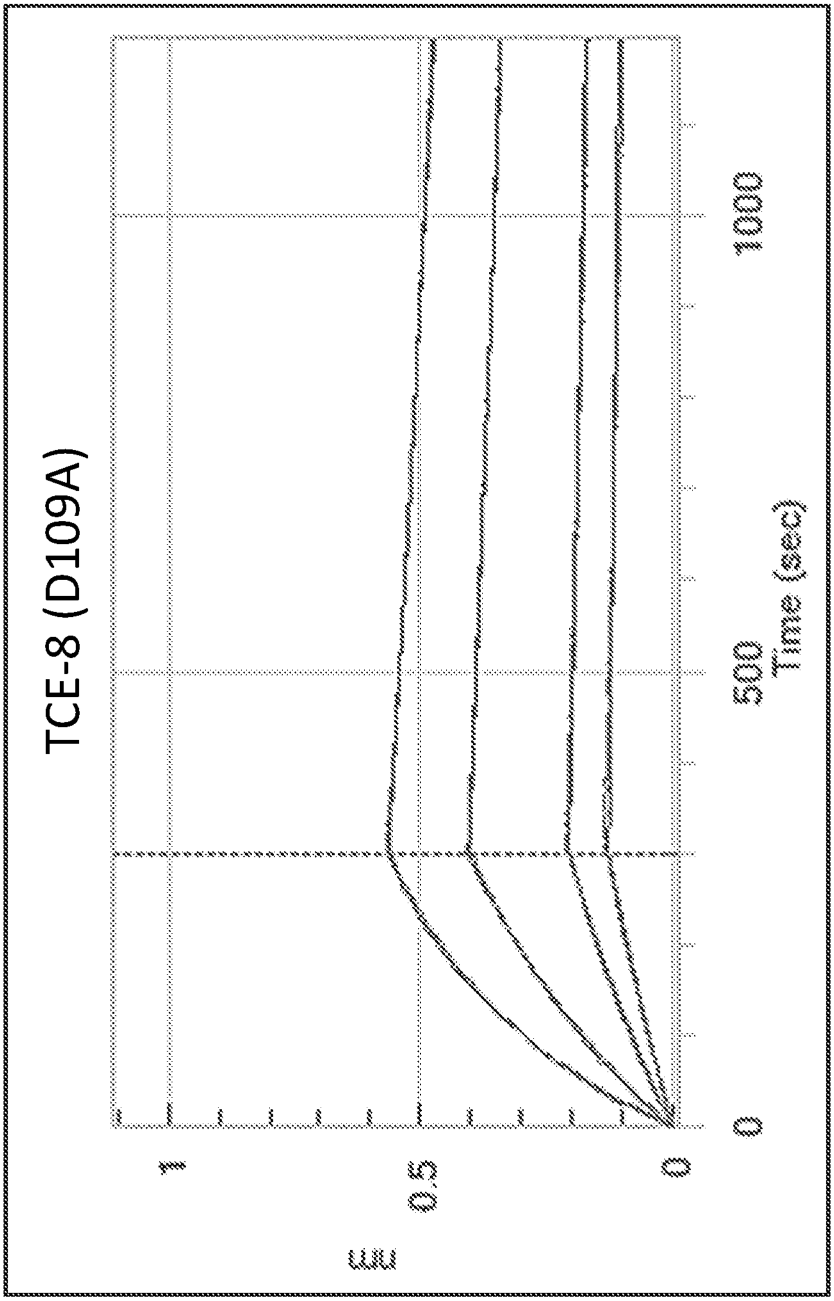
Figure 19A:
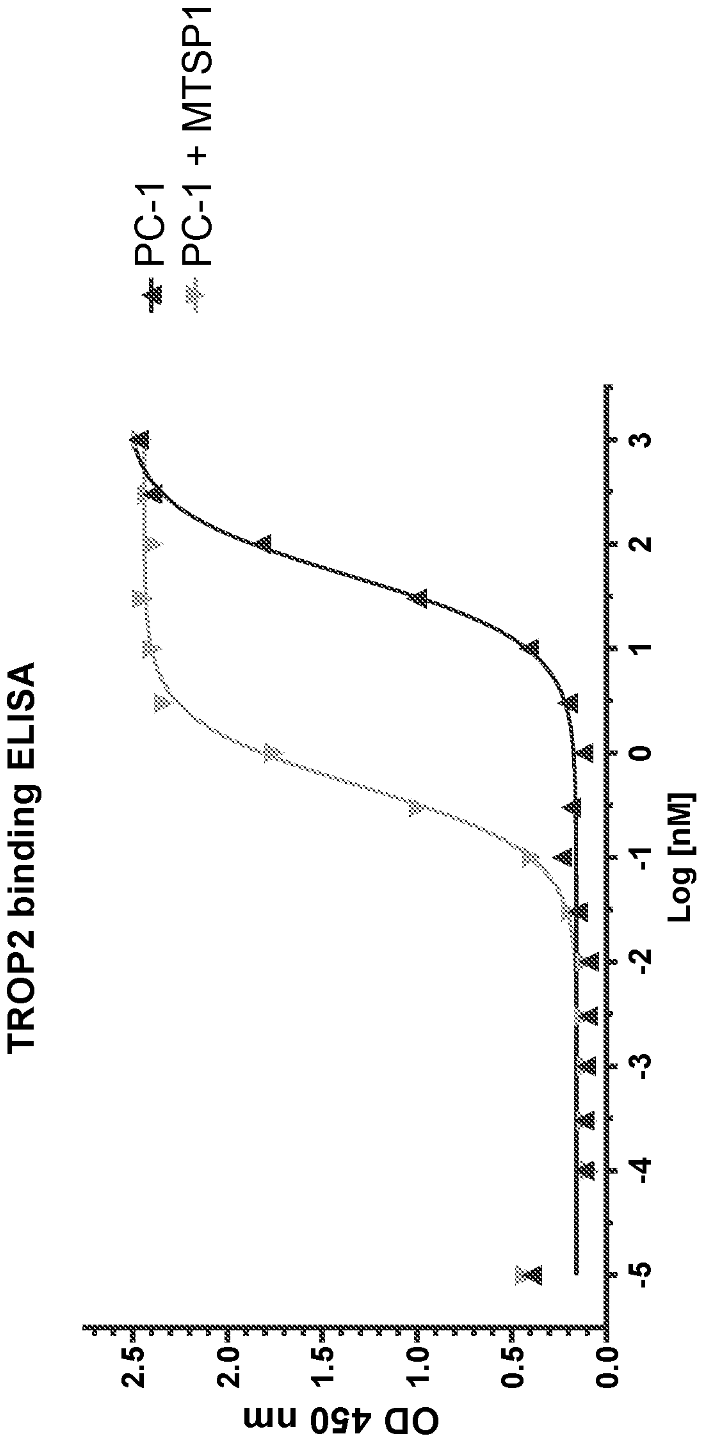
FIGS. 19A-19B show binding curves and $EC_{50}$s for binding of TROP2 (FIG. 19A) and CDRε (FIG. 19B) by polypeptide complex PC-1 as measured by ELISA.
Figure 19B:
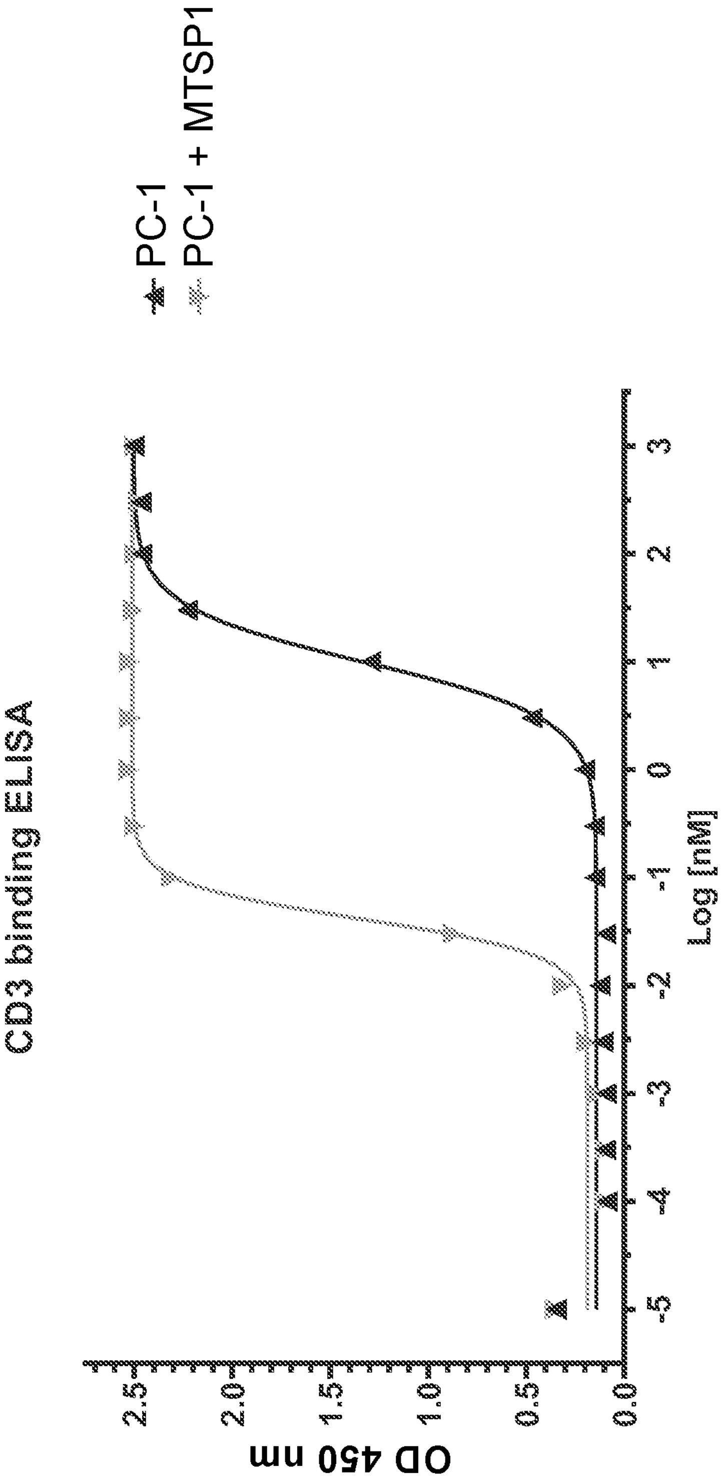
Figure 20A:
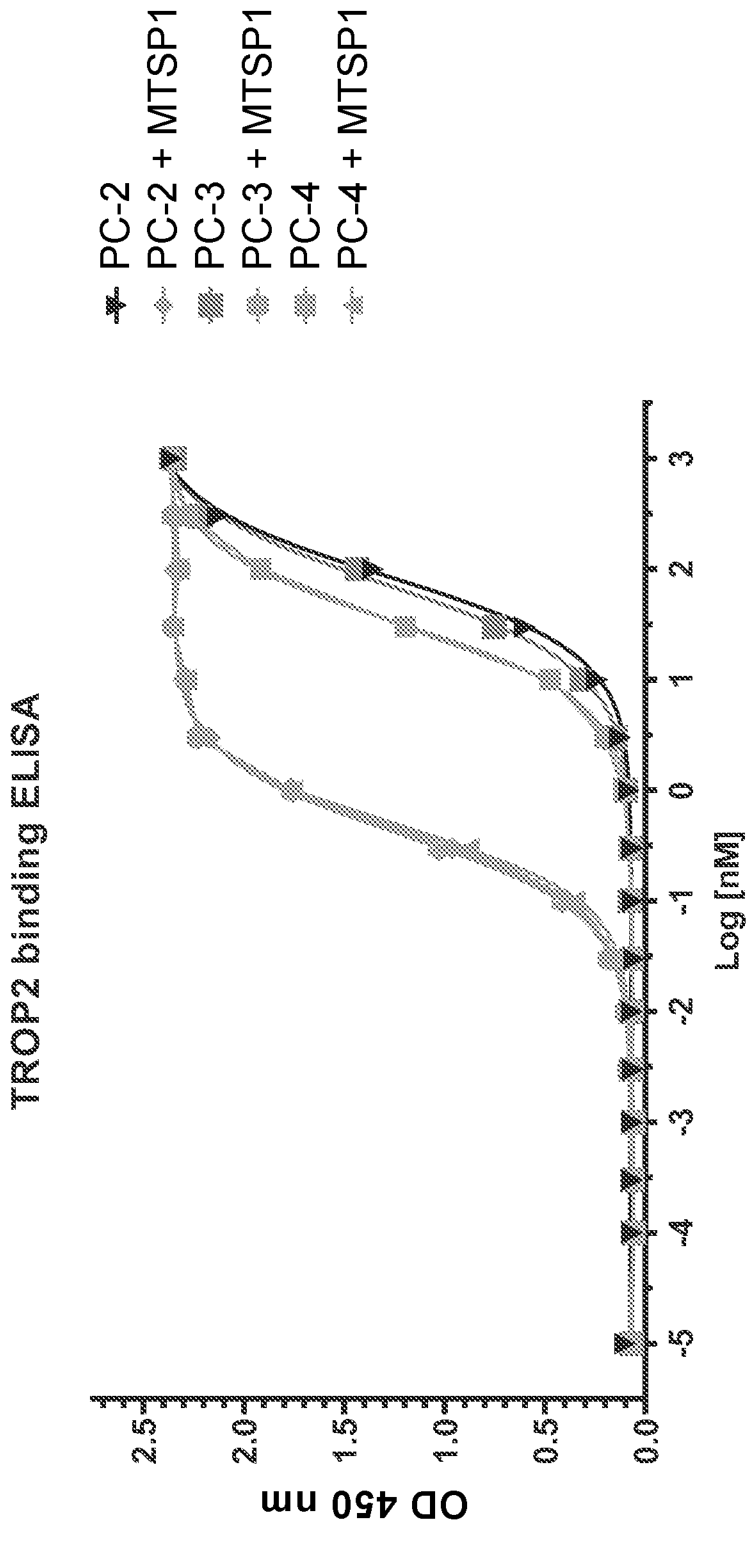
FIGS. 20A-20B show binding curves and $EC_{50}$s for binding of TROP2 (FIG. 20A) and CD3e (FIG. 20B) by polypeptide complexes as measured by ELISA.
Figure 20B:
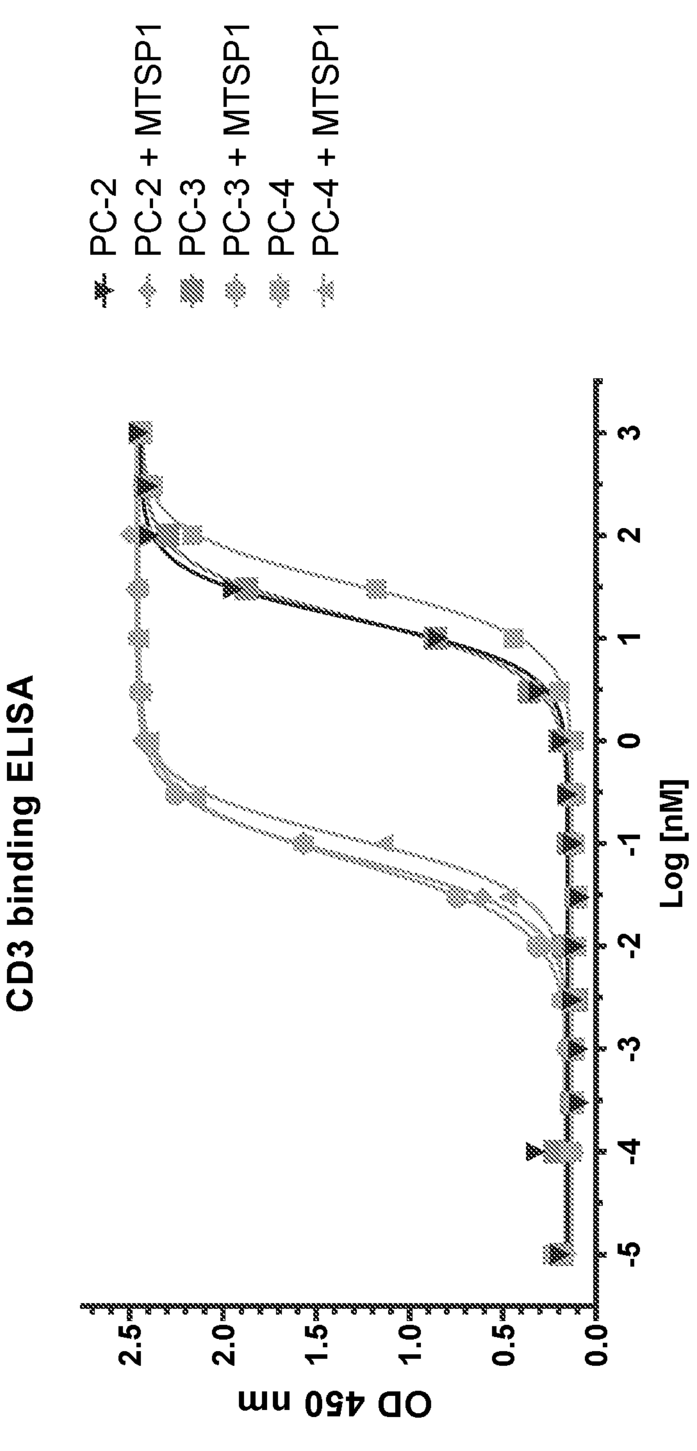
Figure 21A:
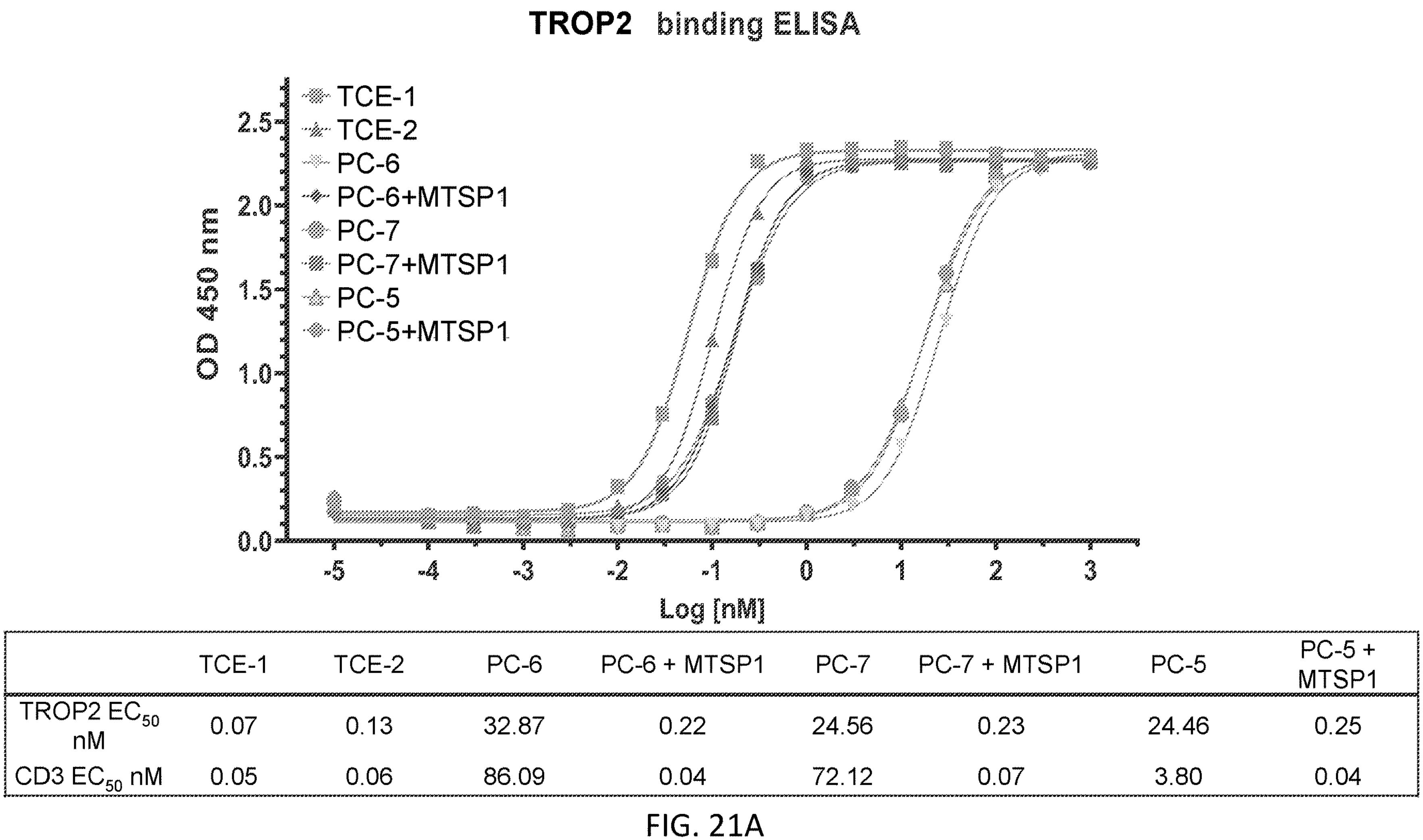
FIGS. 21A-21B show binding curves and $EC_{50}$s for binding of TROP2 (FIG. 21A) and CDRε (FIG. 21B) by TCEs and polypeptide complexes ad measured by ELISA.
Figure 21B:
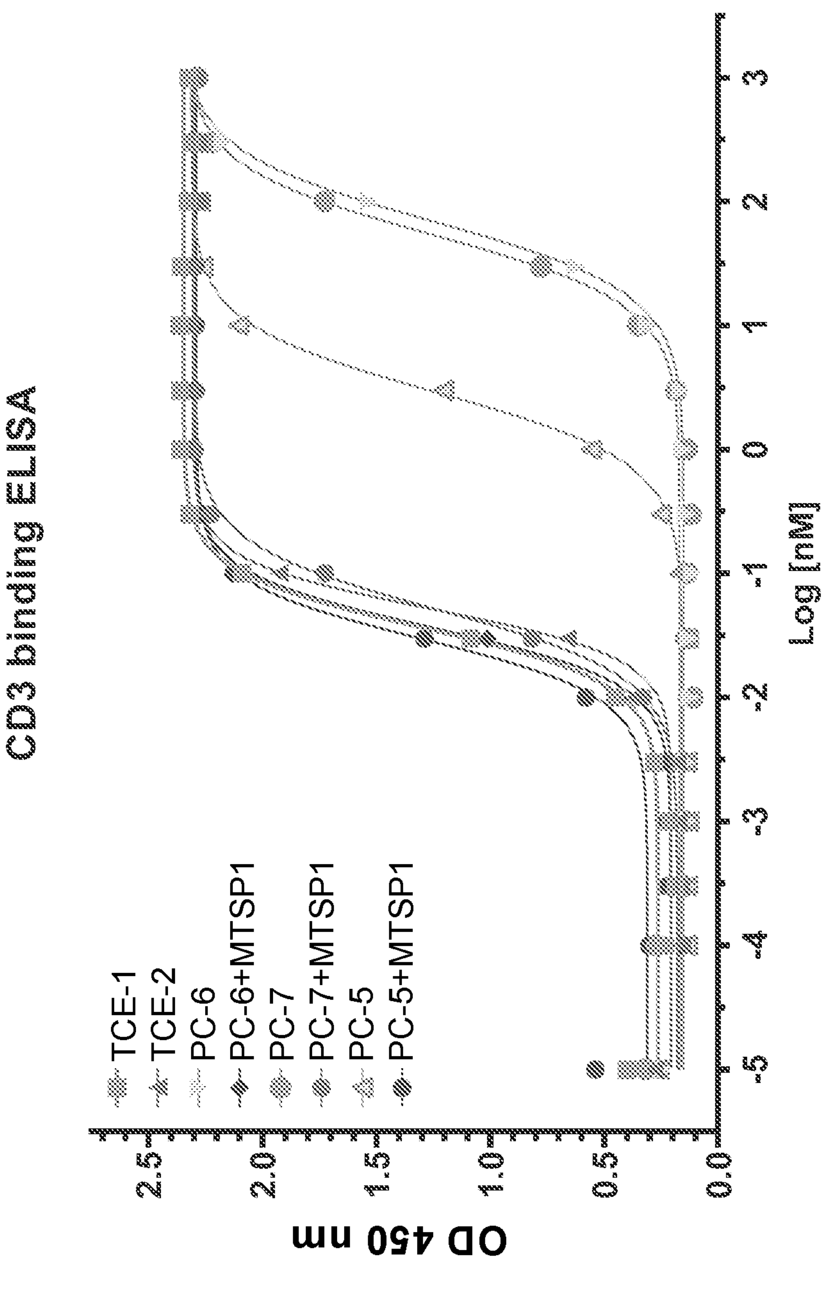
Figure 22A:
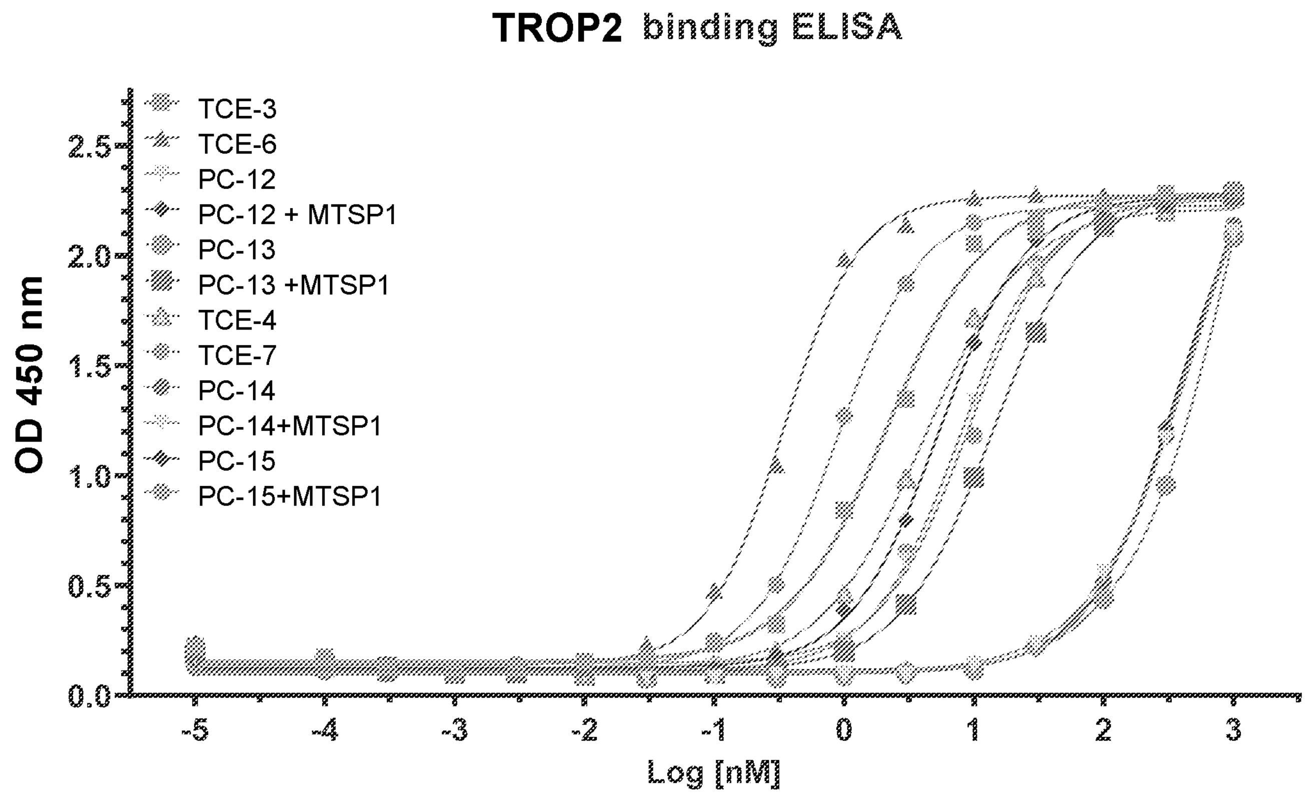
FIGS. 22A-22B show binding curves and $EC_{50}$s for binding of TROP2 (FIG. 22A) and CDRε (FIG. 22B) by TCEs and polypeptide complexes as measured by ELISA.
Figure 22B:
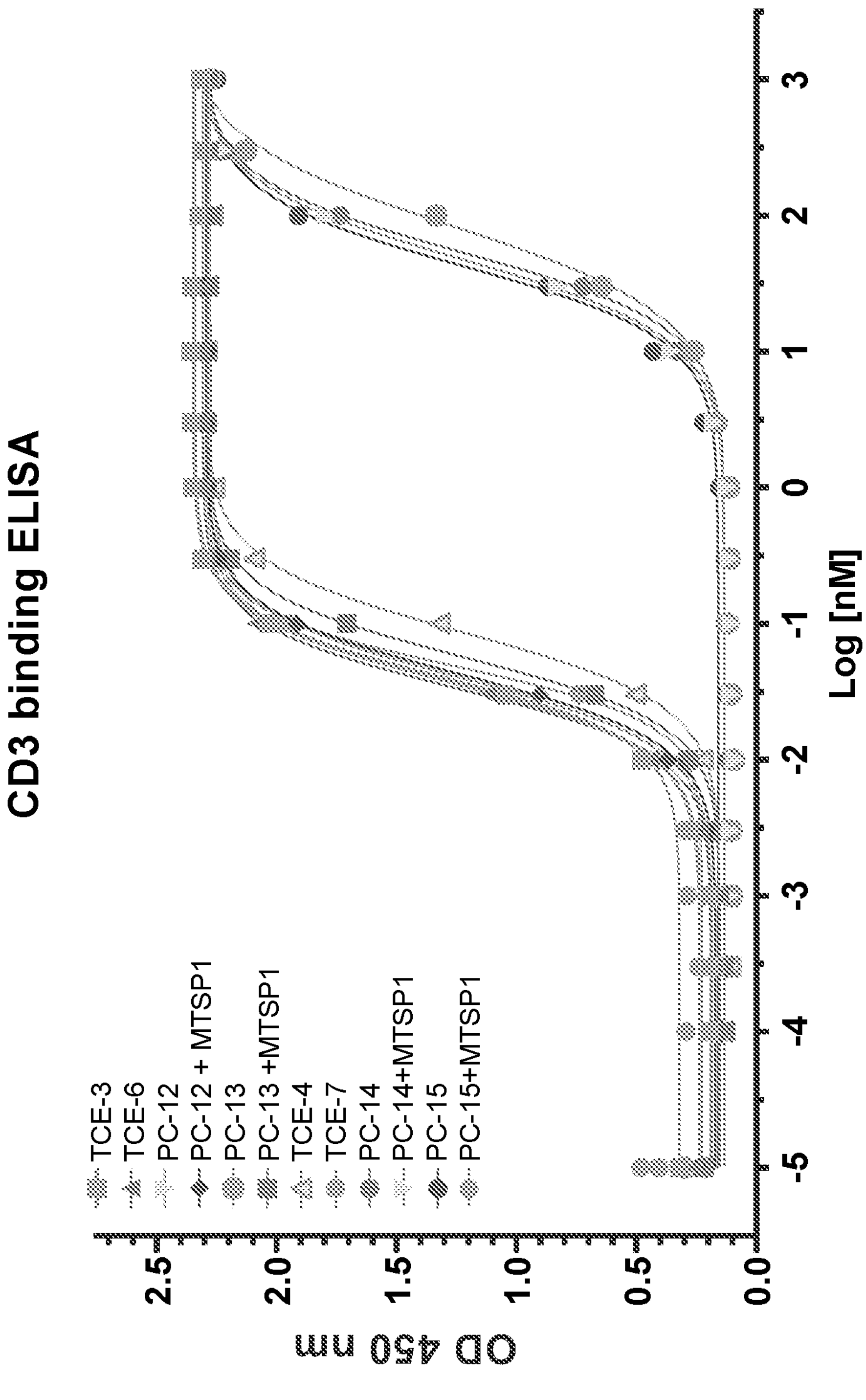
Figure 23A:
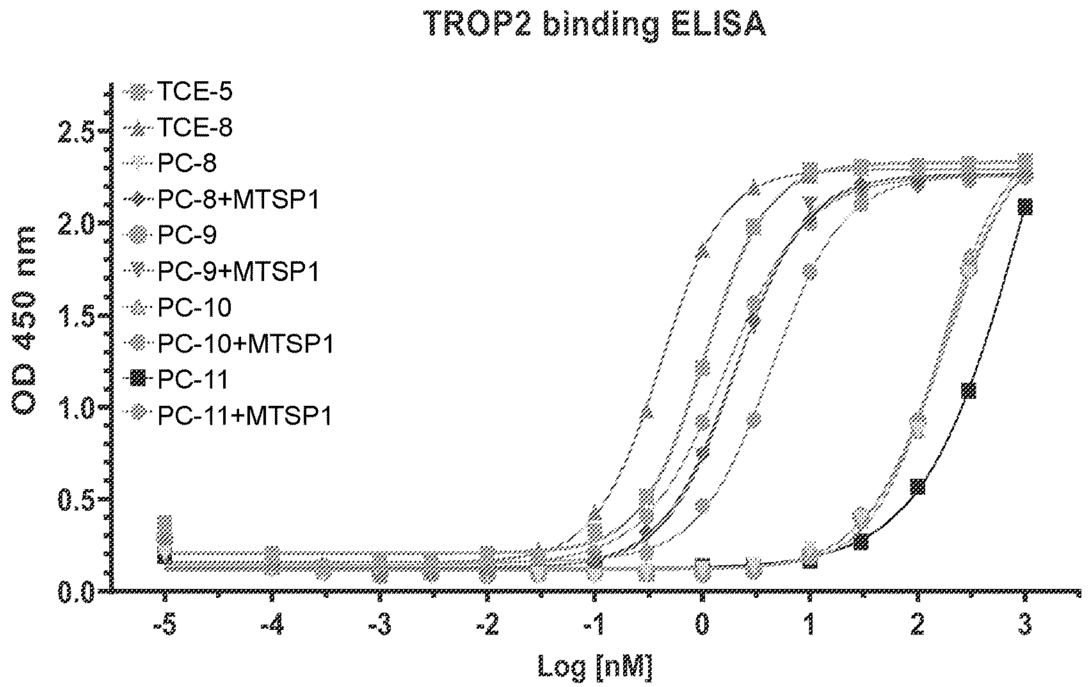
FIGS. 23A-23B show binding curves and $EC_{50}$s for binding of TROP2 (FIG. 23A) and CDRε (FIG. 23B) by TCEs and polypeptide complexes as measured by ELISA.
Figure 23B:
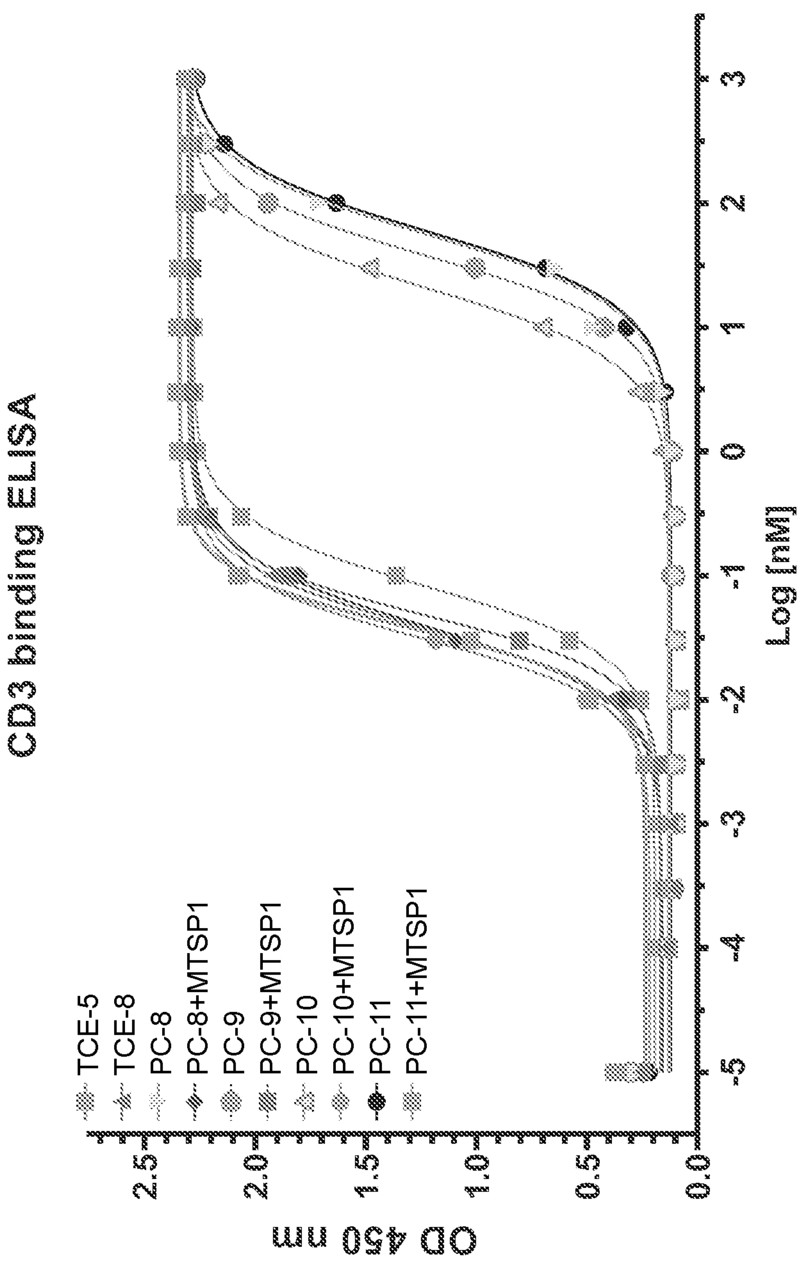
Figure 24A:
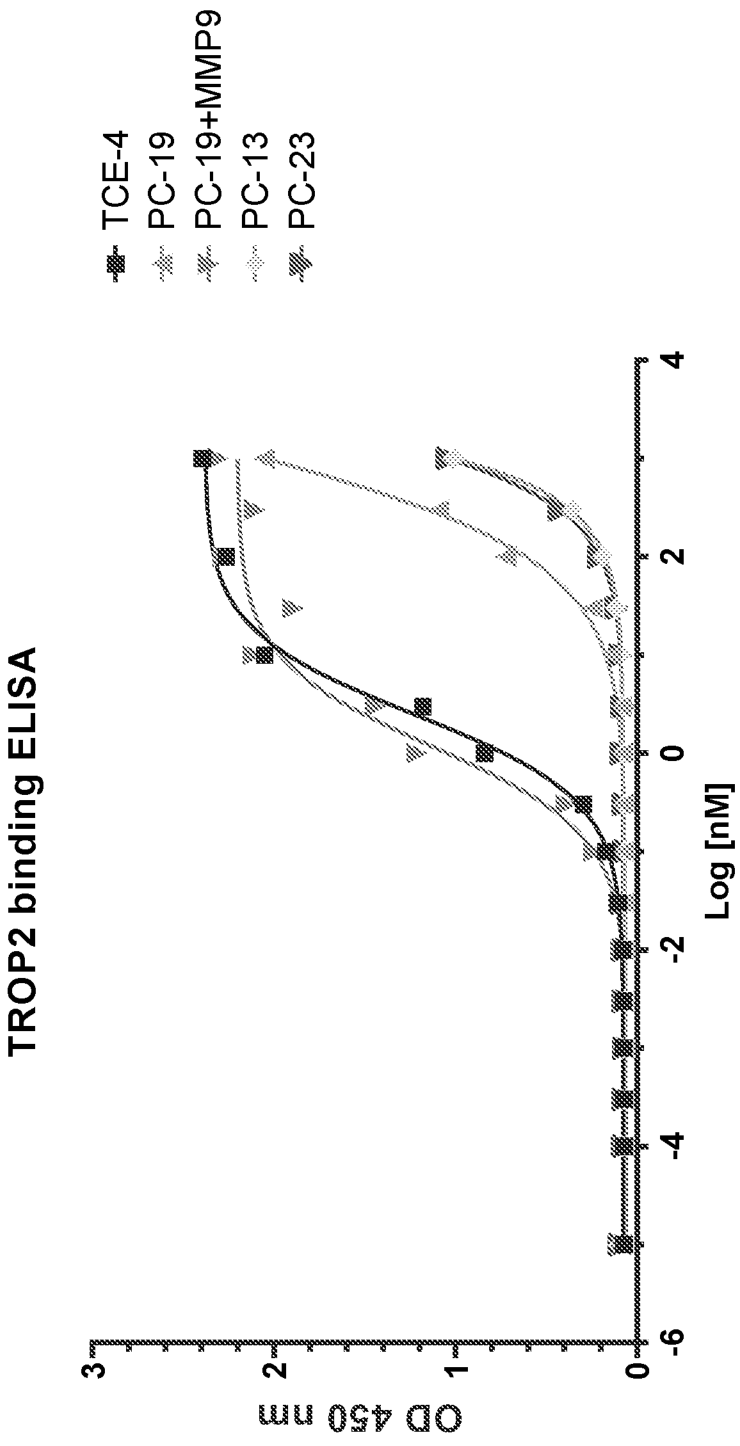
FIGS. 24A-24B show binding curves and $EC_{50}$s for binding of TROP2 (FIG. 24A) and CDRε (FIG. 24B) by TCEs and polypeptide complexes as measured by ELISA.
Figure 24B:
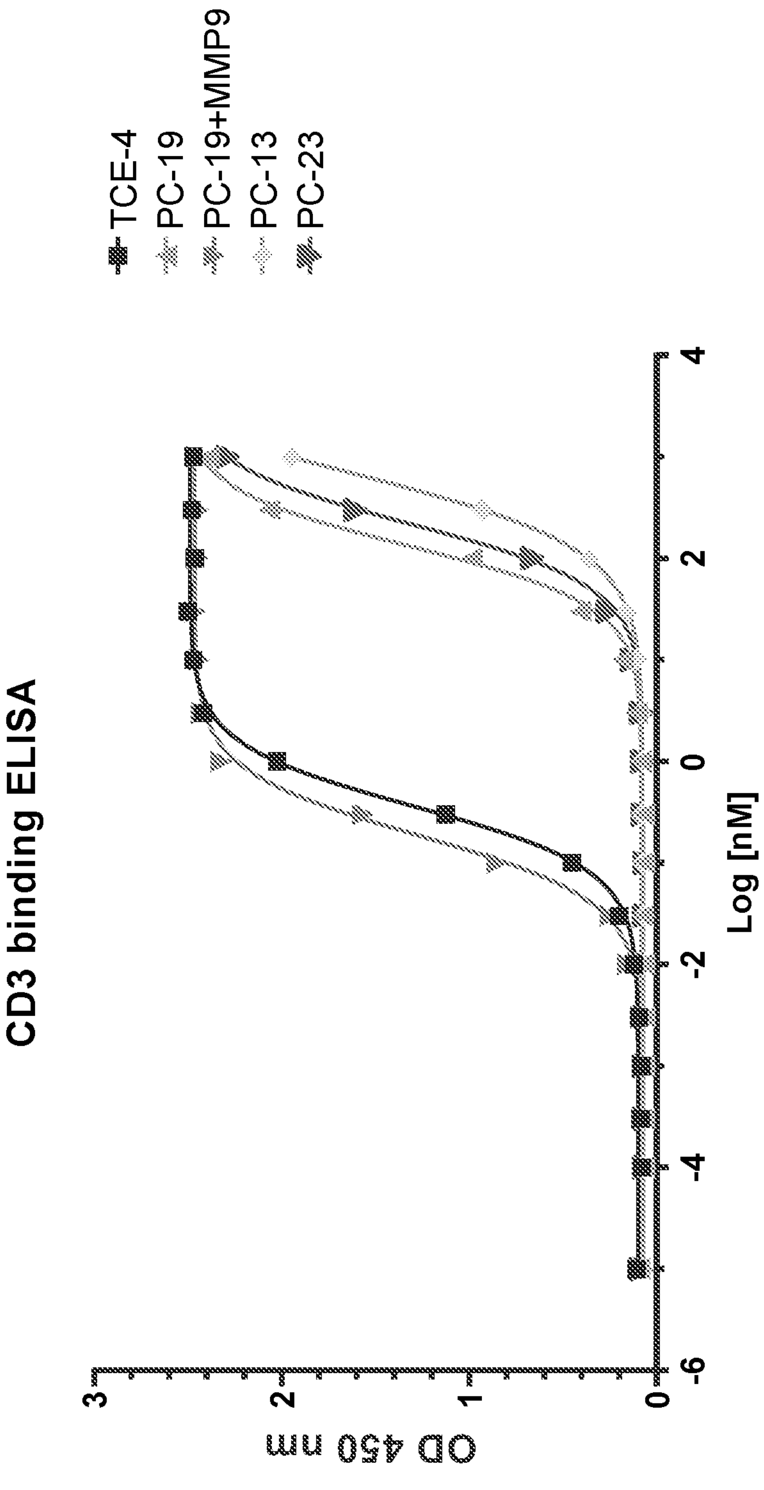
Figure 25A:
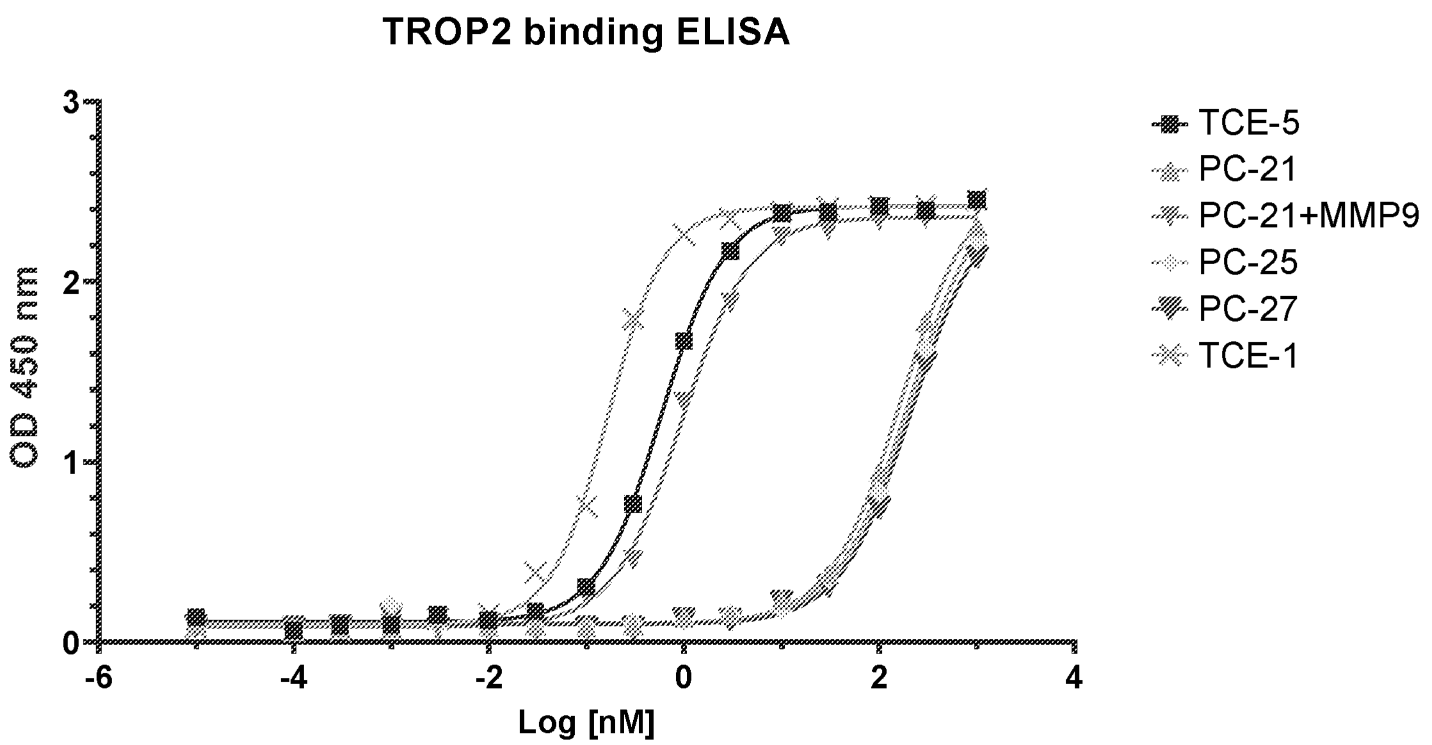
FIGS. 25A-25B show binding curves and $EC_{50}$s for binding of TROP2 (FIG. 25A) and CDRε (FIG. 25B) by TCEs and polypeptide complexes as measured by ELISA.
Figure 25B:
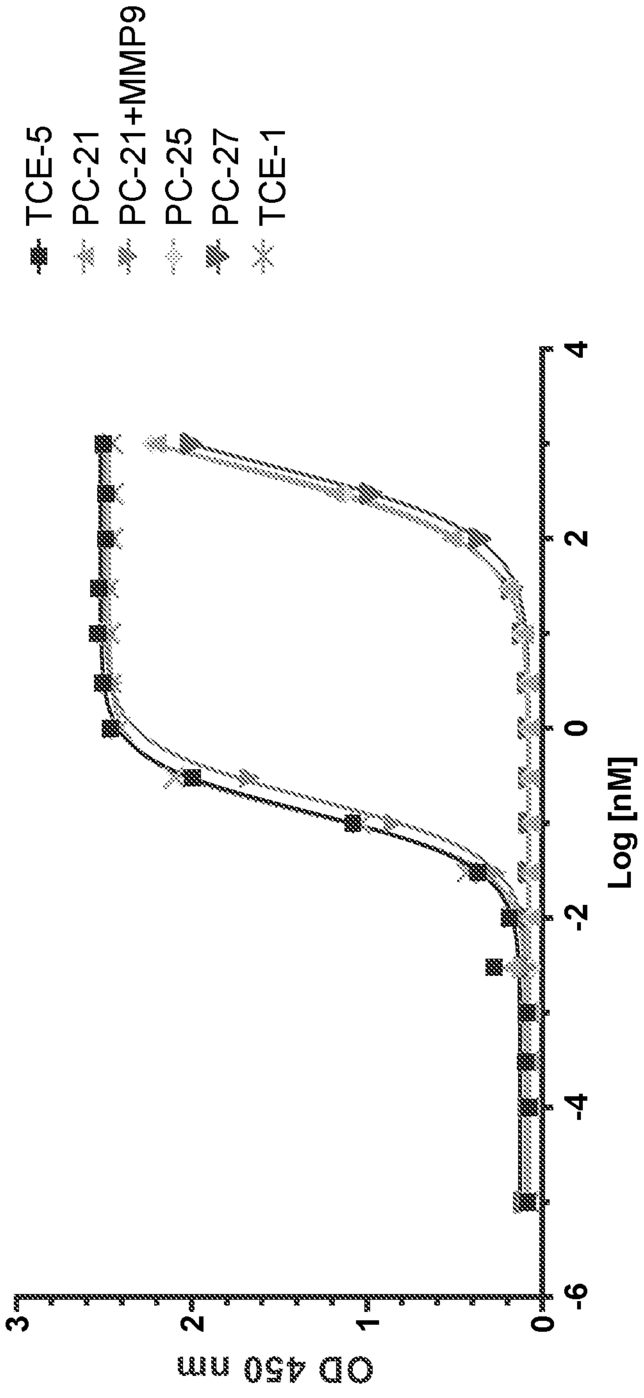
Figure 26A:
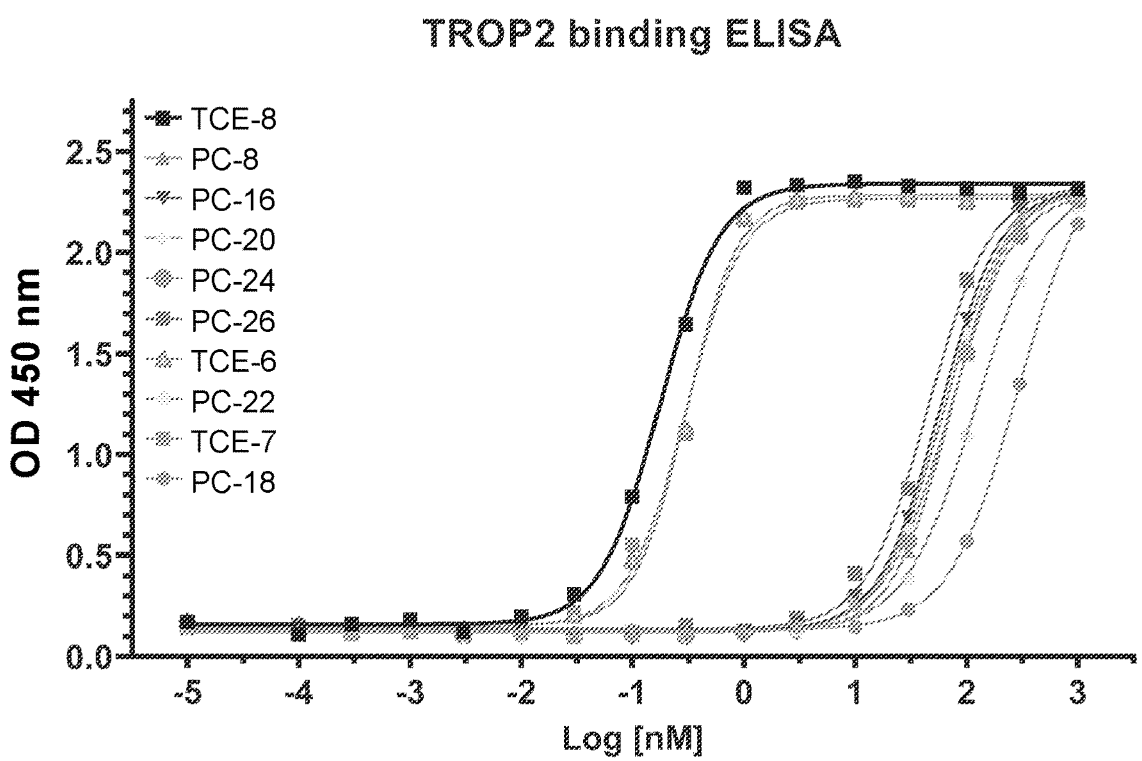
FIGS. 26A-26B show binding curves and $EC_{50}$s for binding of TROP2 (FIG. 26A) and CDRε (FIG. 26B) by TCEs and polypeptide complexes as measured by ELISA.
Figure 26B:
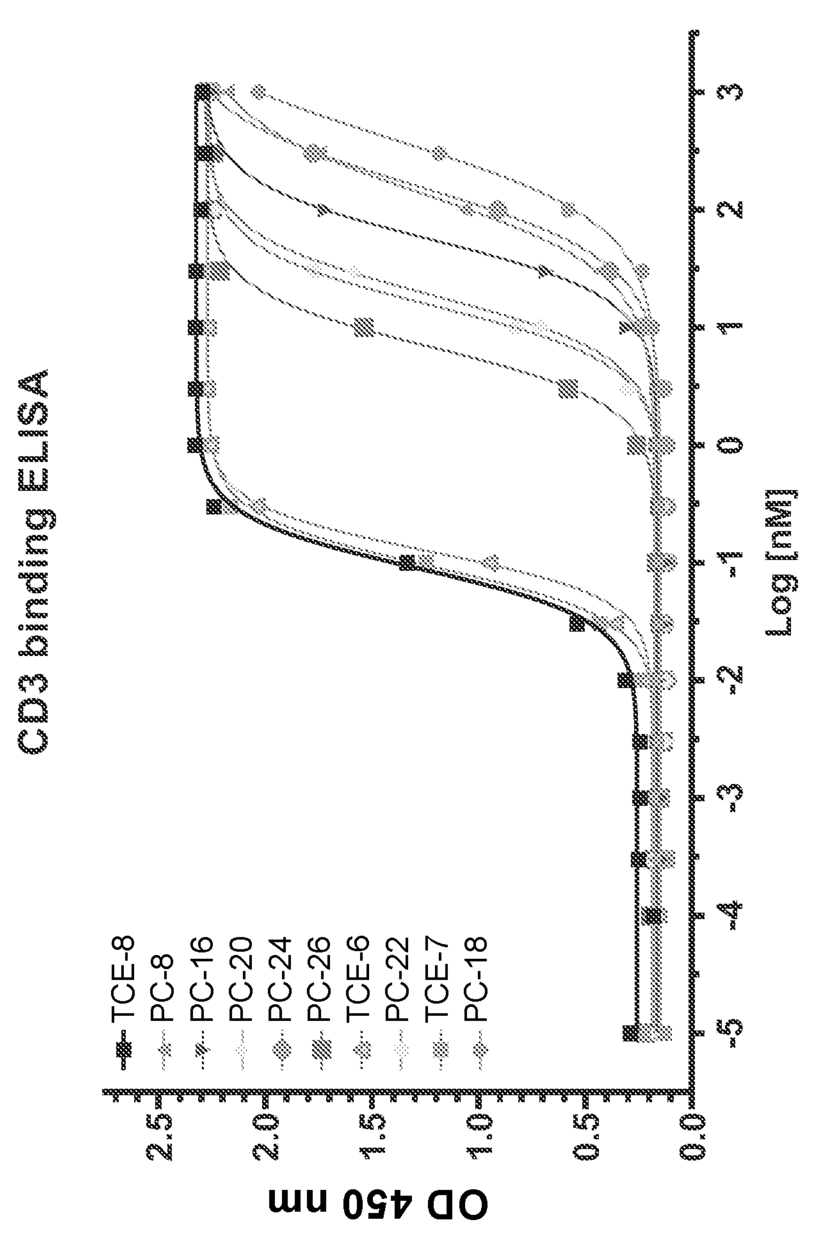
Figure 27A:
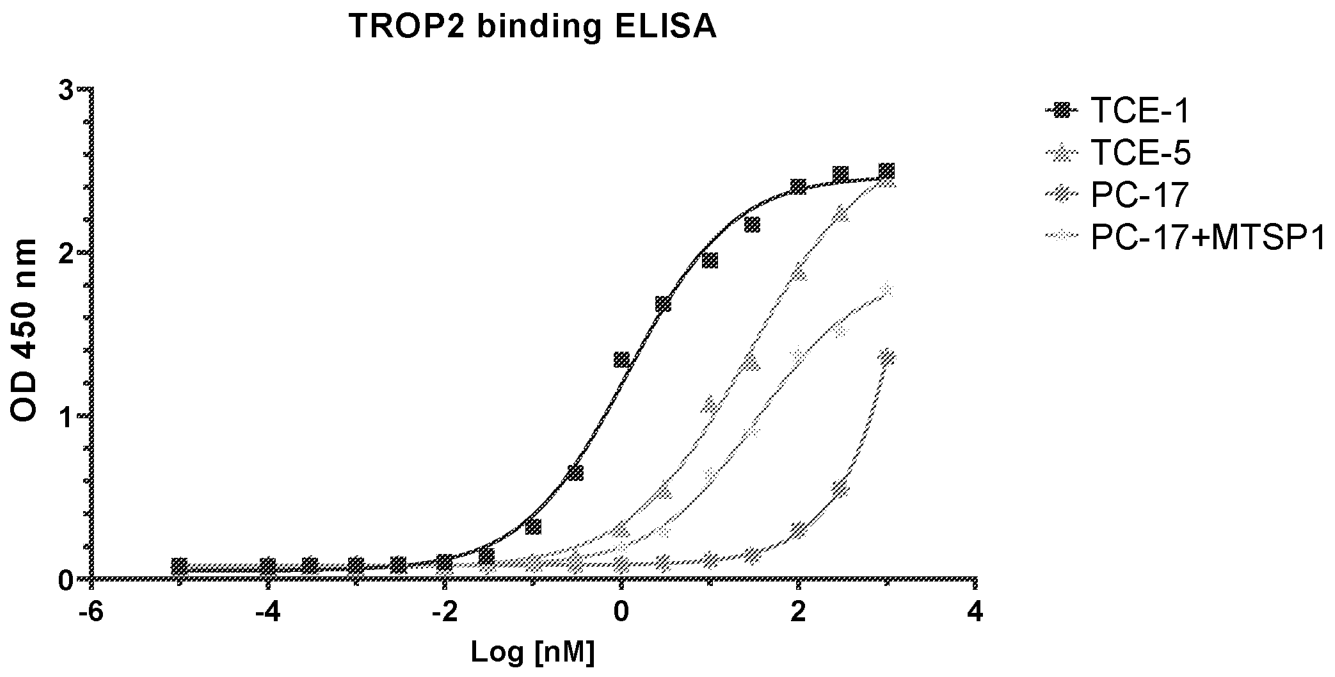
FIGS. 27A-27B show binding curves and $EC_{50}$s for binding of TROP2 (FIG. 27A) and CDRε (FIG. 27B) by TCEs and polypeptide complexes as measured by ELISA.
Figure 27B:
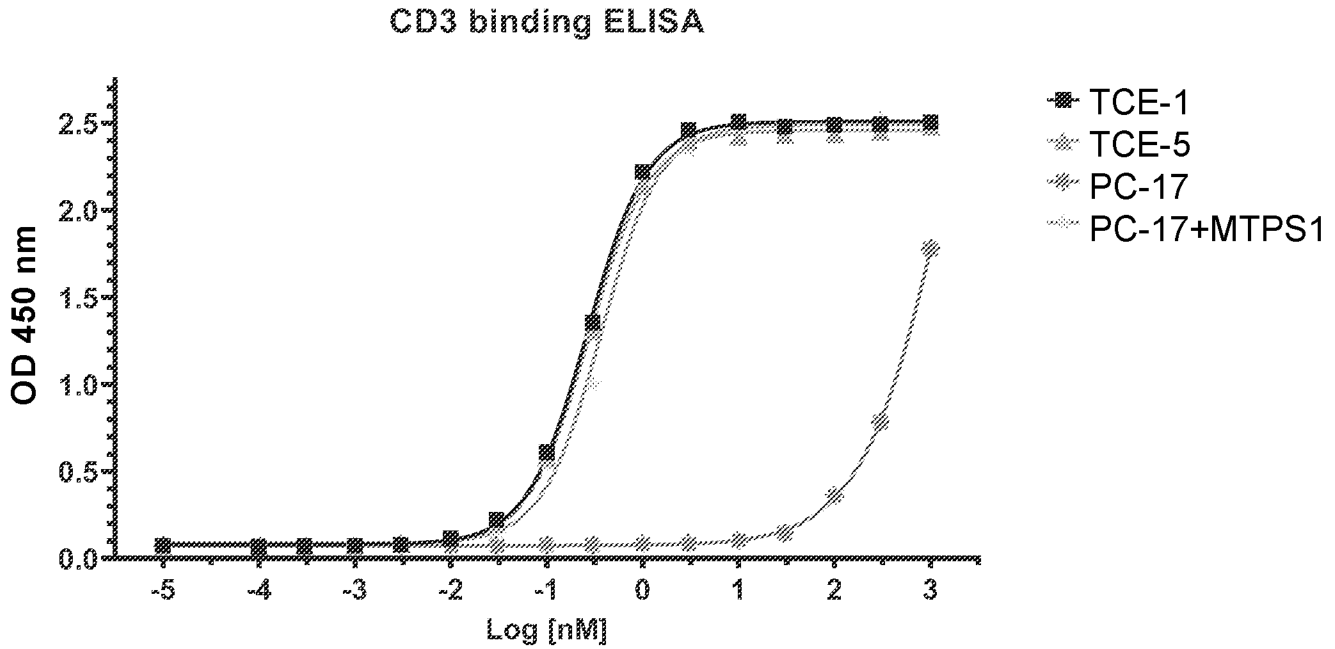
Figure 28A:
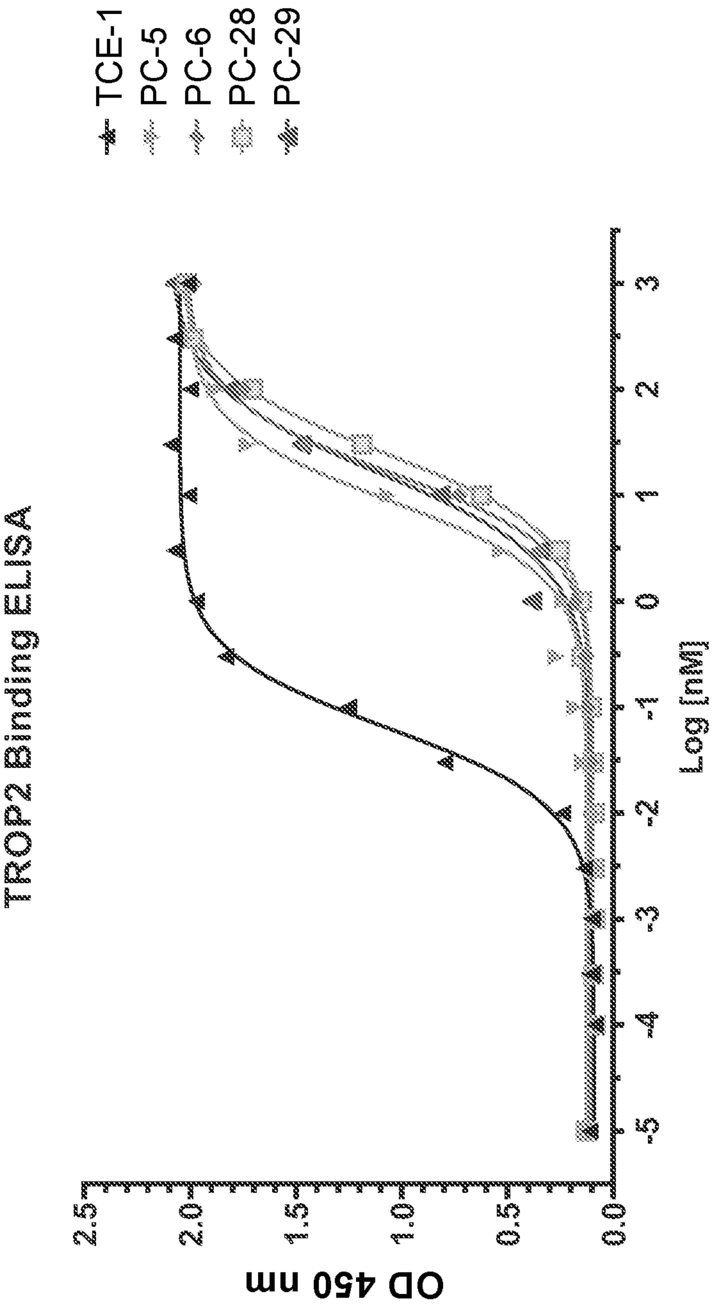
FIGS. 28A-28B show binding curves and $EC_{50}$s for binding of TROP2 (FIG. 28A) and CDRε (FIG. 28B) by TCEs and polypeptide complexes as measured by ELISA.
Figure 28B:
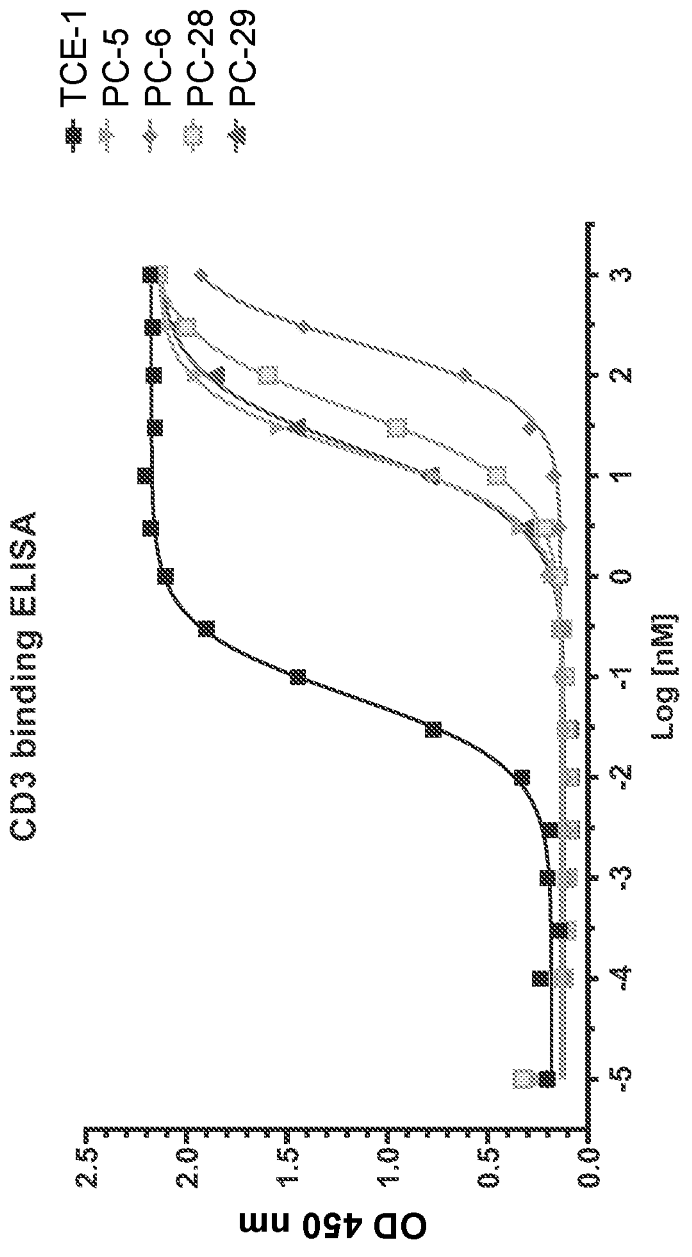
Figure 29A:
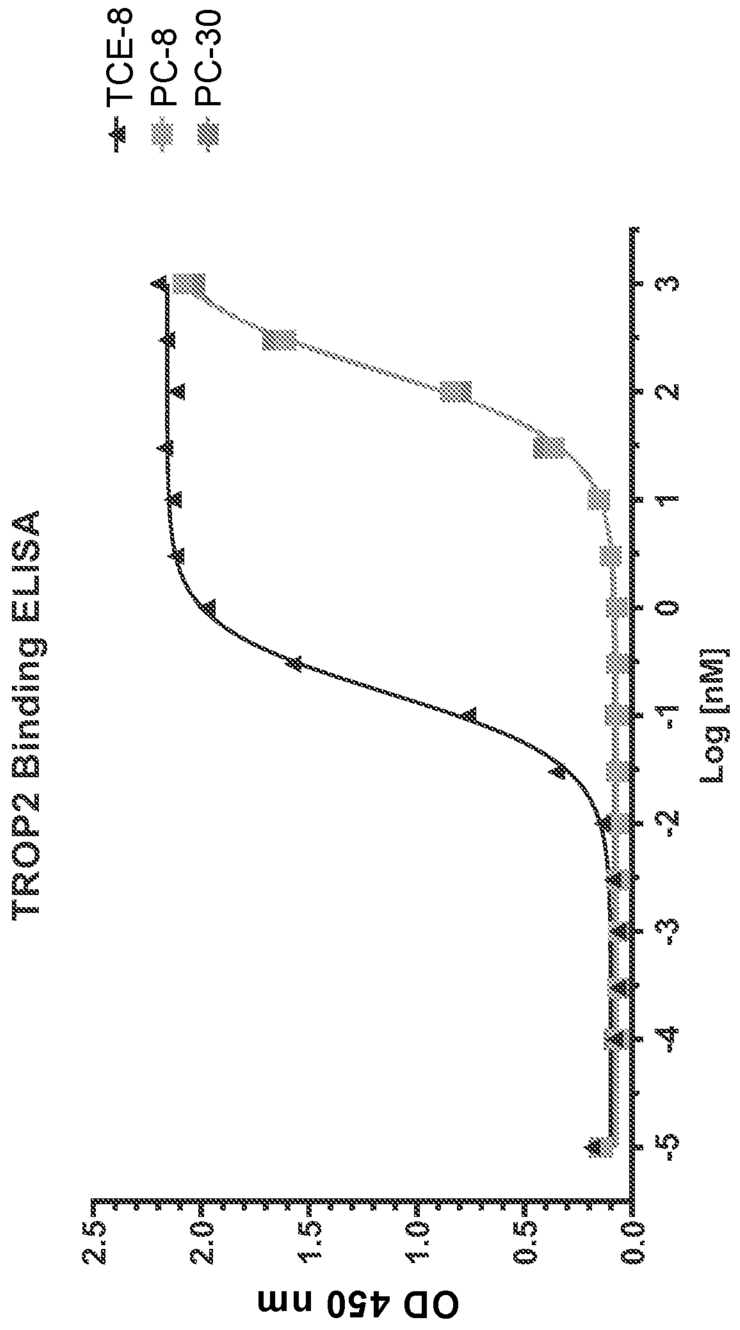
FIGS. 29A-29B show binding curves and $EC_{50}$s for binding of TROP2 (FIG. 29A) and CDRε (FIG. 29B) by TCEs and polypeptide complexes as measured by ELISA.
Figure 29B:
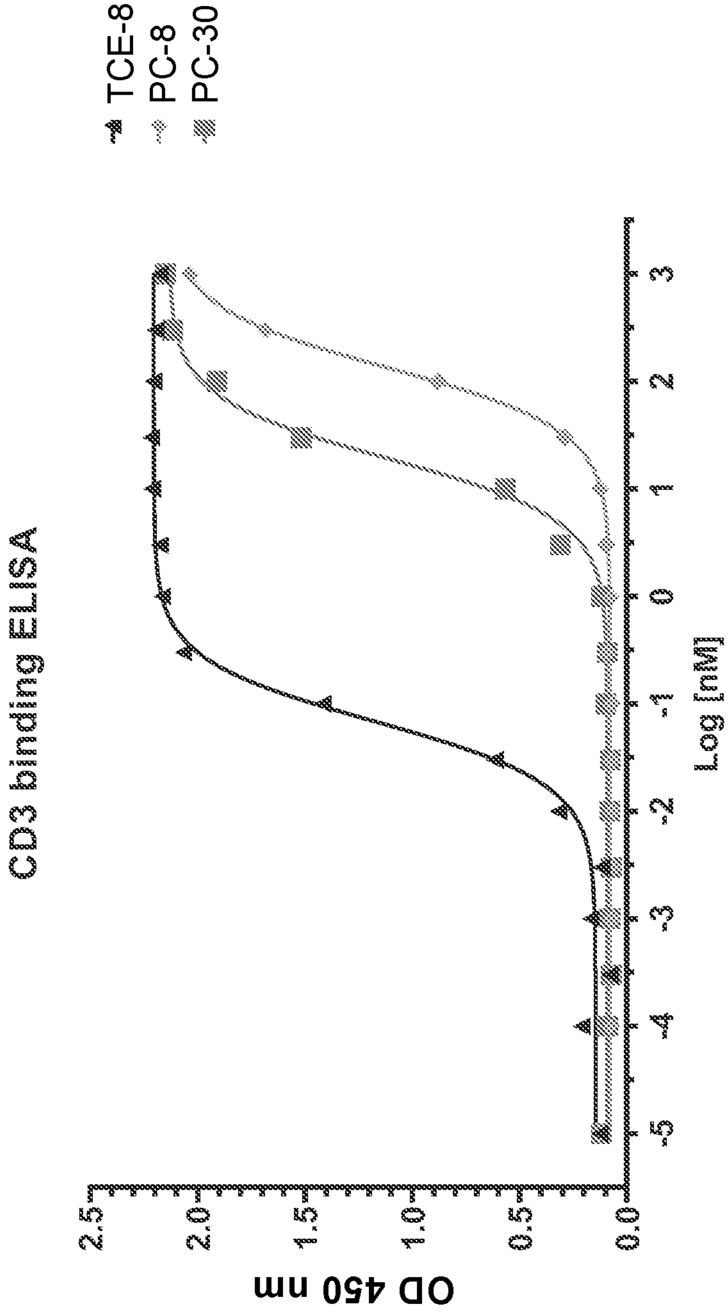
Figure 30A:
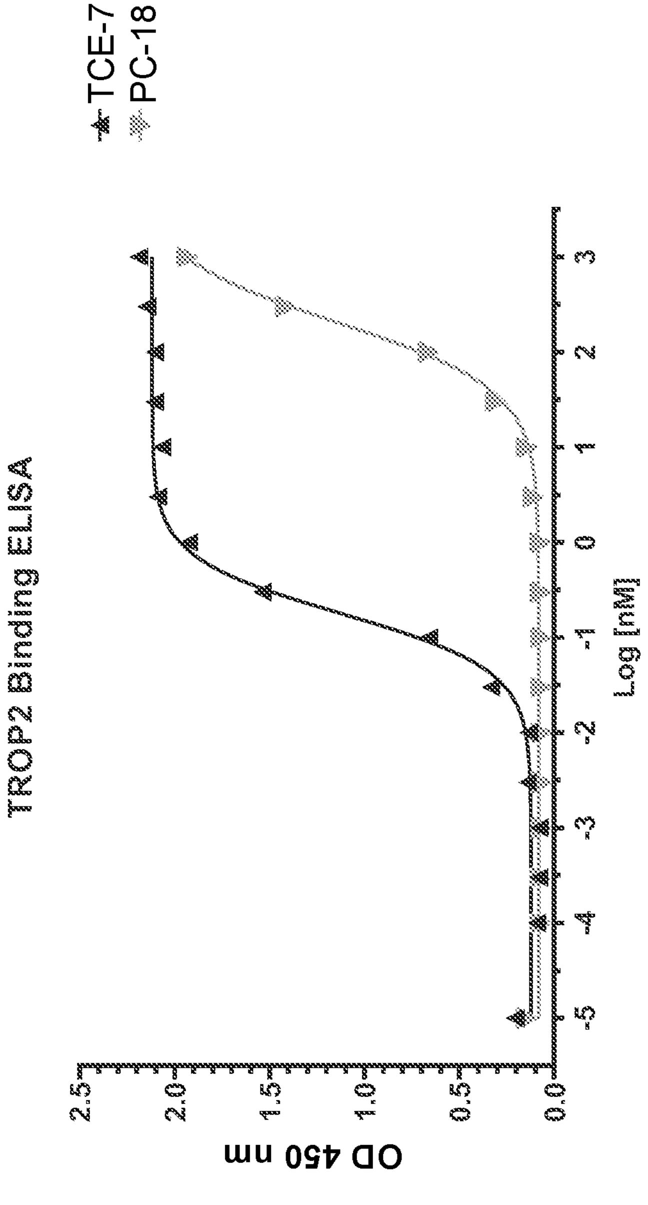
FIGS. 30A-30B show binding curves and $EC_{50}$s for binding of TROP2 (FIG. 30A) and CDRε (FIG. 30B) by TCEs and polypeptide complexes as measured by ELISA.
Figure 30B:
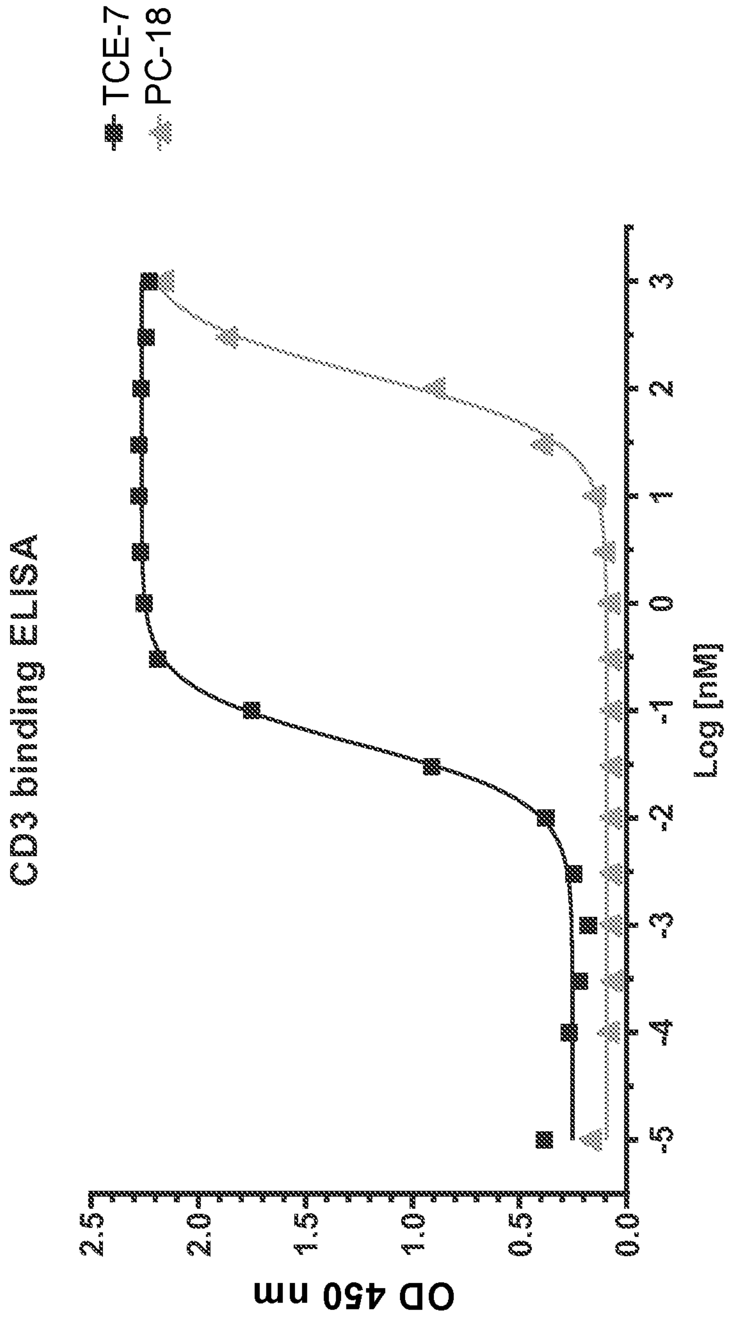

The wild-type and alanine mutated TBDs of Example 1 were also evaluated for their ability to bind TROP2 using a standard enzyme-linked immunosorbent assay (ELISA) format. Briefly, biotinylated TROP2 was captured on neutravidin coated plates. The TROP2 Fab constructs (TBDs)

diluted in buffer were then added to the antigen coated plates. Binding was detected using a standard horse radish peroxidase secondary antibody. The concentration of the TBD required to achieve 50% maximal signal ($EC_{50}$) was calculated. Binding curves for the TBD CDR3 LC and CDR3 HC alanine scanning mutants (TBD-2 to TBD-12) relative to the wild-type TBD (TBD-1) are shown in FIG. 3 along with calculated $EC_{50}$s. Binding curves for CDR3 HC alanine scanning mutants (TBD-13 to TBD-23) relative to the wild-type TBD (TBD-1) are shown in FIG. 4 along with calculated $EC_{50}$s.

Sequence Activity Relationships

Data summarizing the TROP2 binding parameters obtained from the above kinetic and equilibrium binding studies are provided in Table 15 (CDR3 LC alanine mutated constructs) and Tables 16-17 (CDR3 HC alanine mutated constructs). The tables also designate each alanine mutation in the CDR3 LC and CDR3 HC regions as tolerated (T), moderately tolerated (MT), or not tolerated (NT). Alanine mutations which resulted in significantly weakened binding relative to the non-mutated TROP2 Fab (TBD-1) were characterized as NT, and those residues were considered key residues for TROP2 binding. Alanine mutations which showed comparable binding parameters to the non-mutated TROP2 Fab were characterized as T, and those residues were considered non-critical for TROP2 binding Alanine mutations which resulted in somewhat weakened binding relative to the non-mutated TROP2 Fab were characterized as MT.

As can be seen from Table 15, the H91A and Y92A mutations in the CDR3 LC region were not tolerated and weakened the binding interaction with TROP2 substantially. Also disruptive to the TROP2 binding interaction was the L96A mutation. The Q89A mutation was moderately tolerated, whereas the remaining alanine mutations in the CDR3 LC region were tolerated. The data indicates that H91A and Y92A of the CDR3 LC region are critical for binding to TROP2.

Regarding the alanine mutations in the CDR3 HC region, the G100A, Y105A, and W106A mutations were not tolerated and disrupted the binding interaction with TROP2 substantially, indicating that these residues are critical for binding. The F101A and G102A mutations were also significantly disruptive to binding, suggesting that these residues are also important for the binding interaction with the TROP2 antigen.

TABLE 15

TROP2 Binding and SAR Data for TROP2 Fab CDR3 LC Alanine Scanning Mutants

| TROP2 Fab | TBD1 wt | TBD2 | TBD3 | TBD4 | TBD5 | TBD6 | TBD7 | TBD8 | TBD9 | TBD10 |
|---|---|---|---|---|---|---|---|---|---|---|
| $K_D$ (nM) | 0.6 | 10.4 | 0.7 | low binding | low binding | 0.7 | 0.6 | 0.3 | 8.4 | 0.6 |
| $t_{1/2}$ (min) | 50 | 24 | 27 | — | — | 28 | 39 | 61 | 5 | 37 |
| $EC_{50}$ - ELISA (nM) | 0.2 | 4.7 | 0.3 | >1000 | >1000 | 0.3 | 0.2 | 0.2 | 16.8 | 0.3 |
| Fold shift in $EC_{50}$ relative to wt | N/A | 23.5 | 1.5 | ND | ND | 1.5 | 1 | 1 | 84 | 1.5 |
| CDR3 LC Ala scan | N/A | Q | Q | H | Y | I | T | P | L | T |
| Amino acid position | N/A | 89 | 90 | 91 | 92 | 93 | 94 | 95 | 96 | 97 |
| Mutation tolerated? | N/A | MT | T | NT | NT | T | T | T | NT | T |

TABLE 16

TROP2 Binding and SAR Data for TROP2 Fab CDR3 HC Alanine Scanning Mutants

| TROP2 Fab | TBD1 wt | — | TBD11 | TBD12 | TBD13 | TBD14 | TBD15 | TBD16 |
|---|---|---|---|---|---|---|---|---|
| $K_D$ (nM) | 0.6 | | 3.88 | 0.492 | low binding | 18.7 | 5.71 | 0.211 |
| $t_{1/2}$ (min) | 50 | | 10 | 39 | — | 4 | 1 | 103 |
| $EC_{50}$ -ELISA (nM) | 0.2 | | 3.8 | 0.2 | >1000 | 38.6 | 72.2 | 0.2 |
| Fold shift in $EC_{50}$ relative to wt | N/A | | 19 | 1 | ND | 193 | 361 | 1 |
| CDR3 LC Ala scan | N/A | A | R | G | G | F | G | S |
| Amino acid position | N/A | 97 | 98 | 99 | 100 | 101 | 102 | 103 |
| Mutation tolerated? | N/A | N/A | MT | T | NT | NT | NT | T |

TABLE 17

TROP2 Binding and SAR Data for TROP2 Fab CDR3 HC Alanine Scanning Mutants

| TROP2 Fab | TBD1 wt | TBD17 | TBD18 | TBD19 | TBD20 | TBD21 | TBD22 | TBD23 |
|---|---|---|---|---|---|---|---|---|
| $K_D$ (nM) | 0.6 | 0.9 | low binding | low binding | 6.34 | 4.76 | 2.35 | 0.401 |
| $t_{1/2}$ (min) | 50 | 24 | — | — | 10 | 8 | 33 | 34 |
| $EC_{50}$-ELISA (nM) | 0.2 | 0.4 | 800.7 | 701.9 | 52.3 | 4.1 | 1.1 | 0.2 |
| Fold shift in $EC_{50}$ relative to wt | N/A | 2 | 4004 | 3510 | 262 | 20.5 | 5.5 | 1 |
| CDR3 LC Ala scan | N/A | S | Y | W | Y | F | D | V |
| Amino acid position | N/A | 104 | 105 | 106 | 107 | 108 | 109 | 110 |
| Mutation tolerated? | N/A | T | NT | NT | MT | MT | MT | T |

Example 3: Binding of Peptide Masks to TROP2 Binding Domain (TBD) Alanine Scanning Sequences The peptide masks of Table 3 were evaluated for binding to non-mutated and mutated anti-TROP2 Fab constructs (TBDs) that showed faster off rates for binding to TROP2. Binding was measured in a standard ELISA format. Briefly, biotinylated peptides were captured on neutravidin coated plates. The anti-TROP2 Fab constructs (TBDs) diluted in buffer were then added to the peptide coated plates. Bound TBDs were detected using a standard horse radish peroxidase conjugate secondary antibody. The ELISA signal was plotted versus the log-scale concentration of TBD. The concentrations of TBD required to observe half maximal binding signal ($EC_{50}$s) were calculated using Graphpad Prism software. FIGS. 5A-5G show binding curves for binding of peptides to the non-mutated construct TBD-1. FIGS. 6A-6F show binding curves for binding of peptides to TBD-6 (LC I93A mutant). FIGS. 7A-7F show binding curves for binding of peptides to TBD-11 (HC R98A mutant). FIGS. 8A-8D show binding curves for peptide binding to TBD-17 (HC S104A mutant). FIGS. 9A-9D show binding curves for peptide binding to TBD-21 (HC F108A mutant). FIGS. 10A-10D show binding curves for peptide binding to TBD-22 (HC D109A mutant). $EC_{50}$s are provided in Tables 18-20.

TABLE 18

TROP2 Fab (TBD) Binding to Peptides by ELISA

| | TBD-6 (LC 193A) $EC_{50}$ (nM) | TBD-11 (HC R98A) $EC_{50}$ (nM) | TBD-17 (HC S104A) $EC_{50}$ (nM) | TBD-21 (HC F108A) $EC_{50}$ (nM) | TBD-22 (HC D109A) $EC_{50}$ (nM) | TBD-1 wt $EC_{50}$ (nM) |
|---|---|---|---|---|---|---|
| TROP2-biotin | 0.3 | 3.4 | 0.3 | 4.2 | 1.1 | 0.2 |
| Peptide-24 | >1000 | >1000 | 132.7 | 141.6 | unknown | unknown |
| Peptide-25 | 38.3 | >1000 | 38.8 | 48.4 | 1.9 | 48.2 |
| Peptide-1 | 14.8 | 291.9 | 7.3 | 13.5 | 1.0 | 22.5 |
| Peptide-2 | 9.9 | 203.6 | 5.7 | 12.9 | 1.1 | 13.7 |
| Peptide-3 | 11.4 | 245.6 | 6.4 | 12.3 | 1.6 | 12.8 |
| Peptide-4 | 15.3 | 179.4 | 6.5 | 12.7 | 1.2 | 9.2 |
| Peptide-5 | 9.9 | 232.0 | 5.4 | 15.6 | 0.9 | 16.5 |
| Peptide-6 | 15.0 | 362.8 | 10.1 | 24.9 | 1.4 | 28.5 |
| Peptide-7 | 59.6 | 342.9 | 15.6 | 27.4 | 3.6 | 37.5 |
| Peptide-26 | >1000 | >1000 | 379.0 | 390.0 | >1000 | 85.0 |
| Peptide-27 | 178.1 | >1000 | 107.3 | 148.6 | unknown | 23.9 |
| Peptide-28 | 681.1 | >1000 | 247.1 | 146.5 | unknown | unknown |
| Peptide-29 | 43.8 | >1000 | 24.8 | 23.4 | unknown | 6.7 |
| Peptide-30 | >1000 | >1000 | >1000 | >1000 | unknown | 9.1 |
| Peptide-31 | 791.0 | >1000 | 164.2 | >1000 | unknown | 42.1 |
| Peptide-8 | 18.8 | 156.2 | 8.2 | 13.0 | 0.6 | 40.2 |
| Peptide-10 | 8.5 | 271.9 | 6.5 | 15.2 | 1.0 | 62.6 |
| Peptide-12 | 18.2 | 157.1 | 6.8 | 10.1 | 0.6 | 35.9 |
| Peptide-13 | 21.4 | 387.7 | 10.0 | 22.6 | 3.9 | 157.4 |
| Peptide-14 | 145.0 | 331.9 | 71.0 | 53.3 | 5.3 | 378.9 |
| Peptide-17 | 16.5 | 191.2 | 8.5 | 16.4 | 2.6 | 132.5 |
| Peptide-18 | 83.2 | 297.9 | 36.7 | 38.0 | 7.8 | 474.5 |
| Peptide-20 | 139.8 | >1000 | 114.8 | 89.0 | 5.3 | 599.7 |

TABLE 19

| TROP2 Fab (TBD) Binding to Peptides by ELISA, $EC_{50}$ (nM) | | | | | | |
|---|---|---|---|---|---|---|
| | TBD-6 (LC 193A) $EC_{50}$ (nM) | TBD-11 (HC R98A) $EC_{50}$ (nM) | TBD-17 (HC S104A) $EC_{50}$ (nM) | TBD-21 (HC F108A) $EC_{50}$ (nM) | TBD-22 (HC D109A) $EC_{50}$ (nM) | TBD-1 wt $EC_{50}$ (nM) |
| Trop2-biotin | 0.3 | 3.4 | 0.3 | 4.2 | 1.1 | 0.2 |
| Peptide-25 | 10.9 | 453.0 | 35.0 | 42.3 | 2.8 | 216.7 |
| Peptide-3 | 18.3 | 296.3 | 23.0 | 30.8 | 3.0 | 163.6 |
| Peptide-8 | 8.5 | 86.4 | 8.0 | 12.9 | 0.6 | 35.2 |
| Peptide-32 | 20.1 | 87.7 | 35.1 | 27.1 | 2.1 | 34.56 |
| Peptide-62 | 5.1 | 135.5 | 9.2 | 14.3 | 0.9 | 81.38 |
| Peptide-33 | 9.6 | 143.8 | 24.1 | 22.9 | 1.5 | 29.71 |
| Peptide-34 | >1000 | >1000 | >1000 | >1000 | >1000 | >1000 |
| Peptide-35 | 130.7 | >1000 | 214.6 | 331.1 | 7.7 | 260.6 |
| Peptide-36 | 23.8 | 60.1 | 30.2 | 27.0 | 2.2 | 41.4 |
| Peptide-37 | 9.3 | 148.9 | 19.5 | 27.3 | 1.7 | 31.72 |
| Peptide-63 | 9.5 | 228.9 | 30.0 | 39.7 | 1.7 | 162.3 |
| Peptide-38 | 9.8 | 289.8 | 31.8 | 26.1 | 2.0 | 178.2 |
| Peptide-64 | 6.4 | 61.7 | 3.8 | 11.0 | 1.7 | 28.3 |
| Peptide-39 | 32.1 | 151.3 | 16.4 | 32.7 | 4.6 | 95.2 |
| Peptide-40 | 30.4 | 310.1 | 27.0 | 45.8 | 4.6 | 39.7 |
| Peptide-41 | 41.0 | 158.7 | 28.9 | 47.2 | 6.0 | 101.8 |
| Peptide-42 | 5.7 | 86.4 | 5.5 | 13.8 | 0.8 | 28.5 |
| Peptide-43 | 7.2 | 77.5 | 4.9 | 12.0 | 0.9 | 27.5 |

TABLE 20

| Trop2 Fab (TBD) Binding to Peptides by ELISA, $EC_{50}$ (nM) | | | |
|---|---|---|---|
| | TBD-6 (LC 193A) $EC_{50}$ (nM) | TBD-11 (HC R98A) $EC_{50}$ (nM) | TBD-1 wt $EC_{50}$ (nM) |
| Trop2-biotin | 0.3 | 3.4 | 0.2 |
| Peptide-3 | 12.5 | 295.5 | 91.5 |
| Peptide-8 | 12.2 | 318.8 | 55.6 |
| Peptide-43 | 5.3 | 43.6 | 28.6 |
| Peptide-44 | >1000 | 112.3 | >1000 |
| Peptide-45 | 32.6 | 138.1 | 50.8 |
| Peptide-46 | 102.2 | >1000 | 668.5 |
| Peptide-47 | 79.9 | 303.6 | 113.0 |
| Peptide-48 | 12.2 | 42.4 | 21.5 |
| Peptide-49 | 18.3 | 129.9 | 295.5 |
| Peptide-50 | 21.9 | 35.5 | 96.2 |
| Peptide-51 | 13.5 | 243.5 | 45.1 |
| Peptide-52 | 39.3 | >1000 | 127.1 |
| Peptide-53 | 4.4 | 32.5 | 45.3 |
| Peptide-54 | 30.0 | 147.3 | 63.5 |
| Peptide-55 | 6.1 | 36.8 | 15.7 |
| Peptide-56 | 33.3 | 126.6 | 52.8 |
| Peptide-57 | 9.2 | 85.6 | 25.7 |
| Peptide-58 | >1000 | 10.7 | >1000 |
| Peptide-59 | 5.4 | 92.8 | 61.1 |
| Peptide-60 | 7.7 | 60.4 | 47.8 |
| Peptide-61 | 11.8 | 272.5 | 191.3 |

Example 4: Binding Inhibition of TBD Alanine Scanning Sequences by Peptide Masks The peptides of Table 3 were further screened for their ability to inhibit the non-mutated and mutated anti-TROP2 Fab constructs (TBDs) from binding to the TROP2 antigen. The TBDs that showed faster off rates for binding to TROP2 were evaluated. ELISA-based competitive inhibition studies were used to test the ability of each peptide to inhibit the TBDs from binding to TROP2. Biotinylated antigen was captured on neutravidin coated plates, quenched using biocytin, and washed. Inhibitory peptides were titrated in a dilution series and pre-incubated with a constant concentration of antibody. Inhibitory peptide and antibody mixtures were then incubated on the antigen captured plates. A horseradish peroxidase conjugate secondary antibody was then used to detect the antibody binding to the plate-bound antigen. The ELISA signal was plotted versus log-scale peptide concentration. A dose dependent decrease of signal was indicative of peptides that compete for antibody binding to the cognate antigen. Graphpad Prism software was used to calculate the inhibitory concentrations of peptide required to achieve 50% maximal signal ($IC_{50}$s). FIGS. 11A-11G show inhibition curves for peptide inhibition of TBD-1 binding to TROP2. FIGS. 12A-12F show inhibition curves for peptide inhibition of TBD-6 (LC I93A mutant) binding to TROP2. FIGS. 13A-13F show inhibition curves for peptide inhibition of TBD-11 (HC R98A mutant) binding to TROP2. FIGS. 14A-14F show inhibition curves for peptide inhibition of TBD-17 (HC S104A mutant) binding to TROP2. FIGS. 15A-15F show inhibition curves for peptide inhibition of the TBD-21 (HC F108A mutant) binding to TROP2. FIGS. 16A-16F show inhibition curves for peptide inhibition of TBD-22 (HC D109A) binding to TROP2. $IC_{50}$s are provided in Tables 21-23.

TABLE 21

| Peptide Inhibition of TROP2 Fab (TBD) by ELISA | | | | | | |
|---|---|---|---|---|---|---|
| | TBD-6 (LC I93A) $IC_{50}$ (μM) | TBD-11 (HC R98A) $IC_{50}$ (μM) | TBD-17 (HC S104A) $IC_{50}$ (μM) | TBD-21 (HC F108A) $IC_{50}$ (μM) | TBD-22 (HC D109A) $IC_{50}$ (μM) | TBD-1 wt $IC_{50}$ (μM) |
| Trop2-biotin | — | — | — | — | — | — |
| Peptide-24 | — | — | — | — | — | 2.78 |
| Peptide-25 | 1.03 | 8.10 | 3.04 | 6.45 | 0.14 | 2.58 |

TABLE 21-continued

Peptide Inhibition of TROP2 Fab (TBD) by ELISA

| | TBD-6 (LC I93A) $IC_{50}$ (μM) | TBD-11 (HC R98A) $IC_{50}$ (μM) | TBD-17 (HC S104A) $IC_{50}$ (μM) | TBD-21 (HC F108A) $IC_{50}$ (μM) | TBD-22 (HC D109A) $IC_{50}$ (μM) | TBD-1 wt $IC_{50}$ (μM) |
|---|---|---|---|---|---|---|
| Peptide-1 | 0.35 | 2.49 | 1.02 | 2.89 | 0.07 | 0.78 |
| Peptide-2 | 1.10 | 5.85 | 2.08 | 5.88 | 0.16 | 2.23 |
| Peptide-3 | 0.37 | 1.48 | 1.01 | 2.64 | 0.09 | 0.34 |
| Peptide-4 | 0.40 | 3.24 | 2.04 | 3.30 | 0.13 | 0.46 |
| Peptide-5 | 1.05 | 7.23 | 1.79 | 7.16 | 0.10 | 1.59 |
| Peptide-6 | 1.86 | 8.84 | 3.09 | 7.94 | 0.09 | 2.25 |
| Peptide-7 | 1.41 | 1.00 | 3.77 | 4.01 | 0.13 | 0.65 |
| Peptide-26 | — | — | — | — | — | 2.23 |
| Peptide-27 | — | — | — | — | — | 0.74 |
| Peptide-28 | — | — | — | — | — | 1.63 |
| Peptide-29 | 0.80 | 9.17 | 1.11 | 1.49 | 33.56 | 0.92 |
| Peptide-30 | — | — | — | — | — | 1.91 |
| Peptide-31 | — | — | — | — | — | 2.94 |
| Peptide-8 | 0.34 | 0.30 | 0.89 | 0.61 | 0.02 | 0.18 |
| Peptide-10 | 0.62 | 4.04 | 1.52 | 2.90 | 0.06 | 1.22 |
| Peptide-12 | 1.46 | 0.85 | 2.23 | 2.24 | 0.07 | 0.46 |
| Peptide-13 | 0.97 | 2.68 | 2.99 | 3.20 | 0.20 | 1.01 |
| Peptide-14 | 1.54 | 3.42 | 5.72 | 6.92 | 0.19 | 2.19 |
| Peptide-17 | 0.76 | 1.95 | 2.07 | 2.94 | 0.07 | 0.43 |
| Peptide-18 | 6.11 | 3.96 | 7.08 | 7.56 | 0.35 | 1.27 |
| Peptide-20 | — | — | — | — | — | 1.61 |

TABLE 22

Peptide Inhibition of TROP2 Fab (TBD) by ELISA

| | TBD-6 (LC 193A) $IC_{50}$ (μM) | TBD-11 (HC R98A) $IC_{50}$ (μM) | TBD-17 (HC S104A) $IC_{50}$ (μM) | TBD-21 (HC F108A) $IC_{50}$ (μM) | TBD-22 (HC D109A) $IC_{50}$ (μM) | TBD-1 wt $IC_{50}$ (μM) |
|---|---|---|---|---|---|---|
| Trop2-biotin | — | — | — | — | — | — |
| Peptide-25 | 1.28 | 18.00 | 3.75 | 6.73 | 0.29 | 3.03 |
| Peptide-3 | 0.53 | 2.72 | 1.48 | 2.00 | 0.12 | 0.43 |
| Peptide-8 | 0.37 | 0.62 | 0.87 | 1.01 | 0.08 | 0.25 |
| Peptide-32 | 3.29 | 9.93 | 9.44 | 13.17 | 0.33 | 4.94 |
| Peptide-62 | 0.55 | 4.87 | 1.42 | 3.01 | 0.08 | 1.47 |
| Peptide-33 | 2.16 | 18.03 | 6.01 | 15.72 | 0.33 | 5.60 |
| Peptide-34 | >100 | >100 | >100 | >100 | >100 | >100 |
| Peptide-35 | 3.20 | 21.88 | 9.40 | 19.19 | 0.87 | 4.40 |
| Peptide-36 | 3.80 | 19.85 | 14.82 | 19.94 | 1.72 | 5.11 |
| Peptide-37 | 2.60 | 16.61 | 4.08 | 15.54 | 0.37 | 6.28 |
| Peptide-63 | 0.80 | 6.81 | 1.40 | 5.89 | 0.11 | 2.15 |
| Peptide-38 | 0.52 | 4.42 | 2.03 | 3.54 | 0.17 | 1.63 |
| Peptide-64 | 0.54 | 1.78 | 1.60 | 1.63 | 0.12 | 0.42 |
| Peptide-39 | 0.67 | 1.64 | 1.69 | 2.23 | 0.14 | 0.46 |
| Peptide-40 | 2.28 | 14.55 | 7.26 | 10.02 | 0.58 | 3.63 |
| Peptide-41 | 0.58 | 1.51 | 1.55 | 1.50 | 0.11 | 0.64 |
| Peptide-42 | 0.22 | 1.21 | 0.59 | 0.94 | 0.06 | 0.30 |
| Peptide-43 | 0.44 | 0.77 | 0.56 | 0.69 | 0.05 | 0.30 |

TABLE 23

Peptide Inhibition of TROP2 Fab (TBD) by ELISA

| | TBD-6 (LC I93A) $IC_{50}$ (μM) | TBD-11 (HC R98A) $IC_{50}$ (μM) | TBD-17 (HC S104A) $IC_{50}$ (μM) | TBD-21 (HC F108A) $IC_{50}$ (μM) | TBD-22 (HC D109A) $IC_{50}$ (μM) | TBD-1 wt $IC_{50}$ (μM) |
|---|---|---|---|---|---|---|
| Trop2-biotin | — | — | — | — | — | — |
| Peptide-3 | — | — | — | — | — | — |
| Peptide-8 | 0.76 | 0.94 | 1.25 | 2.12 | 0.10 | 0.37 |
| Peptide-43 | 0.48 | 0.87 | 0.51 | 1.04 | 0.05 | 0.27 |
| Peptide-44 | >100 | 3.55 | >100 | >100 | >100 | >100 |
| Peptide-45 | 14.50 | 408.70 | 39.55 | >100 | 2.50 | 9.29 |
| Peptide-46 | 5.18 | 22.29 | 11.48 | 25.91 | 0.70 | 5.14 |

TABLE 23-continued

| Peptide Inhibition of TROP2 Fab (TBD) by ELISA | | | | | | |
|---|---|---|---|---|---|---|
| | TBD-6 (LC I93A) $IC_{50}$ (μM) | TBD-11 (HC R98A) $IC_{50}$ (μM) | TBD-17 (HC S104A) $IC_{50}$ (μM) | TBD-21 (HC F108A) $IC_{50}$ (μM) | TBD-22 (HC D109A) $IC_{50}$ (μM) | TBD-1 wt $IC_{50}$ (μM) |
| Peptide-47 | 7.54 | 46.16 | 27.19 | >100 | 2.01 | 6.48 |
| Peptide-48 | 6.26 | 31.31 | 8.86 | 75.24 | 0.31 | 10.00 |
| Peptide-49 | 2.25 | 6.37 | 2.53 | 8.67 | 0.07 | 3.73 |
| Peptide-50 | 0.92 | 1.97 | 1.54 | 3.70 | 0.02 | 0.56 |
| Peptide-51 | 0.42 | 0.62 | 0.55 | 1.27 | 0.01 | 0.18 |
| Peptide-52 | 12.33 | 19.14 | 15.71 | >100 | 0.89 | 14.31 |
| Peptide-53 | 4.51 | 16.07 | 7.56 | 22.67 | 0.59 | 8.93 |
| Peptide-54 | 23.42 | >100 | 29.87 | 160.80 | 3.62 | 27.09 |
| Peptide-55 | 3.12 | 14.02 | 7.21 | 16.83 | 0.33 | 4.39 |
| Peptide-56 | 5.62 | 20.96 | 24.13 | 106.10 | 3.03 | 10.12 |
| Peptide-57 | 12.71 | >100 | 17.27 | 88.14 | 1.91 | 16.66 |
| Peptide-58 | >100 | 1.13 | >100 | >100 | >100 | >100 |
| Peptide-59 | 1.94 | 7.55 | 3.49 | 9.64 | 0.10 | 3.49 |
| Peptide-60 | 0.67 | 2.56 | 2.09 | 5.45 | 0.16 | 0.47 |
| Peptide-61 | 1.19 | 12.22 | 1.83 | 7.75 | 0.26 | 1.83 |

Example 5: Polypeptide Sequences that Bind to CD3 and TROP2

Selected alanine mutations in the TROP2 binding domain CDR3 HC region were carried out in T-cell engager (TCE) sequences composed of the TROP2 binding domain linked to a CD3ε binding domain. In these sequences, the CD3ε binding domain is an anti-CD3ε single chain variable fragment (scFv). The amino acid sequences of the non-mutated and mutated TCE constructs are provided in Table 8. TCE-1 and TCE-2 are non-mutated constructs having the CD3 binding domain connected to the TROP2 binding domain HC and the TROP2 binding domain LC, respectively. TCE-3 to TCE-5 include individual alanine mutations in the CDR3 HC region of the TROP2 binding domain and have the CD3 binding domain connected to the TROP2 binding domain LC. Specifically, TCE-3 includes a R98A mutation, TCE-4 includes a F108A mutation, and TCE-5 includes a D109A mutation. TCE-6 to TCE-8 include individual alanine mutations in the CDR3 HC region of the TROP2 binding domain and have the CD3 binding domain connected to the TROP2 binding domain HC. TCE-6 includes a R98A mutation, TCE-7 includes a F108A mutation, and TCE-8 includes a D109A mutation. Additionally, certain peptide mask and TROP2 Fab combinations were converted into polypeptide complexes that bind to TROP2 and CD3ε. These polypeptide complex sequences (PC-1 to PC-30) are provided in Table 12.

Example 6: Binding of TROP-2 TCEs to TROP2 and CD3s

Kinetic Binding to TROP2 Via BLI

The non-mutated and alanine mutated TCEs of Example 5 were evaluated for their ability to bind TROP2. Binding kinetics was measured using BLI as described above in Example 2. Example sensorgrams for non-mutated construct TCE-2 and mutated constructs TCE-3 to TCE-5 are shown in FIGS. 17A-17D. Example sensorgrams for non-mutated construct TCE-1 and mutated constructs TCE-6 to TCE-8 are shown in FIGS. 18A-18D. Exemplary experimental conditions and steps used for the kinetic binding measurements are shown in Table 24.

TABLE 24

| Step | Time |
|---|---|
| Sensor: SAX | |
| Baseline: Octet buffer | 60 seconds |
| Loading: Human TROP2-biotin (10 nM) | 300 seconds |
| Biocytin quench (100 μM) | 300 seconds |
| Baseline: Octet buffer | 300 seconds |
| Association: | 300 seconds |
| 50 nM TCE | |
| 25 nM TCE | |
| 12.5 nM TCE | |
| 6.25 nM TCE | |
| Dissociation: Octet buffer | 600 seconds |

Equilibrium Binding to TROP2 and CD3 Via ELISA

The non-mutated and alanine mutated TCEs of Table 8 and non-mutated and alanine mutated PCs of Table 12 were evaluated for their ability to bind TROP2 and CD3ε using an ELISA format. ELISA binding measurements were carried out as described in Example 2 using immobilized TROP2 or immobilized CD3ε. Binding curves and $EC_{50}$s for TROP2 and CD3ε binding by TCEs and polypeptide complexes are shown in FIGS. 19-30. Masked polypeptide complexes were treated with protease (MTSP1, MMP9) where indicated.

Example 7: Peptides that Inhibit αCD3 scFv from Binding CD3

Figure 31:
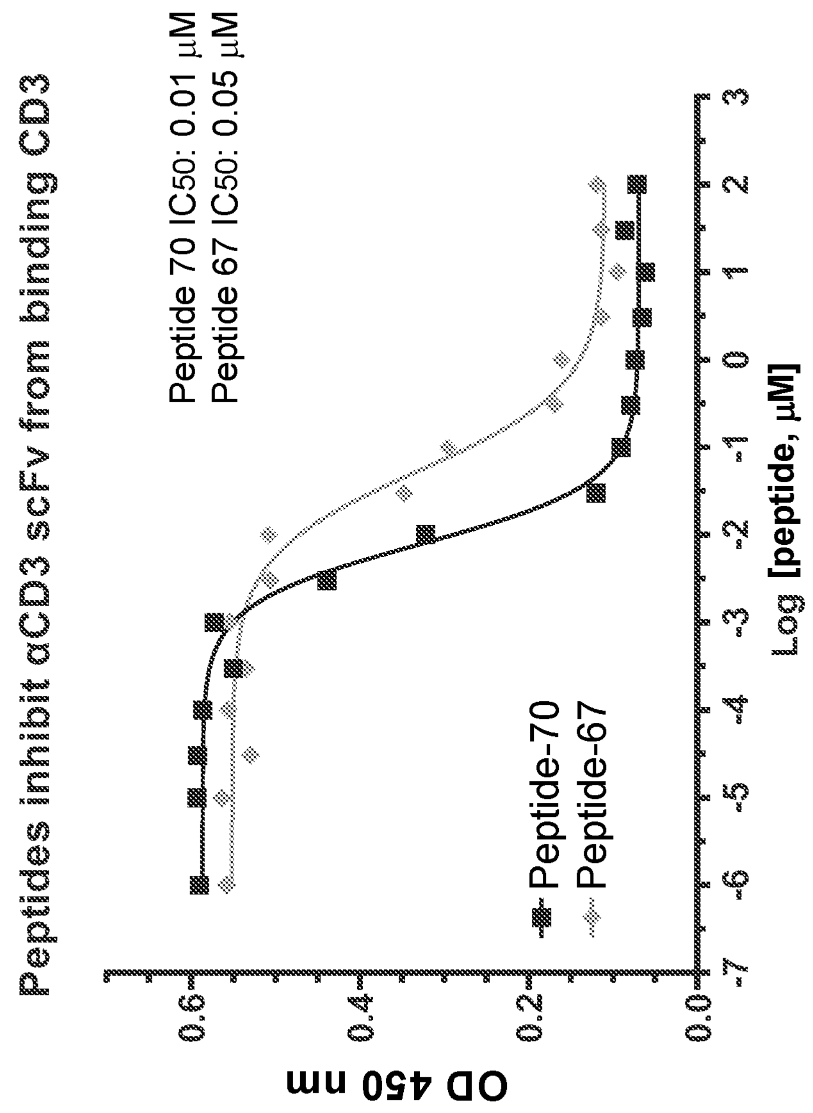
FIG. 31 shows inhibition of αCD3 scFv binding to CD3 by peptides as measured by ELISA.
Figure 32A:
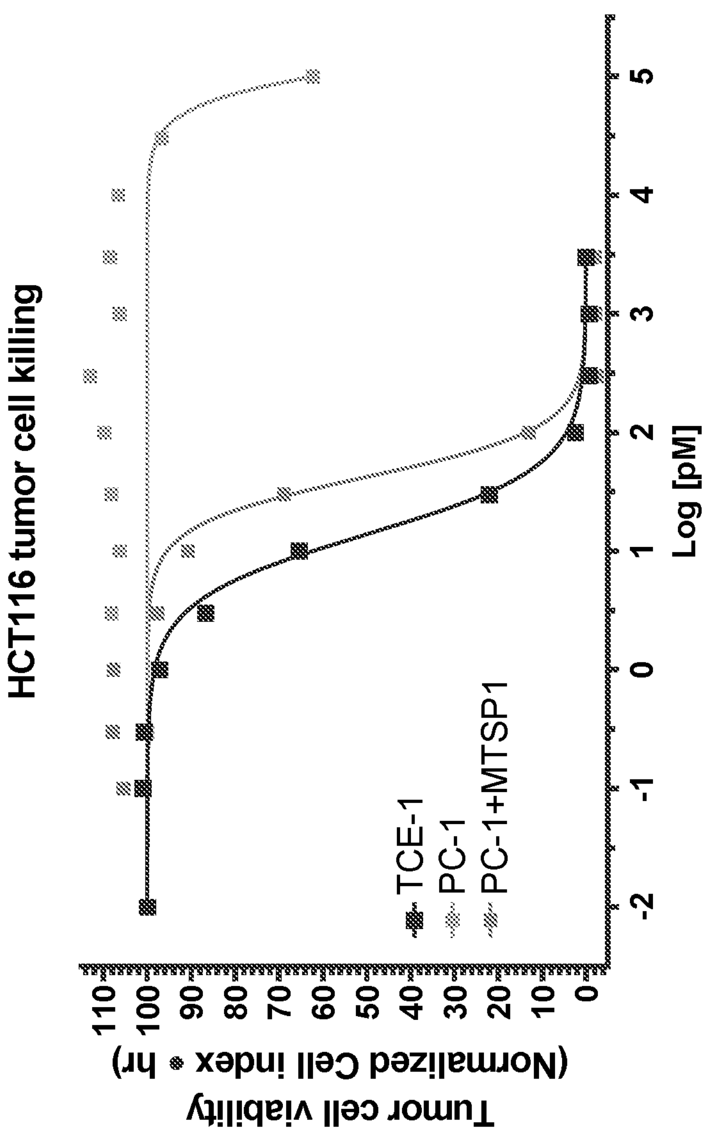
FIGS. 32A-32J illustrate killing of TROP2 positive HCT116 tumor cells by polypeptide complexes in the presence of CD8+ T-cells.
Figure 32B:
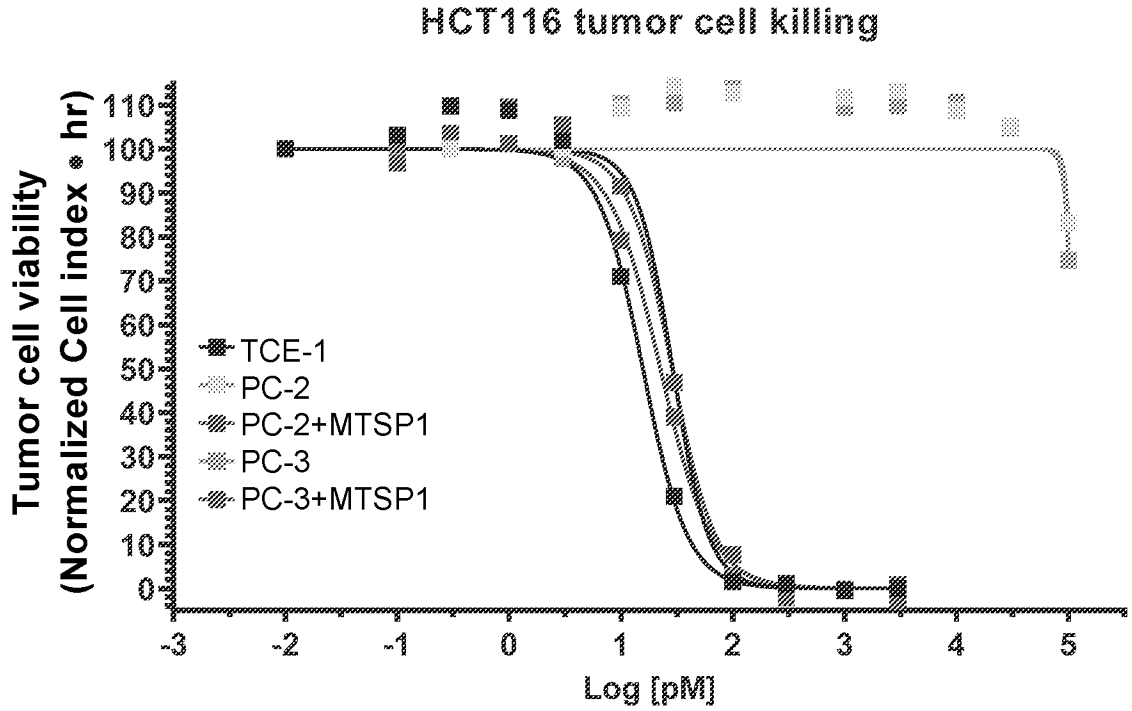
Figure 32C:
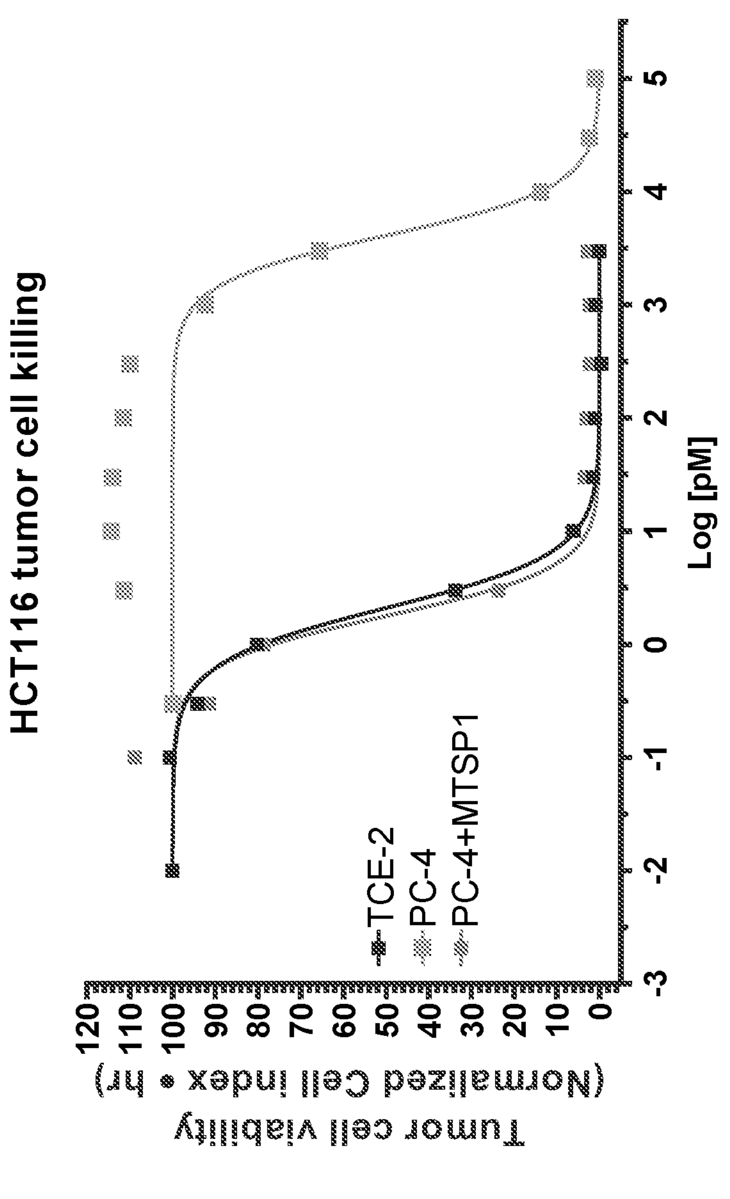
Figure 32D:
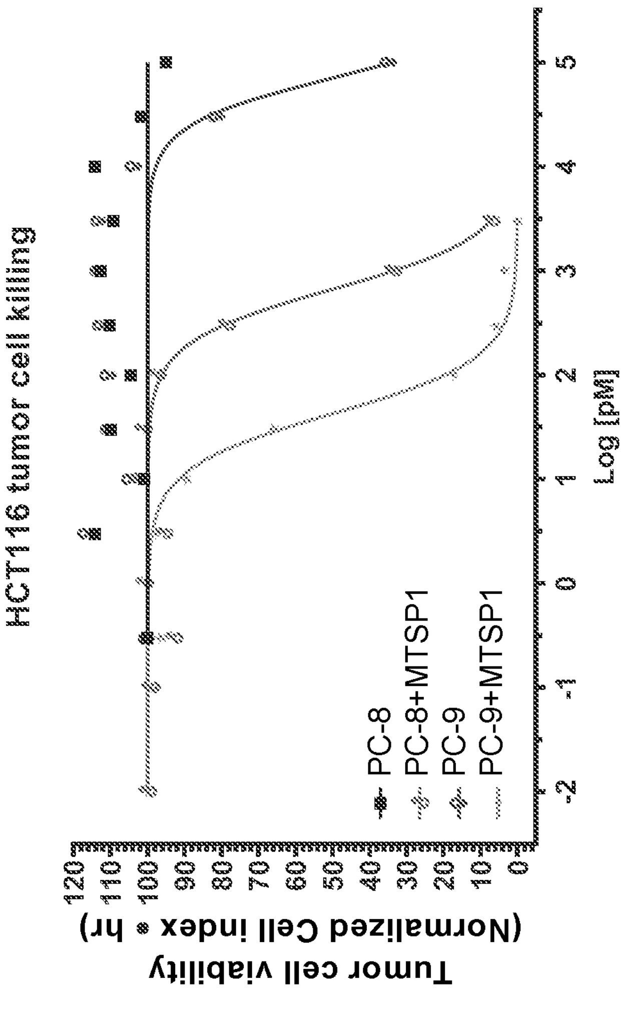
Figure 32E:
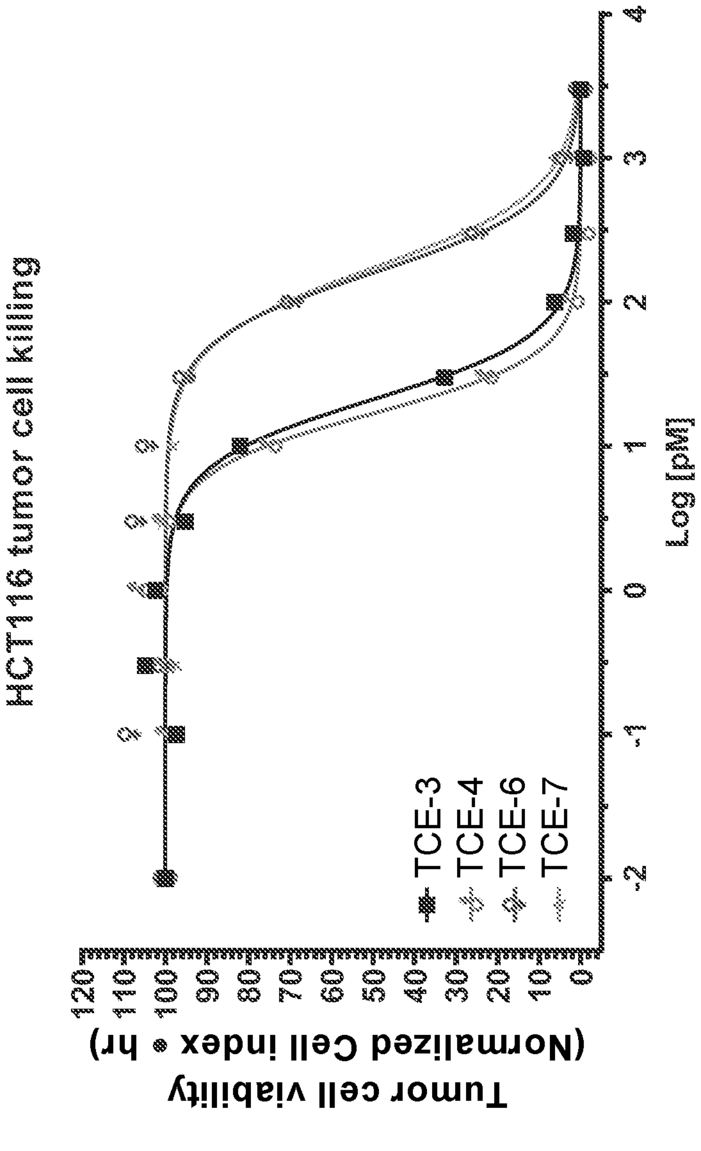
Figure 32F:
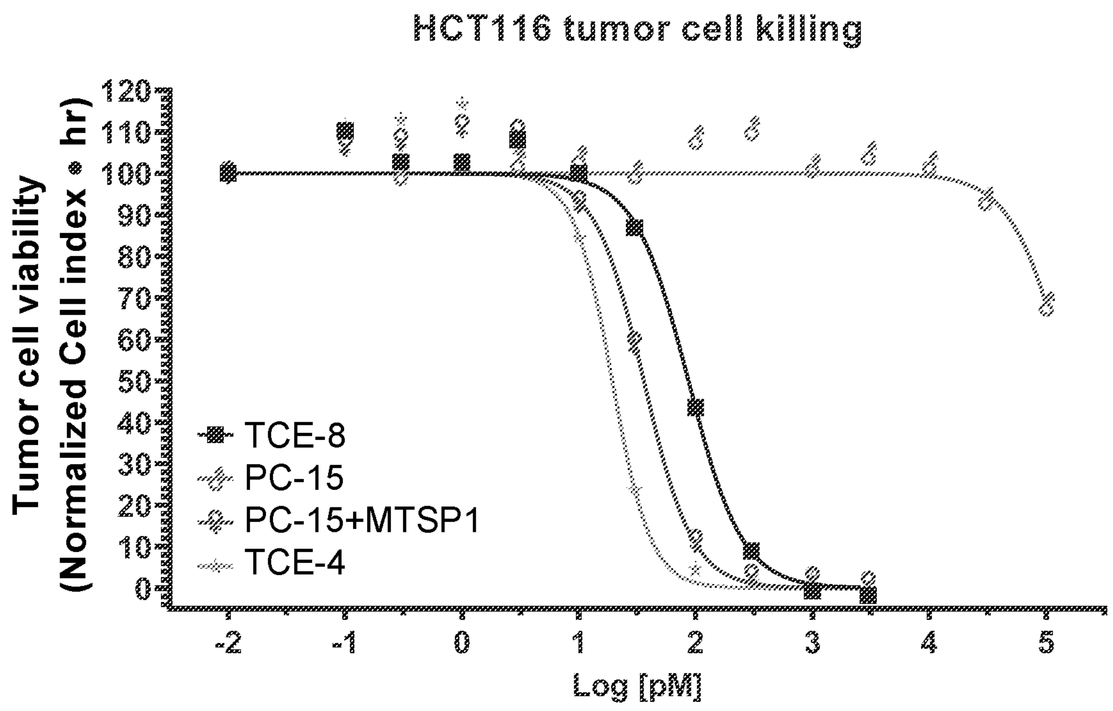
Figure 32G:
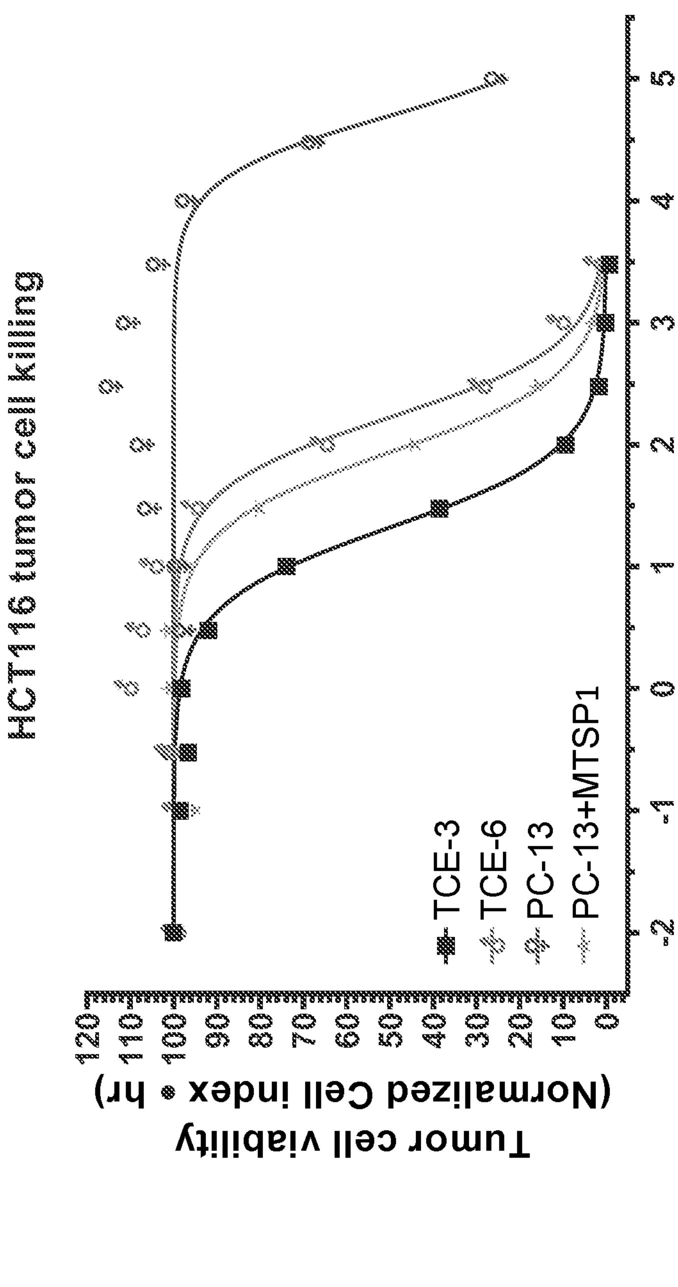
Figure 32H:
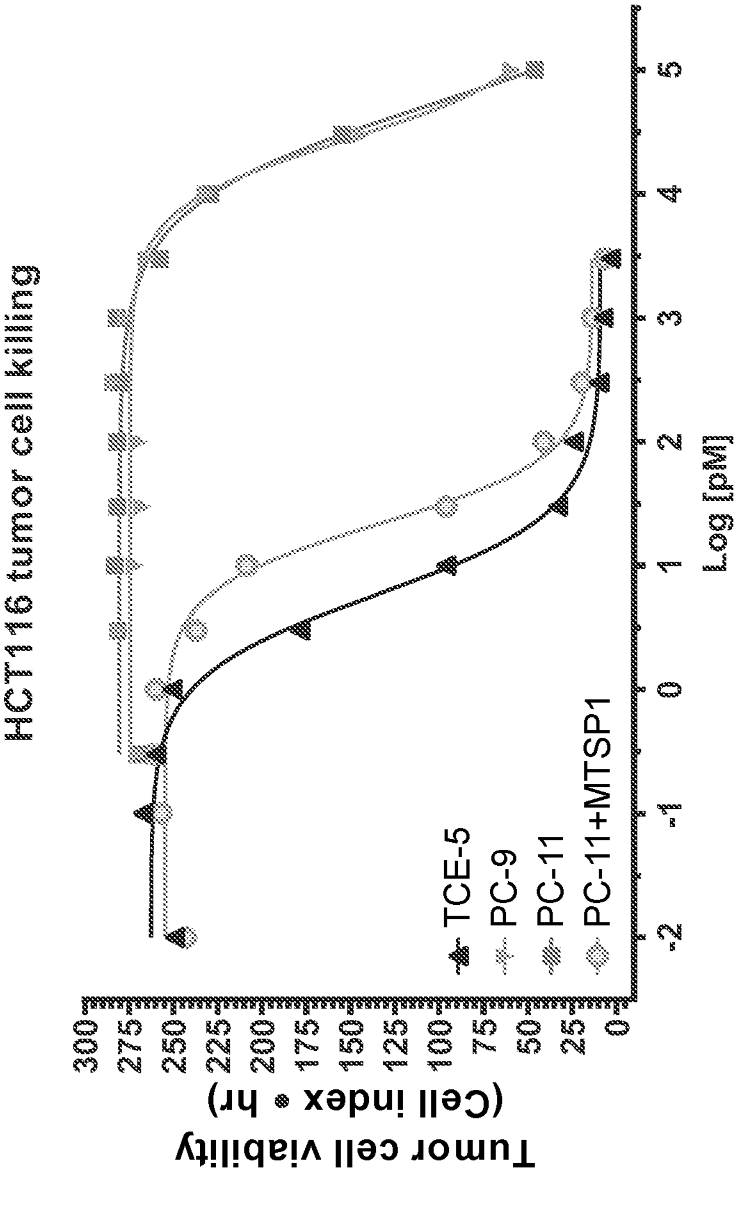
Figure 32I:
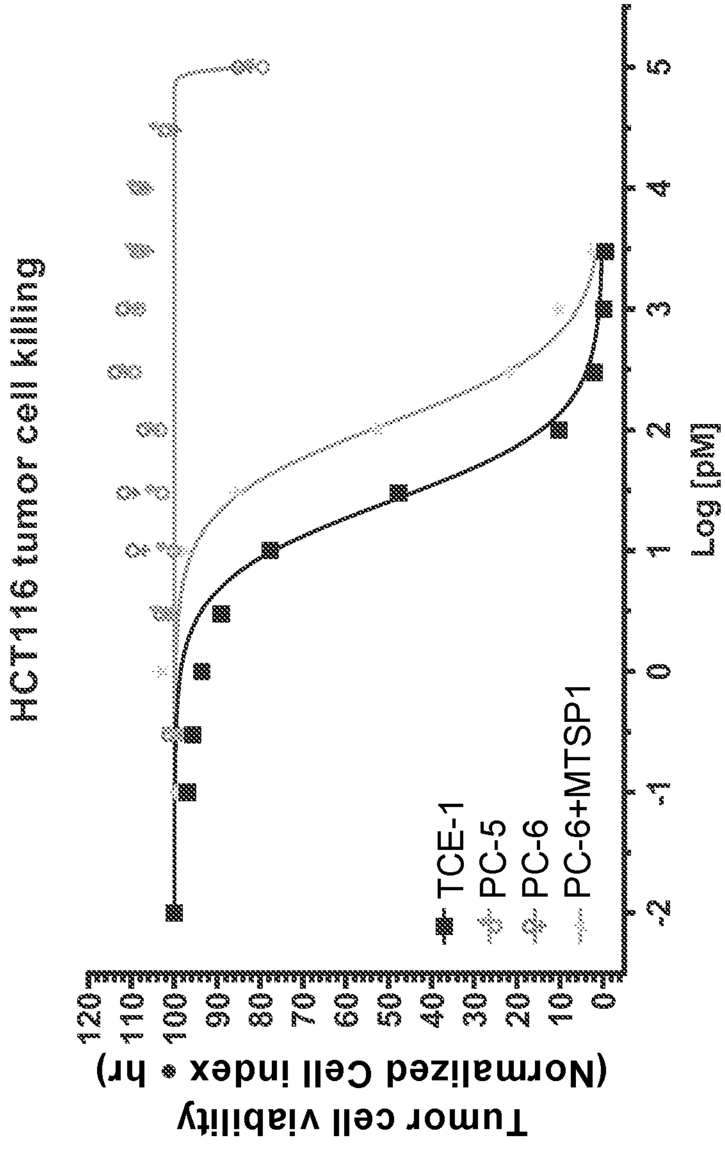
Figure 32J:
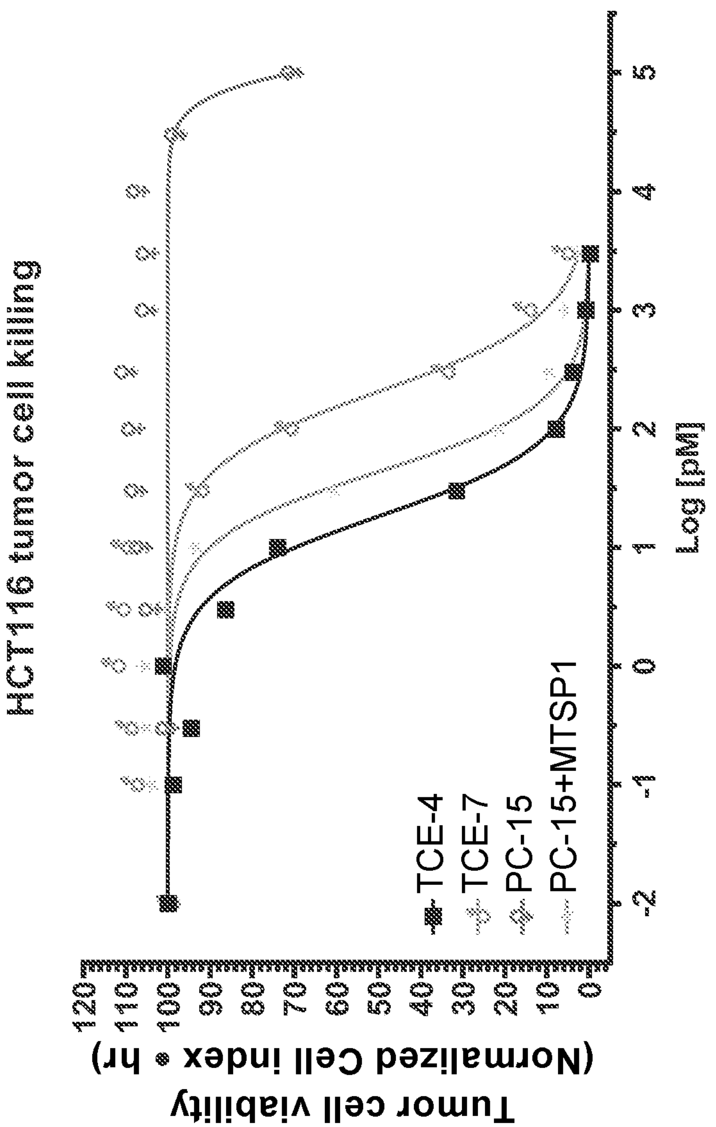

Certain peptides of Table 9 were evaluated for their ability to inhibit αCD3 scFv from binding to the CD3 antigen using ELISA-based competitive inhibition studies. Biotinylated antigen was captured on neutravidin coated plates, quenched using biocytin, and washed. Inhibitory peptides were titrated in a dilution series and pre-incubated with a constant concentration of antibody. Inhibitory peptide and antibody mixtures were then incubated on the antigen captured plates. A horseradish peroxidase conjugate secondary antibody was then used to detect the antibody binding to the plate-bound antigen. The ELISA signal was plotted versus log-scale peptide concentration. A dose dependent decrease of signal was indicative of peptides that compete for antibody binding to the cognate antigen. Graphpad Prism software was used to calculate the inhibitory concentrations of peptide required to achieve 50% maximal signal ($IC_{50}$s). FIG. 31 shows inhibition of αCD3 scFV binding to CD3 by peptide-67 and peptide-70. $IC_{50}$s for peptide-67 and peptide-70 are also shown in FIG. 31.

Example 8: Cytotoxicity Studies in TROP2 Positive Tumor Cell Lines HCT116, NCI-11292, and MDAMB231

Figure 33A:
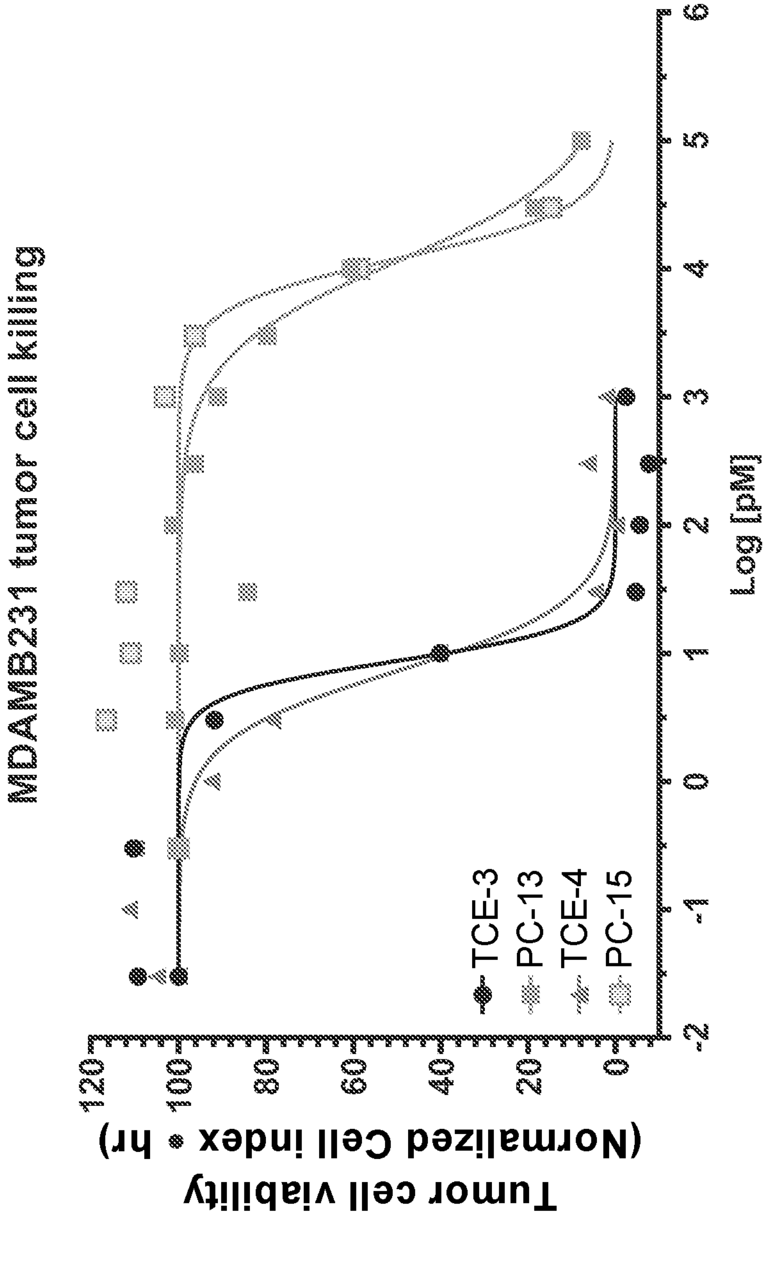
FIGS. 33A-33P illustrate killing of TROP2 positive MDAMB231 tumor cells by polypeptide complexes in the presence of CD8+ T-cells.
Figure 33B:
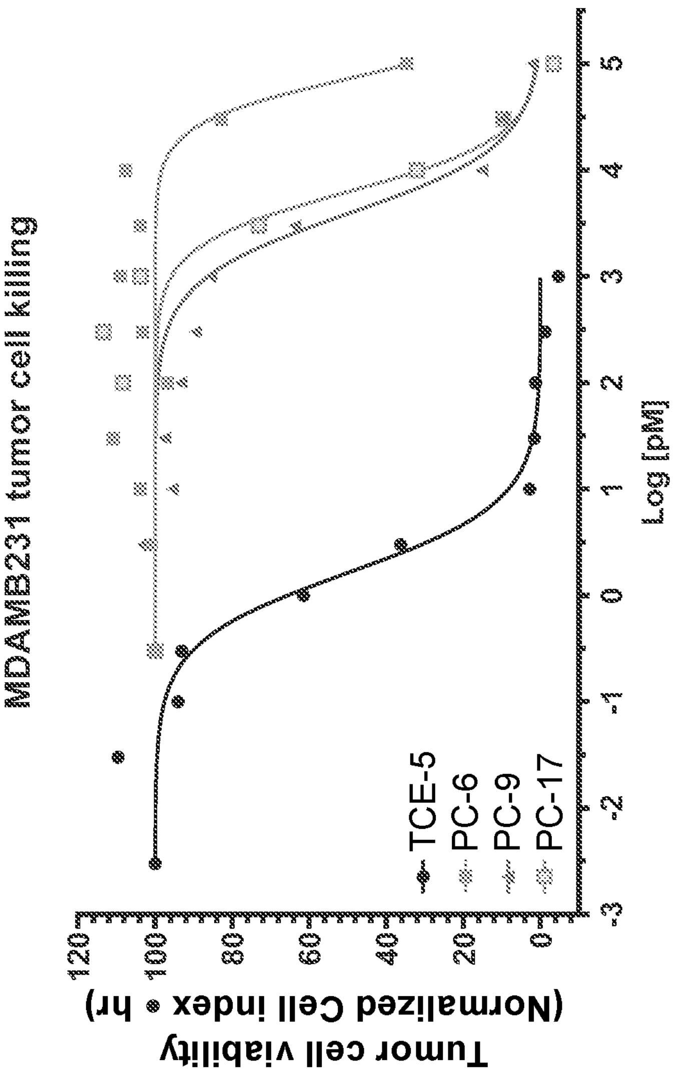
Figure 33C:
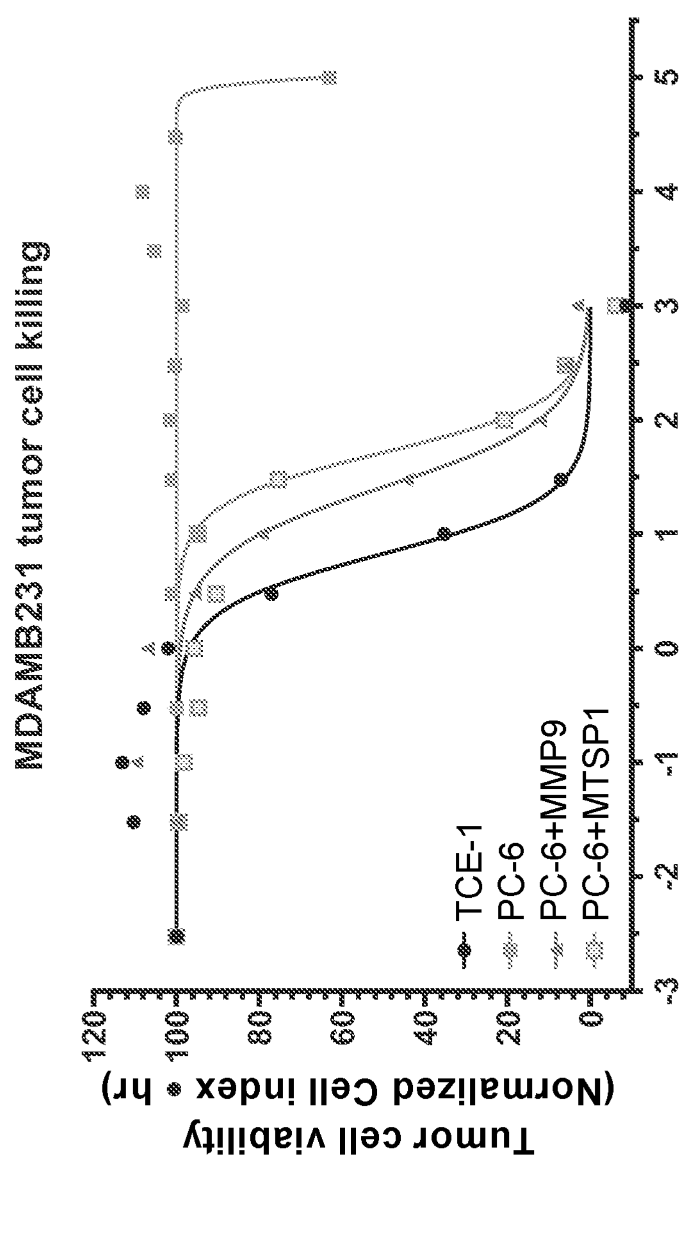
Figure 33D:
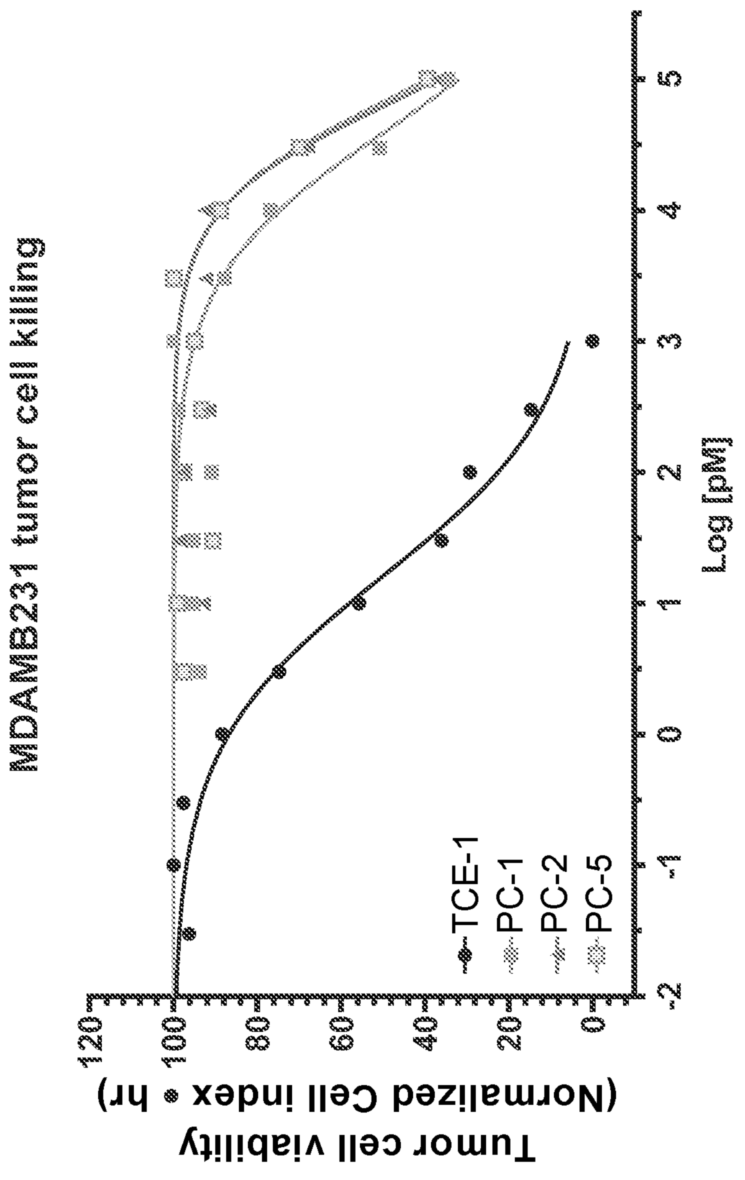
Figure 33E:
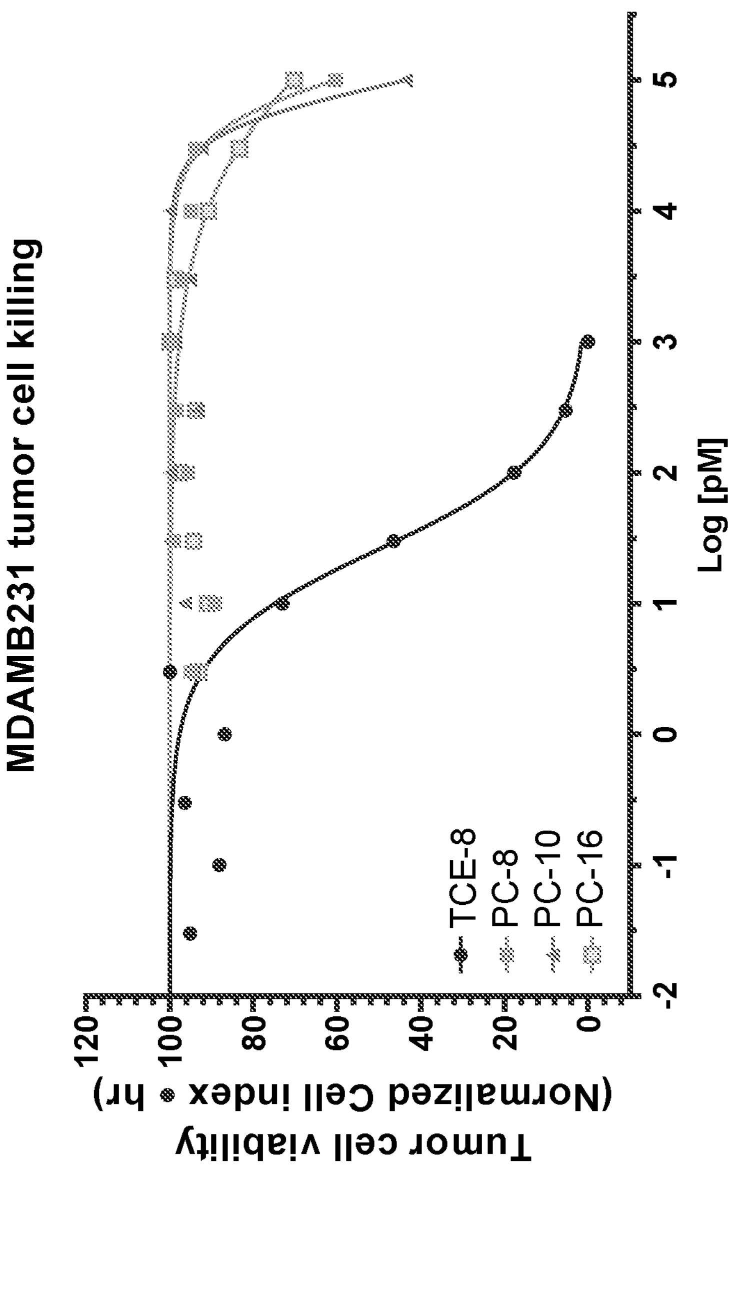
Figure 33F:
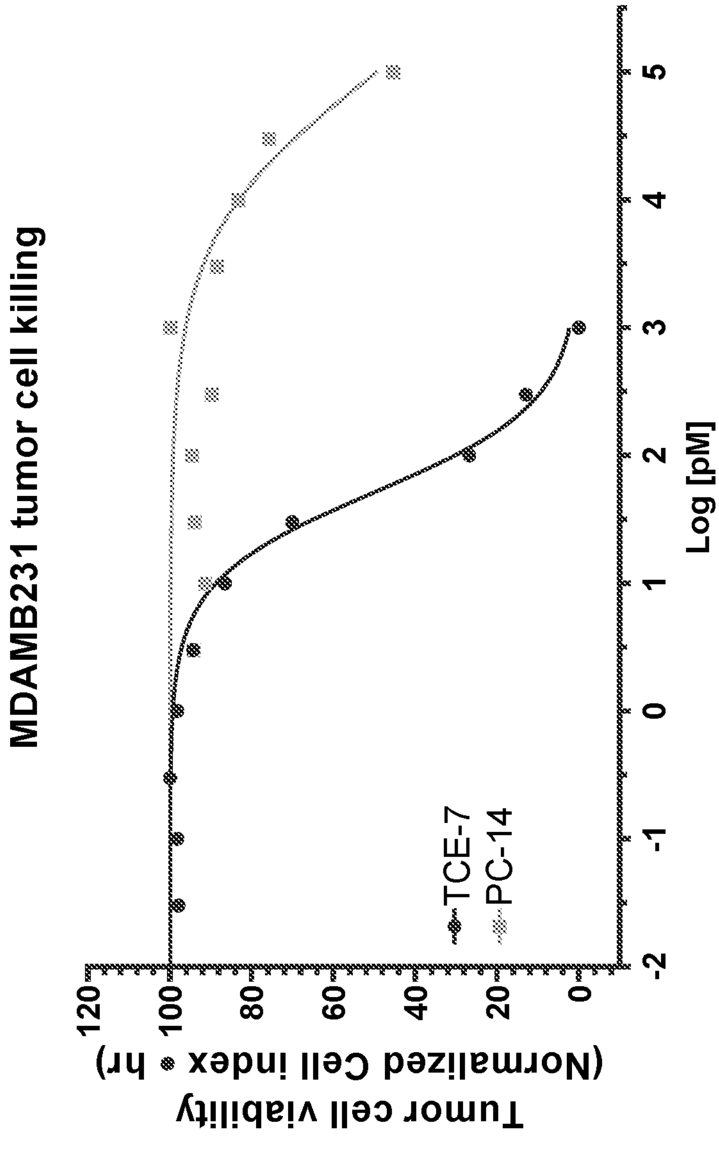
Figure 33G:
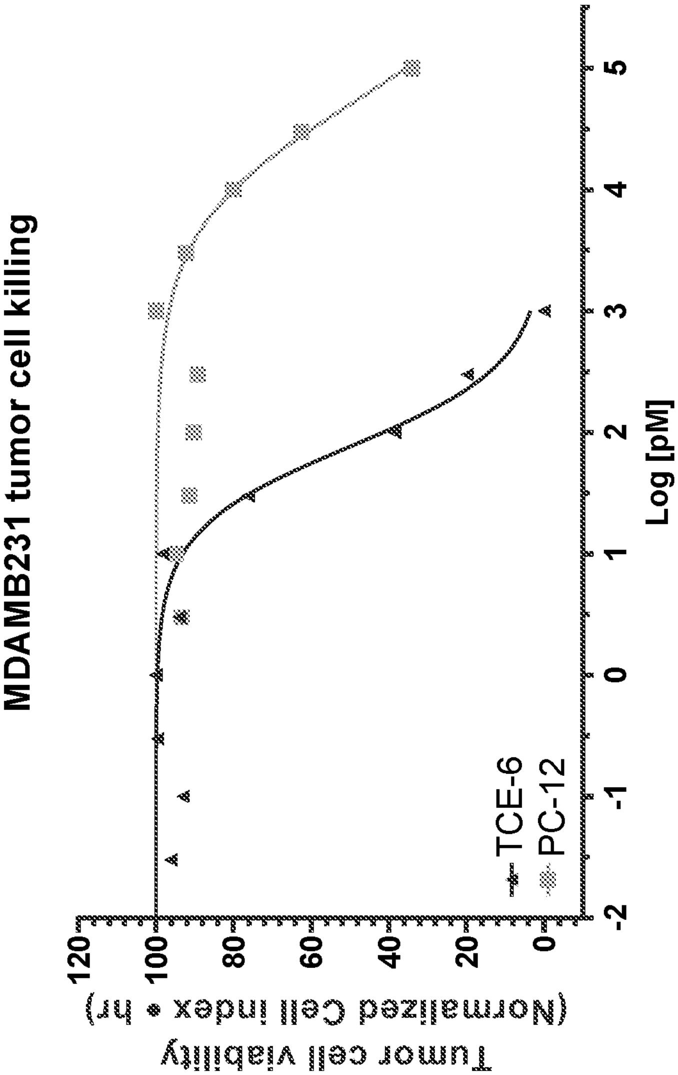
Figure 33H:
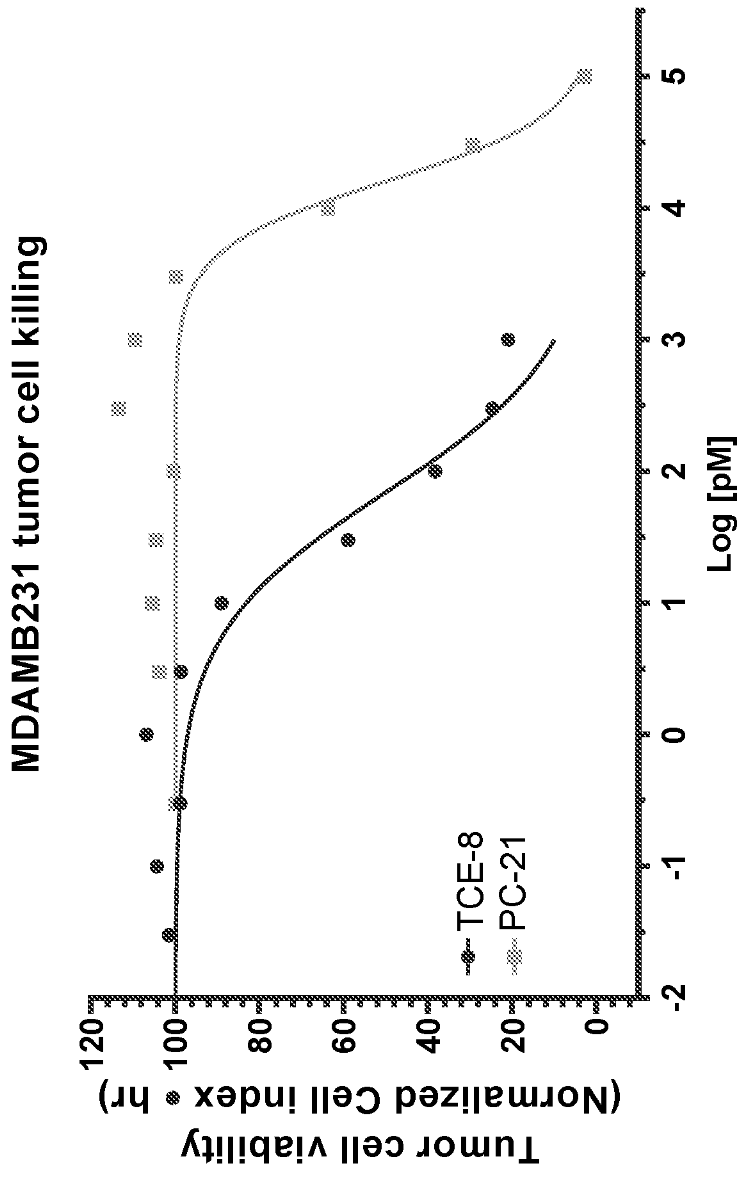
Figure 33I:
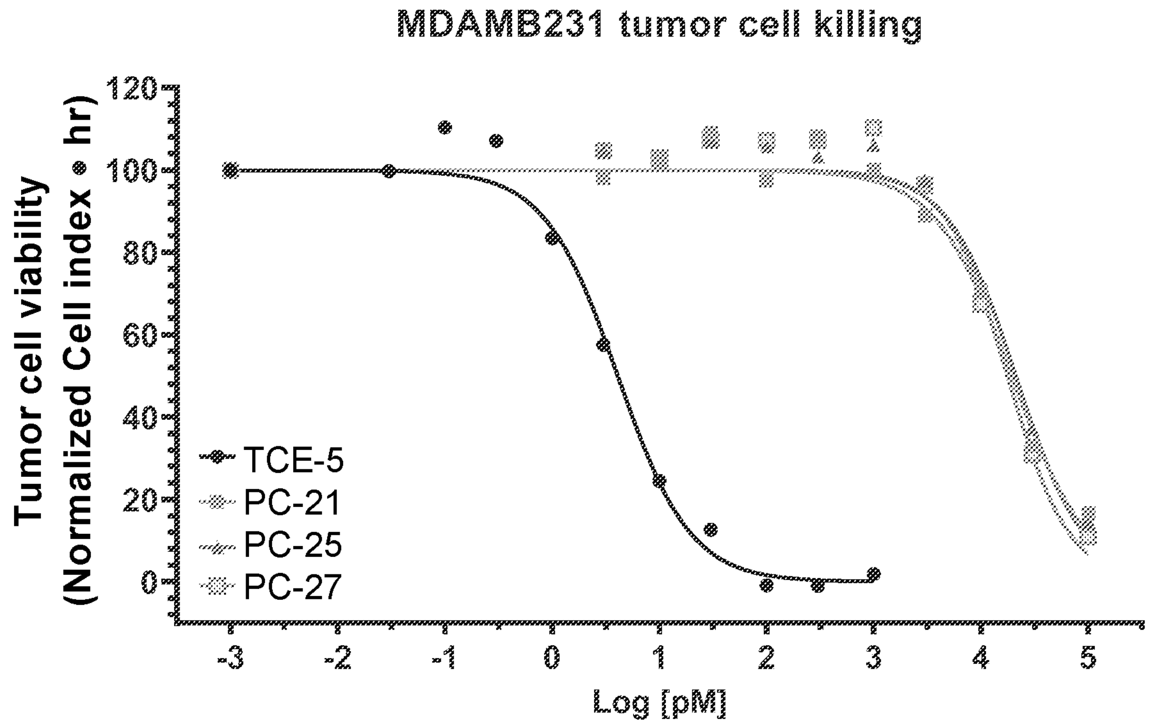
Figure 33J:
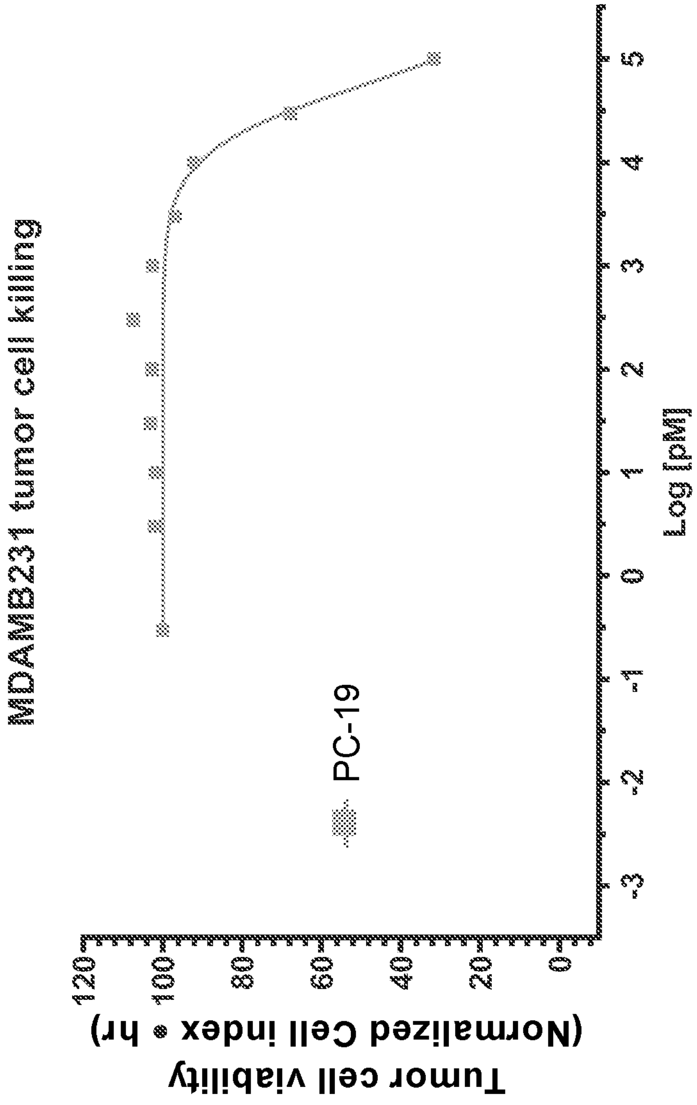
Figure 33K:
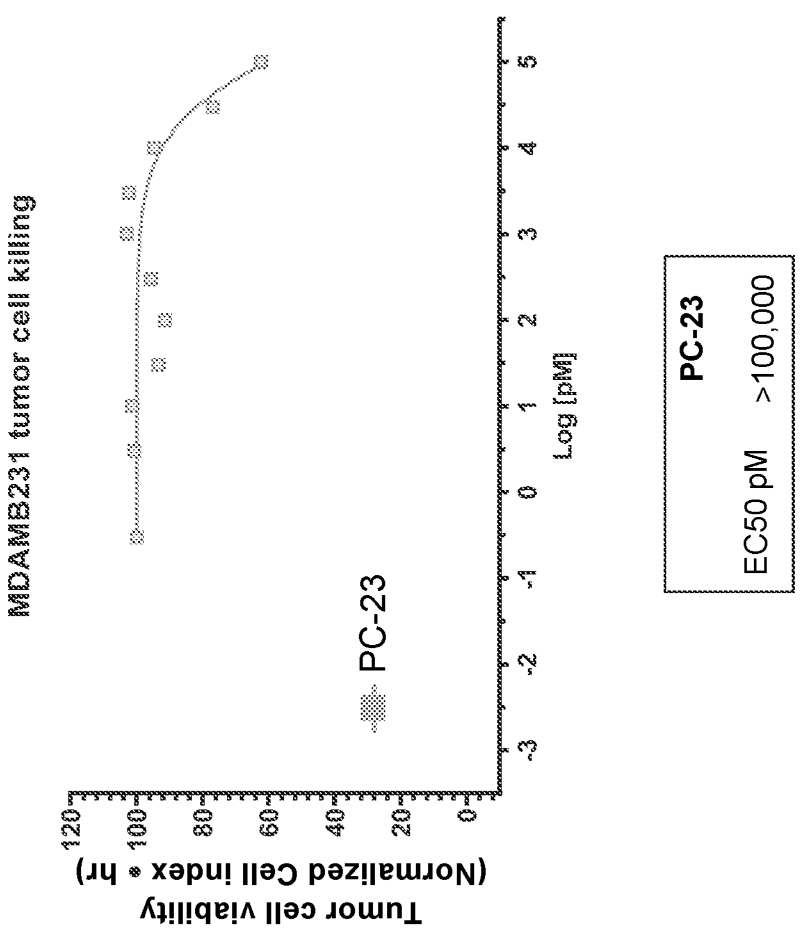
Figure 33L:
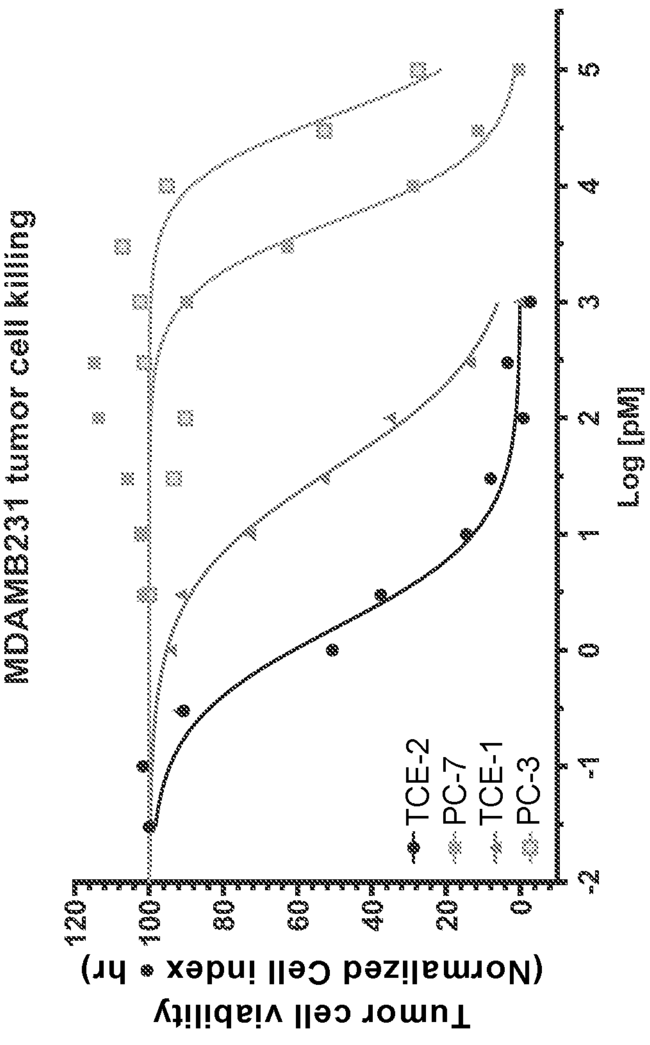
Figure 33M:
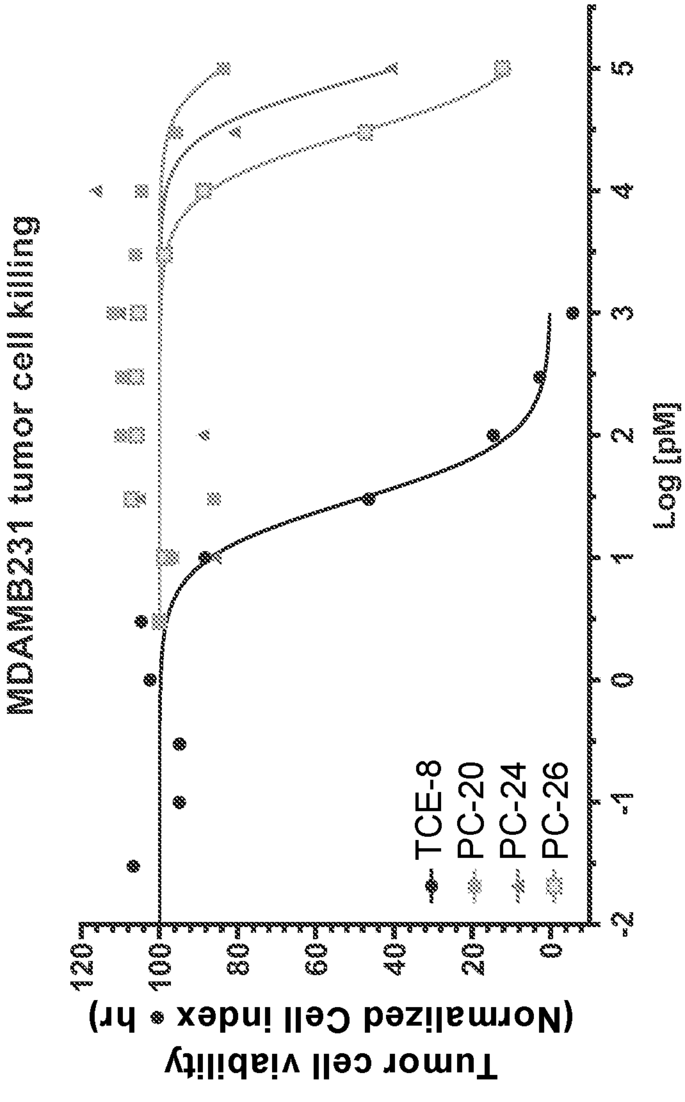
Figure 33N:
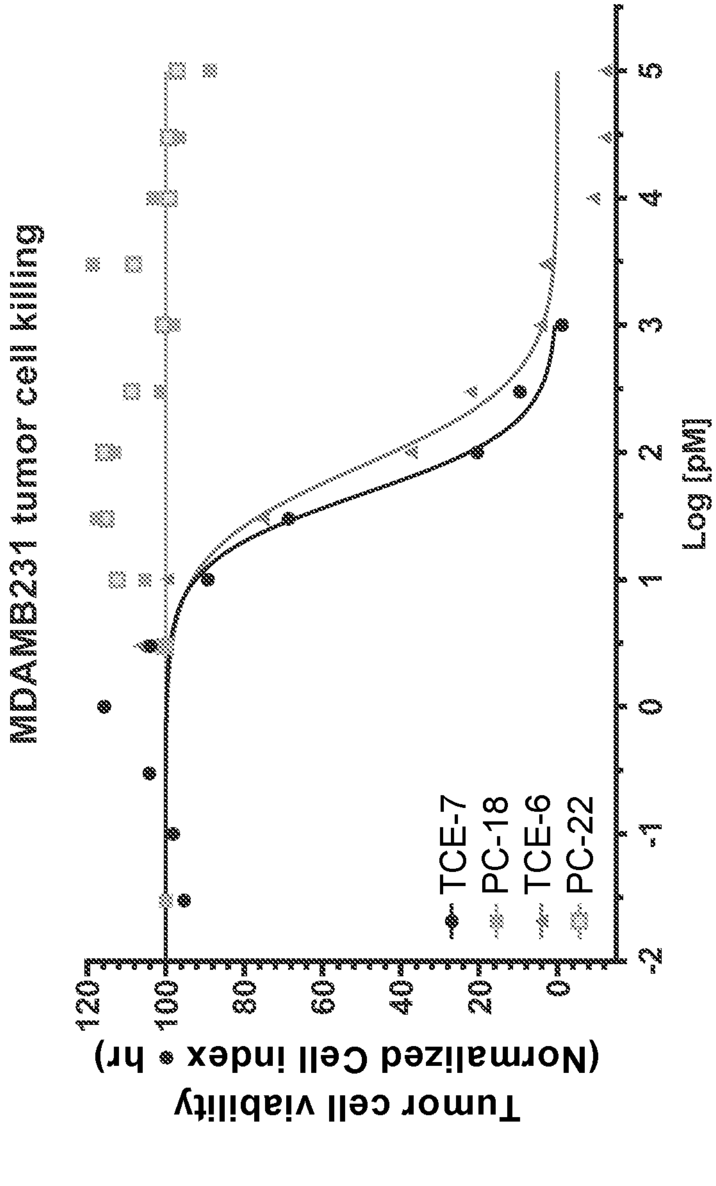
Figure 33O:
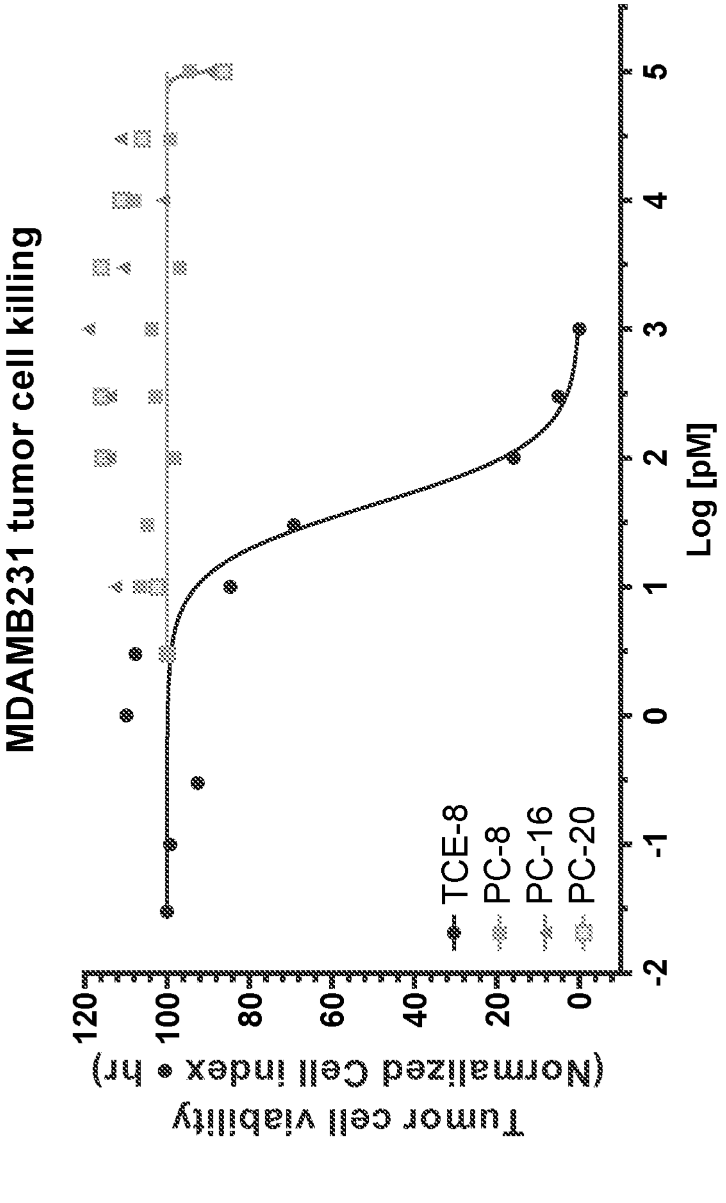
Figure 33P:
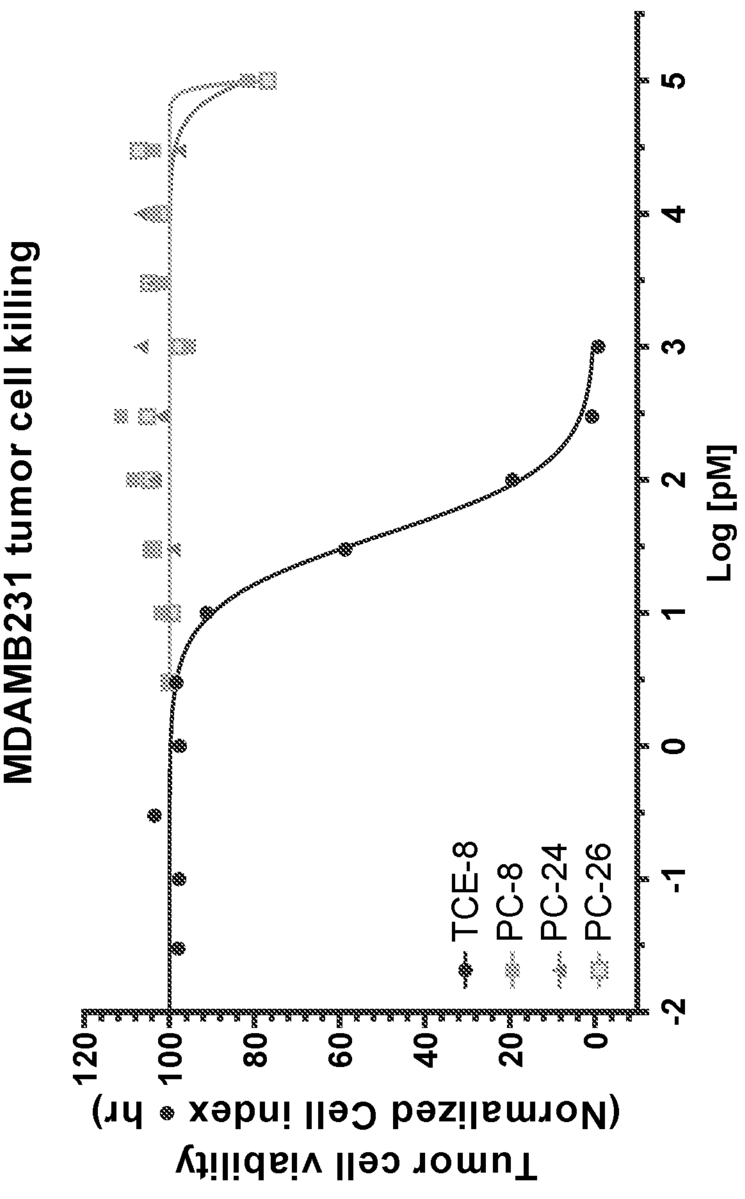
Figure 34A:
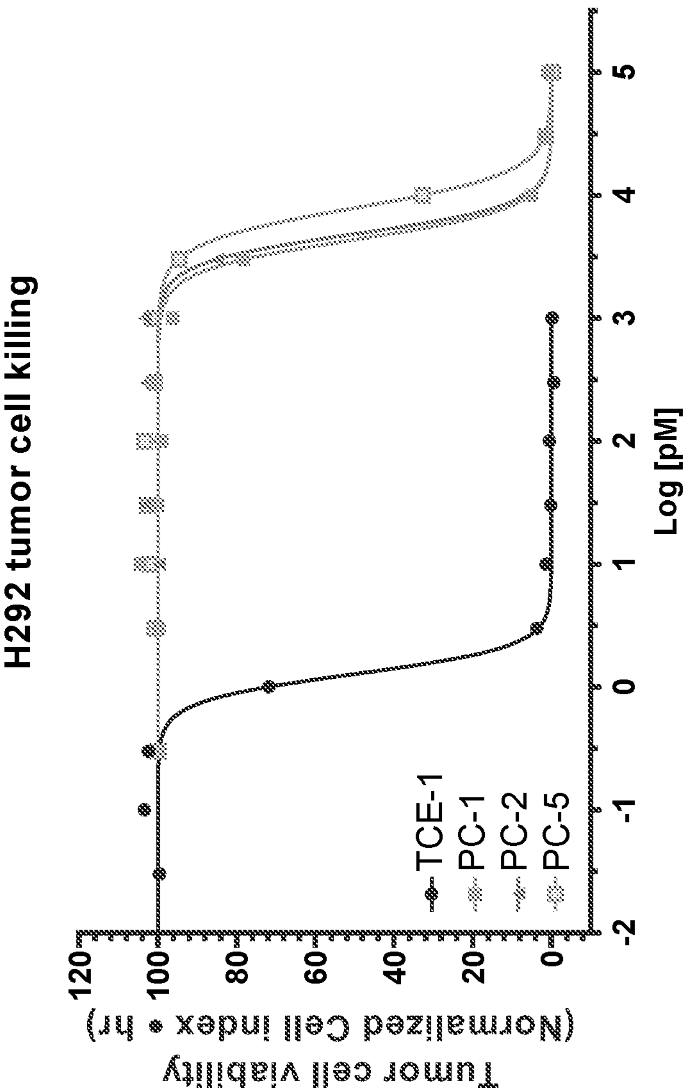
FIGS. 34A-34T illustrate killing of TROP2 positive NCI-H292 tumor cells by polypeptide complexes in the presence of CD8+ T-cells.
Figure 34B:
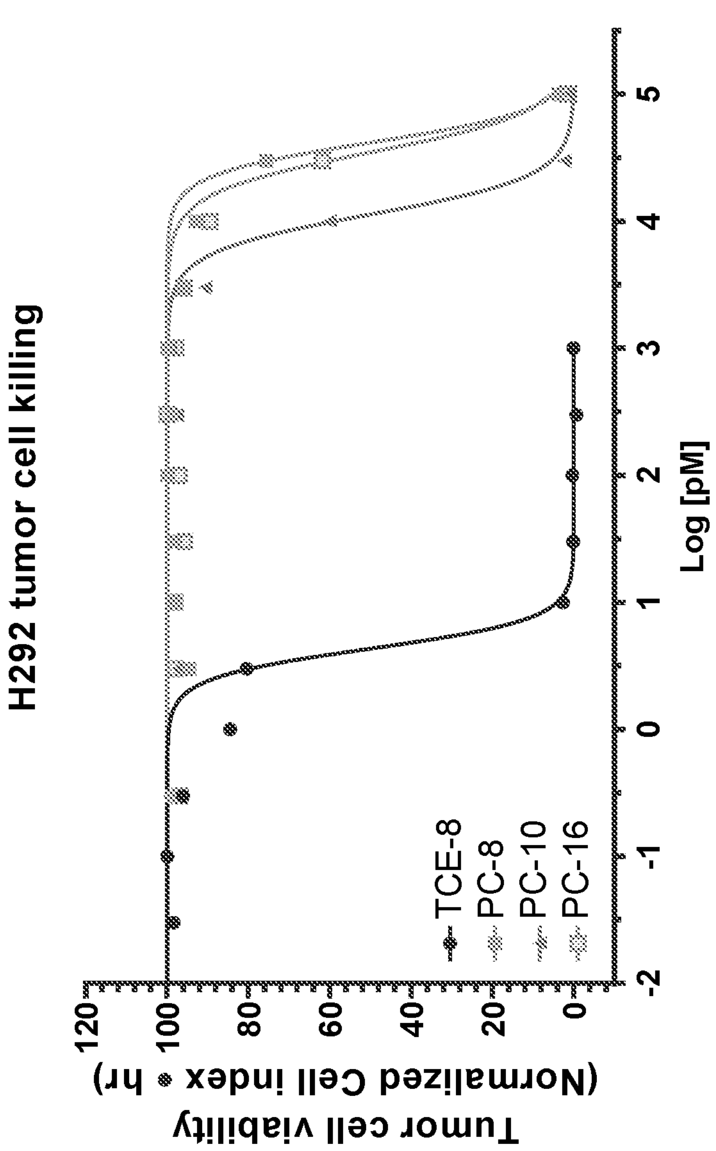
Figure 34C:
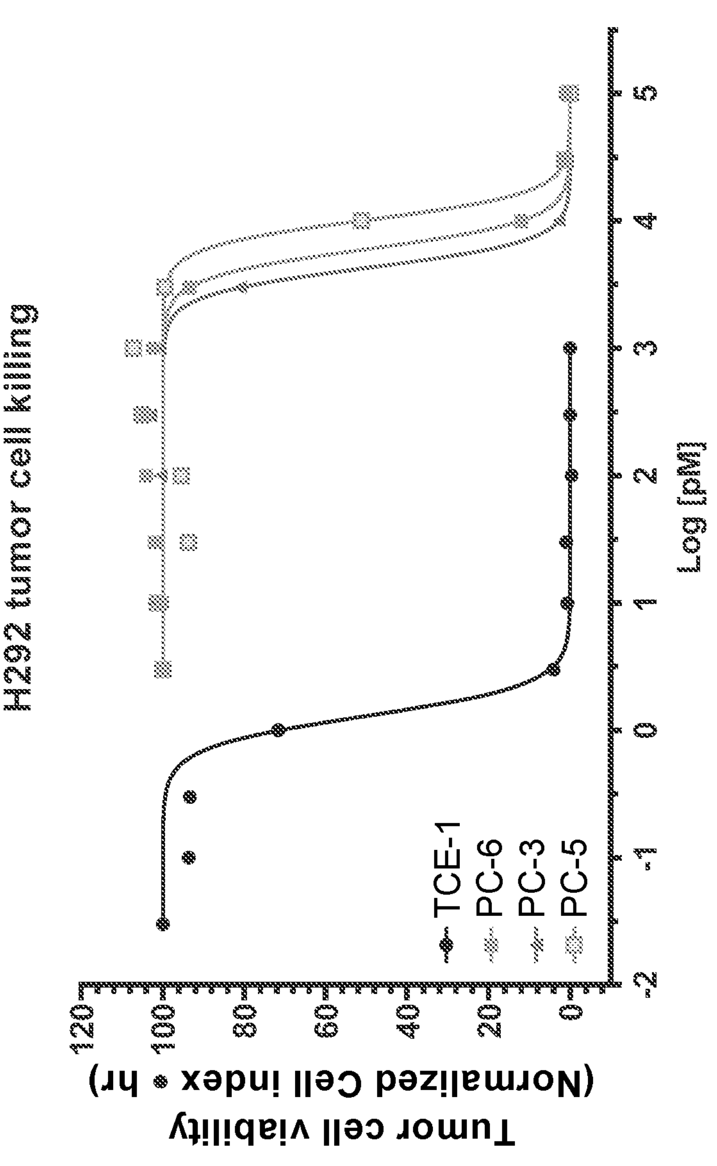
Figure 34D:
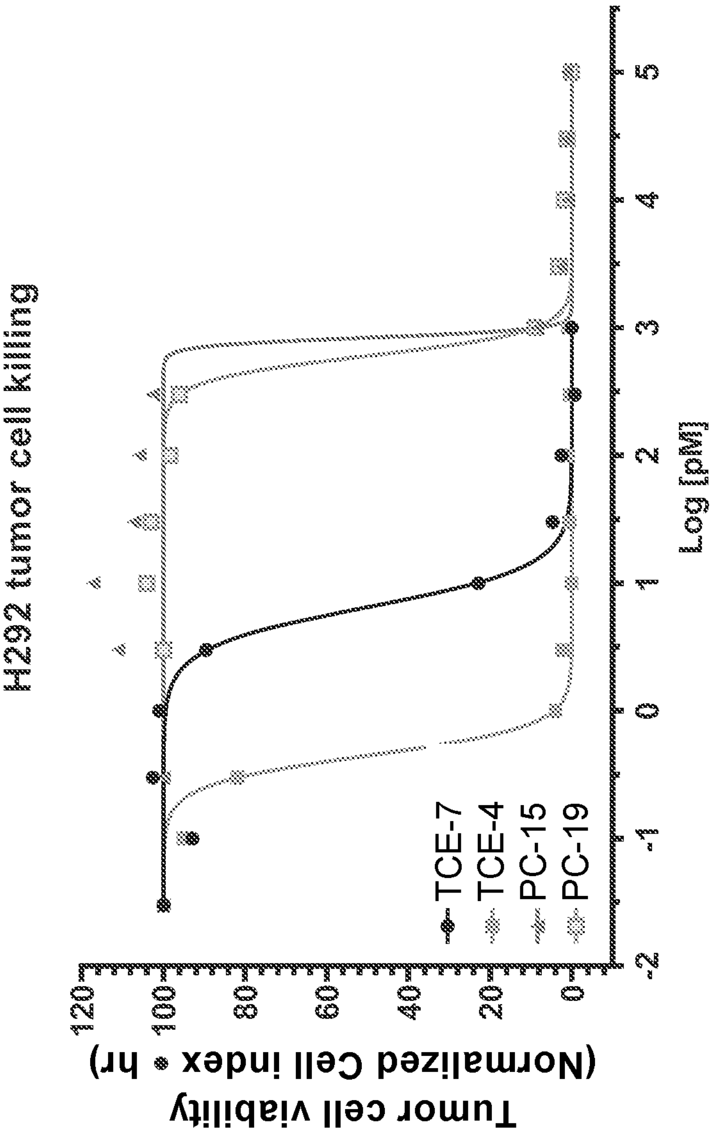
Figure 34E:
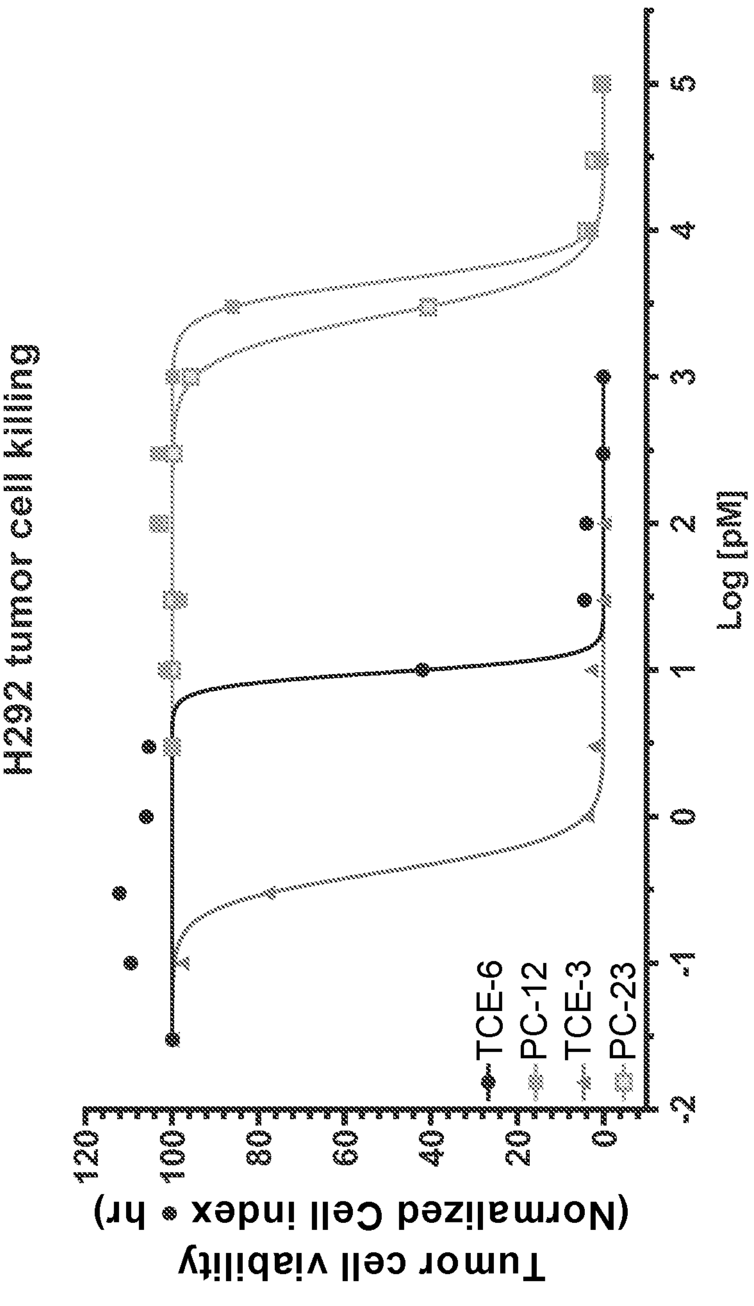
Figure 34F:
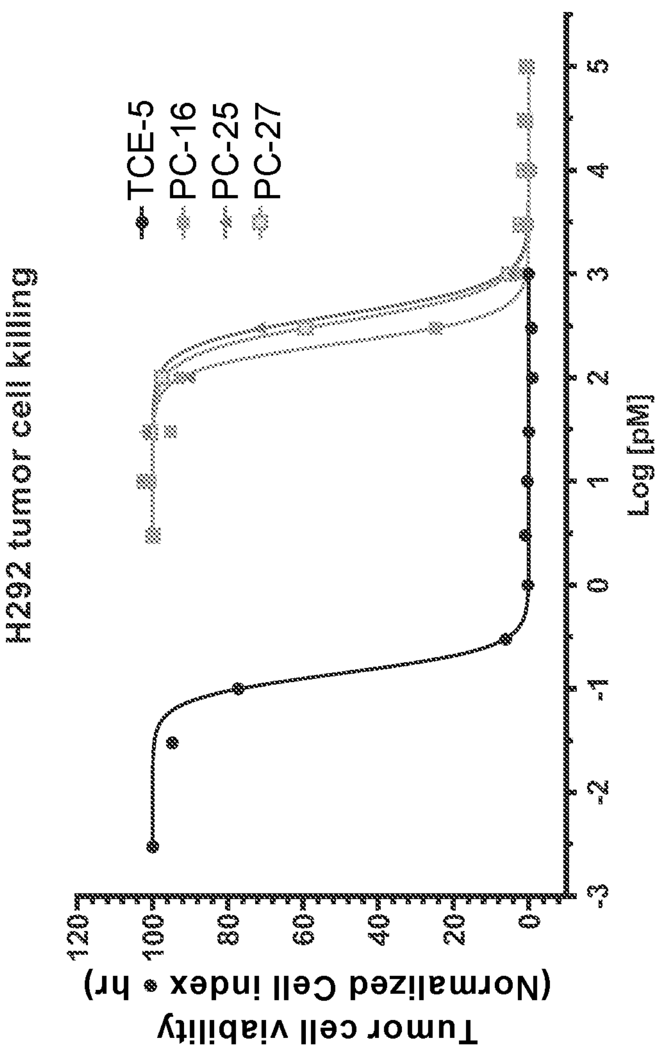
Figure 34G:
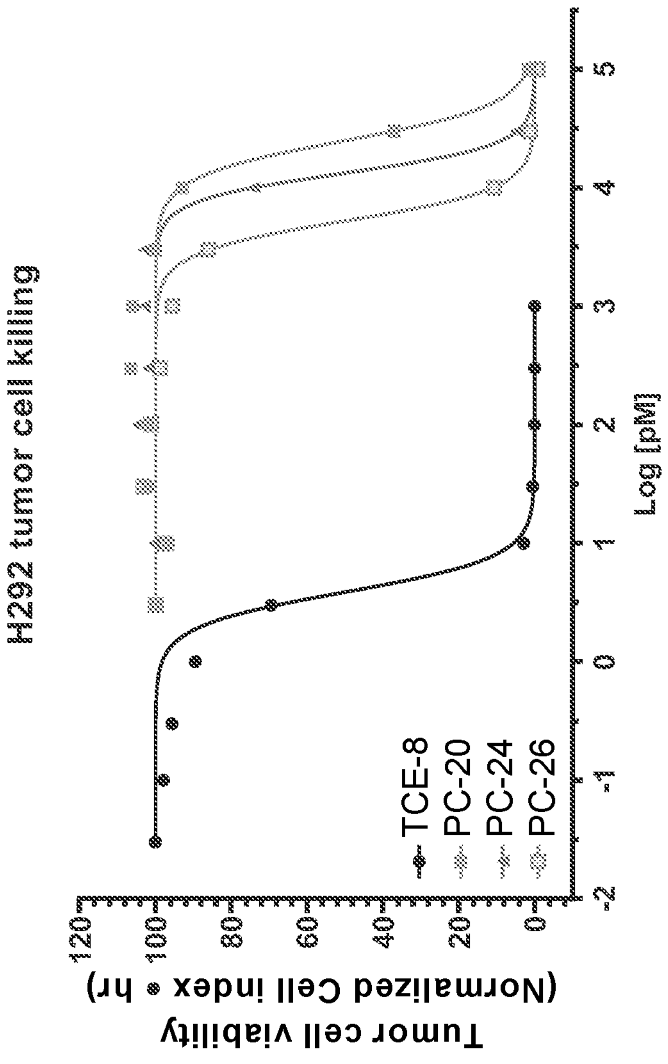
Figure 34H:
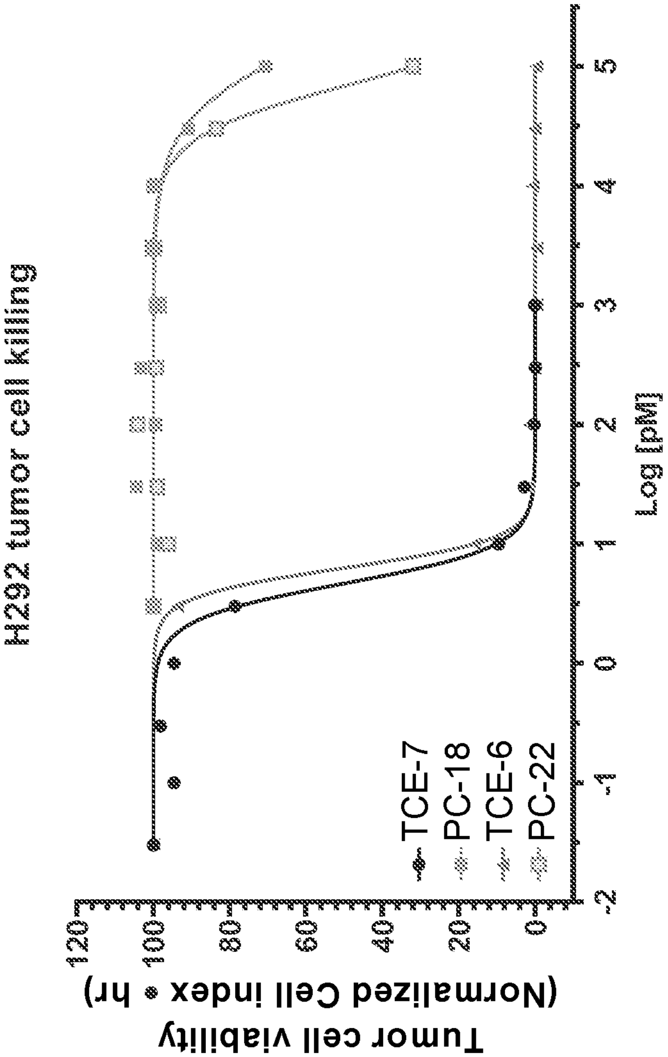
Figure 34I:
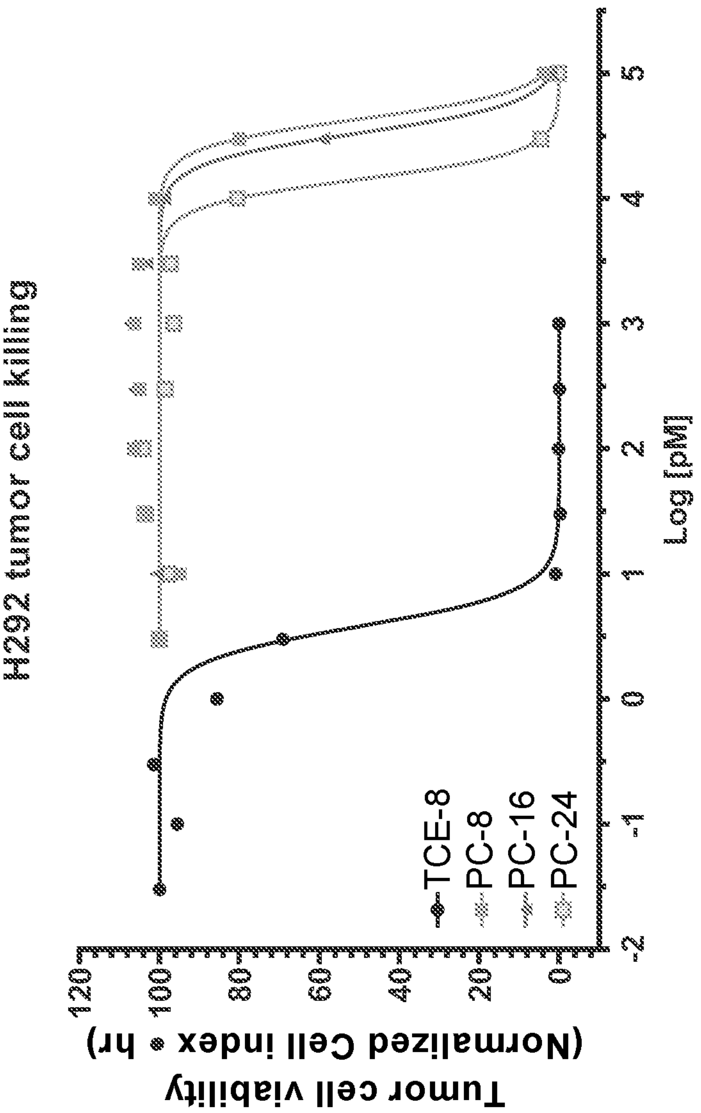
Figure 34J:
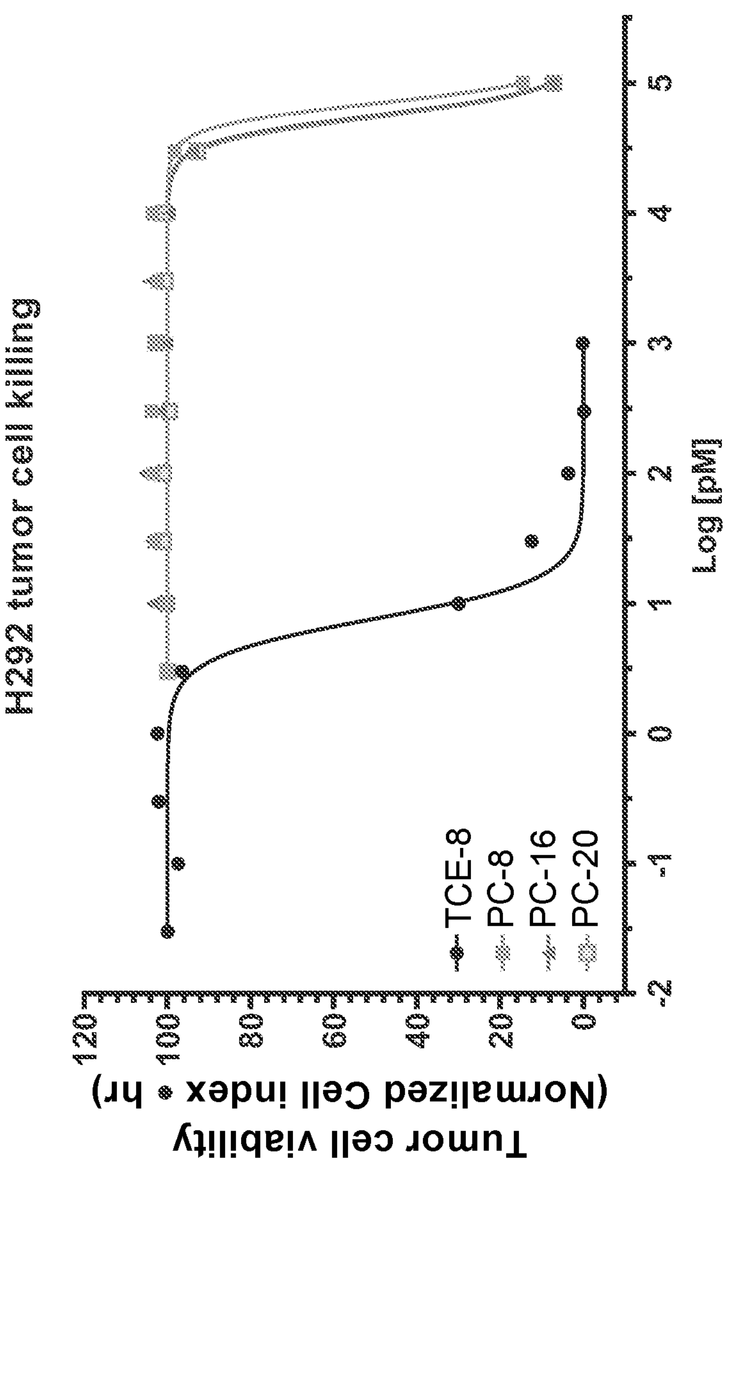
Figure 34K:
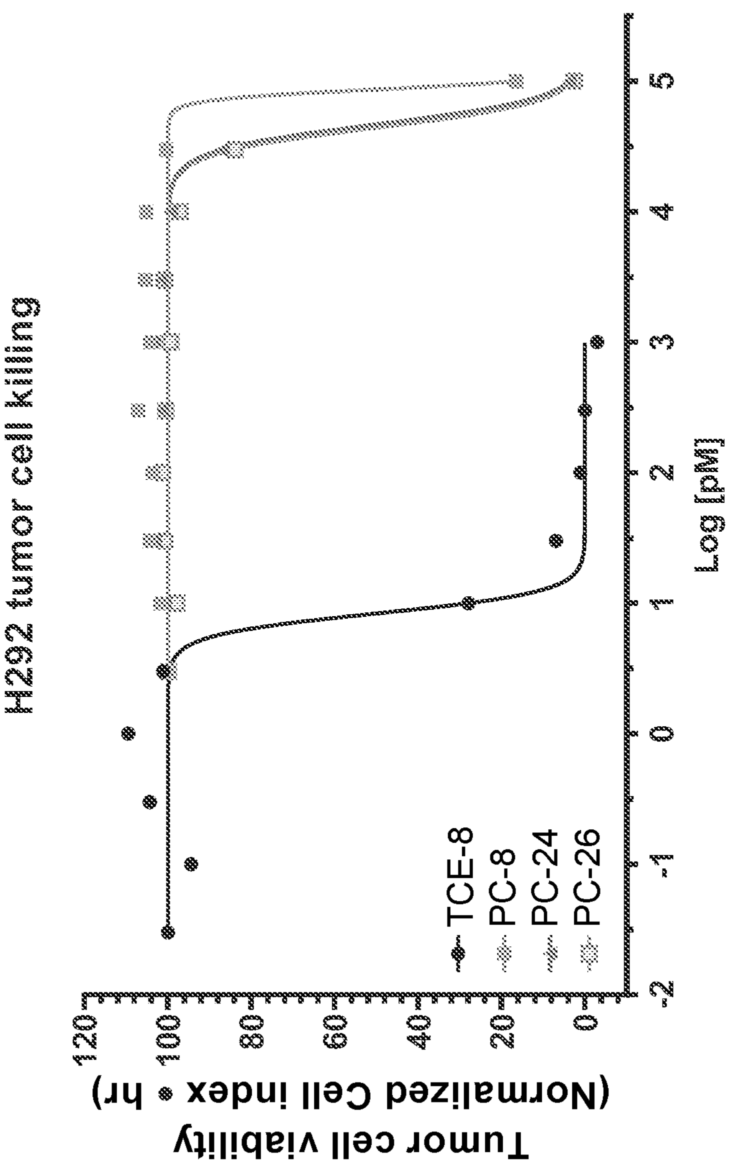
Figure 34L:
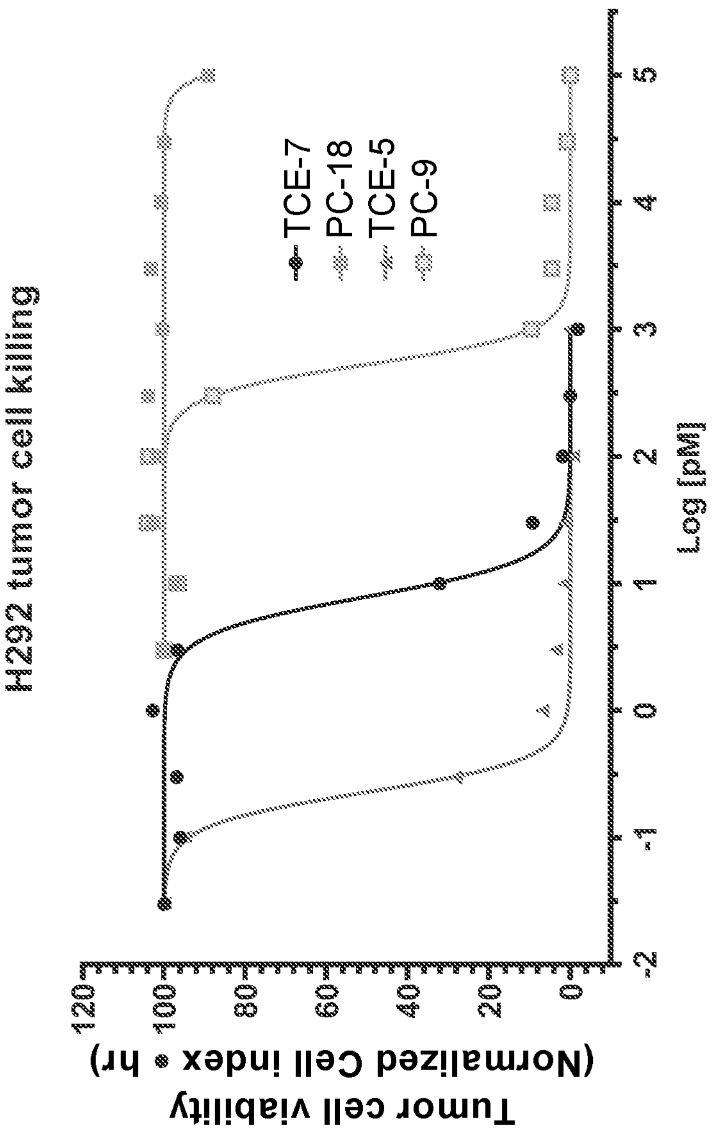
Figure 34M:
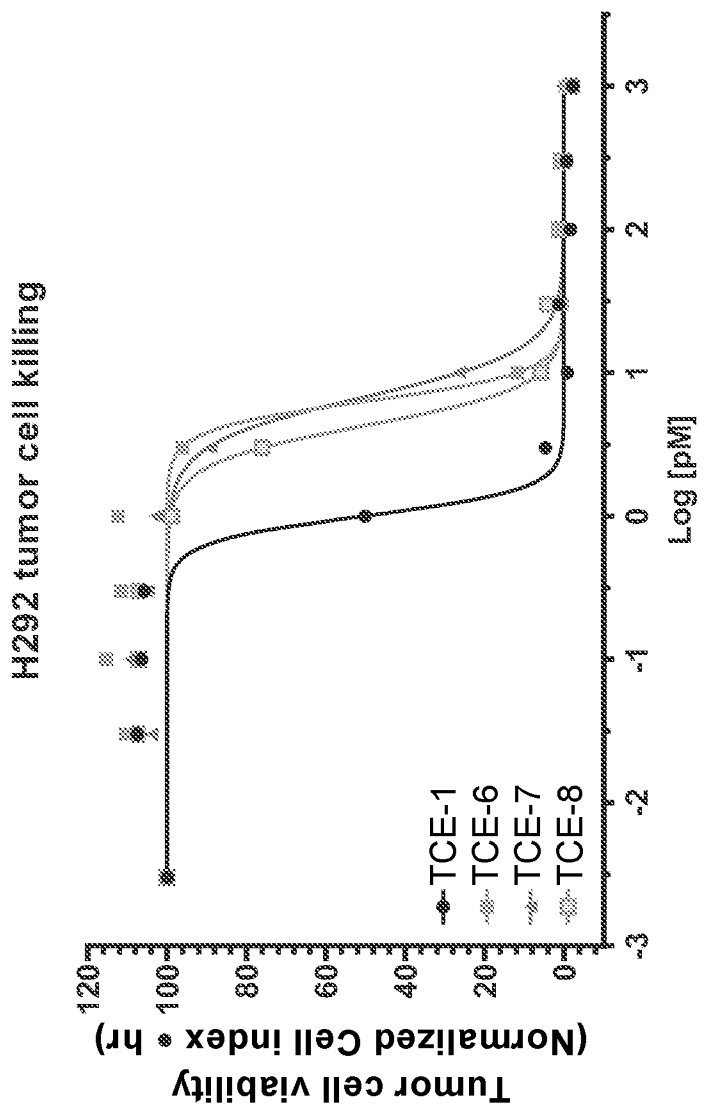
Figure 34N:
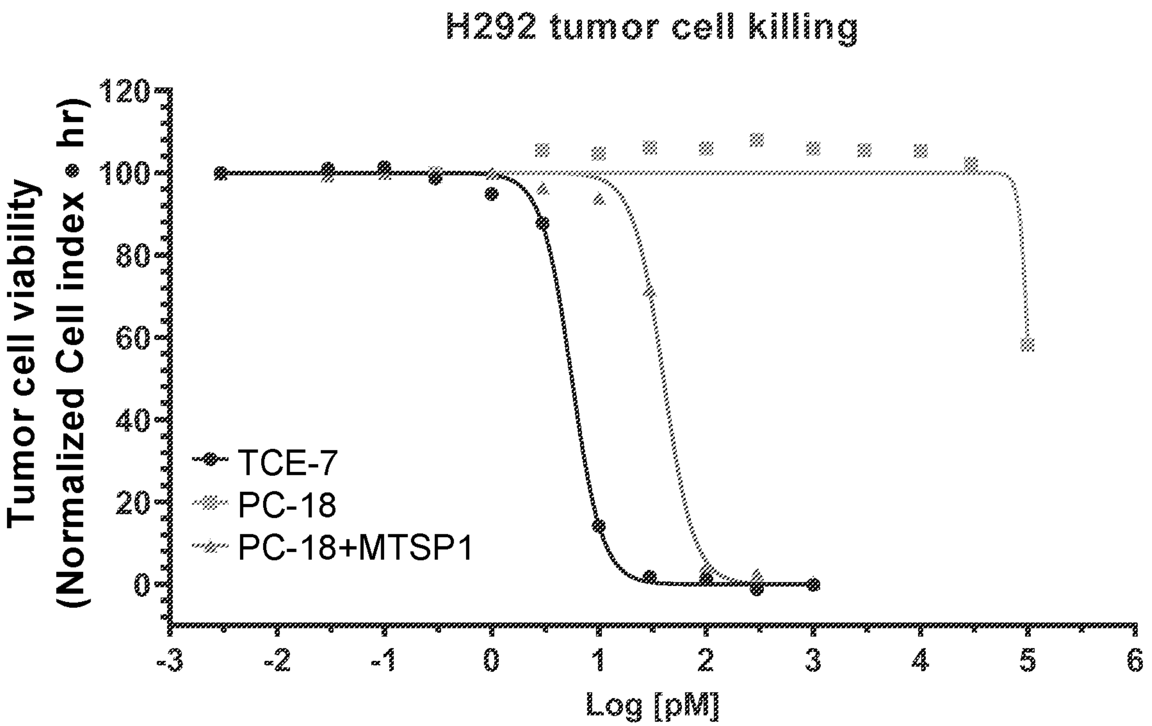
Figure 34O:
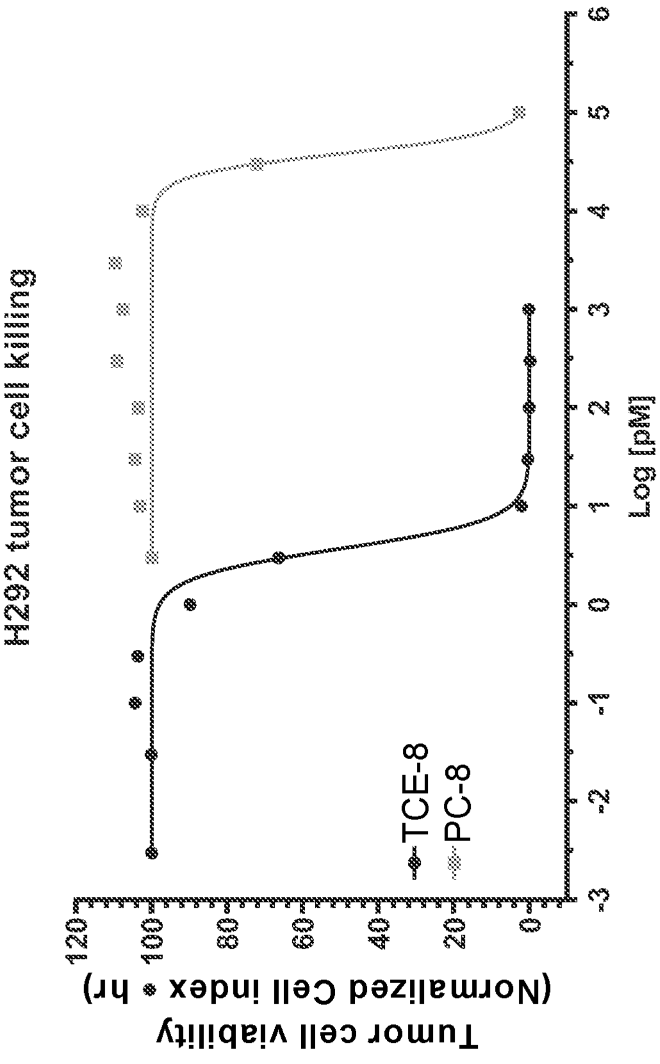
Figure 34P:
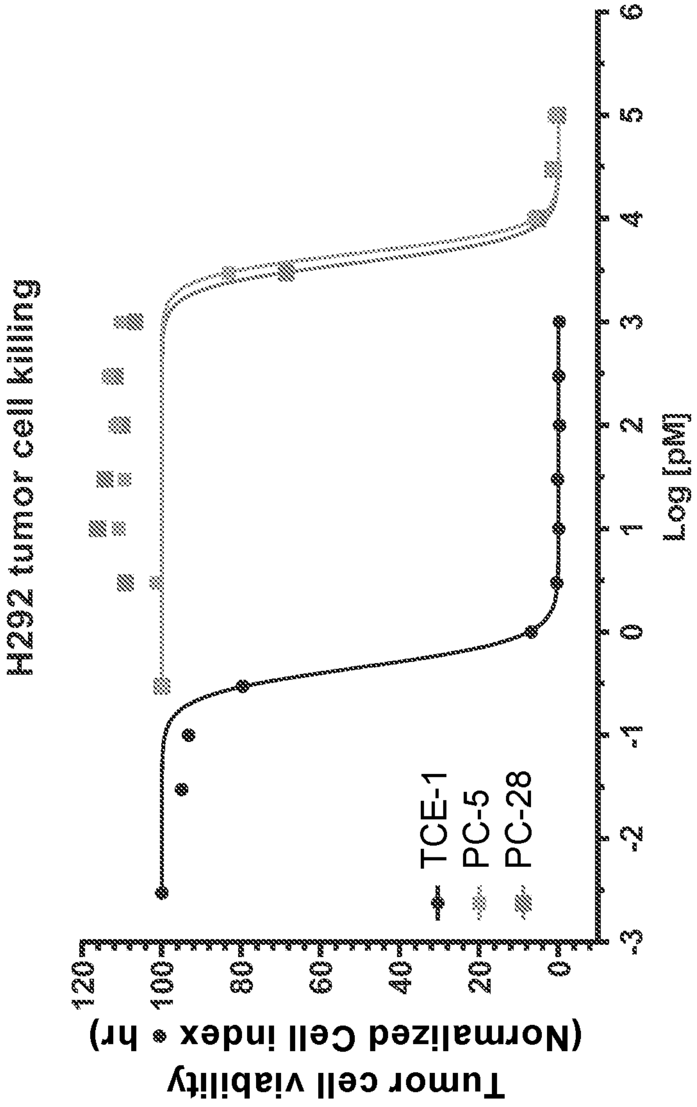
Figure 34Q:
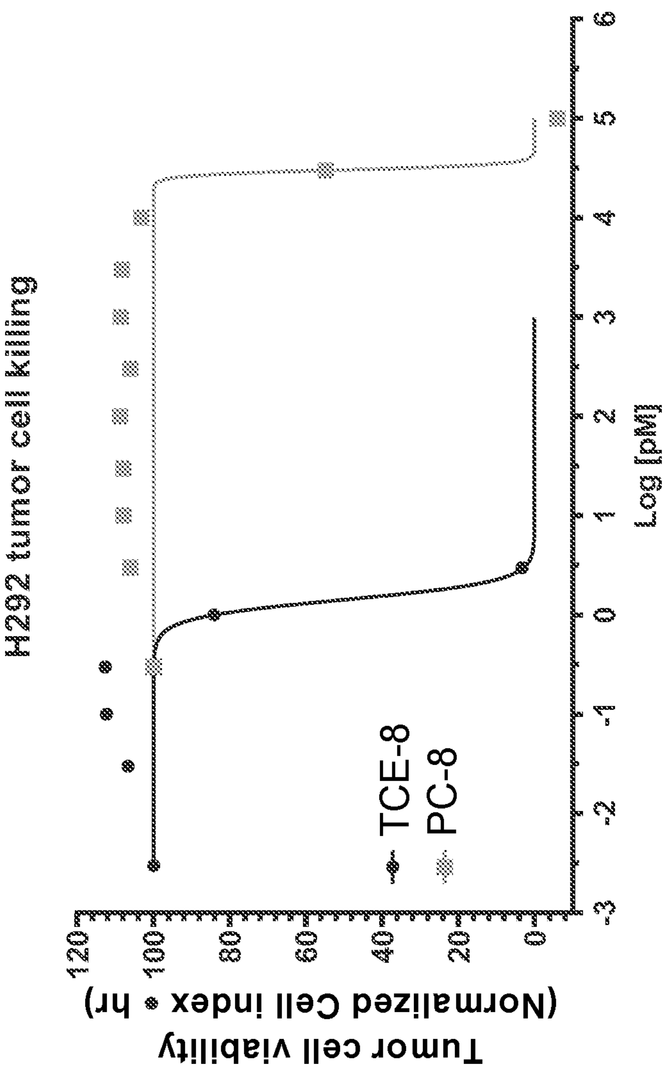
Figure 34R:
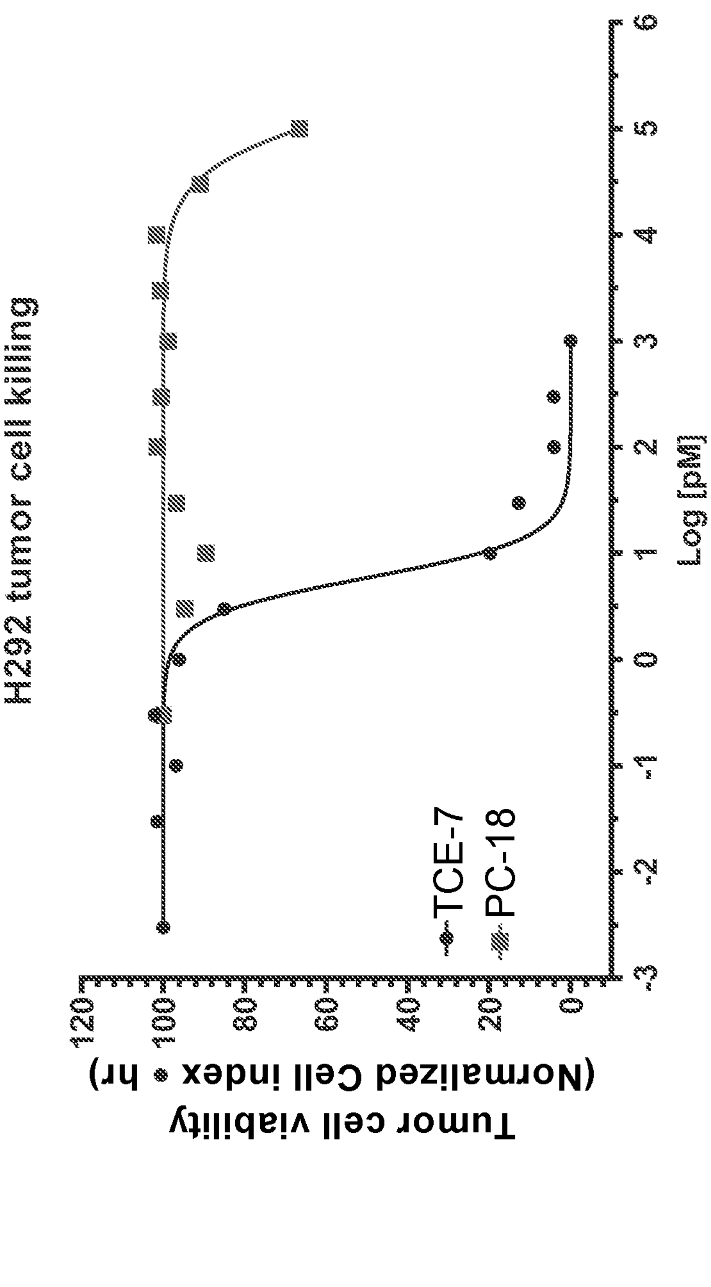
Figure 34S:
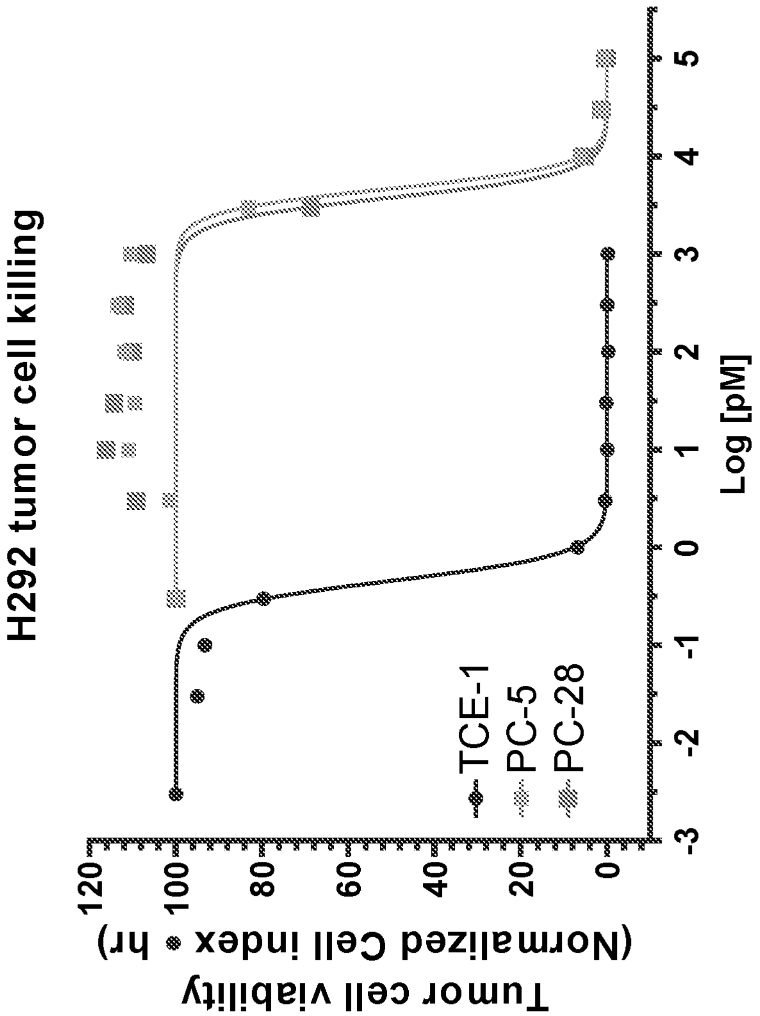
Figure 34T:
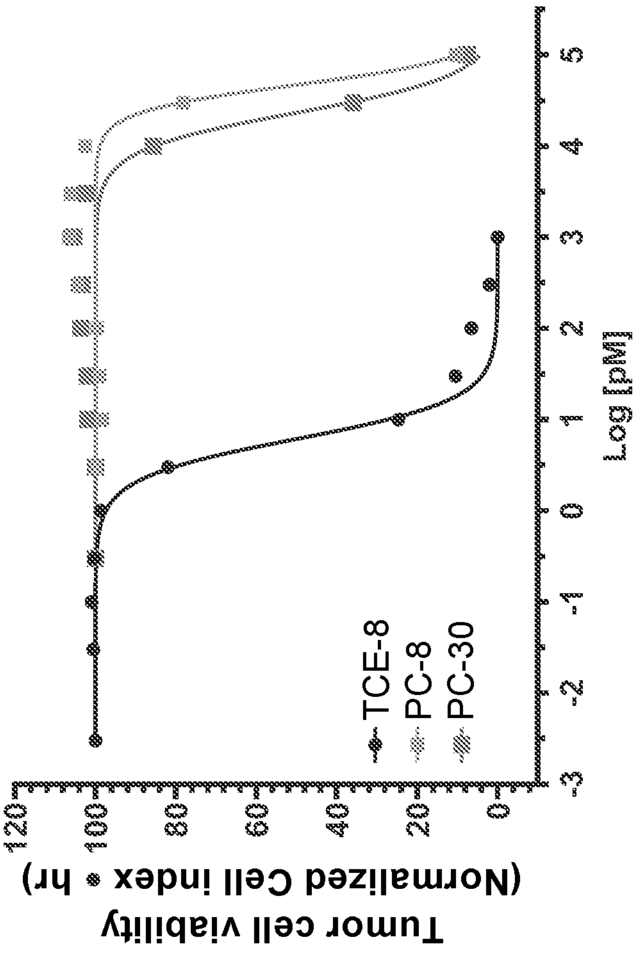

Polypeptide complexes were evaluated in a functional in vitro tumor cell killing assay using the TROP2 positive tumor cell lines HCT116, NCI-H292, and MDAMB231. The number of TROP2 binding sites for the different cell types are provided in Table 25. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 tumor cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% ($IC_{50}$) was calculated using Graphpad Prism software. Polypeptide complexes were treated with protease (MTSP1, MMP9) where indicated. Data plots of tumor cell viability vs. polypeptide complex concentration and $IC_{50}$s are shown in FIGS. 32A-32J (HCT116 cells), FIGS. 33A-33P (MDAMB231 cells), and FIGS. 34A-34T (NCI-H292 cells).

Example 9: Cytotoxicity Studies in TROP2 Expressing HEK293 Cells

Figure 35:
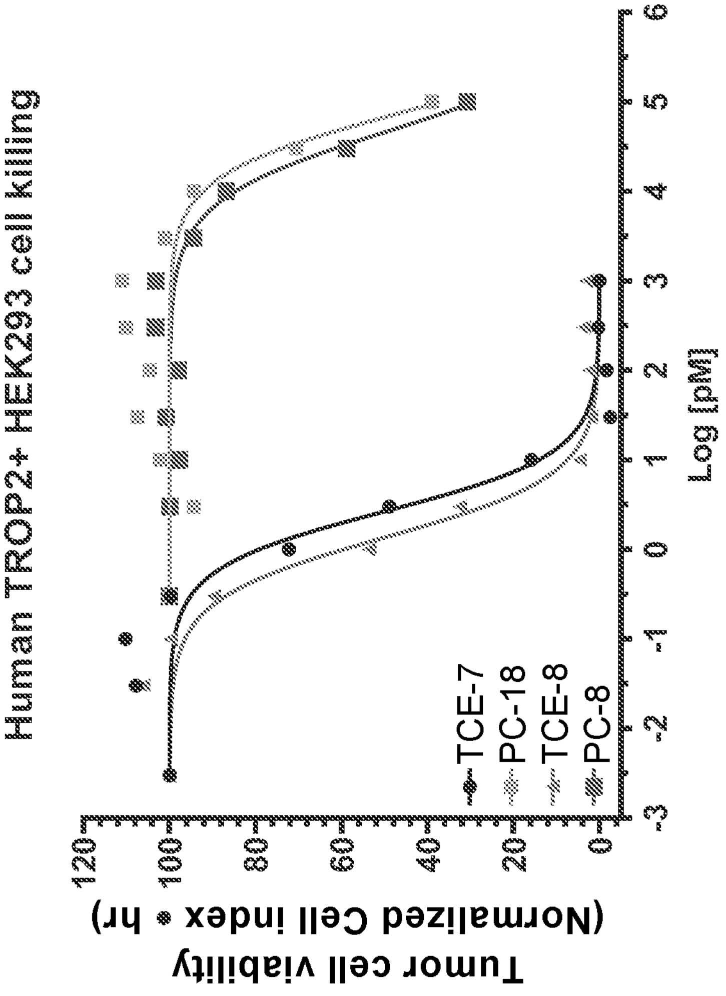
FIG. 35 illustrates killing of recombinant HEK293 cells expressing human TROP2 by polypeptide complexes in the presence of CD8+ T cells.
Figure 36:
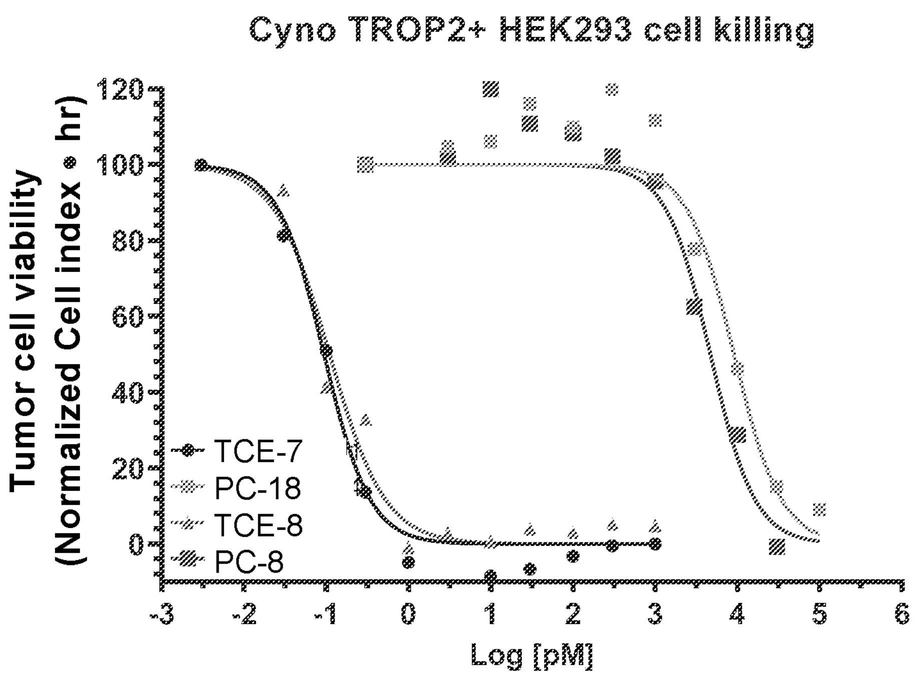
FIG. 36 illustrates killing of recombinant HEK293 cells expressing cynomolgus monkey TROP2 by polypeptide complexes in the presence of CD8+ T cells.
Figure 37:
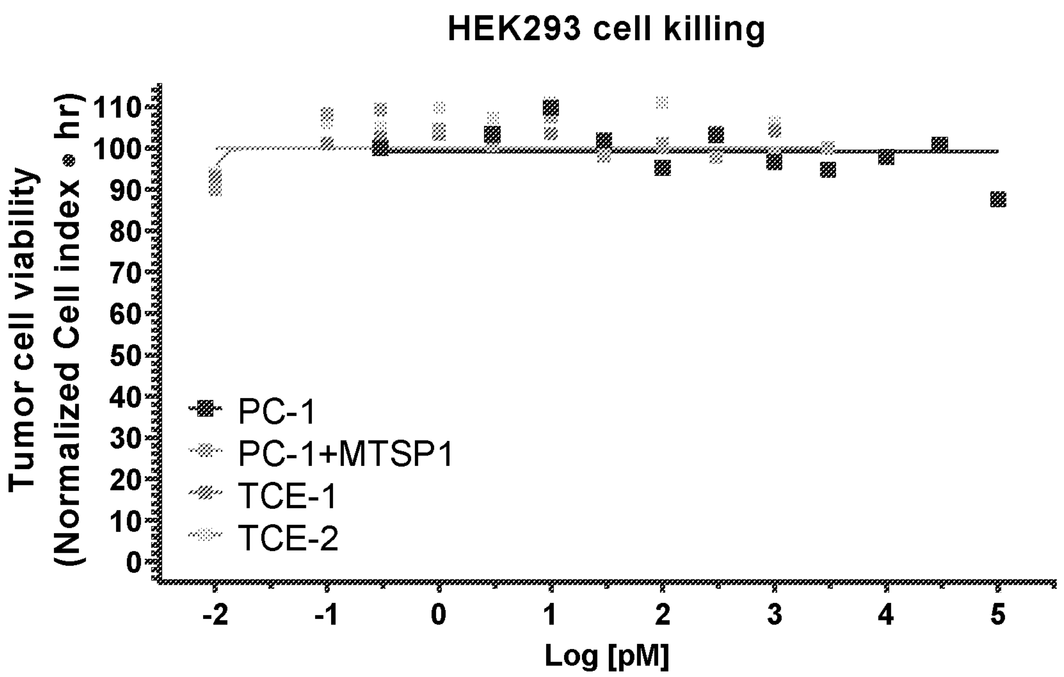
FIG. 37 illustrates tumor cell viability of wildtype HEK293 cells with increasing concentrations of polypeptide complexes in the presence of CD8+ T cells.
Figure 38A:
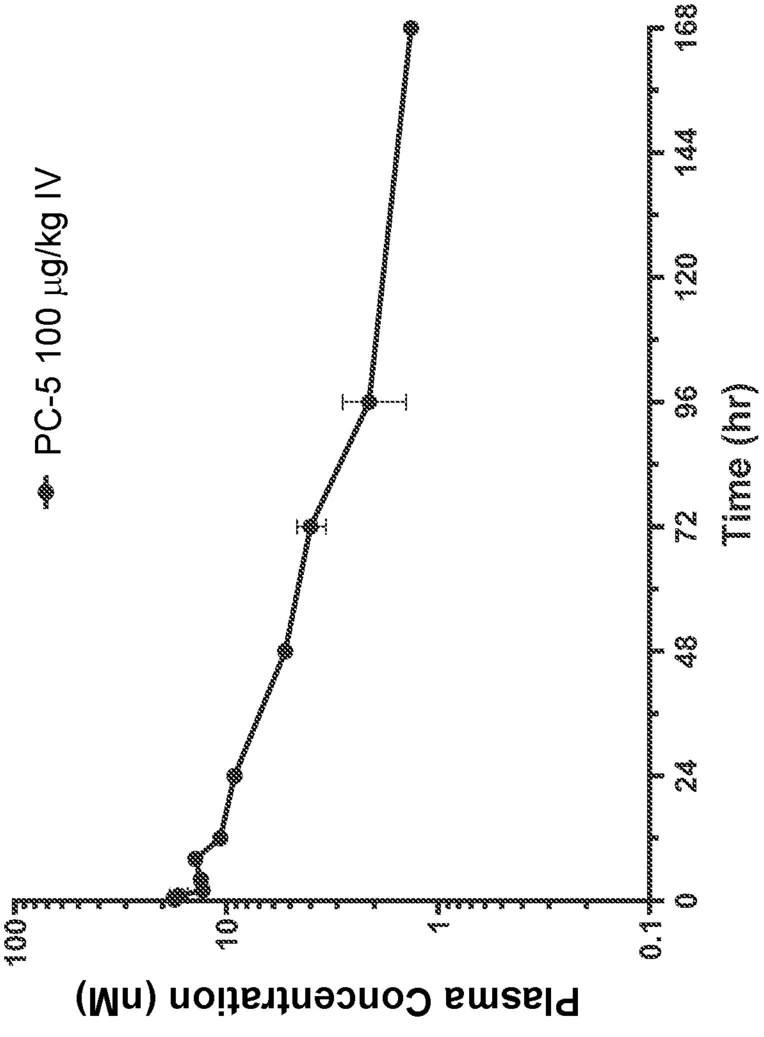
FIGS. 38A-38I illustrate polypeptide pharmacokinetics in cynomolgus monkeys after a single IV bolus injection.
Figure 38B:
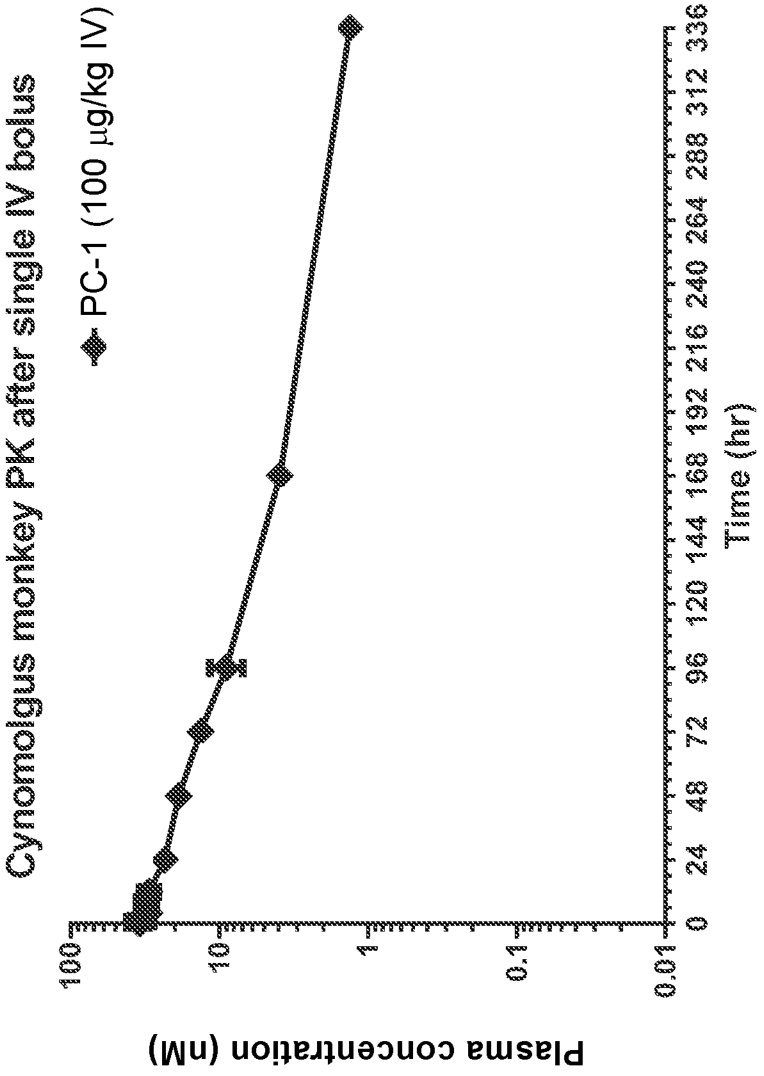
Figure 38C:
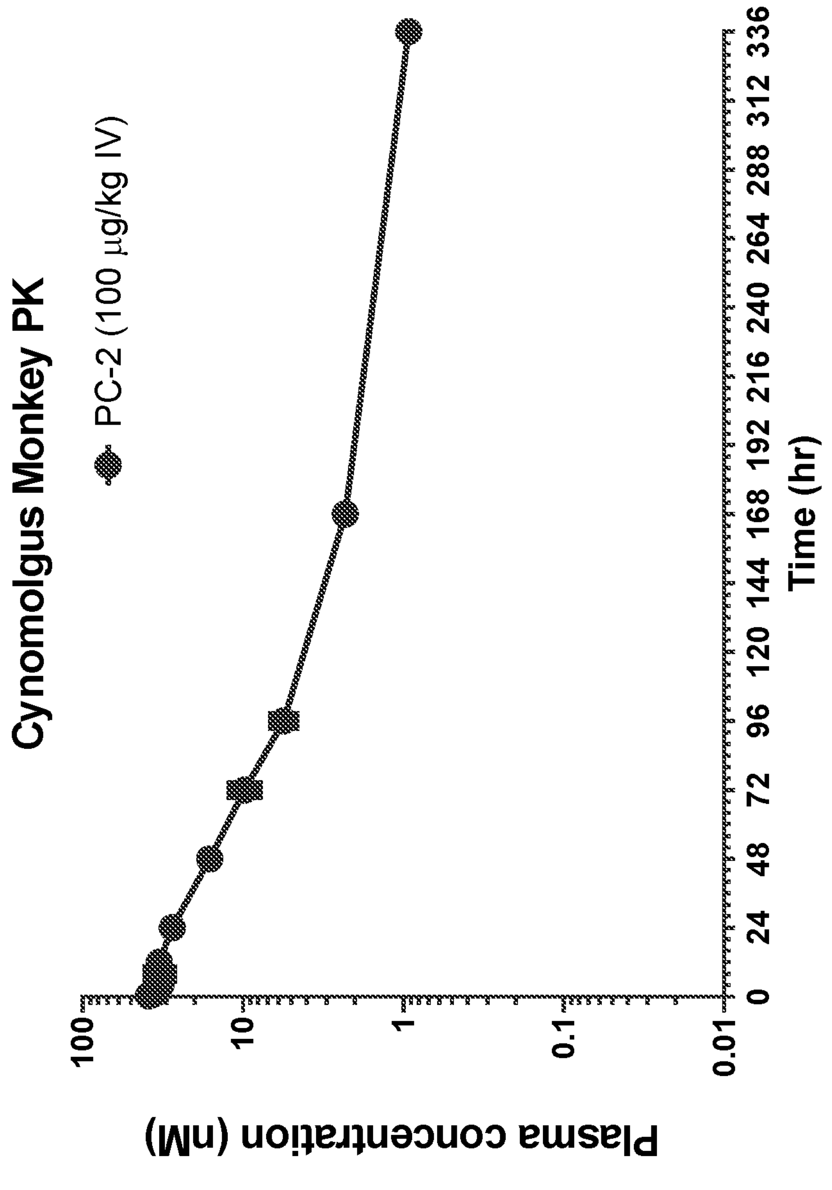
Figure 38D:
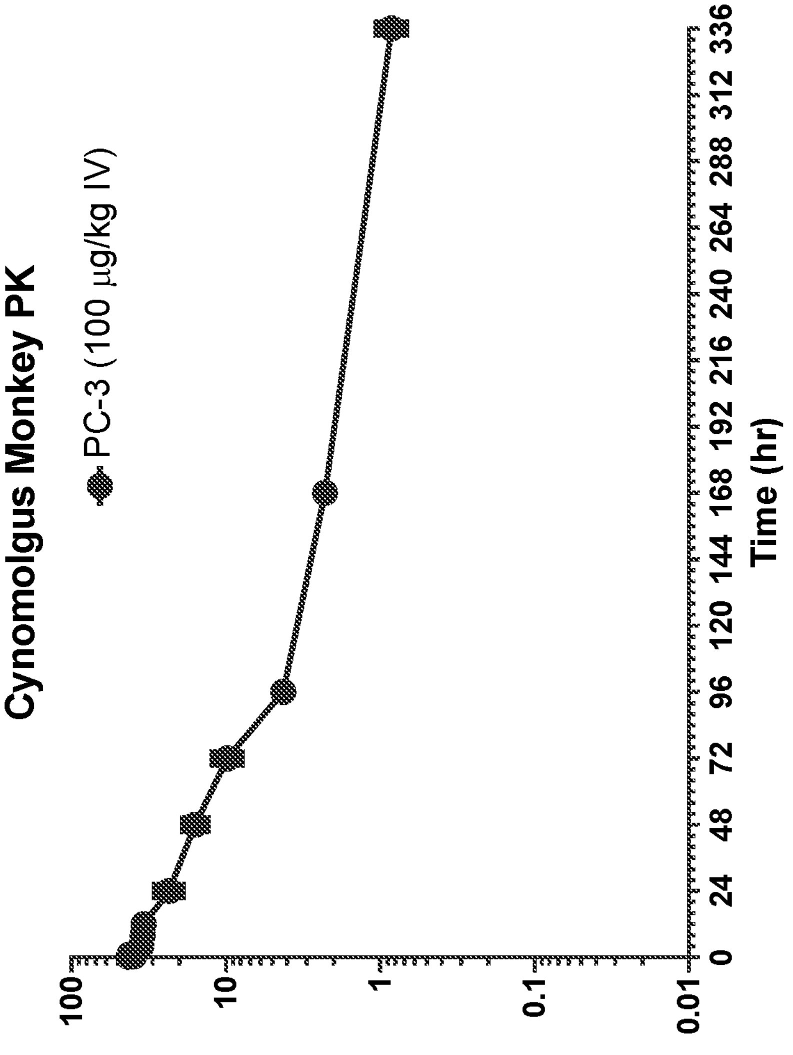
Figure 38E:
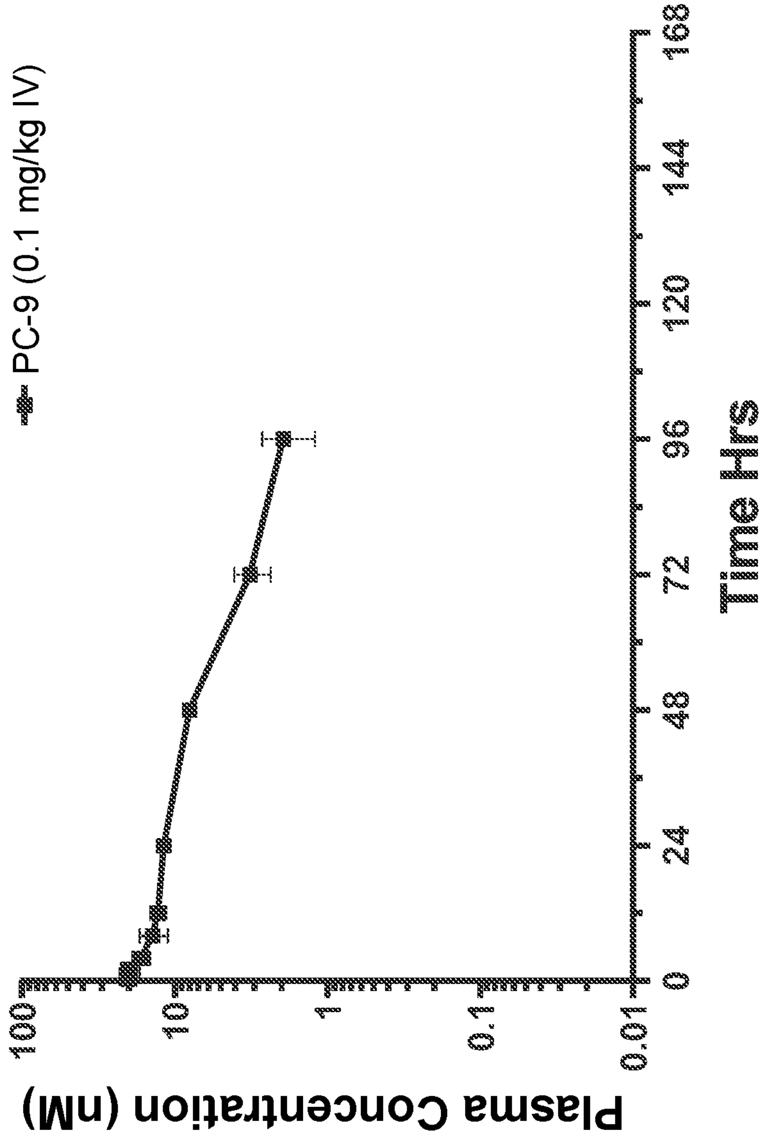
Figure 38F:
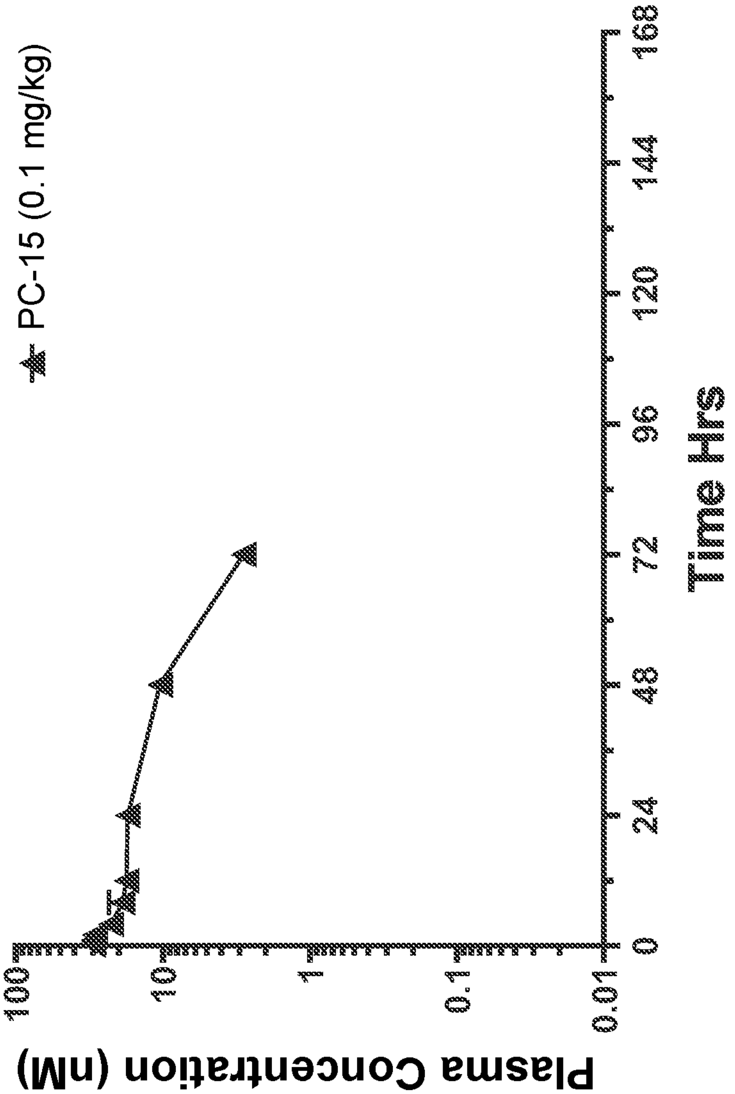
Figure 38G:
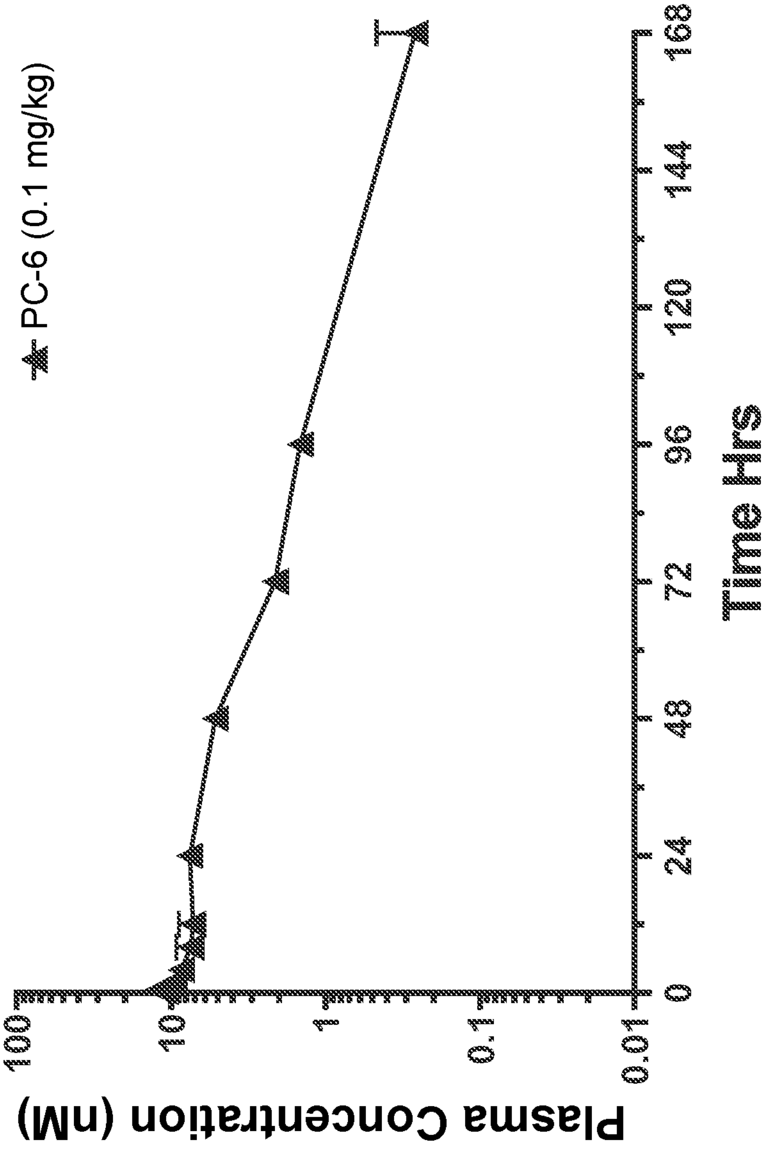
Figure 38H:
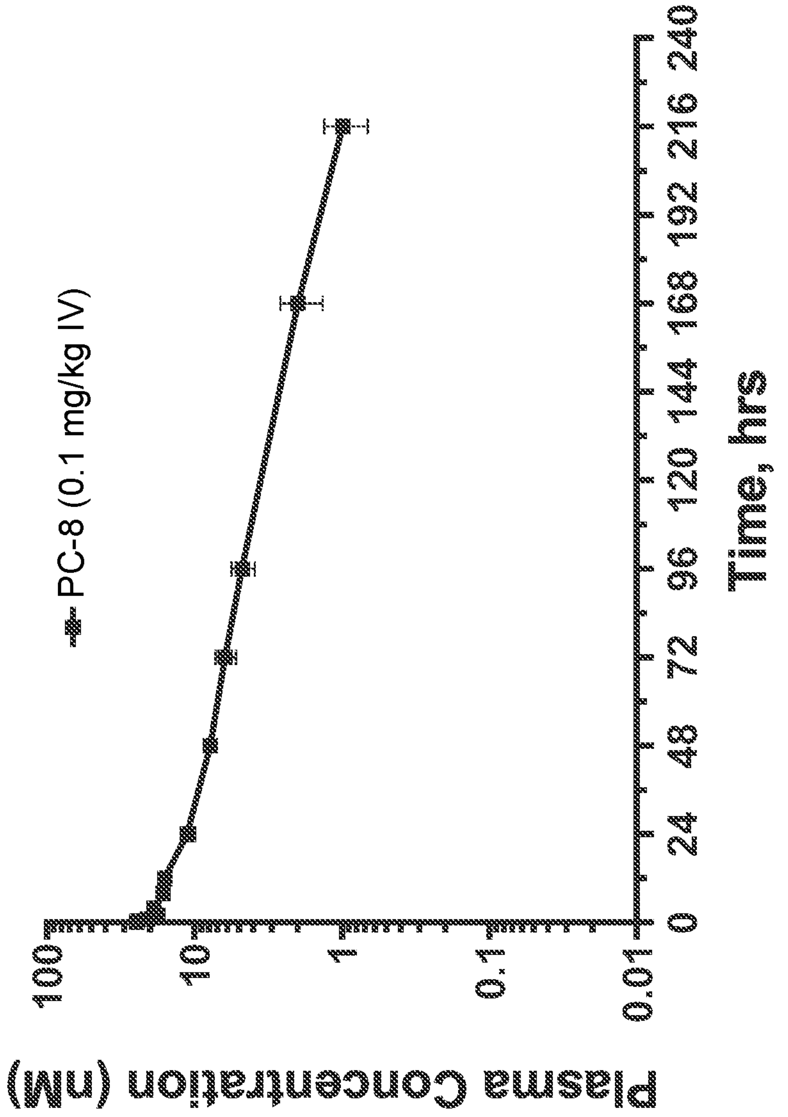
Figure 38I:
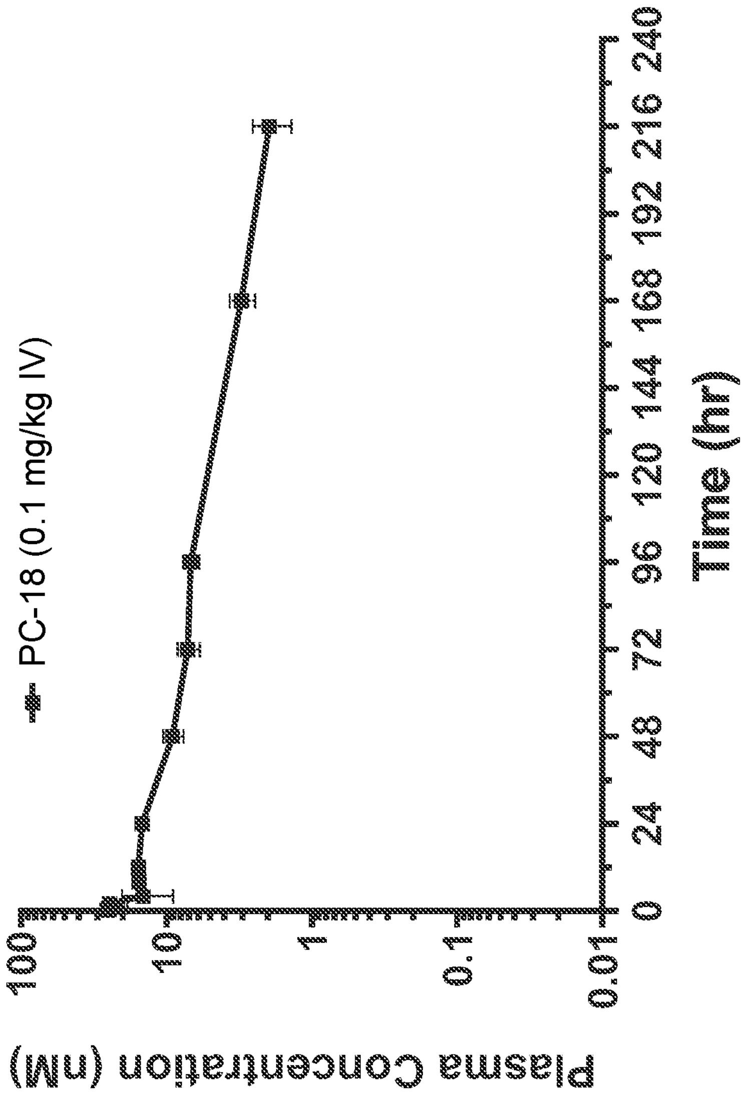
Figure 39A:
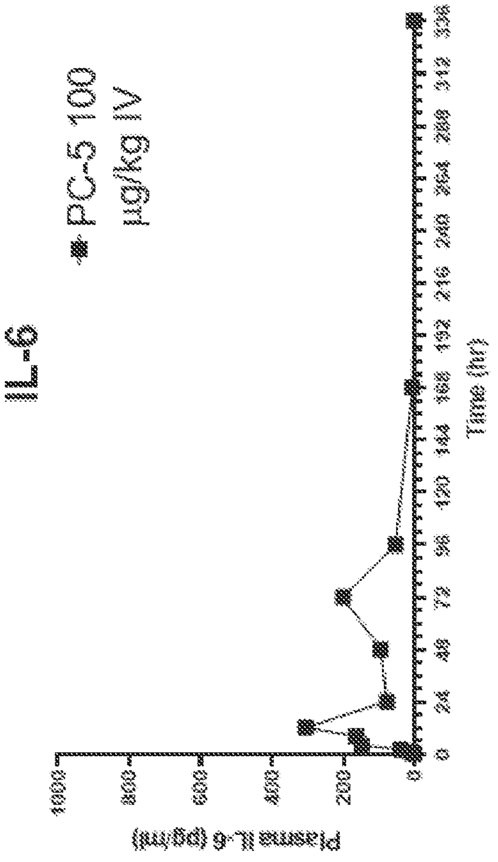
FIGS. 39A-39F shows cytokine release in cynomolgus monkeys after single IV bolus injection of polypeptide complex PC-5.
Figure 39B:
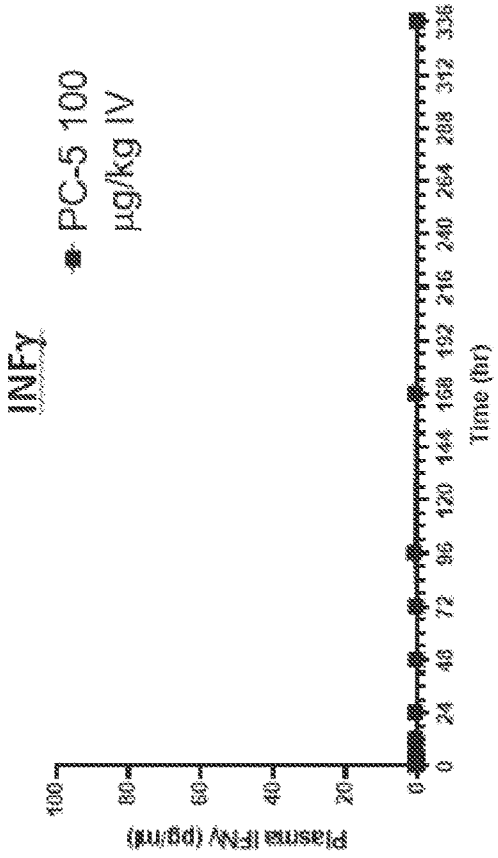
Figure 39D:
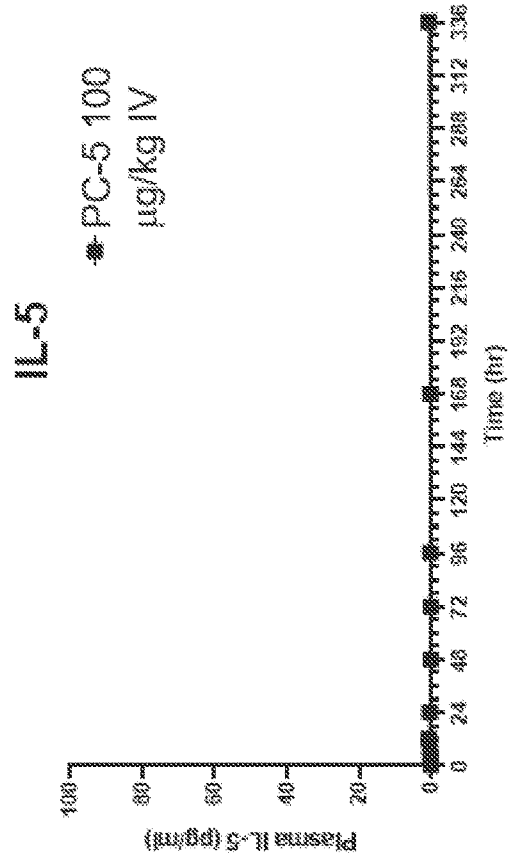
Figure 39C:
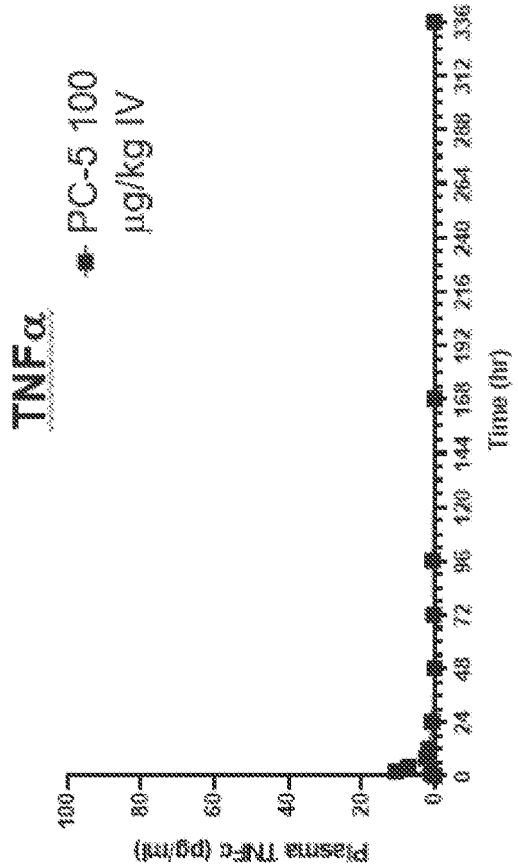
Figure 39E:
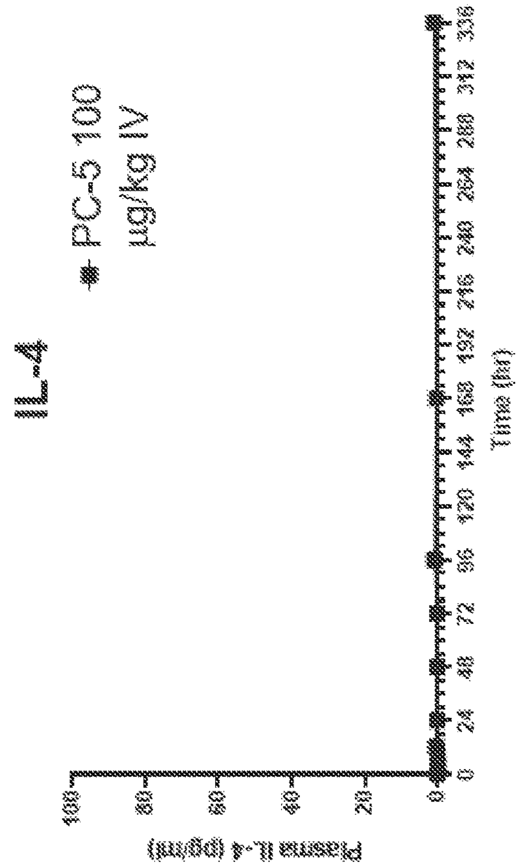
Figure 39F:
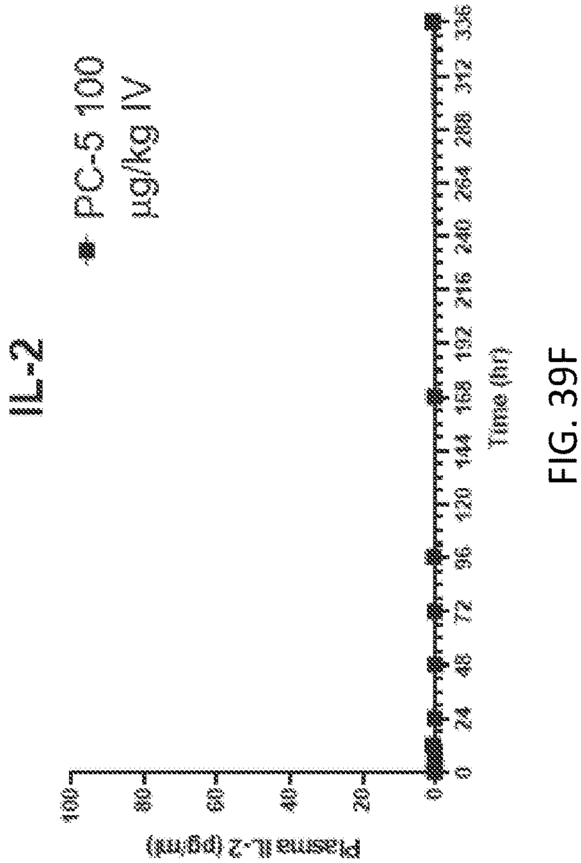
Figure 40:
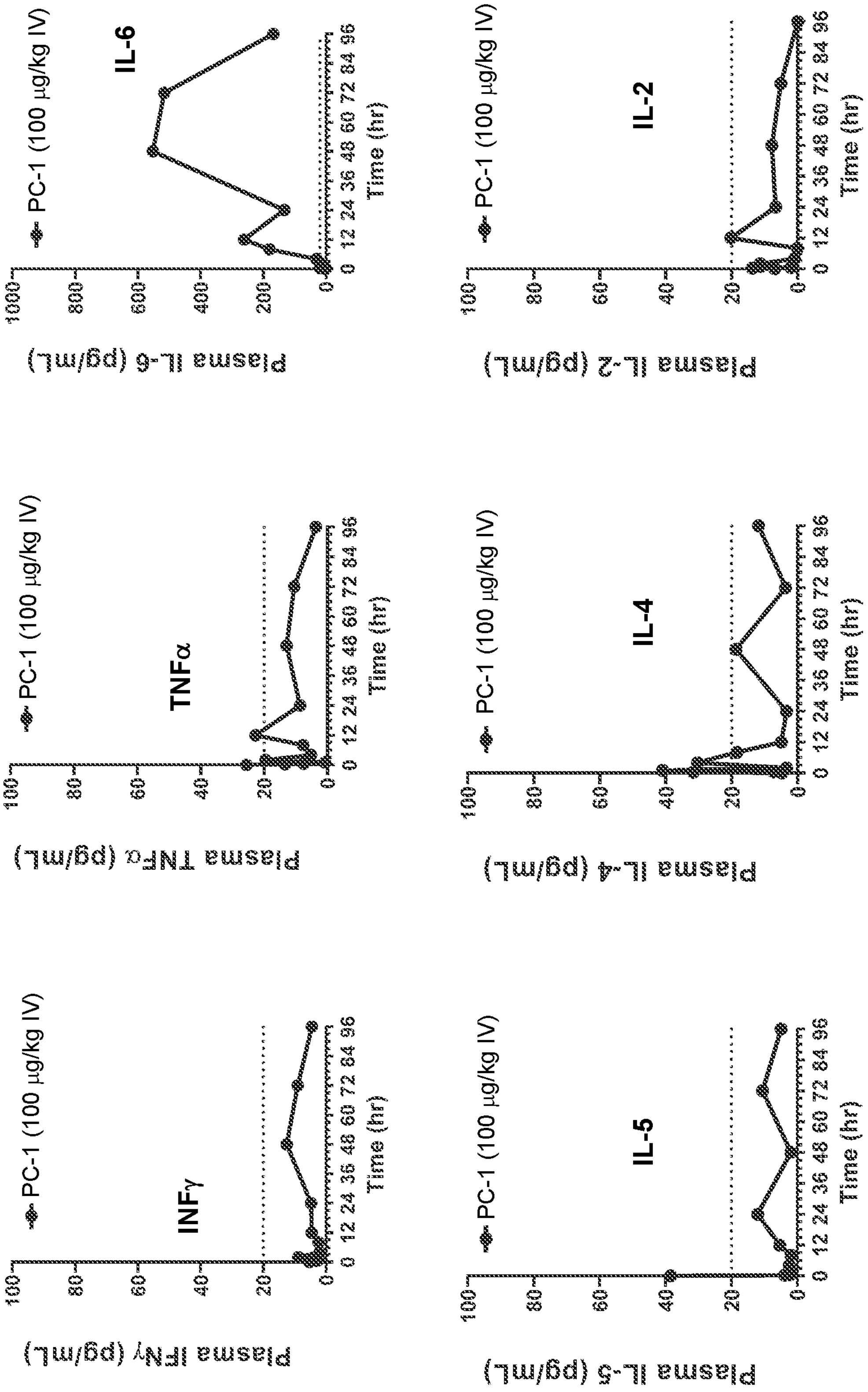
FIG. 40 shows cytokine release in cynomolgus monkeys after single IV bolus injection of polypeptide complex PC-1.
Figure 41:
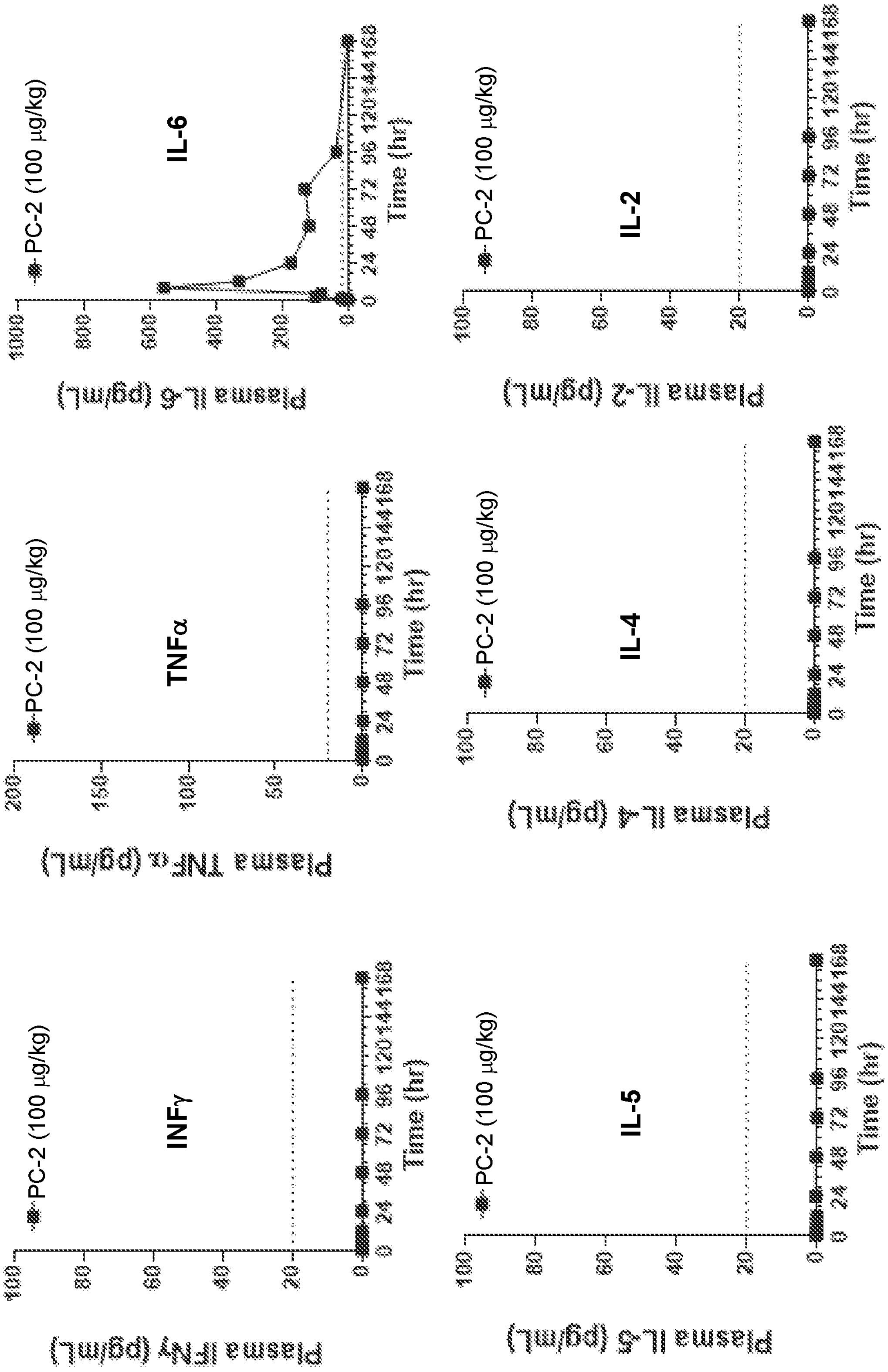
FIG. 41 shows cytokine release in cynomolgus monkeys after single IV bolus injection of polypeptide complex PC-2.
Figure 42:
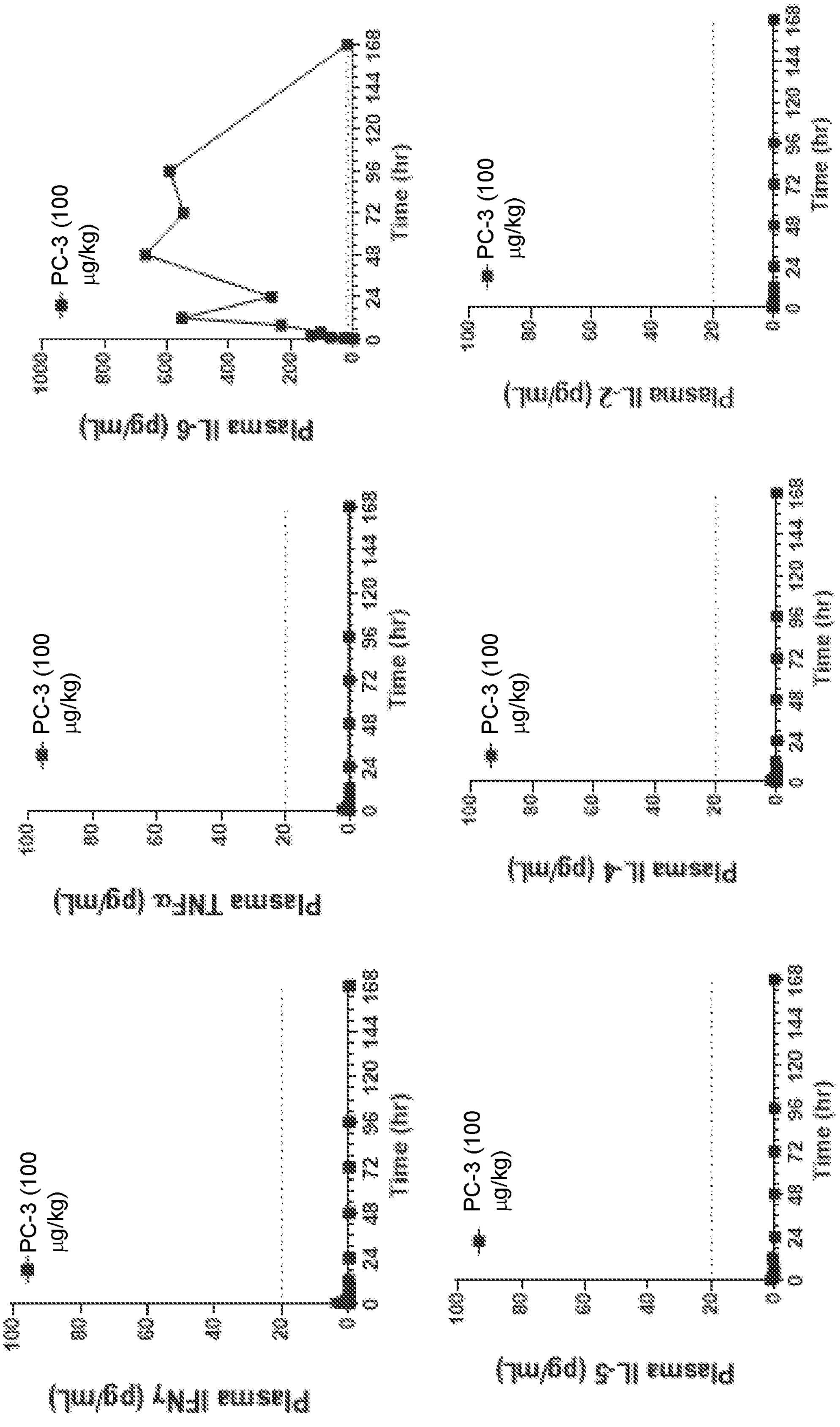
FIG. 42 shows cytokine release in cynomolgus monkeys after single IV bolus injection of polypeptide complex PC-3.
Figure 43:
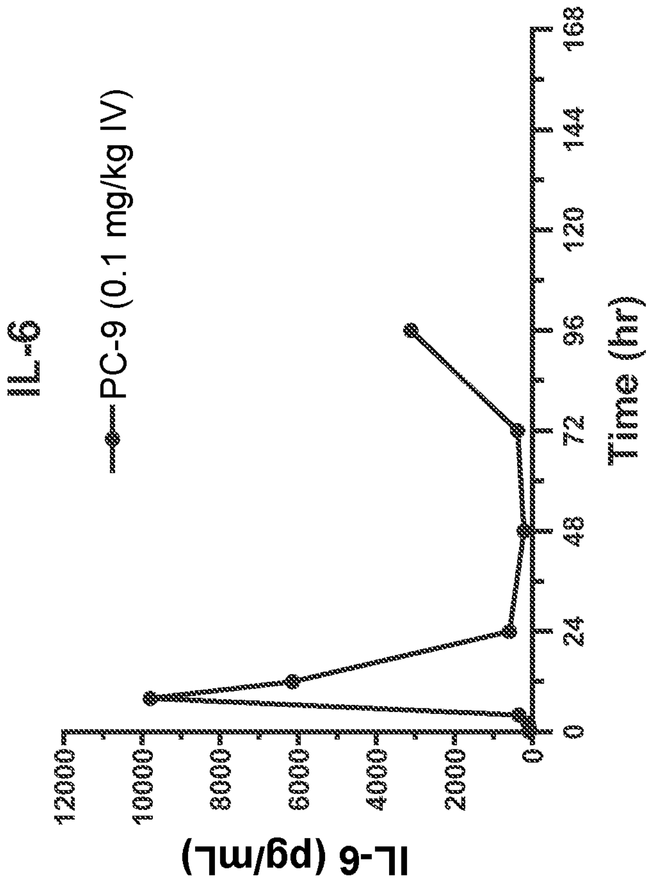
FIG. 43 shows cytokine release in cynomolgus monkeys after single IV bolus injection of polypeptide complex PC-9.
Figure 44:
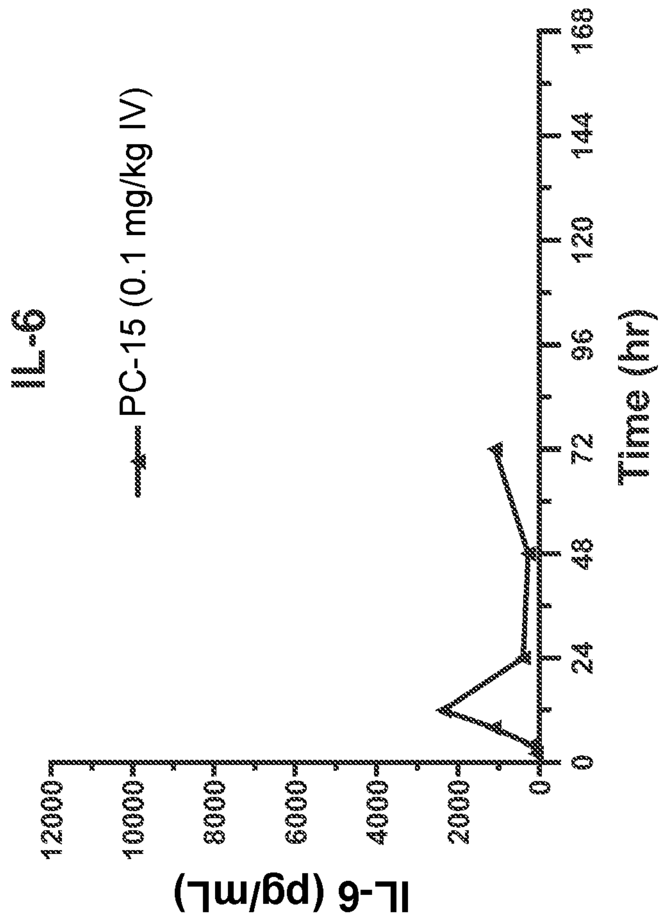
FIG. 44 shows cytokine release in cynomolgus monkeys after single IV bolus injection of polypeptide complex PC-15.
Figure 45:
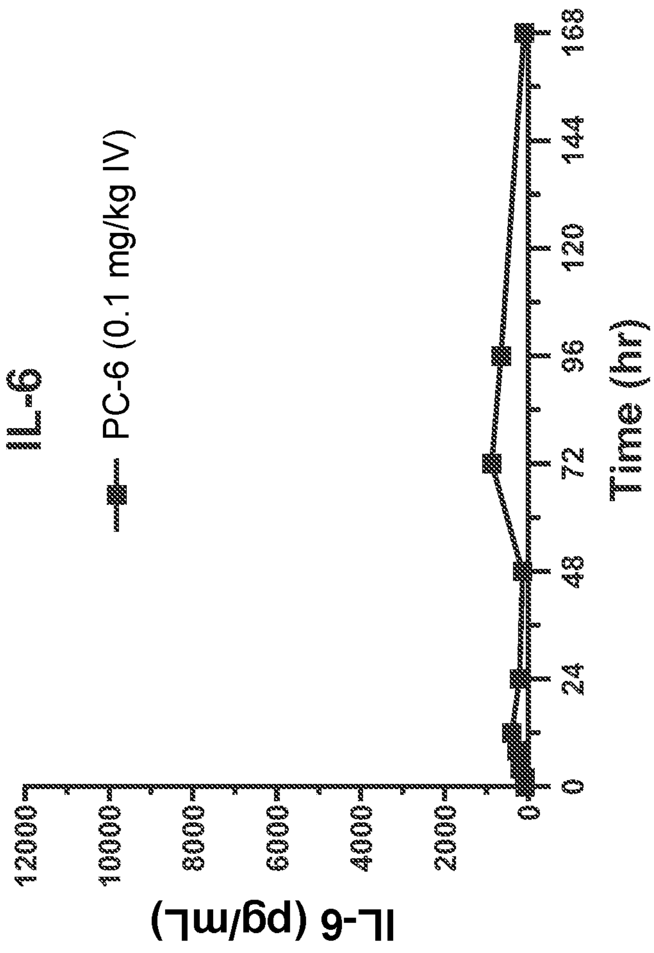
FIG. 45 shows cytokine release in cynomolgus monkeys after single IV bolus injection of polypeptide complex PC-6.
Figure 46:
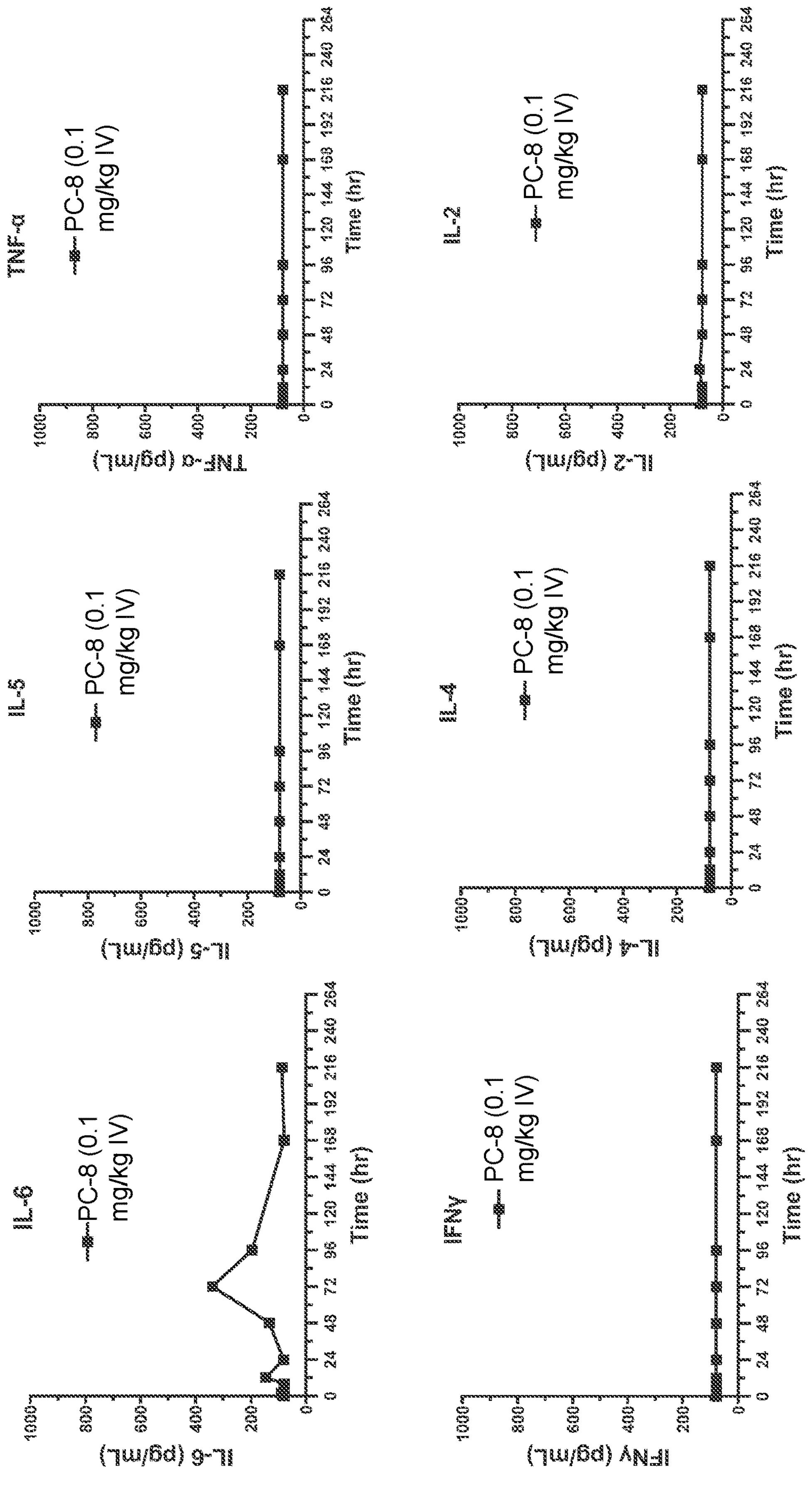
FIG. 46 shows cytokine release in cynomolgus monkeys after single IV bolus injection of polypeptide complex PC-8.

Polypeptide complexes were evaluated in a functional in vitro tumor cell killing assay using wildtype HEK293 or recombinant human or cynomolgus monkey TROP2 expressing HEK293 cells. The number of TROP2 binding sites for the HEK293 cells are provided in Table 25. Cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 HEK293 cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% ($IC_{50}$) was calculated using Graphpad Prism software. Polypeptide complexes were treated with protease (MTSP1) where indicated. Data plots of tumor cell viability vs. polypeptide complex concentration and $IC_{50}$s are shown in FIG. 35 (HEK293 cells expressing human TROP2), FIG. 36 (HEK293 cells expressing cyno TROP2), and FIG. 37 (wild type HEK293). As can be seen, no detectable killing was observed in wildtype HEK293 cells not expressing TROP2 (see FIG. 37).

TABLE 25

Cellular TROP2 Expression Densities

| Cellular TROP2 expression density | TROP2 binding sites per cell |
|---|---|
| HCT116 | 25,000 |
| MDAMB231 | 50,000 |
| NCI-H292 | 225,000 |
| Human TROP2 + HEK293 | 75,000 |
| Cyno TROP2 + HEK293 | 100,000 |
| HEK293 | none detectable |

Example 10: Polypeptide Pharmacokinetics in Cynomoglus Monkeys

Pharmacokinetics and exploratory safety of polypeptide molecules were evaluated in cynomolgus monkeys. Briefly, cynomolgus monkeys of approximately 3 kg bodyweight were administered polypeptides as an IV bolus and observed daily for signs of adverse events. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cyno plasma. Plasma concentration curves were fit to a standard two phase exponential equation representing distribution and elimination phases. Plots of plasma concentration of polypeptide complex versus time after a single IV bolus injections of PC-5, PC-1, PC-2, PC-3, PC-9, PC-15, PC-6, PC-8, and PC-18 are shown in FIG. 38A-38I. Fitting of pharmacokinetics enabled the calculation of $C_{MAX}$, half-life ($t_{1/2}$), volume of distribution, clearance, and 7 day area under the curve (AUC). The results of the data fitting are shown in Tables 26-34.

TABLE 26

PC-5 pharmacokinetics

| | PC-5, 100 μg/kg | units |
|---|---|---|
| $C_{MAX}$ | 17.38 | nM |
| $t_{1/2}$ | 68.97 | hr |
| Vd | 0.18 | L |
| VSS | 0.44 | L |
| CL | 0.61 | mL/hr/kg |
| BW | 3.00 | kg |
| 7 day AUC | 45640 | nM · min |

TABLE 27

PC-1 pharmacokinetics

| | PC-1, 100 μg/kg | units |
|---|---|---|
| $C_{MAX}$ | 34.32 | nM |
| $t_{1/2}$ | 90.16 | hr |
| Vd | 0.09 | L |
| VSS | 0.19 | L |
| CL | 0.23 | mL/hr/kg |
| BW | 3.00 | kg |
| 7 day AUC | 142,182 | nM · min |

TABLE 28

| PC-2 pharmacokinetics | | |
|---|---|---|
| | PC-2, 100 μg/kg | units |
| $C_{MAX}$ | 37.94 | nM |
| $t_{1/2}$ | 97.31 | hr |
| Vd | 0.08 | L |
| VSS | 0.33 | L |
| CL | 0.19 | mL/hr/kg |
| BW | 3.00 | kg |
| 7 day AUC | 127,094 | nM · min |

TABLE 29

| PC-3 pharmacokinetics | | |
|---|---|---|
| | PC-3, 100 μg/kg | units |
| $C_{MAX}$ | 42.12 | nM |
| $t_{1/2}$ | 100.73 | hr |
| Vd | 0.07 | L |
| VSS | 0.39 | L |
| CL | 0.17 | mL/hr/kg |
| BW | 3.00 | kg |
| 7 day AUC | 137,581 | nM · min |

TABLE 30

| PC-9 pharmacokinetics | | |
|---|---|---|
| | PC-9, 100 μg/kg | units |
| $C_{MAX}$ | 21.19 | nM |
| $t_{1/2}$ | 29.03 | hr |
| Vd | 0.15 | L |
| VSS | 0.16 | L |
| CL | 1.17 | mL/hr/kg |
| BW | 3.00 | kg |
| 7 day AUC | 47,086 | nM · min |

TABLE 31

| PC-15 pharmacokinetics | | |
|---|---|---|
| | PC-15, 100 μg/kg | units |
| $C_{MAX}$ | 31.20 | nM |
| $t_{1/2}$ | 24.69 | hr |
| Vd | 0.10 | L |
| VSS | 0.11 | L |
| CL | 0.93 | mL/hr/kg |
| BW | 3.00 | kg |
| 7 day AUC | 80,991 | nM · min |

TABLE 32

| PC-6 pharmacokinetics | | |
|---|---|---|
| | PC-6, 100 μg/kg | units |
| $C_{MAX}$ | 11.93 | nM |
| $t_{1/2}$ | 36.94 | hr |
| Vd | 0.26 | L |
| VSS | 0.31 | L |
| CL | 1.63 | mL/hr/kg |
| BW | 3.00 | kg |
| 7 day AUC | 27,830 | nM · min |

TABLE 33

| PC-8 pharmacokinetics | | |
|---|---|---|
| | PC-18, 100 μg/kg | units |
| $C_{MAX}$ | 26.94 | nM |
| $t_{1/2}$ | 60.00 | hr |
| Vd | 0.12 | L |
| VSS | 0.17 | L |
| CL | 0.44 | mL/hr/kg |
| BW | 3.00 | kg |
| 7 day AUC | 68,067 | nM · min |

TABLE 34

| PC-18 pharmacokinetics | | |
|---|---|---|
| | PC-5, 1000 μg/kg | units |
| $C_{MAX}$ | 26.21 | nM |
| $t_{1/2}$ | 76.97 | hr |
| Vd | 0.12 | L |
| VSS | 0.17 | L |
| CL | 0.36 | mL/hr/kg |
| BW | 3.00 | kg |
| 7 day AUC | 83,211 | nM · min |

Example 11: Cytokine Release in Cynomolgus Monkeys

Figure 47:
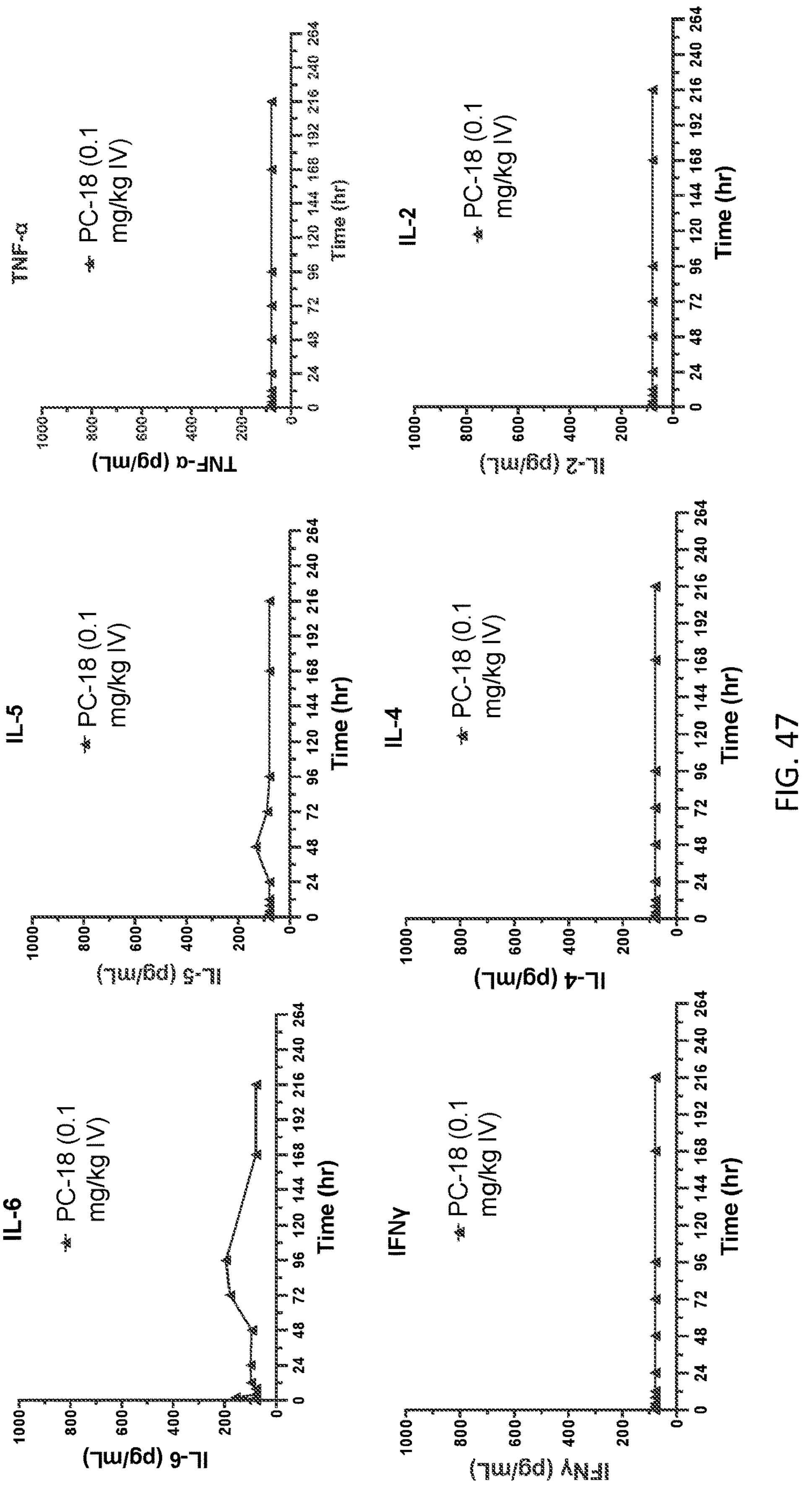
FIG. 47 shows cytokine release in cynomolgus monkeys after single IV bolus injection of polypeptide complex PC-18.

Cytokine release after polypeptide administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for cytokines using a non-human primate cytometric Th1/Th2 bead array kit from BD biosciences following the manufacturers instructions. Interferon gamma, tumor necrosis factor alpha, interleukin 6, interleukin 5, interleukin 4, and interleukin 2 levels in plasma were calculated relative to reference standards provided with the bead array kit. FIGS. 39-47 show plots of cytokine concentrations after administration of PC-5 (FIG. 39), PC-1 (FIG. 40), PC-2 (FIG. 41), PC-3 (FIG. 42), PC-9 (FIG. 43), PC-15 (FIG. 44), PC-6 (FIG. 45), PC-8 (FIG. 46), and PC-18 (FIG. 47).

Example 12: Serum Liver Enzymes in Cynomolgus Monkeys

Figure 48:
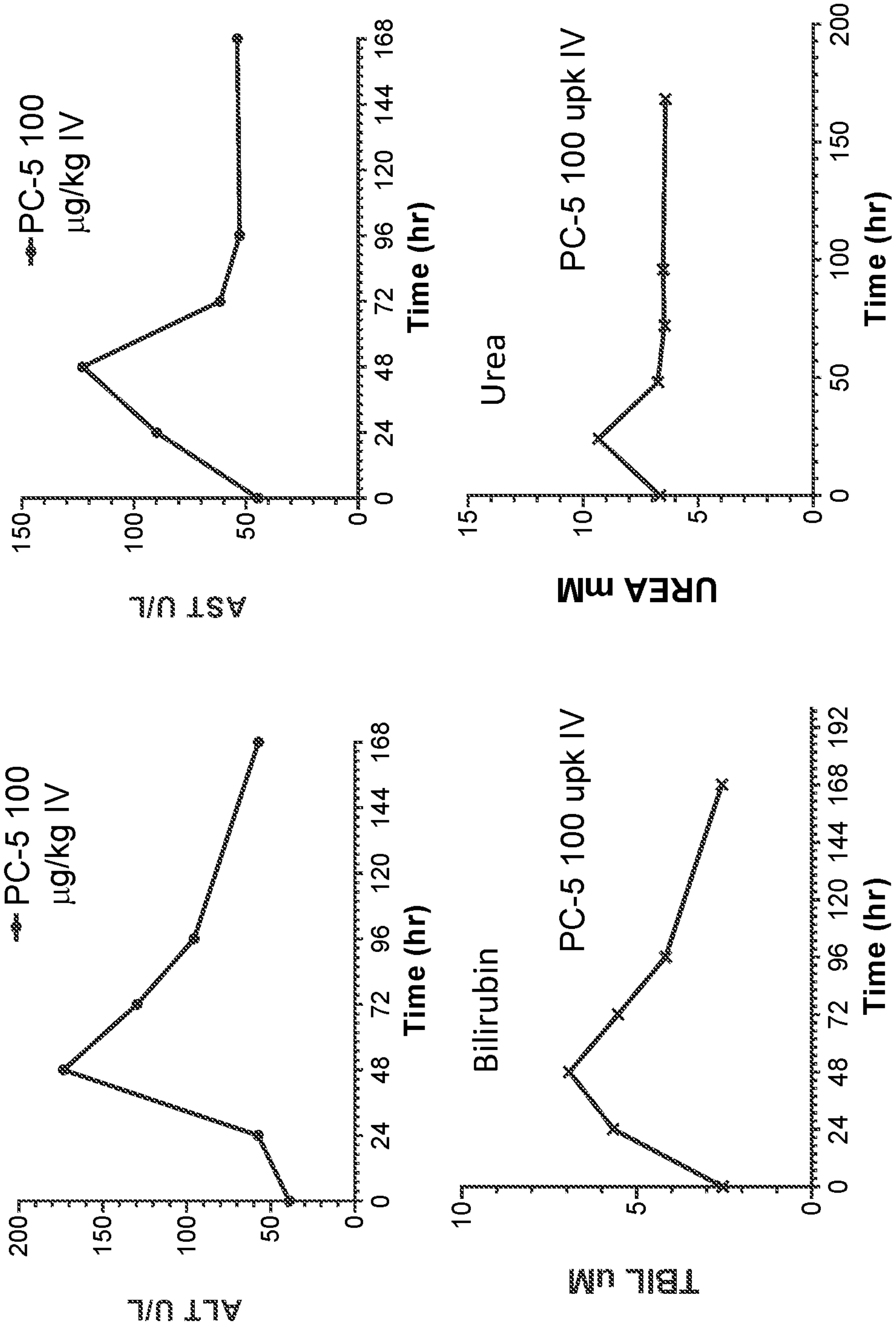
FIG. 48 shows serum liver enzymes, bilirubin, and urea in cynomolgus monkeys after single IV bolus of PC-5.
Figure 49:
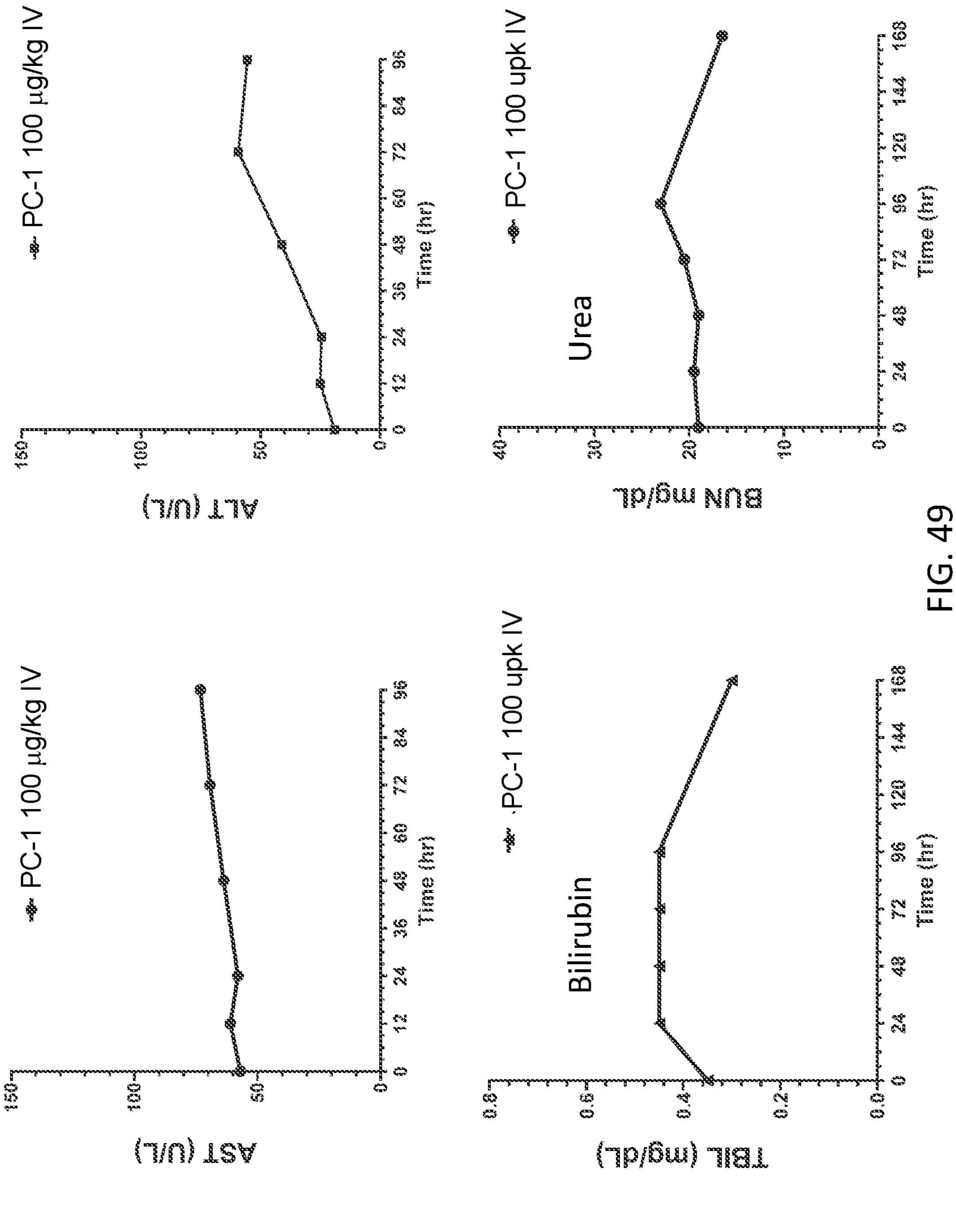
FIG. 49 shows serum liver enzymes, bilirubin, and urea in cynomolgus monkeys after single IV bolus of PC-1.
Figure 50:
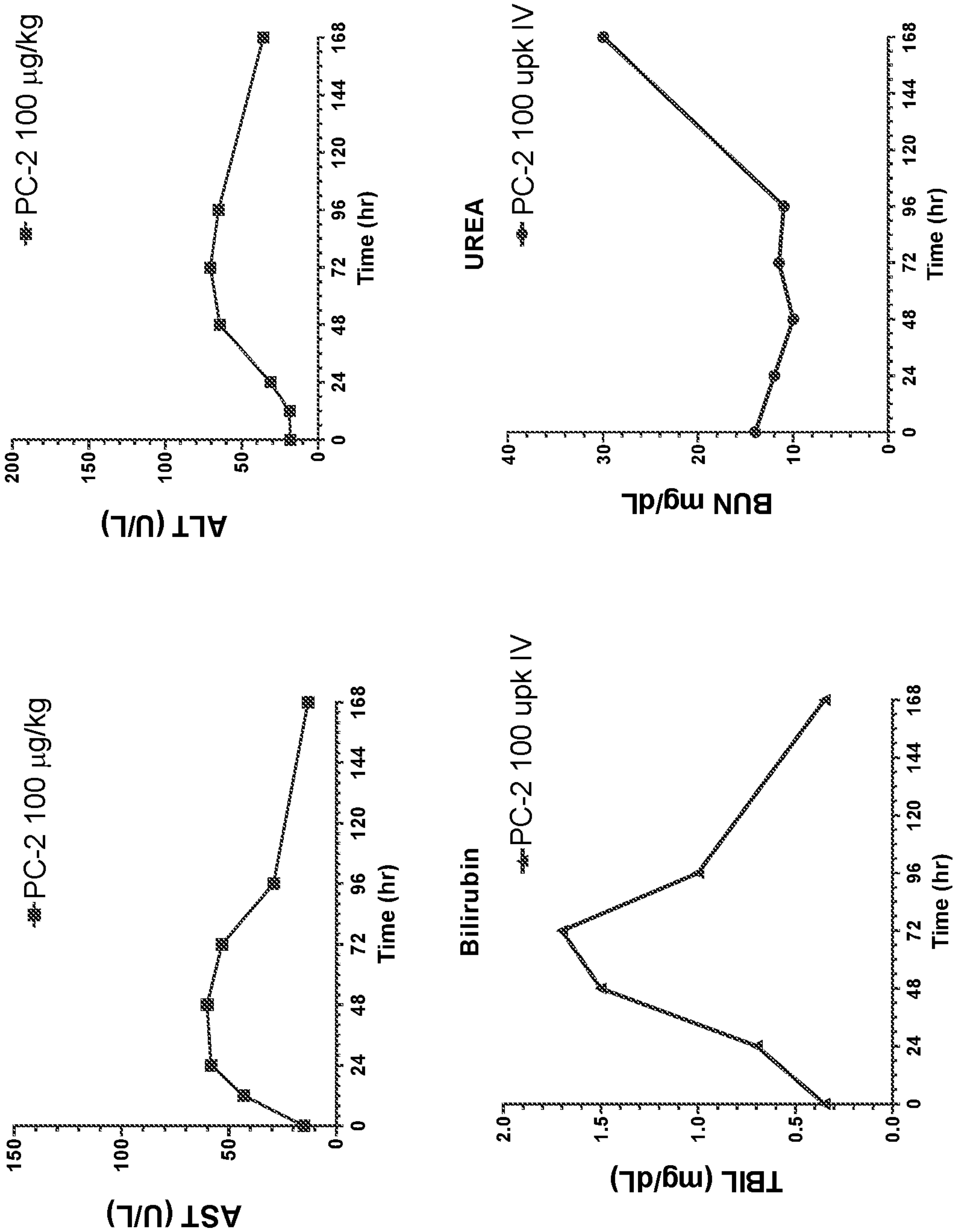
FIG. 50 shows serum liver enzymes, bilirubin, and urea in cynomolgus monkeys after single IV bolus of PC-2.
Figure 51:
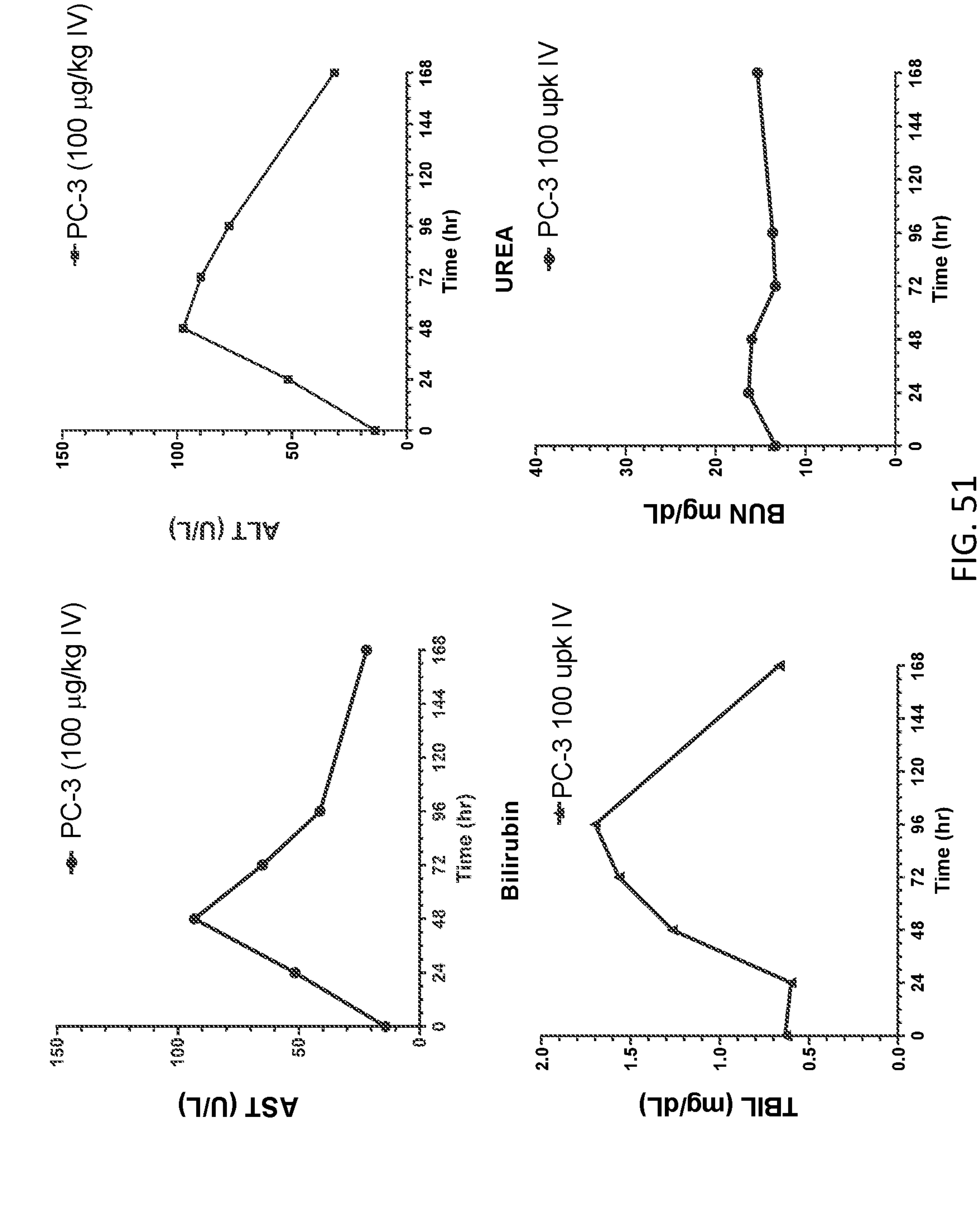
FIG. 51 shows serum liver enzymes, bilirubin, and urea in cynomolgus monkeys after single IV bolus of PC-3.
Figure 52:
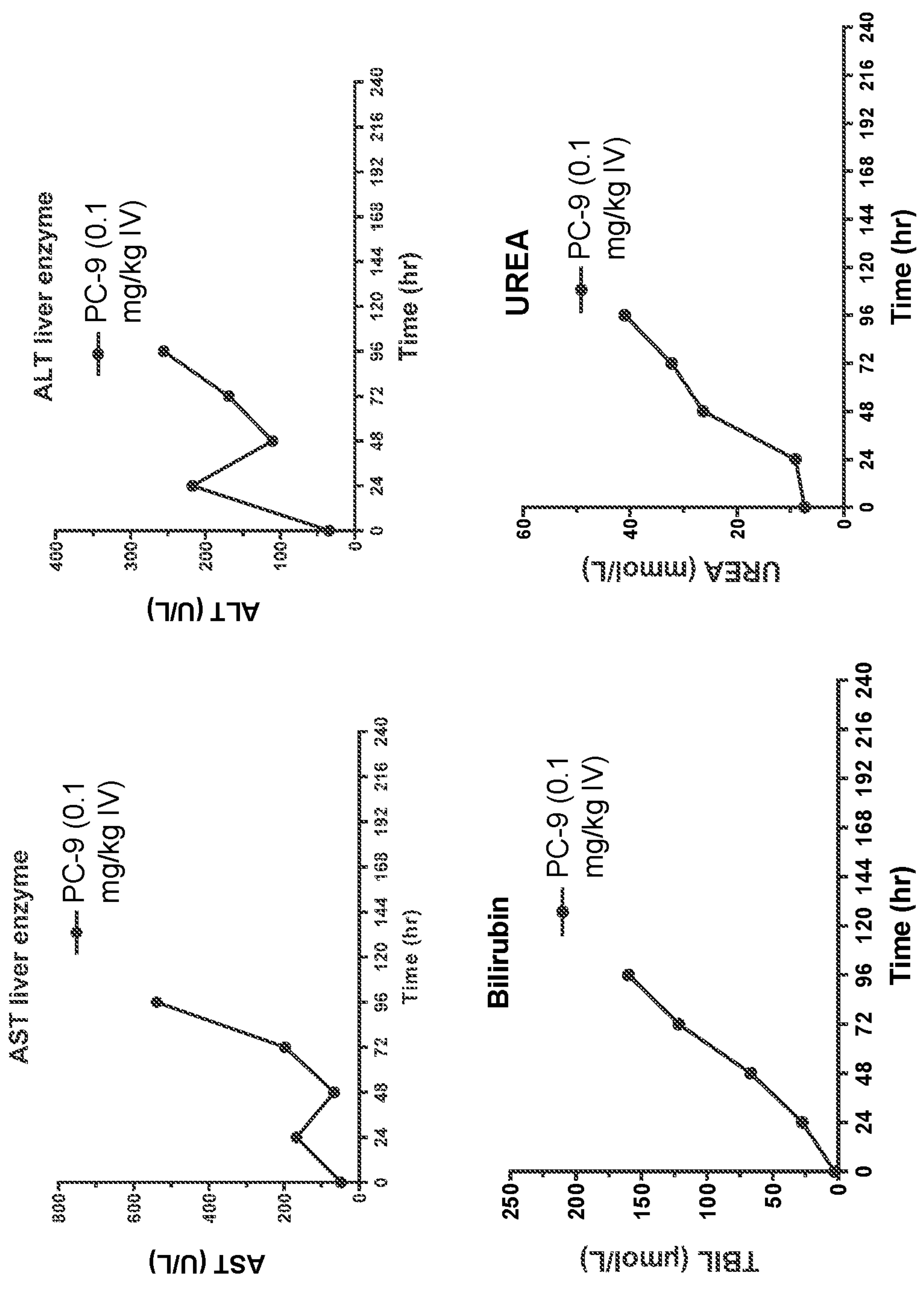
FIG. 52 shows serum liver enzymes, bilirubin, and urea in cynomolgus monkeys after single IV bolus of PC-9.
Figure 53:
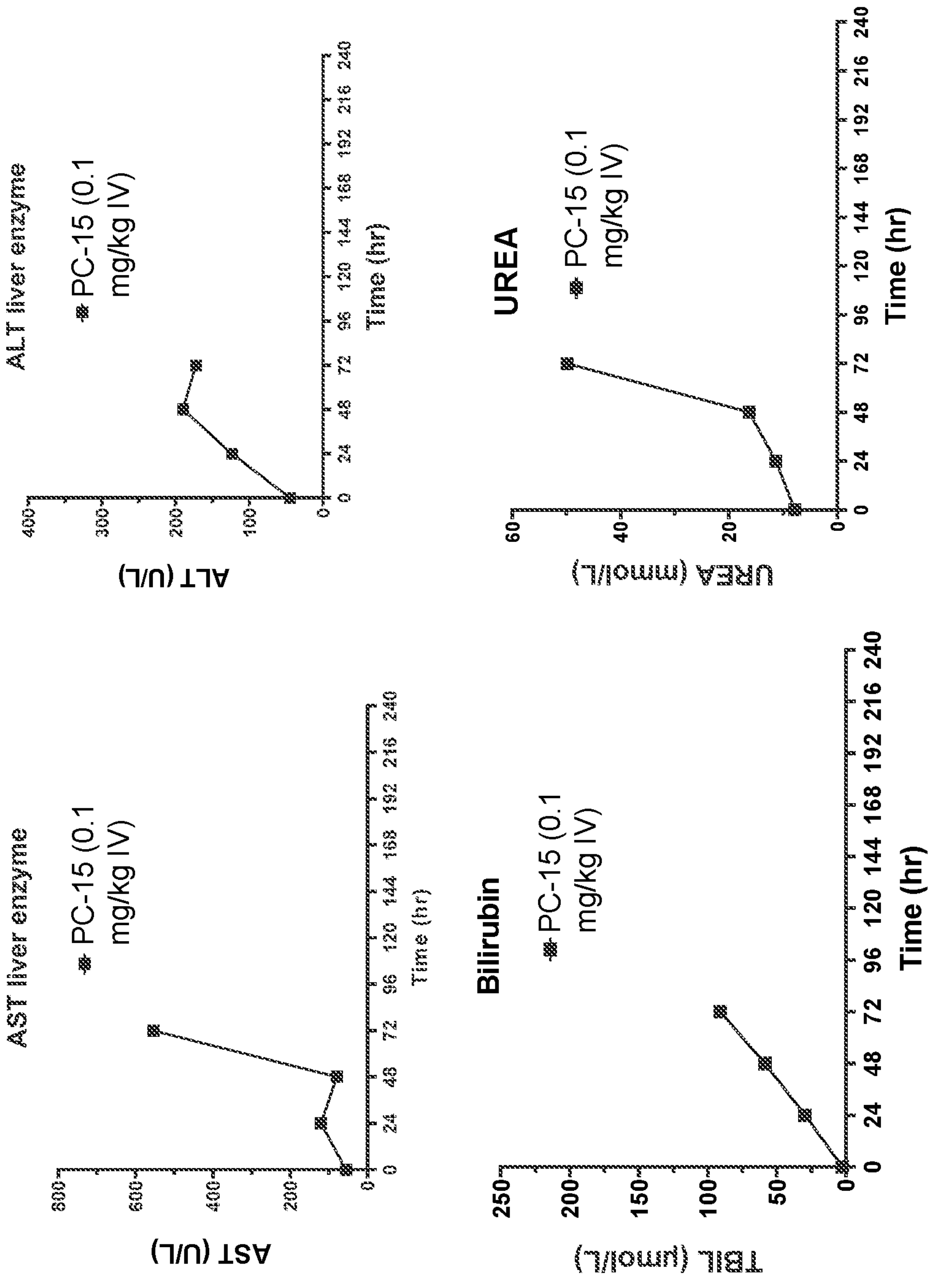
FIG. 53 shows serum liver enzymes, bilirubin, and urea in cynomolgus monkeys after single IV bolus of PC-15.
Figure 54:
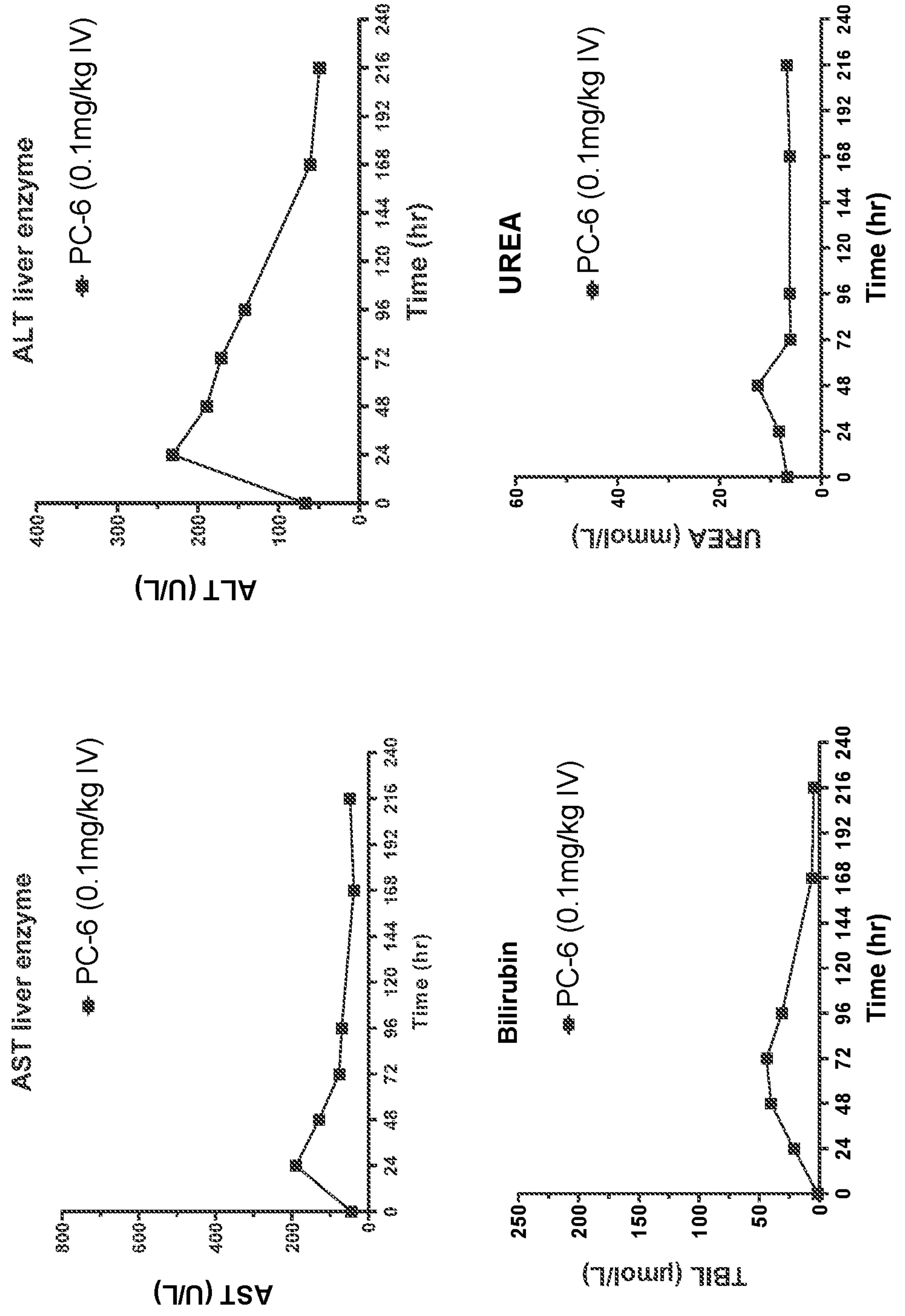
FIG. 54 shows serum liver enzymes, bilirubin, and urea in cynomolgus monkeys after single IV bolus of PC-6.
Figure 55:
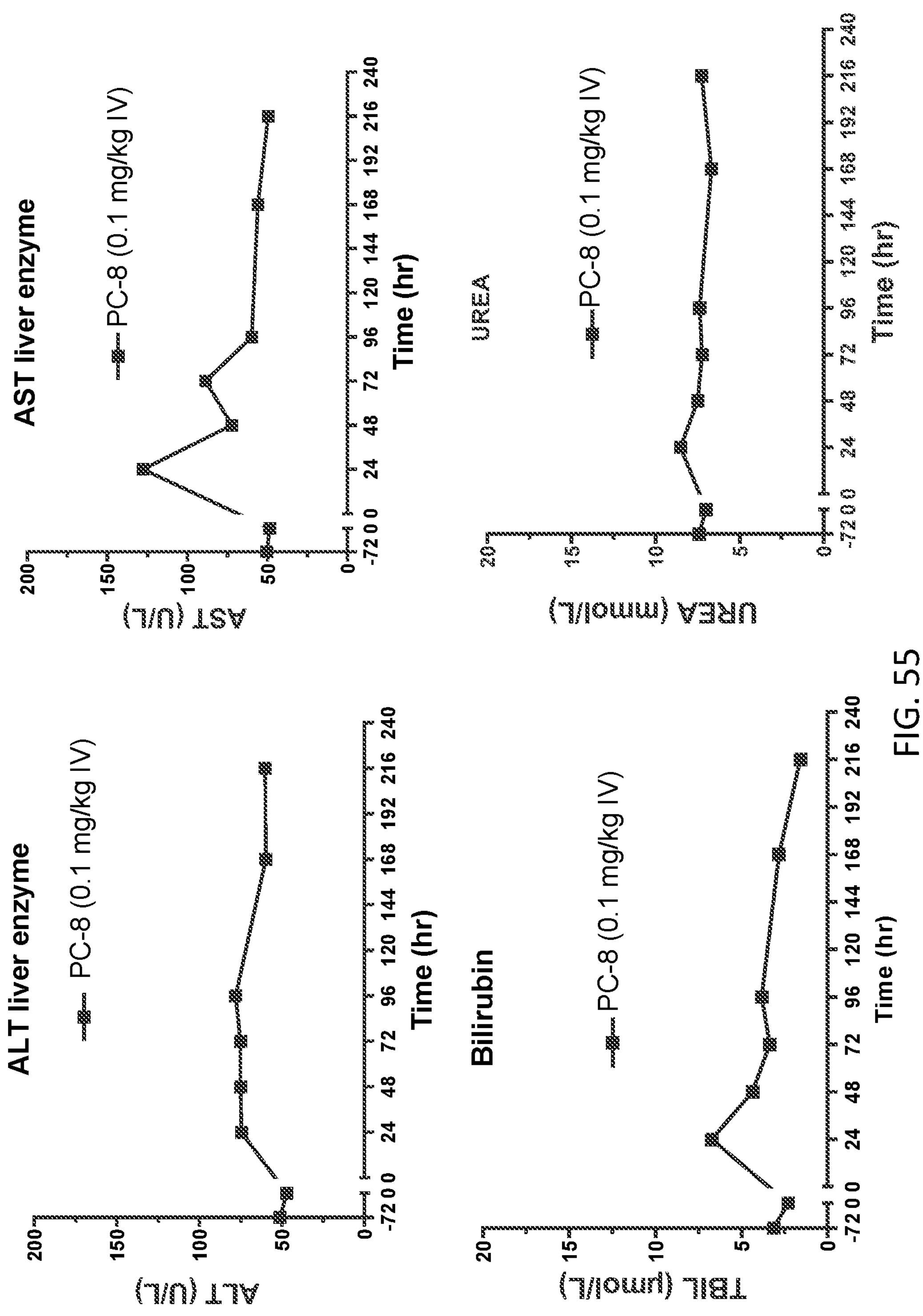
FIG. 55 shows serum liver enzymes, bilirubin, and urea in cynomolgus monkeys after single IV bolus of PC-8.

Systemic liver enzymes after polypeptide molecule administration by IV bolus were evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for the presence of liver enzymes aspartate transaminase (AST) and alanine aminotransferase (ALT) as signs of potential liver toxicity. AST and ALT levels were remained within the normal ranges for all timepoints tested after dosing suggesting a lack of liver toxicity. AST and ALT were quantified following the instructions provided in a commercially available kit from Millipore. AST and ALT levels were calculated according to manufacturers instructions relative to a positive control reference standard. FIG. 48 show plots of liver enzyme levels in cynomolgus monkeys after administration of PC-5.

Example 13: Serum Liver Enzymes in Cynomolgus Monkeys

Figure 56:
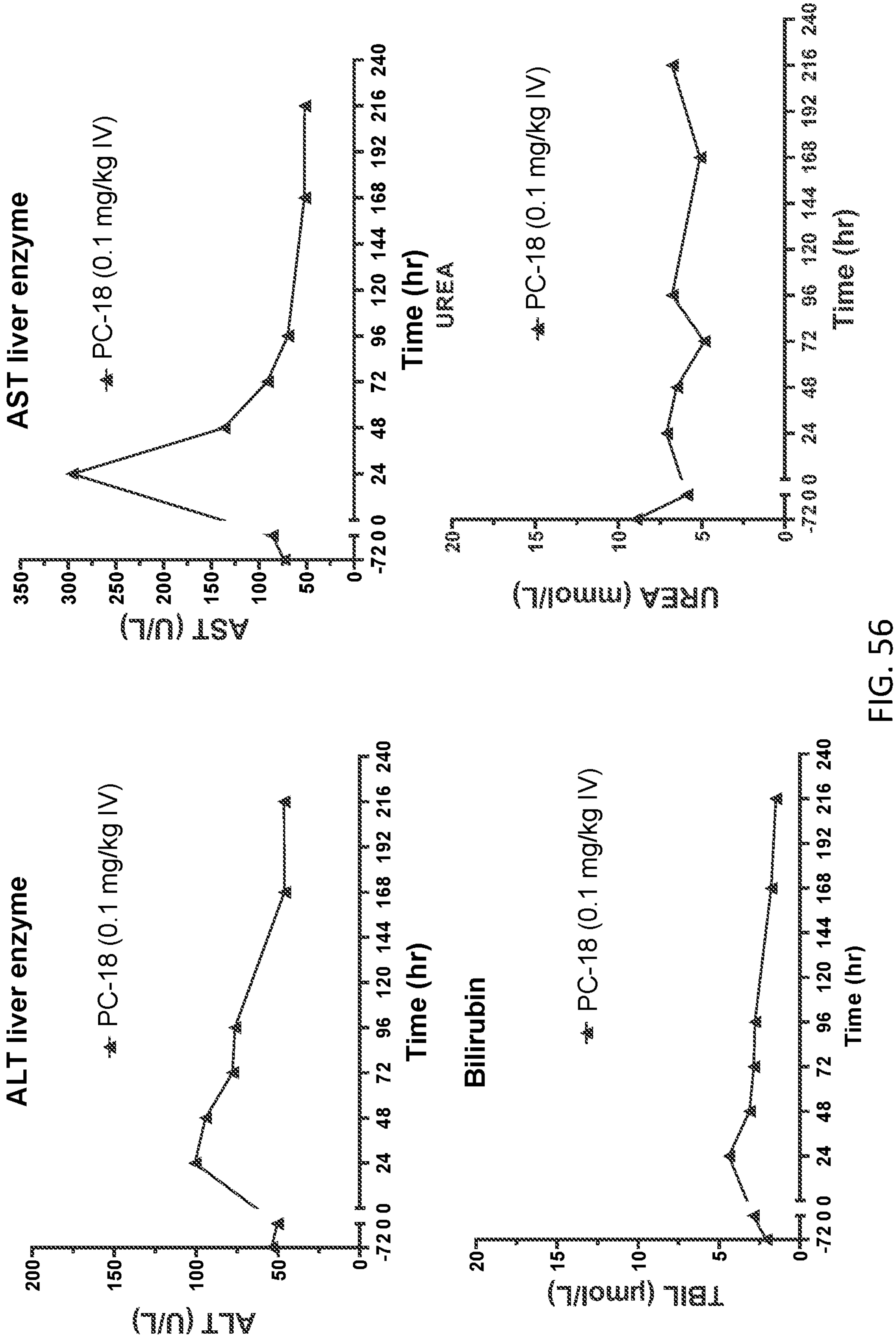
FIG. 56 shows serum liver enzymes, bilirubin, and urea in cynomolgus monkeys after single IV bolus of PC-18.

Clinical chemistry parameters after polypeptide molecule administration by IV bolus in cynomolgus monkeys were measured through standard panel analyses. Briefly, cynomolgus monkeys of approximately 3 kg bodyweight were administered polypeptides as an IV bolus and observed daily for signs of adverse events. After dosing, blood was collected in K2 EDTA tubes at specific timepoints and processed to plasma. Clinical chemistry parameters were run on freshly prepared plasma samples, including aspartate transaminase (AST), alanine aminotransferase (ALT), bilirubin (TBIL), and Urea as signs of liver and kidney related toxicity. FIGS. 49-56 show plots of liver enzyme levels in cynomolgus monkeys after administration of PC-1 (FIG. 49), PC-2 (FIG. 50), PC-3 (FIG. 51), PC-9 (FIG. 52), PC-15 (FIG. 53), PC-6 (FIG. 54), PC-8 (FIG. 55), and PC-18 (FIG. 56).

Figure 57:
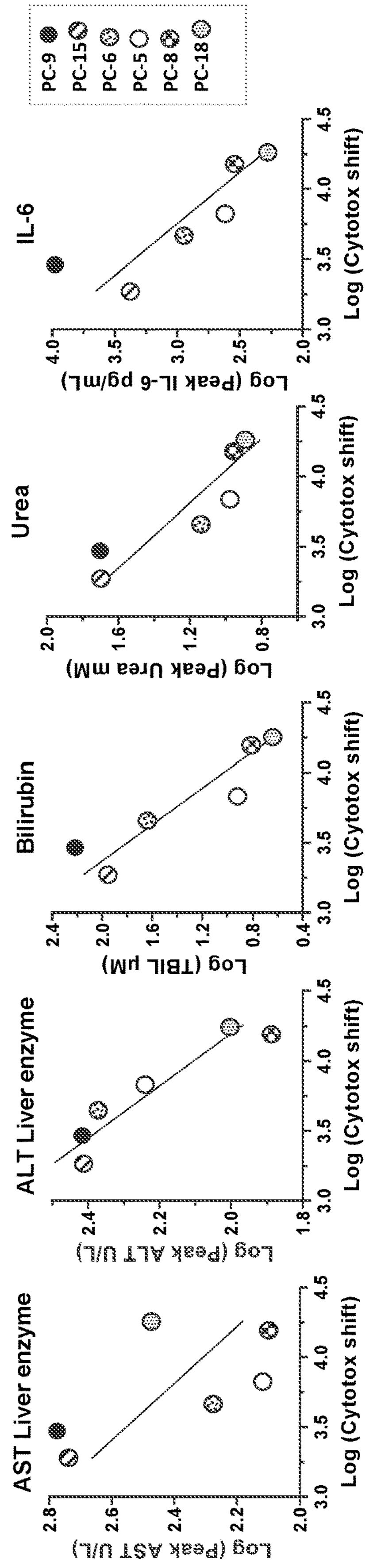
FIG. 57 shows a comparison of in vitro cytotoxicity shifts and cynomolgus monkey clinical chemistry safety signals for PC-9, PC-15, PC-6, PC-5, PC8, and PC-18.

Example 14: Correlation Between In Vitro Cytotoxicity Shifts and Cynomolgus Monkey Clinical Chemistry Safety Signals Comparison of clinical chemistry parameters measured in cynomolgus monkeys relative to the in vitro cytotoxicity activity revealed a strong in vitro to in vivo correlation. FIG. 57 shows plots of log peak concentrations for AST, ALT, bilirubin, urea, and IL-6 versus the log of the cytotoxic shift between the cytotoxicity of polypeptide complexes PC-9, PC-15, PC-6, PC-5, PC-8, and PC-18 and their non-masked polypeptide controls. Polypeptide complexes that exhibit weaker activity relative to their non-masked polypeptide controls appeared to be safer in cynomolgus monkeys based on clinical observations and clinical chemistry parameters measured. Table 35 compares the ratio of the cytotoxicity of the masked polypeptide complexes relative to their non-masked controls in H292 tumor cells and nonhuman primate (NHP) clinical observations after IV bolus injections in cynomolgus monkeys.

TABLE 35

| Polypeptide complex | H292 cytotoxicity Masked: non-masked | NHP clinical observations (100 μg/kg IV bolus) |
|---|---|---|
| PC-9 | 2916x | Liver injury; morbidity |
| PC-15 | 1882x | Liver injury; morbidity |
| PC-6 | 4598x | Skin rash; dehydration |
| PC-5 | 6852x | Skin rash; dehydration |
| PC-8 | 15606x | None |
| PC-18 | 18182x | None |

Example 15: Pharmacokinetics in Cynomolgus Monkey

Figure 58:
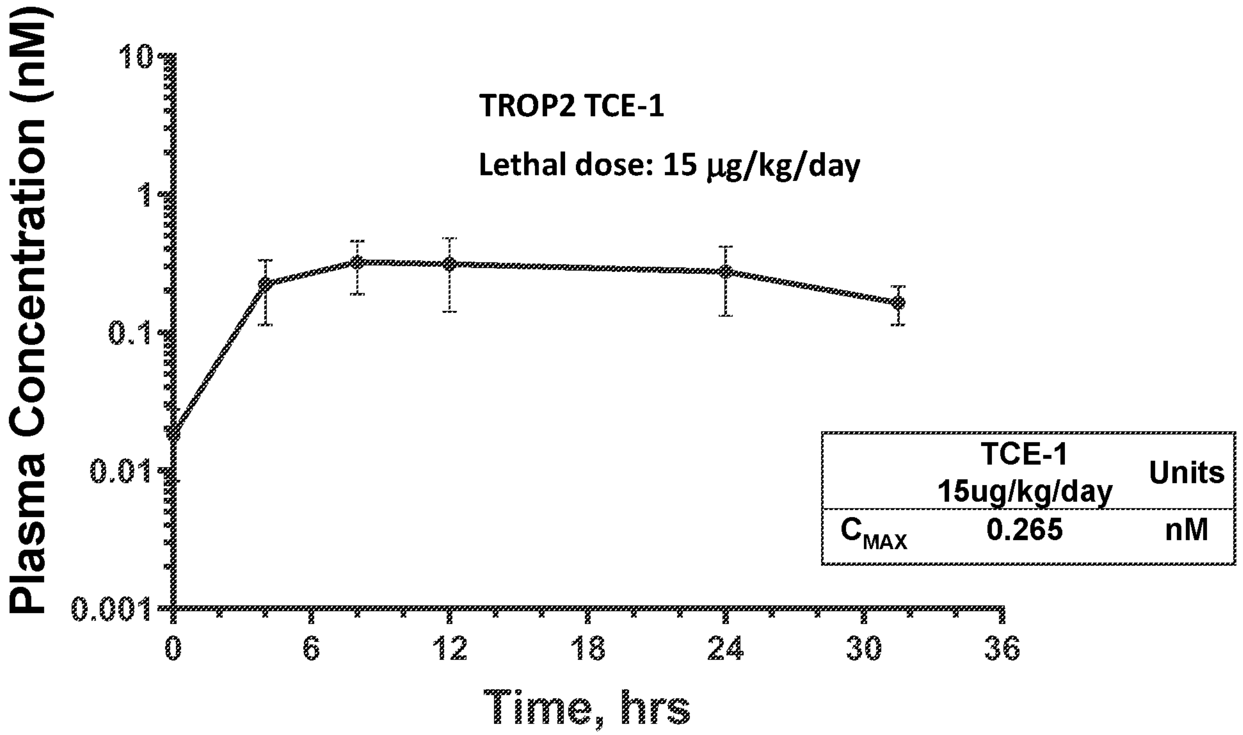
FIG. 58 shows polypeptide pharmacokinetics in cynomolgus monkeys after a continuous IV infusion of TCE-1.
Figure 59:
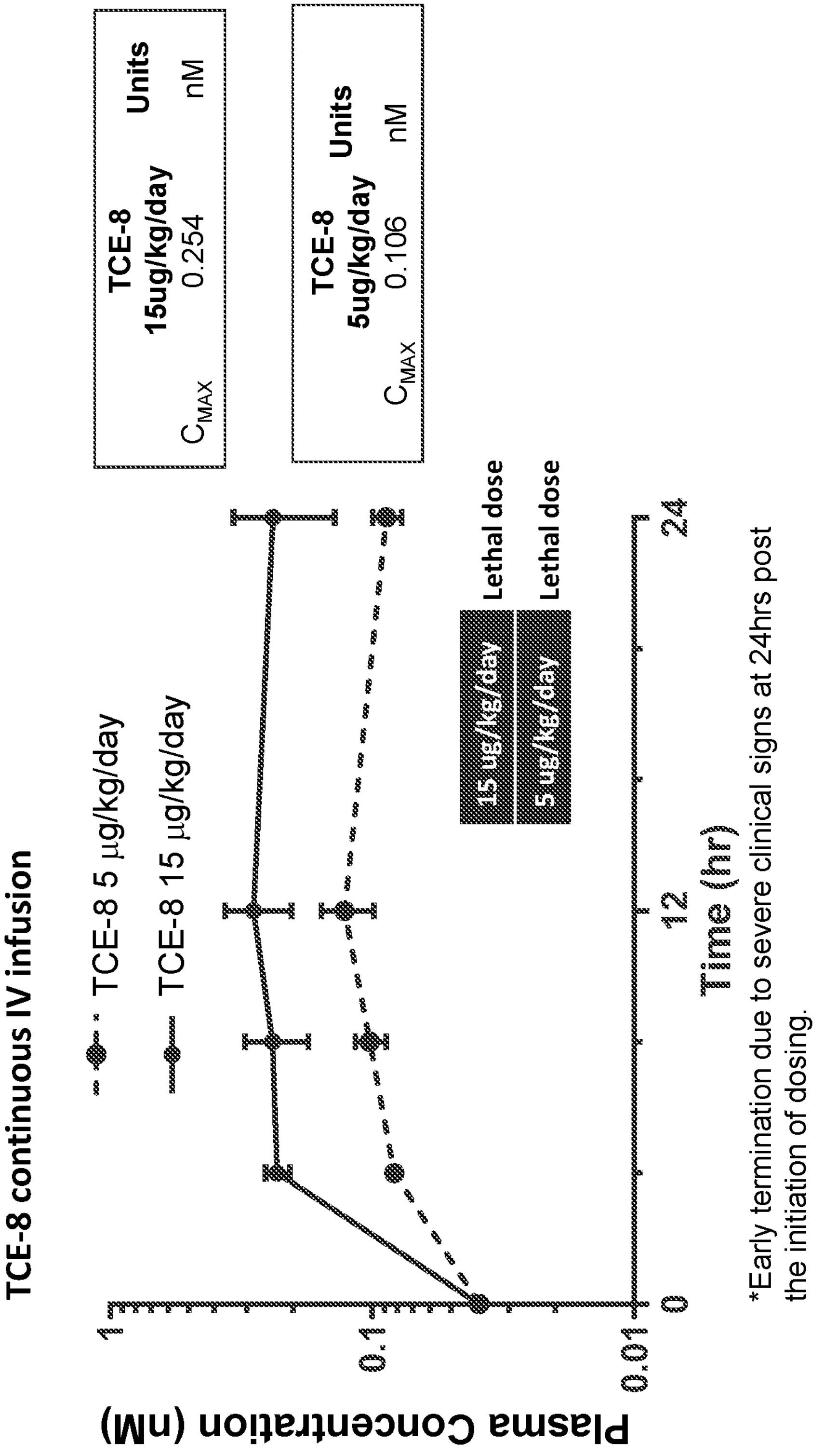
FIG. 59 shows polypeptide pharmacokinetics in cynomolgus monkeys after continuous IV infusions of TCE-8 at different dosing rates.
Figure 60:
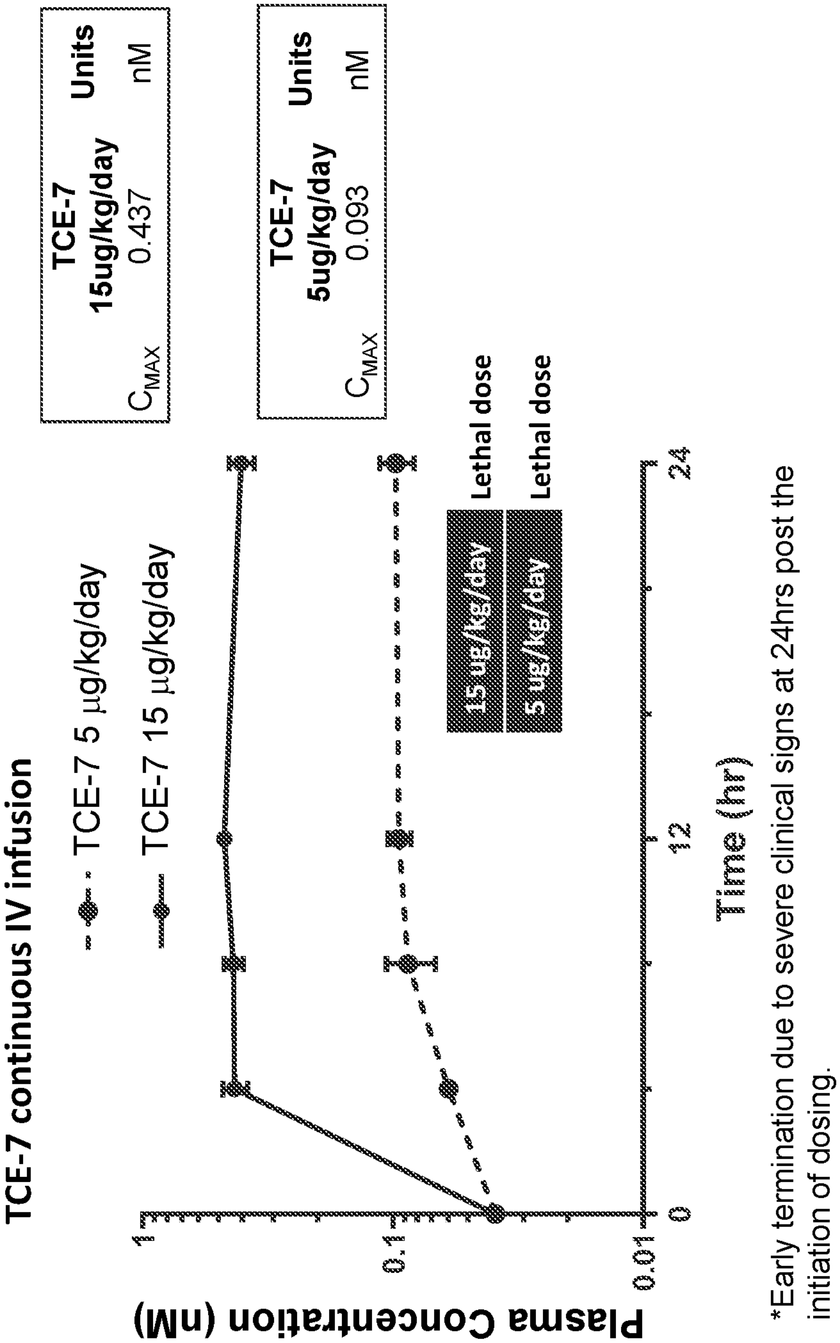
FIG. 60 shows polypeptide pharmacokinetics in cynomolgus monkeys after continuous IV infusions of TCE-7 at different dosing rates.

Pharmacokinetics and exploratory safety of polypeptide molecules were evaluated in cynomolgus monkeys. Briefly, cynomolgus monkeys of approximately 3 kg bodyweight were implanted with an infusion pump subcutaneously. Two weeks later the pump was filled with polypeptide dosing solution and administered via constant infusion. After dosing started, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cyno plasma. Plasma concentration curves were plotted overtime. FIGS. 58-59 show polypeptide pharmacokinetics in cynomolgus monkeys after continuous IV infusions of TCE-1 (FIG. 58), TCE-8 (FIG. 59), and TCE-7 (FIG. 60).

Example 16: Cytokine Release in Cynomolgus Monkey

Figure 61:
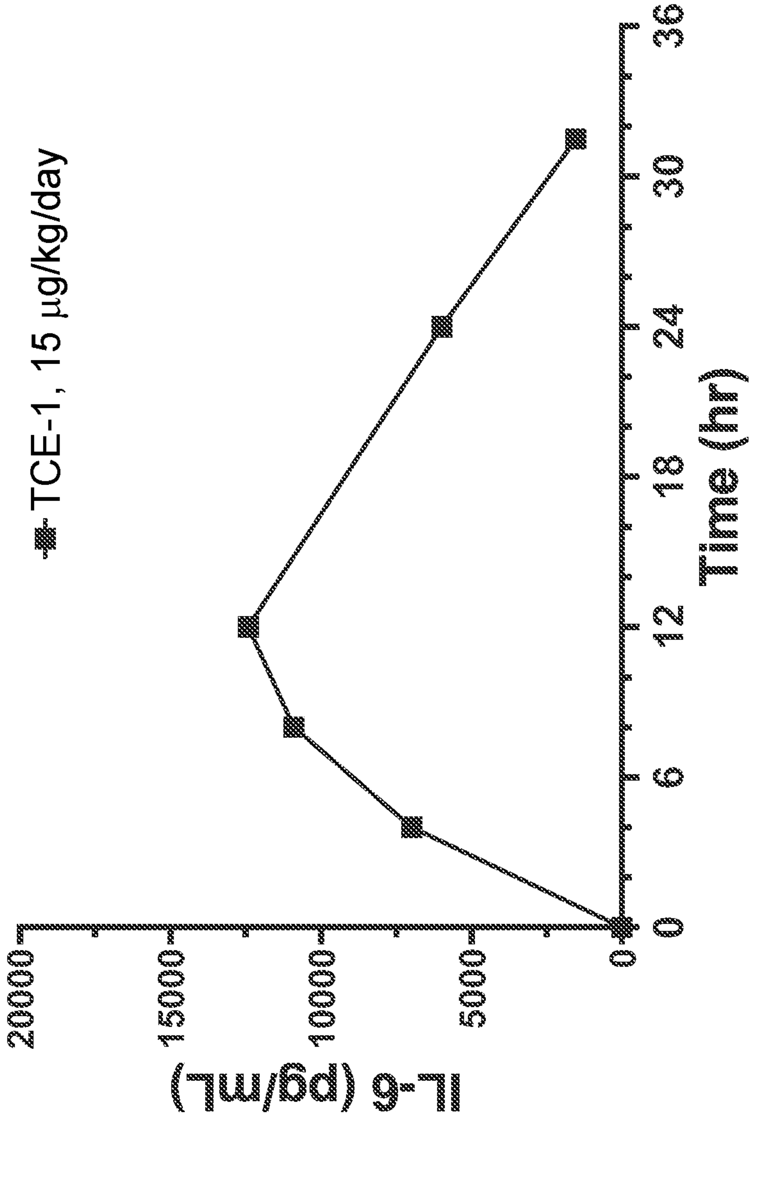
FIG. 61 shows cytokine release in cynomolgus monkey after continuous IV infusion of TCE-1.
Figure 62:
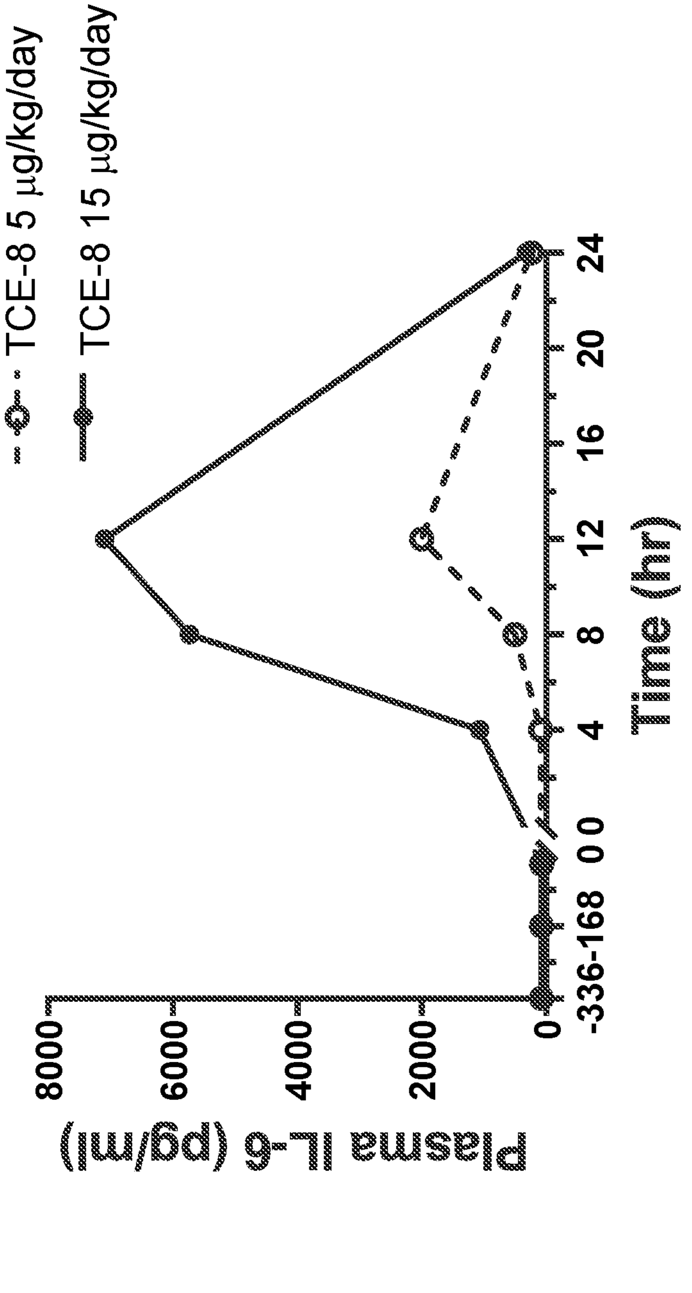
FIG. 62 shows cytokine release in cynomolgus monkey after continuous infusions of TCE-8 at different dosing rates.
Figure 63:
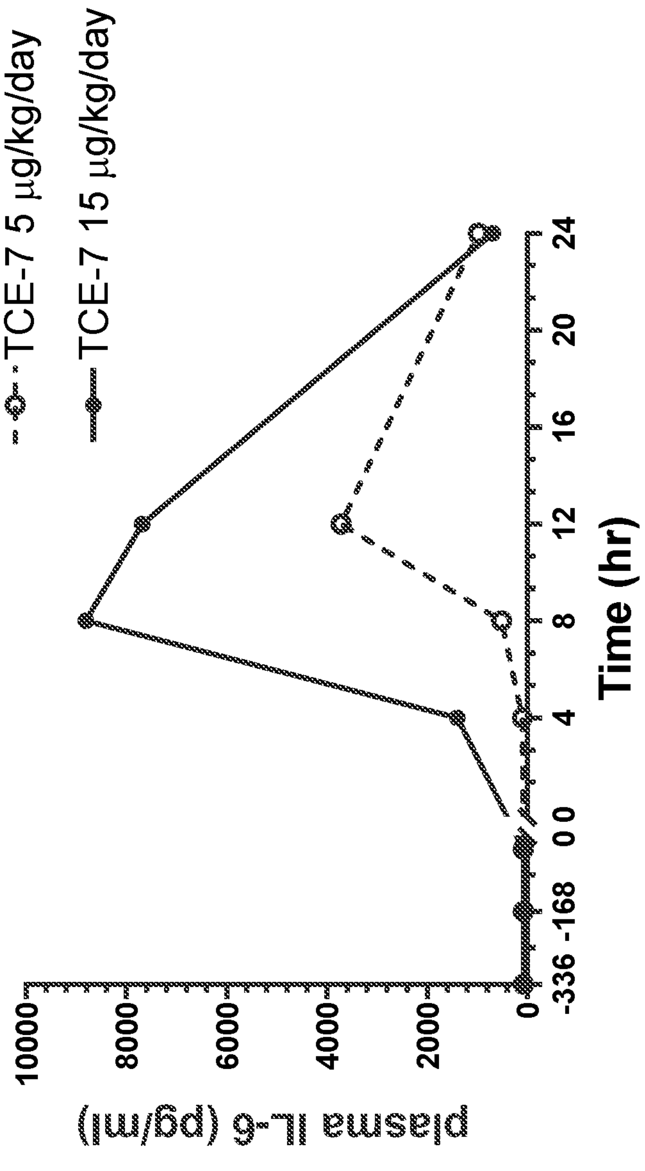
FIG. 63 shows cytokine release in cynomolgus monkey after continuous infusions of TCE-7 at different dosing rates.

Cytokine release after polypeptide molecule administration by continuous IV infusion was evaluated in cynomolgus monkeys. Briefly, cynomolgus monkeys of approximately 3 kg bodyweight were implanted with an infusion pump subcutaneously. Two weeks later the pump was filled with polypeptide dosing solution and administered via constant infusion. After dosing started, blood was collected in K2 EDTA tubes at specific timepoints and processed to plasma. Plasma samples were analyzed for cytokines using a non-human primate cytometric Th1/Th2 bead array kit from BD biosciences following the manufacturers instructions. Interferon gamma, tumor necrosis factor alpha, interleukin 6, interleukin 5, interleukin 4, and interleukin 2 levels in plasma were calculated relative to reference standards provided with the bead array kit. FIGS. 61-63 shows cytokine release in cynomolgus monkey after continuous IV infusions of TCE-1 (FIG. 61), TCE-8 (FIG. 62), and TCE-7 (FIG. 63).

Example 17: Non-Human Primate (NHP) Toxicity Studies of PC-8 and TCE-8

Figure 64:
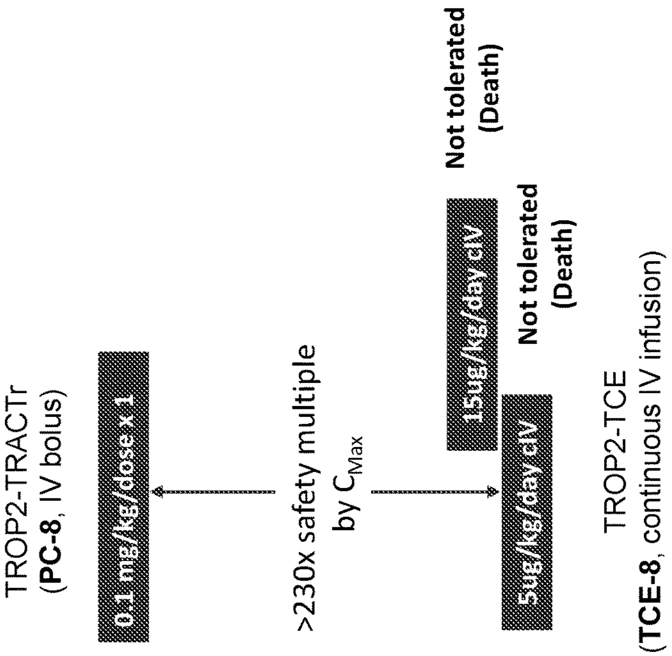
FIGS. 64-65 show results of non-human primate (NHP) toxicity studies of PC-8 and TCE-8.
Figure 65:
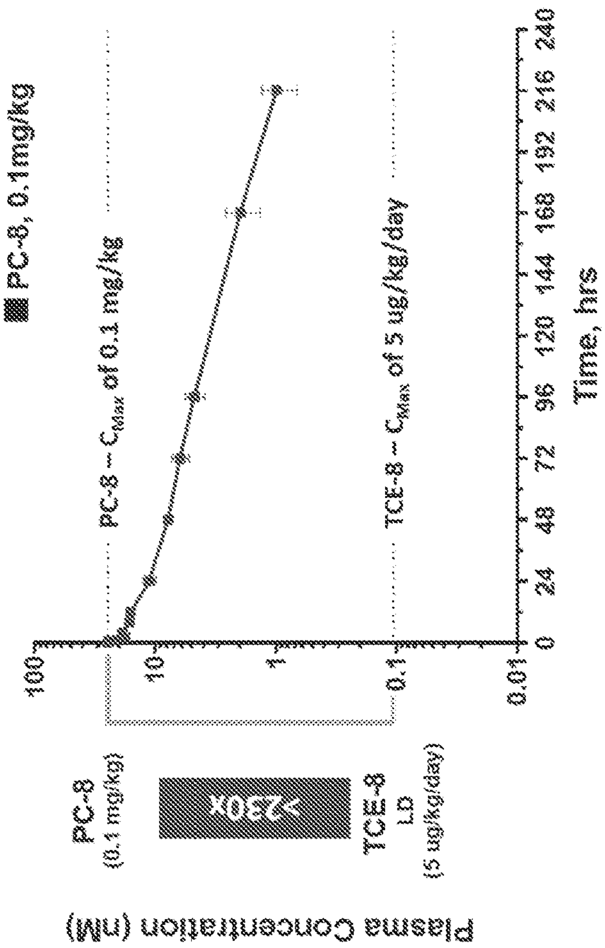

Pharmacokinetics and exploratory safety of masked PC-8 and non-masked TCE-8 were evaluated in cynomolgus monkeys. Briefly, cynomolgus monkeys of approximately 3 kg bodyweight were administered polypeptides as an IV bolus or via continuous IV infusion. Animals were observed for signs of adverse events. PC-8 was dosed at 0.1 mg/kg/dose. TCE-8 was dosed at 5 μg/kg/day and 15 μg/kg/day. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cynomolgus monkey plasma. Maximum plasma concentrations achieved in animals for masked polypeptide complex were compared to those achieved using the non-masked polypeptide complex. Comparison of the maximum plasma concentration achieved with the masked polypeptide complex compared to the maximum tolerated plasma concentration for the non-masked polypeptide complex revealed a >230× multiple (see FIGS. 64-65). As can be seen, TCE-8 is active at low concentrations while masked PC-8 is safe at high exposures in cynomolgus monkeys. Masked PC-8 demonstrates a large in vivo safety multiple relative to non-masked PC-8.

Example 18: Non-Human Primate (NHP) Toxicity Studies of PC-18 and TCE-7

Figure 67:
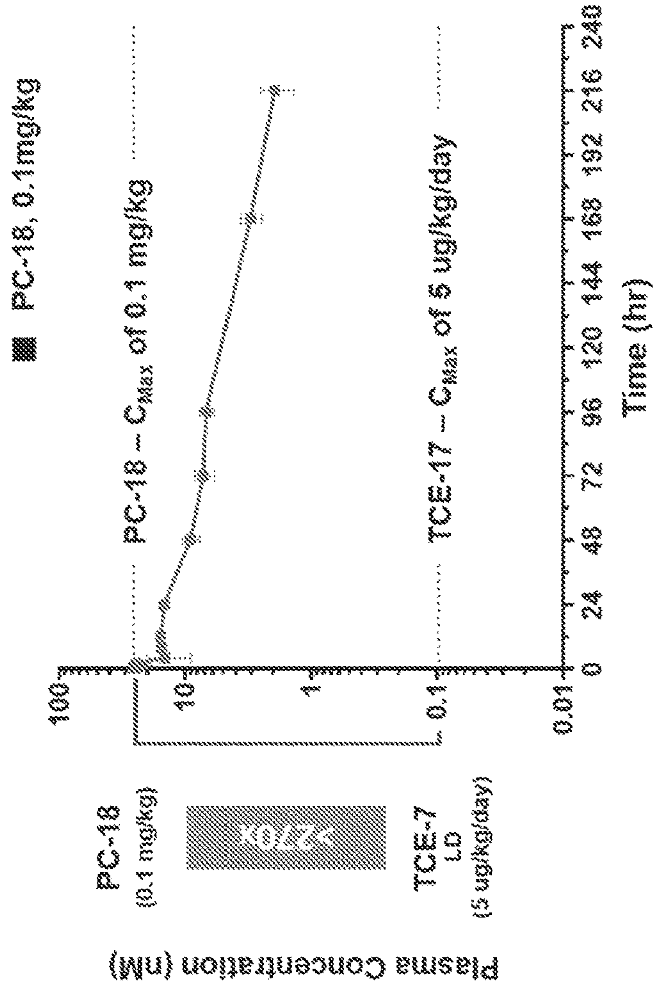
FIGS. 66-67 show results of NHP toxicity studies of PC-18 and TCE-7 in cynomolgus monkeys.
Figure 66:
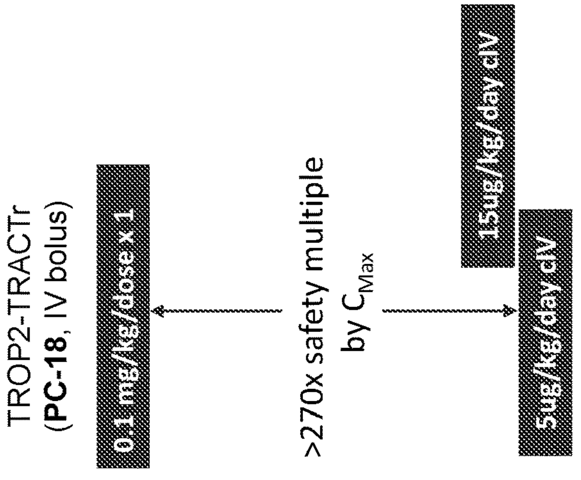

Pharmacokinetics and exploratory safety of masked PC-18 and non-masked TCE-7 were evaluated in cynomolgus monkeys. Observations and measurements were carried out as described in Example 17. PC-18 was dosed at 0.1 mg/kg/dose. TCE-7 was dosed at 5 μg/kg/day and 15 μg/kg/day. Comparison of the maximum plasma concentration achieved with the masked polypeptide complex compared to the maximum tolerated plasma concentration for the non-masked polypeptide complex revealed a >270× multiple (see FIGS. 66-67). As can be seen, TCE-7 is active at low concentrations while masked PC-18 is safe at high exposures in cynomolgus monkeys. Masked PC-18 demonstrates a large in vivo safety multiple relative to non-masked TCE-7.

Example 19: Binding of TROP2 TCEs to CD3 (Alanine Mutated CD3 Binding Domain)

Figure 68:
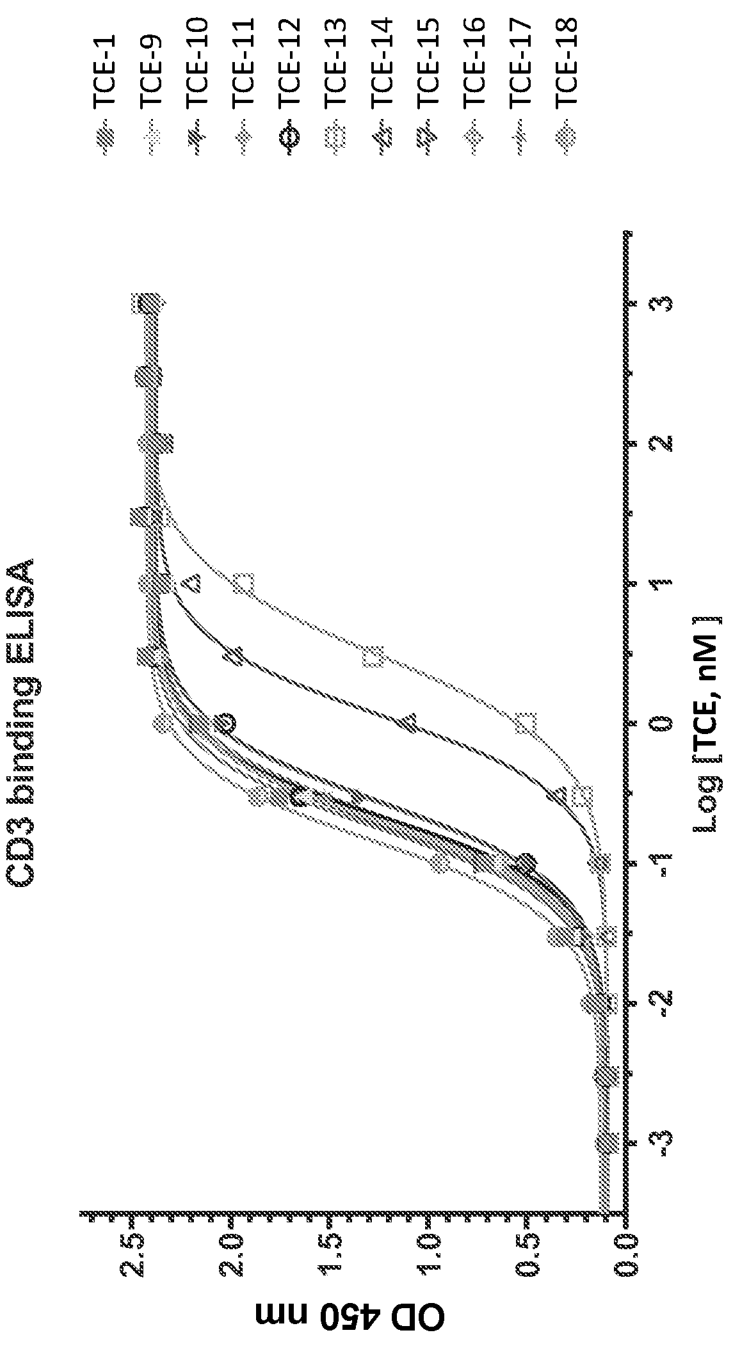
FIG. 68 illustrates binding curves and $EC_{50}$s for binding of human CD3 by TCE-1 and TCE-9 to TCE-18 as measured by ELISA.
Figure 69:
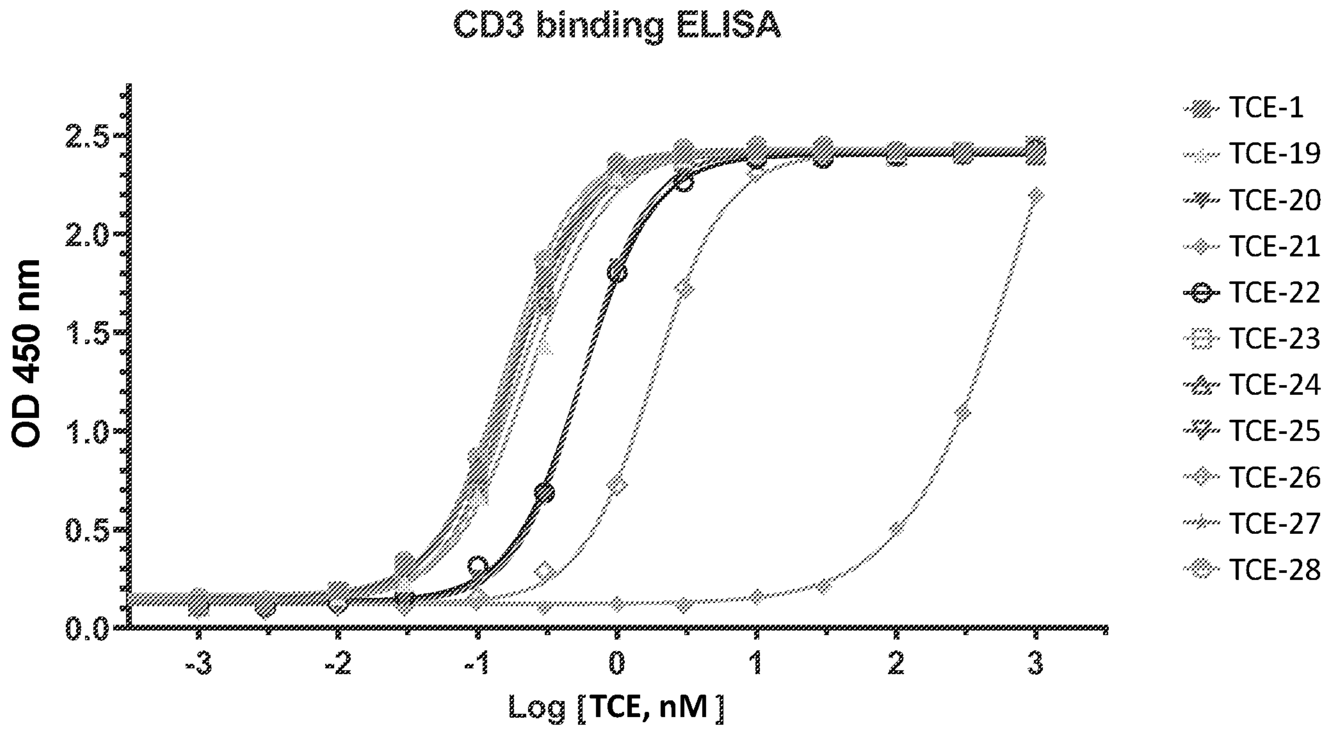
FIG. 69 illustrates binding curves and $EC_{50}$s for binding of human CD3 by TCE-1 and TCE-19 to TCE-28 as measured by ELISA.
Figure 70:
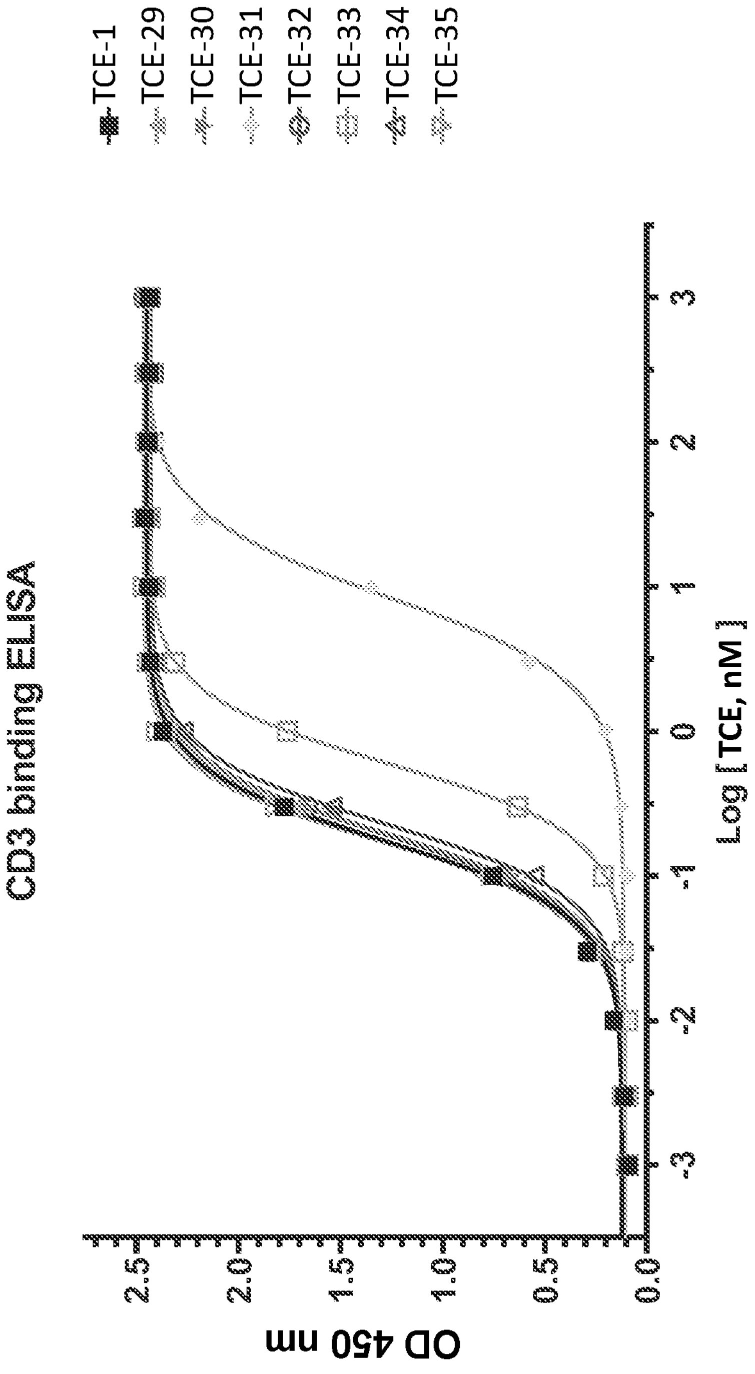
FIG. 70 illustrates binding curves and $EC_{50}$s for binding of human CD3 by TCE-1 and TCE-29 to TCE-35 as measured by ELISA.
Figure 71:
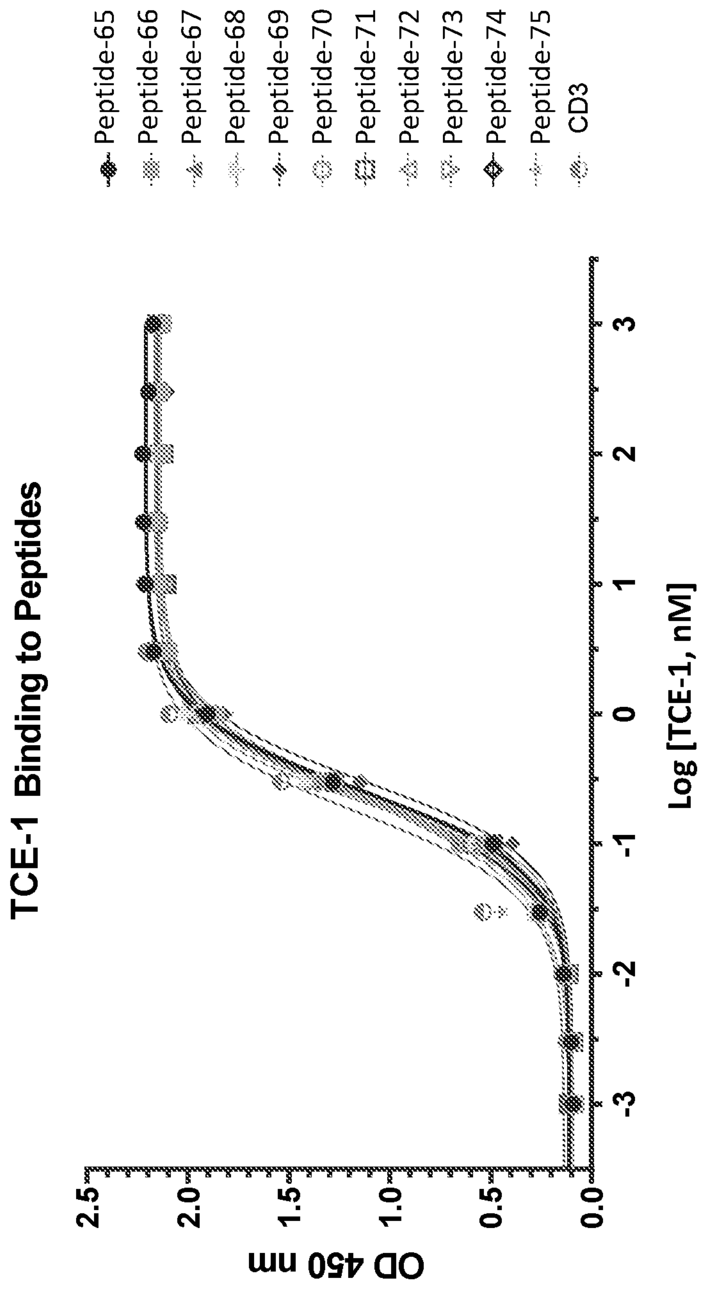
FIG. 71 illustrates binding curves for peptide binding to TCE-1 as measured by ELISA.
Figure 72:
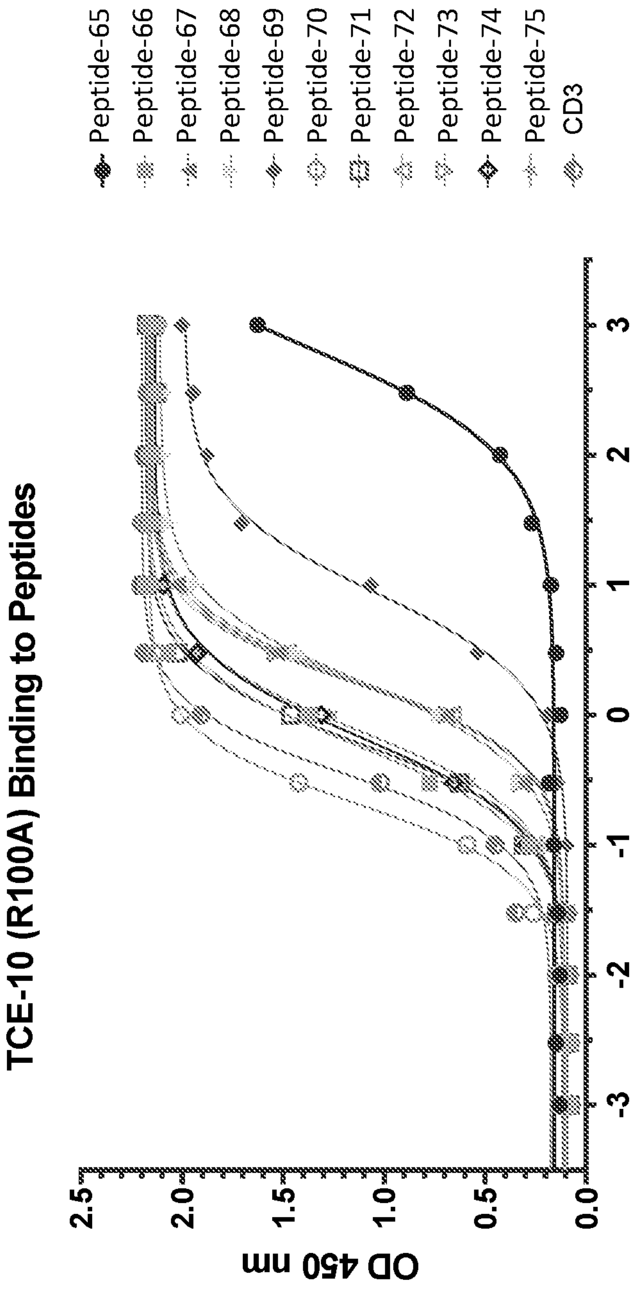
FIG. 72 illustrates binding curves for peptide binding to TCE-10 as measured by ELISA.
Figure 73:
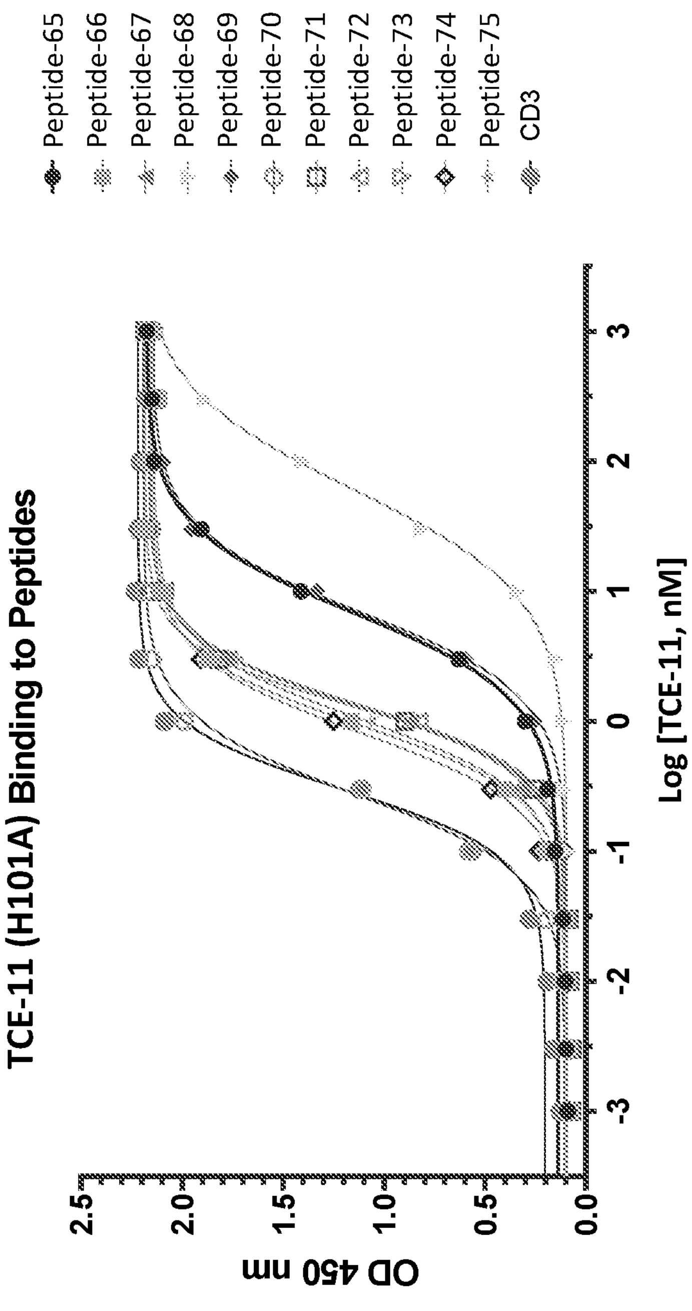
FIG. 73 illustrates binding curves for peptide binding to TCE-11 as measured by ELISA.
Figure 74:
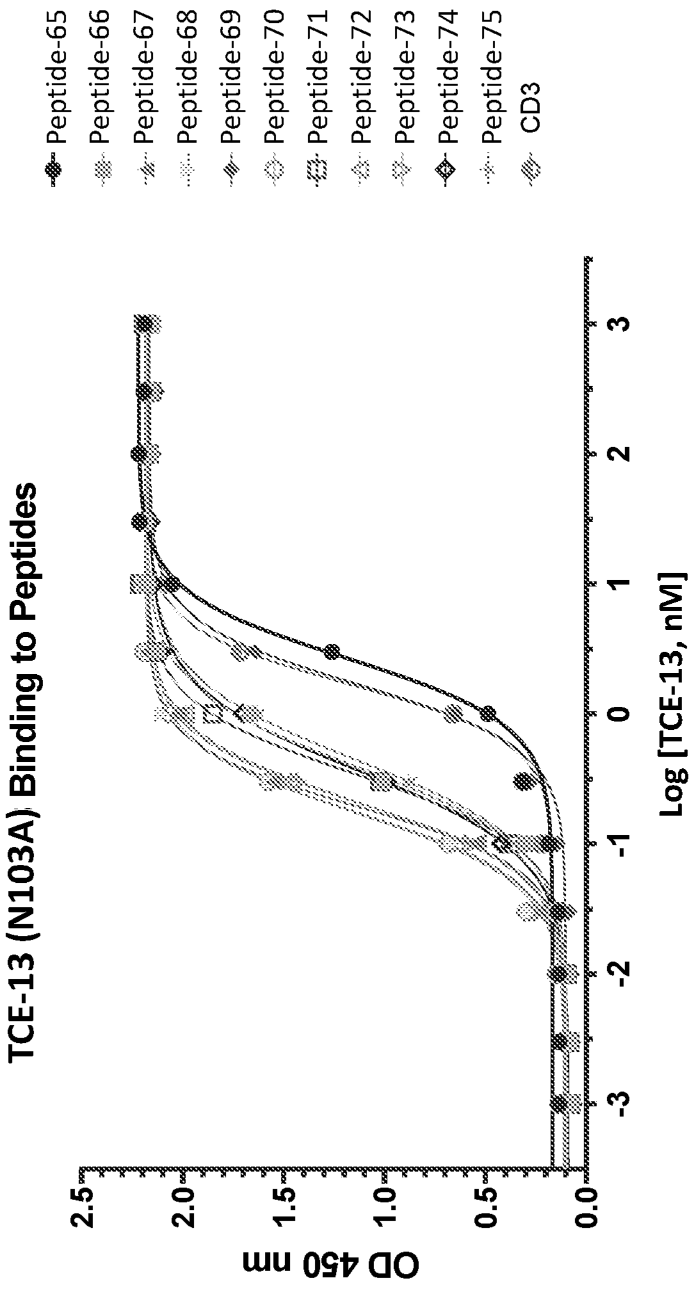
FIG. 74 illustrates binding curves for peptide binding to TCE-13 as measured by ELISA.
Figure 75:
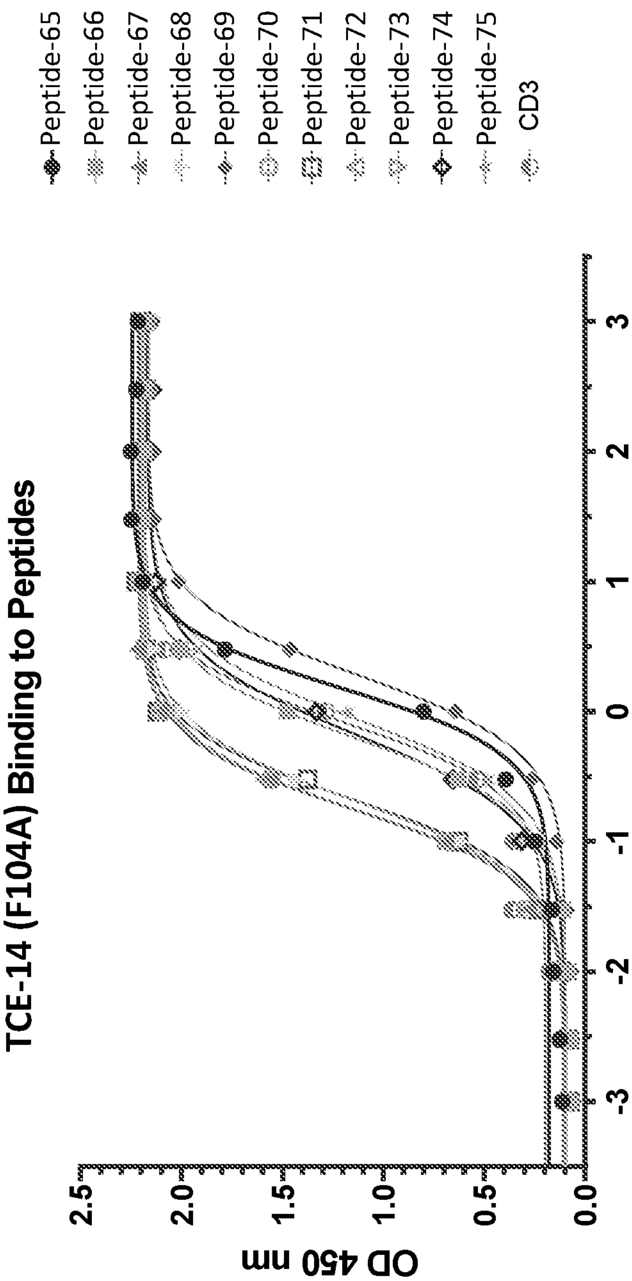
FIG. 75 illustrates binding curves for peptide binding to TCE-14 as measured by ELISA.
Figure 76:
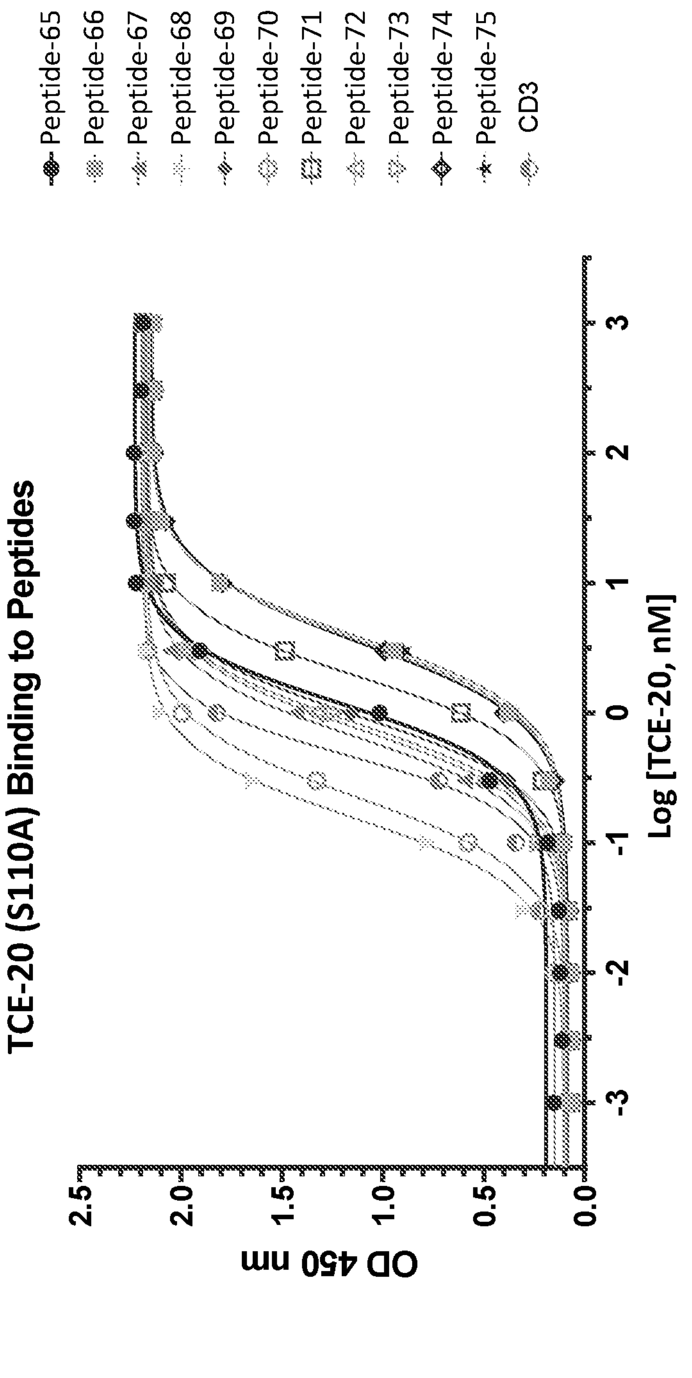
FIG. 76 illustrates binding curves for peptide binding to TCE-20 as measured by ELISA.
Figure 77:
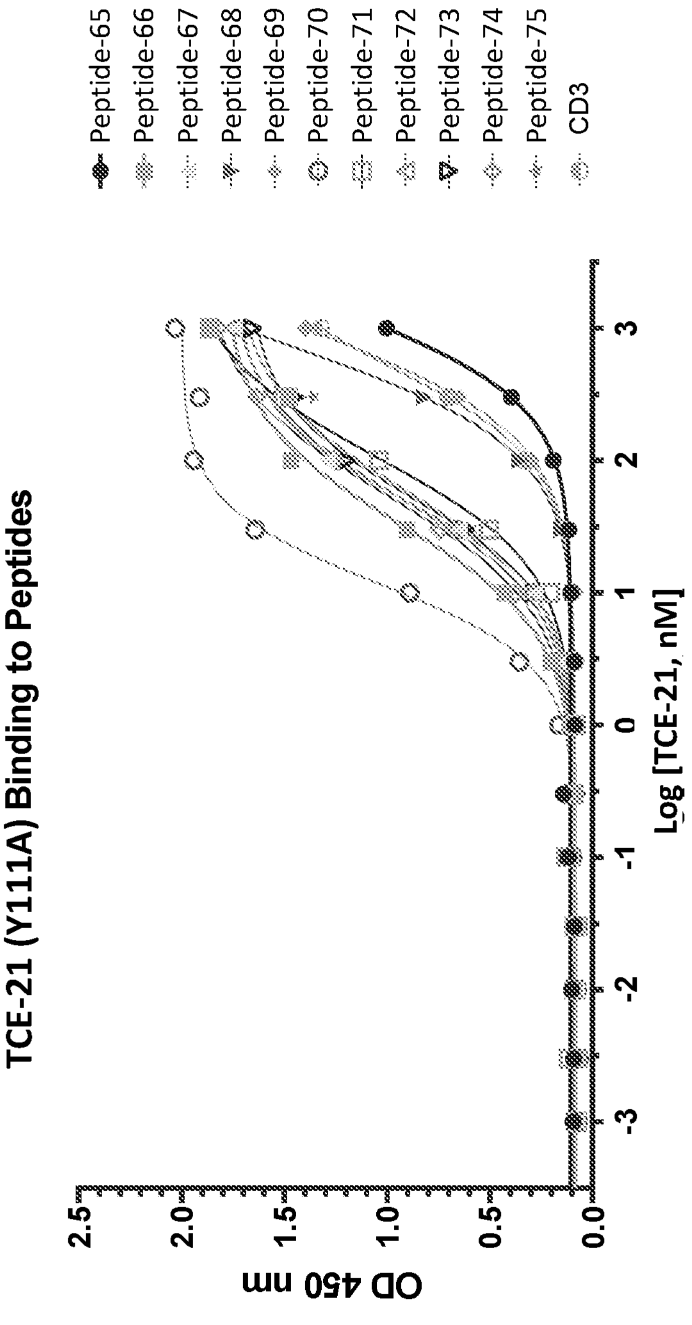
FIG. 77 illustrates binding curves for peptide binding to TCE-21 as measured by ELISA.
Figure 78:
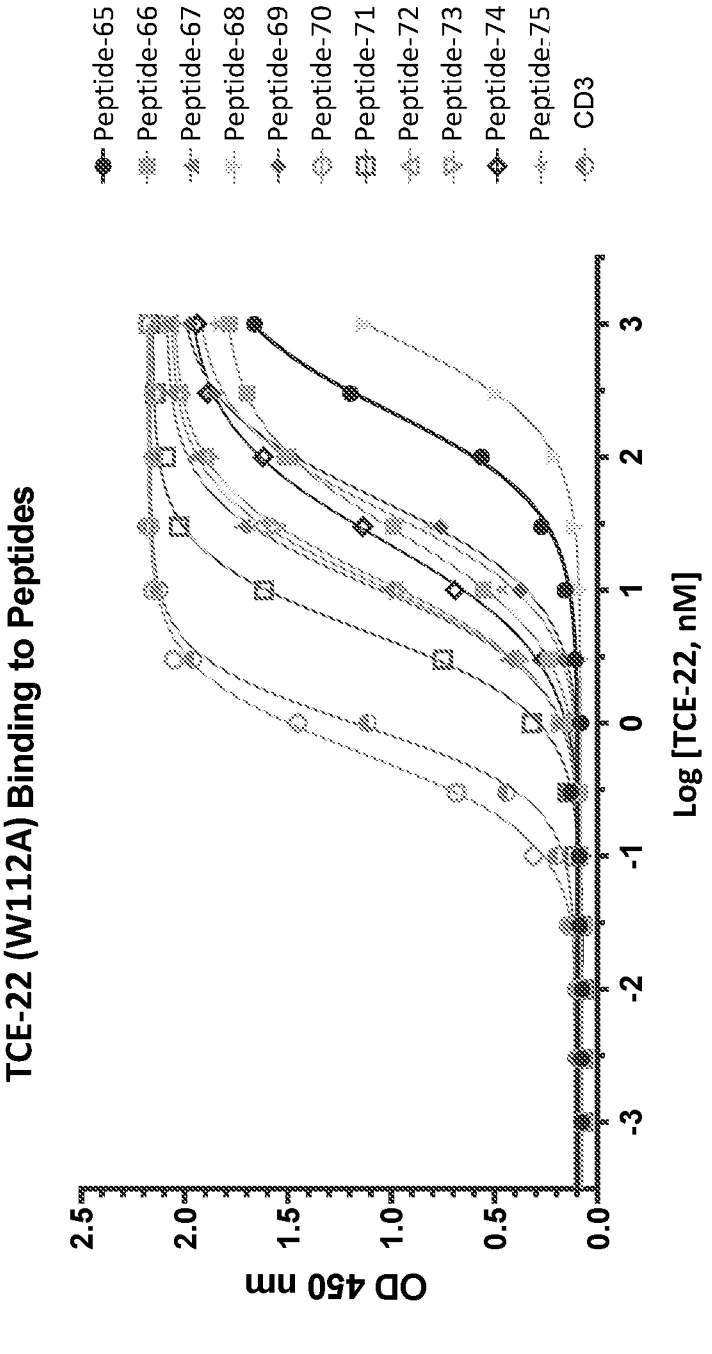
FIG. 78 illustrates binding curves for peptide binding to TCE-22 as measured by ELISA.
Figure 79:
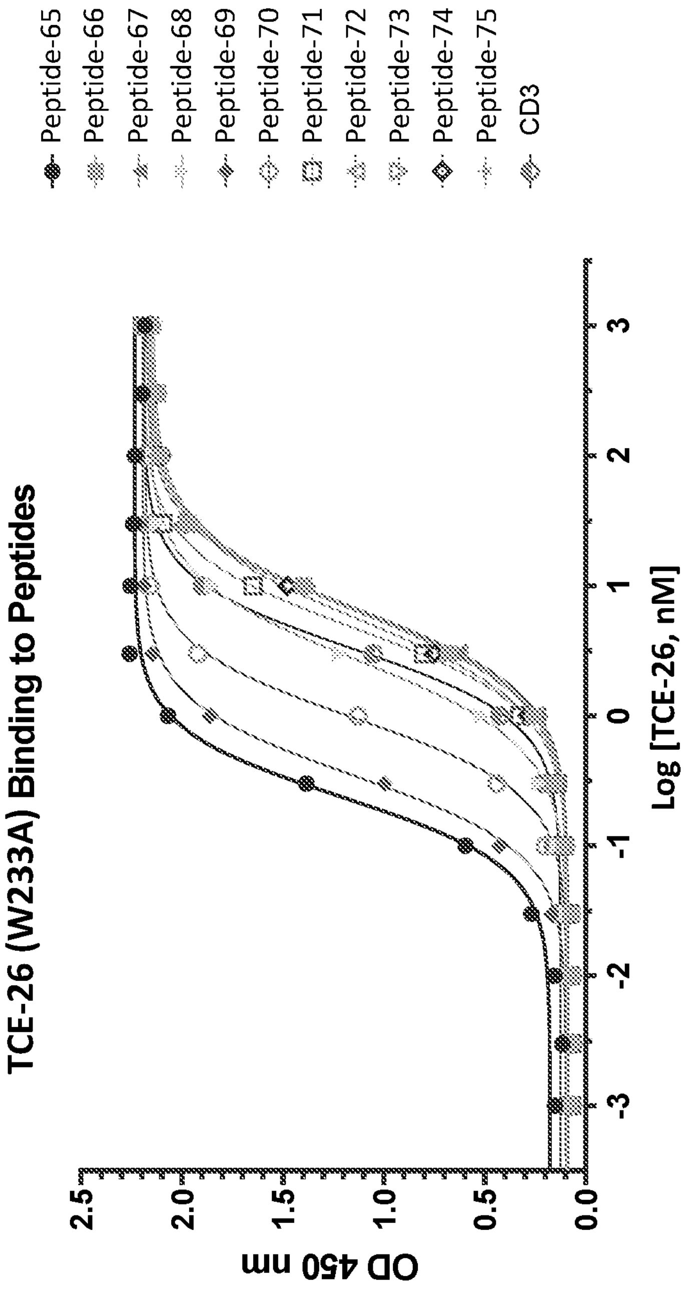
FIG. 79 illustrates binding curves for peptide binding to TCE-26 as measured by ELISA.
Figure 80:
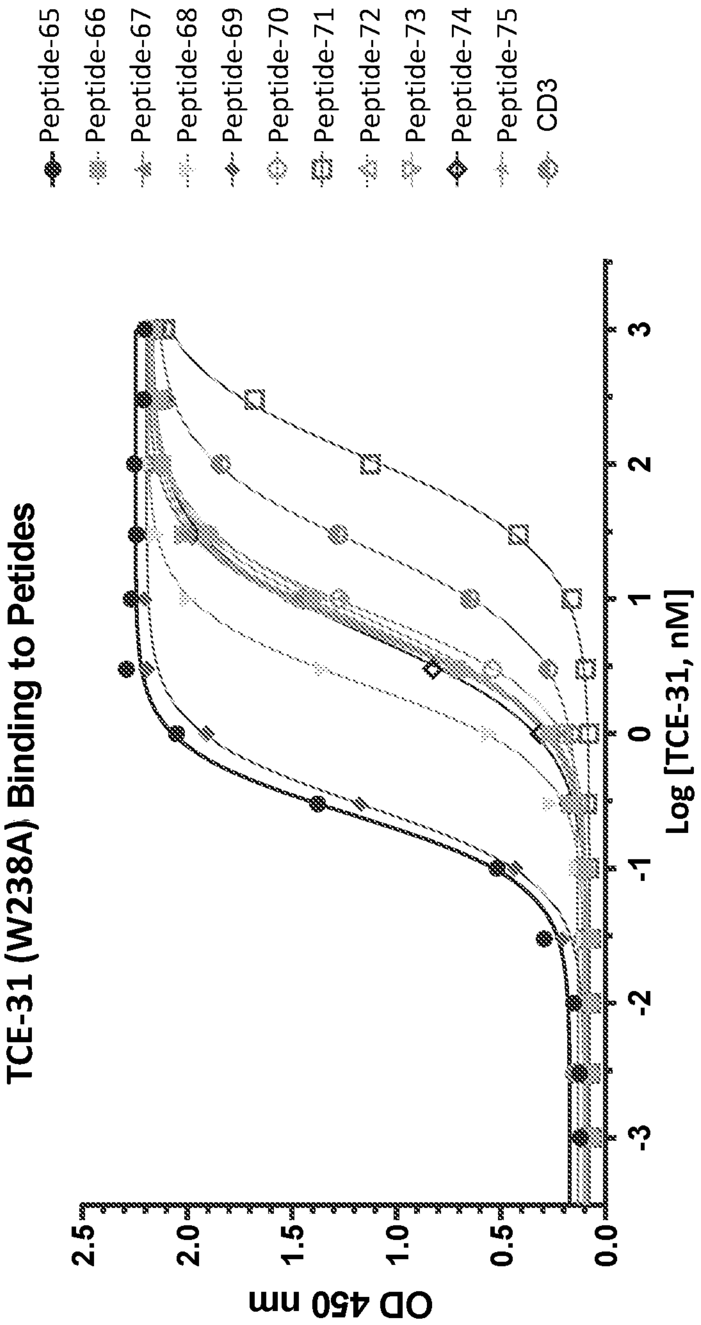
FIG. 80 illustrates binding curves for peptide binding to TCE-31 as measured by ELISA.
Figure 81:
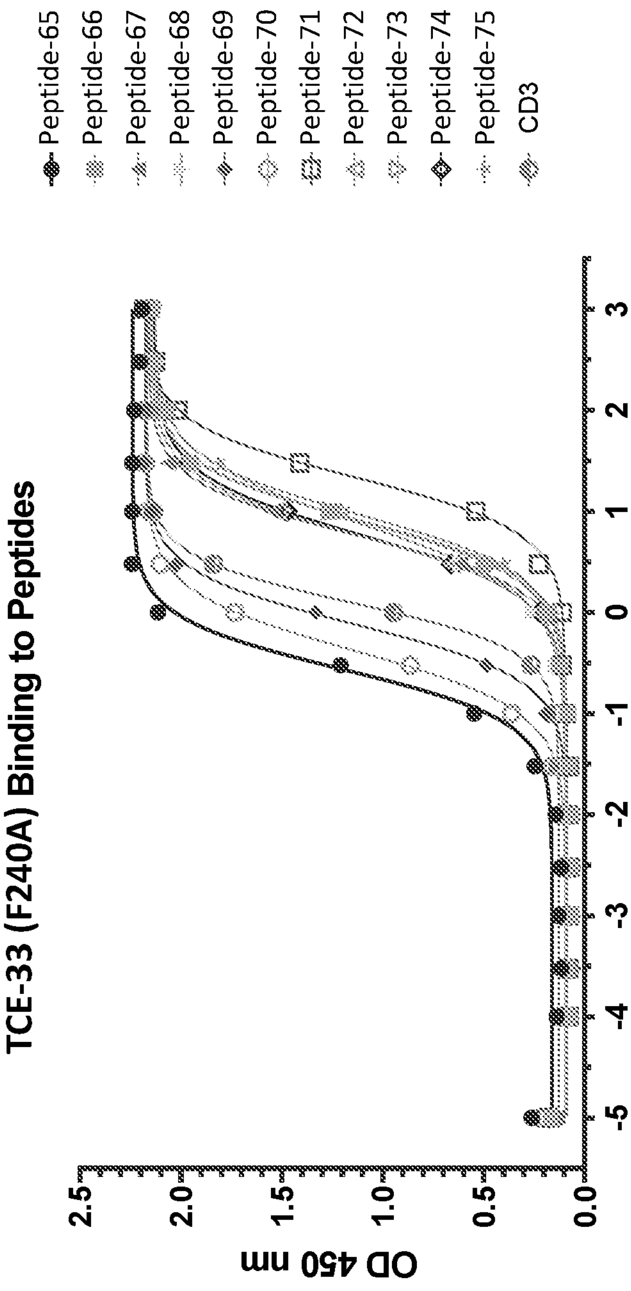
FIG. 81 illustrates binding curves for peptide binding to TCE-33 as measured by ELISA.
Figure 82:
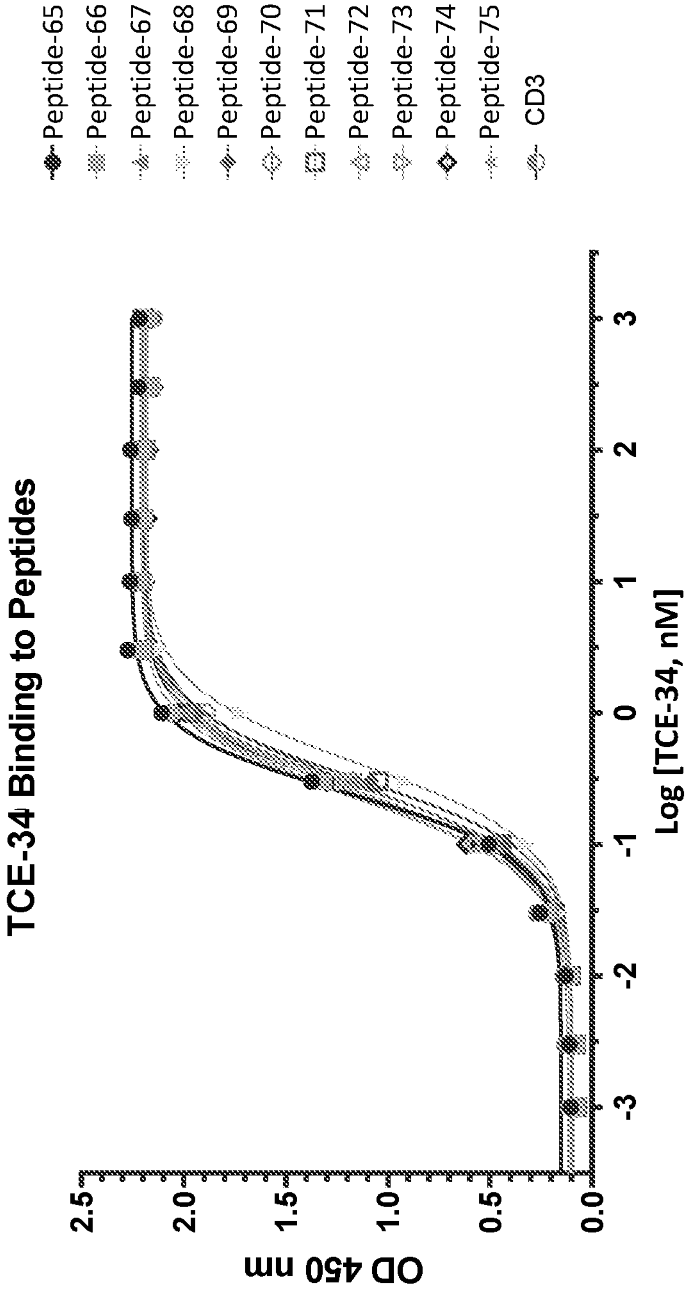
FIG. 82 illustrates binding curves for peptide binding to TCE-34 as measured by ELISA.
Figure 83:
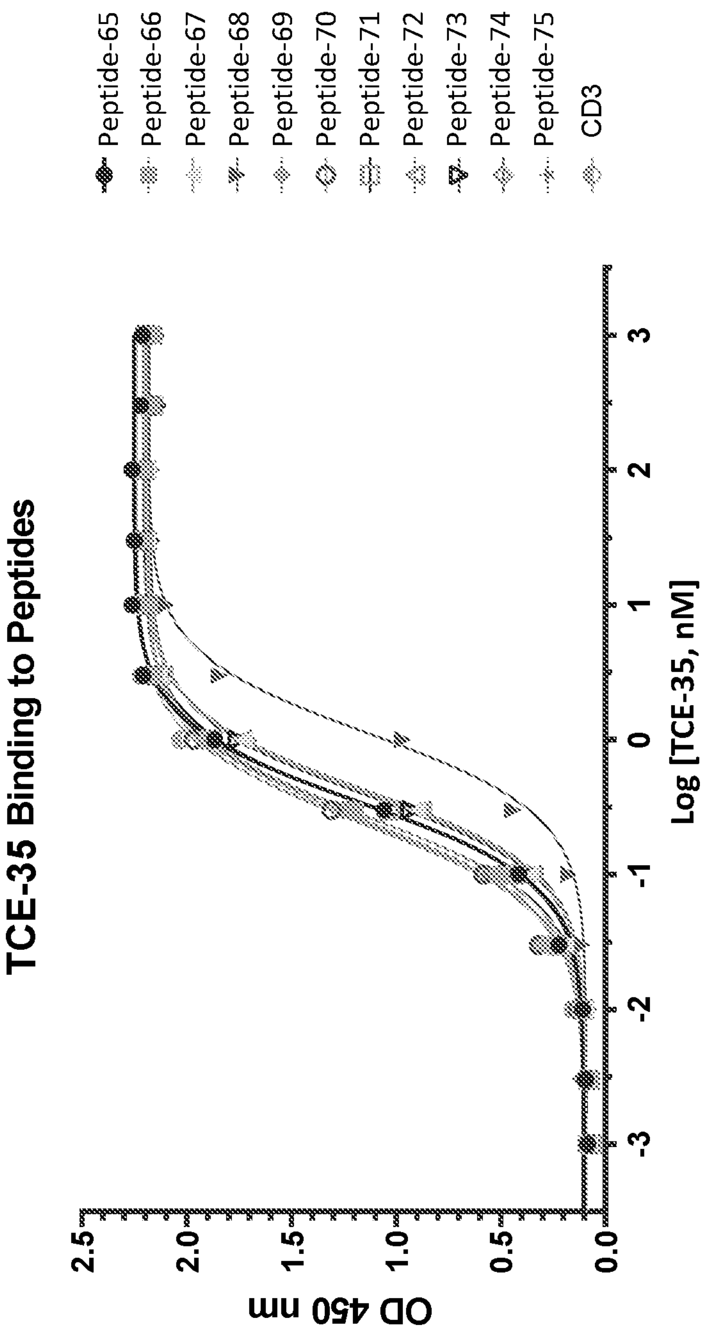
FIG. 83 illustrates binding curves for peptide binding to TCE-35 as measured by ELISA.

Wild-type and alanine mutated T cell engager (TCE) constructs were evaluated for their ability to bind CD3. The alanine mutated TCEs include single alanine mutations in the CDR3 light chain or CDR3 heavy chain of the CD3 binding domain. Binding to CD3 was evaluated using an ELISA format. Briefly, biotinylated CD3 was captured on neutravidin coated plates. TCE constructs diluted in buffer were then added to the CD3 captured plates. TCE binding was detected using a standard horse radish peroxidase secondary antibody. The concentration of TCE required to achieve 50% maximal signal ($EC_{50}$) was calculated. Binding curves for TCE-1 and TCE-9 to TCE-18 to human CD3 along with calculated $EC_{50}$s are shown in FIG. 68. Binding curves for TCE-1 and TCE-19 to TCE-28 to human CD3 along with calculated $EC_{50}$s are shown in FIG. 69. Binding curves and $EC_{50}$s for TCE-1 and TCE-29 to TCE-35 binding to human CD3 are shown in FIG. 70.

Example 20: Binding of Peptide Masks to Wild-Type and Mutated TROP2 TCEs

Select peptide mask sequences of Table 9 were screened for their binding affinities against wild-type and mutant CD3 binding domains harbored within TROP2 TCE constructs of Table 8. Binding was measured in a standard ELISA format. Briefly, biotinylated peptides (or biotinylated CD3) were captured on neutravidin coated plates. The TROP2 TCE constructs diluted in buffer were then added to the peptide coated plates. Bound TCEs were detected using a standard horse radish peroxidase conjugate secondary antibody. The ELISA signal was plotted versus the log-scale concentration of TCE. The concentrations of TCE required to observe half maximal binding signal ($EC_{50}$s) were calculated using Graphpad Prism software. FIGS. 71-83 show ELISA binding curves for peptide binding to TROP2-TCE sequences with a wild-type CD3 binding domain or TROP2-TCE sequences with alanine mutations in the CD3 binding domain. $EC_{50}$s for peptide binding to wild-type and mutated TROP2 TCE sequences are provided in Tables 36-37.

TABLE 36

TROP2 TCE Binding to Peptides by ELISA (wild-type and anti-CD3 CDR3 HC mutants)

| | TCE-1 (wt) $EC_{50}$ (nM) | TCE-10 (R100A) $EC_{50}$ (nM) | TCE-11 (H101A) $EC_{50}$ (nM) | TCE-13 (N103A) $EC_{50}$ (nM) | TCE-14 (F104A) $EC_{50}$ (nM) | TCE-20 (S110A) $EC_{50}$ (nM) |
|---|---|---|---|---|---|---|
| CD3-biotin | 0.18 | 0.35 | 0.30 | 1.69 | 0.83 | 0.47 |
| Peptide-65 | 0.26 | 473.40 | 6.92 | 2.71 | 1.52 | 1.18 |
| Peptide-66 | 0.25 | 0.58 | 0.94 | 0.39 | 0.63 | 3.65 |
| Peptide-67 | 0.23 | 1.76 | 1.31 | 0.20 | 0.18 | 0.66 |
| Peptide-68 | 0.21 | 1.78 | 60.93 | 0.18 | 0.21 | 0.16 |
| Peptide-69 | 0.30 | 8.73 | 6.94 | 1.69 | 1.93 | 0.95 |
| Peptide-70 | 0.22 | 0.21 | 0.28 | 0.18 | 0.18 | 0.23 |
| Peptide-71 | 0.25 | 0.63 | 1.28 | 0.34 | 0.21 | 1.92 |
| Peptide-72 | 0.23 | 1.85 | 1.36 | 0.21 | 0.18 | 0.76 |
| Peptide-73 | 0.22 | 1.74 | 1.31 | 0.21 | 0.18 | 0.83 |
| Peptide-74 | 0.21 | 0.68 | 0.83 | 0.36 | 0.66 | 3.46 |
| Peptide-75 | 0.22 | 0.76 | 1.05 | 0.44 | 0.88 | 3.82 |

TABLE 37

TROP2-TCE Binding to Peptides by ELISA (anti-CD3 CDR3 LC and CDR3 HC mutants)

| | TCE-21 (Y111A) $EC_{50}$ (nM) | TCE-22 (W112A) $EC_{50}$ (nM) | TCE-26 (W233A) $EC_{50}$ (nM) | TCE-31 (W238A) $EC_{50}$ (nM) | TCE-33 (F240A) $EC_{50}$ (nM) | TCE-34 $EC_{50}$ (nM) | TCE-35 $EC_{50}$ (nM) |
|---|---|---|---|---|---|---|---|
| CD3-biotin | 592.30 | 0.95 | 3.29 | 24.01 | 1.24 | 0.26 | 0.25 |
| Peptide-65 | 1083.00 | 219.80 | 0.24 | 0.25 | 0.27 | 0.25 | 0.34 |
| Peptide-66 | 49.12 | 26.35 | 6.28 | 6.34 | 8.02 | 0.24 | 0.27 |
| Peptide-67 | 77.73 | 10.51 | 6.46 | 5.96 | 5.78 | 0.28 | 0.41 |
| Peptide-68 | 381.20 | 794.10 | 2.68 | 2.29 | 7.71 | 0.41 | 1.12 |
| Peptide-69 | 571.80 | 48.24 | 0.35 | 0.29 | 0.76 | 0.31 | 0.42 |
| Peptide-70 | 11.93 | 0.59 | 0.95 | 8.00 | 0.42 | 0.29 | 0.23 |
| Peptide-71 | 105.70 | 4.87 | 4.69 | 112.10 | 21.66 | 0.32 | 0.33 |
| Peptide-72 | 76.86 | 11.15 | 6.43 | 5.66 | 5.78 | 0.27 | 0.42 |
| Peptide-73 | 94.18 | 12.16 | 6.63 | 6.10 | 8.15 | 0.25 | 0.38 |
| Peptide-74 | 64.17 | 23.39 | 5.47 | 5.33 | 5.90 | 0.23 | 0.27 |
| Peptide-75 | 95.61 | 38.18 | 6.26 | 7.08 | 9.20 | 0.22 | 0.25 |

Figure 84A:
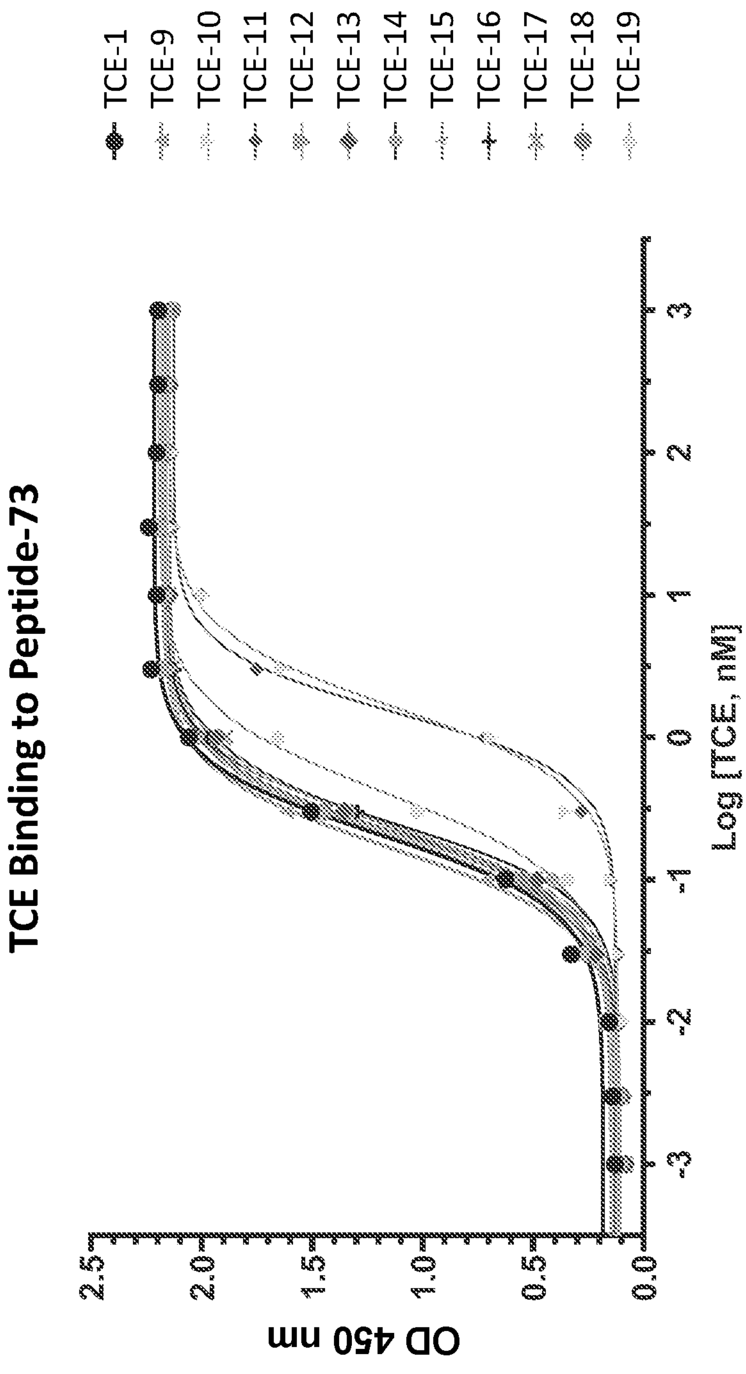
FIGS. 84A-84C illustrate binding curves for peptide-73 binding to TROP2 TCEs as measured by ELISA.
Figure 84B:
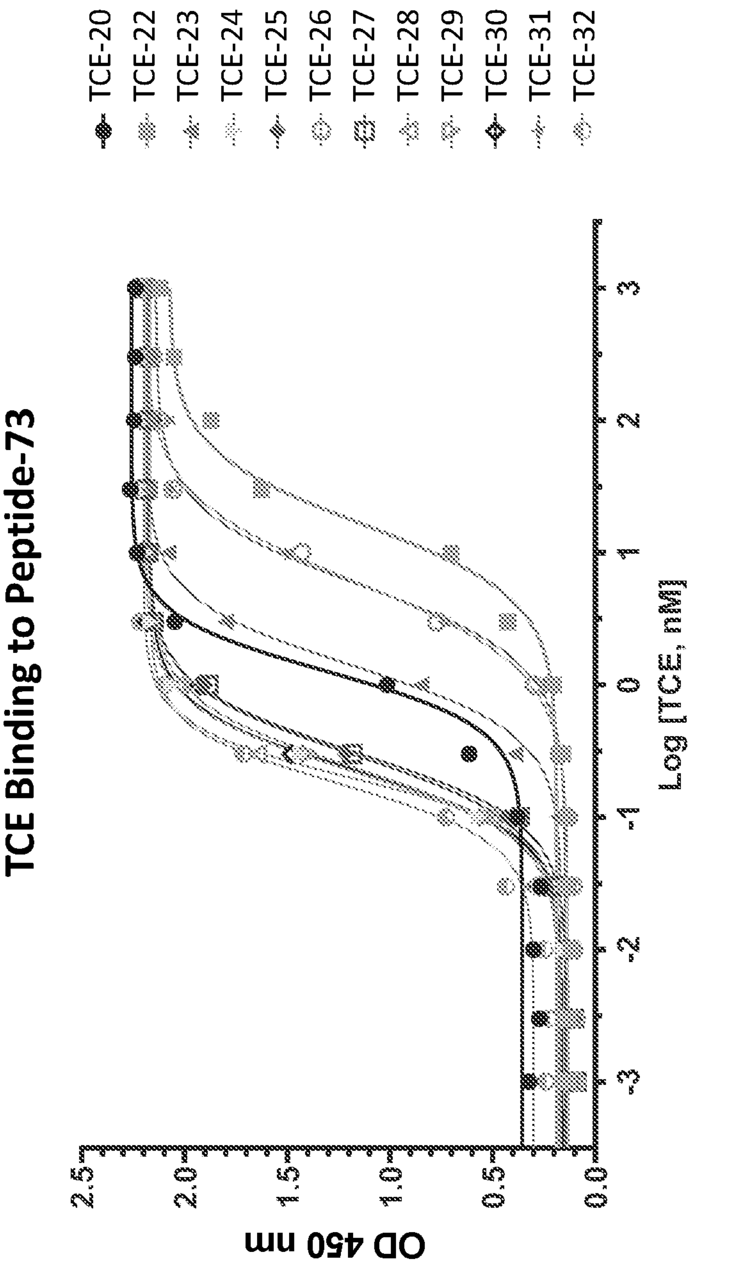
Figure 84C:
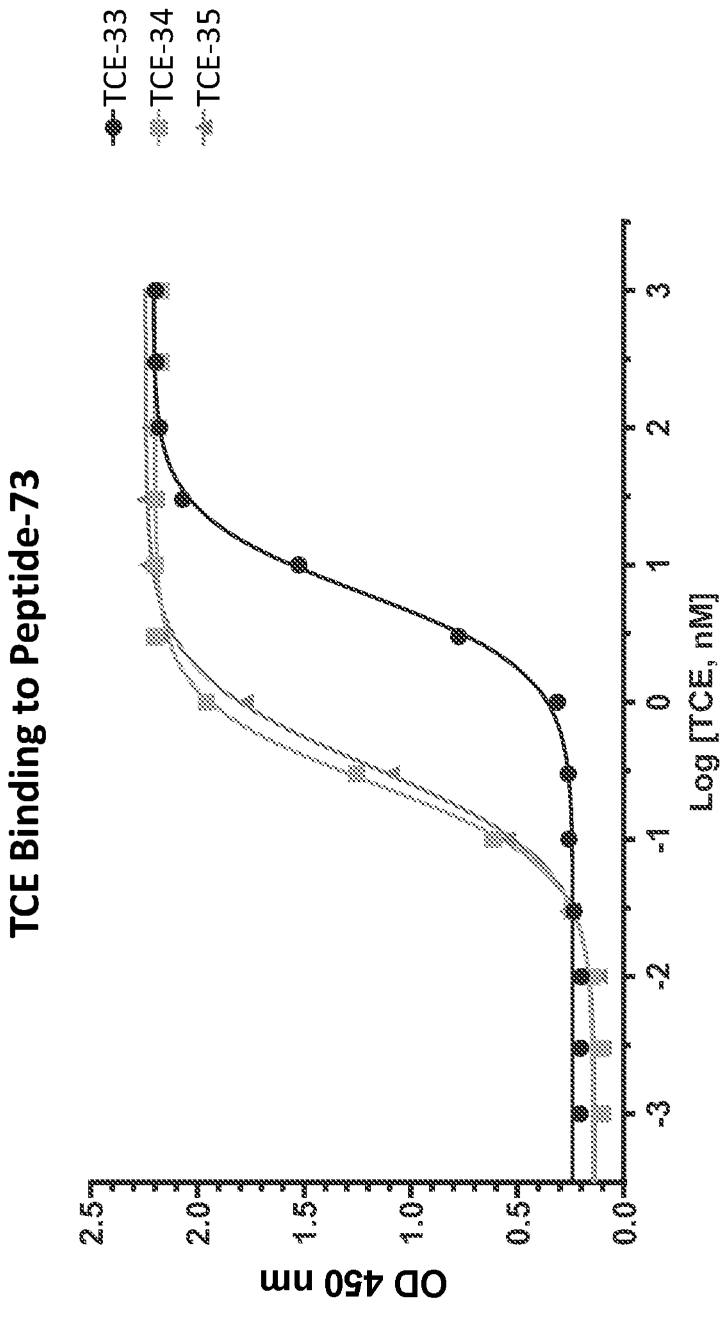
Figure 85:
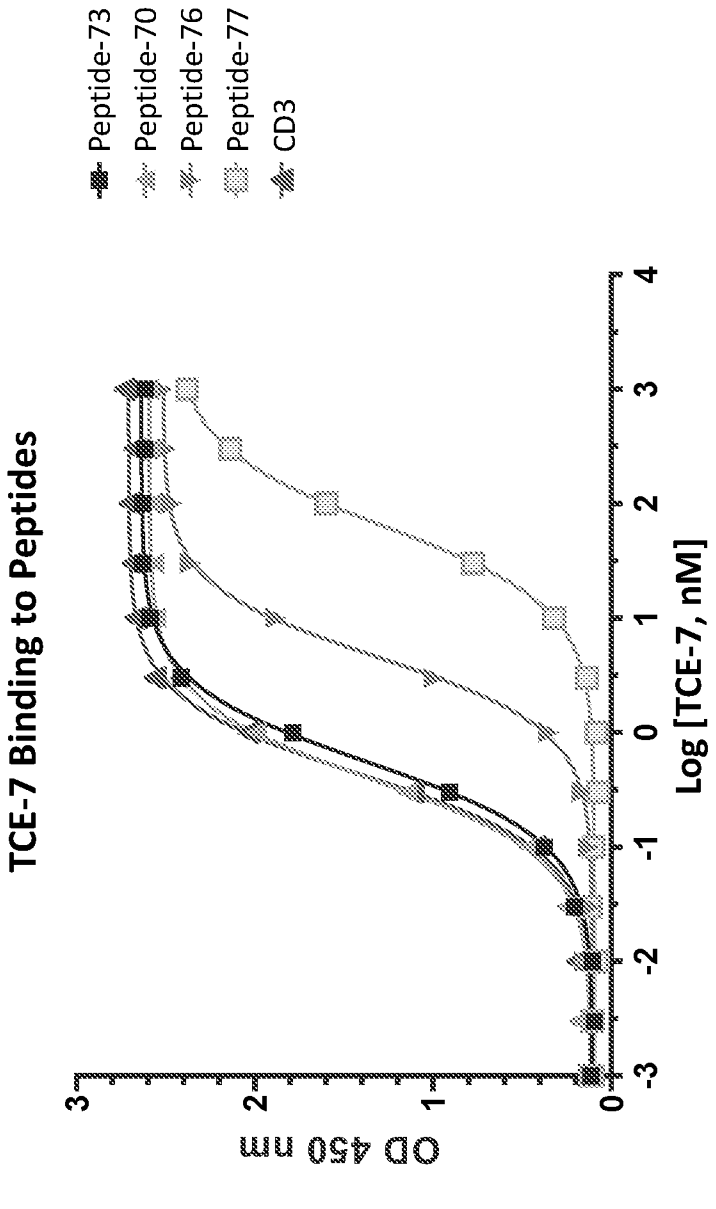
FIG. 85 illustrates binding curves for binding of peptides to TCE-7 as measured by ELISA.
Figure 86:
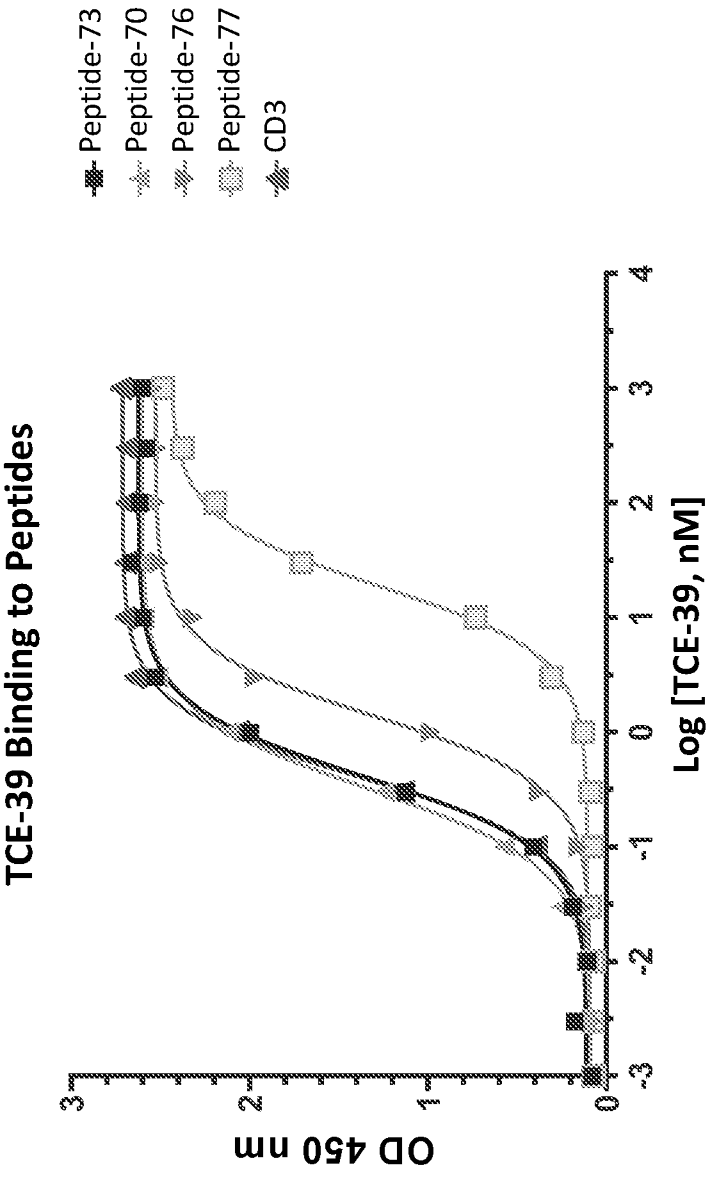
FIG. 86 illustrates binding curves for binding of peptides to TCE-39 as measured by ELISA.
Figure 87:
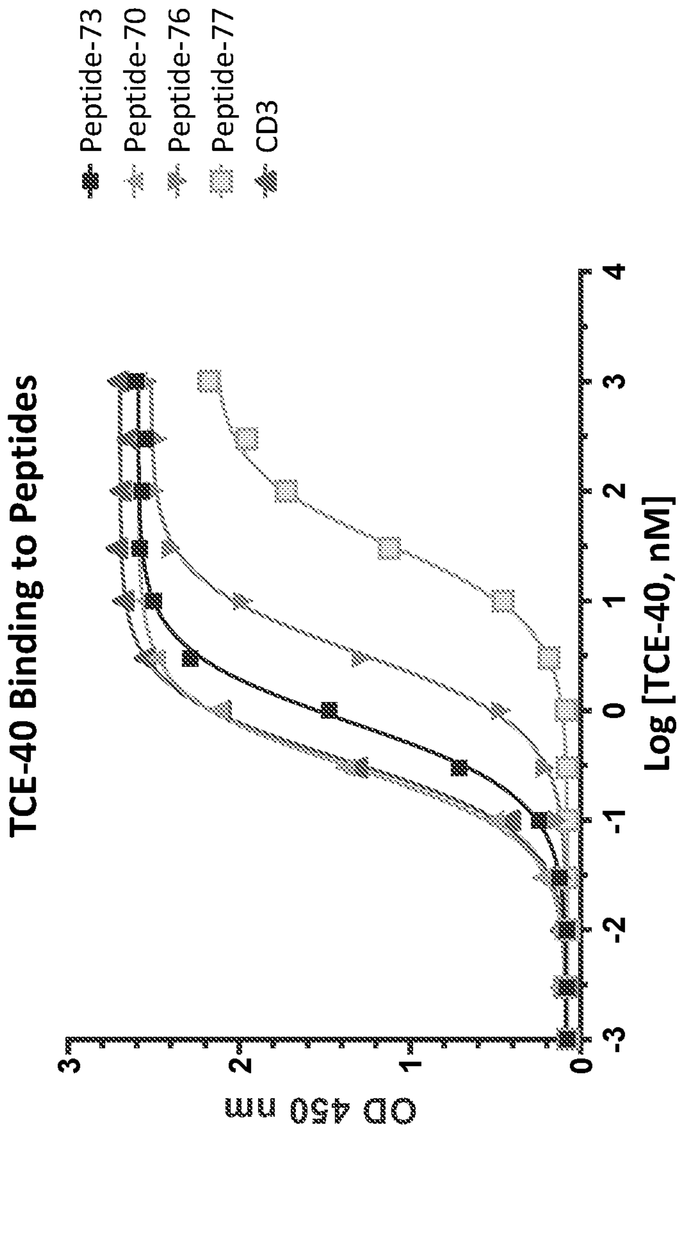
FIG. 87 illustrates binding curves for binding of peptides to TCE-40 as measured by ELISA.
Figure 88:
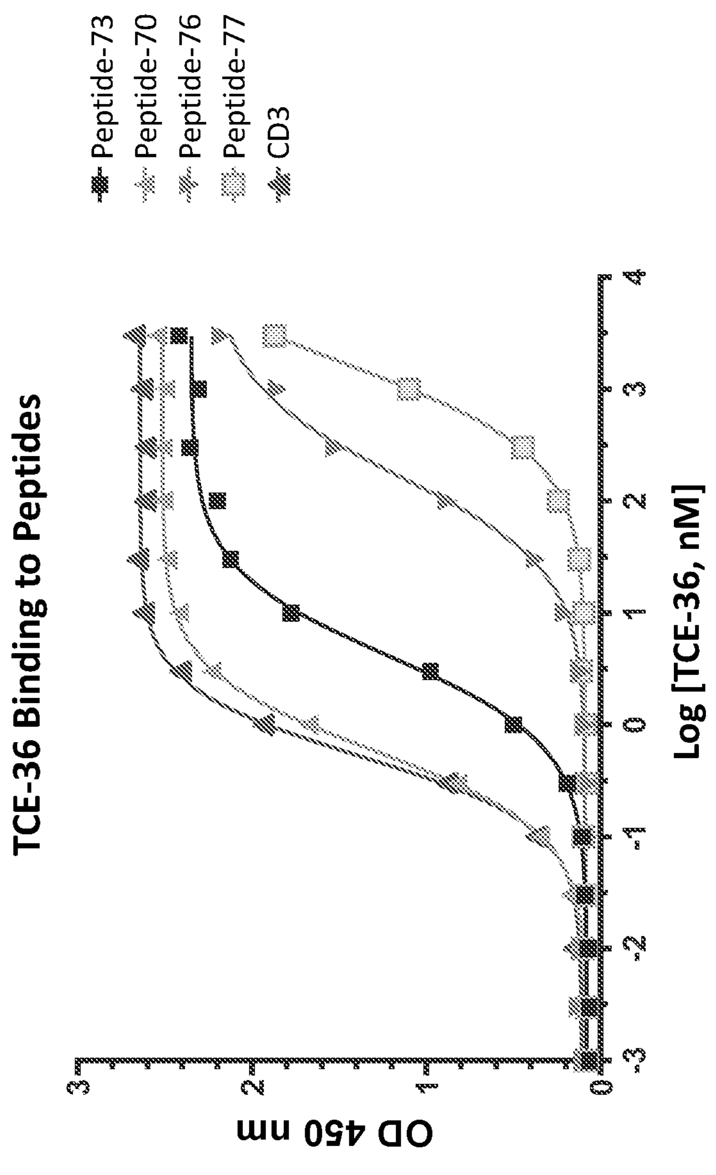
FIG. 88 illustrates binding curves for binding of peptides to TCE-36 as measured by ELISA.
Figure 89:
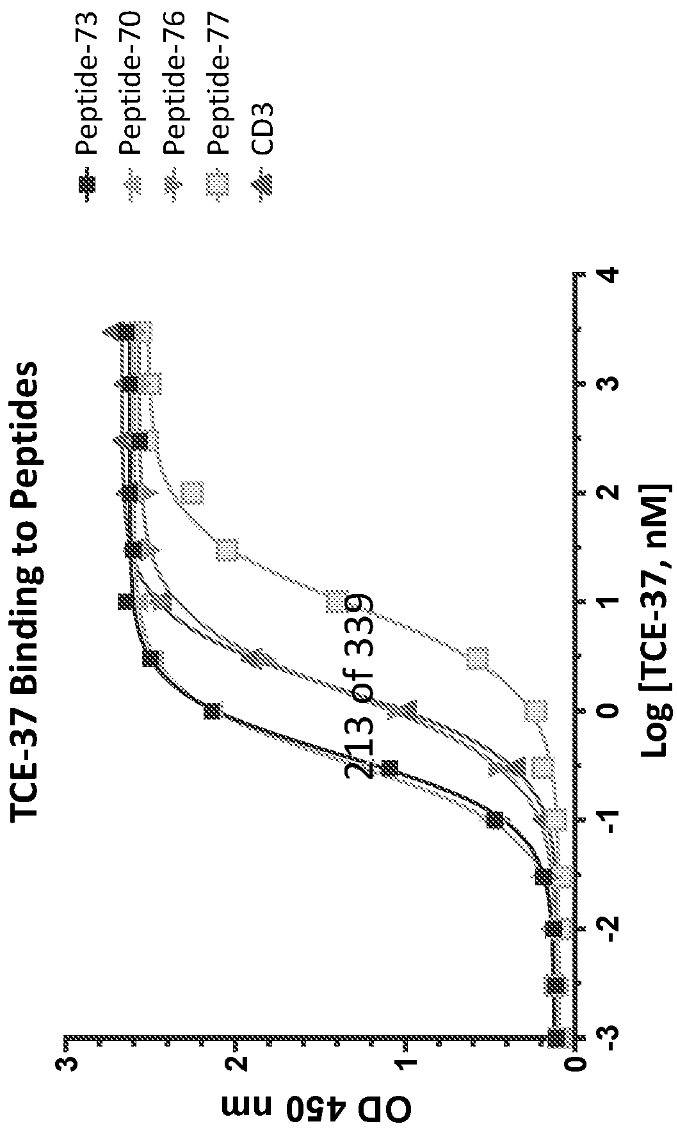
FIG. 89 illustrates binding curves for binding of peptides to TCE-37 as measured by ELISA.
Figure 90:
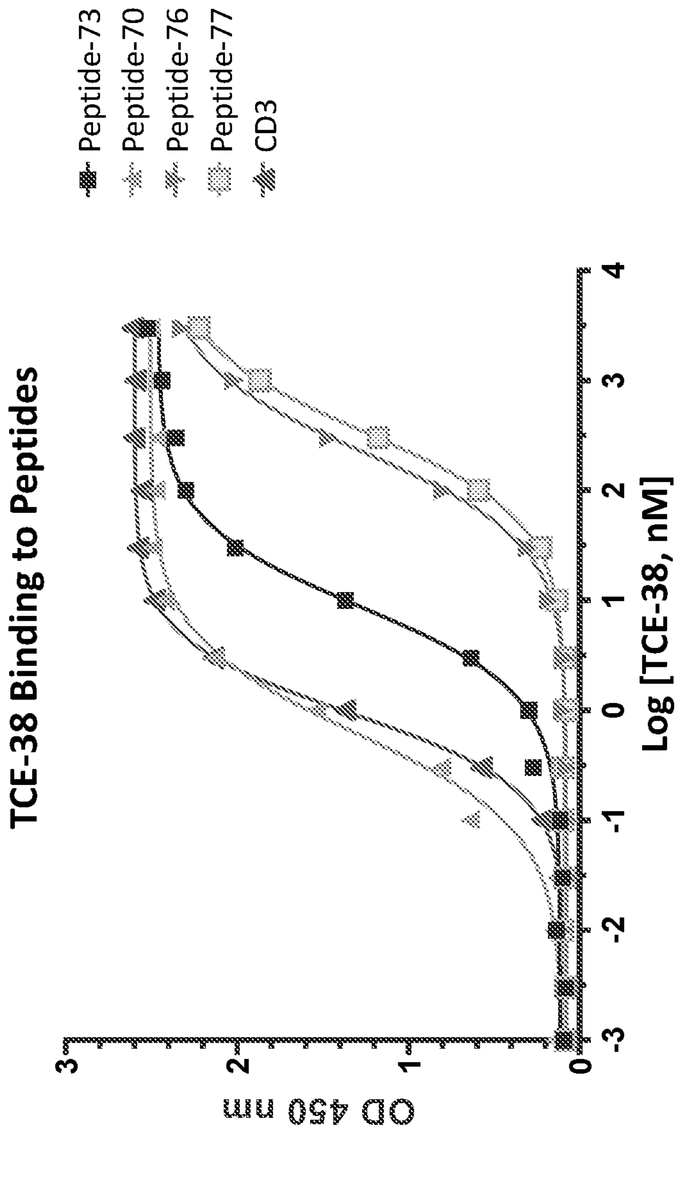
FIG. 90 illustrates binding curves for binding of peptides to TCE-38 as measured by ELISA.
Figure 91:
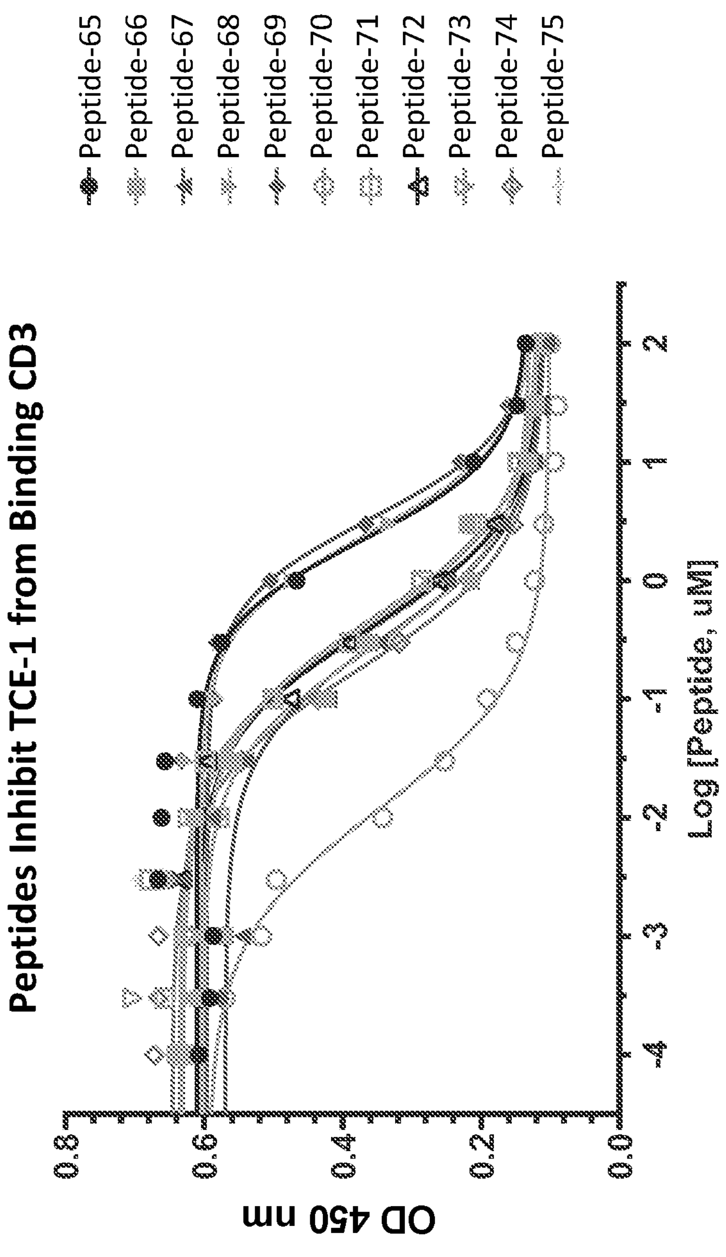
FIG. 91 illustrates inhibition of TCE-1 binding to CD3 by peptides as measured by ELISA.
Figure 92:
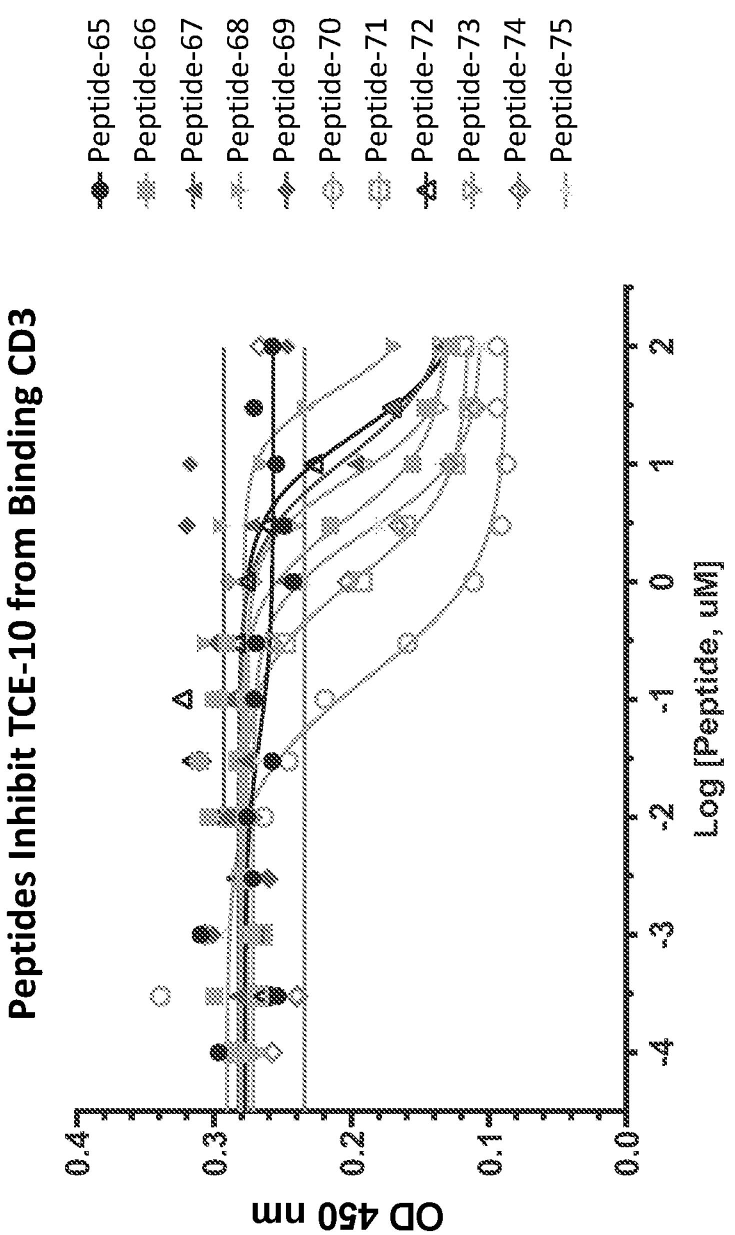
FIG. 92 illustrates inhibition of TCE-10 binding to CD3 by peptides as measured by ELISA.
Figure 93:
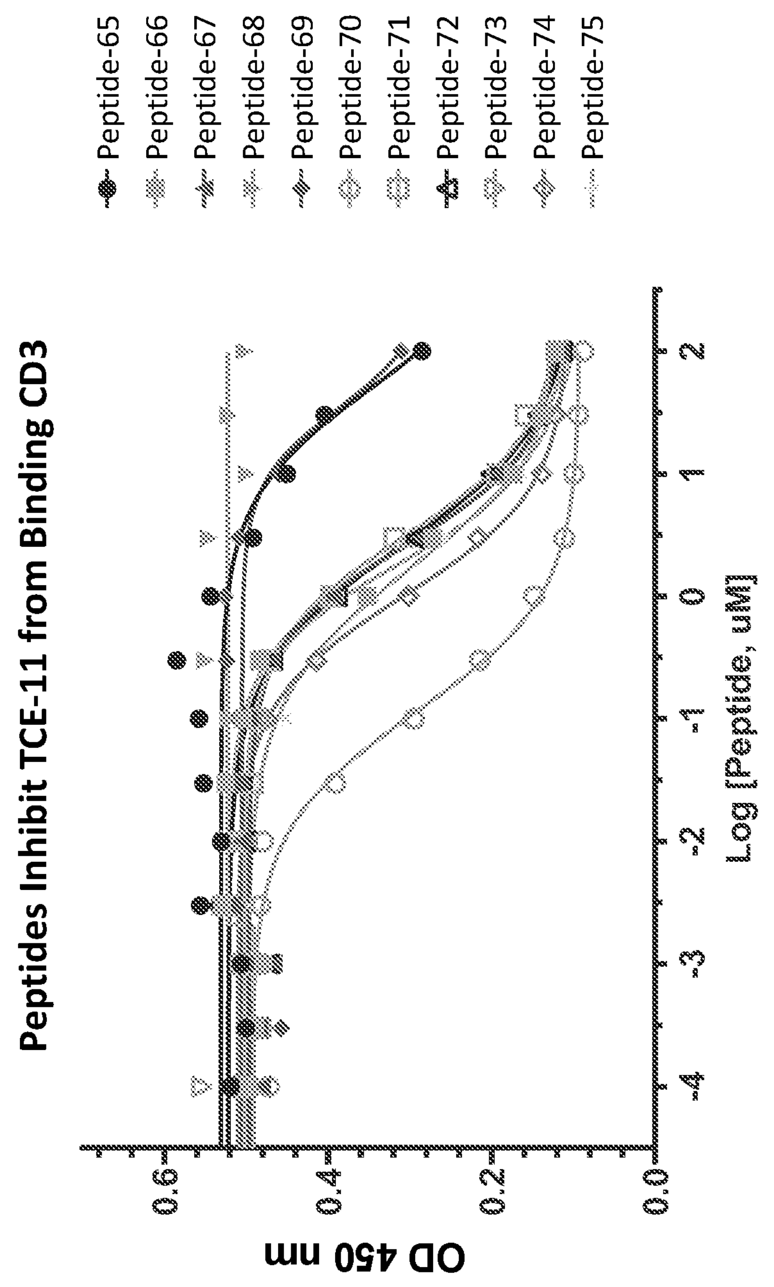
FIG. 93 illustrates inhibition of TCE-11 binding to CD3 by peptides as measured by ELISA.
Figure 94:
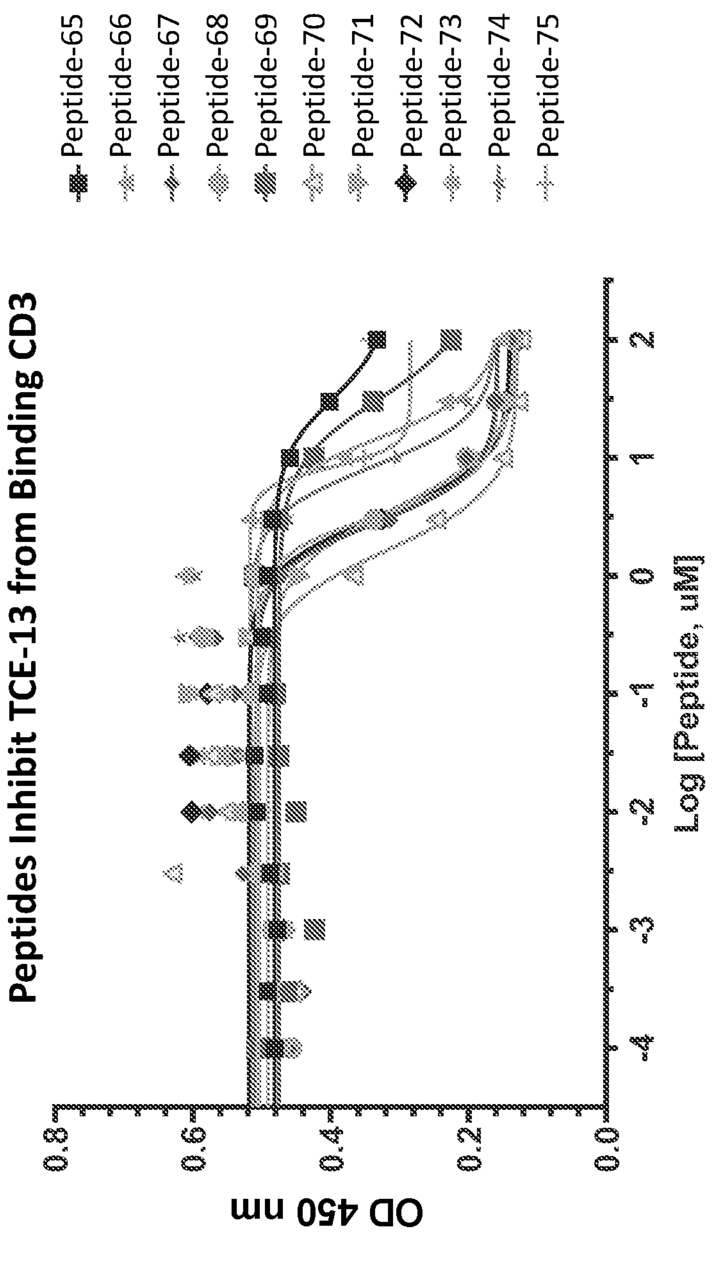
FIG. 94 illustrates inhibition of TCE-13 binding to CD3 by peptides as measured by ELISA.
Figure 95:
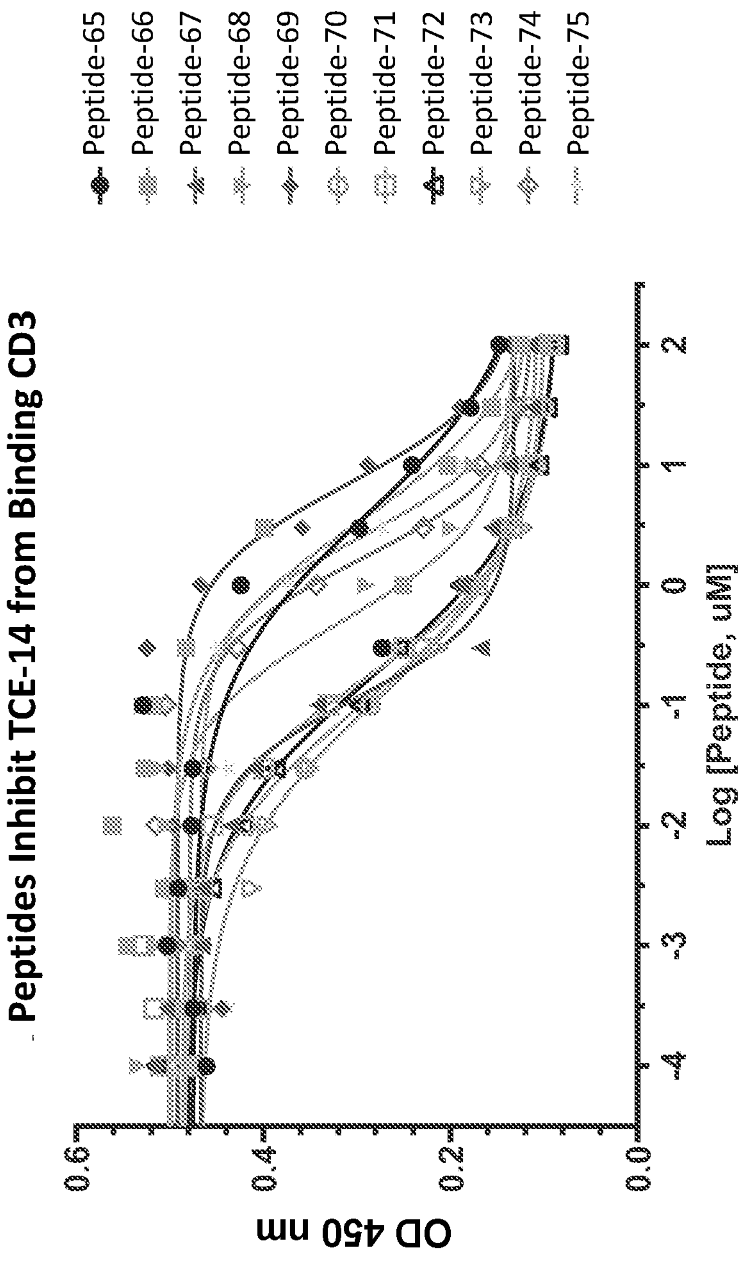
FIG. 95 illustrates inhibition of TCE-14 binding to CD3 by peptides as measured by ELISA.
Figure 96:
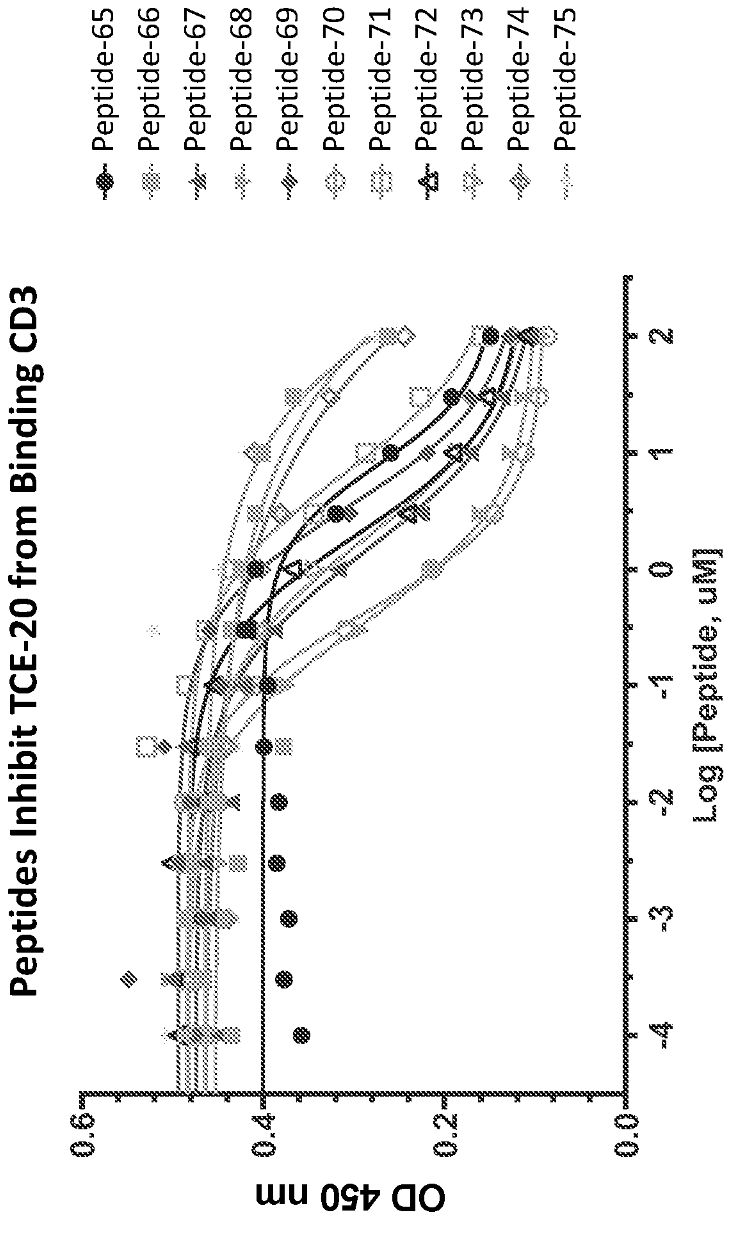
FIG. 96 illustrates inhibition of TCE-20 binding to CD3 by peptides as measured by ELISA.
Figure 97:
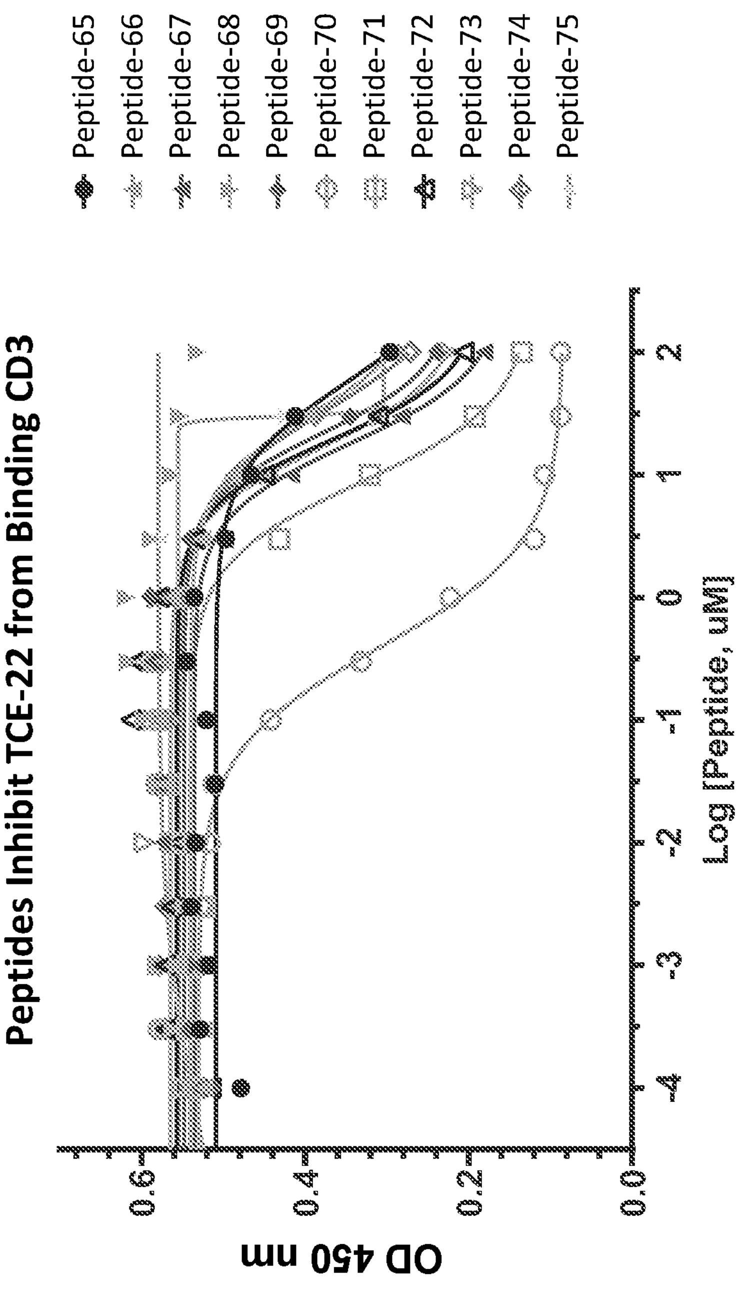
FIG. 97 illustrates inhibition of TCE-22 binding to CD3 by peptides as measured by ELISA.
Figure 98:
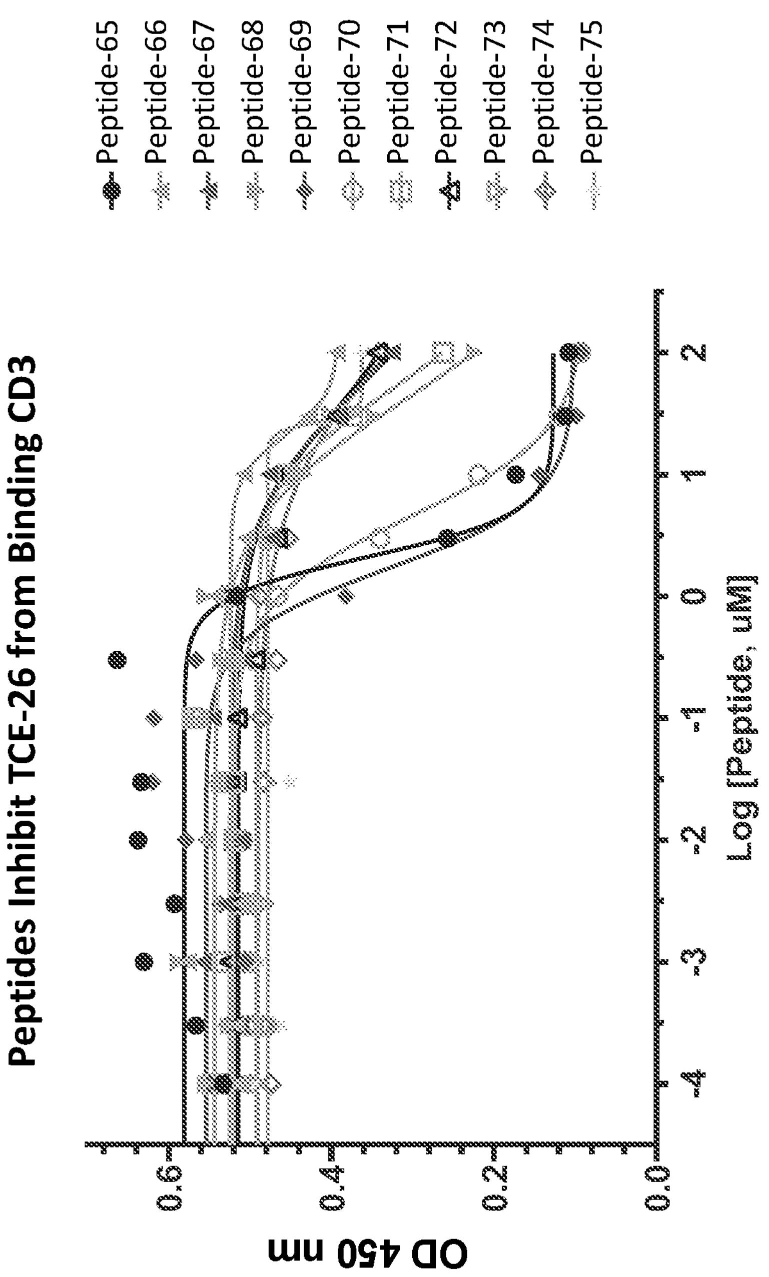
FIG. 98 illustrates inhibition of TCE-26 binding to CD3 by peptides as measured by ELISA.
Figure 99:
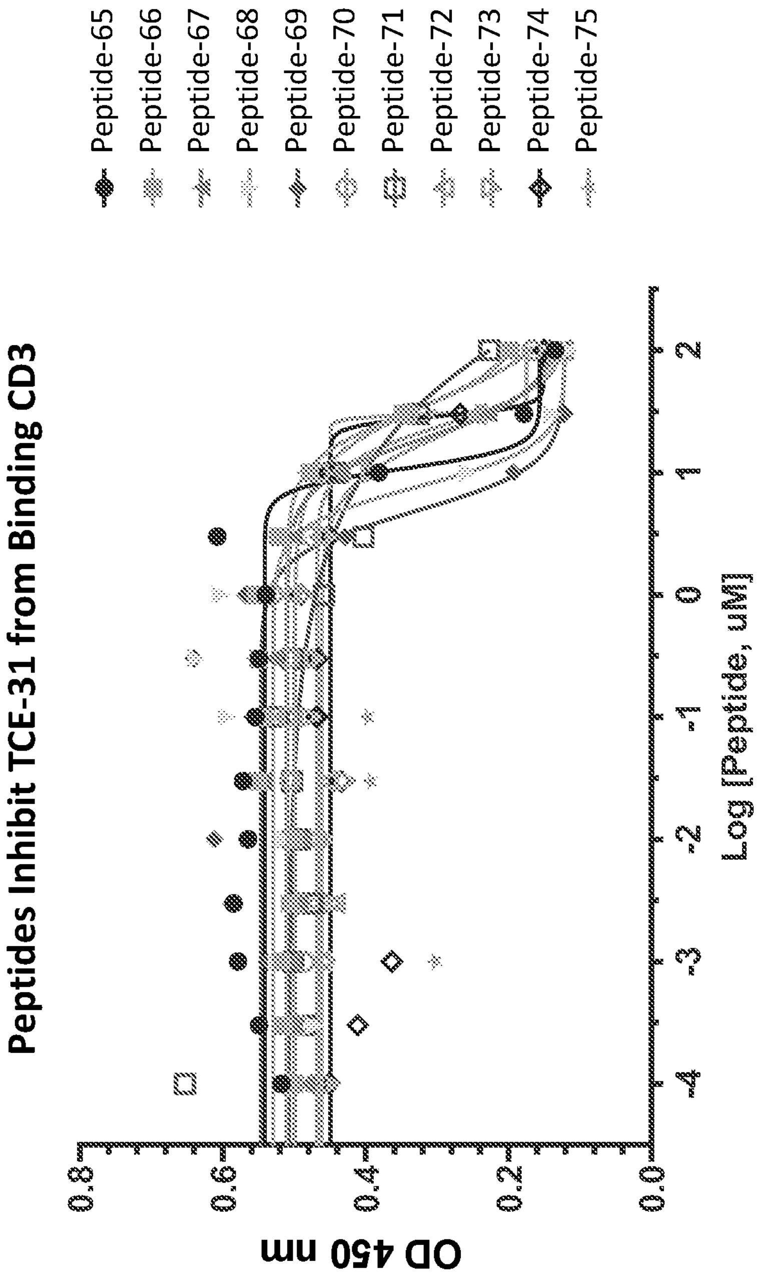
FIG. 99 illustrates inhibition of TCE-31 binding to CD3 by peptides as measured by ELISA.
Figure 100:
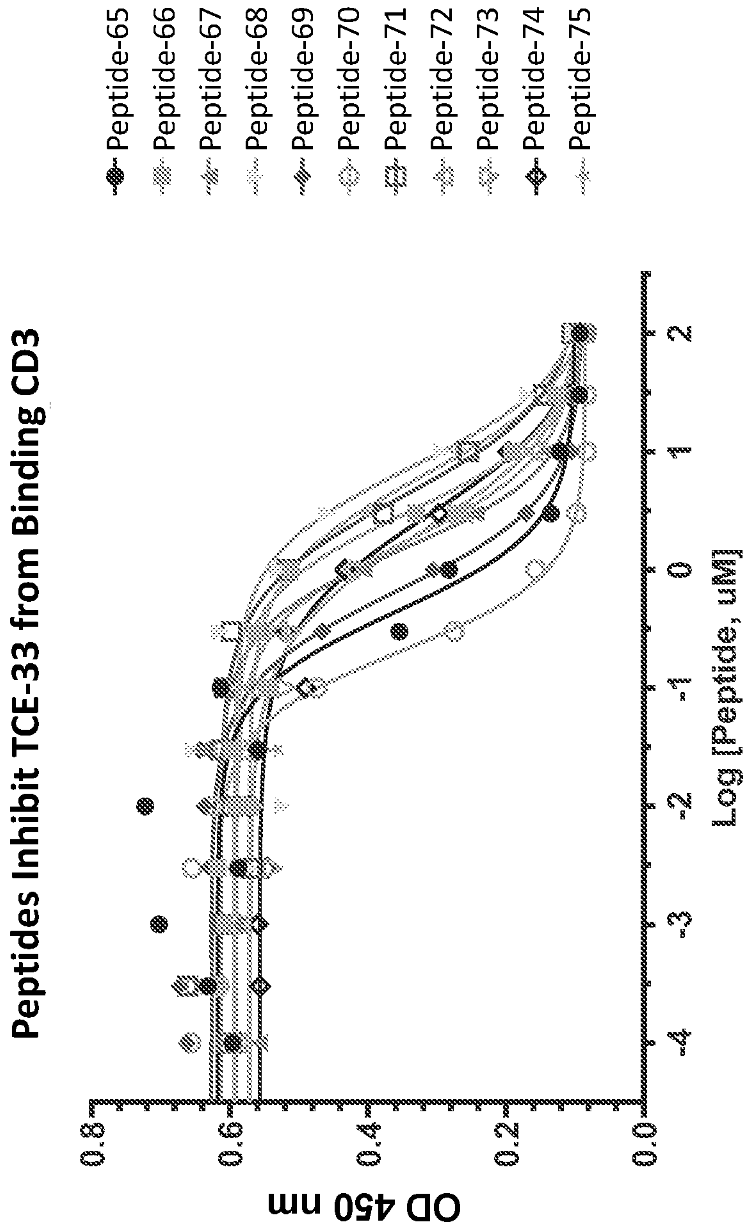
FIG. 100 illustrates inhibition of TCE-33 binding to CD3 by peptides as measured by ELISA.
Figure 101:
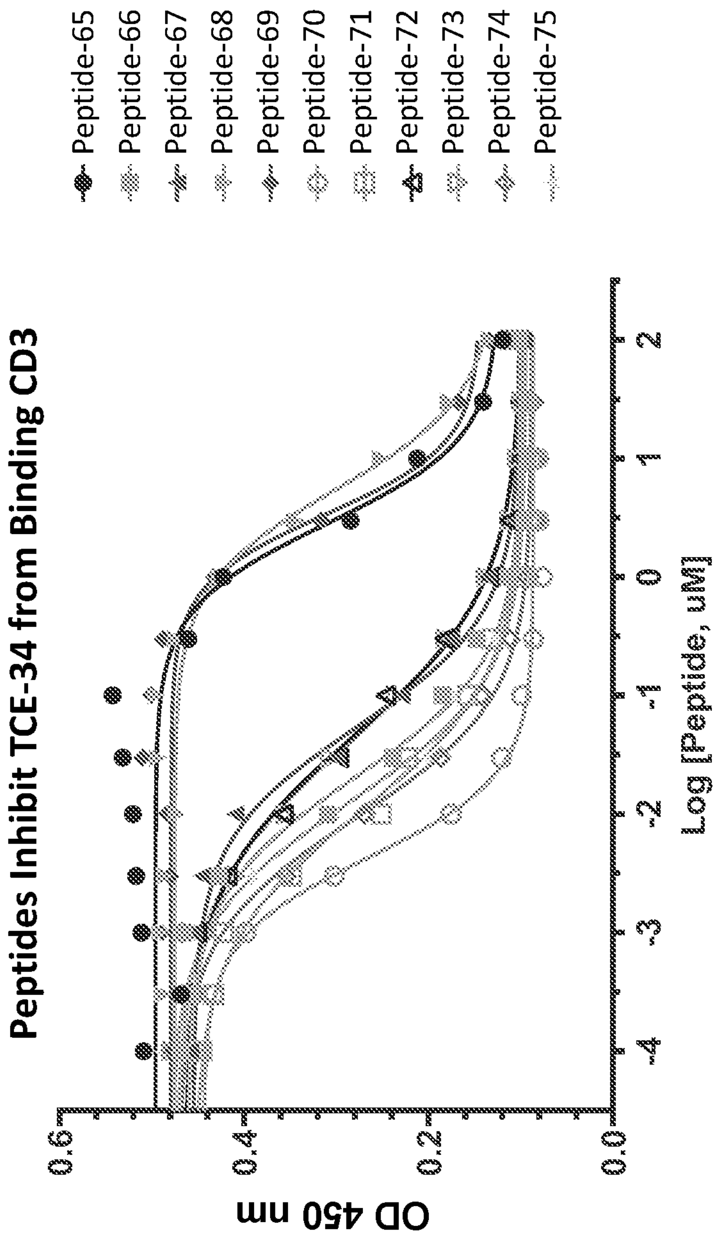
FIG. 101 illustrates inhibition of TCE-34 binding to CD3 by peptides as measured by ELISA.
Figure 102:
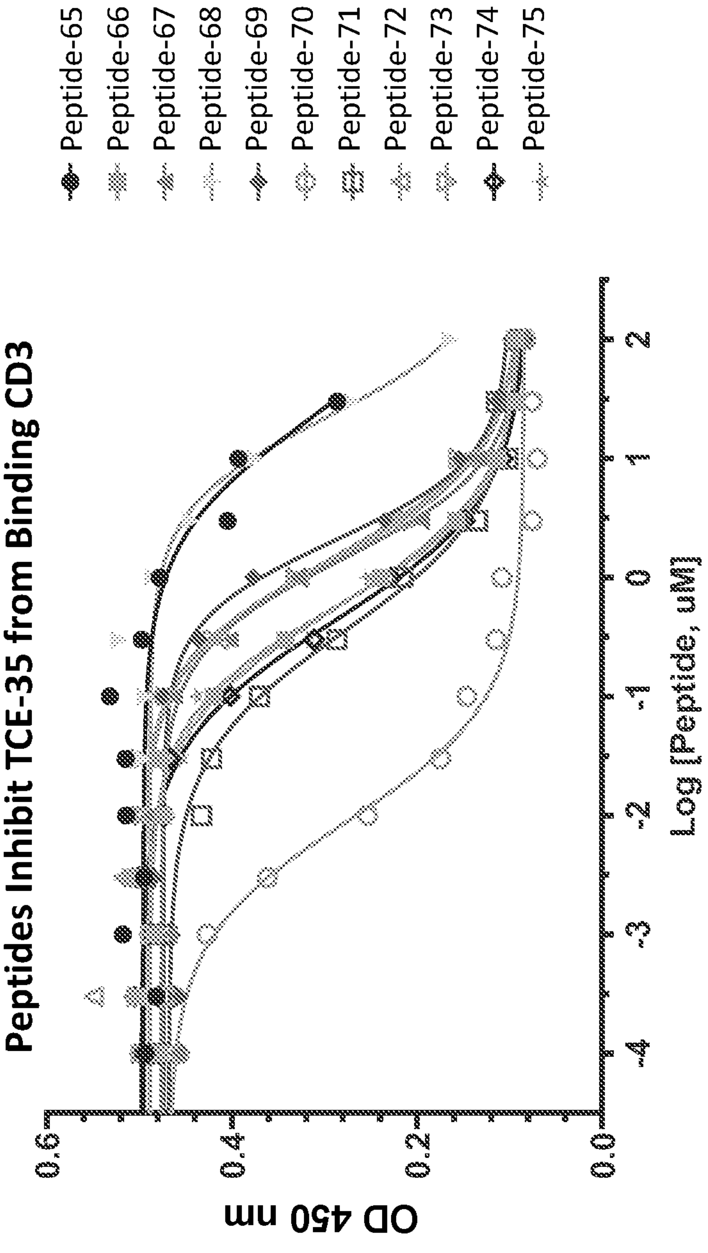
FIG. 102 illustrates inhibition of TCE-35 binding to CD3 by peptides as measured by ELISA.

ELISA binding curves for peptide-73 binding to wild-type TROP2 TCEs and to TROP2 TCEs having alanine mutations in the CD3 binding domain are shown in FIGS. 84A-84C. The $EC_{50}$s calculated from the binding curves are provided in Table 38.

TABLE 38

$EC_{50}$s for Peptide-73 Binding to TROP2 TCEs

| TROP2-TCE Construct | $EC_{50}$ (nM) |
|---|---|
| TCE-1 | 0.19 |
| TCE-9 | 0.17 |
| TCE-10 | 1.72 |
| TCE-11 | 1.58 |
| TCE-12 | 0.21 |
| TCE-13 | 0.25 |
| TCE-14 | 0.26 |
| TCE-15 | 0.23 |
| TCE-16 | 0.24 |
| TCE-17 | 0.25 |
| TCE-18 | 0.22 |
| TCE-19 | 0.40 |
| TCE-20 | 1.16 |
| TCE-21 | 94.18 |
| TCE-22 | 20.92 |
| TCE-23 | 1.57 |
| TCE-24 | 0.25 |
| TCE-25 | 0.33 |
| TCE-26 | 7.25 |
| TCE-27 | 0.35 |
| TCE-28 | 0.22 |
| TCE-29 | 0.27 |
| TCE-30 | 0.25 |
| TCE-31 | 7.03 |
| TCE-32 | 0.18 |
| TCE-33 | 6.58 |
| TCE-34 | 0.30 |
| TCE-35 | 0.39 |

Peptide mask sequences were also evaluated for their binding affinities against TROP2 TCE sequences harboring alanine mutations in the CDR3 regions of either or both of the TROP2 and CD3 binding domains. FIGS. 85-90 show ELISA binding curves for peptide-73, peptide-70, peptide-76, and peptide-77 binding to TCE-7 (anti-CD3 wt, anti-TROP2 F108A), TCE-36 (anti-CD3 H101A, anti-TROP2 F108A), TCE-37 (anti-CD3 F104A, anti-TROP2 F108A), TCE-38 (anti-CD3 F240A, anti-TROP2 F108A), TCE-39 (anti-CD3 several mutations, anti-TROP2 F108A), and TCE-40 (anti-CD3 several mutations, anti-TROP2 F108A). Table 39 provides the $EC_{50}$s calculated from the binding curves of FIGS. 85-90.

TABLE 39

$EC_{50}$s for Peptide Binding to TROP2-TCEs

| | TCE-7 $EC_{50}$ (nM) | TCE-39 $EC_{50}$ (nM) | TCE-40 $EC_{50}$ (nM) | TCE-36 $EC_{50}$ (nM) | TCE-37 $EC_{50}$ (nM) | TCE-38 $EC_{50}$ (nM) |
|---|---|---|---|---|---|---|
| CD3 | 0.43 | 0.41 | 0.36 | 0.52 | 1.59 | 0.95 |
| Peptide-73 | 0.55 | 0.41 | 0.77 | 4.11 | 0.39 | 8.87 |
| Peptide-70 | 0.40 | 0.33 | 0.30 | 0.59 | 0.34 | 0.62 |
| Peptide-76 | 4.56 | 1.39 | 3.33 | 166 | 1.44 | 222 |
| Peptide-77 | 63.2 | 18.8 | 31.9 | 1616 | 9.21 | 336 |

Example 21: Inhibition of TROP2-TCE Binding to CD3 by Peptides

The peptide sequences of Table 9 were further screened for their ability to inhibit the mutated and non-mutated TROP2 TCE constructs from binding to the CD3 antigen via ELISA-based competitive inhibition studies. Specifically, biotinylated CD3 antigen was captured on neutravidin coated plates, quenched using biocytin, and washed. Inhibitory peptides were titrated in a dilution series and pre-incubated with a constant concentration of the respective TROP2 TCE construct. Inhibitory peptide and TROP2 TCE antibody mixtures were then incubated on the antigen captured plates. A horseradish peroxidase conjugate secondary antibody was then used to detect the TROP2 TCE binding to the plate-bound antigen. The ELISA signal was plotted versus log-scale peptide concentration. A dose dependent decrease of signal was indicative of peptides that compete for TROP2 TCE binding to the cognate antigen, CD3. Graphpad Prism software was used to calculate the inhibitory concentrations of peptide required to achieve 50% maximal signal ($IC_{50}$s). FIGS. 91-102 show inhibition curves for peptide inhibition of CD3 binding to TROP2 TCEs having a wild-type or alanine mutated CD3 binding domain. The calculated $IC_{50}$s are provided in Tables 40-41.

TABLE 40

$IC_{50}$s for Peptide Inhibition of CD3 Binding to TROP2-TCEs

| Peptide | TCE-10 $IC_{50}$ (μM) | TCE-11 $IC_{50}$ (μM) | TCE-13 $IC_{50}$ (μM) | TCE-14 $IC_{50}$ (μM) | TCE-20 $IC_{50}$ (μM) |
|---|---|---|---|---|---|
| Peptide-65 | >100 | 84.97 | >100 | 6.46 | 6.54 |
| Peptide-66 | 13.05 | 2.62 | 21.36 | 7.09 | 720.80 |
| Peptide-67 | 18.64 | 2.82 | 3.36 | 0.24 | 1.32 |
| Peptide-68 | 88.87 | >100 | 4.59 | 1.08 | 0.40 |
| Peptide-69 | >100 | >100 | 50.45 | 11.83 | 4.24 |
| Peptide-70 | 0.24 | 0.11 | 2.11 | 0.18 | 0.37 |
| Peptide-71 | 1.35 | 3.72 | 5.08 | 0.23 | 11.78 |
| Peptide-72 | 45.64 | 0.79 | 3.96 | 0.32 | 3.65 |
| Peptide-73 | 16.77 | 2.93 | 4.07 | 0.20 | 2.20 |
| Peptide-74 | 16.10 | 1.11 | 10.63 | 2.47 | 86.60 |
| Peptide-75 | 4.74 | 2.08 | 47.74 | 4.21 | 119.80 |

TABLE 41

| IC50s for Peptide Inhibition of CD3 Binding to TROP2-TCEs | | | | | | |
|---|---|---|---|---|---|---|
| Peptide | TCE-22 $IC_{50}$ (μM) | TCE-26 $IC_{50}$ (μM) | TCE-31 $IC_{50}$ (μM) | TCE-33 $IC_{50}$ (μM) | TCE-34 $IC_{50}$ (μM) | TCE-35 IC50 (μM) |
| Peptide-65 | >100 | 2.64 | 17.73 | 0.62 | 5.53 | 34.52 |
| Peptide-66 | >100 | >100 | 51.52 | 3.71 | 0.03 | 0.57 |
| Peptide-67 | 38.50 | >100 | 21.60 | 1.25 | 0.08 | 1.54 |
| Peptide-68 | >100 | 43.01 | 9.47 | 7.35 | 9.14 | 25.52 |
| Peptide-69 | 56.79 | 2.02 | 6.57 | 0.81 | 6.40 | 2.23 |
| Peptide-70 | 0.47 | 5.00 | 43.49 | 0.23 | 0.004 | 0.01 |
| Peptide-71 | 13.76 | 75.40 | 50.96 | 4.83 | 0.01 | 0.39 |
| Peptide-72 | 40.17 | >100 | 29.88 | 2.70 | 0.06 | 1.53 |
| Peptide-73 | 39.06 | >100 | 25.90 | 3.02 | 0.05 | 1.42 |
| Peptide-74 | 75.36 | >100 | 33.83 | 3.08 | 0.01 | 0.43 |
| Peptide-75 | >100 | >100 | >100 | 7.46 | 0.01 | 0.56 |

Figure 103A:
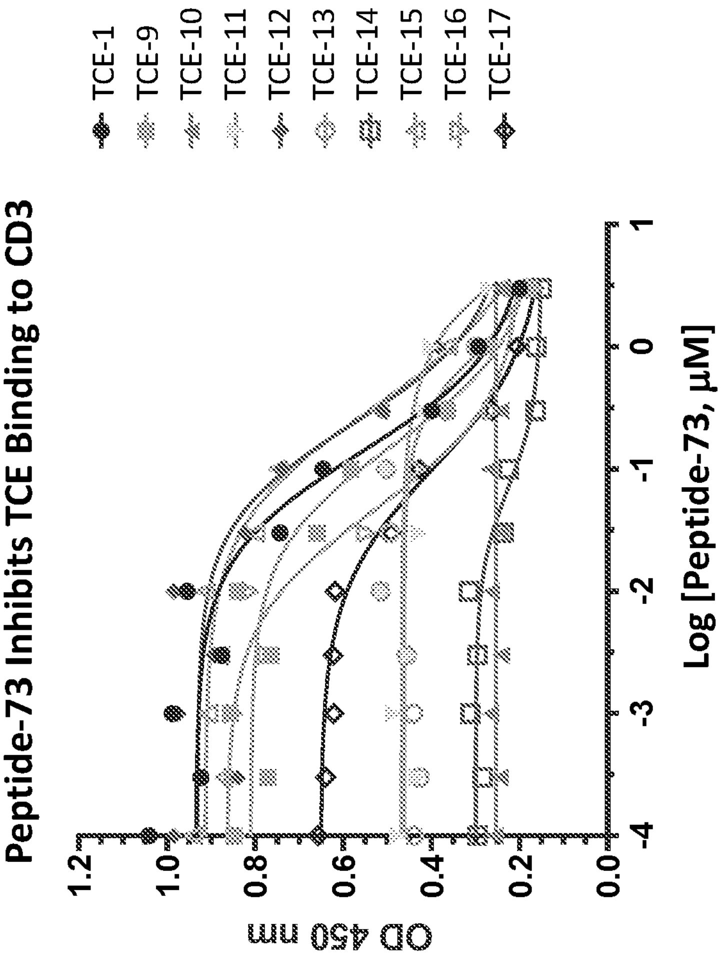
FIGS. 103A-103C illustrate inhibition of TCE binding to CD3 by peptide-73 as measured by ELISA.
Figure 103B:
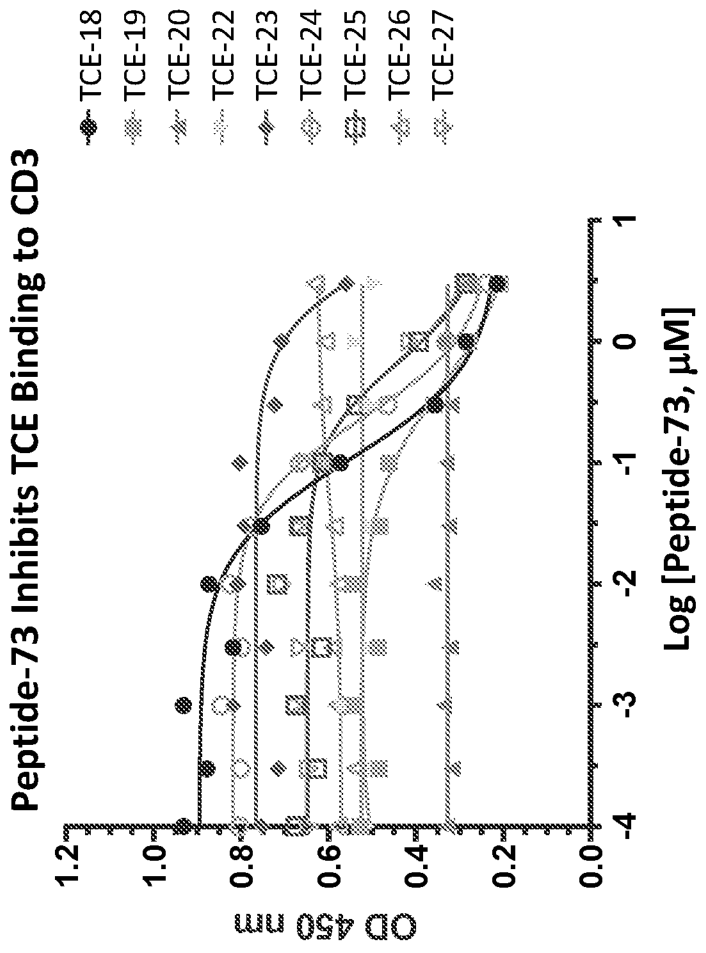
Figure 103C:
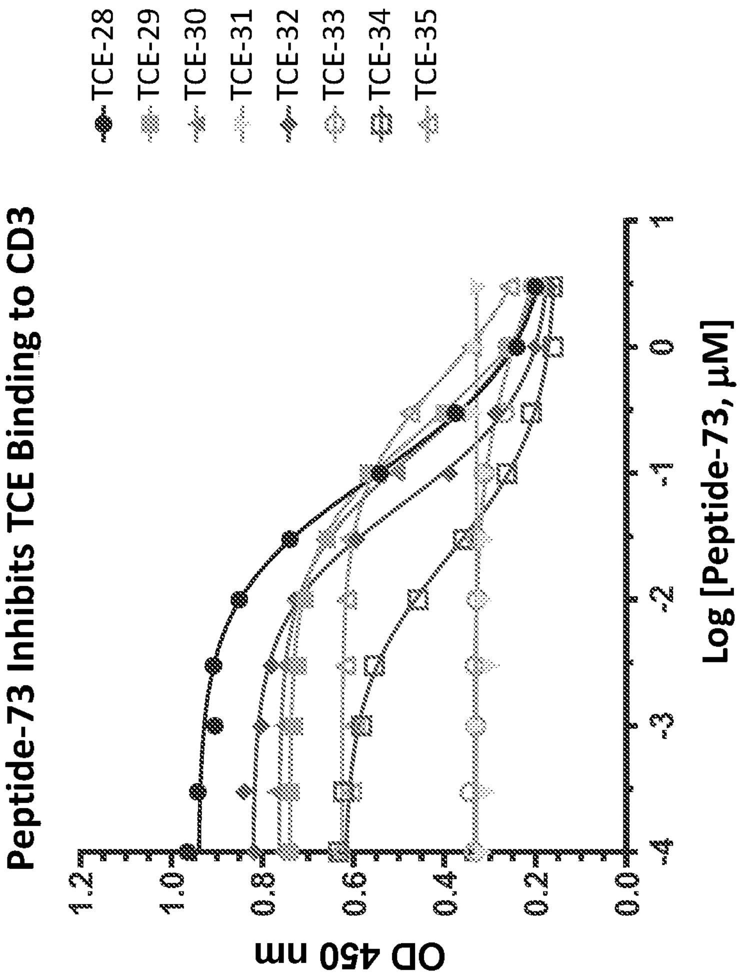
Figure 104:
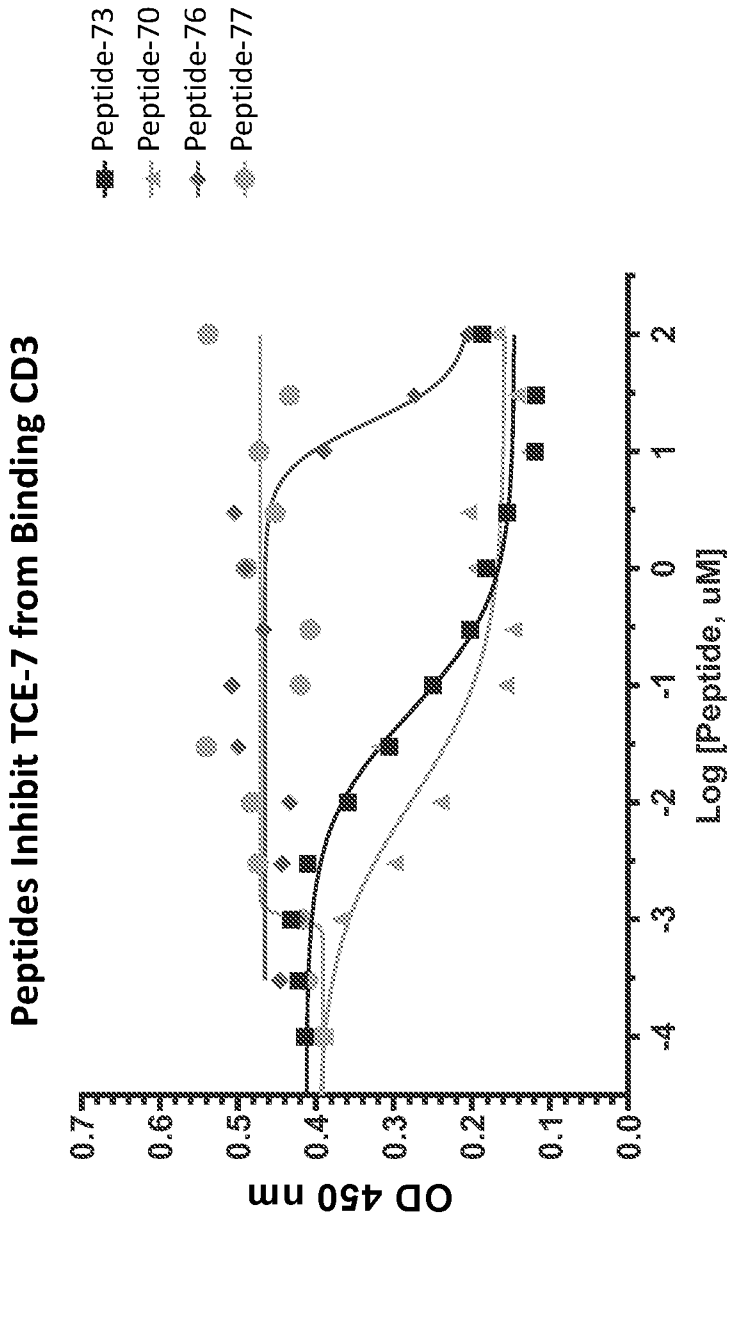
FIG. 104 illustrates inhibition of TCE-7 binding to CD3 by peptides as measured by ELISA.
Figure 105:
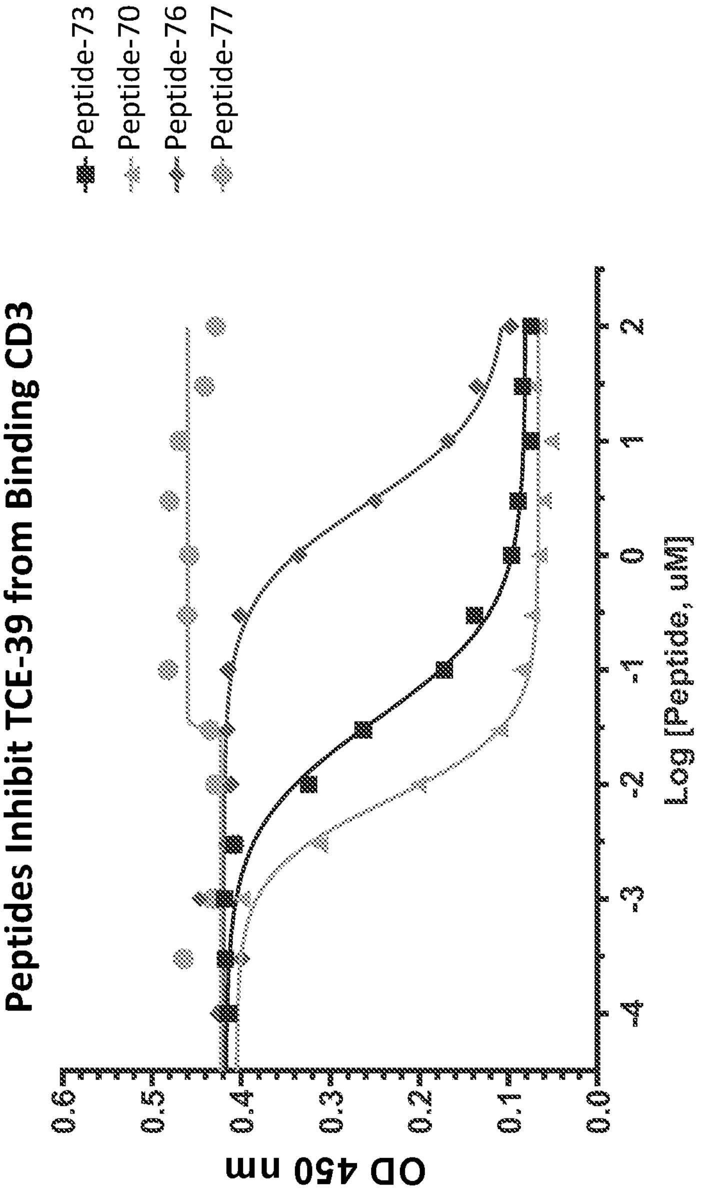
FIG. 105 illustrates inhibition of TCE-39 binding to CD3 by peptides as measured by ELISA.
Figure 106:
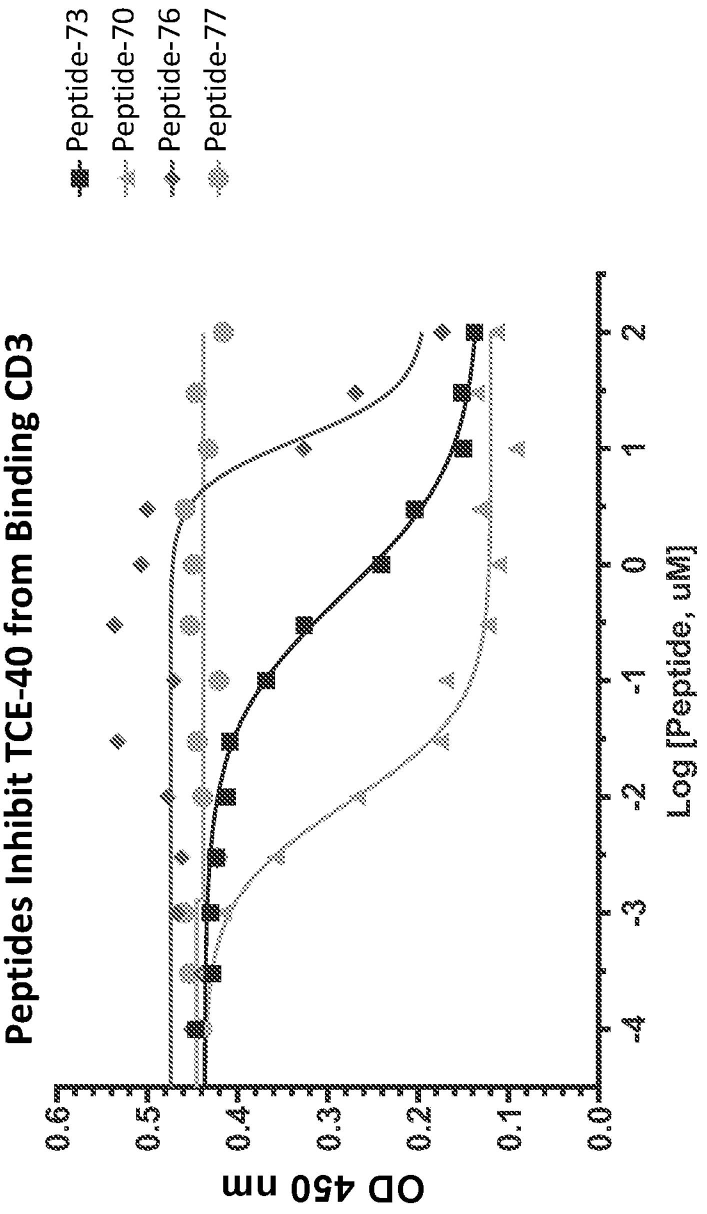
FIG. 106 illustrates inhibition of TCE-40 binding to CD3 by peptides as measured by ELISA.
Figure 107:
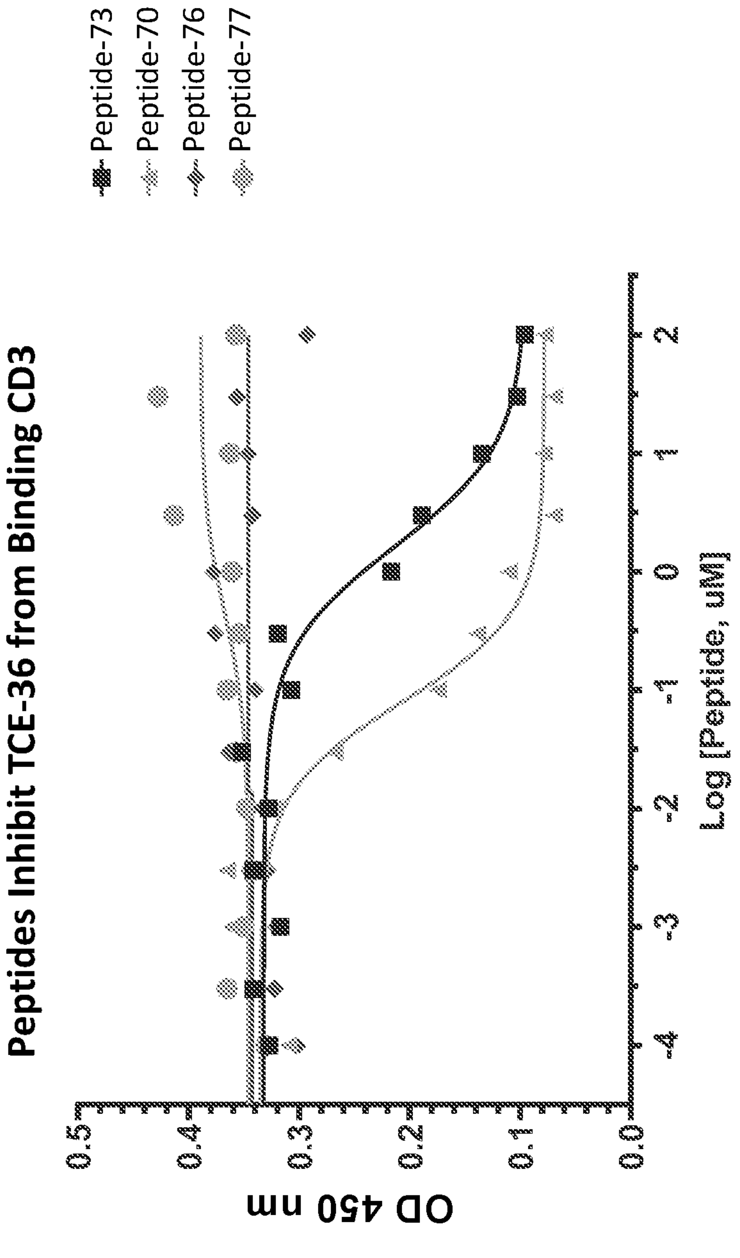
FIG. 107 illustrates inhibition of TCE-36 binding to CD3 by peptides as measured by ELISA.
Figure 108:
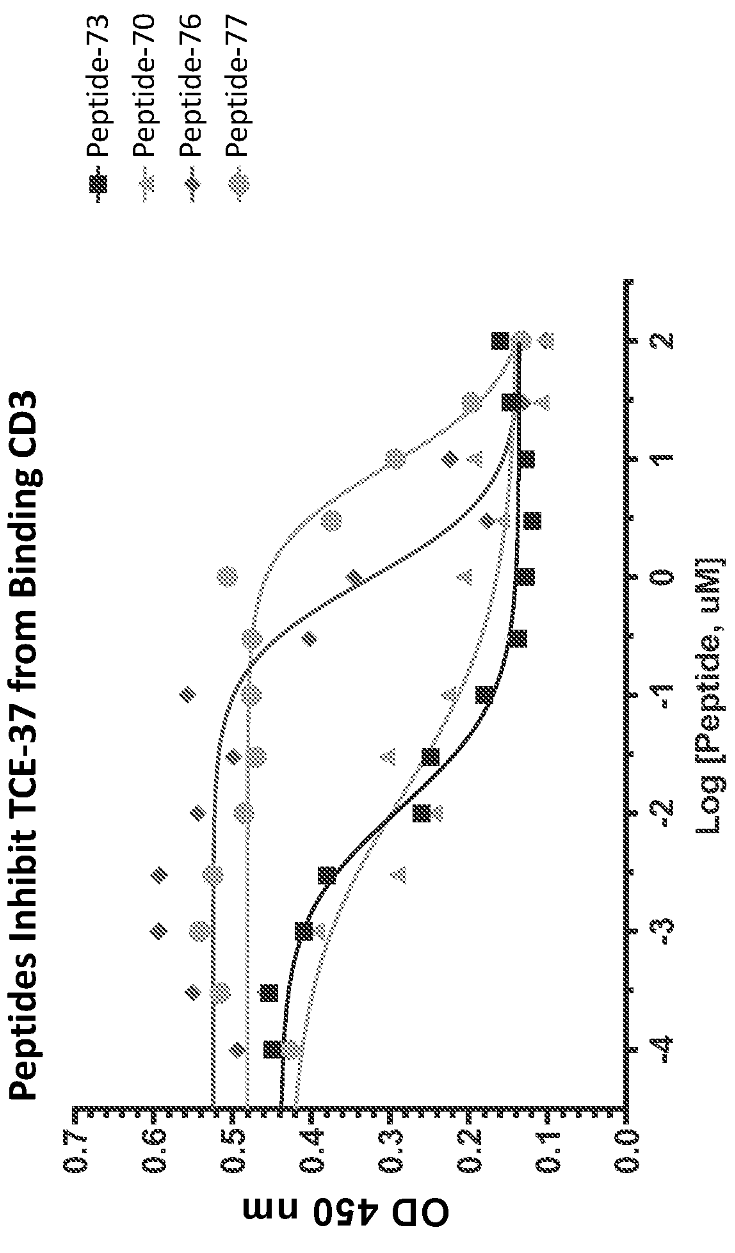
FIG. 108 illustrates inhibition of TCE-37 binding to CD3 by peptides as measured by ELISA.
Figure 109:
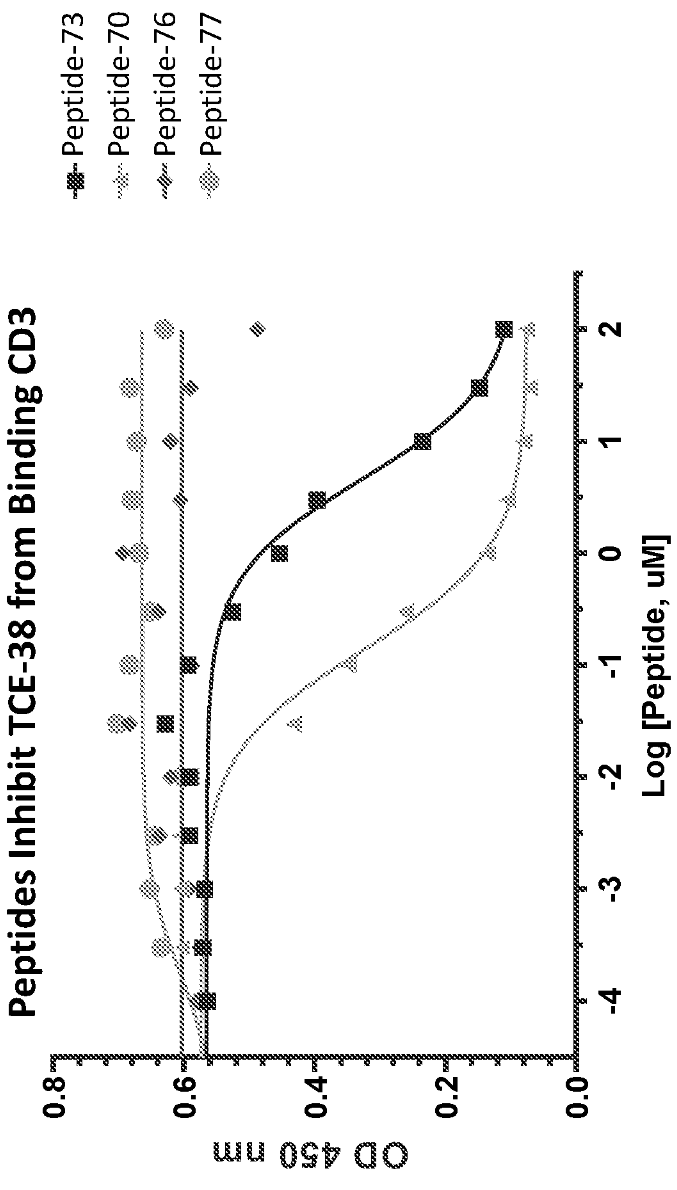
FIG. 109 illustrates inhibition of TCE-38 binding to CD3 by peptides as measured by ELISA.
Figure 110:
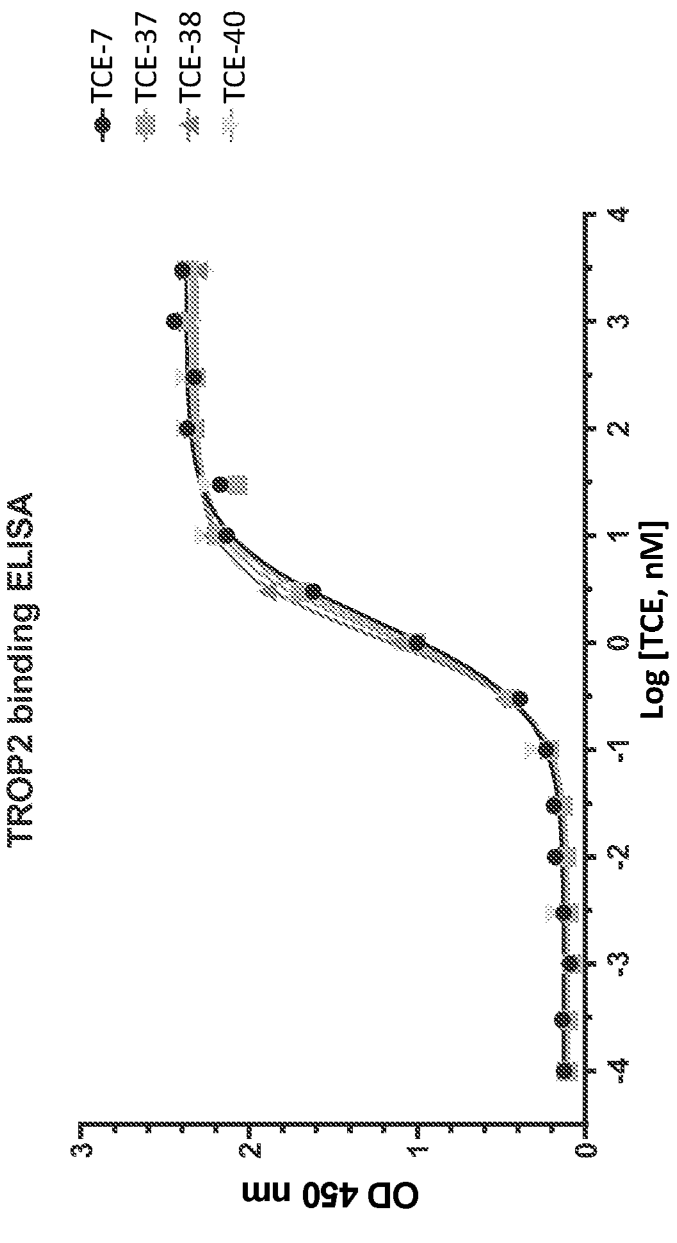
FIG. 110 illustrates binding curves for binding of TROP2 by TCEs as measured by ELISA.
Figure 111:
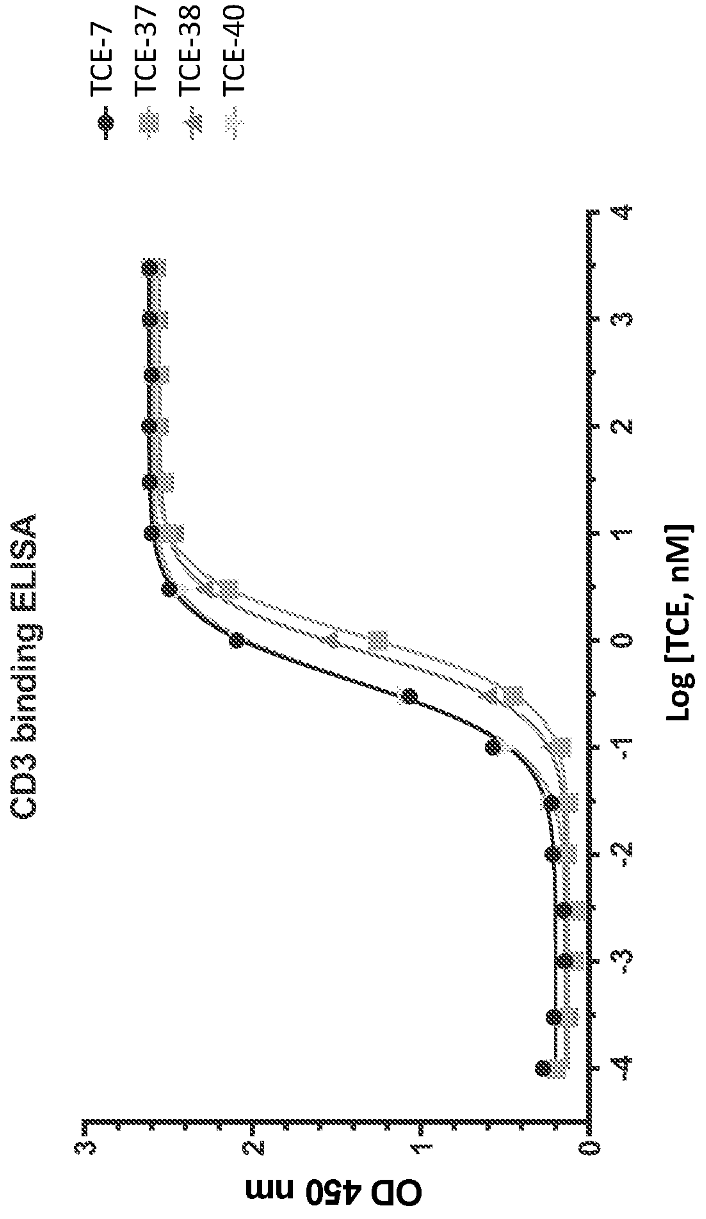
FIG. 111 illustrates binding curves for binding of CD3 by TCEs as measured by ELISA.
Figure 112:
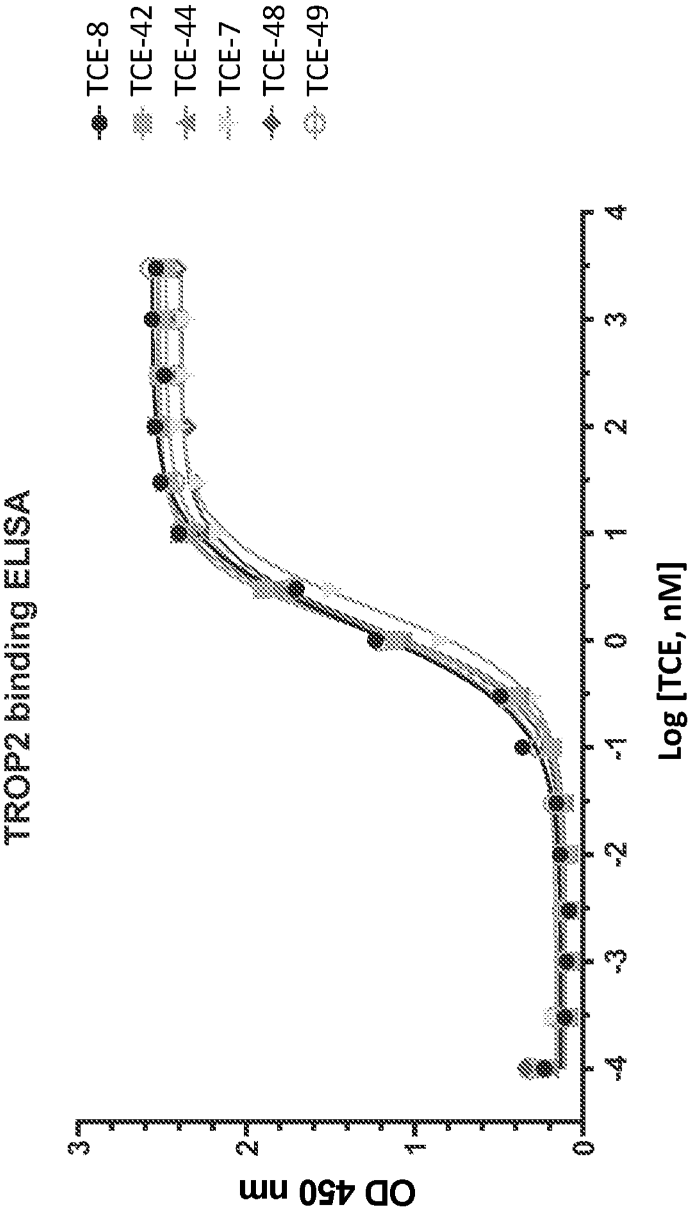
FIG. 112 illustrates binding curves for binding of TROP2 by TCEs as measured by ELISA.
Figure 113:
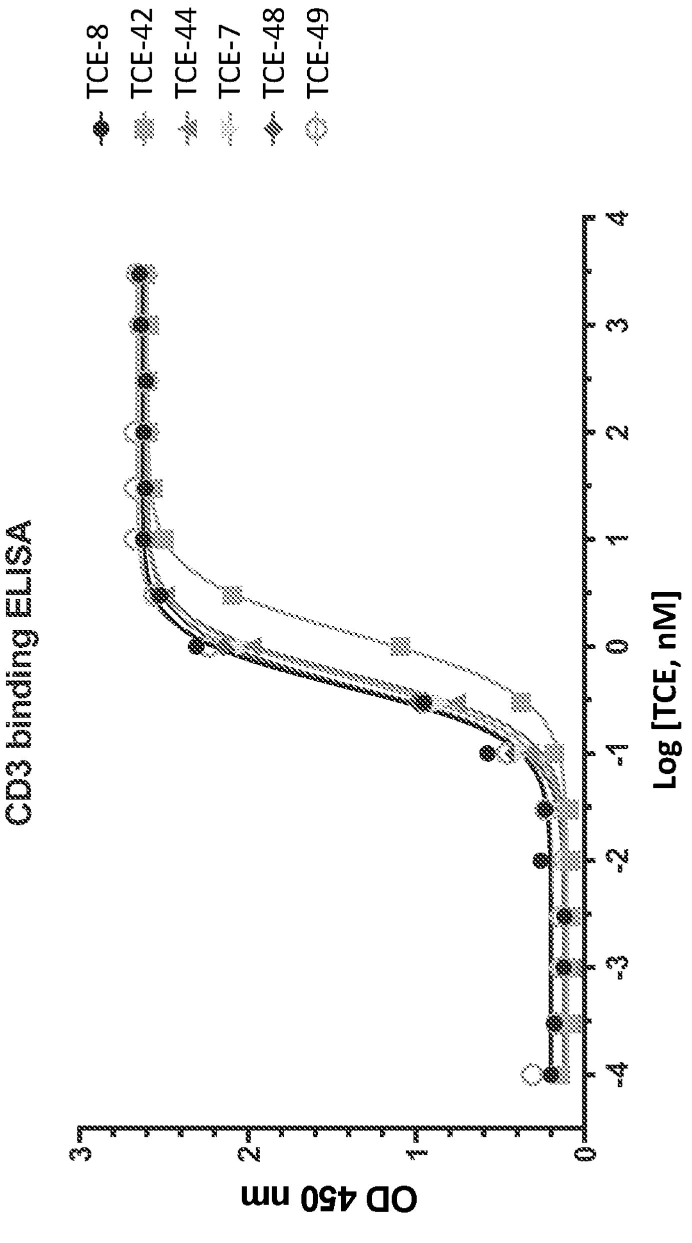
FIG. 113 illustrates binding curves for binding of CD3 by TCEs as measured by ELISA.
Figure 114:
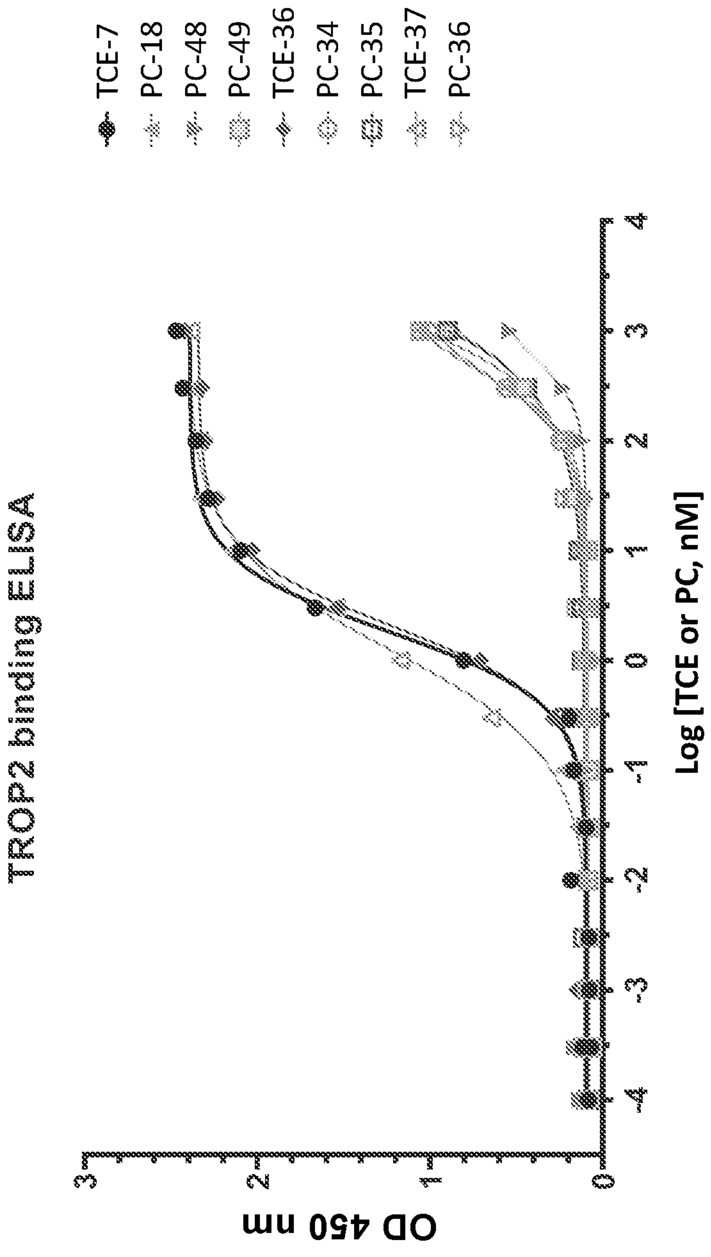
FIG. 114 illustrates binding curves for binding of TROP2 by TCEs and PCs as measured by ELISA.
Figure 115:
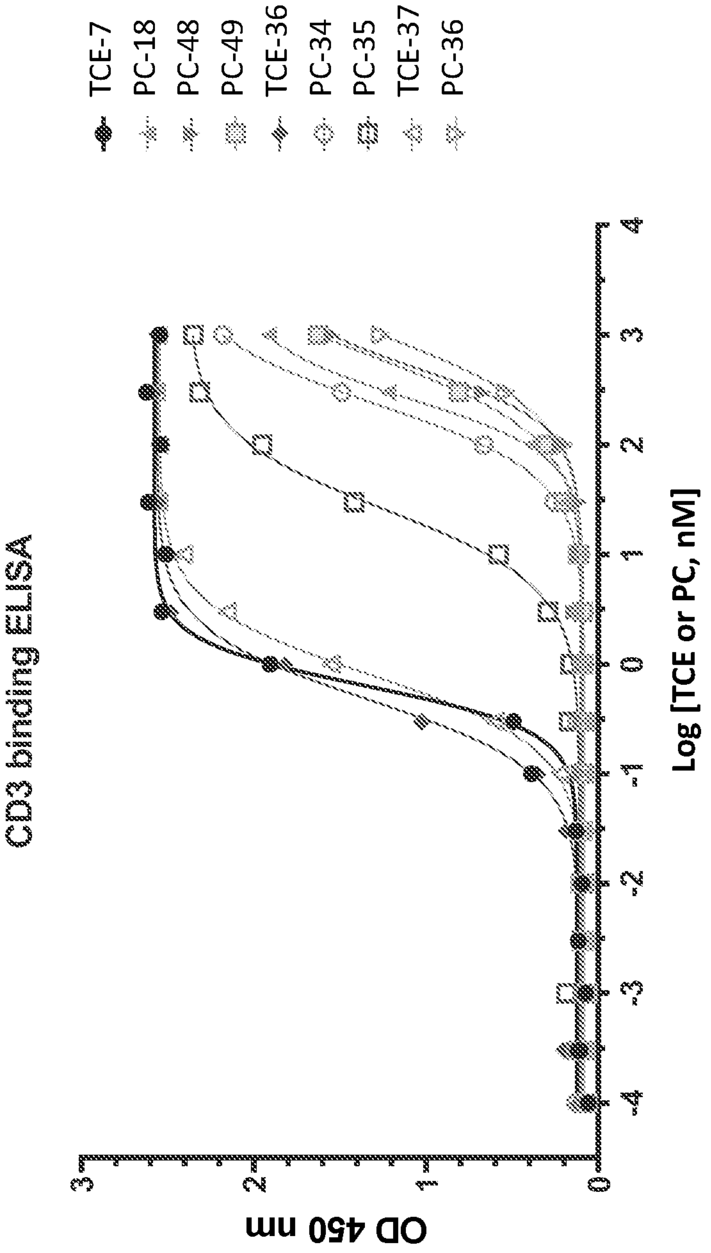
FIG. 115 illustrates binding curves for binding of CD3 by TCEs and PCs as measured by ELISA.
Figure 116:
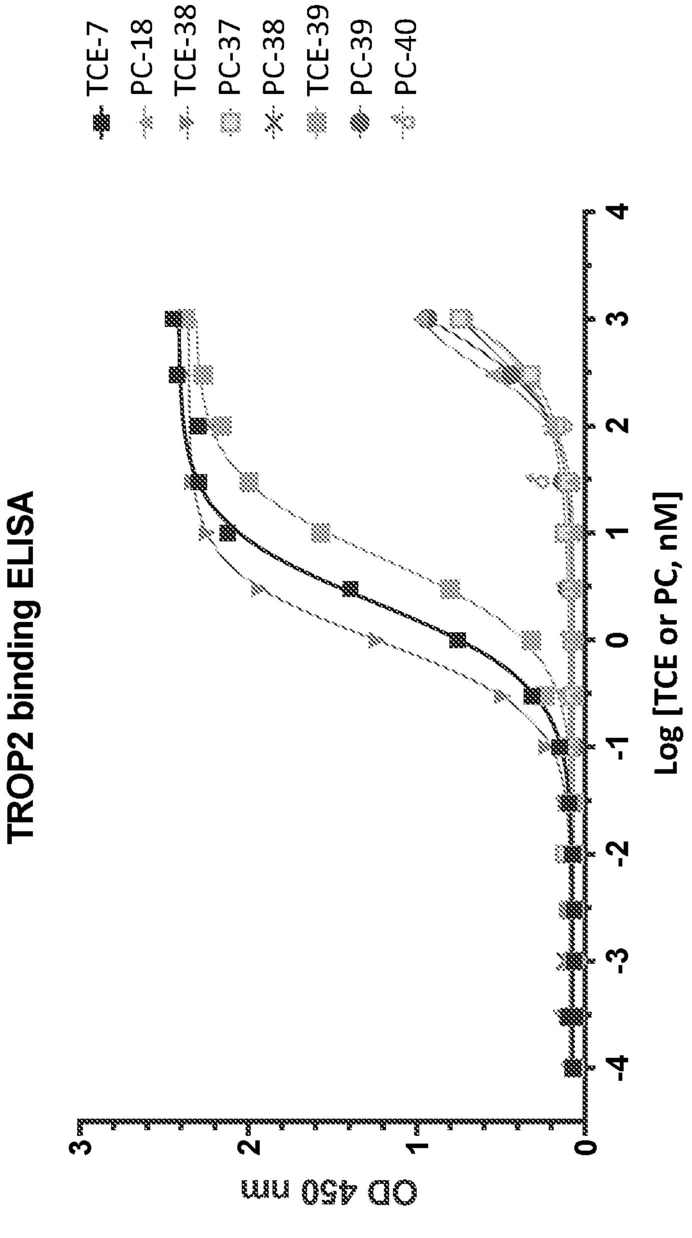
FIG. 116 illustrates binding curves for binding of TROP2 by TCEs and PCs as measured by ELISA.
Figure 117:
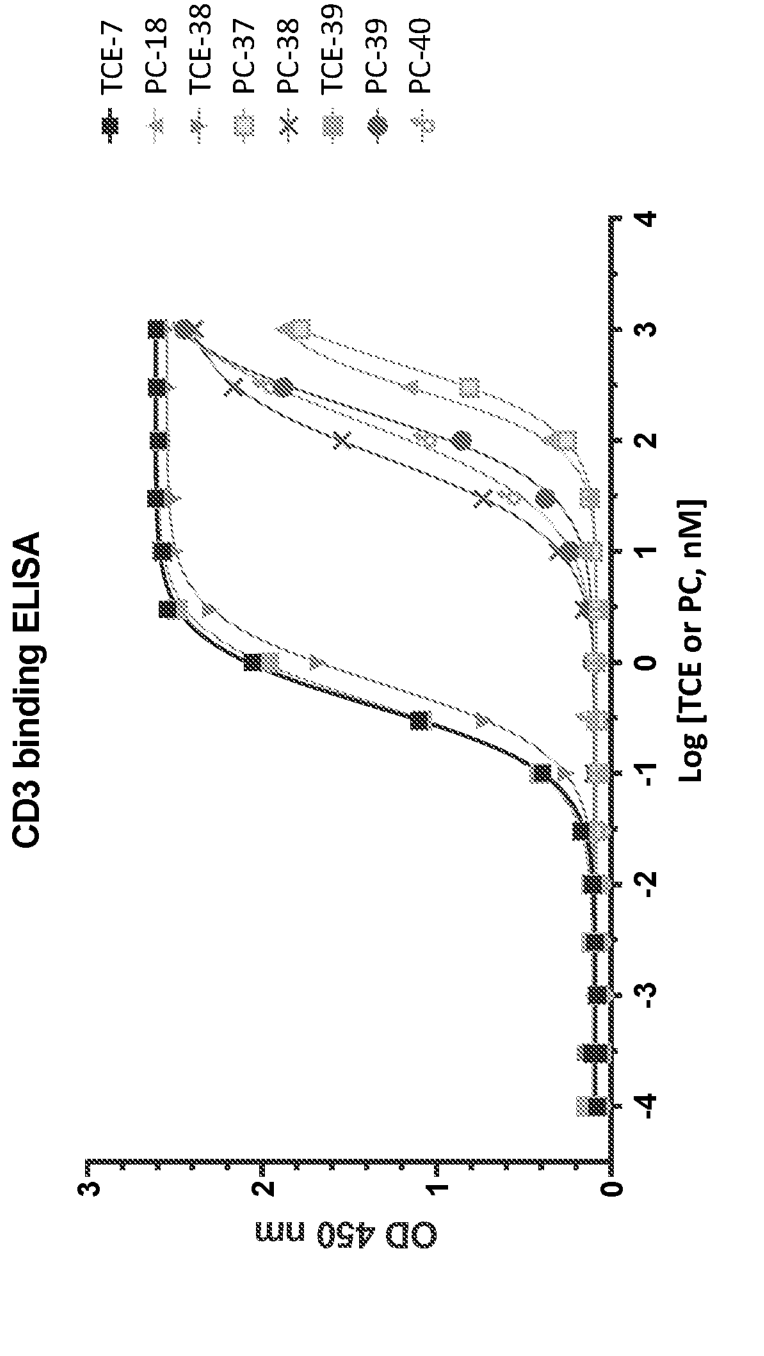
FIG. 117 illustrates binding curves for binding of CD3 by TCEs and PCs as measured by ELISA.
Figure 118:
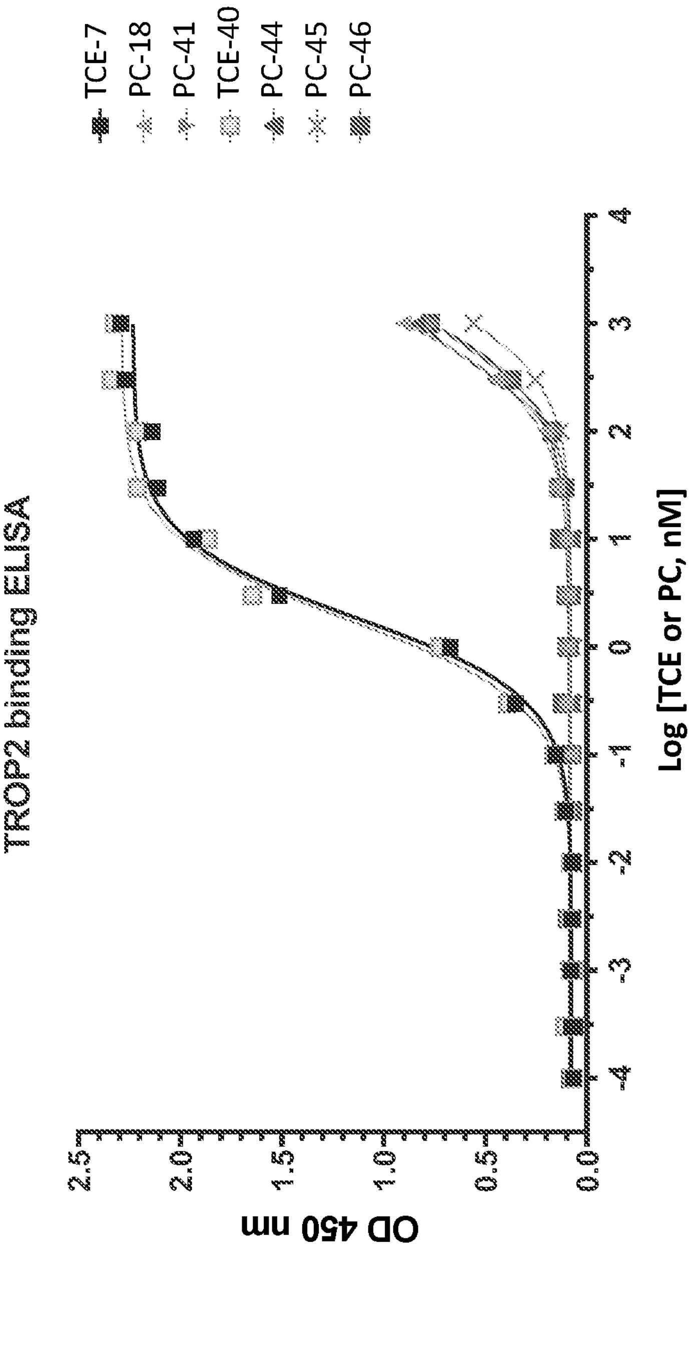
FIG. 118 illustrates binding curves for binding of TROP2 by TCEs and PCs as measured by ELISA.
Figure 119:
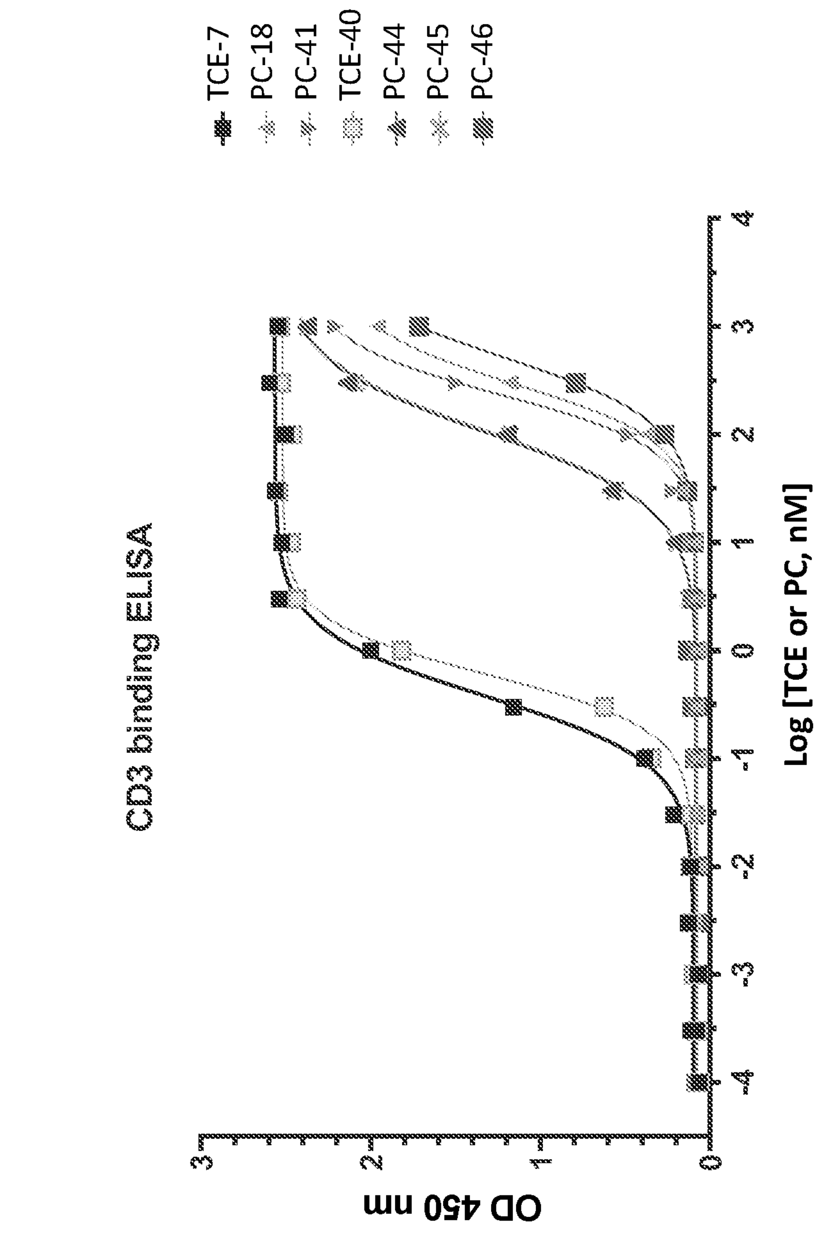
FIG. 119 illustrates binding curves for binding of CD3 by TCEs and PCs as measured by ELISA.
Figure 120:
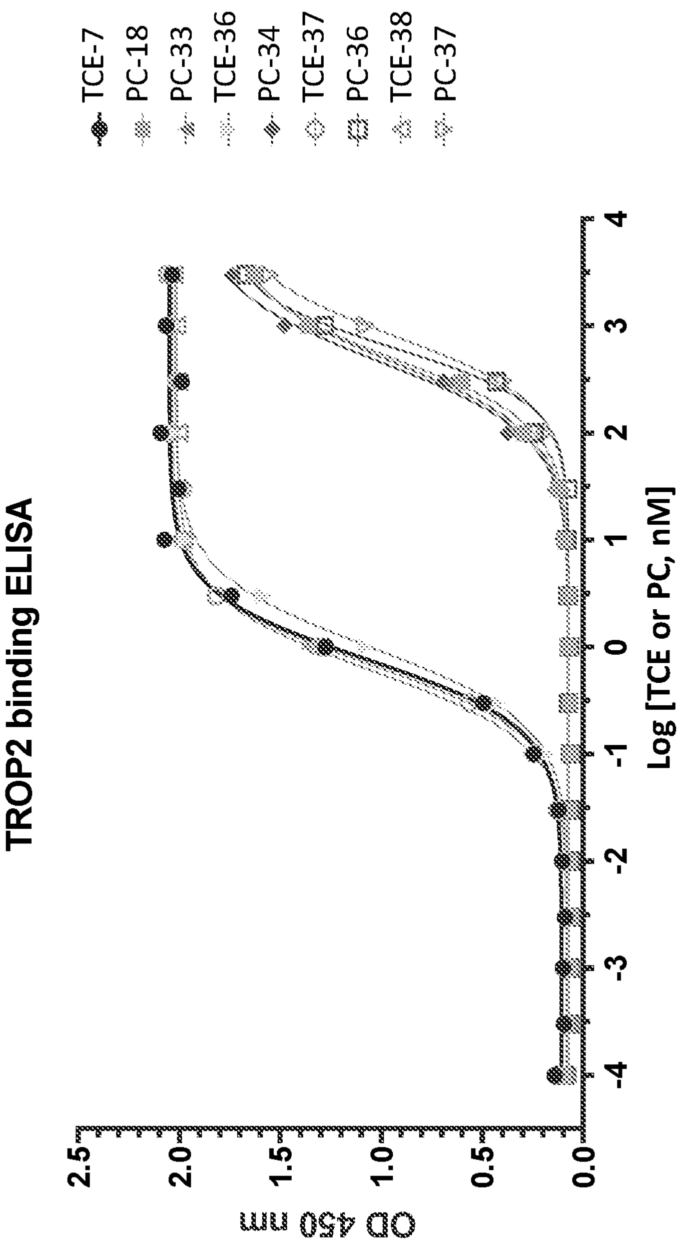
FIG. 120 illustrates binding curves for binding of TROP2 by TCEs and PCs as measured by ELISA.
Figure 121:
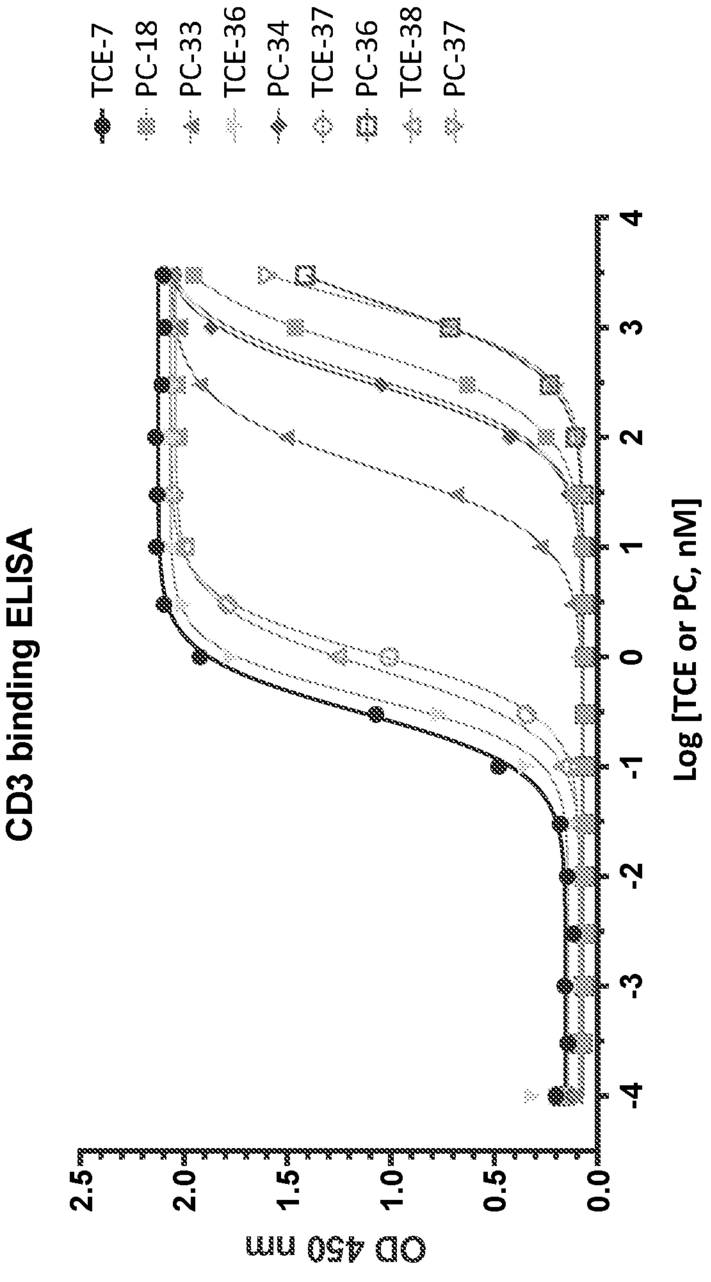
Figure 122:
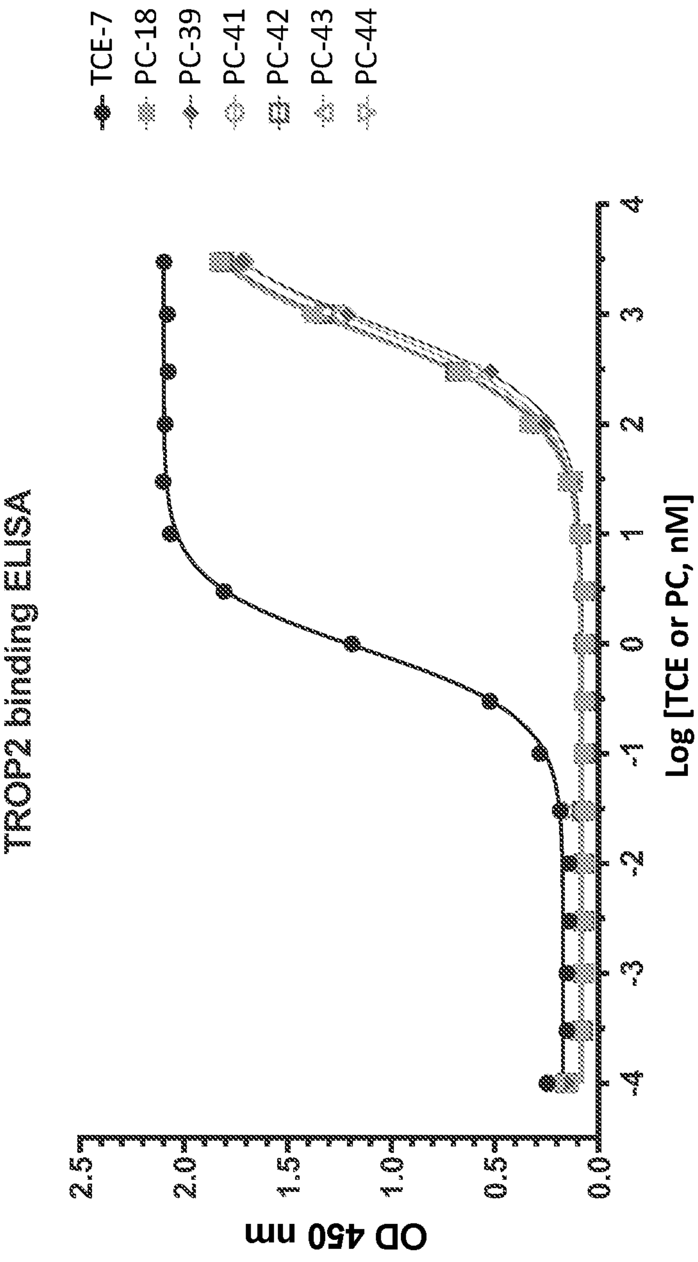
Figure 123:
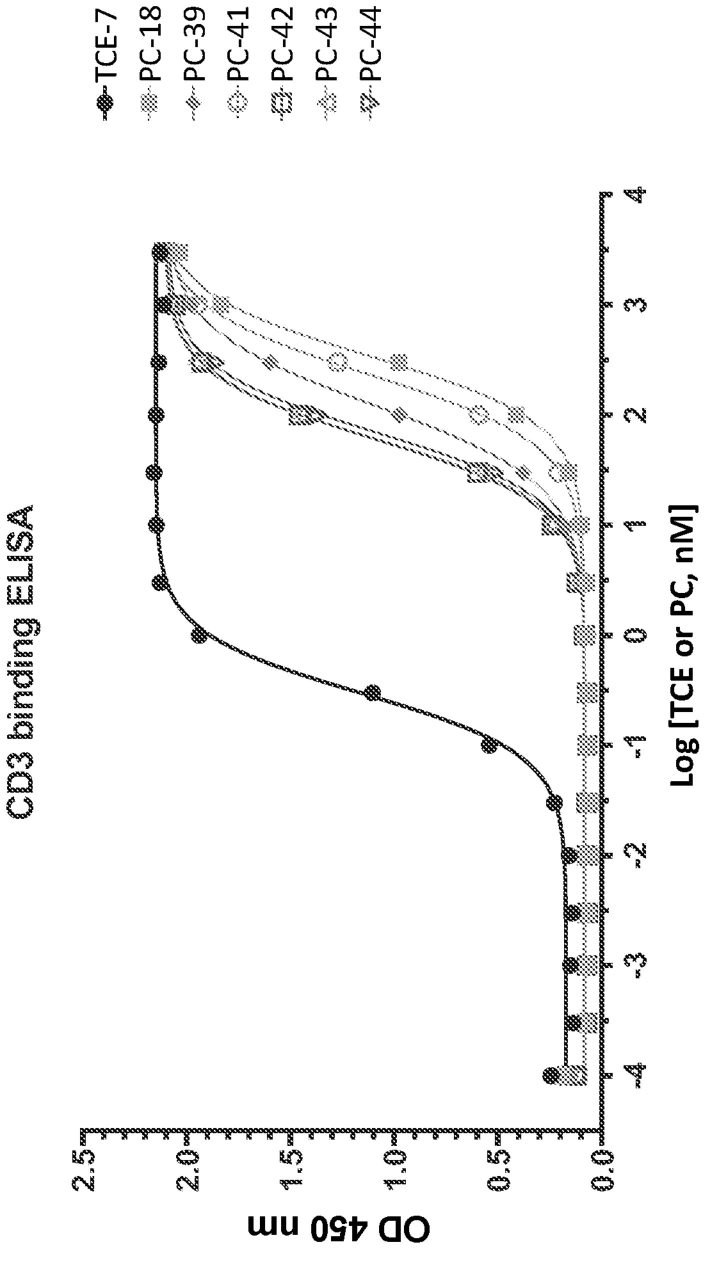
Figure 124:
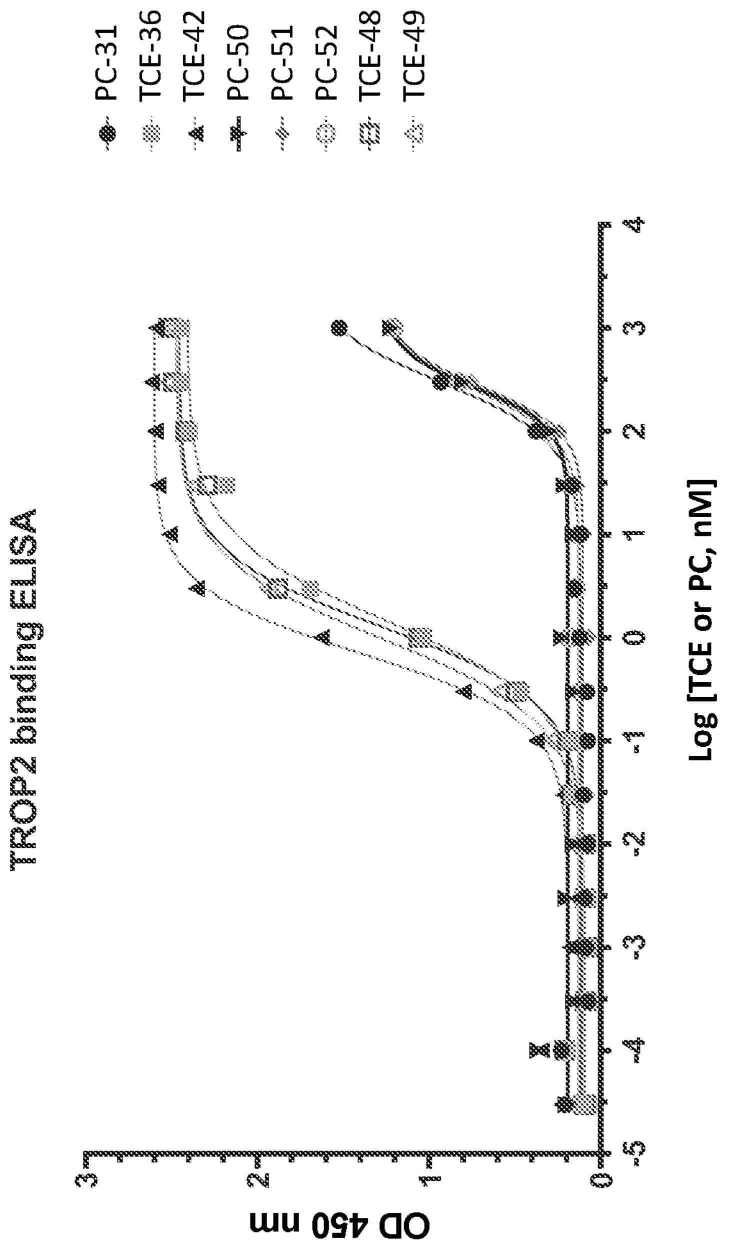
Figure 125:
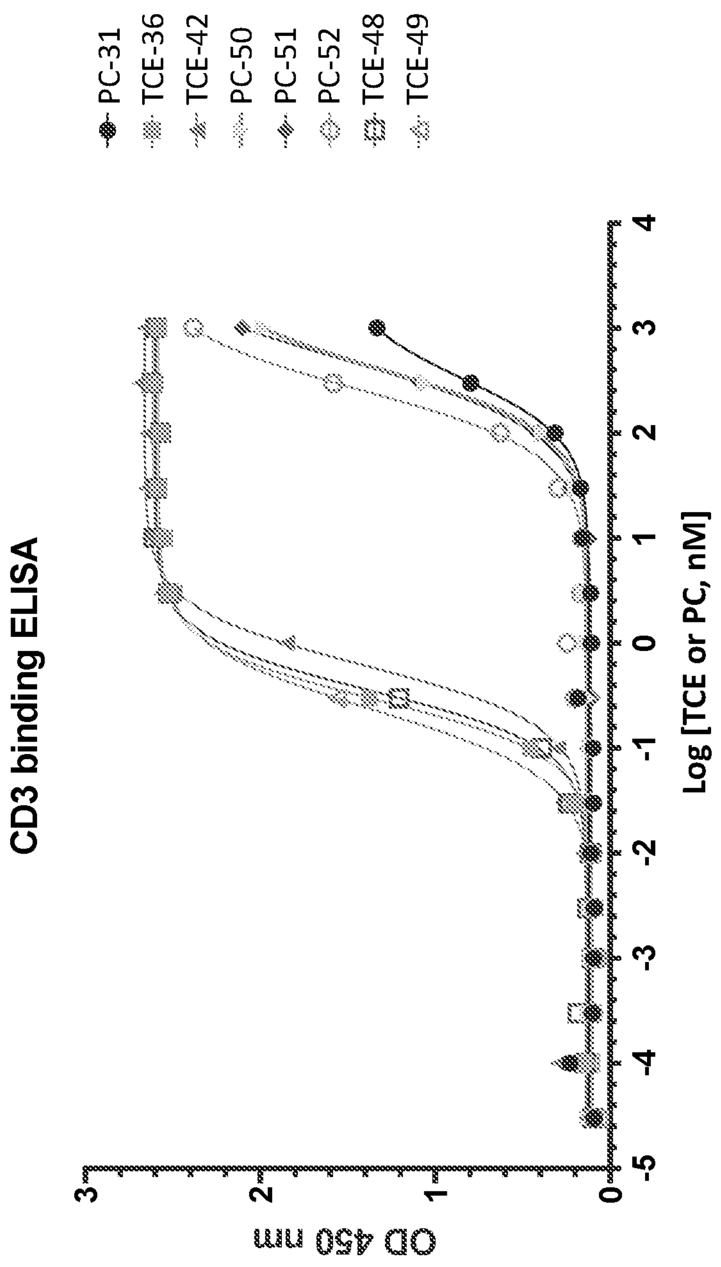
Figure 126:
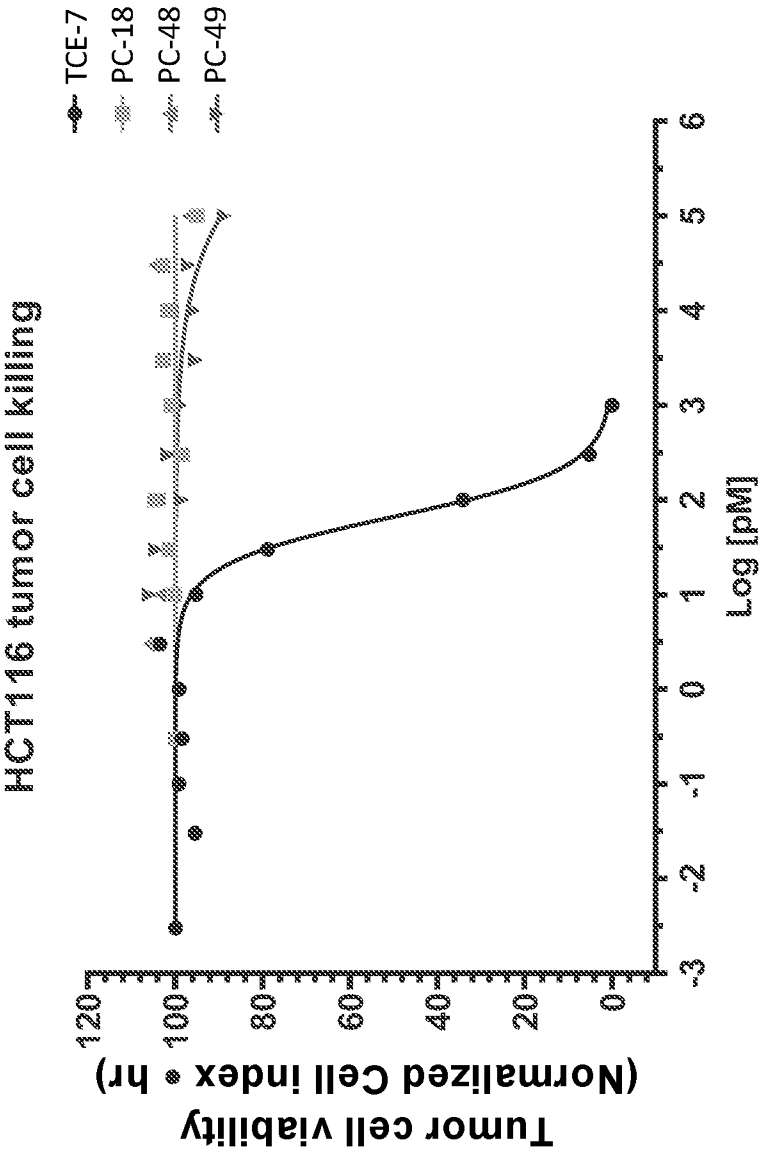
Figure 127:
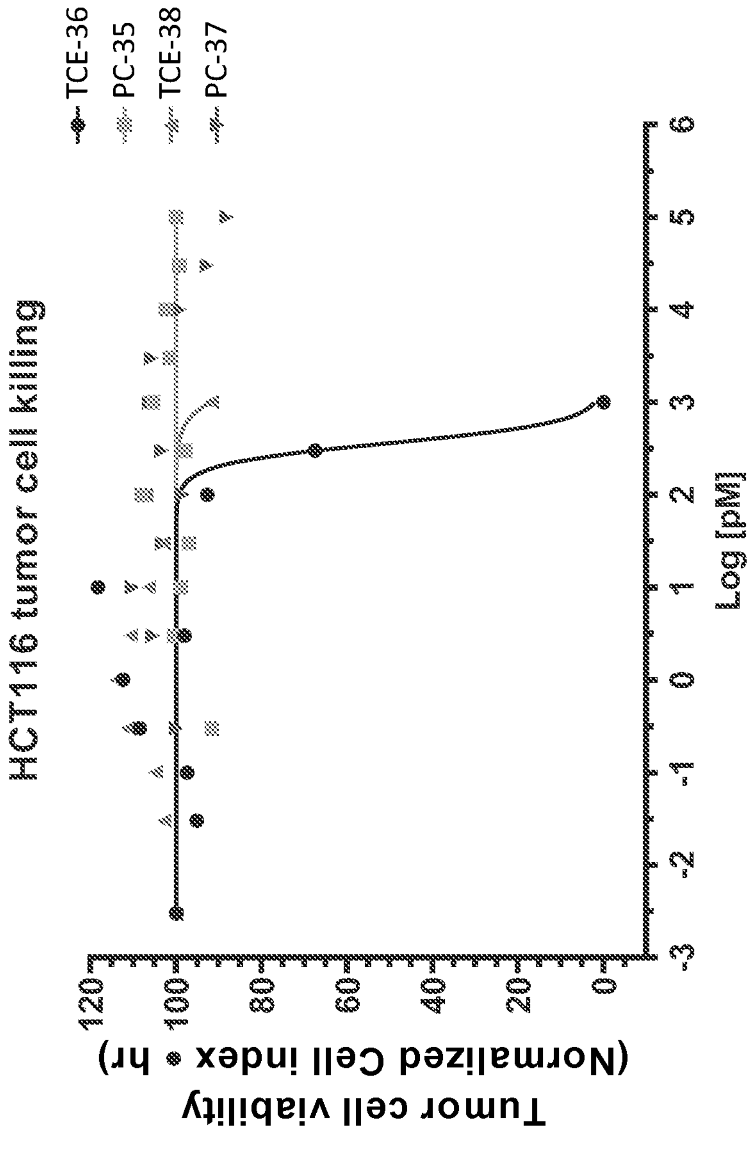
Figure 128:
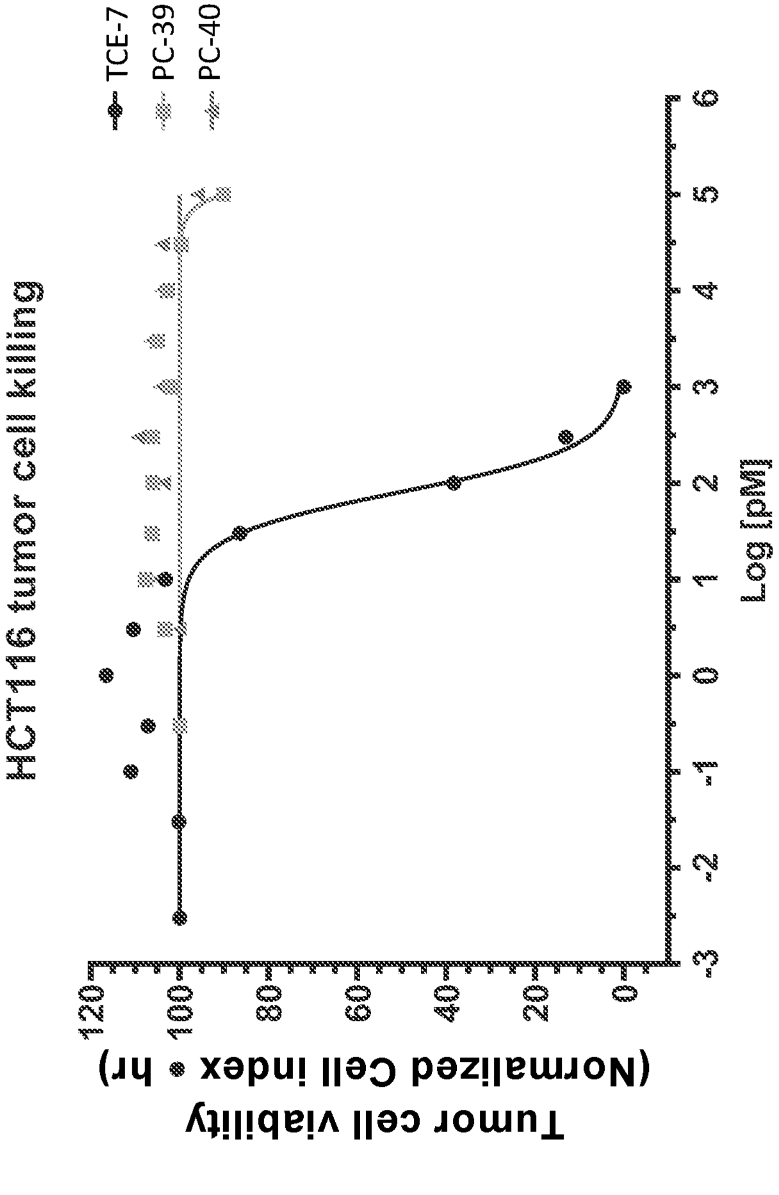
Figure 129:
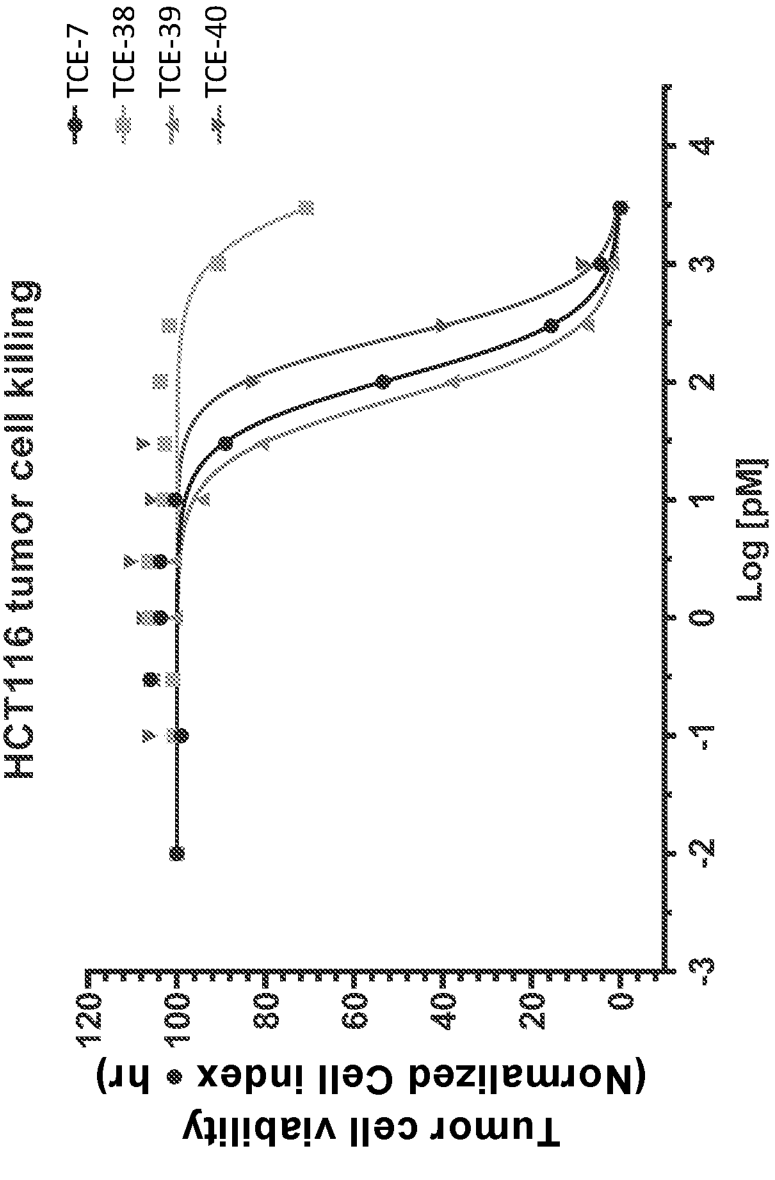
Figure 130:
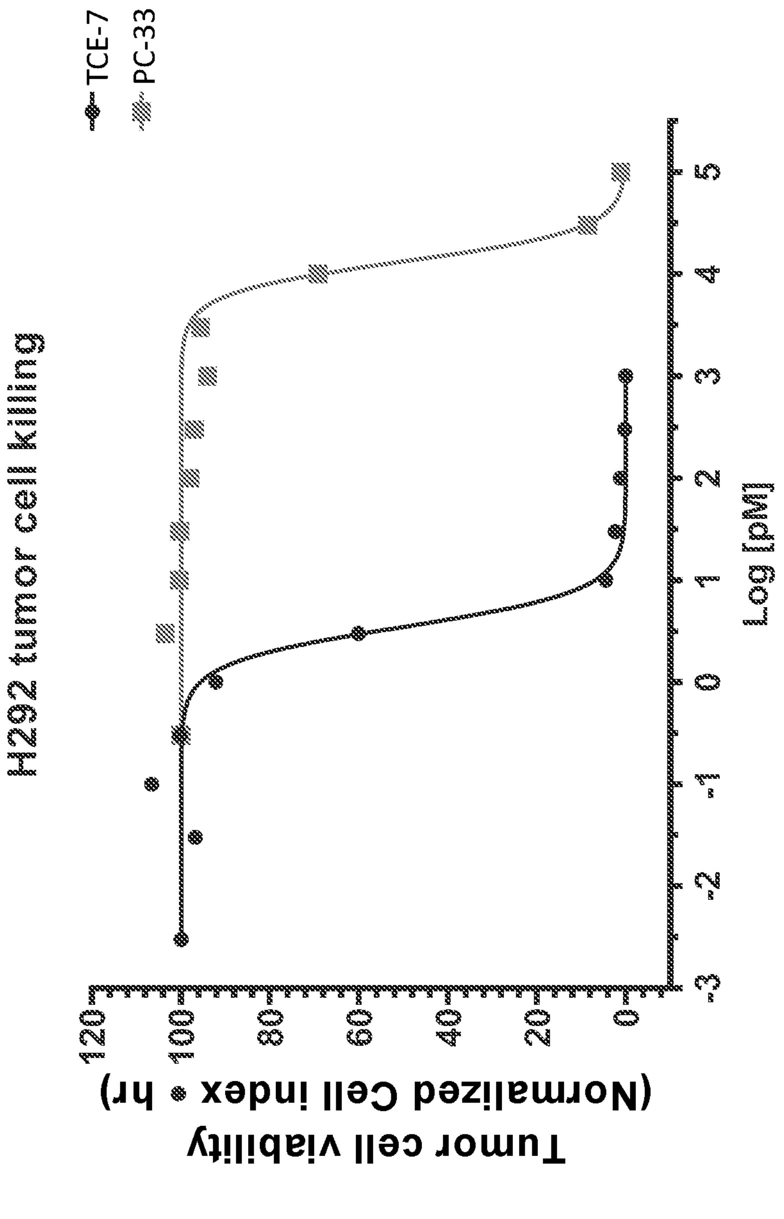
Figure 131:
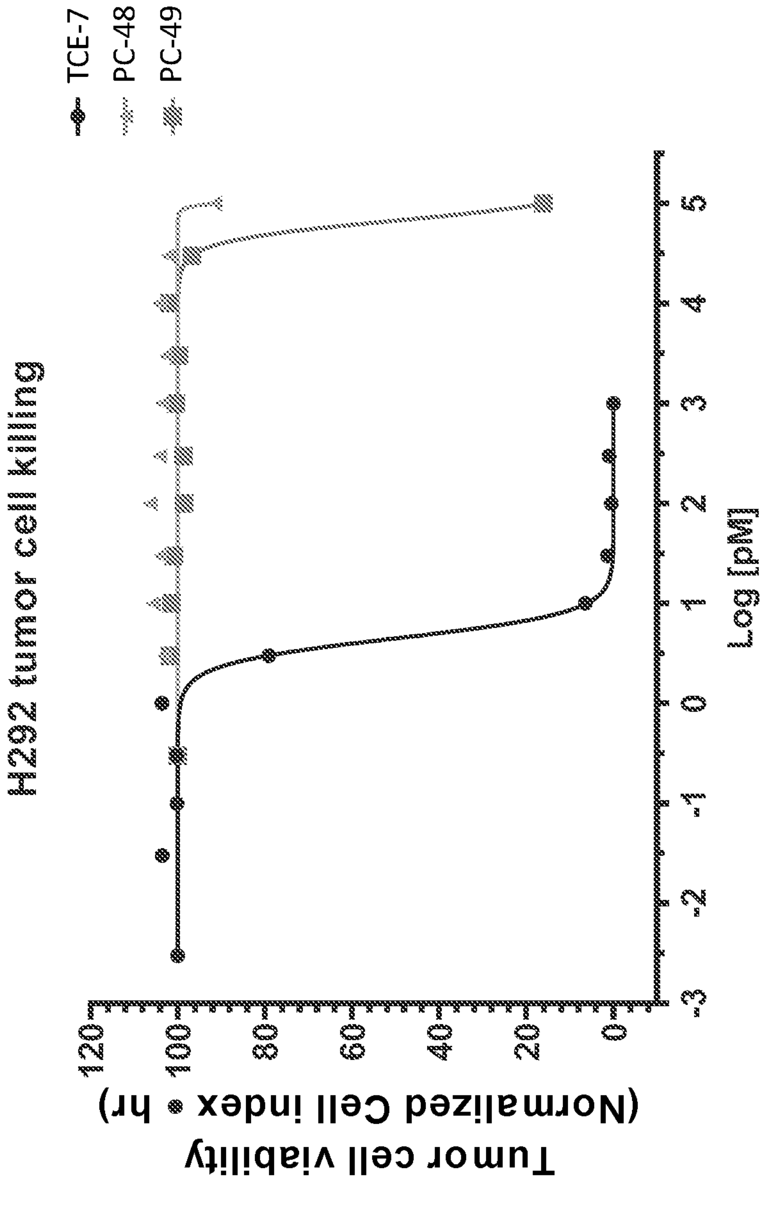
Figure 132:
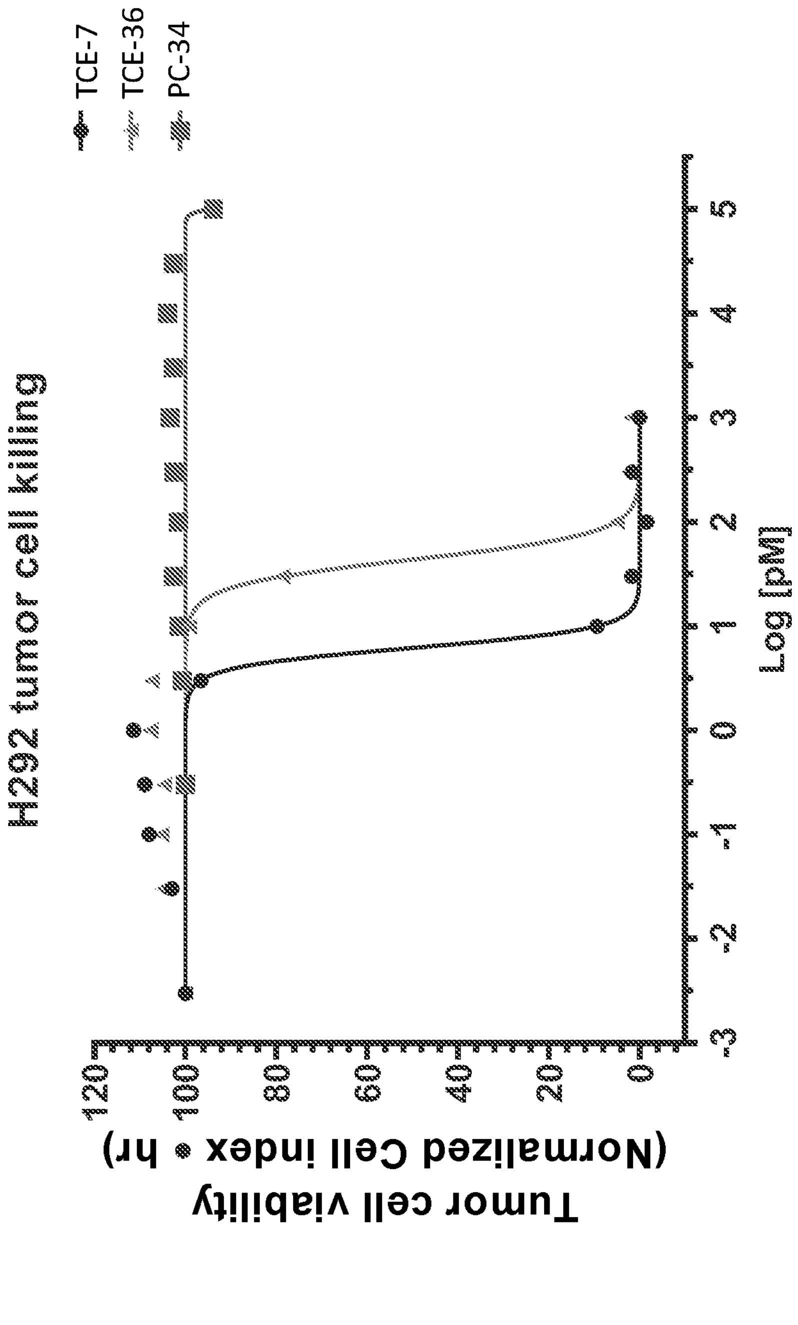
Figure 133:
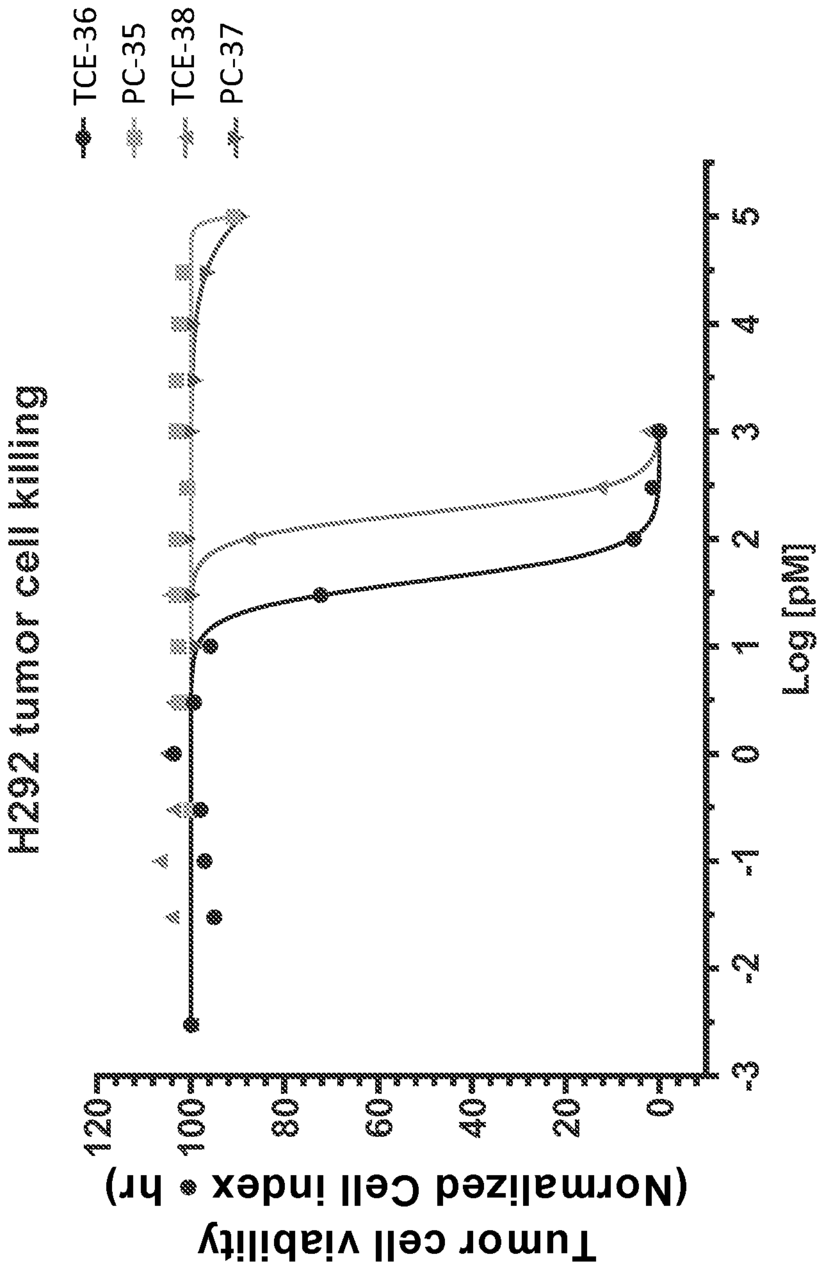
Figure 134:
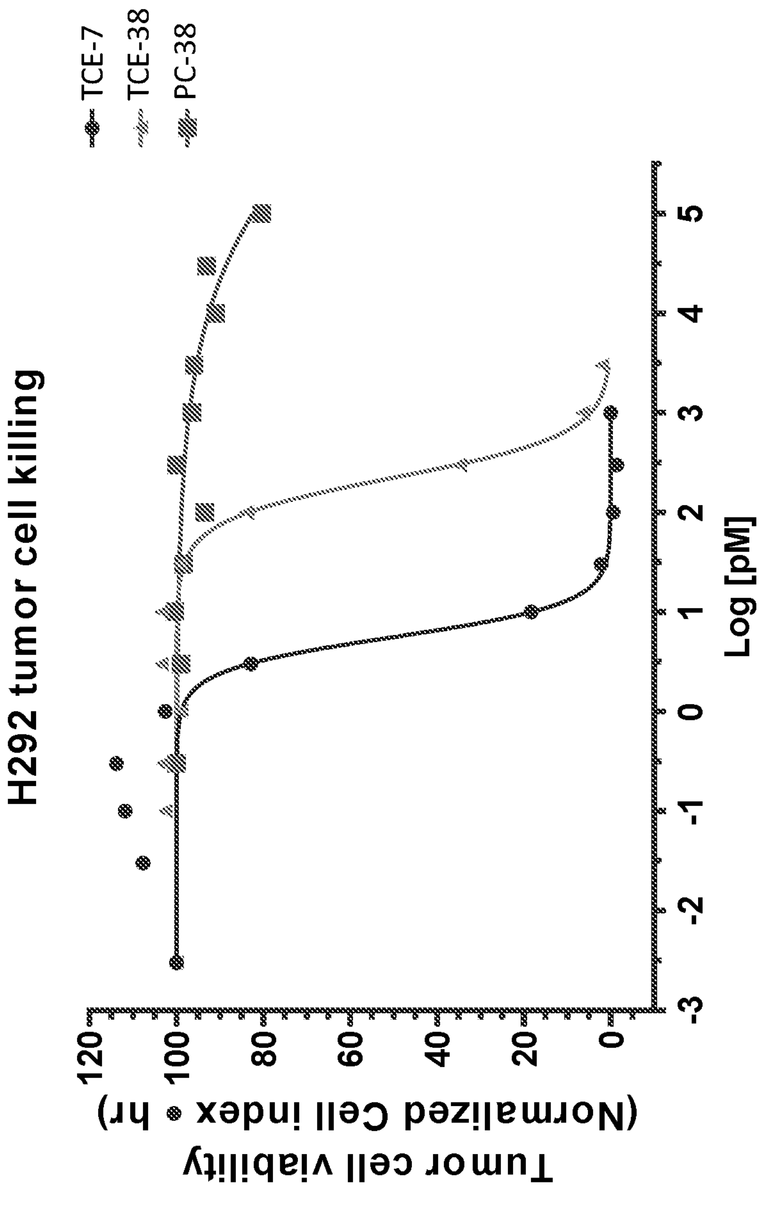
Figure 135:
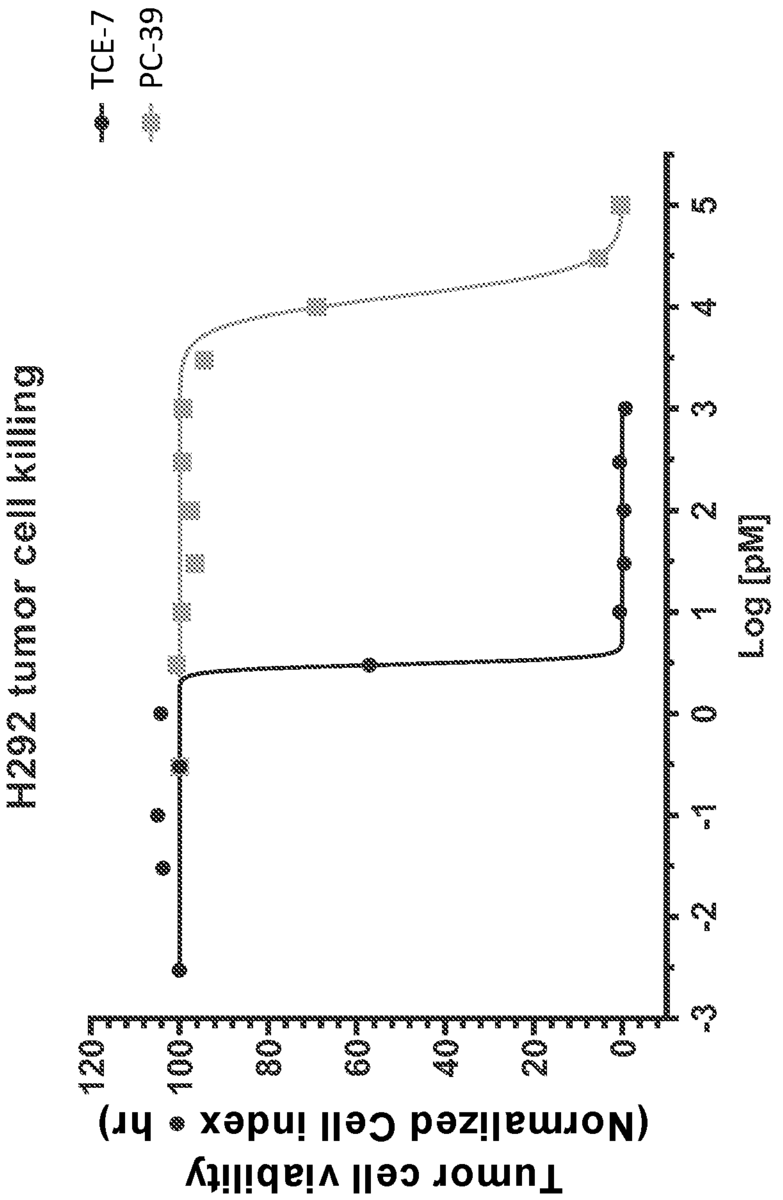
Figure 136:
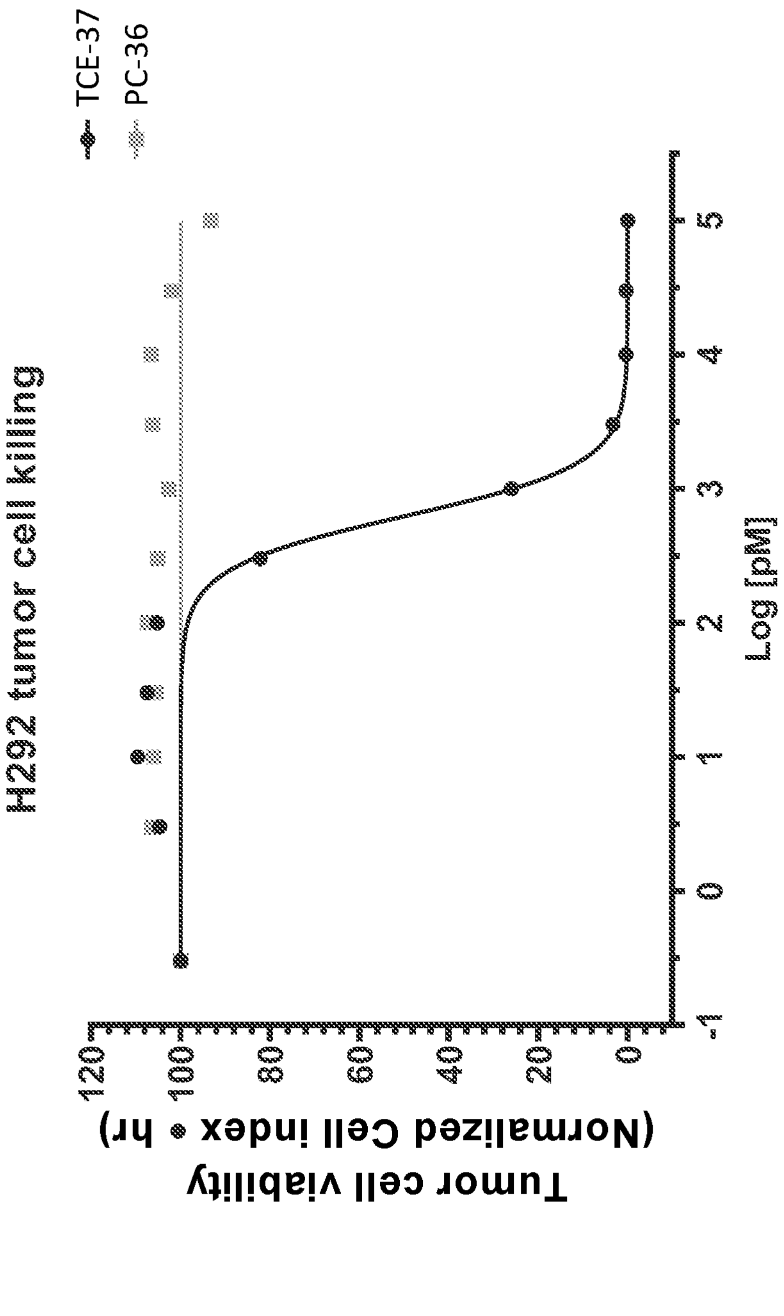
Figure 137:
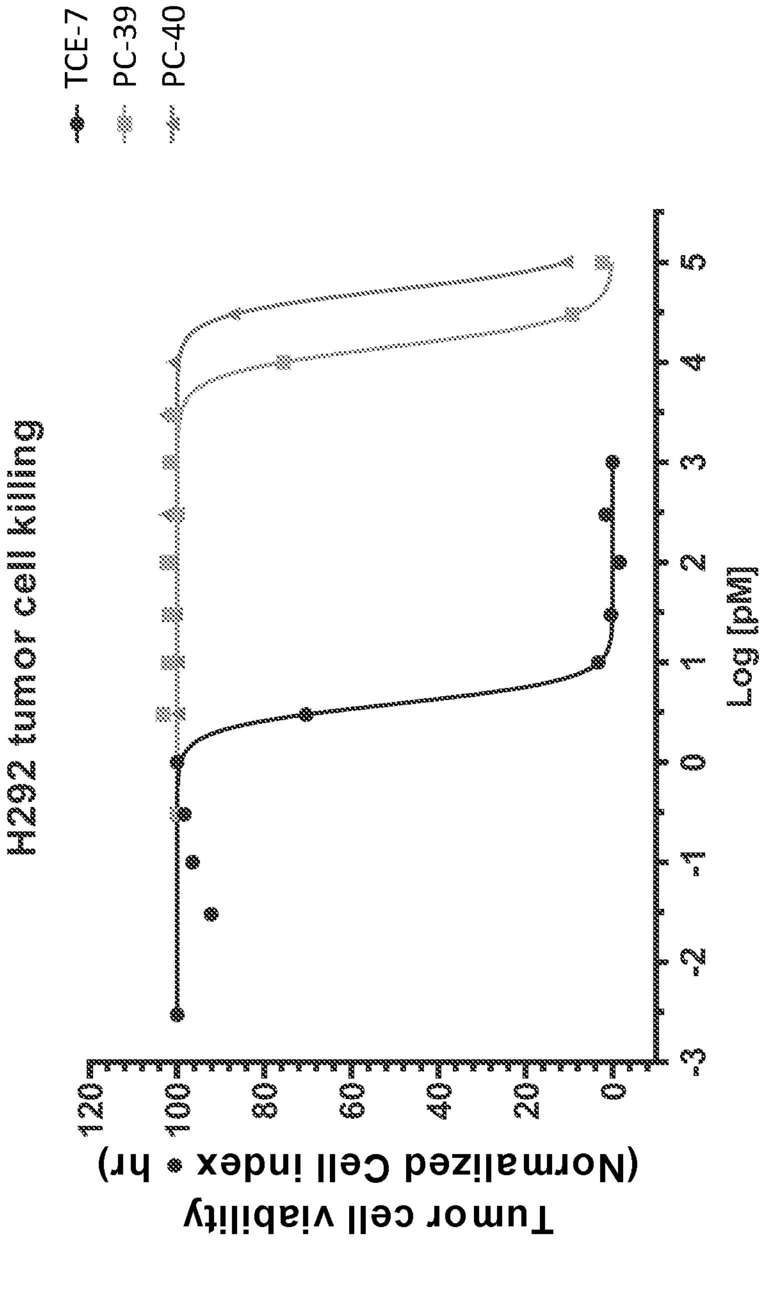
Figure 138:
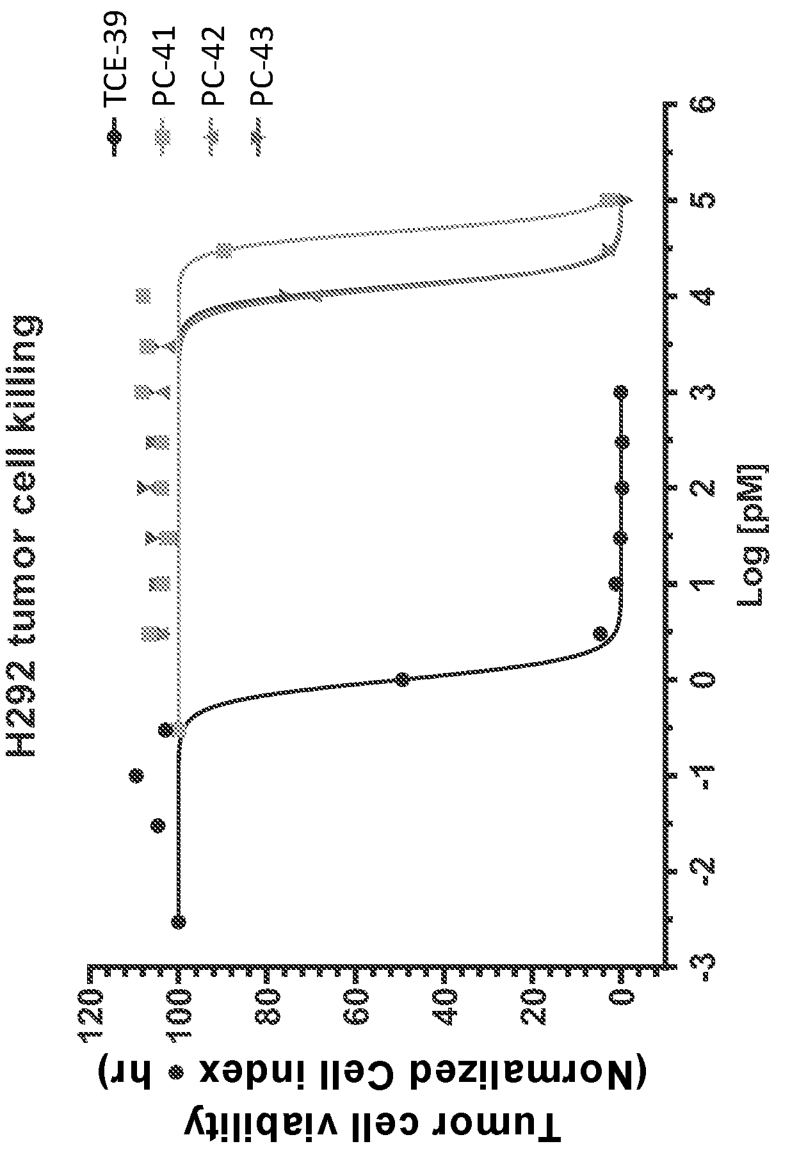
Figure 139:
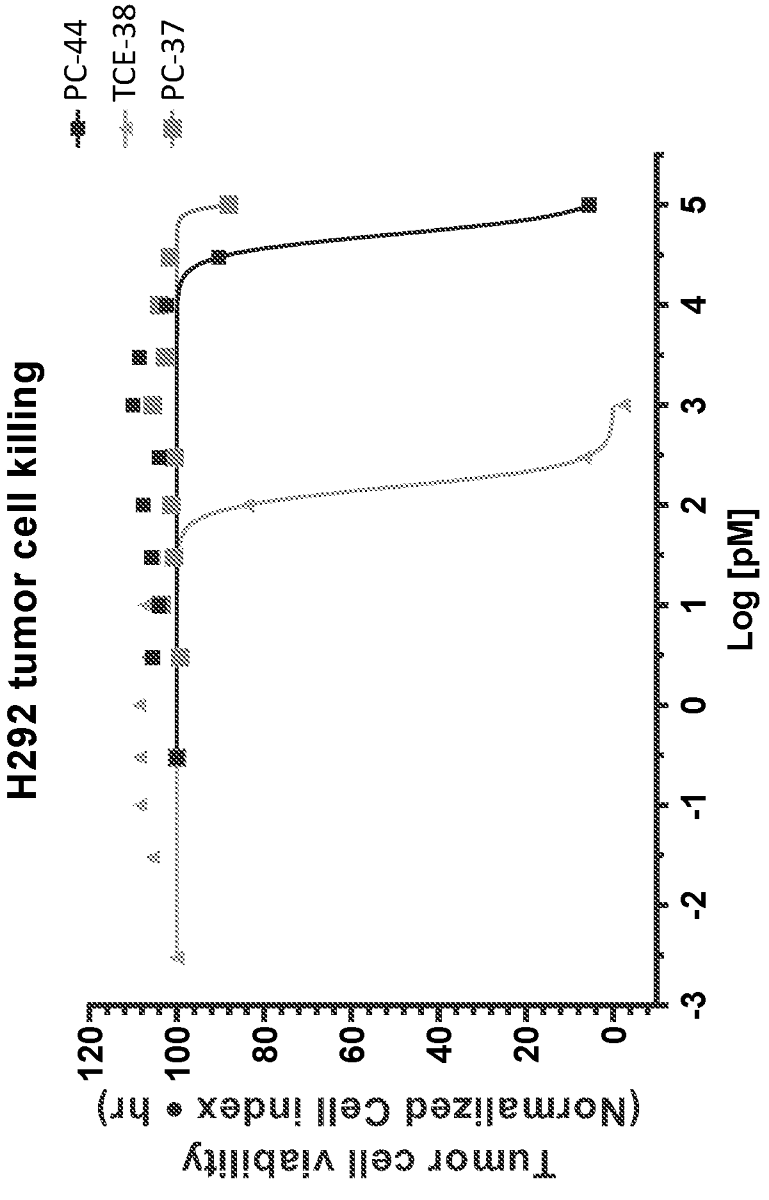
Figure 140:
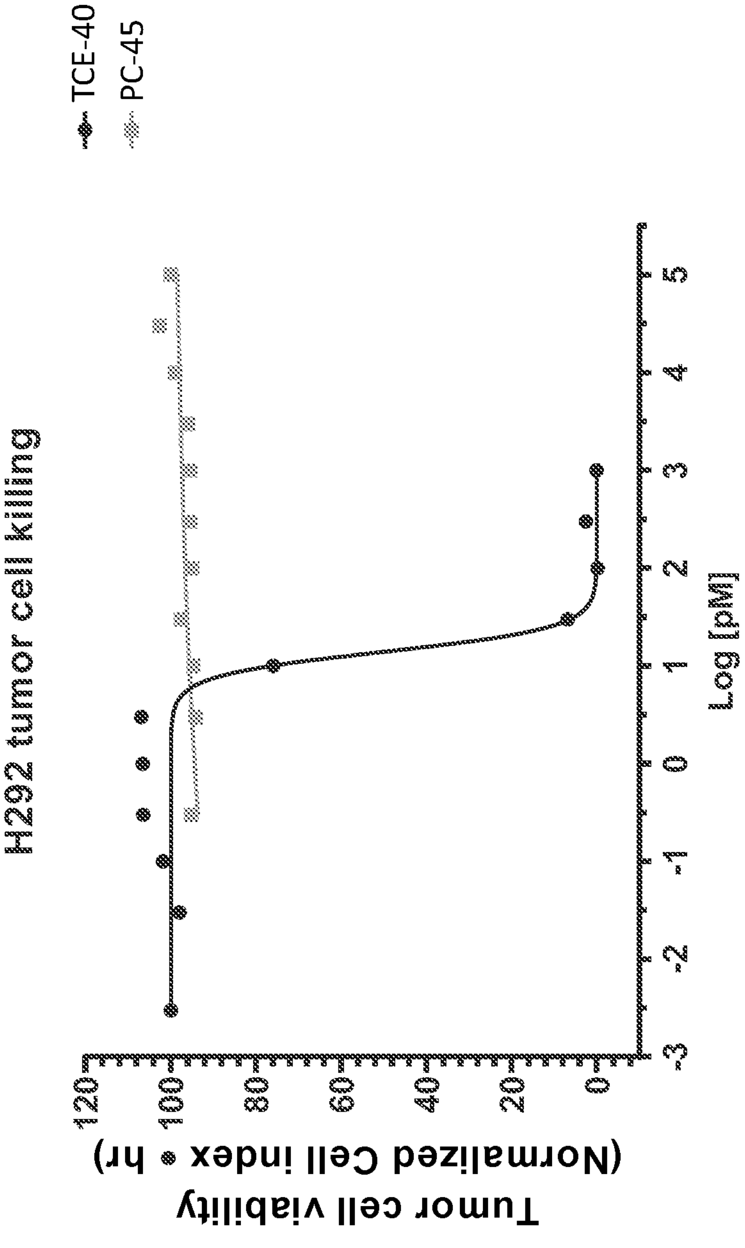
Figure 141:
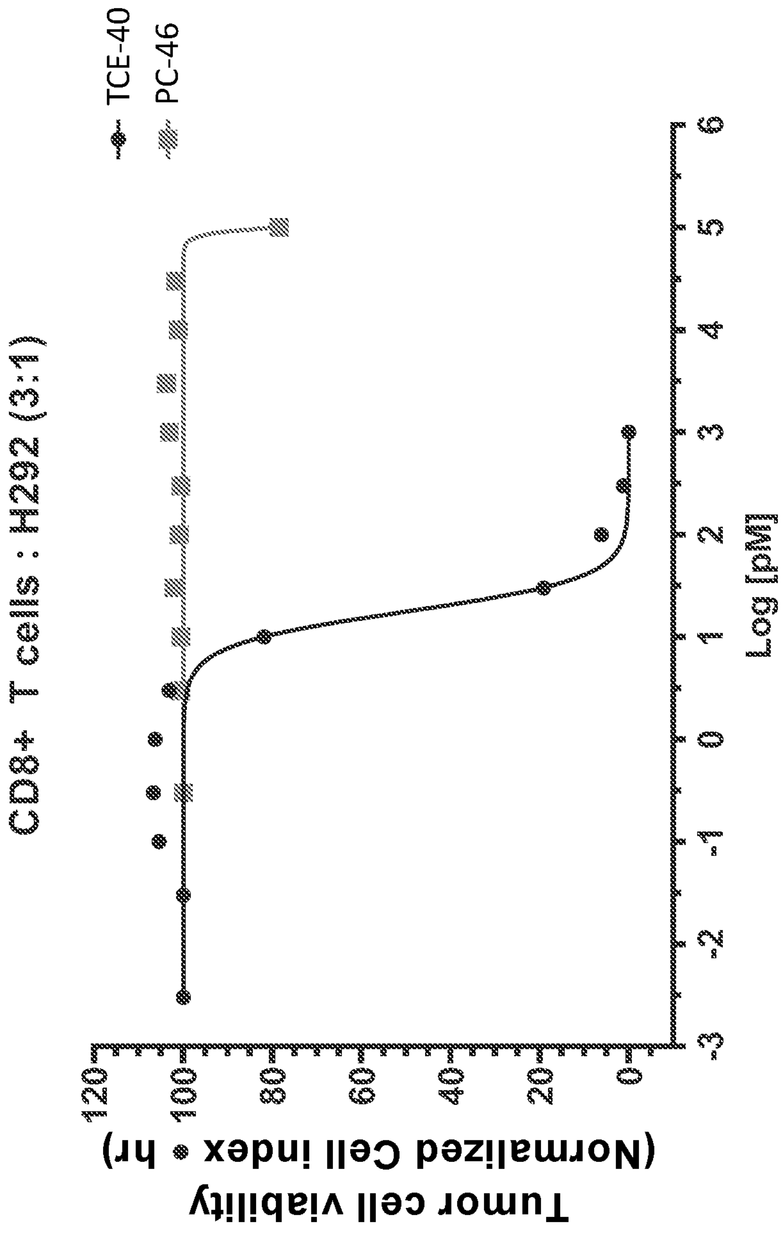
Figure 142:
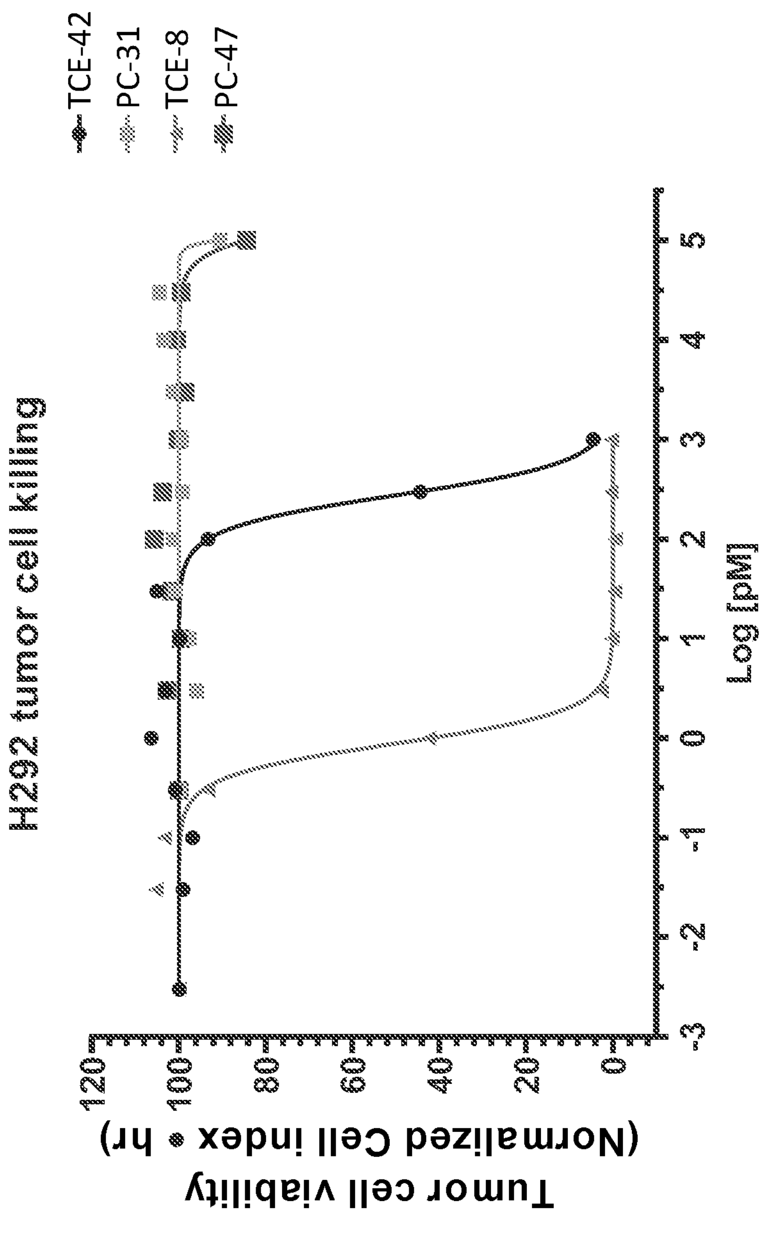
Figure 143:
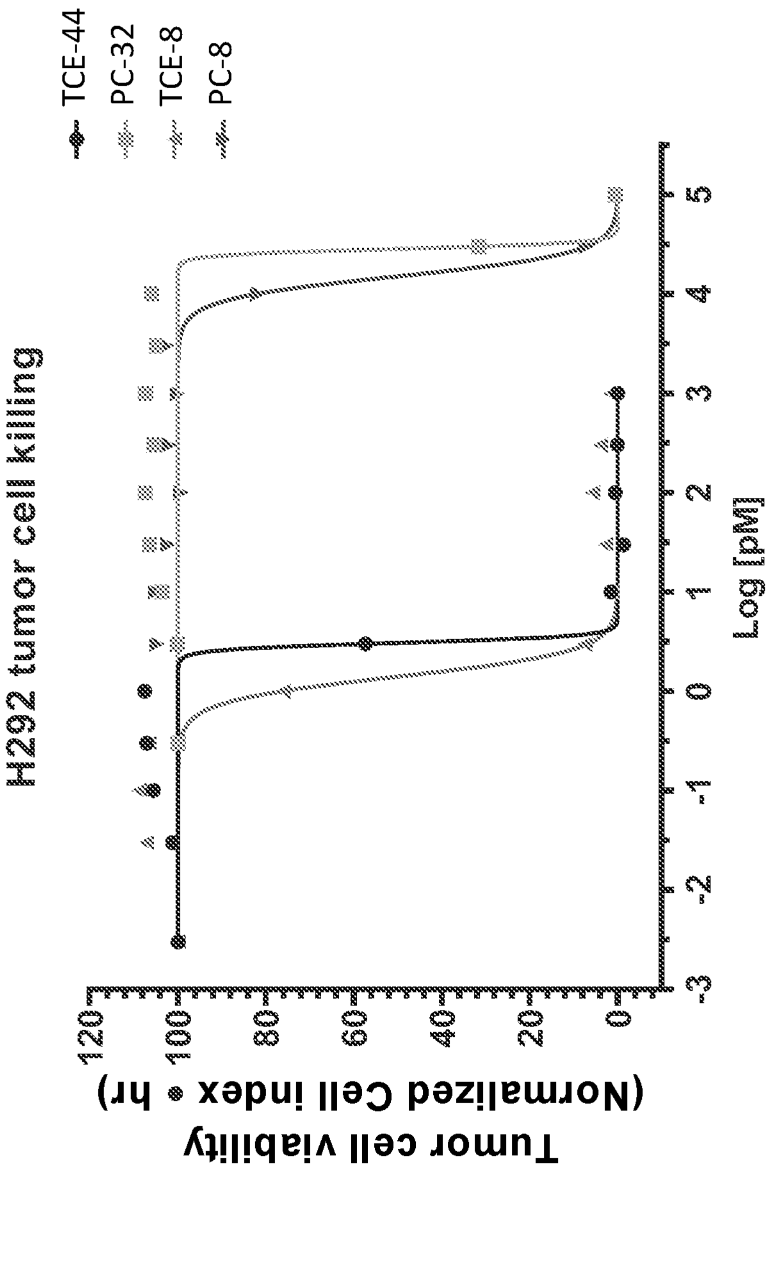
Figure 144:
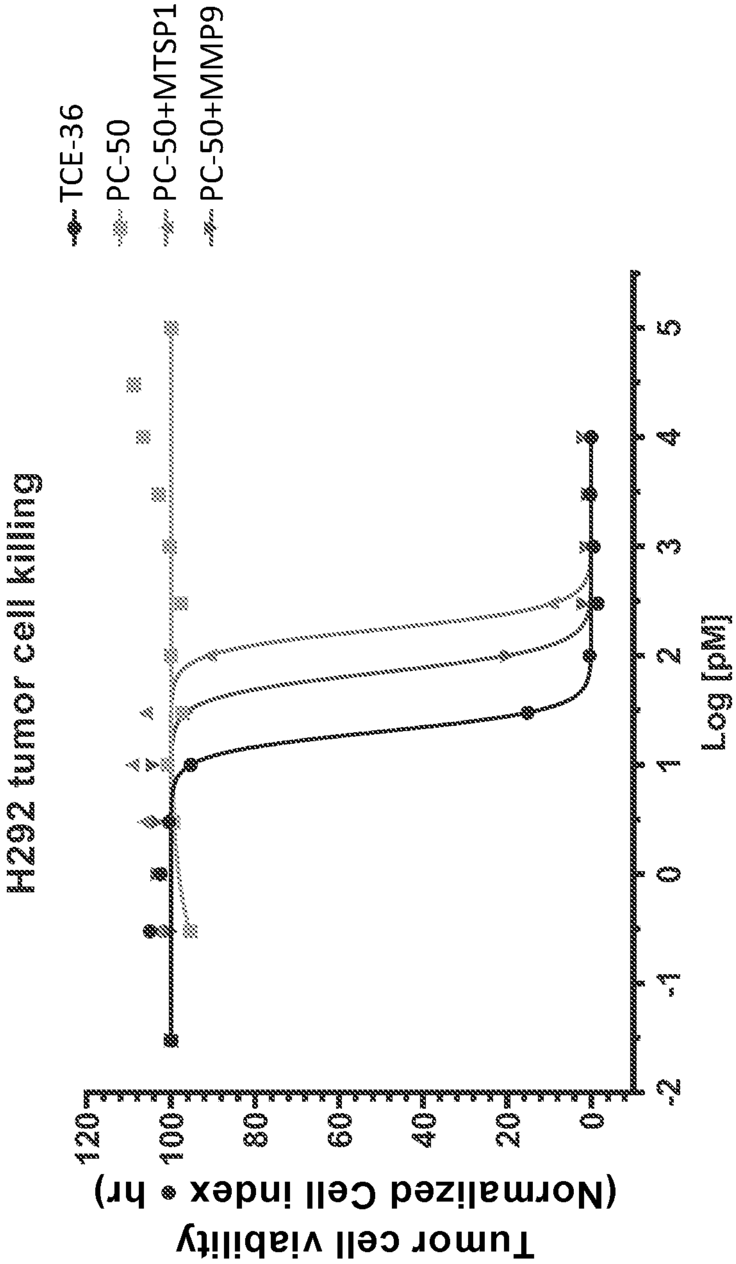
Figure 145:
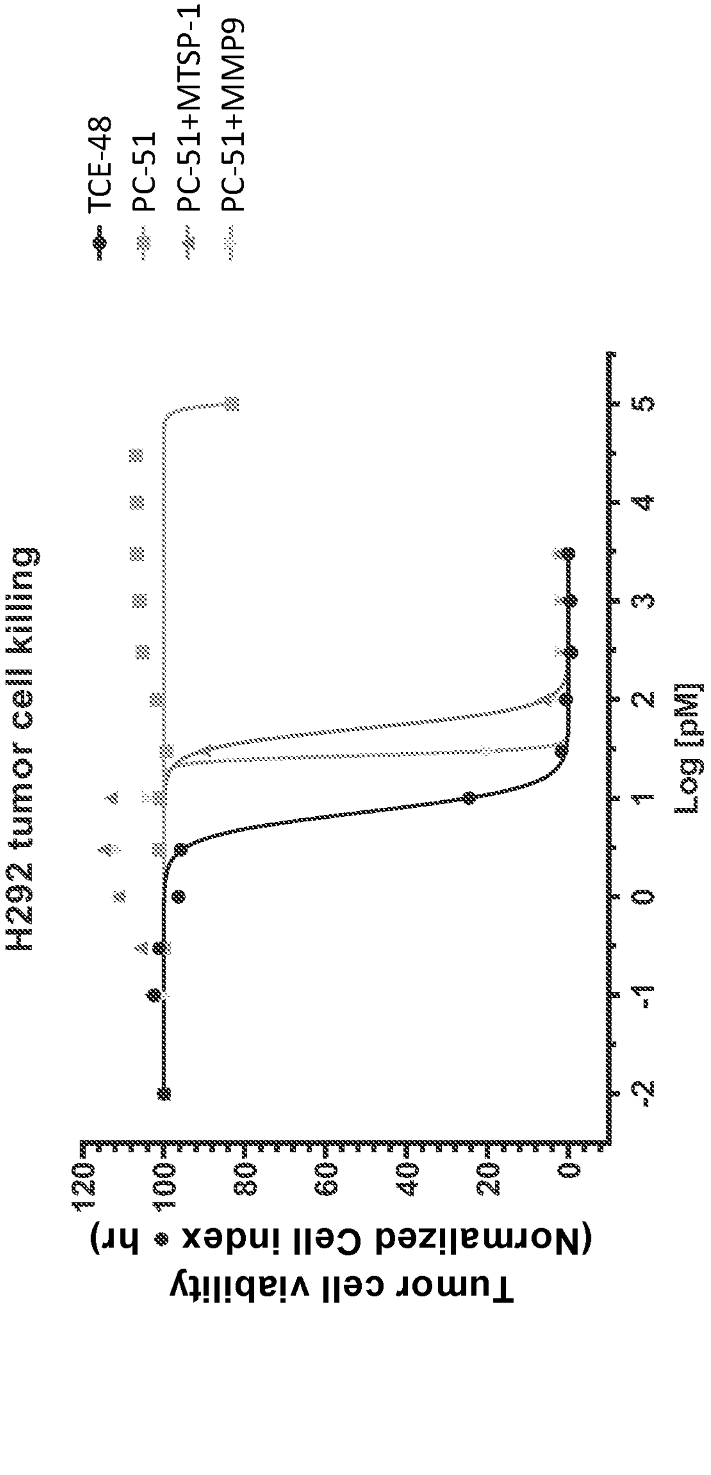
Figure 146:
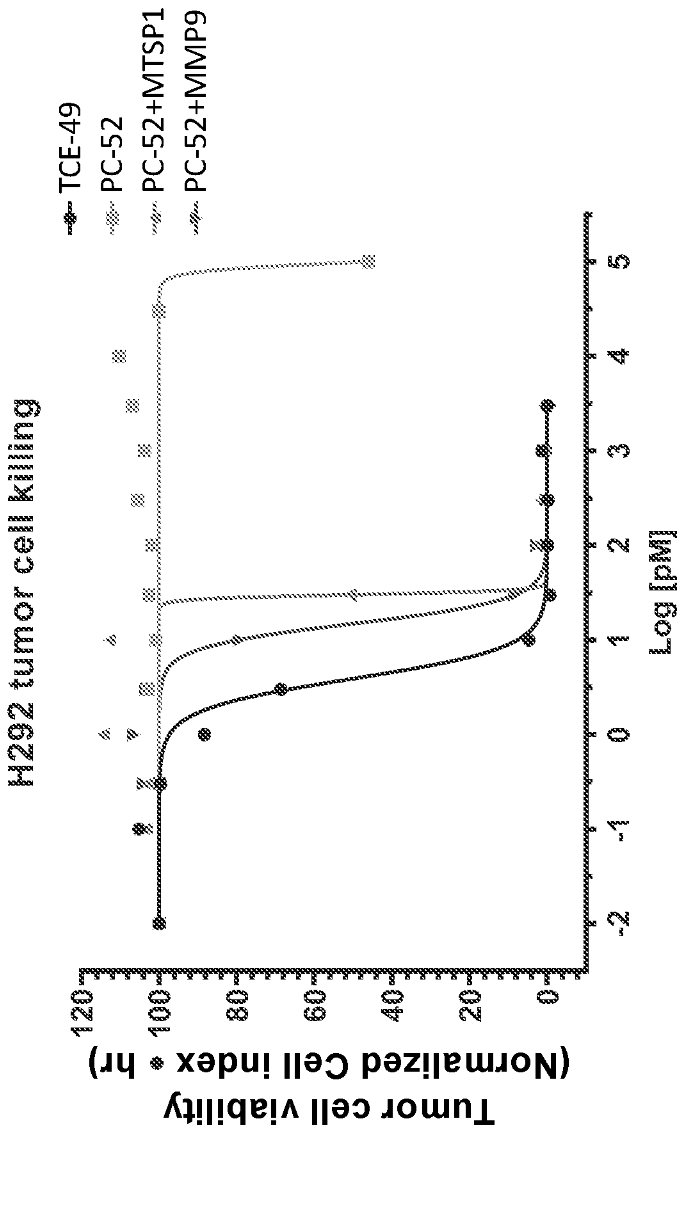
Figure 147:
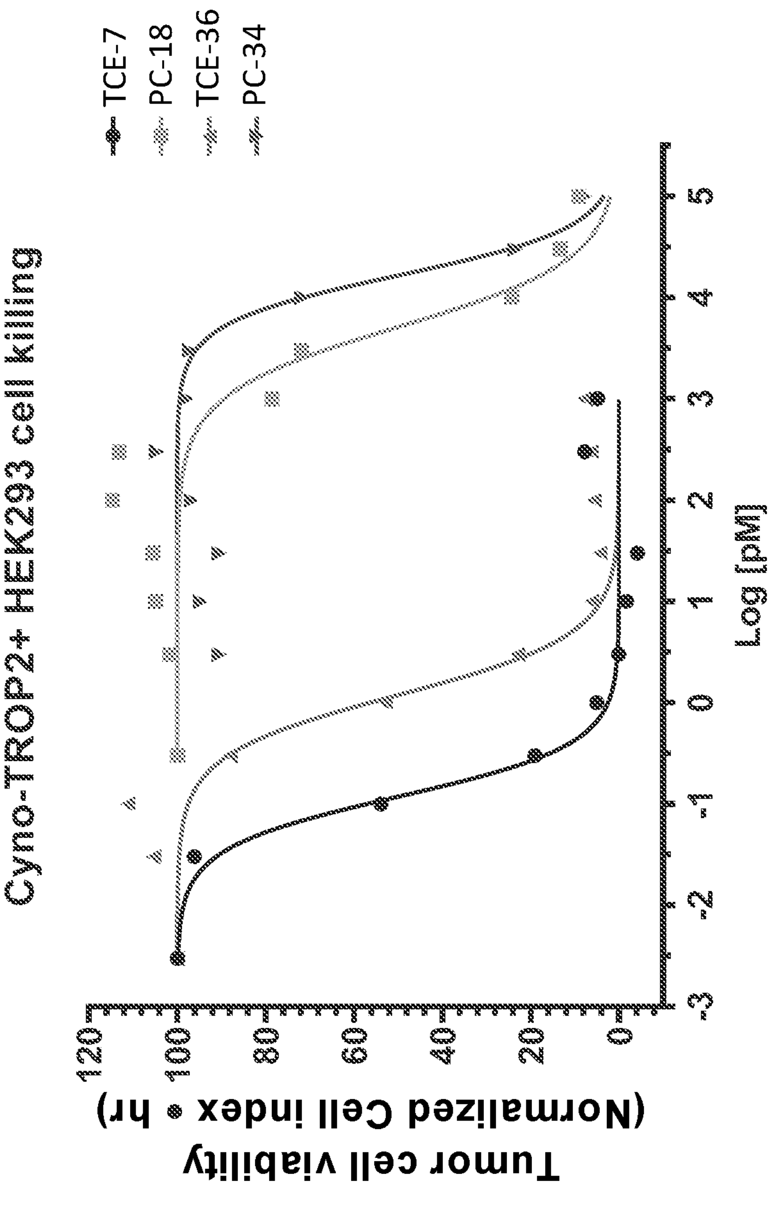
Figure 148:
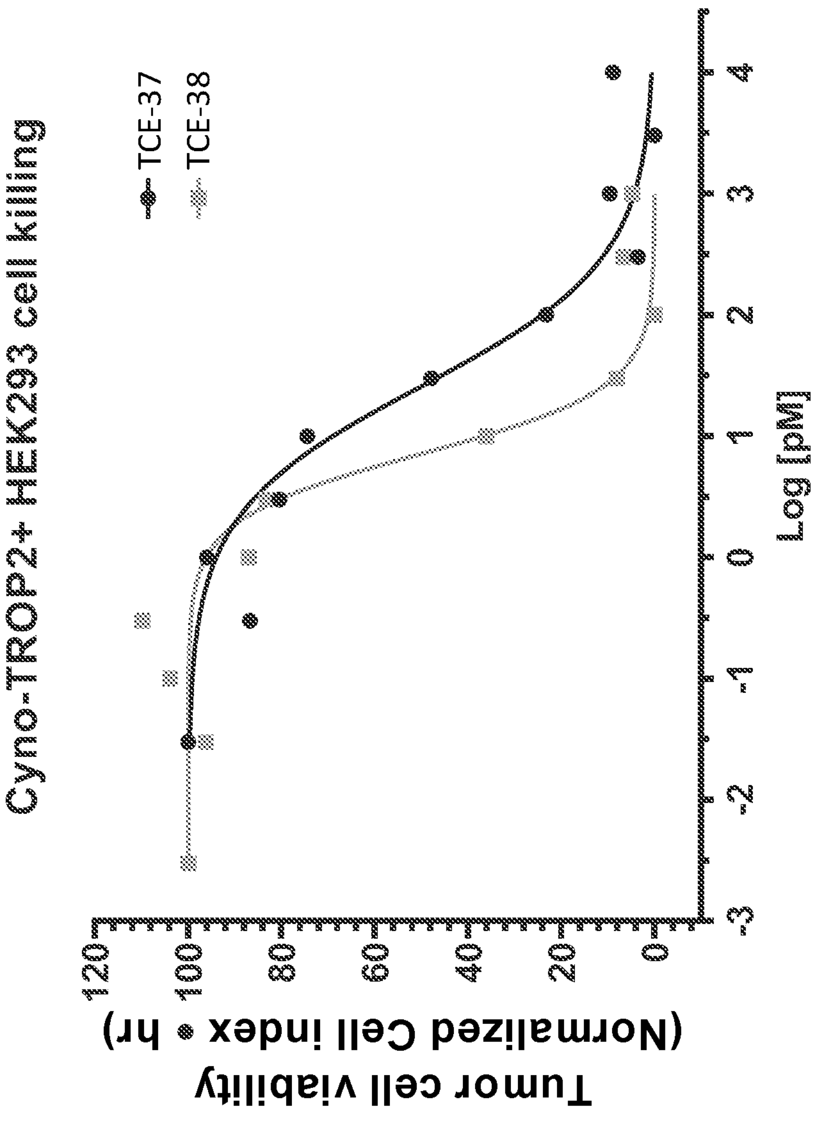
Figure 149:
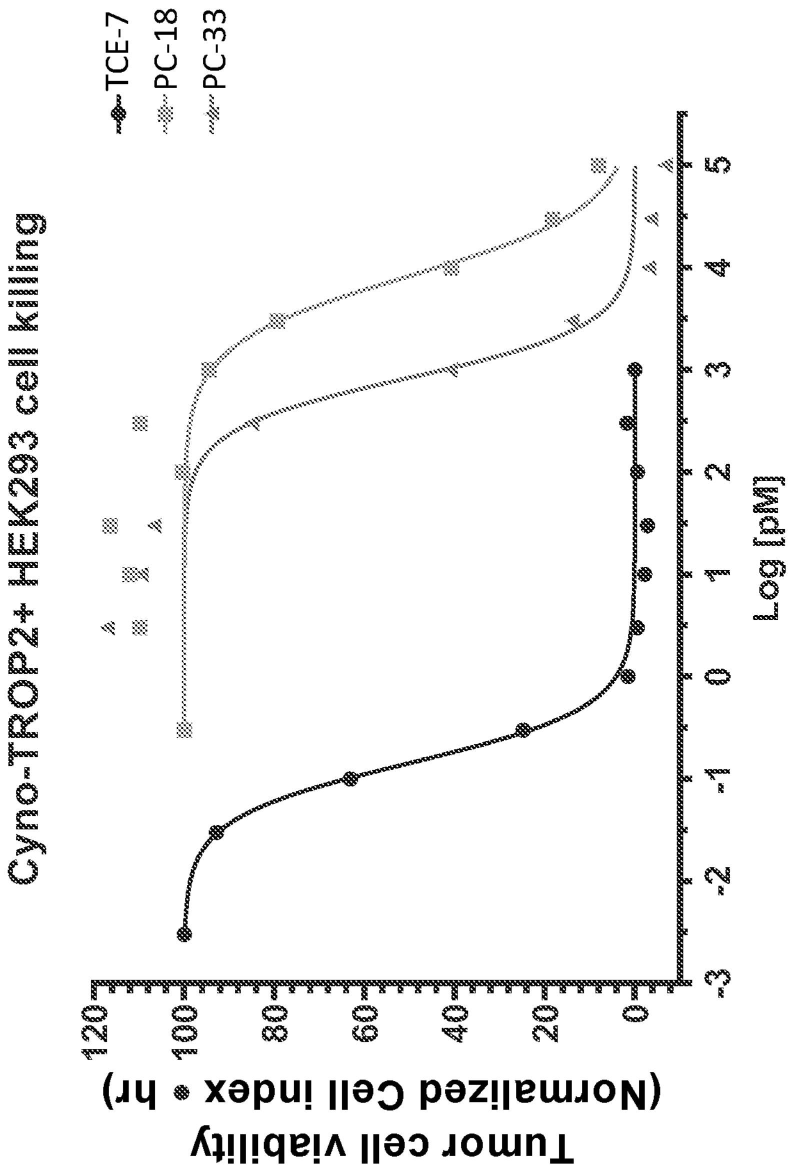
Figure 150:
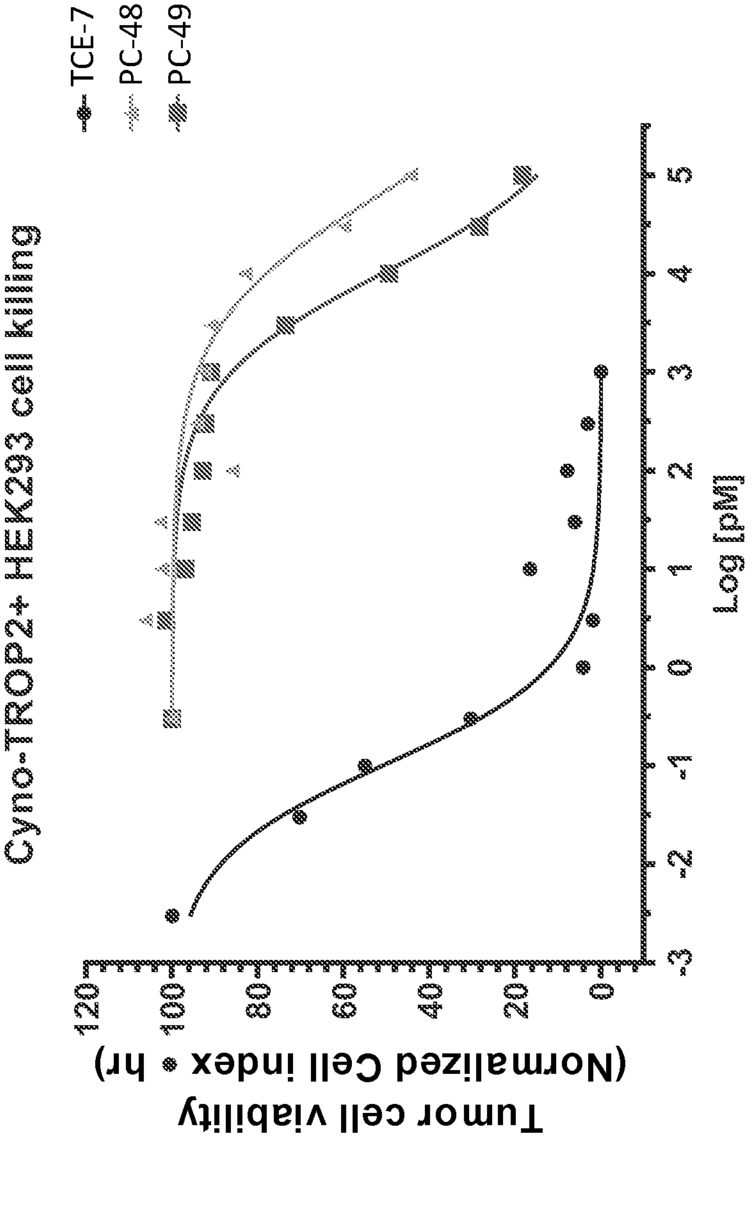
Figure 151:
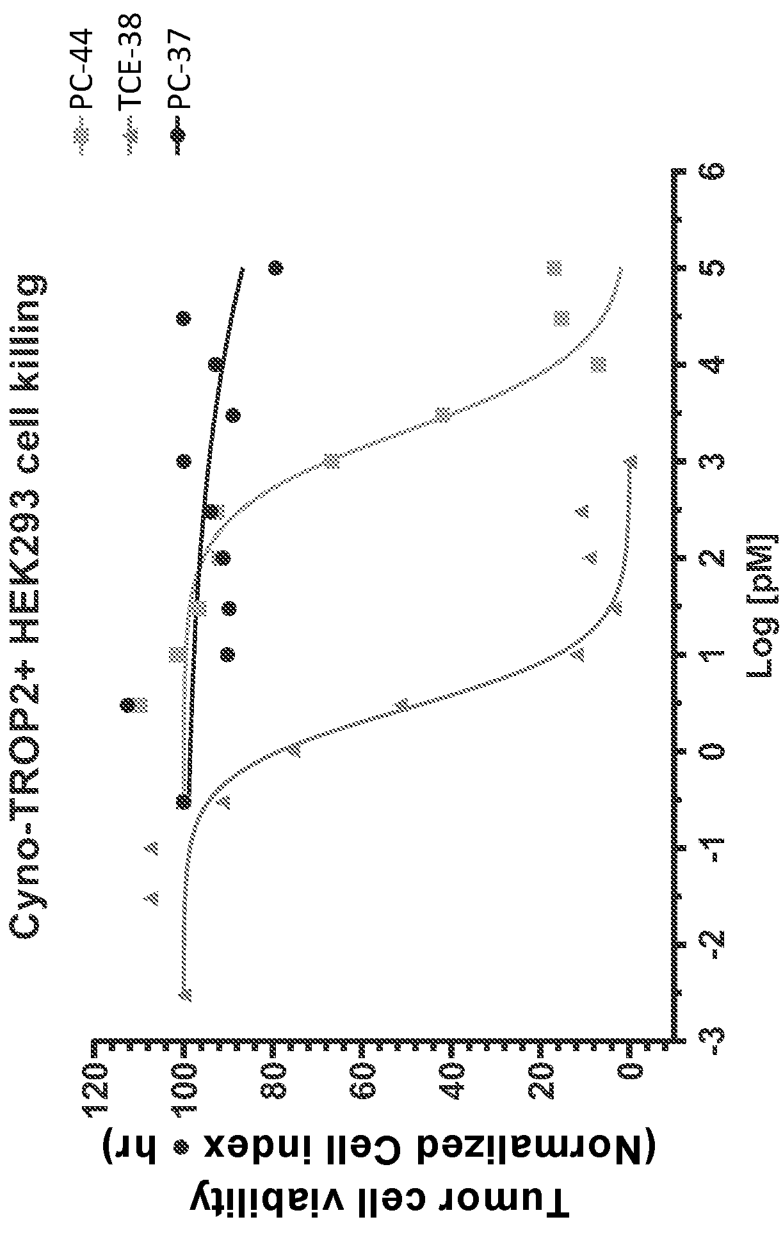
Figure 152:
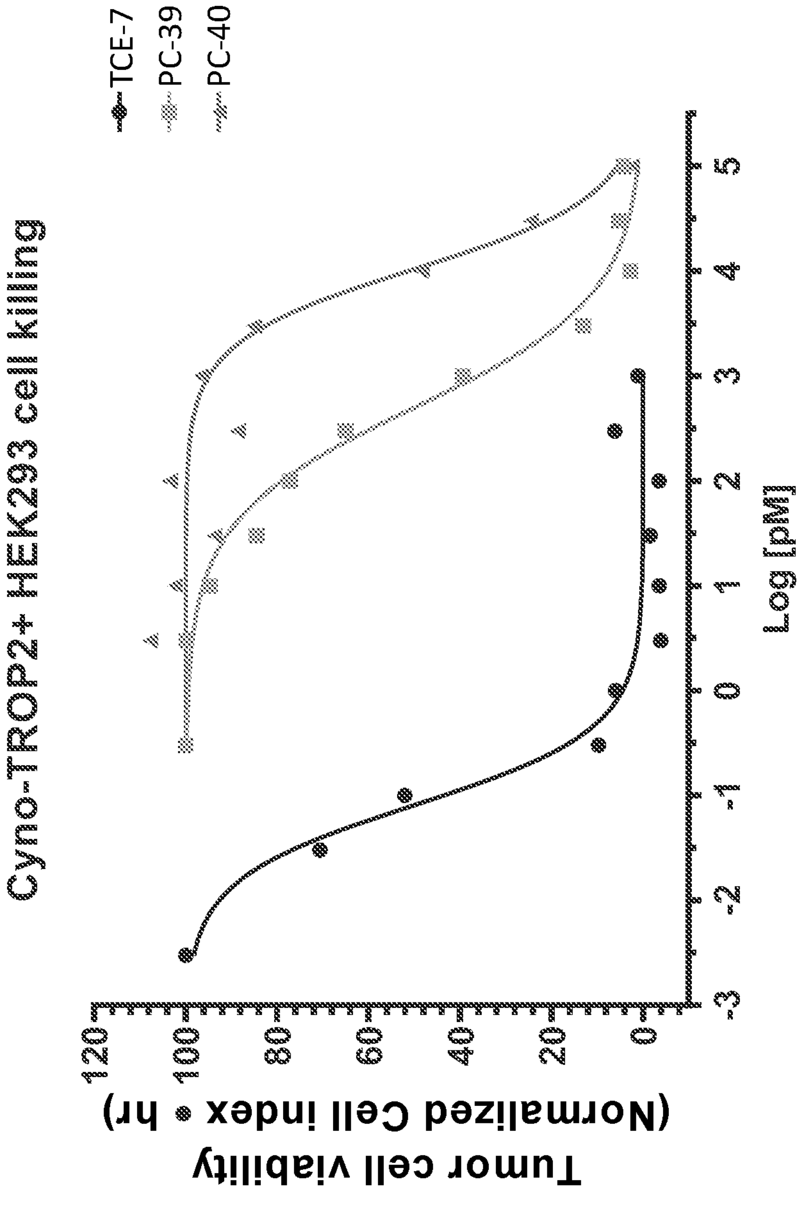
Figure 153:
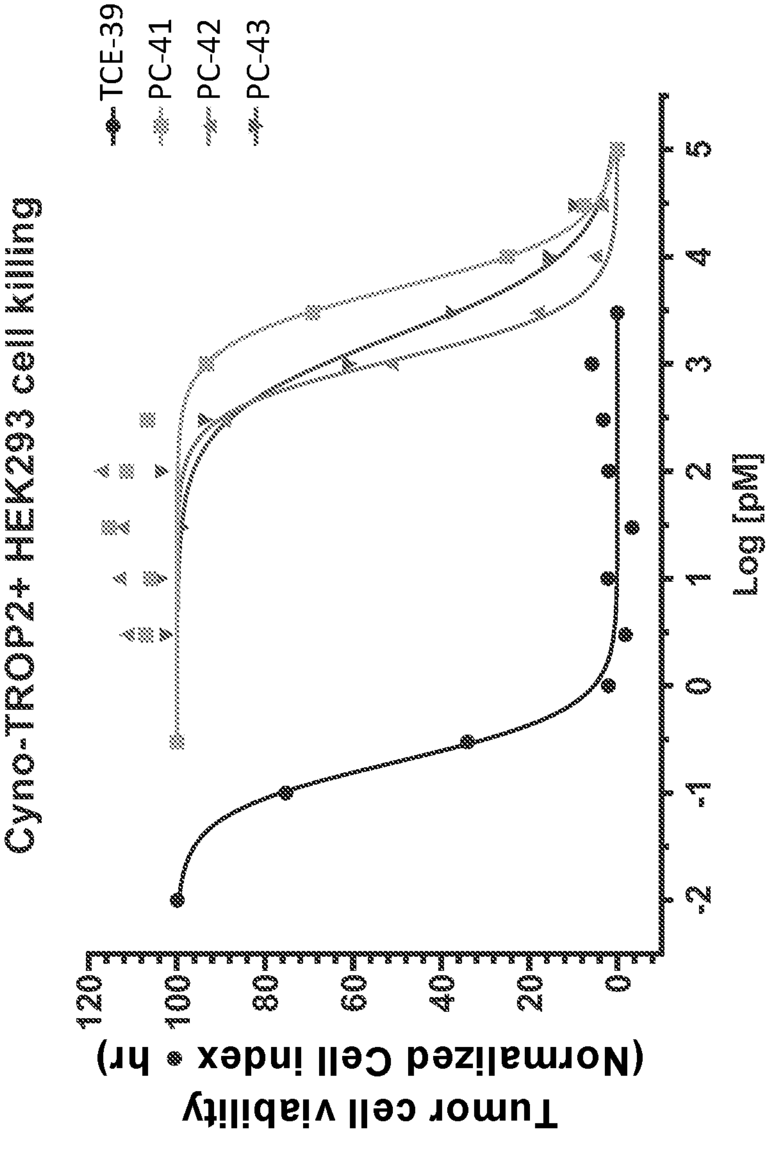
Figure 154:
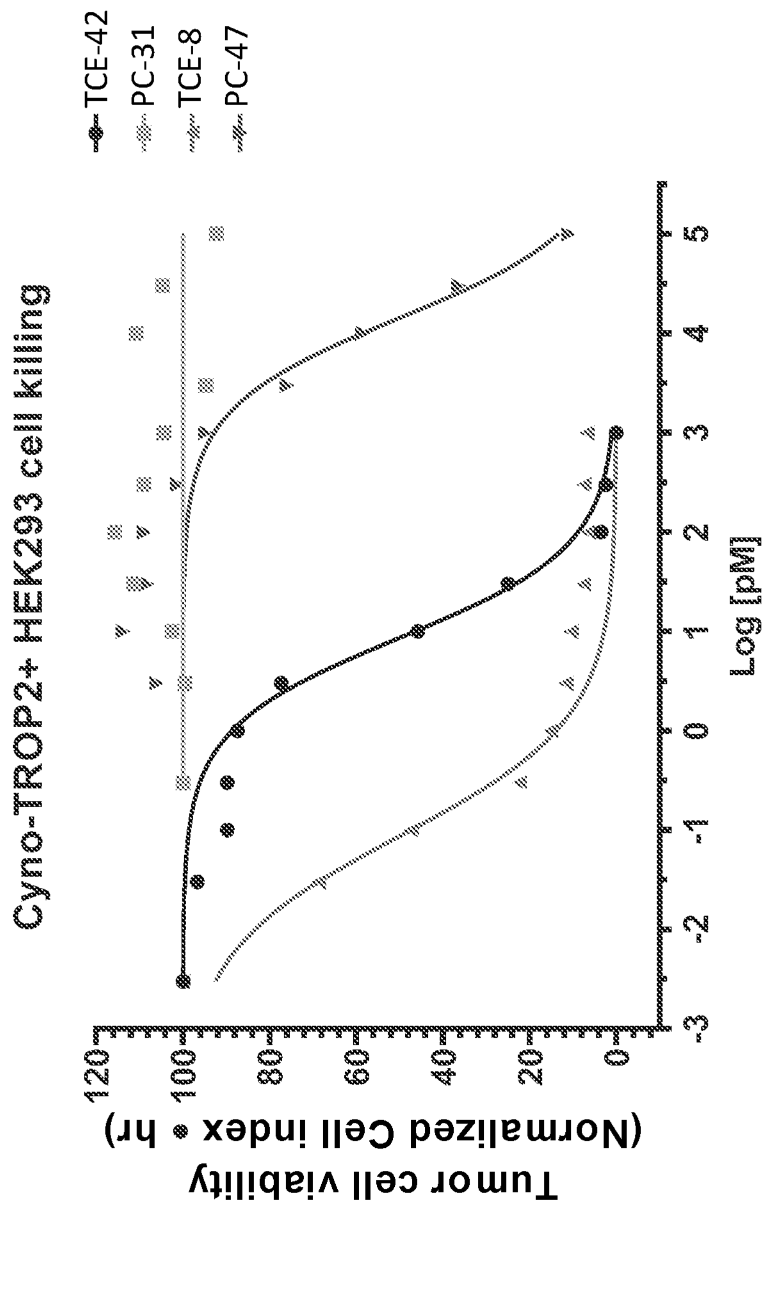
Figure 155:
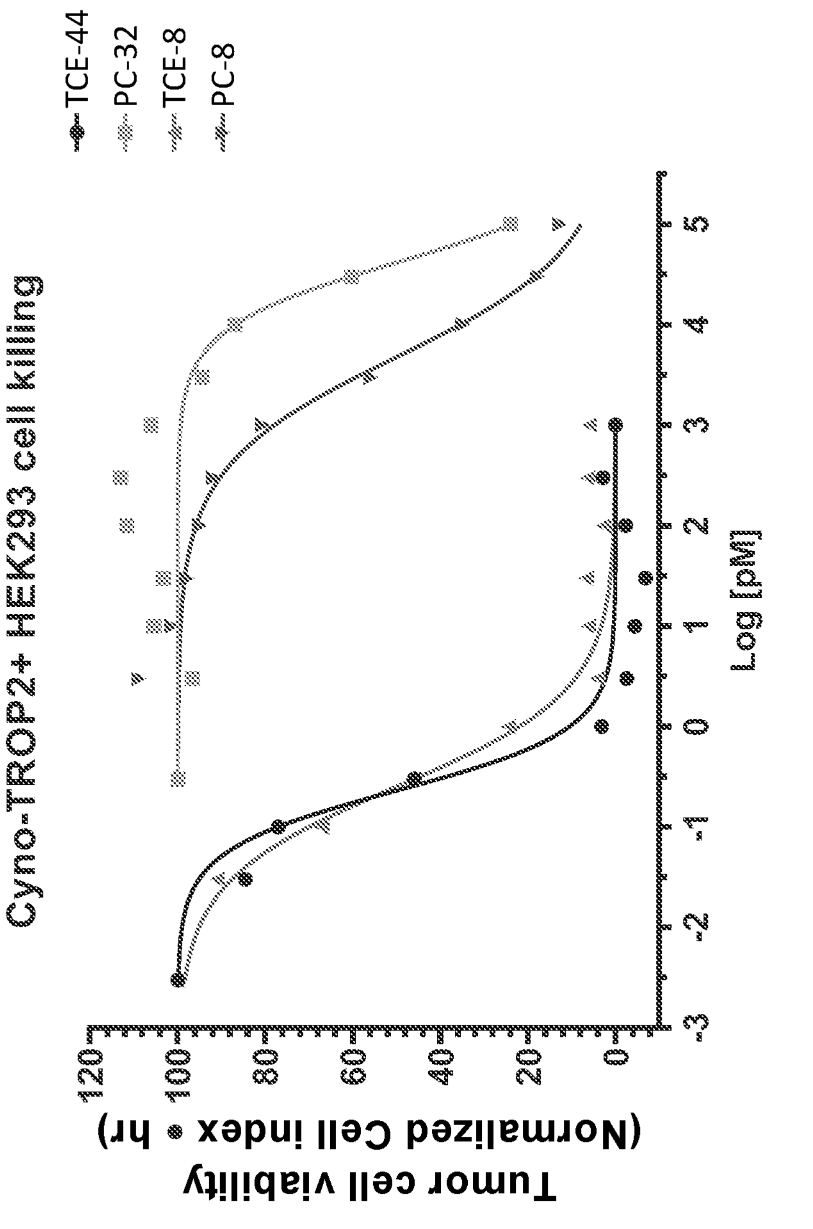
Figure 156:
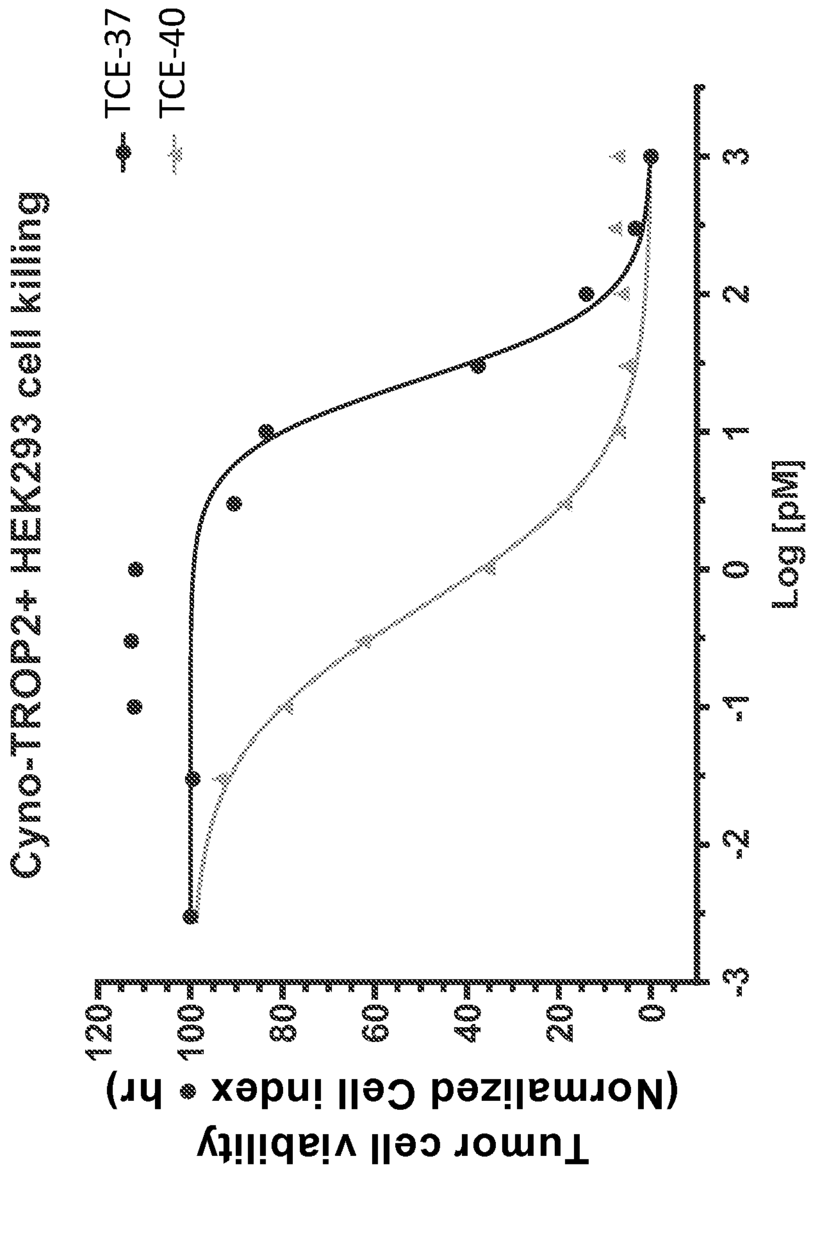
Figure 157:
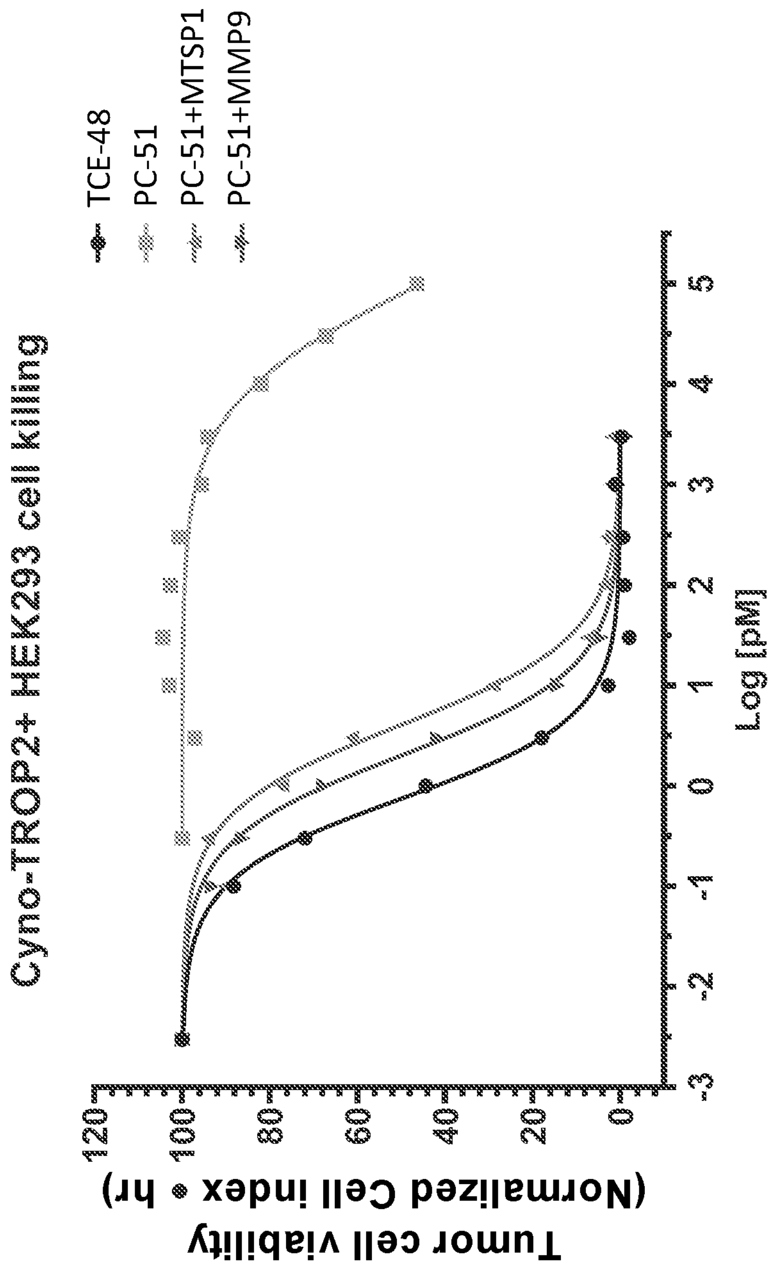
Figure 158:
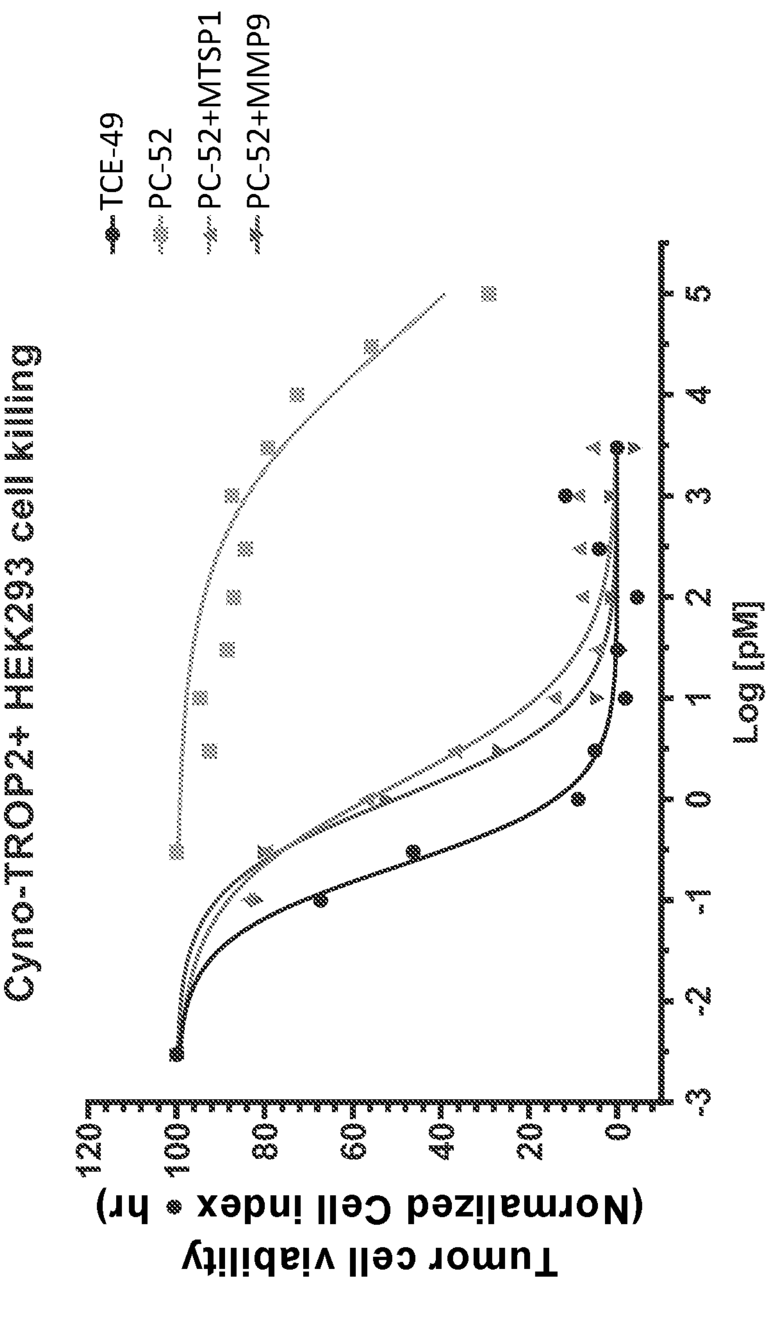
Figure 159:
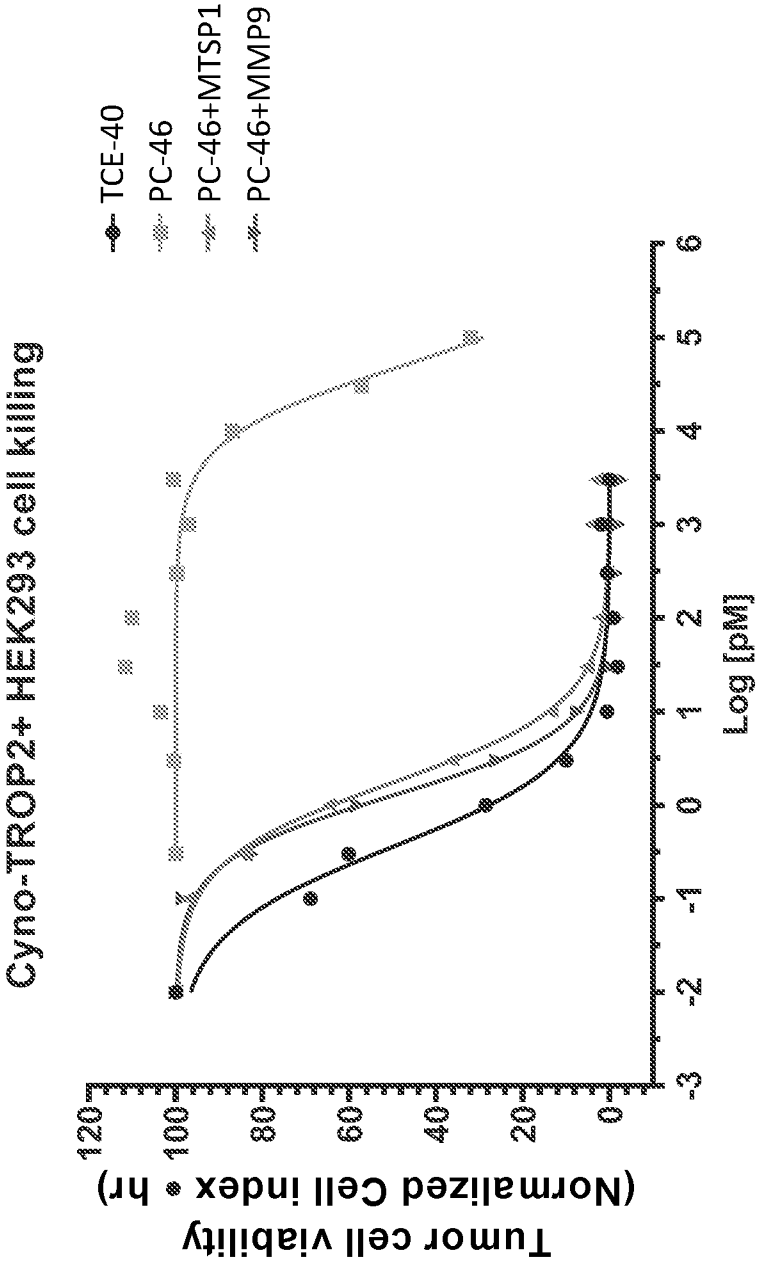
Figure 160:
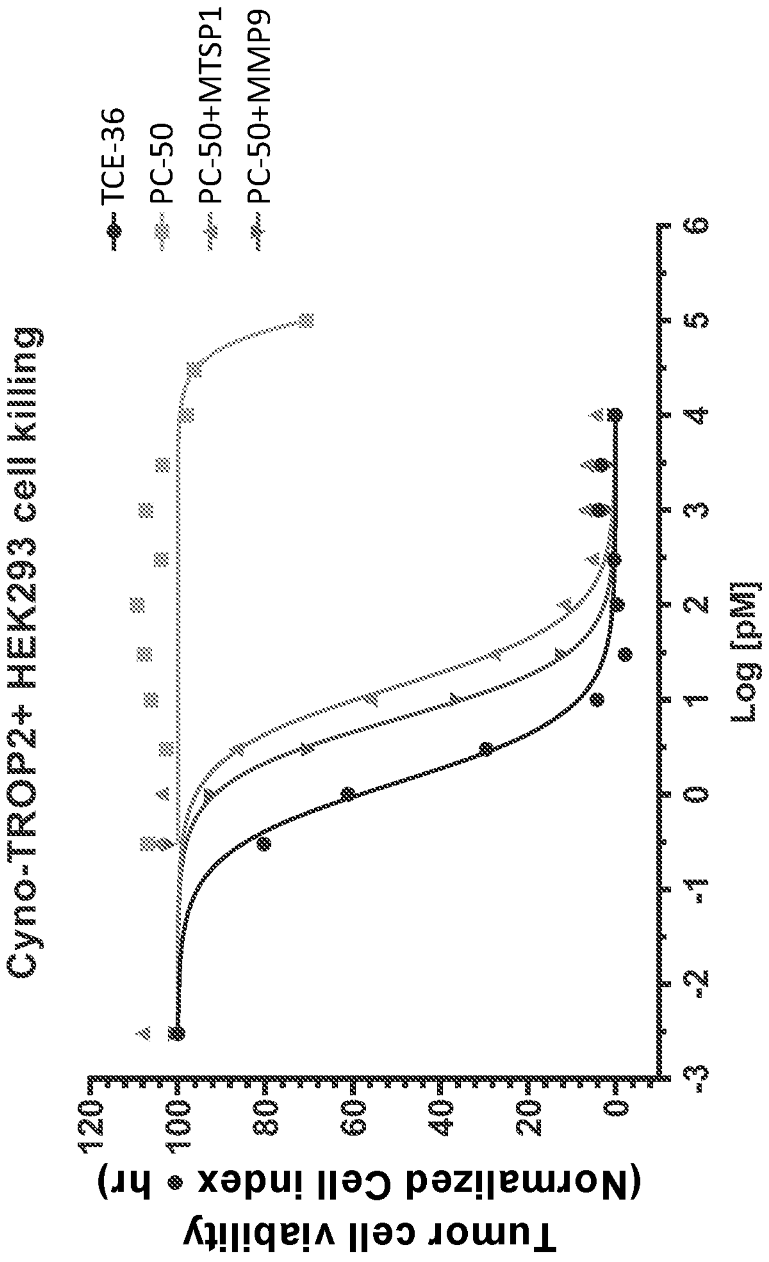
Figure 161:
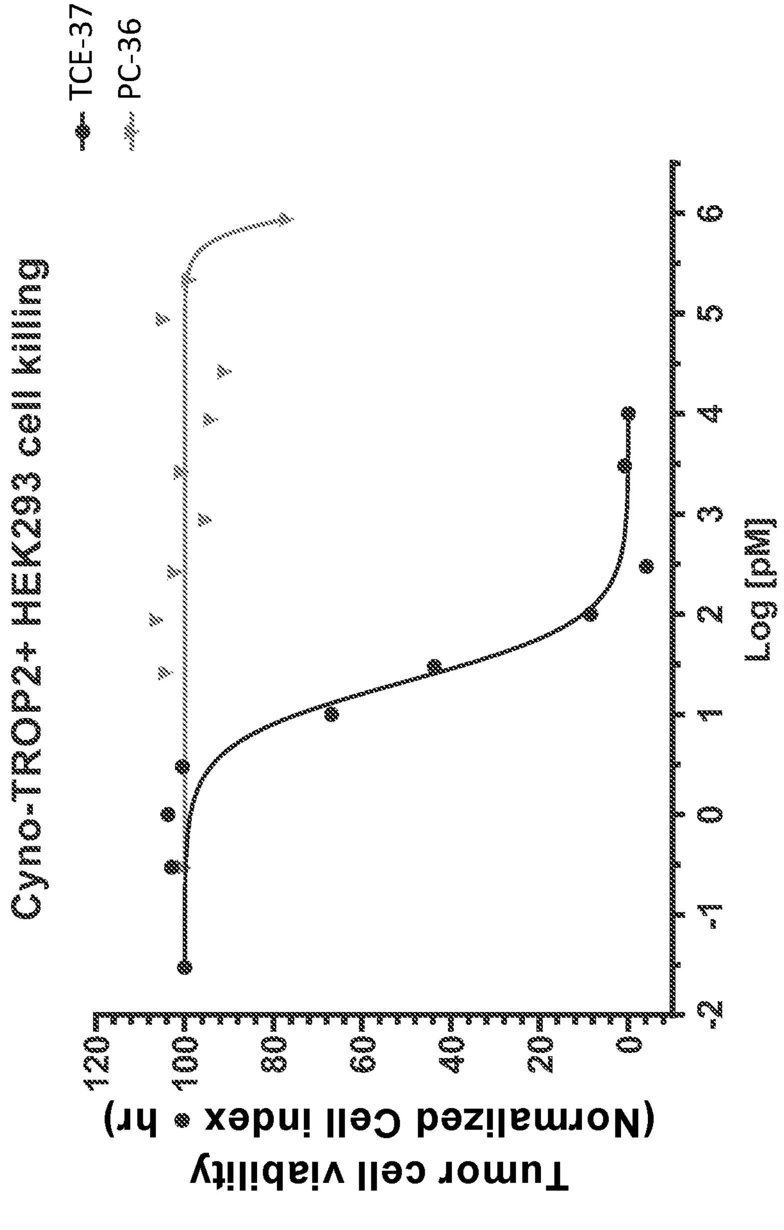
Figure 162:
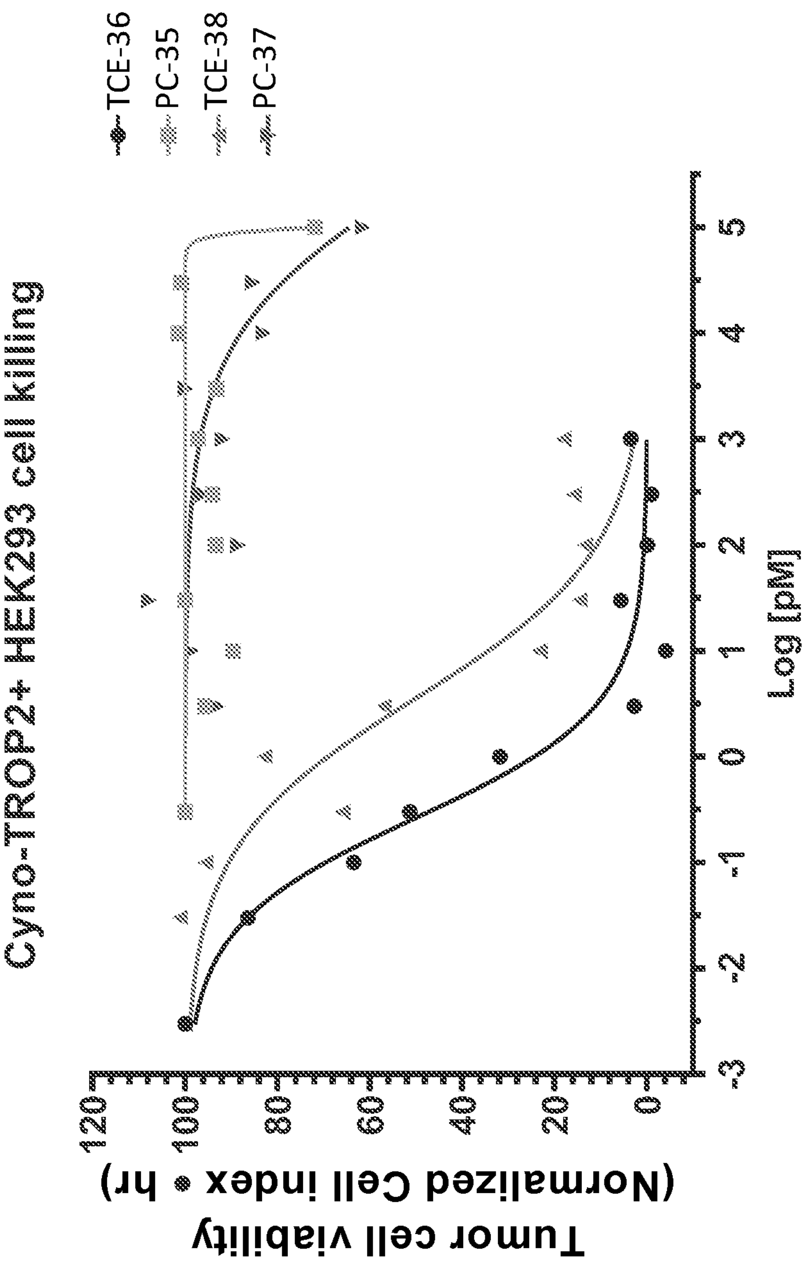

Inhibition curves for peptide-73 inhibition of TROP2 TCE binding to CD3 are provided in FIGS. 103A-103C. The mutated TROP2 TCEs of FIGS. 103A-103C have alanine mutations in the CD3 binding domain. The $IC_{50}$s calculated from the binding curves of FIGS. 103A-103C are provided in Table 42.

TABLE 42

| IC50s for Peptide-73 Inhibition of CD3 Binding to TROP2-TCEs | |
|---|---|
| TROP2-TCE Construct | $IC_{50}$ (μM) |
| TCE-1 | 0.14 |
| TCE-9 | 0.16 |
| TCE-10 | >3 |
| TCE-11 | 1.22 |
| TCE-12 | 0.23 |
| TCE-13 | 0.82 |
| TCE-14 | 0.07 |
| TCE-15 | 0.31 |
| TCE-16 | 0.05 |
| TCE-17 | 0.10 |
| TCE-18 | 0.11 |
| TCE-19 | 0.42 |
| TCE-20 | >3 |

TABLE 42-continued

| IC50s for Peptide-73 Inhibition of CD3 Binding to TROP2-TCEs | |
|---|---|
| TROP2-TCE Construct | $IC_{50}$ (μM) |
| TCE-22 | >3 |
| TCE-23 | >3 |
| TCE-24 | 0.23 |
| TCE-25 | 0.65 |
| TCE-26 | >3 |
| TCE-27 | 0.62 |
| TCE-28 | 0.10 |
| TCE-29 | 0.23 |
| TCE-30 | 0.14 |
| TCE-31 | >3 |
| TCE-32 | 0.06 |
| TCE-33 | 1.9 |
| TCE-34 | 0.02 |
| TCE-35 | 0.58 |

FIGS. 104-109 show inhibition curves for peptide-73, peptide-70, peptide-76, and peptide-77 inhibition of TROP2 TCEs (having an F108A mutation in the TROP2 binding domain and either a wild-type or alanine mutated CD3 binding domain) binding to CD3. $IC_{50}$s calculated from the inhibition curves are provided in Table 43.

TABLE 43

| IC50s for Peptide Inhibition of CD3 Binding to TROP2-TCEs | | | | | | |
|---|---|---|---|---|---|---|
| Peptide | TCE-7 $IC_{50}$ (μM) | TCE-39 $IC_{50}$ (μM) | TCE-40 $IC_{50}$ (μM) | TCE-36 $IC_{50}$ (μM) | TCE-37 $IC_{50}$ (μM) | TCE-38 $IC_{50}$ (μM) |
| Peptide-73 | 0.06 | 0.04 | 0.55 | 1.63 | 0.01 | 4.62 |
| Peptide-70 | 0.01 | 0.01 | 0.01 | 0.08 | 0.01 | 0.14 |
| Peptide-76 | 17.49 | 2.79 | 11.96 | >100 | 0.95 | >100 |
| Peptide-77 | >100 | >100 | >100 | >100 | 8.87 | >100 |

Example 22: Binding to TROP2 and CD3 by TROP2 TCEs and PCs Via ELISA

TROP2 TCEs and masked polypeptide complexes (PCs) were evaluated for their ability to bind TROP2 and CD3 by ELISA. Briefly, biotinylated CD3 or biotinylated TROP2 was captured on neutravidin coated plates. The TCE or PC constructs diluted in buffer were then added to the antigen coated plates. Binding was measured using a standard horse radish peroxidase secondary antibody. The concentration of TCE or PC required to achieve 50% maximal signal ($EC_{50}$) was calculated. Tables 44-46 provide $EC_{50}$s for TROP2 and CD3 binding by TCEs and PCs having alanine mutations in the TROP2 binding domain (D109A or F108A) and either a wild-type or alanine mutated CD3 binding domain. Binding curves for TROP2 and CD3 binding by mutated TCEs and PCs are shown in FIGS. 110-125.

TABLE 44

$EC_{50}$s for TROP2 and CD3 Binding by Mutated TCEs and PCs

| TROP2 Fab Mutation | Anti-CD3 scFV Mutation | Construct Description | TROP2 ELISA $EC_{50}$ (nM) | CD3 ELISA $EC_{50}$ (nM) |
|---|---|---|---|---|
| D109A | wild-type | TCE-8 | 1.31 | 0.40 |
| D109A | F104A | TCE-42 | 0.99 | 0.96 |
| D109A | F104A | PC-31 | 694 | 1077 |
| D109A | N30Q, I109V, G172A, V231A | TCE-44 | 1.48 | 0.56 |

TABLE 45

$EC_{50}$s for TROP2 and CD3 Binding by Mutated TCEs and PCs

| TROP2 Fab Mutation | Anti-CD3 scFV Mutation | Construct Description | TROP2 ELISA $EC_{50}$ (nM) | CD3 ELISA $EC_{50}$ (nM) |
|---|---|---|---|---|
| F108A | wild-type | TCE-7 | 1.46 | 0.38 |
| F108A | H101A | TCE-36 | 1.49 | 0.43 |
| F108A | F104A | TCE-37 | 1.41 | 1.25 |
| F108A | F240A | TCE-38 | 0.80 | 0.75 |
| F108A | P41S, A49G, N87S, L150F, T151S, G163R, P175A, K181T, T200V, A202D, L208I, G211N, L217I, S218T, V220A, P222A, E223D, A226S, E227D | TCE-39 | 5.92 | 0.43 |
| F108A | N30Q, I109V, G172A, V231A | TCE-40 | 1.60 | 0.47 |
| F108A | L232A | TCE-48 | 1.68 | 0.44 |
| F108A | N236A | TCE-49 | 1.41 | 0.42 |

TABLE 46

$EC_{50}$s for TROP2 and CD3 Binding by Mutated PCs

| TROP2 Fab Mutation | Anti-CD3 scFV Mutation | Construct Description | TROP2 ELISA $EC_{50}$ (nM) | CD3 ELISA $EC_{50}$ (nM) |
|---|---|---|---|---|
| F108A | wild-type | PC-18 | 957 | 620 |
| F108A | wild-type | PC-33 | 574 | 53 |
| F108A | wild-type | PC-48 | 3963 | 729 |
| F108A | wild-type | PC-49 | 1359 | 625 |
| F108A | H101A | PC-34 | 828 | 283 |
| F108A | H101A | PC-50 | 1223 | 454 |
| F108A | H101A | PC-35 | 2082 | 30 |
| F108A | F104A | PC-36 | 1473 | 2921 |
| F108A | F240A | PC-37 | 1513 | 1297 |
| F108A | F240A | PC-38 | 3025 | 77.6 |
| F108A | P41S, A49G, N87S, L150F, T151S, G163R, P175A, K181T, T200V, A202D, L208I, G211N, L217I, S218T, V220A, P222A, E223D, A226S, E227D | PC-39 | 1087 | 135.7 |

TABLE 46-continued $EC_{50}$s for TROP2 and CD3 Binding by Mutated PCs

| TROP2 Fab Mutation | Anti-CD3 scFV Mutation | Construct Description | TROP2 ELISA $EC_{50}$ (nM) | CD3 ELISA $EC_{50}$ (nM) |
|---|---|---|---|---|
| F108A | P41S, A49G, N87S, L150F, T151S, G163R, P175A, K181T, T200V, A202D, L208I, G211N, L217I, S218T, V220A, P222A, E223D, A226S, E227D | PC-40 | 3511 | 124.3 |
| F108A | P41S, A49G, N87S, L150F, T151S, G163R, P175A, K181T, T200V, A202D, L208I, G211N, L217I, S218T, V220A, P222A, E223D, A226S, E227D | PC-41 | 1377 | 230.1 |
| F108A | P41S, A49G, N87S, L150F, T151S, G163R, P175A, K181T, T200V, A202D, L208I, G211N, L217I, S218T, V220A, P222A, E223D, A226S, E227D | PC-42 | 630 | 60.2 |
| F108A | P41S, A49G, N87S, L150F, T151S, G163R, P175A, K181T, T200V, A202D, L208I, G211N, L217I, S218T, V220A, P222A, E223D, A226S, E227D | PC-43 | 587 | 60.7 |
| F108A | N30Q, I109V, G172A, V231A | PC-44 | 1141 | 77.3 |
| F108A | N30Q, I109V, G172A, V231A | PC-45 | 4010 | 97.04 |
| F108A | N30Q, I109V, G172A, V231A | PC-46 | 2547 | 555.5 |
| F108A | L232A | PC-51 | 1160 | 409.8 |
| F108A | N236A | PC-52 | 1212 | 241.7 |

Example 23: Cytotoxic Activity of TROP2 TCEs and Masked PCs

TROP2 TCEs and masked PCs were evaluated in a functional in vitro tumor cell killing assay using TROP2 positive tumor cell lines HCT116 or H292 or cynomolgus TROP2 expressing HEK293 (CyTROP2 HEK293) cells. These studies looked at the cytotoxicity of TROP2 TCEs and masked PCs with mutated CD3 binding domains relative to wild-type CD3 binding domains. Tumor cell killing was measured and $EC_{50}$s were calculated as described above in Examples 8-9. $EC_{50}$s for tumor cell killing with various TCEs and PCs of the present disclosure are provided in Tables 47-50. The mutations in the TROP2 Fab and the anti-CD3 scFv for each TCE and PC are listed in the Tables. FIGS. 126-129 show data plots of tumor cell viability vs. TCE or PC concentration in HCT116 cells. FIGS. 130-146 show data plots of tumor cell viability vs. TCE or PC concentration in H292 cells. FIGS. 147-162 show data plots of tumor cell viability vs. TCE or PC concentration in CyTROP2 HEK293 cells. PCs were treated with membrane type serine protease 1 (MTSP1) or matrix metalloprotease 9 (MMP9) where indicated. As can be seen, the masked PCs exhibit weaker cytotoxicities than their corresponding unmasked TCEs with the same TROP2 Fab and/or anti-CD3 scFv mutations. Protease treatment (mask cleavage) of the PCs increased their cytotoxic efficiencies (see, for example, FIG. 144 and FIGS. 157-160).

TABLE 47

Cytotoxicity $EC_{50}$s in HCT116, H292, and CyTROP2 Cells (D109A TROP2 Fab) mutations)

| TROP2 Fab mutation | Anti-CD3 scFv mutation | Construct Description | HCT116 Cytotoxicity $EC_{50}$ (pM) | H292 Cytotoxicity $EC_{50}$ (pM) | CyTROP2 HEK293 $EC_{50}$ (pM) |
|---|---|---|---|---|---|
| D109A | wild-type | TCE-8 | 83 | 0.9 | 0.1 |
| D109A | F104A | TCE-42 | | 268.9 | 14.8 |
| D109A | N30Q, I109V, G172A, V231A | TCE-44 | | 3.0 | 0.3 |

TABLE 48

Cytotoxicity $EC_{50}$s in HCT116, H292, and CyTROP2 Cells (D109A TROP2 Fab)

| TROP2 Fab mutation | Anti-CD3 scFv mutation | Construct Description | HCT116 Cytotoxicity $EC_{50}$ (pM) | H292 Cytotoxicity $EC_{50}$ (pM) | CyTROP2 HEK293 $EC_{50}$ (pM) |
|---|---|---|---|---|---|
| D109A | wild-type | PC-8 | >100,000 | 14,555 | 3,447 |
| D109A | wild-type | PC-47 | | >100,000 | 17,333 |
| D109A | F104A | PC-31 | | >100,000 | >100,000 |
| D109A | N30Q, I109V, G172A, V231A | PC-32 | | 28,113 | 35,914 |

TABLE 49

Cytotoxicity $EC_{50}$s in HCT116, H292, and CyTROP2 Cells (F108A TROP2 Fab)

| TROP2 Fab mutation | Anti-CD3 scFv mutation | Construct Description | HCT116 Cytotoxicity $EC_{50}$ (pM) | H292 Cytotoxicity $EC_{50}$ (pM) | CyTROP2 HEK293 $EC_{50}$ (pM) |
|---|---|---|---|---|---|
| F108A | wild-type | TCE-7 | 112.6 | 4.4 | 0.11 |
| F108A | H101A | TCE-36 | 488.9 | 33.6 | 0.9 |
| F108A | F104A | TCE-37 | | 566.6 | 24.9 |
| F108A | F240A | TCE-38 | >3,000 | 172.0 | 3.6 |
| F108A | P41S, A49G, N87S, L150F, T151S, G163R, P175A, K181T, T200V, A202D, L208I, G211N, L217I, S218T, V220A, P222A, E223D, A226S, E227D | TCE-39 | 73.2 | 2.9 | 0.2 |
| F108A | N30Q, I109V, G172A, V231A | TCE-40 | 225.7 | 11.3 | 0.4 |
| F108A | L232A | TCE-48 | | 7.2 | 0.8 |
| F108A | N236A | TCE-49 | | 3.9 | 0.2 |

TABLE 50

Cytotoxicity $EC_{50}$s in HCT116, H292, and CyTROP2 Cells (F108A TROP2 Fab)

| TROP2 Fab mutation | Anti-CD3 scFv mutation | Construct Description | HCT116 Cytotoxicity $EC_{50}$ (pM) | H292 Cytotoxicity $EC_{50}$ (pM) | CyTROP2 HEK293 $EC_{50}$ (pM) |
|---|---|---|---|---|---|
| F108A | wild-type | PC-18 | >100,000 | >100,000 | 8,249 |
| F108A | wild-type | PC-33 | | 13,240 | 837 |
| F108A | wild-type | PC-48 | >100,000 | >100,000 | 69,887 |
| F108A | wild-type | PC-49 | >100,000 | 67,411 | 10,555 |
| F108A | H101A | PC-50 | | >100,000 | >100,000 |
| F108A | H101A | PC-34 | | >100,000 | 16,485 |
| F108A | H101A | PC-35 | >100,000 | >100,000 | >100,000 |
| F108A | F104A | PC-36 | | >100,000 | >870,000 |
| F108A | F240A | PC-37 | >100,000 | >100,000 | >100,000 |
| F108A | F240A | PC-38 | | >100,000 | |
| F108A | P41S, A49G, N87S, L150F, T151S, G163R, P175A, K181T, T200V, A202D, L208I, G211N, L217I, S218T, V220A, P222A, E223D, A226S, E227D | PC-39 | >100,000 | 13,688 | 665 |
| F108A | P41S, A49G, N87S, L150F, T151S, G163R, P175A, K181T, T200V, A202D, L208I, G211N, L217I, S218T, V220A, P222A, E223D, A226S, E227D | PC-40 | >100,000 | 53,224 | 10,432 |
| F108A | P41S, A49G, N87S, L150F, T151S, G163R, P175A, K181T T200V, A202D, L208I, G211N, L217I, S218T, V220A, P222A, E223D, A226S, E227D | PC-41 | | 46,982 | 5,134 |
| F108A | P41S, A49G, N87S, L150F, T151S, G163R, P175A, K181T, T200V, A202D, L208I, G211N, L217I, S218T, V220A, P222A, E223D, A226S, E227D | PC-42 | | 12,189 | 1,000 |
| F108A | P41S, A49G, N87S, L150F, T151S, G163R, P175A, K181T, T200V, A202D, L208I, G211N, L217I, S218T, V220A, P222A, E223D, A226S, E227D | PC-43 | | 12,698 | 1,224 |
| F108A | N30Q, I109V, G172A, V231A | PC-44 | | 51,035 | 1,679 |
| F108A | N30Q, I109V, G172A, V231A | PC-45 | | >100,000 | |
| F108A | N30Q, I109V, G172A, V231A | PC-46 | | >100,000 | 45,572 |
| F108A | L232A | PC-51 | | >100,000 | 79,289 |
| F108A | N236A | PC-52 | | 98,294 | 37,655 |

Example 24: Non-Human Primate (NHP) Studies of TROP2 TCEs

NHP Toxicity Studies of TCE-7 and TCE-8

Figure 163:
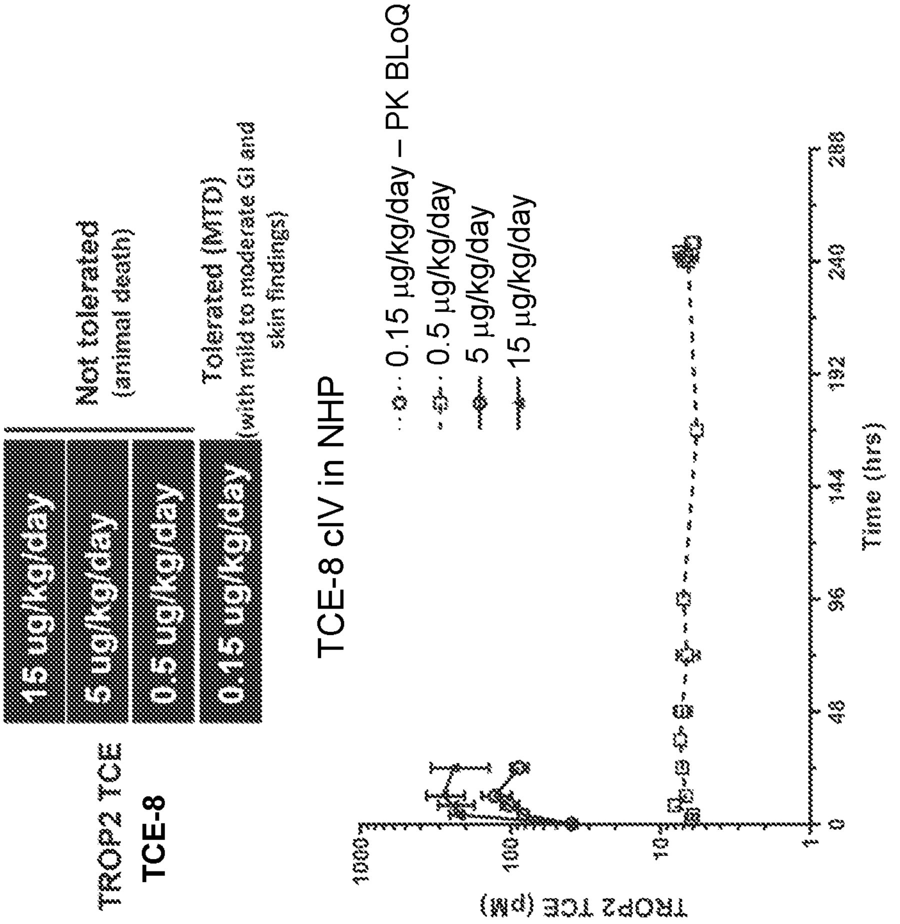
Figure 164:
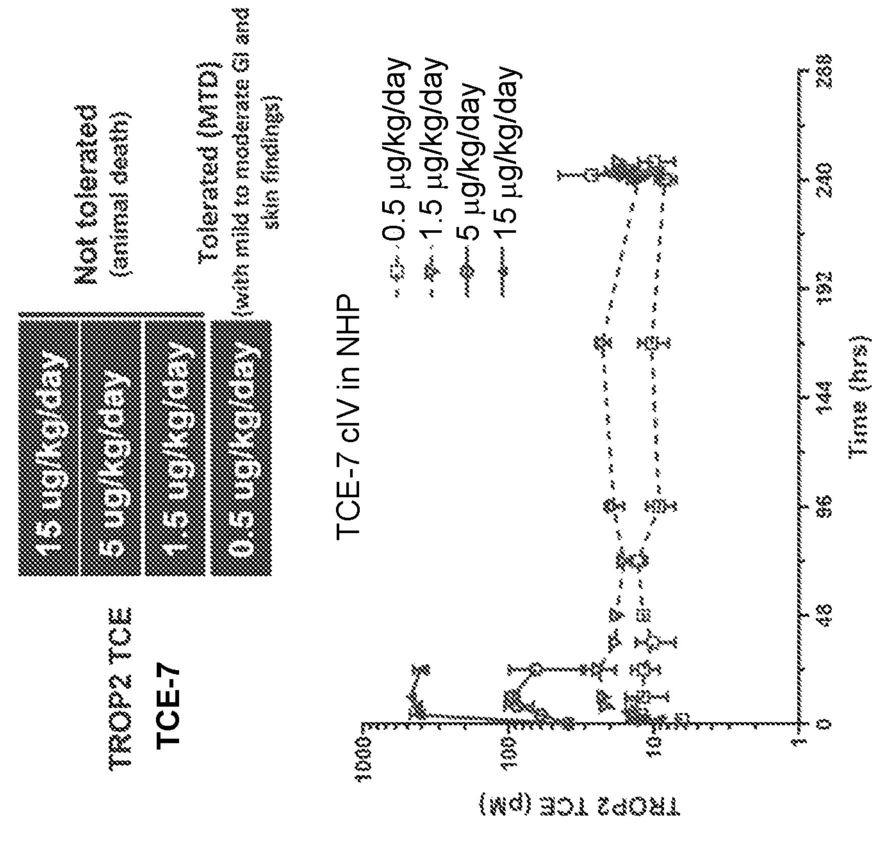

Pharmacokinetics and exploratory safety of TCE-7 (wt anti-CD3, anti-TROP2 F108A mutant) and TCE-8 (wt anti-CD3, anti-TROP2 D109A mutant) were evaluated in cynomolgus monkeys. Briefly, monkeys of approximately 3 kilograms (kg) bodyweight were administered TCEs as a continuous IV (cIV) infusion via a subcutaneous infusion pump. Animals were observed for signs of adverse events. TCE-8 was dosed at 0.15 micrograms/kilogram/day (μg/kg/day), 0.5 μg/kg/day, 5 μg/kg/day, and 15 μg/kg/day. TCE-7 was dosed at 0.5 μg/kg/day, 1.5 μg/kg/day, 5 μg/kg/day, and 15 μg/kg/day. After dosing, blood was collected in K2 EDTA tubes at specific time points and processed to plasma. Plasma was frozen until analysis. Concentrations of TCEs in plasma were measured via a Meso Scale Discovery (MSD) based method relative to a reference standard diluted in control cynomolgus monkey plasma. Pharmacokinetic profiles and toxicity results are shown in FIG. 163 (TCE-8) and FIG. 164 (TCE-7). Both TCE-8 and TCE-7 showed a dose proportional exposure increase. As shown in the figures, the maximum tolerated doses (MTD) for TCE-8 and TCE-7 were 0.15 μg/kg/day and 0.5 μg/kg/day, respectively. Mild to moderate gastrointestinal (GI) and skin findings were observed at these doses.

Cytokine Induction in NHPs with TCE-7 and TCE-8

Figure 165:
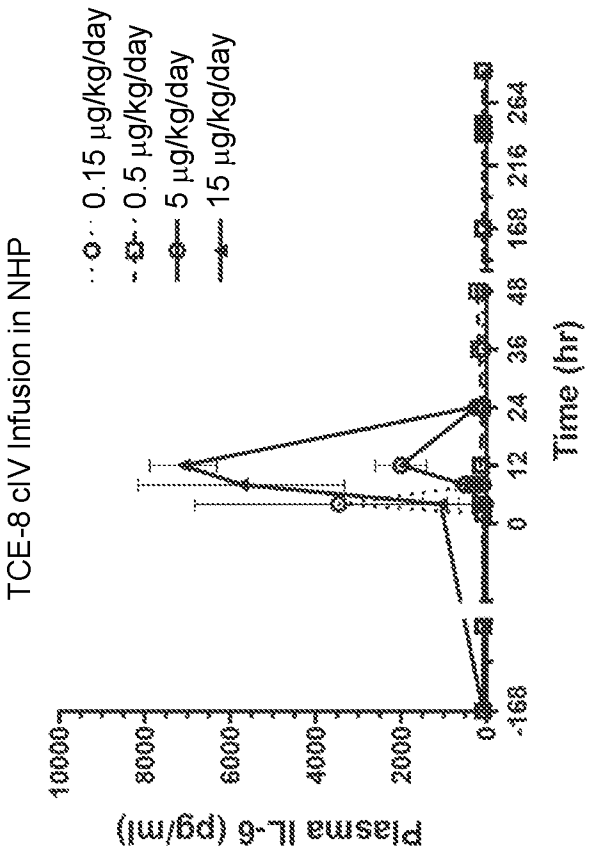
Figure 166:
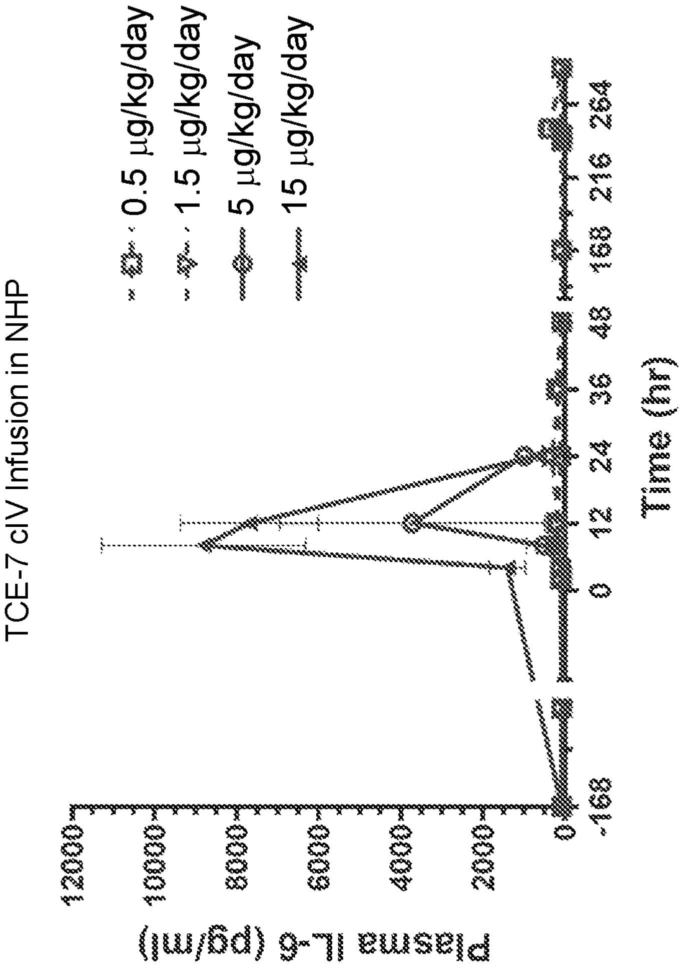
Figure 167B:
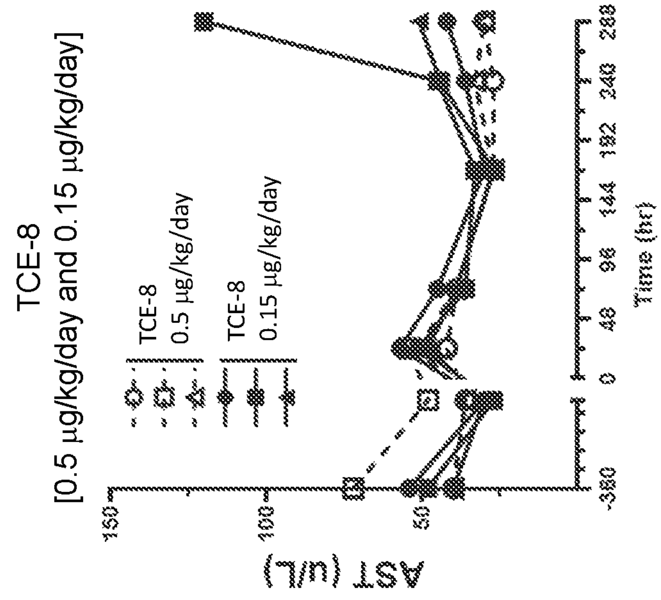
Figure 167A:
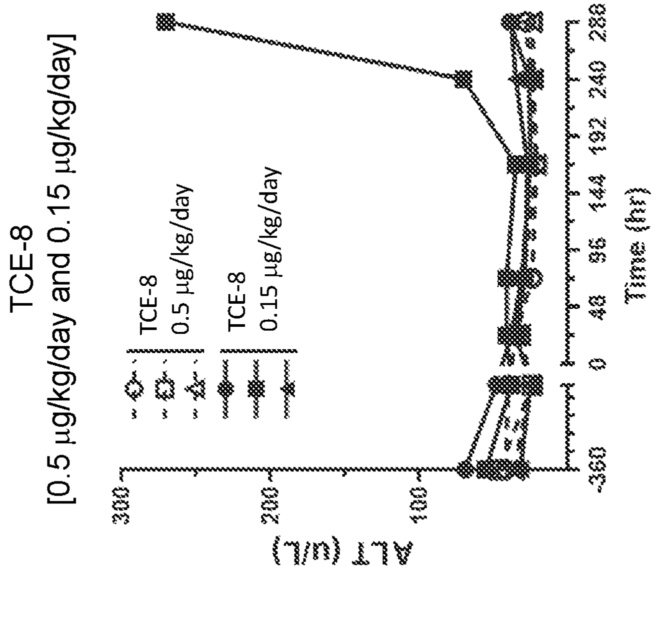
Figure 167D:
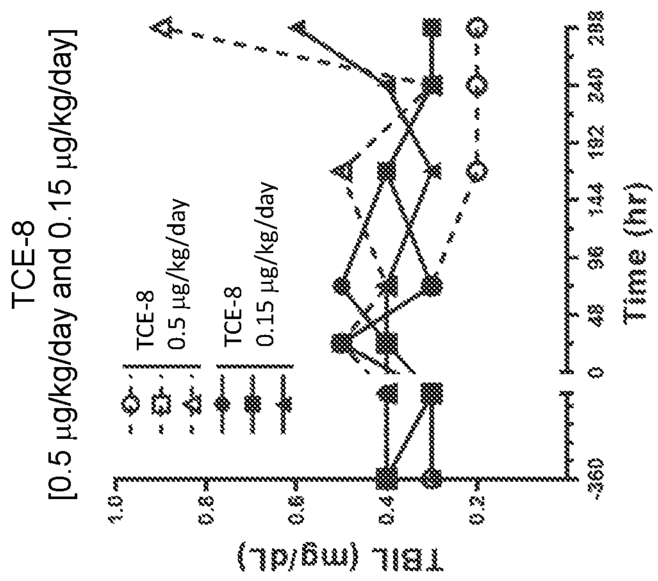
Figure 167C:
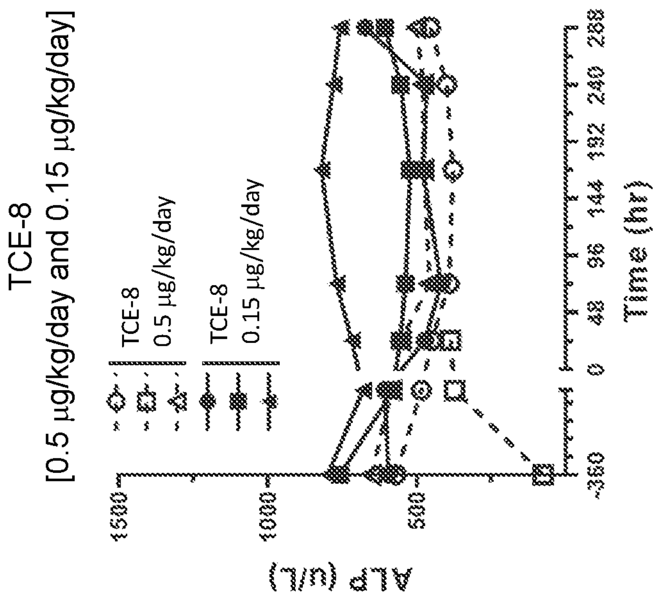
Figure 167E:
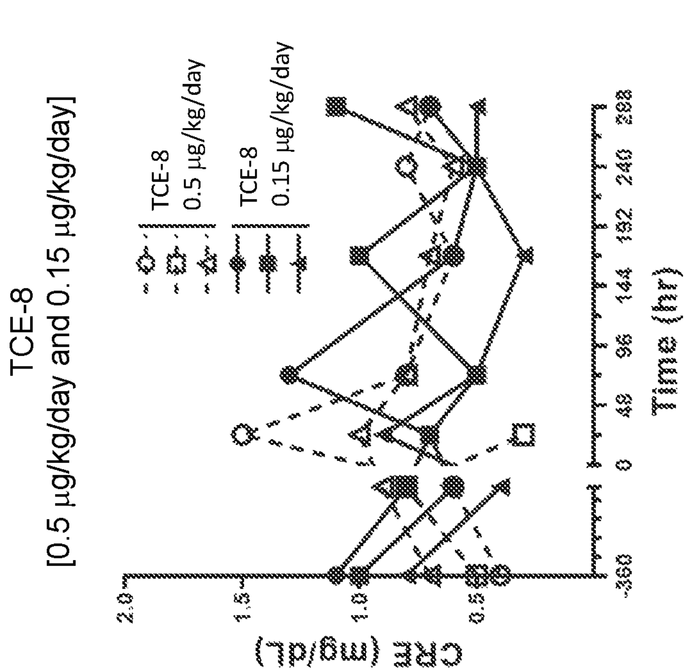
Figure 167F:
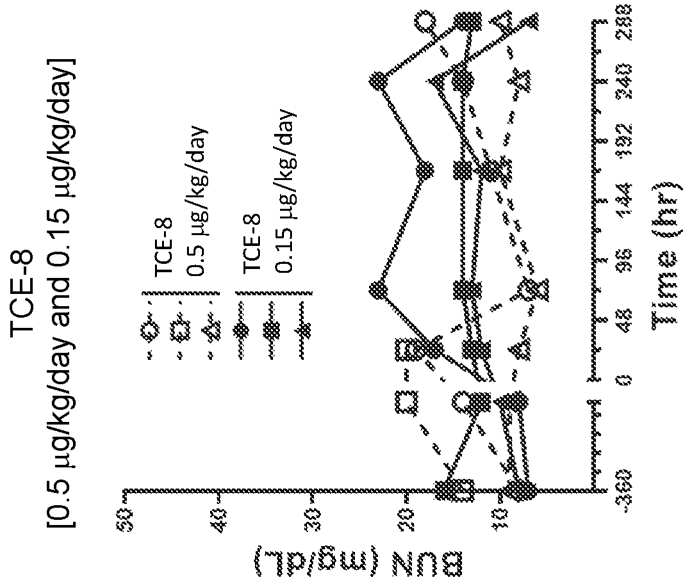
Figure 168B:
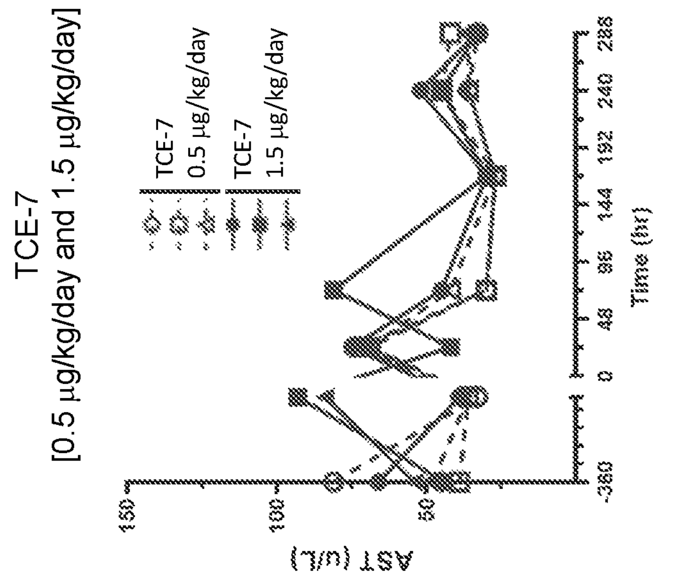
Figure 168A:
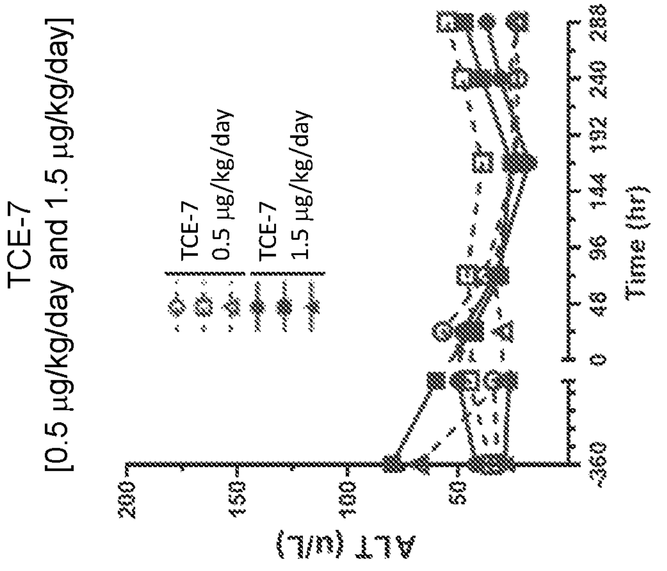
Figure 168C:
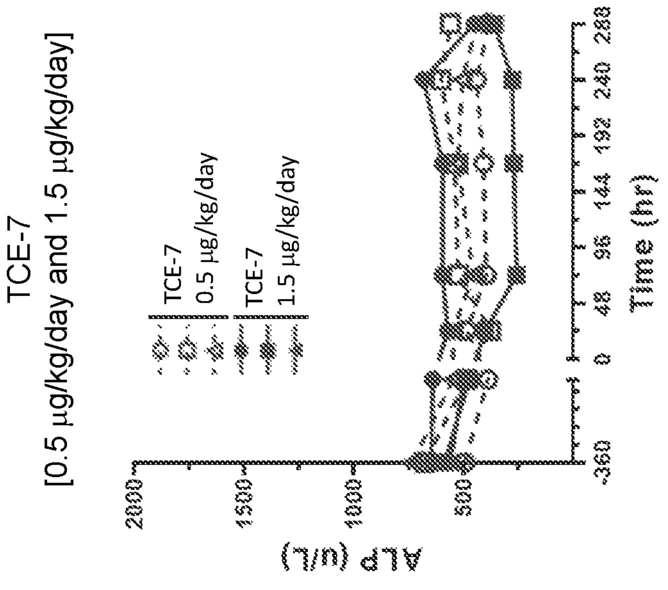
Figure 168D:
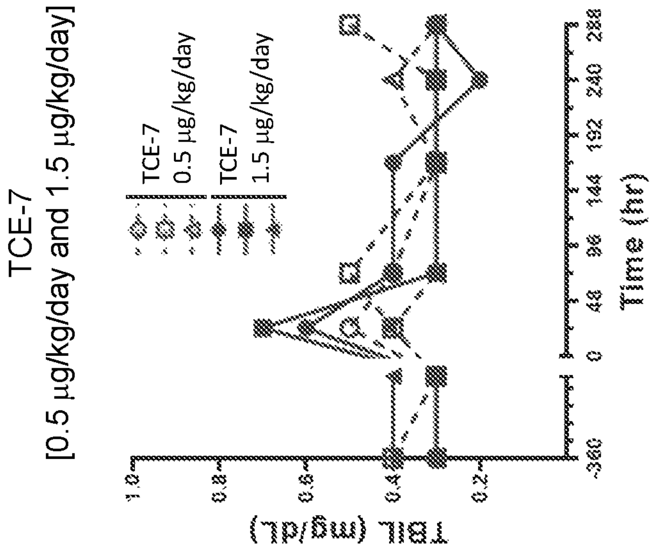
Figure 168E:
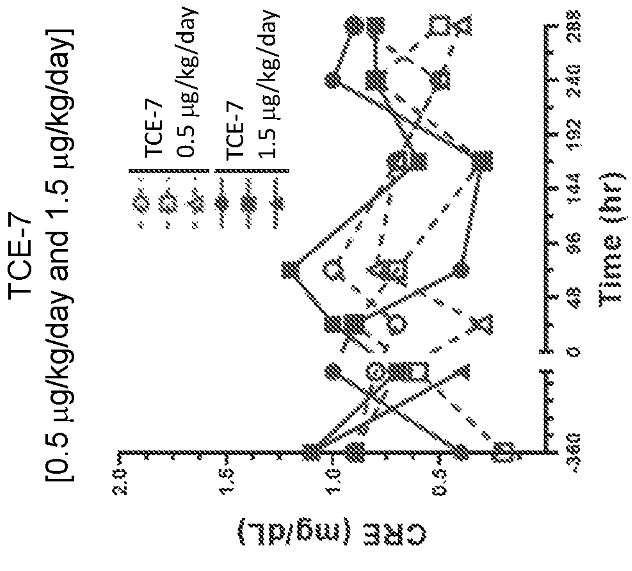
Figure 168F:
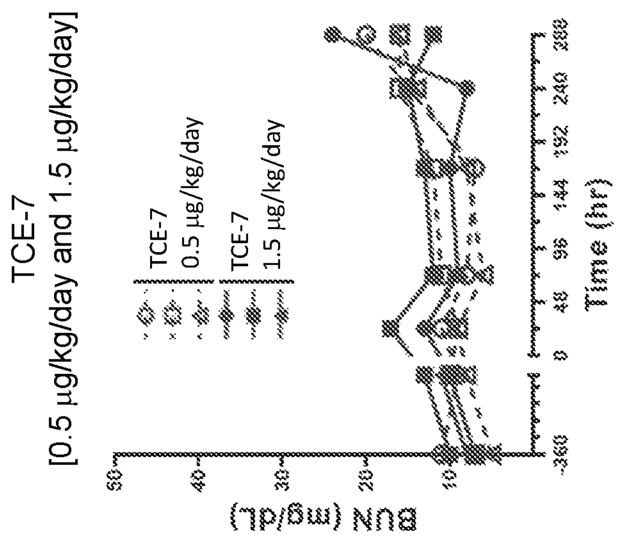

Cytokine release after TCE-7 and TCE-8 administration by cIV was evaluated in cynomolgus monkeys. Briefly, cynomolgus monkeys of approximately 3 kg bodyweight were implanted with an infusion pump subcutaneously. Two weeks later the pump was filled with TCE dosing solution and administered via constant infusion. After dosing started, blood was collected in K2 EDTA tubes at specific timepoints and processed to plasma. Plasma samples were analyzed for cytokines using a non-human primate cytometric Th1/Th2 bead array kid from BD biosciences following the manufacturer's instructions. Interleukin 6 (IL-6) levels in plasma were calculated relative to reference standards provided with the bead array kit. FIGS. 165-166 show IL-6 release in cynomolgus monkey after continuous infusion of TCE-8 (FIG. 165) and TCE-7 (FIG. 166) at different doses. IL-6 levels (in picograms/milliliter (pg/mL)) following cIV infusion for 10 days at different doses are provided in Table 51 for TCE-8 and Table 52 for TCE-7.

TABLE 51

| NHP Continuous IV Infusion of TCE-8 for 10 Days | | | |
|---|---|---|---|
| 0.15 μg/kg/day | 0.5 μg/kg/day | 5 μg/kg/day | 15 μg/kg/day |
| 3458 pg/mL IL-6 | 298 pg/mL IL-6 | 2006 pg/mL IL-6 | 7098 pg/mL IL-6 |

TABLE 52

| NHP Continuous IV Infusion of TCE-7 for 10 Days | | | |
|---|---|---|---|
| 0.5 μg/kg/day | 1.5 μg/kg/day | 5 μg/kg/day | 15 μg/kg/day |
| 356 pg/mL IL-6 | 324 pg/mL IL-6 | 3719 pg/mL IL-6 | 8811 pg/mL IL-6 |

Clinical Chemistry of TCE-7 and TCE-8 in NHP

Clinical chemistry after TCE-7 and TCE-8 administration by cIV in cynomolgus monkeys was measured through standard panel analyses. Briefly, cynomolgus monkeys of approximately 3 kg bodyweight were administered TCEs by cIV and observed daily for signs of adverse events. After dosing, blood was collected in K2 EDTA tubes at specific timepoints and processed to plasma. Clinical chemistry parameters were run on freshly prepared plasma samples, including alanine aminotransferase (ALT), aspartate transaminase (AST), alkaline phosphatase (ALP), bilirubin (TBIL), creatinine (CRE), and blood urea nitrogen (BUN) as signs of liver and kidney related toxicity. FIGS. 167-168 show plots of ALT, AST, ALP, TBIL, CRE, and BUN levels in cynomolgus monkeys after administration of TCE-8 (FIG. 167A-F) and TCE-7 (FIG. 168A-F).

NHP Toxicity Studies of TCE-37, TCE-38, and TCE-40

Pharmacokinetics and exploratory safety of TCE-37, TCE-38, and TCE-40 were evaluated as described above. Pharmacokinetic profiles and toxicity results are shown in FIG. 169 (TCE-37), FIG. 170 (TCE-40), and FIG. 171 (TCE-38). Maximum tolerated doses were 30 μg/kg/day for TCE-37, 1 μg/kg/day for TCE-40, and 30 μg/kg/day for TCE-38.

Cytokine Induction in NHPs with TCE-37, TCE-38, and TCE-40

Cytokine release after TCE-37, TCE-38, and TCE-40 administration by cIV was evaluated in cynomolgus monkeys as described above. FIGS. 172A-172D show release of IL-6, tumor necrosis factor alpha (TNFα), interferon gamma (IFNγ), and interleukin-2 (IL-2) in cynomolgus monkey after continuous infusion of TCE-37. FIGS. 173A-173D show release of IL-6, TNFα, IFNγ, and IL-2 in cynomolgus monkey after continuous infusion of TCE-40. FIG. 174 shows release of IL-6 in cynomolgus monkey after continuous infusion of TCE-38. IL-6 levels in pg/mL following cIV infusion for 10 days at different doses are provided in Table 53 for TCE-37, Table 54 for TCE-38, and Table 55 for TCE-40. Notably, TCE-37 (F104A anti-CD3 mutant) and TCE-38 (F240A anti-CD3 mutant) resulted in reduced IL-6 levels at the maximum tolerated doses after 10 days compared to TCE-7 which has the wild-type anti-CD3 sequence (compare Tables 52-54), suggesting a potential advantage for the anti-CD3 alanine mutants related to cytokine release syndrome.

TABLE 53

| NHP Continuous IV Infusion of TCE-37 for 10 Days | |
|---|---|
| 30 μg/kg/day | 100 μg/kg/day |
| 197 pg/mL IL-6 | 100 pg/mL IL-6 |

TABLE 54

| NHP Continuous IV Infusion of TCE-38 for 10 Days | |
|---|---|
| 30 μg/kg/day | 100 μg/kg/day |
| 183 pg/mL IL-6 | 213 pg/mL IL-6 |

TABLE 55

| NHP Continuous IV Infusion of TCE-40 for 10 Days | |
|---|---|
| 1 μg/kg/day | 3 μg/kg/day |
| IL-6, below limit of quantitation | 133 pg/mL IL-6 |

Clinical Chemistry of TCE-37, TCE-38, and TCE-40

Clinical chemistry after TCE-37, TCE-38, and TCE-40 administration by cIV in cynomolgus monkeys was measured through standard panel analyses as described above. FIGS. 175-177 show plots of ALT, AST, ALP, TBIL, CRE, and BUN levels in cynomolgus monkeys after administration of TCE-37 (FIGS. 175A-F), TCE-40 (FIGS. 176A-F), and TCE-38 (FIGS. 177A-F).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An isolated polypeptide or polypeptide complex according to Formula I:

$$A_1\text{-}L_1\text{-}P_1 \quad \text{(Formula I)}$$

wherein:

- $A_1$ comprises a recombinant antibody or antigen binding fragment thereof that comprises a tumor-associated calcium signal transducer 2 (TROP2) binding domain, wherein the TROP2 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of:
- CDR1-L: SEQ ID NO: 1, CDR2-L: SEQ ID NO: 2 (SA), CDR3-L: SEQ ID NO: 4, and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 5 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 6 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 7 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 8 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 9 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 10 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 11 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 12 and
- CDR1-H: SEQ ID NO: 13, CDR2-H: SEQ ID NO: 14, CDR3-H: SEQ ID NO: 15;
- CDR1-L: SEQ ID NO: 1, CDR2-L: SEQ ID NO: 2 (SA), CDR3-L: SEQ ID NO: 3, and
- CDR1-H: SEQ ID NO: 13, CDR2-H: SEQ ID NO: 14, CDR3-H: SEQ ID NO: 16;
- CDR1-L: SEQ ID NO: 1, CDR2-L: SEQ ID NO: 2 (SA), CDR3-L: SEQ ID NO: 3, and
- CDR1-H: SEQ ID NO: 13, CDR2-H: SEQ ID NO: 14, CDR3-H: SEQ ID NO: 17;
- CDR1-L: SEQ ID NO: 1, CDR2-L: SEQ ID NO: 2 (SA), CDR3-L: SEQ ID NO: 3, and
- CDR1-H: SEQ ID NO: 13, CDR2-H: SEQ ID NO: 14, CDR3-H: SEQ ID NO: 18;
- CDR1-L: SEQ ID NO: 1, CDR2-L: SEQ ID NO: 2 (SA), CDR3-L: SEQ ID NO: 3, and
- CDR1-H: SEQ ID NO: 13, CDR2-H: SEQ ID NO: 14, CDR3-H: SEQ ID NO: 19;
- CDR1-L: SEQ ID NO: 1, CDR2-L: SEQ ID NO: 2 (SA), CDR3-L: SEQ ID NO: 3, and
- CDR1-H: SEQ ID NO: 13, CDR2-H: SEQ ID NO: 14, CDR3-H: SEQ ID NO: 20;
- CDR1-L: SEQ ID NO: 1, CDR2-L: SEQ ID NO: 2 (SA); CDR3-L: SEQ ID NO: 3, and

CDR1-H: SEQ ID NO: 13, CDR2-H: SEQ ID NO: 14, CDR3-H: SEQ ID NO: 21;

CDR1-L: SEQ ID NO: 1, CDR2-L: SEQ ID NO: 2 (SA); CDR3-L: SEQ ID NO: 3, and

CDR1-H: SEQ ID NO: 13, CDR2-H: SEQ ID NO: 14; CDR3-H: SEQ ID NO: 22;

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 23;

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 24;

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 25;

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 26;

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 27; and

CDR1-L: SEQ ID NO: 1, CDR2-L: SEQ ID NO: 2 (SA), CDR3-L: SEQ ID NO: 3, and

CDR1-H: SEQ ID NO: 13, CDR2-H: SEQ ID NO: 14, CDR3-H: SEQ ID NO: 28;

$P_1$ comprises a peptide that binds to $A_1$, wherein $P_1$ comprises an amino acid sequence according to any one of SEQ ID NOs: 100-163, or an amino acid sequence that has 1, 2, or 3 amino acid mutations, substitutions or deletions relative to any one SEQ ID NOs: 100-163; and $L_1$ comprises a linking moiety that connects $A_1$ to $P_1$ and is a substrate for a tumor specific protease.

2. The isolated polypeptide or polypeptide complex according to claim 1, wherein the TROP2 binding domain is a Fab.

3. The isolated polypeptide or polypeptide complex according to claim 1, wherein the immunoglobulin light chain comprises a variable domain of an immunoglobulin kappa (IgK) or immunoglobulin lambda (IgL) light chain, and wherein the immunoglobulin heavy chain comprises a variable domain of an IgG1, IgG2, IgG3, or IgG4 heavy chain.

4. The isolated polypeptide or polypeptide complex according to claim 1, wherein the immunoglobulin light chain comprises an amino acid sequence with at least 90%, 95%, 96%, 97%, 98%, 99%, or 100% identity to any one of SEQ ID NOs: 31, 33, 35, 37, 39, 41, 43, 45, 47, 49, 51, 53, 55, 57, 59, 61, 63, 65, 67, 69, 71, or 73, and wherein the immunoglobulin heavy chain comprises an amino acid sequence with at least 90%, 95%, 96%, 97%, 98%, 99%, or 100% identity to any one of SEQ ID NOs: 32, 34, 36, 38, 40, 42, 44, 46, 48, 50, 52, 54, 56, 58, 60, 62, 64, 66, 68, 70, 72, or 74.

5. The isolated polypeptide or polypeptide complex according to claim 1, wherein the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70.

6. The isolated polypeptide or polypeptide complex according to claim 1, wherein the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72.

7. The isolated polypeptide or polypeptide complex according to claim 1, wherein the immunoglobulin light chain and the immunoglobulin heavy chain comprise a set of CDRs comprising CDR1-L: SEQ ID NO: 1, CDR2-L: SEQ ID NO: 2 (SA), CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

8. The isolated polypeptide or polypeptide complex according to claim 1, wherein the immunoglobulin light chain and the immunoglobulin heavy chain comprise a set of CDRs comprising CDR1-L: SEQ ID NO: 1, CDR2-L: SEQ ID NO: 2 (SA), CDR3-L: SEQ ID NO: 3, CDR1-H: SEQ ID NO: 13, CDR2-H: SEQ ID NO: 14, and CDR3-H: SEQ ID NO: 26, and wherein $P_1$ comprises an amino acid sequence according to any one of SEQ ID NOs: 107, 141, 142, and 150, or an amino acid sequence that has 1, 2, or 3 amino acid mutations, substitutions, or deletions relative to any one of SEQ ID NOs: 107, 141, 142, and 150.

9. The isolated polypeptide or polypeptide complex according to claim 1, wherein the immunoglobulin light chain comprises an amino acid sequence with at least 90%, 95%, 96%, 97%, 98%, 99%, or 100% identity to SEQ ID NO: 69 and the immunoglobulin heavy chain comprises an amino acid sequence with at least 90%, 95%, 96%, 97%, 98%, 99%, or 100% identity to SEQ ID NO: 70, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

10. The isolated polypeptide or polypeptide complex according to claim 1, wherein the immunoglobulin light chain and the immunoglobulin heavy chain comprise a set of CDRs comprising CDR1-L: SEQ ID NO: 1, CDR2-L: SEQ ID NO: 2 (SA), CDR3-L: SEQ ID NO: 3, CDR1-H: SEQ ID NO: 13, CDR2-H: SEQ ID NO: 14, and CDR3-H: SEQ ID NO: 27, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

11. The isolated polypeptide or polypeptide complex according to claim 1, wherein the immunoglobulin light chain and the immunoglobulin heavy chain comprise a set of CDRs comprising CDR1-L: SEQ ID NO: 1, CDR2-L: SEQ ID NO: 2 (SA), CDR3-L: SEQ ID NO: 3, CDR1-H: SEQ ID NO: 13, CDR2-H: SEQ ID NO: 14, and CDR3-H: SEQ ID NO: 27, and wherein $P_1$ comprises an amino acid sequence according to any one of SEQ ID NOs: 107, 109, 116, 141, 142, 148, 149, 150, 158, or an amino acid sequence that has 1, 2, or 3 amino acid mutations, substitutions, or deletions relative to any one of SEQ ID NOs: 107, 109, 116, 141, 142, 148, 149, 150, 158.

12. The isolated polypeptide or polypeptide complex according to claim 1, wherein the immunoglobulin light chain comprises an amino acid sequence with at least 90%, 95%, 96%, 97%, 98%, 99%, or 100% identity to SEQ ID NO: 71 and the immunoglobulin heavy chain comprises an amino acid sequence with at least 90%, 95%, 96%, 97%, 98%, 99%, or 100% identity to SEQ ID NO: 72, and wherein $P_1$ comprises an amino acid sequence according to any one of SEQ ID NOs: 100-107, 109, 111-113, 116-117, 119, and 123-163, or an amino acid sequence that has 1, 2, or 3 amino acid mutations, substitutions, or deletions relative to any one of SEQ ID NOs: 100-107, 109, 111-113, 116-117, 119, and 123-163.

13. The isolated polypeptide or polypeptide complex according to claim 1, wherein the isolated polypeptide or polypeptide complex further comprises a CD3 binding domain.

14. The isolated polypeptide or polypeptide complex according to claim 13, wherein the isolated polypeptide or polypeptide complex is according to the following formula $P_2$-$L_2$-$B_2$-$A_1$-$L_1$-$P_1$ (Formula Ia), wherein $B_2$ comprises the CD3 binding domain, $P_2$ comprises a peptide that binds to $B_2$ and $L_2$ comprises a linking moiety that connects $B_2$ to $P_2$ and is a substrate for a tumor specific protease.

15. The isolated polypeptide or polypeptide complex according to claim 13, wherein the CD3 binding domain comprises an immunoglobulin light chain comprising complementarity determining regions (CDRs) CDR1-L, CDR2-L, and CDR3-L, and an immunoglobulin heavy chain comprising CDRs: CDR1-H, CDR2-H, and CDR3-H, wherein the immunoglobulin light chain and the immunoglobulin heavy chain comprise a set of CDR sequences selected from the group consisting of:

CDR1-L: SEQ ID NO: 75, CDR2-L: SEQ ID NO: 76 (GTK), CDR3-L SEQ ID NO: 77, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 260, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 261, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 262, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 263, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 264, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 265, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 266, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 267, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 268, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 269, and
CDR1-H: SEQ ID NO: 78, CDR2-H: SEQ ID NO: 79, CDR3-H: SEQ ID NO: 80;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 271;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 272;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 273;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 274;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 275;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 276;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 277;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 278;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 279;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 280;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 281;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 282;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 283;
CDR1-L: SEQ ID NO: 75, CDR2-L: SEQ ID NO: 76 (GTK), CDR3-L: SEQ ID NO: 77, and
CDR1-H: SEQ ID NO: 78, CDR2-H: SEQ ID NO: 79, CDR3-H: SEQ ID NO: 284;

CDR1-L: SEQ ID NO: 75, CDR2-L: SEQ ID NO: 76 (GTK), CDR3-L: SEQ ID NO: 77, and

CDR1-H: SEQ ID NO: 78, CDR2-H: SEQ ID NO: 79, CDR3-H: SEQ ID NO: 285; and

CDR1-L: SEQ ID NO: 259, CDR2-L: SEQ ID NO: 76 (GTK), CDR3-L: SEQ ID NO: 260, and

CDR1-H: SEQ ID NO: 270, CDR2-H: SEQ ID NO: 79, CDR3-H: SEQ ID NO: 286.

16. The isolated polypeptide or polypeptide complex according to claim 13, wherein the CD3 binding domain comprises an amino acid sequence with at least 90%, 95%, 96%, 97%, 98%, 99%, or 100% identity to any one of SEQ ID NOs: 99 and 303-329.

17. The isolated polypeptide or polypeptide complex according to claim 13, wherein the CD3 binding domain is a single chain variable fragment (scFv).

18. The isolated polypeptide or polypeptide complex according to claim 13, wherein the recombinant antibody or antigen binding fragment thereof comprises an amino acid sequence with at least 90%, 95%, 96%, 97%, 98%, 99%, or 100% identity to any one of SEQ ID NOs: 87, 89, 91, 93, 95, 97, 330, 332, 334, 336, 338, 340, 342, 344, 346, 348, and 350 and an amino acid sequence with at least 90%, 95%, 96%, 97%, 98%, 99%, or 100% identity to any one of SEQ ID NOs: 88, 90, 92, 94, 96, 98, 331, 333, 335, 337, 339, 341, 343, 345, 347, 349, and 351.

19. The isolated polypeptide or polypeptide complex according to claim 14, wherein $P_2$ comprises an amino acid sequence according to any one of SEQ ID NOs: 287-302, or an amino acid sequence that has 1, 2, or 3 amino acid mutations, substitutions or deletions relative to any one of SEQ ID NOs: 287-302.

20. The isolated polypeptide or polypeptide complex according to claim 1, wherein the isolated polypeptide or polypeptide complex comprises amino acid sequences with at least 90%, 95%, 96%, 97%, 98%, 99%, or 100% identity to any one of SEQ ID NOs: 180, 182, 184, 186, 188, 190, 192, 194, 196, 198, 200, 202, 204, 206, 208, 210, 212, 214, 216, 218, 224, and 356 and any one of SEQ ID NOs: 181, 183, 185, 187, 189, 191, 193, 195, 197, 199, 201, 203, 205, 207, 209, 211, 213, 215, 217, 219, 225, and 357.

21. The isolated polypeptide or polypeptide complex according to claim 1, wherein the isolated polypeptide or polypeptide complex comprises amino acid sequences with at least 90%, 95%, 96%, 97%, 98%, 99%, or 100% identity to any one of SEQ ID NOs: 352, 354, 358, 360, 362, 364, 366, 368, 370, 372, 374, 376, 378, 380, 382, 388, 390, 392, and 394 and any one of SEQ ID NOs: 353, 355, 359, 361, 363, 365, 367, 369, 371, 373, 375, 377, 379, 381, 383, 390, 391, 393, and 395.

22. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 180 and SEQ ID NO: 181.

23. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 200 and SEQ ID NO: 201.

24. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 352 and SEQ ID NO: 353.

25. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 354 and SEQ ID NO: 355.

26. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 362 and SEQ ID NO: 363.

27. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 382 and SEQ ID NO: 383.

28. The isolated polypeptide or polypeptide complex according to claim 1, wherein the isolated polypeptide or polypeptide complex comprises amino acid sequences with at least 90%, 95%, 96%, 97%, 98%, 99%, or 100% identity to SEQ ID NO: 390 and SEQ ID NO: 391.

* * * * *

SEQUENCE LISTING

```
Sequence total quantity: 453
SEQ ID NO: 1           moltype = AA  length = 6
FEATURE                Location/Qualifiers
source                 1..6
                       mol_type = protein
                       organism = synthetic construct
SEQUENCE: 1
QDVSIA                                                                6

SEQ ID NO: 2           moltype =   length =
SEQUENCE: 2
000

SEQ ID NO: 3           moltype = AA  length = 9
FEATURE                Location/Qualifiers
source                 1..9
                       mol_type = protein
                       organism = synthetic construct
SEQUENCE: 3
QQHYITPLT                                                             9

SEQ ID NO: 4           moltype = AA  length = 9
FEATURE                Location/Qualifiers
source                 1..9
                       mol_type = protein
                       organism = synthetic construct
SEQUENCE: 4
AQHYITPLT                                                             9

SEQ ID NO: 5           moltype = AA  length = 9
FEATURE                Location/Qualifiers
source                 1..9
                       mol_type = protein
                       organism = synthetic construct
SEQUENCE: 5
QAHYITPLT                                                             9

SEQ ID NO: 6           moltype = AA  length = 9
FEATURE                Location/Qualifiers
source                 1..9
                       mol_type = protein
                       organism = synthetic construct
SEQUENCE: 6
QQAYITPLT                                                             9

SEQ ID NO: 7           moltype = AA  length = 9
FEATURE                Location/Qualifiers
source                 1..9
                       mol_type = protein
                       organism = synthetic construct
SEQUENCE: 7
QQHAITPLT                                                             9

SEQ ID NO: 8           moltype = AA  length = 9
FEATURE                Location/Qualifiers
source                 1..9
                       mol_type = protein
                       organism = synthetic construct
SEQUENCE: 8
```

-continued

```
QQHYATPLT                                                            9

SEQ ID NO: 9           moltype = AA  length = 9
FEATURE                Location/Qualifiers
source                 1..9
                       mol_type = protein
                       organism = synthetic construct
SEQUENCE: 9
QQHYIAPLT                                                            9

SEQ ID NO: 10          moltype = AA  length = 9
FEATURE                Location/Qualifiers
source                 1..9
                       mol_type = protein
                       organism = synthetic construct
SEQUENCE: 10
QQHYITALT                                                            9

SEQ ID NO: 11          moltype = AA  length = 9
FEATURE                Location/Qualifiers
source                 1..9
                       mol_type = protein
                       organism = synthetic construct
SEQUENCE: 11
QQHYITPAT                                                            9

SEQ ID NO: 12          moltype = AA  length = 9
FEATURE                Location/Qualifiers
source                 1..9
                       mol_type = protein
                       organism = synthetic construct
SEQUENCE: 12
QQHYITPLA                                                            9

SEQ ID NO: 13          moltype = AA  length = 8
FEATURE                Location/Qualifiers
source                 1..8
                       mol_type = protein
                       organism = synthetic construct
SEQUENCE: 13
GYTFTNYG                                                             8

SEQ ID NO: 14          moltype = AA  length = 8
FEATURE                Location/Qualifiers
source                 1..8
                       mol_type = protein
                       organism = synthetic construct
SEQUENCE: 14
INTYTGEP                                                             8

SEQ ID NO: 15          moltype = AA  length = 14
FEATURE                Location/Qualifiers
source                 1..14
                       mol_type = protein
                       organism = synthetic construct
SEQUENCE: 15
ARGGFGSSYW YFDV                                                      14

SEQ ID NO: 16          moltype = AA  length = 14
FEATURE                Location/Qualifiers
source                 1..14
                       mol_type = protein
                       organism = synthetic construct
SEQUENCE: 16
AAGGFGSSYW YFDV                                                      14

SEQ ID NO: 17          moltype = AA  length = 14
FEATURE                Location/Qualifiers
source                 1..14
                       mol_type = protein
                       organism = synthetic construct
SEQUENCE: 17
ARAGFGSSYW YFDV                                                      14

SEQ ID NO: 18          moltype = AA  length = 14
FEATURE                Location/Qualifiers
source                 1..14
                       mol_type = protein
                       organism = synthetic construct
```

```
SEQUENCE: 18
ARGAFGSSYW YFDV                                                   14

SEQ ID NO: 19          moltype = AA  length = 14
FEATURE                Location/Qualifiers
source                 1..14
                       mol_type = protein
                       organism = synthetic construct
SEQUENCE: 19
ARGGAGSSYW YFDV                                                   14

SEQ ID NO: 20          moltype = AA  length = 14
FEATURE                Location/Qualifiers
source                 1..14
                       mol_type = protein
                       organism = synthetic construct
SEQUENCE: 20
ARGGFASSYW YFDV                                                   14

SEQ ID NO: 21          moltype = AA  length = 14
FEATURE                Location/Qualifiers
source                 1..14
                       mol_type = protein
                       organism = synthetic construct
SEQUENCE: 21
ARGGFGASYW YFDV                                                   14

SEQ ID NO: 22          moltype = AA  length = 14
FEATURE                Location/Qualifiers
source                 1..14
                       mol_type = protein
                       organism = synthetic construct
SEQUENCE: 22
ARGGFGSAYW YFDV                                                   14

SEQ ID NO: 23          moltype = AA  length = 14
FEATURE                Location/Qualifiers
source                 1..14
                       mol_type = protein
                       organism = synthetic construct
SEQUENCE: 23
ARGGFGSSAW YFDV                                                   14

SEQ ID NO: 24          moltype = AA  length = 14
FEATURE                Location/Qualifiers
source                 1..14
                       mol_type = protein
                       organism = synthetic construct
SEQUENCE: 24
ARGGFGSSYA YFDV                                                   14

SEQ ID NO: 25          moltype = AA  length = 14
FEATURE                Location/Qualifiers
source                 1..14
                       mol_type = protein
                       organism = synthetic construct
SEQUENCE: 25
ARGGFGSSYW AFDV                                                   14

SEQ ID NO: 26          moltype = AA  length = 14
FEATURE                Location/Qualifiers
source                 1..14
                       mol_type = protein
                       organism = synthetic construct
SEQUENCE: 26
ARGGFGSSYW YADV                                                   14

SEQ ID NO: 27          moltype = AA  length = 14
FEATURE                Location/Qualifiers
source                 1..14
                       mol_type = protein
                       organism = synthetic construct
SEQUENCE: 27
ARGGFGSSYW YFAV                                                   14

SEQ ID NO: 28          moltype = AA  length = 14
FEATURE                Location/Qualifiers
source                 1..14
                       mol_type = protein
```

```
                         organism = synthetic construct
SEQUENCE: 28
ARGGFGSSYW YFDA                                                14

SEQ ID NO: 29            moltype = AA  length = 214
FEATURE                  Location/Qualifiers
source                   1..214
                         mol_type = protein
                         organism = synthetic construct
SEQUENCE: 29
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 30            moltype = AA  length = 224
FEATURE                  Location/Qualifiers
source                   1..224
                         mol_type = protein
                         organism = synthetic construct
SEQUENCE: 30
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 31            moltype = AA  length = 214
FEATURE                  Location/Qualifiers
source                   1..214
                         mol_type = protein
                         organism = synthetic construct
SEQUENCE: 31
DIQLTQSPSS LSASVGDRVS ITCKASQDVS IAVAWYQQKP GKAPKLLIYS ASYRYTGVPD  60
RFSGSGSGTD FTLTISSLQP EDFAVYYCAQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 32            moltype = AA  length = 224
FEATURE                  Location/Qualifiers
source                   1..224
                         mol_type = protein
                         organism = synthetic construct
SEQUENCE: 32
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 33            moltype = AA  length = 214
FEATURE                  Location/Qualifiers
source                   1..214
                         mol_type = protein
                         organism = synthetic construct
SEQUENCE: 33
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQA HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 34            moltype = AA  length = 224
FEATURE                  Location/Qualifiers
source                   1..224
                         mol_type = protein
                         organism = synthetic construct
SEQUENCE: 34
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 35            moltype = AA  length = 214
FEATURE                  Location/Qualifiers
source                   1..214
                         mol_type = protein
                         organism = synthetic construct
SEQUENCE: 35
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ AYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                             214

SEQ ID NO: 36          moltype = AA  length = 224
FEATURE                Location/Qualifiers
source                 1..224
                       mol_type = protein
                       organism = synthetic construct
SEQUENCE: 36
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 37          moltype = AA  length = 214
FEATURE                Location/Qualifiers
source                 1..214
                       mol_type = protein
                       organism = synthetic construct
SEQUENCE: 37
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HAITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 38          moltype = AA  length = 224
FEATURE                Location/Qualifiers
source                 1..224
                       mol_type = protein
                       organism = synthetic construct
SEQUENCE: 38
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 39          moltype = AA  length = 214
FEATURE                Location/Qualifiers
source                 1..214
                       mol_type = protein
                       organism = synthetic construct
SEQUENCE: 39
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYATPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 40          moltype = AA  length = 224
FEATURE                Location/Qualifiers
source                 1..224
                       mol_type = protein
                       organism = synthetic construct
SEQUENCE: 40
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 41          moltype = AA  length = 214
FEATURE                Location/Qualifiers
source                 1..214
                       mol_type = protein
                       organism = synthetic construct
SEQUENCE: 41
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYIAPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 42          moltype = AA  length = 224
FEATURE                Location/Qualifiers
source                 1..224
                       mol_type = protein
                       organism = synthetic construct
SEQUENCE: 42
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224
```

-continued

```
SEQ ID NO: 43          moltype = AA  length = 214
FEATURE                Location/Qualifiers
source                 1..214
                       mol_type = protein
                       organism = synthetic construct
SEQUENCE: 43
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITALTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 44          moltype = AA  length = 224
FEATURE                Location/Qualifiers
source                 1..224
                       mol_type = protein
                       organism = synthetic construct
SEQUENCE: 44
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 45          moltype = AA  length = 214
FEATURE                Location/Qualifiers
source                 1..214
                       mol_type = protein
                       organism = synthetic construct
SEQUENCE: 45
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPATFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 46          moltype = AA  length = 224
FEATURE                Location/Qualifiers
source                 1..224
                       mol_type = protein
                       organism = synthetic construct
SEQUENCE: 46
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 47          moltype = AA  length = 214
FEATURE                Location/Qualifiers
source                 1..214
                       mol_type = protein
                       organism = synthetic construct
SEQUENCE: 47
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLAFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 48          moltype = AA  length = 224
FEATURE                Location/Qualifiers
source                 1..224
                       mol_type = protein
                       organism = synthetic construct
SEQUENCE: 48
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 49          moltype = AA  length = 214
FEATURE                Location/Qualifiers
source                 1..214
                       mol_type = protein
                       organism = synthetic construct
SEQUENCE: 49
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 50          moltype = AA  length = 224
FEATURE                Location/Qualifiers
```

-continued

```
source                  1..224
                        mol_type = protein
                        organism = synthetic construct
SEQUENCE: 50
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCAAGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 51           moltype = AA  length = 214
FEATURE                 Location/Qualifiers
source                  1..214
                        mol_type = protein
                        organism = synthetic construct
SEQUENCE: 51
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 52           moltype = AA  length = 224
FEATURE                 Location/Qualifiers
source                  1..224
                        mol_type = protein
                        organism = synthetic construct
SEQUENCE: 52
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARAG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 53           moltype = AA  length = 214
FEATURE                 Location/Qualifiers
source                  1..214
                        mol_type = protein
                        organism = synthetic construct
SEQUENCE: 53
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 54           moltype = AA  length = 224
FEATURE                 Location/Qualifiers
source                  1..224
                        mol_type = protein
                        organism = synthetic construct
SEQUENCE: 54
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGA FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 55           moltype = AA  length = 214
FEATURE                 Location/Qualifiers
source                  1..214
                        mol_type = protein
                        organism = synthetic construct
SEQUENCE: 55
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 56           moltype = AA  length = 224
FEATURE                 Location/Qualifiers
source                  1..224
                        mol_type = protein
                        organism = synthetic construct
SEQUENCE: 56
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG AGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 57           moltype = AA  length = 214
FEATURE                 Location/Qualifiers
source                  1..214
                        mol_type = protein
```

```
                         organism = synthetic construct
SEQUENCE: 57
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 58            moltype = AA  length = 224
FEATURE                  Location/Qualifiers
source                   1..224
                         mol_type = protein
                         organism = synthetic construct
SEQUENCE: 58
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FASSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 59            moltype = AA  length = 214
FEATURE                  Location/Qualifiers
source                   1..214
                         mol_type = protein
                         organism = synthetic construct
SEQUENCE: 59
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 60            moltype = AA  length = 224
FEATURE                  Location/Qualifiers
source                   1..224
                         mol_type = protein
                         organism = synthetic construct
SEQUENCE: 60
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGASYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 61            moltype = AA  length = 214
FEATURE                  Location/Qualifiers
source                   1..214
                         mol_type = protein
                         organism = synthetic construct
SEQUENCE: 61
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 62            moltype = AA  length = 224
FEATURE                  Location/Qualifiers
source                   1..224
                         mol_type = protein
                         organism = synthetic construct
SEQUENCE: 62
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSAYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 63            moltype = AA  length = 214
FEATURE                  Location/Qualifiers
source                   1..214
                         mol_type = protein
                         organism = synthetic construct
SEQUENCE: 63
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 64            moltype = AA  length = 224
FEATURE                  Location/Qualifiers
source                   1..224
                         mol_type = protein
                         organism = synthetic construct
SEQUENCE: 64
```

```
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSAWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 65          moltype = AA  length = 214
FEATURE                Location/Qualifiers
source                 1..214
                       mol_type = protein
                       organism = synthetic construct
SEQUENCE: 65
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 66          moltype = AA  length = 224
FEATURE                Location/Qualifiers
source                 1..224
                       mol_type = protein
                       organism = synthetic construct
SEQUENCE: 66
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYAYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 67          moltype = AA  length = 214
FEATURE                Location/Qualifiers
source                 1..214
                       mol_type = protein
                       organism = synthetic construct
SEQUENCE: 67
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 68          moltype = AA  length = 224
FEATURE                Location/Qualifiers
source                 1..224
                       mol_type = protein
                       organism = synthetic construct
SEQUENCE: 68
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWAFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 69          moltype = AA  length = 214
FEATURE                Location/Qualifiers
source                 1..214
                       mol_type = protein
                       organism = synthetic construct
SEQUENCE: 69
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 70          moltype = AA  length = 224
FEATURE                Location/Qualifiers
source                 1..224
                       mol_type = protein
                       organism = synthetic construct
SEQUENCE: 70
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYADV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 71          moltype = AA  length = 214
FEATURE                Location/Qualifiers
source                 1..214
                       mol_type = protein
                       organism = synthetic construct
SEQUENCE: 71
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
```

-continued

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 72           moltype = AA  length = 224
FEATURE                 Location/Qualifiers
source                  1..224
                        mol_type = protein
                        organism = synthetic construct
SEQUENCE: 72
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFAV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 73           moltype = AA  length = 214
FEATURE                 Location/Qualifiers
source                  1..214
                        mol_type = protein
                        organism = synthetic construct
SEQUENCE: 73
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 74           moltype = AA  length = 224
FEATURE                 Location/Qualifiers
source                  1..224
                        mol_type = protein
                        organism = synthetic construct
SEQUENCE: 74
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDA WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 75           moltype = AA  length = 9
FEATURE                 Location/Qualifiers
source                  1..9
                        mol_type = protein
                        organism = synthetic construct
SEQUENCE: 75
TGAVTSGNY                                                          9

SEQ ID NO: 76           moltype =   length =
SEQUENCE: 76
000

SEQ ID NO: 77           moltype = AA  length = 9
FEATURE                 Location/Qualifiers
source                  1..9
                        mol_type = protein
                        organism = synthetic construct
SEQUENCE: 77
VLWYSNRWV                                                          9

SEQ ID NO: 78           moltype = AA  length = 8
FEATURE                 Location/Qualifiers
source                  1..8
                        mol_type = protein
                        organism = synthetic construct
SEQUENCE: 78
GFTFNKYA                                                           8

SEQ ID NO: 79           moltype = AA  length = 10
FEATURE                 Location/Qualifiers
source                  1..10
                        mol_type = protein
                        organism = synthetic construct
SEQUENCE: 79
IRSKYNNYAT                                                         10

SEQ ID NO: 80           moltype = AA  length = 16
FEATURE                 Location/Qualifiers
source                  1..16
                        mol_type = protein
                        organism = synthetic construct
SEQUENCE: 80
VRHGNFGNSY ISYWAY                                                  16
```

```
SEQ ID NO: 81          moltype = AA  length = 109
FEATURE                Location/Qualifiers
source                 1..109
                       mol_type = protein
                       organism = synthetic construct
SEQUENCE: 81
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVL              109

SEQ ID NO: 82          moltype = AA  length = 125
FEATURE                Location/Qualifiers
source                 1..125
                       mol_type = protein
                       organism = synthetic construct
SEQUENCE: 82
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSS                                                              125

SEQ ID NO: 83          moltype = AA  length = 214
FEATURE                Location/Qualifiers
source                 1..214
                       mol_type = protein
                       organism = synthetic construct
SEQUENCE: 83
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 84          moltype = AA  length = 478
FEATURE                Location/Qualifiers
source                 1..478
                       mol_type = protein
                       organism = synthetic construct
SEQUENCE: 84
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 85          moltype = AA  length = 468
FEATURE                Location/Qualifiers
source                 1..468
                       mol_type = protein
                       organism = synthetic construct
SEQUENCE: 85
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSDIQLTQ SPSSLSASVG DRVSITCKAS QDVSIAVAWY QQKPGKAPKL  300
LIYSASYRYT GVPDRFSGSG SGTDFTLTIS SLQPEDFAVY YCQQHYITPL TFGAGTKVEI  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC               468

SEQ ID NO: 86          moltype = AA  length = 224
FEATURE                Location/Qualifiers
source                 1..224
                       mol_type = protein
                       organism = synthetic construct
SEQUENCE: 86
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 87          moltype = AA  length = 468
FEATURE                Location/Qualifiers
source                 1..468
                       mol_type = protein
                       organism = synthetic construct
SEQUENCE: 87
EVQLVESGGG LVQPGGSLKL SCAASGFTFN KYAMNWVRQA PGKGLEWVAR IRSKYNNYAT  60
```

-continued

```
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSDIQLTQ SPSSLSASVG DRVSITCKAS QDVSIAVAWY QQKPGKAPKL  300
LIYSASYRYT GVPDRFSGSG SGTDFTLTIS SLQPEDFAVY YCQQHYITPL TFGAGTKVEI  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC                468

SEQ ID NO: 88          moltype = AA  length = 224
FEATURE                Location/Qualifiers
source                 1..224
                       mol_type = protein
                       organism = synthetic construct
SEQUENCE: 88
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCAAGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                    224

SEQ ID NO: 89          moltype = AA  length = 468
FEATURE                Location/Qualifiers
source                 1..468
                       mol_type = protein
                       organism = synthetic construct
SEQUENCE: 89
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSDIQLTQ SPSSLSASVG DRVSITCKAS QDVSIAVAWY QQKPGKAPKL  300
LIYSASYRYT GVPDRFSGSG SGTDFTLTIS SLQPEDFAVY YCQQHYITPL TFGAGTKVEI  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC                468

SEQ ID NO: 90          moltype = AA  length = 224
FEATURE                Location/Qualifiers
source                 1..224
                       mol_type = protein
                       organism = synthetic construct
SEQUENCE: 90
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYADV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                    224

SEQ ID NO: 91          moltype = AA  length = 468
FEATURE                Location/Qualifiers
source                 1..468
                       mol_type = protein
                       organism = synthetic construct
SEQUENCE: 91
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSDIQLTQ SPSSLSASVG DRVSITCKAS QDVSIAVAWY QQKPGKAPKL  300
LIYSASYRYT GVPDRFSGSG SGTDFTLTIS SLQPEDFAVY YCQQHYITPL TFGAGTKVEI  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC                468

SEQ ID NO: 92          moltype = AA  length = 224
FEATURE                Location/Qualifiers
source                 1..224
                       mol_type = protein
                       organism = synthetic construct
SEQUENCE: 92
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFAV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                    224

SEQ ID NO: 93          moltype = AA  length = 214
FEATURE                Location/Qualifiers
source                 1..214
                       mol_type = protein
                       organism = synthetic construct
SEQUENCE: 93
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 94          moltype = AA  length = 478
FEATURE                Location/Qualifiers
source                 1..478
                       mol_type = protein
                       organism = synthetic construct
SEQUENCE: 94
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC AAGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 95          moltype = AA  length = 214
FEATURE                Location/Qualifiers
source                 1..214
                       mol_type = protein
                       organism = synthetic construct
SEQUENCE: 95
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 96          moltype = AA  length = 478
FEATURE                Location/Qualifiers
source                 1..478
                       mol_type = protein
                       organism = synthetic construct
SEQUENCE: 96
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 97          moltype = AA  length = 214
FEATURE                Location/Qualifiers
source                 1..214
                       mol_type = protein
                       organism = synthetic construct
SEQUENCE: 97
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 98          moltype = AA  length = 478
FEATURE                Location/Qualifiers
source                 1..478
                       mol_type = protein
                       organism = synthetic construct
SEQUENCE: 98
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFAVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 99          moltype = AA  length = 249
FEATURE                Location/Qualifiers
source                 1..249
                       mol_type = protein
                       organism = synthetic construct
SEQUENCE: 99
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
```

-continued

```
KPGQAPRGLI GGTKFLAPGT PARFSGSLLG GKAALTLSGV QPEDEAEYYC VLWYSNRWVF  240
GGGTKLTVL                                                          249

SEQ ID NO: 100          moltype = AA  length = 14
FEATURE                 Location/Qualifiers
source                  1..14
                        mol_type = protein
                        organism = synthetic construct
SEQUENCE: 100
IDFCAMYQWP ICDT                                                    14

SEQ ID NO: 101          moltype = AA  length = 14
FEATURE                 Location/Qualifiers
source                  1..14
                        mol_type = protein
                        organism = synthetic construct
SEQUENCE: 101
IDFCAVYKWP VCQV                                                    14

SEQ ID NO: 102          moltype = AA  length = 14
FEATURE                 Location/Qualifiers
source                  1..14
                        mol_type = protein
                        organism = synthetic construct
SEQUENCE: 102
IDFCMLYNWP ICAG                                                    14

SEQ ID NO: 103          moltype = AA  length = 14
FEATURE                 Location/Qualifiers
source                  1..14
                        mol_type = protein
                        organism = synthetic construct
SEQUENCE: 103
VDFCKIYAWP ICGS                                                    14

SEQ ID NO: 104          moltype = AA  length = 14
FEATURE                 Location/Qualifiers
source                  1..14
                        mol_type = protein
                        organism = synthetic construct
SEQUENCE: 104
VDFCKLYNWP VCQT                                                    14

SEQ ID NO: 105          moltype = AA  length = 14
FEATURE                 Location/Qualifiers
source                  1..14
                        mol_type = protein
                        organism = synthetic construct
SEQUENCE: 105
IDFCLIYNWP VCDT                                                    14

SEQ ID NO: 106          moltype = AA  length = 14
FEATURE                 Location/Qualifiers
source                  1..14
                        mol_type = protein
                        organism = synthetic construct
SEQUENCE: 106
EDFCKLYNWP ICYQ                                                    14

SEQ ID NO: 107          moltype = AA  length = 14
FEATURE                 Location/Qualifiers
source                  1..14
                        mol_type = protein
                        organism = synthetic construct
SEQUENCE: 107
VDFCGLYHWP ICYQ                                                    14

SEQ ID NO: 108          moltype = AA  length = 14
FEATURE                 Location/Qualifiers
source                  1..14
                        mol_type = protein
                        organism = synthetic construct
SEQUENCE: 108
VDFCYLYNWP VCSK                                                    14

SEQ ID NO: 109          moltype = AA  length = 14
FEATURE                 Location/Qualifiers
source                  1..14
                        mol_type = protein
```

```
                        organism = synthetic construct
SEQUENCE: 109
IDFCAIYQWP VCRS                                                          14

SEQ ID NO: 110          moltype = AA  length = 14
FEATURE                 Location/Qualifiers
source                  1..14
                        mol_type = protein
                        organism = synthetic construct
SEQUENCE: 110
VDFCALYNWP VCET                                                          14

SEQ ID NO: 111          moltype = AA  length = 14
FEATURE                 Location/Qualifiers
source                  1..14
                        mol_type = protein
                        organism = synthetic construct
SEQUENCE: 111
PDFCAVYRWP ICYQ                                                          14

SEQ ID NO: 112          moltype = AA  length = 14
FEATURE                 Location/Qualifiers
source                  1..14
                        mol_type = protein
                        organism = synthetic construct
SEQUENCE: 112
VDFCELYRWP ICNS                                                          14

SEQ ID NO: 113          moltype = AA  length = 14
FEATURE                 Location/Qualifiers
source                  1..14
                        mol_type = protein
                        organism = synthetic construct
SEQUENCE: 113
LDFCKIYDWP ICHL                                                          14

SEQ ID NO: 114          moltype = AA  length = 14
FEATURE                 Location/Qualifiers
source                  1..14
                        mol_type = protein
                        organism = synthetic construct
SEQUENCE: 114
LDFCKLYQWP VCFT                                                          14

SEQ ID NO: 115          moltype = AA  length = 14
FEATURE                 Location/Qualifiers
source                  1..14
                        mol_type = protein
                        organism = synthetic construct
SEQUENCE: 115
IDFCLLYDWP VCAS                                                          14

SEQ ID NO: 116          moltype = AA  length = 14
FEATURE                 Location/Qualifiers
source                  1..14
                        mol_type = protein
                        organism = synthetic construct
SEQUENCE: 116
IDFCLLYDWP ICGR                                                          14

SEQ ID NO: 117          moltype = AA  length = 14
FEATURE                 Location/Qualifiers
source                  1..14
                        mol_type = protein
                        organism = synthetic construct
SEQUENCE: 117
MDFCQIYDWP ICRL                                                          14

SEQ ID NO: 118          moltype = AA  length = 14
FEATURE                 Location/Qualifiers
source                  1..14
                        mol_type = protein
                        organism = synthetic construct
SEQUENCE: 118
PDFCQLYNWP VCAG                                                          14

SEQ ID NO: 119          moltype = AA  length = 14
FEATURE                 Location/Qualifiers
source                  1..14
```

```
                        mol_type = protein
                        organism = synthetic construct
SEQUENCE: 119
VDFCSFYRWP ICET                                                    14

SEQ ID NO: 120          moltype = AA  length = 14
FEATURE                 Location/Qualifiers
source                  1..14
                        mol_type = protein
                        organism = synthetic construct
SEQUENCE: 120
IDFCSLYQWP VCGT                                                    14

SEQ ID NO: 121          moltype = AA  length = 14
FEATURE                 Location/Qualifiers
source                  1..14
                        mol_type = protein
                        organism = synthetic construct
SEQUENCE: 121
VDFCTIYKWP VCEG                                                    14

SEQ ID NO: 122          moltype = AA  length = 14
FEATURE                 Location/Qualifiers
source                  1..14
                        mol_type = protein
                        organism = synthetic construct
SEQUENCE: 122
VDFCYQYGWP ICSR                                                    14

SEQ ID NO: 123          moltype = AA  length = 14
FEATURE                 Location/Qualifiers
source                  1..14
                        mol_type = protein
                        organism = synthetic construct
SEQUENCE: 123
SVLFCVKNLY CWVT                                                    14

SEQ ID NO: 124          moltype = AA  length = 14
FEATURE                 Location/Qualifiers
source                  1..14
                        mol_type = protein
                        organism = synthetic construct
SEQUENCE: 124
VDFCKIYSWP VCHQ                                                    14

SEQ ID NO: 125          moltype = AA  length = 14
FEATURE                 Location/Qualifiers
source                  1..14
                        mol_type = protein
                        organism = synthetic construct
SEQUENCE: 125
DNLICVKNLW CWIA                                                    14

SEQ ID NO: 126          moltype = AA  length = 14
FEATURE                 Location/Qualifiers
source                  1..14
                        mol_type = protein
                        organism = synthetic construct
SEQUENCE: 126
FSLVCVRNLY CWNV                                                    14

SEQ ID NO: 127          moltype = AA  length = 14
FEATURE                 Location/Qualifiers
source                  1..14
                        mol_type = protein
                        organism = synthetic construct
SEQUENCE: 127
NYLLCVKNLY CWIV                                                    14

SEQ ID NO: 128          moltype = AA  length = 14
FEATURE                 Location/Qualifiers
source                  1..14
                        mol_type = protein
                        organism = synthetic construct
SEQUENCE: 128
SYLVCVKNVY CWTA                                                    14

SEQ ID NO: 129          moltype = AA  length = 14
FEATURE                 Location/Qualifiers
```

```
source                 1..14
                       mol_type = protein
                       organism = synthetic construct
SEQUENCE: 129
TSLICFRNVY CWNV                                                    14

SEQ ID NO: 130         moltype = AA  length = 14
FEATURE                Location/Qualifiers
source                 1..14
                       mol_type = protein
                       organism = synthetic construct
SEQUENCE: 130
YSLVCVKNLY CWNL                                                    14

SEQ ID NO: 131         moltype = AA  length = 14
FEATURE                Location/Qualifiers
source                 1..14
                       mol_type = protein
                       organism = synthetic construct
SEQUENCE: 131
PDFCYMYGWP ICDS                                                    14

SEQ ID NO: 132         moltype = AA  length = 14
FEATURE                Location/Qualifiers
source                 1..14
                       mol_type = protein
                       organism = synthetic construct
SEQUENCE: 132
PDFCYMYNWP VCVT                                                    14

SEQ ID NO: 133         moltype = AA  length = 14
FEATURE                Location/Qualifiers
source                 1..14
                       mol_type = protein
                       organism = synthetic construct
SEQUENCE: 133
WTFCATSMWR YCVD                                                    14

SEQ ID NO: 134         moltype = AA  length = 14
FEATURE                Location/Qualifiers
source                 1..14
                       mol_type = protein
                       organism = synthetic construct
SEQUENCE: 134
EDFCYWYQWP ICSD                                                    14

SEQ ID NO: 135         moltype = AA  length = 14
FEATURE                Location/Qualifiers
source                 1..14
                       mol_type = protein
                       organism = synthetic construct
SEQUENCE: 135
VDFCYQYGWP ICSR                                                    14

SEQ ID NO: 136         moltype = AA  length = 14
FEATURE                Location/Qualifiers
source                 1..14
                       mol_type = protein
                       organism = synthetic construct
SEQUENCE: 136
VDFCYLYNWP VCSK                                                    14

SEQ ID NO: 137         moltype = AA  length = 14
FEATURE                Location/Qualifiers
source                 1..14
                       mol_type = protein
                       organism = synthetic construct
SEQUENCE: 137
VDFCSIYHWP VCYV                                                    14

SEQ ID NO: 138         moltype = AA  length = 16
FEATURE                Location/Qualifiers
source                 1..16
                       mol_type = protein
                       organism = synthetic construct
SEQUENCE: 138
VDFCGLYHWP ICYQVD                                                  16

SEQ ID NO: 139         moltype = AA  length = 14
```

```
FEATURE                Location/Qualifiers
source                 1..14
                       mol_type = protein
                       organism = synthetic construct
SEQUENCE: 139
VDFCYLYSWP ICTK                                                   14

SEQ ID NO: 140         moltype = AA  length = 16
FEATURE                Location/Qualifiers
source                 1..16
                       mol_type = protein
                       organism = synthetic construct
SEQUENCE: 140
VDFCGLYHWP ICYQVY                                                 16

SEQ ID NO: 141         moltype = AA  length = 14
FEATURE                Location/Qualifiers
source                 1..14
                       mol_type = protein
                       organism = synthetic construct
SEQUENCE: 141
IDFCAMYHWP ICDT                                                   14

SEQ ID NO: 142         moltype = AA  length = 14
FEATURE                Location/Qualifiers
source                 1..14
                       mol_type = protein
                       organism = synthetic construct
SEQUENCE: 142
VDFCALYHWP ICYQ                                                   14

SEQ ID NO: 143         moltype = AA  length = 14
FEATURE                Location/Qualifiers
source                 1..14
                       mol_type = protein
                       organism = synthetic construct
SEQUENCE: 143
VEFCKQWTWF GCMT                                                   14

SEQ ID NO: 144         moltype = AA  length = 16
FEATURE                Location/Qualifiers
source                 1..16
                       mol_type = protein
                       organism = synthetic construct
SEQUENCE: 144
VDFCYQYGWP ICSRVD                                                 16

SEQ ID NO: 145         moltype = AA  length = 14
FEATURE                Location/Qualifiers
source                 1..14
                       mol_type = protein
                       organism = synthetic construct
SEQUENCE: 145
VEFCAIYSWP ICKI                                                   14

SEQ ID NO: 146         moltype = AA  length = 16
FEATURE                Location/Qualifiers
source                 1..16
                       mol_type = protein
                       organism = synthetic construct
SEQUENCE: 146
VDFCYQYGWP ICSRLY                                                 16

SEQ ID NO: 147         moltype = AA  length = 14
FEATURE                Location/Qualifiers
source                 1..14
                       mol_type = protein
                       organism = synthetic construct
SEQUENCE: 147
VDFCYMYKWP VCYP                                                   14

SEQ ID NO: 148         moltype = AA  length = 14
FEATURE                Location/Qualifiers
source                 1..14
                       mol_type = protein
                       organism = synthetic construct
SEQUENCE: 148
IDFCLLYKWP VCEL                                                   14
```

```
SEQ ID NO: 149          moltype = AA  length = 14
FEATURE                 Location/Qualifiers
source                  1..14
                        mol_type = protein
                        organism = synthetic construct
SEQUENCE: 149
VDFCAIYSWP ICKI                                                 14

SEQ ID NO: 150          moltype = AA  length = 15
FEATURE                 Location/Qualifiers
source                  1..15
                        mol_type = protein
                        organism = synthetic construct
SEQUENCE: 150
VDFCGLYHWP ICYQV                                                15

SEQ ID NO: 151          moltype = AA  length = 16
FEATURE                 Location/Qualifiers
source                  1..16
                        mol_type = protein
                        organism = synthetic construct
SEQUENCE: 151
VDFCYQYAWP VCSTGD                                               16

SEQ ID NO: 152          moltype = AA  length = 14
FEATURE                 Location/Qualifiers
source                  1..14
                        mol_type = protein
                        organism = synthetic construct
SEQUENCE: 152
IDFCRVYDWP VCSL                                                 14

SEQ ID NO: 153          moltype = AA  length = 14
FEATURE                 Location/Qualifiers
source                  1..14
                        mol_type = protein
                        organism = synthetic construct
SEQUENCE: 153
VDFCYRYSWP VCWA                                                 14

SEQ ID NO: 154          moltype = AA  length = 14
FEATURE                 Location/Qualifiers
source                  1..14
                        mol_type = protein
                        organism = synthetic construct
SEQUENCE: 154
VDFCYKYNWP ICSR                                                 14

SEQ ID NO: 155          moltype = AA  length = 15
FEATURE                 Location/Qualifiers
source                  1..15
                        mol_type = protein
                        organism = synthetic construct
SEQUENCE: 155
VDFCYQYGWP ICSRV                                                15

SEQ ID NO: 156          moltype = AA  length = 14
FEATURE                 Location/Qualifiers
source                  1..14
                        mol_type = protein
                        organism = synthetic construct
SEQUENCE: 156
IDFCYRYGWP VCQT                                                 14

SEQ ID NO: 157          moltype = AA  length = 14
FEATURE                 Location/Qualifiers
source                  1..14
                        mol_type = protein
                        organism = synthetic construct
SEQUENCE: 157
VEICKQWFYT VCLS                                                 14

SEQ ID NO: 158          moltype = AA  length = 14
FEATURE                 Location/Qualifiers
source                  1..14
                        mol_type = protein
                        organism = synthetic construct
SEQUENCE: 158
VDFCALYNWP VCAI                                                 14
```

```
SEQ ID NO: 159          moltype = AA  length = 14
FEATURE                 Location/Qualifiers
source                  1..14
                        mol_type = protein
                        organism = synthetic construct
SEQUENCE: 159
VDFCNLYHWP ICAI                                                  14

SEQ ID NO: 160          moltype = AA  length = 14
FEATURE                 Location/Qualifiers
source                  1..14
                        mol_type = protein
                        organism = synthetic construct
SEQUENCE: 160
VDFCALYHWP VCGL                                                  14

SEQ ID NO: 161          moltype = AA  length = 14
FEATURE                 Location/Qualifiers
source                  1..14
                        mol_type = protein
                        organism = synthetic construct
SEQUENCE: 161
IDFCAVYKWP VCQV                                                  14

SEQ ID NO: 162          moltype = AA  length = 14
FEATURE                 Location/Qualifiers
source                  1..14
                        mol_type = protein
                        organism = synthetic construct
SEQUENCE: 162
IDFCLIYNWP VCDT                                                  14

SEQ ID NO: 163          moltype = AA  length = 14
FEATURE                 Location/Qualifiers
source                  1..14
                        mol_type = protein
                        organism = synthetic construct
SEQUENCE: 163
PDFCAVYRWP ICYQ                                                  14

SEQ ID NO: 164          moltype =   length =
SEQUENCE: 164
000

SEQ ID NO: 165          moltype =   length =
SEQUENCE: 165
000

SEQ ID NO: 166          moltype = AA  length = 256
FEATURE                 Location/Qualifiers
source                  1..256
                        mol_type = protein
                        organism = synthetic construct
SEQUENCE: 166
GGVDFCKIYS WPVCHQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 167          moltype = AA  length = 655
FEATURE                 Location/Qualifiers
source                  1..655
                        mol_type = protein
                        organism = synthetic construct
SEQUENCE: 167
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655
```

-continued

```
SEQ ID NO: 168         moltype = AA  length = 261
FEATURE                Location/Qualifiers
source                 1..261
                       mol_type = protein
                       organism = synthetic construct
SEQUENCE: 168
GGIDFCMLYN WPICAGGGGG SSGGSAAGLL APPGGLSGRS DAGGGGSDIQ LTQSPSSLSA  60
SVGDRVSITC KASQDVSIAV AWYQQKPGKA PKLLIYSASY RYTGVPDRFS GSGSGTDFTL  120
TISSLQPEDF AVYYCQQHYI TPLTFGAGTK VEIKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 169         moltype = AA  length = 655
FEATURE                Location/Qualifiers
source                 1..655
                       mol_type = protein
                       organism = synthetic construct
SEQUENCE: 169
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG SSGGSAAGLL APPGGLSGRS DAGGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 170         moltype = AA  length = 261
FEATURE                Location/Qualifiers
source                 1..261
                       mol_type = protein
                       organism = synthetic construct
SEQUENCE: 170
GGVDFCKIYS WPVCHQGGGG SSGGSAAGLL APPGGLSGRS DAGGGGSDIQ LTQSPSSLSA  60
SVGDRVSITC KASQDVSIAV AWYQQKPGKA PKLLIYSASY RYTGVPDRFS GSGSGTDFTL  120
TISSLQPEDF AVYYCQQHYI TPLTFGAGTK VEIKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 171         moltype = AA  length = 655
FEATURE                Location/Qualifiers
source                 1..655
                       mol_type = protein
                       organism = synthetic construct
SEQUENCE: 171
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG SSGGSAAGLL APPGGLSGRS DAGGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 172         moltype = AA  length = 645
FEATURE                Location/Qualifiers
source                 1..645
                       mol_type = protein
                       organism = synthetic construct
SEQUENCE: 172
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG SSGGSAAGLL APPGGLSGRS DAGGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 173         moltype = AA  length = 271
```

```
FEATURE                Location/Qualifiers
source                 1..271
                       mol_type = protein
                       organism = synthetic construct
SEQUENCE: 173
GGIDFCMLYN WPICAGGGGG SSGGSAAGLL APPGGLSGRS DAGGGGSQVQ LQQSGSELKK  60
PGASVKVSCK ASGYTFTNYG MNWVKQAPGQ GLKWMGWINT YTGEPTYTDD FKGRFAFSLD  120
TSVSTAYLQI SSLKADDTAV YFCARGGFGS SYWYFDVWGQ GSLVTVSSAS TKGPSVFPLA  180
PSSKSTSGGT AALGCLVKDY FPEPVTVSWN SGALTSGVHT FPAVLQSSGL YSLSSVVTVP  240
SSSLGTQTYI CNVNHKPSNT KVDKKVEPKS C                                271

SEQ ID NO: 174         moltype = AA  length = 256
FEATURE                Location/Qualifiers
source                 1..256
                       mol_type = protein
                       organism = synthetic construct
SEQUENCE: 174
GGIDFCMLYN WPICAGGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 175         moltype = AA  length = 655
FEATURE                Location/Qualifiers
source                 1..655
                       mol_type = protein
                       organism = synthetic construct
SEQUENCE: 175
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 176         moltype = AA  length = 256
FEATURE                Location/Qualifiers
source                 1..256
                       mol_type = protein
                       organism = synthetic construct
SEQUENCE: 176
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 177         moltype = AA  length = 655
FEATURE                Location/Qualifiers
source                 1..655
                       mol_type = protein
                       organism = synthetic construct
SEQUENCE: 177
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 178         moltype = AA  length = 645
FEATURE                Location/Qualifiers
source                 1..645
                       mol_type = protein
                       organism = synthetic construct
SEQUENCE: 178
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
```

-continued

```
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 179         moltype = AA  length = 266
FEATURE                Location/Qualifiers
source                 1..266
                       mol_type = protein
                       organism = synthetic construct
SEQUENCE: 179
GGVDFCGLYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF DVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                       266

SEQ ID NO: 180         moltype = AA  length = 256
FEATURE                Location/Qualifiers
source                 1..256
                       mol_type = protein
                       organism = synthetic construct
SEQUENCE: 180
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 181         moltype = AA  length = 655
FEATURE                Location/Qualifiers
source                 1..655
                       mol_type = protein
                       organism = synthetic construct
SEQUENCE: 181
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC        655

SEQ ID NO: 182         moltype = AA  length = 645
FEATURE                Location/Qualifiers
source                 1..645
                       mol_type = protein
                       organism = synthetic construct
SEQUENCE: 182
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 183         moltype = AA  length = 266
FEATURE                Location/Qualifiers
source                 1..266
                       mol_type = protein
                       organism = synthetic construct
SEQUENCE: 183
GGVDFCGLYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF AVWGQGSLVT VSSASTKGPS VFPLAPSSKS  180
```

-continued

```
TSGGTAALGC LVKDYFPEPV TVSWNSGALT SGVHTFPAVL QSSGLYSLSS VVTVPSSSLG  240
TQTYICNVNH KPSNTKVDKK VEPKSC                                       266

SEQ ID NO: 184         moltype = AA  length = 261
FEATURE                Location/Qualifiers
source                 1..261
                       mol_type = protein
                       organism = synthetic construct
SEQUENCE: 184
GGVDFCGLYH WPICYQGGGG SSGGSAAGLL APPGGLSGRS DAGGGGSDIQ LTQSPSSLSA  60
SVGDRVSITC KASQDVSIAV AWYQQKPGKA PKLLIYSASY RYTGVPDRFS GSGSGTDFTL  120
TISSLQPEDF AVYYCQQHYI TPLTFGAGTK VEIKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 185         moltype = AA  length = 655
FEATURE                Location/Qualifiers
source                 1..655
                       mol_type = protein
                       organism = synthetic construct
SEQUENCE: 185
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG SSGGSAAGLL APPGGLSGRS DAGGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC        655

SEQ ID NO: 186         moltype = AA  length = 645
FEATURE                Location/Qualifiers
source                 1..645
                       mol_type = protein
                       organism = synthetic construct
SEQUENCE: 186
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG SSGGSAAGLL APPGGLSGRS DAGGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 187         moltype = AA  length = 271
FEATURE                Location/Qualifiers
source                 1..271
                       mol_type = protein
                       organism = synthetic construct
SEQUENCE: 187
GGVDFCGLYH WPICYQGGGG SSGGSAAGLL APPGGLSGRS DAGGGGSQVQ LQQSGSELKK  60
PGASVKVSCK ASGYTFTNYG MNWVKQAPGQ GLKWMGWINT YTGEPTYTDD FKGRFAFSLD  120
TSVSTAYLQI SSLKADDTAV YFCARGGFGS SYWYFAVWGQ GSLVTVSSAS TKGPSVFPLA  180
PSSKSTSGGT AALGCLVKDY FPEPVTVSWN SGALTSGVHT FPAVLQSSGL YSLSSVVTVP  240
SSSLGTQTYI CNVNHKPSNT KVDKKVEPKS C                                 271

SEQ ID NO: 188         moltype = AA  length = 256
FEATURE                Location/Qualifiers
source                 1..256
                       mol_type = protein
                       organism = synthetic construct
SEQUENCE: 188
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 189         moltype = AA  length = 655
FEATURE                Location/Qualifiers
source                 1..655
                       mol_type = protein
```

```
                         organism = synthetic construct
SEQUENCE: 189
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCAAG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 190           moltype = AA  length = 645
FEATURE                  Location/Qualifiers
source                   1..645
                         mol_type = protein
                         organism = synthetic construct
SEQUENCE: 190
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 191           moltype = AA  length = 266
FEATURE                  Location/Qualifiers
source                   1..266
                         mol_type = protein
                         organism = synthetic construct
SEQUENCE: 191
GGVDFCGLYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAA GGFGSSYWYF DVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                       266

SEQ ID NO: 192           moltype = AA  length = 256
FEATURE                  Location/Qualifiers
source                   1..256
                         mol_type = protein
                         organism = synthetic construct
SEQUENCE: 192
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 193           moltype = AA  length = 655
FEATURE                  Location/Qualifiers
source                   1..655
                         mol_type = protein
                         organism = synthetic construct
SEQUENCE: 193
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 194           moltype = AA  length = 645
FEATURE                  Location/Qualifiers
source                   1..645
                         mol_type = protein
                         organism = synthetic construct
```

```
SEQUENCE: 194
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                645

SEQ ID NO: 195          moltype = AA  length = 266
FEATURE                 Location/Qualifiers
source                  1..266
                        mol_type = protein
                        organism = synthetic construct
SEQUENCE: 195
GGVDFCGLYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYA DVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                     266

SEQ ID NO: 196          moltype = AA  length = 256
FEATURE                 Location/Qualifiers
source                  1..256
                        mol_type = protein
                        organism = synthetic construct
SEQUENCE: 196
GGIDFCAIYQ WPVCRSGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 197          moltype = AA  length = 655
FEATURE                 Location/Qualifiers
source                  1..655
                        mol_type = protein
                        organism = synthetic construct
SEQUENCE: 197
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC      655

SEQ ID NO: 198          moltype = AA  length = 645
FEATURE                 Location/Qualifiers
source                  1..645
                        mol_type = protein
                        organism = synthetic construct
SEQUENCE: 198
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                645

SEQ ID NO: 199          moltype = AA  length = 266
FEATURE                 Location/Qualifiers
source                  1..266
                        mol_type = protein
                        organism = synthetic construct
SEQUENCE: 199
```

```
GGIDFCAIYQ WPVCRSGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF AVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                      266

SEQ ID NO: 200          moltype = AA  length = 256
FEATURE                 Location/Qualifiers
source                  1..256
                        mol_type = protein
                        organism = synthetic construct
SEQUENCE: 200
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 201          moltype = AA  length = 655
FEATURE                 Location/Qualifiers
source                  1..655
                        mol_type = protein
                        organism = synthetic construct
SEQUENCE: 201
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 202          moltype = AA  length = 645
FEATURE                 Location/Qualifiers
source                  1..645
                        mol_type = protein
                        organism = synthetic construct
SEQUENCE: 202
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                 645

SEQ ID NO: 203          moltype = AA  length = 266
FEATURE                 Location/Qualifiers
source                  1..266
                        mol_type = protein
                        organism = synthetic construct
SEQUENCE: 203
GGVDFCALYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYA DVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                      266

SEQ ID NO: 204          moltype = AA  length = 256
FEATURE                 Location/Qualifiers
source                  1..256
                        mol_type = protein
                        organism = synthetic construct
SEQUENCE: 204
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 205          moltype = AA  length = 655
```

```
FEATURE                 Location/Qualifiers
source                  1..655
                        mol_type = protein
                        organism = synthetic construct
SEQUENCE: 205
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 206          moltype = AA  length = 645
FEATURE                 Location/Qualifiers
source                  1..645
                        mol_type = protein
                        organism = synthetic construct
SEQUENCE: 206
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                 645

SEQ ID NO: 207          moltype = AA  length = 266
FEATURE                 Location/Qualifiers
source                  1..266
                        mol_type = protein
                        organism = synthetic construct
SEQUENCE: 207
GGVDFCALYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF AVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                      266

SEQ ID NO: 208          moltype = AA  length = 256
FEATURE                 Location/Qualifiers
source                  1..256
                        mol_type = protein
                        organism = synthetic construct
SEQUENCE: 208
GGVDFCGLYH WPICYQVGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 209          moltype = AA  length = 655
FEATURE                 Location/Qualifiers
source                  1..655
                        mol_type = protein
                        organism = synthetic construct
SEQUENCE: 209
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCAAG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 210          moltype = AA  length = 645
FEATURE                 Location/Qualifiers
```

```
source                1..645
                      mol_type = protein
                      organism = synthetic construct
SEQUENCE: 210
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 211        moltype = AA  length = 266
FEATURE               Location/Qualifiers
source                1..266
                      mol_type = protein
                      organism = synthetic construct
SEQUENCE: 211
GGVDFCGLYH WPICYQVGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAA GGFGSSYWYF DVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                       266

SEQ ID NO: 212        moltype = AA  length = 256
FEATURE               Location/Qualifiers
source                1..256
                      mol_type = protein
                      organism = synthetic construct
SEQUENCE: 212
GGVDFCGLYH WPICYQVGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 213        moltype = AA  length = 655
FEATURE               Location/Qualifiers
source                1..655
                      mol_type = protein
                      organism = synthetic construct
SEQUENCE: 213
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 214        moltype = AA  length = 645
FEATURE               Location/Qualifiers
source                1..645
                      mol_type = protein
                      organism = synthetic construct
SEQUENCE: 214
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                  645

SEQ ID NO: 215        moltype = AA  length = 266
FEATURE               Location/Qualifiers
source                1..266
```

```
                        mol_type = protein
                        organism = synthetic construct
SEQUENCE: 215
GGVDFCALYH WPICYQGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF AVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                      266

SEQ ID NO: 216          moltype = AA  length = 256
FEATURE                 Location/Qualifiers
source                  1..256
                        mol_type = protein
                        organism = synthetic construct
SEQUENCE: 216
GGVDFCAIYS WPICKIGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 217          moltype = AA  length = 655
FEATURE                 Location/Qualifiers
source                  1..655
                        mol_type = protein
                        organism = synthetic construct
SEQUENCE: 217
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 218          moltype = AA  length = 645
FEATURE                 Location/Qualifiers
source                  1..645
                        mol_type = protein
                        organism = synthetic construct
SEQUENCE: 218
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQLTQSPS SLSASVGDRV SITCKASQDV SIAVAWYQQK PGKAPKLLIY  480
SASYRYTGVP DRFSGSGSGT DFTLTISSLQ PEDFAVYYCQ QHYITPLTFG AGTKVEIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC                 645

SEQ ID NO: 219          moltype = AA  length = 266
FEATURE                 Location/Qualifiers
source                  1..266
                        mol_type = protein
                        organism = synthetic construct
SEQUENCE: 219
GGVDFCAIYS WPICKIGGGG SGGLSGRSDA GSPLGLAGSG GSQVQLQQSG SELKKPGASV  60
KVSCKASGYT FTNYGMNWVK QAPGQGLKWM GWINTYTGEP TYTDDFKGRF AFSLDTSVST  120
AYLQISSLKA DDTAVYFCAR GGFGSSYWYF AVWGQGSLVT VSSASTKGPS VFPLAPSSKS  180
TSGGTAALGC LVKDYFPEPV TVSWNSGALT SGVHTFPAVL QSSGLYSLSS VVTVPSSSLG  240
TQTYICNVNH KPSNTKVDKK VEPKSC                                      266

SEQ ID NO: 220          moltype = AA  length = 256
FEATURE                 Location/Qualifiers
source                  1..256
                        mol_type = protein
                        organism = synthetic construct
SEQUENCE: 220
GGIDFCMLYN WPICAGGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
```

```
QGLSSPVTKS FNRGEC                                                256

SEQ ID NO: 221         moltype = AA  length = 655
FEATURE                Location/Qualifiers
source                 1..655
                       mol_type = protein
                       organism = synthetic construct
SEQUENCE: 221
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 222         moltype = AA  length = 256
FEATURE                Location/Qualifiers
source                 1..256
                       mol_type = protein
                       organism = synthetic construct
SEQUENCE: 222
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 223         moltype = AA  length = 655
FEATURE                Location/Qualifiers
source                 1..655
                       mol_type = protein
                       organism = synthetic construct
SEQUENCE: 223
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 224         moltype = AA  length = 256
FEATURE                Location/Qualifiers
source                 1..256
                       mol_type = protein
                       organism = synthetic construct
SEQUENCE: 224
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 225         moltype = AA  length = 655
FEATURE                Location/Qualifiers
source                 1..655
                       mol_type = protein
                       organism = synthetic construct
SEQUENCE: 225
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655
```

```
SEQ ID NO: 226          moltype = AA  length = 15
FEATURE                 Location/Qualifiers
source                  1..15
                        mol_type = protein
                        organism = synthetic construct
SEQUENCE: 226
GGGGSGGGGS GGGGS                                                    15

SEQ ID NO: 227          moltype = AA  length = 5
FEATURE                 Location/Qualifiers
source                  1..5
                        mol_type = protein
                        organism = synthetic construct
SEQUENCE: 227
GGGGS                                                               5

SEQ ID NO: 228          moltype = AA  length = 9
FEATURE                 Location/Qualifiers
source                  1..9
                        mol_type = protein
                        organism = synthetic construct
SEQUENCE: 228
GGGGSGGGS                                                           9

SEQ ID NO: 229          moltype = AA  length = 28
FEATURE                 Location/Qualifiers
source                  1..28
                        mol_type = protein
                        organism = synthetic construct
SEQUENCE: 229
GGGGSGGGLS GRSDAGSPLG LAGSGGGS                                      28

SEQ ID NO: 230          moltype = AA  length = 18
FEATURE                 Location/Qualifiers
source                  1..18
                        mol_type = protein
                        organism = synthetic construct
SEQUENCE: 230
GGGGSLSGRS DNHGSSGT                                                 18

SEQ ID NO: 231          moltype = AA  length = 26
FEATURE                 Location/Qualifiers
source                  1..26
                        mol_type = protein
                        organism = synthetic construct
SEQUENCE: 231
GGGGSSGGSG GSGLSGRSDN HGSSGT                                        26

SEQ ID NO: 232          moltype = AA  length = 8
FEATURE                 Location/Qualifiers
source                  1..8
                        mol_type = protein
                        organism = synthetic construct
SEQUENCE: 232
ASGRSDNH                                                            8

SEQ ID NO: 233          moltype = AA  length = 8
FEATURE                 Location/Qualifiers
source                  1..8
                        mol_type = protein
                        organism = synthetic construct
SEQUENCE: 233
LAGRSDNH                                                            8

SEQ ID NO: 234          moltype = AA  length = 13
FEATURE                 Location/Qualifiers
source                  1..13
                        mol_type = protein
                        organism = synthetic construct
SEQUENCE: 234
ISSGLASGRS DNH                                                      13

SEQ ID NO: 235          moltype = AA  length = 13
FEATURE                 Location/Qualifiers
source                  1..13
                        mol_type = protein
                        organism = synthetic construct
SEQUENCE: 235
```

```
ISSGLLAGRS DNH                                                    13

SEQ ID NO: 236          moltype = AA  length = 8
FEATURE                 Location/Qualifiers
source                  1..8
                        mol_type = protein
                        organism = synthetic construct
SEQUENCE: 236
LSGRSDNH                                                          8

SEQ ID NO: 237          moltype = AA  length = 13
FEATURE                 Location/Qualifiers
source                  1..13
                        mol_type = protein
                        organism = synthetic construct
SEQUENCE: 237
ISSGLLSGRS DNP                                                    13

SEQ ID NO: 238          moltype = AA  length = 13
FEATURE                 Location/Qualifiers
source                  1..13
                        mol_type = protein
                        organism = synthetic construct
SEQUENCE: 238
ISSGLLSGRS DNH                                                    13

SEQ ID NO: 239          moltype = AA  length = 16
FEATURE                 Location/Qualifiers
source                  1..16
                        mol_type = protein
                        organism = synthetic construct
SEQUENCE: 239
LSGRSDNHSP LGLAGS                                                 16

SEQ ID NO: 240          moltype = AA  length = 16
FEATURE                 Location/Qualifiers
source                  1..16
                        mol_type = protein
                        organism = synthetic construct
SEQUENCE: 240
SPLGLAGSLS GRSDNH                                                 16

SEQ ID NO: 241          moltype = AA  length = 12
FEATURE                 Location/Qualifiers
source                  1..12
                        mol_type = protein
                        organism = synthetic construct
SEQUENCE: 241
SPLGLSGRSD NH                                                     12

SEQ ID NO: 242          moltype = AA  length = 16
FEATURE                 Location/Qualifiers
source                  1..16
                        mol_type = protein
                        organism = synthetic construct
SEQUENCE: 242
LAGRSDNHSP LGLAGS                                                 16

SEQ ID NO: 243          moltype = AA  length = 16
FEATURE                 Location/Qualifiers
source                  1..16
                        mol_type = protein
                        organism = synthetic construct
SEQUENCE: 243
LSGRSDNHVP LSLKMG                                                 16

SEQ ID NO: 244          moltype = AA  length = 16
FEATURE                 Location/Qualifiers
source                  1..16
                        mol_type = protein
                        organism = synthetic construct
SEQUENCE: 244
LSGRSDNHVP LSLSMG                                                 16

SEQ ID NO: 245          moltype = AA  length = 31
FEATURE                 Location/Qualifiers
source                  1..31
                        mol_type = protein
                        organism = synthetic construct
```

-continued

```
SEQUENCE: 245
GSSGGSGGSG GSGISSGLLS GRSDNHGSSG T                              31

SEQ ID NO: 246          moltype = AA  length = 28
FEATURE                 Location/Qualifiers
source                  1..28
                        mol_type = protein
                        organism = synthetic construct
SEQUENCE: 246
GSSGGSGGSG GISSGLLSGR SDNHGGGS                                  28

SEQ ID NO: 247          moltype = AA  length = 8
FEATURE                 Location/Qualifiers
source                  1..8
                        mol_type = protein
                        organism = synthetic construct
SEQUENCE: 247
ASGRSDNH                                                        8

SEQ ID NO: 248          moltype = AA  length = 8
FEATURE                 Location/Qualifiers
source                  1..8
                        mol_type = protein
                        organism = synthetic construct
SEQUENCE: 248
LAGRSDNH                                                        8

SEQ ID NO: 249          moltype = AA  length = 13
FEATURE                 Location/Qualifiers
source                  1..13
                        mol_type = protein
                        organism = synthetic construct
SEQUENCE: 249
ISSGLASGRS DNH                                                  13

SEQ ID NO: 250          moltype = AA  length = 8
FEATURE                 Location/Qualifiers
source                  1..8
                        mol_type = protein
                        organism = synthetic construct
SEQUENCE: 250
LSGRSDAG                                                        8

SEQ ID NO: 251          moltype = AA  length = 13
FEATURE                 Location/Qualifiers
source                  1..13
                        mol_type = protein
                        organism = synthetic construct
SEQUENCE: 251
ISSGLLSGRS DAG                                                  13

SEQ ID NO: 252          moltype = AA  length = 18
FEATURE                 Location/Qualifiers
source                  1..18
                        mol_type = protein
                        organism = synthetic construct
SEQUENCE: 252
AAGLLAPPGG LSGRSDAG                                             18

SEQ ID NO: 253          moltype = AA  length = 12
FEATURE                 Location/Qualifiers
source                  1..12
                        mol_type = protein
                        organism = synthetic construct
SEQUENCE: 253
SPLGLSGRSD AG                                                   12

SEQ ID NO: 254          moltype = AA  length = 15
FEATURE                 Location/Qualifiers
source                  1..15
                        mol_type = protein
                        organism = synthetic construct
SEQUENCE: 254
LSGRSDAGSP LGLAG                                                15

SEQ ID NO: 255          moltype = AA  length = 8
FEATURE                 Location/Qualifiers
source                  1..8
                        mol_type = protein
```

```
                        organism = synthetic construct
SEQUENCE: 255
GSTFYTAV                                                        8

SEQ ID NO: 256          moltype = AA  length = 8
FEATURE                 Location/Qualifiers
source                  1..8
                        mol_type = protein
                        organism = synthetic construct
SEQUENCE: 256
IRWTALTT                                                        8

SEQ ID NO: 257          moltype = AA  length = 17
FEATURE                 Location/Qualifiers
source                  1..17
                        mol_type = protein
                        organism = synthetic construct
SEQUENCE: 257
AARGTLGLFT TADSYDY                                              17

SEQ ID NO: 258          moltype = AA  length = 124
FEATURE                 Location/Qualifiers
source                  1..124
                        mol_type = protein
                        organism = synthetic construct
SEQUENCE: 258
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSS                                                            124

SEQ ID NO: 259          moltype = AA  length = 9
FEATURE                 Location/Qualifiers
source                  1..9
                        mol_type = protein
                        organism = synthetic construct
SEQUENCE: 259
TGAVTSANY                                                       9

SEQ ID NO: 260          moltype = AA  length = 9
FEATURE                 Location/Qualifiers
source                  1..9
                        mol_type = protein
                        organism = synthetic construct
SEQUENCE: 260
ALWYSNRWV                                                       9

SEQ ID NO: 261          moltype = AA  length = 9
FEATURE                 Location/Qualifiers
source                  1..9
                        mol_type = protein
                        organism = synthetic construct
SEQUENCE: 261
VAWYSNRWV                                                       9

SEQ ID NO: 262          moltype = AA  length = 9
FEATURE                 Location/Qualifiers
source                  1..9
                        mol_type = protein
                        organism = synthetic construct
SEQUENCE: 262
VLAYSNRWV                                                       9

SEQ ID NO: 263          moltype = AA  length = 9
FEATURE                 Location/Qualifiers
source                  1..9
                        mol_type = protein
                        organism = synthetic construct
SEQUENCE: 263
VLWASNRWV                                                       9

SEQ ID NO: 264          moltype = AA  length = 9
FEATURE                 Location/Qualifiers
source                  1..9
                        mol_type = protein
                        organism = synthetic construct
SEQUENCE: 264
VLWYANRWV                                                       9

SEQ ID NO: 265          moltype = AA  length = 9
```

```
FEATURE                Location/Qualifiers
source                 1..9
                       mol_type = protein
                       organism = synthetic construct
SEQUENCE: 265
VLWYSARWV                                                            9

SEQ ID NO: 266         moltype = AA  length = 9
FEATURE                Location/Qualifiers
source                 1..9
                       mol_type = protein
                       organism = synthetic construct
SEQUENCE: 266
VLWYSNAWV                                                            9

SEQ ID NO: 267         moltype = AA  length = 9
FEATURE                Location/Qualifiers
source                 1..9
                       mol_type = protein
                       organism = synthetic construct
SEQUENCE: 267
VLWYSNRAV                                                            9

SEQ ID NO: 268         moltype = AA  length = 9
FEATURE                Location/Qualifiers
source                 1..9
                       mol_type = protein
                       organism = synthetic construct
SEQUENCE: 268
VLWYSNRWA                                                            9

SEQ ID NO: 269         moltype = AA  length = 10
FEATURE                Location/Qualifiers
source                 1..10
                       mol_type = protein
                       organism = synthetic construct
SEQUENCE: 269
VLWYSNRWVA                                                           10

SEQ ID NO: 270         moltype = AA  length = 8
FEATURE                Location/Qualifiers
source                 1..8
                       mol_type = protein
                       organism = synthetic construct
SEQUENCE: 270
GFTFQKYA                                                             8

SEQ ID NO: 271         moltype = AA  length = 16
FEATURE                Location/Qualifiers
source                 1..16
                       mol_type = protein
                       organism = synthetic construct
SEQUENCE: 271
ARHGNFGNSY ISYWAY                                                    16

SEQ ID NO: 272         moltype = AA  length = 16
FEATURE                Location/Qualifiers
source                 1..16
                       mol_type = protein
                       organism = synthetic construct
SEQUENCE: 272
VAHGNFGNSY ISYWAY                                                    16

SEQ ID NO: 273         moltype = AA  length = 16
FEATURE                Location/Qualifiers
source                 1..16
                       mol_type = protein
                       organism = synthetic construct
SEQUENCE: 273
VRAGNFGNSY ISYWAY                                                    16

SEQ ID NO: 274         moltype = AA  length = 16
FEATURE                Location/Qualifiers
source                 1..16
                       mol_type = protein
                       organism = synthetic construct
SEQUENCE: 274
VRHANFGNSY ISYWAY                                                    16
```

```
SEQ ID NO: 275         moltype = AA  length = 16
FEATURE                Location/Qualifiers
source                 1..16
                       mol_type = protein
                       organism = synthetic construct
SEQUENCE: 275
VRHGAFGNSY ISYWAY                                                  16

SEQ ID NO: 276         moltype = AA  length = 16
FEATURE                Location/Qualifiers
source                 1..16
                       mol_type = protein
                       organism = synthetic construct
SEQUENCE: 276
VRHGNAGNSY ISYWAY                                                  16

SEQ ID NO: 277         moltype = AA  length = 16
FEATURE                Location/Qualifiers
source                 1..16
                       mol_type = protein
                       organism = synthetic construct
SEQUENCE: 277
VRHGNFANSY ISYWAY                                                  16

SEQ ID NO: 278         moltype = AA  length = 16
FEATURE                Location/Qualifiers
source                 1..16
                       mol_type = protein
                       organism = synthetic construct
SEQUENCE: 278
VRHGNFGASY ISYWAY                                                  16

SEQ ID NO: 279         moltype = AA  length = 16
FEATURE                Location/Qualifiers
source                 1..16
                       mol_type = protein
                       organism = synthetic construct
SEQUENCE: 279
VRHGNFGNAY ISYWAY                                                  16

SEQ ID NO: 280         moltype = AA  length = 16
FEATURE                Location/Qualifiers
source                 1..16
                       mol_type = protein
                       organism = synthetic construct
SEQUENCE: 280
VRHGNFGNSA ISYWAY                                                  16

SEQ ID NO: 281         moltype = AA  length = 16
FEATURE                Location/Qualifiers
source                 1..16
                       mol_type = protein
                       organism = synthetic construct
SEQUENCE: 281
VRHGNFGNSY ASYWAY                                                  16

SEQ ID NO: 282         moltype = AA  length = 16
FEATURE                Location/Qualifiers
source                 1..16
                       mol_type = protein
                       organism = synthetic construct
SEQUENCE: 282
VRHGNFGNSY IAYWAY                                                  16

SEQ ID NO: 283         moltype = AA  length = 16
FEATURE                Location/Qualifiers
source                 1..16
                       mol_type = protein
                       organism = synthetic construct
SEQUENCE: 283
VRHGNFGNSY ISAWAY                                                  16

SEQ ID NO: 284         moltype = AA  length = 16
FEATURE                Location/Qualifiers
source                 1..16
                       mol_type = protein
                       organism = synthetic construct
SEQUENCE: 284
VRHGNFGNSY ISYAAY                                                  16
```

```
SEQ ID NO: 285          moltype = AA  length = 16
FEATURE                 Location/Qualifiers
source                  1..16
                        mol_type = protein
                        organism = synthetic construct
SEQUENCE: 285
VRHGNFGNSY ISYWAA                                                  16

SEQ ID NO: 286          moltype = AA  length = 16
FEATURE                 Location/Qualifiers
source                  1..16
                        mol_type = protein
                        organism = synthetic construct
SEQUENCE: 286
VRHGNFGNSY VSYWAY                                                  16

SEQ ID NO: 287          moltype = AA  length = 14
FEATURE                 Location/Qualifiers
source                  1..14
                        mol_type = protein
                        organism = synthetic construct
SEQUENCE: 287
QGCGTIADPE PHCW                                                    14

SEQ ID NO: 288          moltype = AA  length = 14
FEATURE                 Location/Qualifiers
source                  1..14
                        mol_type = protein
                        organism = synthetic construct
SEQUENCE: 288
GSQCLGPEWE VCPY                                                    14

SEQ ID NO: 289          moltype = AA  length = 14
FEATURE                 Location/Qualifiers
source                  1..14
                        mol_type = protein
                        organism = synthetic construct
SEQUENCE: 289
VYCGPEFDES VGCM                                                    14

SEQ ID NO: 290          moltype = AA  length = 14
FEATURE                 Location/Qualifiers
source                  1..14
                        mol_type = protein
                        organism = synthetic construct
SEQUENCE: 290
DWCWYSPDND GLCD                                                    14

SEQ ID NO: 291          moltype = AA  length = 14
FEATURE                 Location/Qualifiers
source                  1..14
                        mol_type = protein
                        organism = synthetic construct
SEQUENCE: 291
SECLVDLQSD PCYW                                                    14

SEQ ID NO: 292          moltype = AA  length = 14
FEATURE                 Location/Qualifiers
source                  1..14
                        mol_type = protein
                        organism = synthetic construct
SEQUENCE: 292
YLCGPDGDET LACY                                                    14

SEQ ID NO: 293          moltype = AA  length = 14
FEATURE                 Location/Qualifiers
source                  1..14
                        mol_type = protein
                        organism = synthetic construct
SEQUENCE: 293
VDCGPDGDES ILCY                                                    14

SEQ ID NO: 294          moltype = AA  length = 14
FEATURE                 Location/Qualifiers
source                  1..14
                        mol_type = protein
                        organism = synthetic construct
SEQUENCE: 294
```

-continued

```
AYCGPEFDES VGCM                                                    14

SEQ ID NO: 295          moltype = AA  length = 14
FEATURE                 Location/Qualifiers
source                  1..14
                        mol_type = protein
                        organism = synthetic construct
SEQUENCE: 295
VYCGPEFDES VGCA                                                    14

SEQ ID NO: 296          moltype = AA  length = 14
FEATURE                 Location/Qualifiers
source                  1..14
                        mol_type = protein
                        organism = synthetic construct
SEQUENCE: 296
ASQCLGPEWE VCPY                                                    14

SEQ ID NO: 297          moltype = AA  length = 14
FEATURE                 Location/Qualifiers
source                  1..14
                        mol_type = protein
                        organism = synthetic construct
SEQUENCE: 297
GSACLGPEWE VCPY                                                    14

SEQ ID NO: 298          moltype = AA  length = 14
FEATURE                 Location/Qualifiers
source                  1..14
                        mol_type = protein
                        organism = synthetic construct
SEQUENCE: 298
YLCGPDADET LACY                                                    14

SEQ ID NO: 299          moltype = AA  length = 14
FEATURE                 Location/Qualifiers
source                  1..14
                        mol_type = protein
                        organism = synthetic construct
SEQUENCE: 299
YLCGPDTDET LACY                                                    14

SEQ ID NO: 300          moltype = AA  length = 14
FEATURE                 Location/Qualifiers
source                  1..14
                        mol_type = protein
                        organism = synthetic construct
SEQUENCE: 300
IDFCAVYKWP VCQV                                                    14

SEQ ID NO: 301          moltype = AA  length = 14
FEATURE                 Location/Qualifiers
source                  1..14
                        mol_type = protein
                        organism = synthetic construct
SEQUENCE: 301
IDFCLIYNWP VCDT                                                    14

SEQ ID NO: 302          moltype = AA  length = 14
FEATURE                 Location/Qualifiers
source                  1..14
                        mol_type = protein
                        organism = synthetic construct
SEQUENCE: 302
PDFCAVYRWP ICYQ                                                    14

SEQ ID NO: 303          moltype = AA  length = 249
FEATURE                 Location/Qualifiers
source                  1..249
                        mol_type = protein
                        organism = synthetic construct
SEQUENCE: 303
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCAR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 304          moltype = AA  length = 249
```

```
FEATURE                 Location/Qualifiers
source                  1..249
                        mol_type = protein
                        organism = synthetic construct
SEQUENCE: 304
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVA HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 305          moltype = AA  length = 249
FEATURE                 Location/Qualifiers
source                  1..249
                        mol_type = protein
                        organism = synthetic construct
SEQUENCE: 305
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR AGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 306          moltype = AA  length = 249
FEATURE                 Location/Qualifiers
source                  1..249
                        mol_type = protein
                        organism = synthetic construct
SEQUENCE: 306
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HANFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 307          moltype = AA  length = 249
FEATURE                 Location/Qualifiers
source                  1..249
                        mol_type = protein
                        organism = synthetic construct
SEQUENCE: 307
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGAFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 308          moltype = AA  length = 249
FEATURE                 Location/Qualifiers
source                  1..249
                        mol_type = protein
                        organism = synthetic construct
SEQUENCE: 308
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNAGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 309          moltype = AA  length = 249
FEATURE                 Location/Qualifiers
source                  1..249
                        mol_type = protein
                        organism = synthetic construct
SEQUENCE: 309
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFANSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 310          moltype = AA  length = 249
FEATURE                 Location/Qualifiers
source                  1..249
                        mol_type = protein
                        organism = synthetic construct
SEQUENCE: 310
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGASYIS YWAYWGQGTL  120
```

-continued

```
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 311         moltype = AA  length = 249
FEATURE                Location/Qualifiers
source                 1..249
                       mol_type = protein
                       organism = synthetic construct
SEQUENCE: 311
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNAYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 312         moltype = AA  length = 249
FEATURE                Location/Qualifiers
source                 1..249
                       mol_type = protein
                       organism = synthetic construct
SEQUENCE: 312
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSAIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 313         moltype = AA  length = 249
FEATURE                Location/Qualifiers
source                 1..249
                       mol_type = protein
                       organism = synthetic construct
SEQUENCE: 313
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYAS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 314         moltype = AA  length = 249
FEATURE                Location/Qualifiers
source                 1..249
                       mol_type = protein
                       organism = synthetic construct
SEQUENCE: 314
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIA YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 315         moltype = AA  length = 249
FEATURE                Location/Qualifiers
source                 1..249
                       mol_type = protein
                       organism = synthetic construct
SEQUENCE: 315
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS AWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 316         moltype = AA  length = 249
FEATURE                Location/Qualifiers
source                 1..249
                       mol_type = protein
                       organism = synthetic construct
SEQUENCE: 316
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YAAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                          249

SEQ ID NO: 317         moltype = AA  length = 249
FEATURE                Location/Qualifiers
source                 1..249
```

```
                         mol_type = protein
                         organism = synthetic construct
SEQUENCE: 317
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAAWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                         249

SEQ ID NO: 318          moltype = AA  length = 249
FEATURE                 Location/Qualifiers
source                  1..249
                        mol_type = protein
                        organism = synthetic construct
SEQUENCE: 318
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC ALWYSNRWVF  240
GGGTKLTVL                                                         249

SEQ ID NO: 319          moltype = AA  length = 249
FEATURE                 Location/Qualifiers
source                  1..249
                        mol_type = protein
                        organism = synthetic construct
SEQUENCE: 319
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VAWYSNRWVF  240
GGGTKLTVL                                                         249

SEQ ID NO: 320          moltype = AA  length = 249
FEATURE                 Location/Qualifiers
source                  1..249
                        mol_type = protein
                        organism = synthetic construct
SEQUENCE: 320
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLAYSNRWVF  240
GGGTKLTVL                                                         249

SEQ ID NO: 321          moltype = AA  length = 249
FEATURE                 Location/Qualifiers
source                  1..249
                        mol_type = protein
                        organism = synthetic construct
SEQUENCE: 321
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWASNRWVF  240
GGGTKLTVL                                                         249

SEQ ID NO: 322          moltype = AA  length = 249
FEATURE                 Location/Qualifiers
source                  1..249
                        mol_type = protein
                        organism = synthetic construct
SEQUENCE: 322
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYANRWVF  240
GGGTKLTVL                                                         249

SEQ ID NO: 323          moltype = AA  length = 249
FEATURE                 Location/Qualifiers
source                  1..249
                        mol_type = protein
                        organism = synthetic construct
SEQUENCE: 323
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSARWVF  240
```

```
GGGTKLTVL                                                        249

SEQ ID NO: 324          moltype = AA  length = 249
FEATURE                 Location/Qualifiers
source                  1..249
                        mol_type = protein
                        organism = synthetic construct
SEQUENCE: 324
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNAWVF  240
GGGTKLTVL                                                        249

SEQ ID NO: 325          moltype = AA  length = 249
FEATURE                 Location/Qualifiers
source                  1..249
                        mol_type = protein
                        organism = synthetic construct
SEQUENCE: 325
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRAVF  240
GGGTKLTVL                                                        249

SEQ ID NO: 326          moltype = AA  length = 249
FEATURE                 Location/Qualifiers
source                  1..249
                        mol_type = protein
                        organism = synthetic construct
SEQUENCE: 326
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWAF  240
GGGTKLTVL                                                        249

SEQ ID NO: 327          moltype = AA  length = 249
FEATURE                 Location/Qualifiers
source                  1..249
                        mol_type = protein
                        organism = synthetic construct
SEQUENCE: 327
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVA  240
GGGTKLTVL                                                        249

SEQ ID NO: 328          moltype = AA  length = 249
FEATURE                 Location/Qualifiers
source                  1..249
                        mol_type = protein
                        organism = synthetic construct
SEQUENCE: 328
EVQLVESGGG LVQPGGSLKL SCAASGFTFN KYAMNWVRQA SGKGLEWVGR IRSKYNNYAT  60
YYADSVKDRF TISRDDSKNT AYLQMNSLKT EDTAVYYCVR HGNFGNSYIS YWAYWGQGTL  120
VTVSSGGGGS GGGGSGGGGS QTVVTQEPSF SVSPGGTVTL TCRSSTGAVT SGNYANWVQQ  180
TPGQAPRGLI GGTKFLAPGV PDRFSGSILG NKAALTITGA QADDESDYYC VLWYSNRWVF  240
GGGTKLTVL                                                        249

SEQ ID NO: 329          moltype = AA  length = 249
FEATURE                 Location/Qualifiers
source                  1..249
                        mol_type = protein
                        organism = synthetic construct
SEQUENCE: 329
EVQLVESGGG LVQPGGSLKL SCAASGFTFQ KYAMNWVRQA PGKGLEWVAR IRSKYNNYAT  60
YYADSVKDRF TISRDDSKNT AYLQMNNLKT EDTAVYYCVR HGNFGNSYVS YWAYWGQGTL  120
VTVSSGGGGS GGGGSGGGGS QTVVTQEPSL TVSPGGTVTL TCGSSTGAVT SANYPNWVQQ  180
KPGQAPRGLI GGTKFLAPGT PARFSGSLLG GKAALTLSGV QPEDEAEYYC ALWYSNRWVF  240
GGGTKLTVL                                                        249

SEQ ID NO: 330          moltype = AA  length = 214
FEATURE                 Location/Qualifiers
source                  1..214
                        mol_type = protein
                        organism = synthetic construct
```

```
SEQUENCE: 330
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 331          moltype = AA  length = 478
FEATURE                 Location/Qualifiers
source                  1..478
                        mol_type = protein
                        organism = synthetic construct
SEQUENCE: 331
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR AGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 332          moltype = AA  length = 214
FEATURE                 Location/Qualifiers
source                  1..214
                        mol_type = protein
                        organism = synthetic construct
SEQUENCE: 332
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 333          moltype = AA  length = 478
FEATURE                 Location/Qualifiers
source                  1..478
                        mol_type = protein
                        organism = synthetic construct
SEQUENCE: 333
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNAGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 334          moltype = AA  length = 214
FEATURE                 Location/Qualifiers
source                  1..214
                        mol_type = protein
                        organism = synthetic construct
SEQUENCE: 334
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 335          moltype = AA  length = 478
FEATURE                 Location/Qualifiers
source                  1..478
                        mol_type = protein
                        organism = synthetic construct
SEQUENCE: 335
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVA  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 336          moltype = AA  length = 214
FEATURE                 Location/Qualifiers
source                  1..214
                        mol_type = protein
                        organism = synthetic construct
SEQUENCE: 336
```

-continued

```
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 337         moltype = AA  length = 478
FEATURE                Location/Qualifiers
source                 1..478
                       mol_type = protein
                       organism = synthetic construct
SEQUENCE: 337
EVQLVESGGG LVQPGGSLKL SCAASGFTFN KYAMNWVRQA SGKGLEWVGR IRSKYNNYAT  60
YYADSVKDRF TISRDDSKNT AYLQMNSLKT EDTAVYYCVR HGNFGNSYIS YWAYWGQGTL  120
VTVSSGGGGS GGGGSGGGGS QTVVTQEPSF SVSPGGTVTL TCRSSTGAVT SGNYANWVQQ  180
TPGQAPRGLI GGTKFLAPGV PDRFSGSILG NKAALTITGA QADDESDYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 338         moltype = AA  length = 214
FEATURE                Location/Qualifiers
source                 1..214
                       mol_type = protein
                       organism = synthetic construct
SEQUENCE: 338
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 339         moltype = AA  length = 478
FEATURE                Location/Qualifiers
source                 1..478
                       mol_type = protein
                       organism = synthetic construct
SEQUENCE: 339
EVQLVESGGG LVQPGGSLKL SCAASGFTFQ KYAMNWVRQA PGKGLEWVAR IRSKYNNYAT  60
YYADSVKDRF TISRDDSKNT AYLQMNNLKT EDTAVYYCVR HGNFGNSYVS YWAYWGQGTL  120
VTVSSGGGGS GGGGSGGGGS QTVVTQEPSL TVSPGGTVTL TCGSSTGAVT SANYPNWVQQ  180
KPGQAPRGLI GGTKFLAPGT PARFSGSLLG GKAALTLSGV QPEDEAEYYC ALWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 340         moltype = AA  length = 214
FEATURE                Location/Qualifiers
source                 1..214
                       mol_type = protein
                       organism = synthetic construct
SEQUENCE: 340
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 341         moltype = AA  length = 478
FEATURE                Location/Qualifiers
source                 1..478
                       mol_type = protein
                       organism = synthetic construct
SEQUENCE: 341
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR AGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFAVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 342         moltype = AA  length = 214
FEATURE                Location/Qualifiers
source                 1..214
                       mol_type = protein
                       organism = synthetic construct
SEQUENCE: 342
DIQLTQSPSS LSASVGDRVS ITCKASQDVS IAVAWYQQKP GKAPKLLIYS ASYRYTGVPD  60
```

```
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 343         moltype = AA  length = 478
FEATURE                Location/Qualifiers
source                 1..478
                       mol_type = protein
                       organism = synthetic construct
SEQUENCE: 343
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNAGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFAVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 344         moltype = AA  length = 214
FEATURE                Location/Qualifiers
source                 1..214
                       mol_type = protein
                       organism = synthetic construct
SEQUENCE: 344
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 345         moltype = AA  length = 478
FEATURE                Location/Qualifiers
source                 1..478
                       mol_type = protein
                       organism = synthetic construct
SEQUENCE: 345
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVA  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFAVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 346         moltype = AA  length = 214
FEATURE                Location/Qualifiers
source                 1..214
                       mol_type = protein
                       organism = synthetic construct
SEQUENCE: 346
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 347         moltype = AA  length = 478
FEATURE                Location/Qualifiers
source                 1..478
                       mol_type = protein
                       organism = synthetic construct
SEQUENCE: 347
EVQLVESGGG LVQPGGSLKL SCAASGFTFQ KYAMNWVRQA PGKGLEWVAR IRSKYNNYAT  60
YYADSVKDRF TISRDDSKNT AYLQMNNLKT EDTAVYYCVR HGNFGNSYVS YWAYWGQGTL  120
VTVSSGGGGS GGGGSGGGGS QTVVTQEPSL TVSPGGTVTL TCGSSTGAVT SANYPNWVQQ  180
KPGQAPRGLI GGTKFLAPGT PARFSGSLLG GKAALTLSGV QPEDEAEYYC ALWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFAVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 348         moltype = AA  length = 214
FEATURE                Location/Qualifiers
source                 1..214
                       mol_type = protein
                       organism = synthetic construct
SEQUENCE: 348
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 349          moltype = AA  length = 478
FEATURE                 Location/Qualifiers
source                  1..478
                        mol_type = protein
                        organism = synthetic construct
SEQUENCE: 349
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VAWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 350          moltype = AA  length = 214
FEATURE                 Location/Qualifiers
source                  1..214
                        mol_type = protein
                        organism = synthetic construct
SEQUENCE: 350
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 351          moltype = AA  length = 478
FEATURE                 Location/Qualifiers
source                  1..478
                        mol_type = protein
                        organism = synthetic construct
SEQUENCE: 351
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSARWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YADVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 352          moltype = AA  length = 256
FEATURE                 Location/Qualifiers
source                  1..256
                        mol_type = protein
                        organism = synthetic construct
SEQUENCE: 352
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 353          moltype = AA  length = 655
FEATURE                 Location/Qualifiers
source                  1..655
                        mol_type = protein
                        organism = synthetic construct
SEQUENCE: 353
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN AGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 354          moltype = AA  length = 256
FEATURE                 Location/Qualifiers
source                  1..256
                        mol_type = protein
                        organism = synthetic construct
```

```
SEQUENCE: 354
GGVDFCGLYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 355          moltype = AA  length = 655
FEATURE                 Location/Qualifiers
source                  1..655
                        mol_type = protein
                        organism = synthetic construct
SEQUENCE: 355
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFQKYA MNWVRQAPGK GLEWVARIRS KYNNYATYYA  240
DSVKDRFTIS RDDSKNTAYL QMNNLKTEDT AVYYCVRHGN FGNSYVSYWA YWGQGTLVTV  300
SSGGGGSGGG GSGGGGSQTV VTQEPSLTVS PGGTVTLTCG SSTGAVTSAN YPNWVQQKPG  360
QAPRGLIGGT KFLAPGTPAR FSGSLLGGKA ALTLSGVQPE DEAEYYCALW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 356          moltype = AA  length = 256
FEATURE                 Location/Qualifiers
source                  1..256
                        mol_type = protein
                        organism = synthetic construct
SEQUENCE: 356
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 357          moltype = AA  length = 655
FEATURE                 Location/Qualifiers
source                  1..655
                        mol_type = protein
                        organism = synthetic construct
SEQUENCE: 357
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 358          moltype = AA  length = 256
FEATURE                 Location/Qualifiers
source                  1..256
                        mol_type = protein
                        organism = synthetic construct
SEQUENCE: 358
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 359          moltype = AA  length = 655
FEATURE                 Location/Qualifiers
source                  1..655
                        mol_type = protein
                        organism = synthetic construct
SEQUENCE: 359
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRAGN FGNSYISYWA YWGQGTLVTV  300
SSGGGGSGGG GSGGGGSQTV VTQEPSLTVS PGGTVTLTCG SSTGAVTSGN YPNWVQQKPG  360
```

```
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 360          moltype = AA  length = 256
FEATURE                 Location/Qualifiers
source                  1..256
                        mol_type = protein
                        organism = synthetic construct
SEQUENCE: 360
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 361          moltype = AA  length = 655
FEATURE                 Location/Qualifiers
source                  1..655
                        mol_type = protein
                        organism = synthetic construct
SEQUENCE: 361
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DADETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRAGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 362          moltype = AA  length = 256
FEATURE                 Location/Qualifiers
source                  1..256
                        mol_type = protein
                        organism = synthetic construct
SEQUENCE: 362
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 363          moltype = AA  length = 655
FEATURE                 Location/Qualifiers
source                  1..655
                        mol_type = protein
                        organism = synthetic construct
SEQUENCE: 363
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN AGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 364          moltype = AA  length = 256
FEATURE                 Location/Qualifiers
source                  1..256
                        mol_type = protein
                        organism = synthetic construct
SEQUENCE: 364
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 365          moltype = AA  length = 655
```

```
FEATURE                Location/Qualifiers
source                 1..655
                       mol_type = protein
                       organism = synthetic construct
SEQUENCE: 365
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVAGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 366         moltype = AA  length = 256
FEATURE                Location/Qualifiers
source                 1..256
                       mol_type = protein
                       organism = synthetic construct
SEQUENCE: 366
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 367         moltype = AA  length = 655
FEATURE                Location/Qualifiers
source                 1..655
                       mol_type = protein
                       organism = synthetic construct
SEQUENCE: 367
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DADETLACYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVAGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 368         moltype = AA  length = 256
FEATURE                Location/Qualifiers
source                 1..256
                       mol_type = protein
                       organism = synthetic construct
SEQUENCE: 368
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 369         moltype = AA  length = 655
FEATURE                Location/Qualifiers
source                 1..655
                       mol_type = protein
                       organism = synthetic construct
SEQUENCE: 369
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFNKYA MNWVRQASGK GLEWVGRIRS KYNNYATYYA  240
DSVKDRFTIS RDDSKNTAYL QMNSLKTEDT AVYYCVRHGN FGNSYISYWA YWGQGTLVTV  300
SSGGGGSGGG GSGGGGSQTV VTQEPSFSVS PGGTVTLTCR SSTGAVTSGN YANWVQQTPG  360
QAPRGLIGGT KFLAPGVPDR FSGSILGNKA ALTITGAQAD DESDYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 370         moltype = AA  length = 256
FEATURE                Location/Qualifiers
```

```
source                 1..256
                       mol_type = protein
                       organism = synthetic construct
SEQUENCE: 370
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 371         moltype = AA  length = 655
FEATURE                Location/Qualifiers
source                 1..655
                       mol_type = protein
                       organism = synthetic construct
SEQUENCE: 371
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DADETLACYG GGGSGGGLSG RSDAGSPLGL AGSGGGSEVQ  180
LVESGGGLVQ PGGSLKLSCA ASGFTFNKYA MNWVRQASGK GLEWVGRIRS KYNNYATYYA  240
DSVKDRFTIS RDDSKNTAYL QMNSLKTEDT AVYYCVRHGN FGNSYISYWA YWGQGTLVTV  300
SSGGGGSGGG GSGGGGSQTV VTQEPSFSVS PGGTVTLTCR SSTGAVTSGN YANWVQQTPG  360
QAPRGLIGGT KFLAPGVPDR FSGSILGNKA ALTITGAQAD DESDYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 372         moltype = AA  length = 256
FEATURE                Location/Qualifiers
source                 1..256
                       mol_type = protein
                       organism = synthetic construct
SEQUENCE: 372
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 373         moltype = AA  length = 655
FEATURE                Location/Qualifiers
source                 1..655
                       mol_type = protein
                       organism = synthetic construct
SEQUENCE: 373
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQASGK GLEWVGRIRS KYNNYATYYA  240
DSVKDRFTIS RDDSKNTAYL QMNSLKTEDT AVYYCVRHGN FGNSYISYWA YWGQGTLVTV  300
SSGGGGSGGG GSGGGGSQTV VTQEPSFSVS PGGTVTLTCR SSTGAVTSGN YANWVQQTPG  360
QAPRGLIGGT KFLAPGVPDR FSGSILGNKA ALTITGAQAD DESDYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 374         moltype = AA  length = 256
FEATURE                Location/Qualifiers
source                 1..256
                       mol_type = protein
                       organism = synthetic construct
SEQUENCE: 374
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 375         moltype = AA  length = 655
FEATURE                Location/Qualifiers
source                 1..655
                       mol_type = protein
                       organism = synthetic construct
SEQUENCE: 375
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGASQCL GPEWEVCPYG GGGSGGGLSG RSDAGSPLGL AGSGGGSEVQ  180
```

```
LVESGGGLVQ PGGSLKLSCA ASGFTFNKYA MNWVRQASGK GLEWVGRIRS KYNNYATYYA  240
DSVKDRFTIS RDDSKNTAYL QMNSLKTEDT AVYYCVRHGN FGNSYISYWA YWGQGTLVTV  300
SSGGGGSGGG GSGGGGSQTV VTQEPSFSVS PGGTVTLTCR SSTGAVTSGN YANWVQQTPG  360
QAPRGLIGGT KFLAPGVPDR FSGSILGNKA ALTITGAQAD DESDYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 376          moltype = AA  length = 256
FEATURE                 Location/Qualifiers
source                  1..256
                        mol_type = protein
                        organism = synthetic construct
SEQUENCE: 376
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 377          moltype = AA  length = 655
FEATURE                 Location/Qualifiers
source                  1..655
                        mol_type = protein
                        organism = synthetic construct
SEQUENCE: 377
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGGSACL GPEWEVCPYG GGGSGGGLSG RSDAGSPLGL AGSGGGSEVQ  180
LVESGGGLVQ PGGSLKLSCA ASGFTFNKYA MNWVRQASGK GLEWVGRIRS KYNNYATYYA  240
DSVKDRFTIS RDDSKNTAYL QMNSLKTEDT AVYYCVRHGN FGNSYISYWA YWGQGTLVTV  300
SSGGGGSGGG GSGGGGSQTV VTQEPSFSVS PGGTVTLTCR SSTGAVTSGN YANWVQQTPG  360
QAPRGLIGGT KFLAPGVPDR FSGSILGNKA ALTITGAQAD DESDYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 378          moltype = AA  length = 256
FEATURE                 Location/Qualifiers
source                  1..256
                        mol_type = protein
                        organism = synthetic construct
SEQUENCE: 378
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 379          moltype = AA  length = 655
FEATURE                 Location/Qualifiers
source                  1..655
                        mol_type = protein
                        organism = synthetic construct
SEQUENCE: 379
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DGDETLACYG GGGSGGGLSG RSDAGSPLGL AGSGGGSEVQ  180
LVESGGGLVQ PGGSLKLSCA ASGFTFQKYA MNWVRQAPGK GLEWVARIRS KYNNYATYYA  240
DSVKDRFTIS RDDSKNTAYL QMNNLKTEDT AVYYCVRHGN FGNSYVSYWA YWGQGTLVTV  300
SSGGGGSGGG GSGGGGSQTV VTQEPSLTVS PGGTVTLTCG SSTGAVTSAN YPNWVQQKPG  360
QAPRGLIGGT KFLAPGTPAR FSGSLLGGKA ALTLSGVQPE DEAEYYCALW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 380          moltype = AA  length = 256
FEATURE                 Location/Qualifiers
source                  1..256
                        mol_type = protein
                        organism = synthetic construct
SEQUENCE: 380
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
```

```
QGLSSPVTKS FNRGEC                                                256

SEQ ID NO: 381          moltype = AA  length = 655
FEATURE                 Location/Qualifiers
source                  1..655
                        mol_type = protein
                        organism = synthetic construct
SEQUENCE: 381
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGYLCGP DADETLACYG GGGSGGGLSG RSDAGSPLGL AGSGGGSEVQ  180
LVESGGGLVQ PGGSLKLSCA ASGFTFQKYA MNWVRQAPGK GLEWVARIRS KYNNYATYYA  240
DSVKDRFTIS RDDSKNTAYL QMNNLKTEDT AVYYCVRHGN FGNSYVSYWA YWGQGTLVTV  300
SSGGGGSGGG GSGGGGSQTV VTQEPSLTVS PGGTVTLTCG SSTGAVTSAN YPNWVQQKPG  360
QAPRGLIGGT KFLAPGTPAR FSGSLLGGKA ALTLSGVQPE DEAEYYCALW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 382          moltype = AA  length = 256
FEATURE                 Location/Qualifiers
source                  1..256
                        mol_type = protein
                        organism = synthetic construct
SEQUENCE: 382
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 383          moltype = AA  length = 655
FEATURE                 Location/Qualifiers
source                  1..655
                        mol_type = protein
                        organism = synthetic construct
SEQUENCE: 383
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFQKYA MNWVRQAPGK GLEWVARIRS KYNNYATYYA  240
DSVKDRFTIS RDDSKNTAYL QMNNLKTEDT AVYYCVRHGN FGNSYVSYWA YWGQGTLVTV  300
SSGGGGSGGG GSGGGGSQTV VTQEPSLTVS PGGTVTLTCG SSTGAVTSAN YPNWVQQKPG  360
QAPRGLIGGT KFLAPGTPAR FSGSLLGGKA ALTLSGVQPE DEAEYYCALW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 384          moltype = AA  length = 256
FEATURE                 Location/Qualifiers
source                  1..256
                        mol_type = protein
                        organism = synthetic construct
SEQUENCE: 384
GGVDFCGLYH WPICYQGGGG SGGGGGSGGG GSGGASSGAG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                256

SEQ ID NO: 385          moltype = AA  length = 655
FEATURE                 Location/Qualifiers
source                  1..655
                        mol_type = protein
                        organism = synthetic construct
SEQUENCE: 385
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGSGG GGSGGASSGA GGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYFA  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655
```

```
SEQ ID NO: 386         moltype = AA  length = 256
FEATURE                Location/Qualifiers
source                 1..256
                       mol_type = protein
                       organism = synthetic construct
SEQUENCE: 386
GGVDFCALYH WPICYQGGGG SGGGSGGSGG ASSGAGGSGG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 387         moltype = AA  length = 655
FEATURE                Location/Qualifiers
source                 1..655
                       mol_type = protein
                       organism = synthetic construct
SEQUENCE: 387
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGSGG GGSGGASSGA GGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 388         moltype = AA  length = 256
FEATURE                Location/Qualifiers
source                 1..256
                       mol_type = protein
                       organism = synthetic construct
SEQUENCE: 388
GGVDFCALYH WPICYQGGGS GGSGGISSGL LSGRSDAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 389         moltype = AA  length = 655
FEATURE                Location/Qualifiers
source                 1..655
                       mol_type = protein
                       organism = synthetic construct
SEQUENCE: 389
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGSGGI SSGLLSGRSD AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 390         moltype = AA  length = 256
FEATURE                Location/Qualifiers
source                 1..256
                       mol_type = protein
                       organism = synthetic construct
SEQUENCE: 390
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 391         moltype = AA  length = 655
FEATURE                Location/Qualifiers
source                 1..655
                       mol_type = protein
                       organism = synthetic construct
SEQUENCE: 391
```

-continued

```
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRAGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 392          moltype = AA  length = 256
FEATURE                 Location/Qualifiers
source                  1..256
                        mol_type = protein
                        organism = synthetic construct
SEQUENCE: 392
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 393          moltype = AA  length = 655
FEATURE                 Location/Qualifiers
source                  1..655
                        mol_type = protein
                        organism = synthetic construct
SEQUENCE: 393
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVAW YSNRWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 394          moltype = AA  length = 256
FEATURE                 Location/Qualifiers
source                  1..256
                        mol_type = protein
                        organism = synthetic construct
SEQUENCE: 394
GGVDFCALYH WPICYQGGGG SGGLSGRSDA GSPLGLAGSG GSDIQLTQSP SSLSASVGDR  60
VSITCKASQD VSIAVAWYQQ KPGKAPKLLI YSASYRYTGV PDRFSGSGSG TDFTLTISSL  120
QPEDFAVYYC QQHYITPLTF GAGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                 256

SEQ ID NO: 395          moltype = AA  length = 655
FEATURE                 Location/Qualifiers
source                  1..655
                        mol_type = protein
                        organism = synthetic construct
SEQUENCE: 395
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCAG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSARWVFGGG  420
TKLTVLGGGG SQVQLQQSGS ELKKPGASVK VSCKASGYTF TNYGMNWVKQ APGQGLKWMG  480
WINTYTGEPT YTDDFKGRFA FSLDTSVSTA YLQISSLKAD DTAVYFCARG GFGSSYWYAD  540
VWGQGSLVTV SSASTKGPSV FPLAPSSKST SGGTAALGCL VKDYFPEPVT VSWNSGALTS  600
GVHTFPAVLQ SSGLYSLSSV VTVPSSSLGT QTYICNVNHK PSNTKVDKKV EPKSC       655

SEQ ID NO: 396          moltype = AA  length = 244
FEATURE                 Location/Qualifiers
source                  1..244
                        mol_type = protein
                        organism = synthetic construct
SEQUENCE: 396
QDNCTCPTNK MTVCSPDGPG GRCQCRALGS GMAVDCSTLT SKCLLLKARM SAPKNARTLV  60
```

```
RPSEHALVDN DGLYDPDCDP EGRFKARQCN QTSVCWCVNS VGVRRTDKGD LSLRCDELVR  120
THHILIDLRH RPTAGAFNHS DLDAELRRLF RERYRLHPKF VAAVHYEQPT IQIELRQNTS  180
QKAAGDVDIG DAAYYFERDI KGESLFQGRG GLDLRVRGEP LQVERTLIYY LDEIPPKFSM  240
KRLT                                                              244

SEQ ID NO: 397         moltype = AA  length = 244
FEATURE                Location/Qualifiers
source                 1..244
                       mol_type = protein
                       organism = synthetic construct
SEQUENCE: 397
QDNCTCPTNK MTVCSPDGPG GRCQCRALGS GVAVDCSTLT SKCLLLKARM SAPKNARTLV  60
RPNEHALVDN DGLYDPDCDP EGRFKARQCN QTSVCWCVNS VGVRRTDKGD LSLRCDELVR  120
THHILIDLRH RPTAGAFNHS DLDAELRRLF RERYRLHPKF VAAVHYEQPT IQIELRQNTS  180
QKAAGDVDIG DAAYYFERDV KGESLFQGRG GLDLRVRGEP LQVERTLIYY LDEIPPKFSM  240
KRLT                                                              244

SEQ ID NO: 398         moltype = AA  length = 293
FEATURE                Location/Qualifiers
source                 1..293
                       mol_type = protein
                       organism = synthetic construct
SEQUENCE: 398
QDNCTCPTNK MTVCSPDGPG GRCQCRALGS GMAVDCSTLT SKCLLLKARM SAPKNARTLV  60
RPSEHALVDN DGLYDPDCDP EGRFKARQCN QTSVCWCVNS VGVRRTDKGD LSLRCDELVR  120
THHILIDLRH RPTAGAFNHS DLDAELRRLF RERYRLHPKF VAAVHYEQPT IQIELRQNTS  180
QKAAGDVDIG DAAYYFERDI KGESLFQGRG GLDLRVRGEP LQVERTLIYY LDEIPPKFSM  240
KRLTAGLIAV IVVVVVALVA GMAVLVITNR RKSGKYKKVE IKELGELRKE PSL         293

SEQ ID NO: 399         moltype = AA  length = 293
FEATURE                Location/Qualifiers
source                 1..293
                       mol_type = protein
                       organism = synthetic construct
SEQUENCE: 399
QDNCTCPTNK MTVCSPDGPG GRCQCRALGS GVAVDCSTLT SKCLLLKARM SAPKNARTLV  60
RPNEHALVDN DGLYDPDCDP EGRFKARQCN QTSVCWCVNS VGVRRTDKGD LSLRCDELVR  120
THHILIDLRH RPTAGAFNHS DLDAELRRLF RERYRLHPKF VAAVHYEQPT IQIELRQNTS  180
QKAAGDVDIG DAAYYFERDV KGESLFQGRG GLDLRVRGEP LQVERTLIYY LDEIPPKFSM  240
KRLTAGLIAV IVVVVVALVA GVAVLVISNR RKSGKYKKVE IKELGELRKE PSL         293

SEQ ID NO: 400         moltype = AA  length = 214
FEATURE                Location/Qualifiers
source                 1..214
                       mol_type = protein
                       organism = synthetic construct
SEQUENCE: 400
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 401         moltype = AA  length = 478
FEATURE                Location/Qualifiers
source                 1..478
                       mol_type = protein
                       organism = synthetic construct
SEQUENCE: 401
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCAR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 402         moltype = AA  length = 214
FEATURE                Location/Qualifiers
source                 1..214
                       mol_type = protein
                       organism = synthetic construct
SEQUENCE: 402
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 403         moltype = AA  length = 478
```

```
FEATURE                Location/Qualifiers
source                 1..478
                       mol_type = protein
                       organism = synthetic construct
SEQUENCE: 403
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVA HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 404         moltype = AA  length = 214
FEATURE                Location/Qualifiers
source                 1..214
                       mol_type = protein
                       organism = synthetic construct
SEQUENCE: 404
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 405         moltype = AA  length = 478
FEATURE                Location/Qualifiers
source                 1..478
                       mol_type = protein
                       organism = synthetic construct
SEQUENCE: 405
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR AGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 406         moltype = AA  length = 214
FEATURE                Location/Qualifiers
source                 1..214
                       mol_type = protein
                       organism = synthetic construct
SEQUENCE: 406
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 407         moltype = AA  length = 478
FEATURE                Location/Qualifiers
source                 1..478
                       mol_type = protein
                       organism = synthetic construct
SEQUENCE: 407
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HANFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 408         moltype = AA  length = 214
FEATURE                Location/Qualifiers
source                 1..214
                       mol_type = protein
                       organism = synthetic construct
SEQUENCE: 408
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 409         moltype = AA  length = 478
FEATURE                Location/Qualifiers
```

```
source                  1..478
                        mol_type = protein
                        organism = synthetic construct
SEQUENCE: 409
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGAFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 410          moltype = AA  length = 214
FEATURE                 Location/Qualifiers
source                  1..214
                        mol_type = protein
                        organism = synthetic construct
SEQUENCE: 410
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 411          moltype = AA  length = 478
FEATURE                 Location/Qualifiers
source                  1..478
                        mol_type = protein
                        organism = synthetic construct
SEQUENCE: 411
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNAGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 412          moltype = AA  length = 214
FEATURE                 Location/Qualifiers
source                  1..214
                        mol_type = protein
                        organism = synthetic construct
SEQUENCE: 412
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 413          moltype = AA  length = 478
FEATURE                 Location/Qualifiers
source                  1..478
                        mol_type = protein
                        organism = synthetic construct
SEQUENCE: 413
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFANSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 414          moltype = AA  length = 214
FEATURE                 Location/Qualifiers
source                  1..214
                        mol_type = protein
                        organism = synthetic construct
SEQUENCE: 414
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 415          moltype = AA  length = 478
FEATURE                 Location/Qualifiers
source                  1..478
```

-continued

```
                        mol_type = protein
                        organism = synthetic construct
SEQUENCE: 415
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGASYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 416          moltype = AA  length = 214
FEATURE                 Location/Qualifiers
source                  1..214
                        mol_type = protein
                        organism = synthetic construct
SEQUENCE: 416
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 417          moltype = AA  length = 478
FEATURE                 Location/Qualifiers
source                  1..478
                        mol_type = protein
                        organism = synthetic construct
SEQUENCE: 417
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNAYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 418          moltype = AA  length = 214
FEATURE                 Location/Qualifiers
source                  1..214
                        mol_type = protein
                        organism = synthetic construct
SEQUENCE: 418
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 419          moltype = AA  length = 478
FEATURE                 Location/Qualifiers
source                  1..478
                        mol_type = protein
                        organism = synthetic construct
SEQUENCE: 419
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSAIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 420          moltype = AA  length = 214
FEATURE                 Location/Qualifiers
source                  1..214
                        mol_type = protein
                        organism = synthetic construct
SEQUENCE: 420
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 421          moltype = AA  length = 478
FEATURE                 Location/Qualifiers
source                  1..478
                        mol_type = protein
```

-continued

```
                        organism = synthetic construct
SEQUENCE: 421
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYAS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 422          moltype = AA  length = 214
FEATURE                 Location/Qualifiers
source                  1..214
                        mol_type = protein
                        organism = synthetic construct
SEQUENCE: 422
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 423          moltype = AA  length = 478
FEATURE                 Location/Qualifiers
source                  1..478
                        mol_type = protein
                        organism = synthetic construct
SEQUENCE: 423
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIA YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 424          moltype = AA  length = 214
FEATURE                 Location/Qualifiers
source                  1..214
                        mol_type = protein
                        organism = synthetic construct
SEQUENCE: 424
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 425          moltype = AA  length = 478
FEATURE                 Location/Qualifiers
source                  1..478
                        mol_type = protein
                        organism = synthetic construct
SEQUENCE: 425
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS AWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 426          moltype = AA  length = 214
FEATURE                 Location/Qualifiers
source                  1..214
                        mol_type = protein
                        organism = synthetic construct
SEQUENCE: 426
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 427          moltype = AA  length = 478
FEATURE                 Location/Qualifiers
source                  1..478
                        mol_type = protein
                        organism = synthetic construct
```

-continued

```
SEQUENCE: 427
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YAAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 428         moltype = AA  length = 214
FEATURE                Location/Qualifiers
source                 1..214
                       mol_type = protein
                       organism = synthetic construct
SEQUENCE: 428
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 429         moltype = AA  length = 478
FEATURE                Location/Qualifiers
source                 1..478
                       mol_type = protein
                       organism = synthetic construct
SEQUENCE: 429
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAAWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 430         moltype = AA  length = 214
FEATURE                Location/Qualifiers
source                 1..214
                       mol_type = protein
                       organism = synthetic construct
SEQUENCE: 430
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 431         moltype = AA  length = 478
FEATURE                Location/Qualifiers
source                 1..478
                       mol_type = protein
                       organism = synthetic construct
SEQUENCE: 431
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC ALWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 432         moltype = AA  length = 214
FEATURE                Location/Qualifiers
source                 1..214
                       mol_type = protein
                       organism = synthetic construct
SEQUENCE: 432
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 433         moltype = AA  length = 478
FEATURE                Location/Qualifiers
source                 1..478
                       mol_type = protein
                       organism = synthetic construct
SEQUENCE: 433
```

-continued

```
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VAWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 434         moltype = AA  length = 214
FEATURE                Location/Qualifiers
source                 1..214
                       mol_type = protein
                       organism = synthetic construct
SEQUENCE: 434
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 435         moltype = AA  length = 478
FEATURE                Location/Qualifiers
source                 1..478
                       mol_type = protein
                       organism = synthetic construct
SEQUENCE: 435
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLAYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 436         moltype = AA  length = 214
FEATURE                Location/Qualifiers
source                 1..214
                       mol_type = protein
                       organism = synthetic construct
SEQUENCE: 436
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 437         moltype = AA  length = 478
FEATURE                Location/Qualifiers
source                 1..478
                       mol_type = protein
                       organism = synthetic construct
SEQUENCE: 437
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWASNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 438         moltype = AA  length = 214
FEATURE                Location/Qualifiers
source                 1..214
                       mol_type = protein
                       organism = synthetic construct
SEQUENCE: 438
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 439         moltype = AA  length = 478
FEATURE                Location/Qualifiers
source                 1..478
                       mol_type = protein
                       organism = synthetic construct
SEQUENCE: 439
EVQLVESGGG LVQPGGSLKL SCAASGFTFN KYAMNWVRQA PGKGLEWVAR IRSKYNNYAT  60
```

```
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYANRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 440         moltype = AA  length = 214
FEATURE                Location/Qualifiers
source                 1..214
                       mol_type = protein
                       organism = synthetic construct
SEQUENCE: 440
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 441         moltype = AA  length = 478
FEATURE                Location/Qualifiers
source                 1..478
                       mol_type = protein
                       organism = synthetic construct
SEQUENCE: 441
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSARWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 442         moltype = AA  length = 214
FEATURE                Location/Qualifiers
source                 1..214
                       mol_type = protein
                       organism = synthetic construct
SEQUENCE: 442
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 443         moltype = AA  length = 478
FEATURE                Location/Qualifiers
source                 1..478
                       mol_type = protein
                       organism = synthetic construct
SEQUENCE: 443
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNAWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 444         moltype = AA  length = 214
FEATURE                Location/Qualifiers
source                 1..214
                       mol_type = protein
                       organism = synthetic construct
SEQUENCE: 444
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 445         moltype = AA  length = 478
FEATURE                Location/Qualifiers
source                 1..478
                       mol_type = protein
                       organism = synthetic construct
SEQUENCE: 445
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
```

```
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRAVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 446         moltype = AA  length = 214
FEATURE                Location/Qualifiers
source                 1..214
                       mol_type = protein
                       organism = synthetic construct
SEQUENCE: 446
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 447         moltype = AA  length = 478
FEATURE                Location/Qualifiers
source                 1..478
                       mol_type = protein
                       organism = synthetic construct
SEQUENCE: 447
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWAF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 448         moltype = AA  length = 214
FEATURE                Location/Qualifiers
source                 1..214
                       mol_type = protein
                       organism = synthetic construct
SEQUENCE: 448
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 449         moltype = AA  length = 478
FEATURE                Location/Qualifiers
source                 1..478
                       mol_type = protein
                       organism = synthetic construct
SEQUENCE: 449
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVA  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 450         moltype = AA  length = 214
FEATURE                Location/Qualifiers
source                 1..214
                       mol_type = protein
                       organism = synthetic construct
SEQUENCE: 450
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 451         moltype = AA  length = 478
FEATURE                Location/Qualifiers
source                 1..478
                       mol_type = protein
                       organism = synthetic construct
SEQUENCE: 451
EVQLVESGGG LVQPGGSLKL SCAASGFTFN KYAMNWVRQA SGKGLEWVGR IRSKYNNYAT  60
YYADSVKDRF TISRDDSKNT AYLQMNSLKT EDTAVYYCVR HGNFGNSYIS YWAYWGQGTL  120
VTVSSGGGGS GGGGSGGGGS QTVVTQEPSF SVSPGGTVTL TCRSSTGAVT SGNYANWVQQ  180
```

-continued

```
TPGQAPRGLI GGTKFLAPGV PDRFSGSILG NKAALTITGA QADDESDYYC VLWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478

SEQ ID NO: 452         moltype = AA  length = 214
FEATURE                Location/Qualifiers
source                 1..214
                       mol_type = protein
                       organism = synthetic construct
SEQUENCE: 452
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 453         moltype = AA  length = 478
FEATURE                Location/Qualifiers
source                 1..478
                       mol_type = protein
                       organism = synthetic construct
SEQUENCE: 453
EVQLVESGGG LVQPGGSLKL SCAASGFTFQ KYAMNWVRQA PGKGLEWVAR IRSKYNNYAT  60
YYADSVKDRF TISRDDSKNT AYLQMNNLKT EDTAVYYCVR HGNFGNSYVS YWAYWGQGTL  120
VTVSSGGGGS GGGGSGGGGS QTVVTQEPSL TVSPGGTVTL TCGSSTGAVT SANYPNWVQQ  180
KPGQAPRGLI GGTKFLAPGT PARFSGSLLG GKAALTLSGV QPEDEAEYYC ALWYSNRWVF  240
GGGTKLTVLG GGGSQVQLQQ SGSELKKPGA SVKVSCKASG YTFTNYGMNW VKQAPGQGLK  300
WMGWINTYTG EPTYTDDFKG RFAFSLDTSV STAYLQISSL KADDTAVYFC ARGGFGSSYW  360
YFDVWGQGSL VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSC    478
```